(12) United States Patent
Chai et al.

(10) Patent No.: US 9,695,149 B2
(45) Date of Patent: Jul. 4, 2017

(54) 1,2,6-SUBSTITUTED BENZIMIDAZOLES AS FLAP MODULATORS

(71) Applicant: JANSSEN PHARMACEUTICA NV, Beerse (BE)

(72) Inventors: Wenying Chai, San Diego, CA (US); Curt A. Dvorak, Poway, CA (US); Wendy Eccles, San Diego, CA (US); James P. Edwards, San Diego, CA (US); Steven D. Goldberg, Encinitas, CA (US); Paul J. Krawczuk, San Diego, CA (US); Alec D. Lebsack, Ladera Ranch, CA (US); Jing Liu, San Diego, CA (US); Daniel J. Pippel, Del Mar, CA (US); Zachary S. Sales, Escondido, CA (US); Virginia M. Tanis, Carlsbad, CA (US); Mark S. Tichenor, San Diego, CA (US); John J. M. Wiener, La Jolla, CA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

(21) Appl. No.: 14/777,492

(22) PCT Filed: Mar. 13, 2014

(86) PCT No.: PCT/US2014/025609
§ 371 (c)(1),
(2) Date: Sep. 15, 2015

(87) PCT Pub. No.: WO2014/151380
PCT Pub. Date: Sep. 25, 2014

(65) Prior Publication Data
US 2016/0039790 A1 Feb. 11, 2016

Related U.S. Application Data

(60) Provisional application No. 61/799,901, filed on Mar. 15, 2013.

(51) Int. Cl.
| C07D 401/12 | (2006.01) |
| C07D 401/14 | (2006.01) |
| C07D 403/12 | (2006.01) |
| C07D 403/14 | (2006.01) |
| A61K 31/4184 | (2006.01) |
| A61K 31/4439 | (2006.01) |
| A61K 31/454 | (2006.01) |
| A61K 31/4545 | (2006.01) |
| A61K 31/506 | (2006.01) |

(52) U.S. Cl.
CPC ........ *C07D 401/12* (2013.01); *A61K 31/4184* (2013.01); *A61K 31/4439* (2013.01); *A61K 31/454* (2013.01); *A61K 31/4545* (2013.01); *A61K 31/506* (2013.01); *C07D 401/14* (2013.01); *C07D 403/12* (2013.01); *C07D 403/14* (2013.01)

(58) Field of Classification Search
None
See application file for complete search history.

(56) References Cited

U.S. PATENT DOCUMENTS

| 5,021,443 | A | 6/1991 | Bru-Magniez |
| 5,124,336 | A | 6/1992 | Bru-Magniez |
| 5,128,359 | A | 7/1992 | Bru-Magniez |
| 8,952,177 | B2 | 2/2015 | Chai et al. |
| 9,067,917 | B2 | 6/2015 | Chai et al. |
| 9,089,569 | B2 | 7/2015 | Chai et al. |
| 9,265,770 | B2 | 2/2016 | Chai et al. |
| 2005/0101647 | A1 | 5/2005 | Oda |
| 2007/0244128 | A1 | 10/2007 | Hutchinson et al. |
| 2011/0190343 | A1 | 8/2011 | Gochin |

(Continued)

FOREIGN PATENT DOCUMENTS

| EP | 1878724 A1 | 1/2008 |
| WO | WO 0157020 A1 | 8/2001 |

(Continued)

OTHER PUBLICATIONS

U.S. Appl. No. 61/799,660, filed Mar. 15, 2013, Chai et al.

(Continued)

*Primary Examiner* — Timothy R Rozof

(57) ABSTRACT

The present invention relates to compounds of Formula (I),

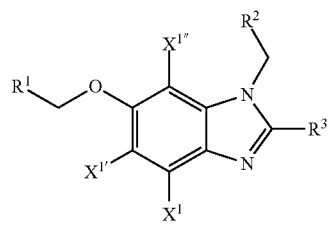

(I)

and solvates, hydrates, and pharmaceutically acceptable salts thereof, wherein $X^1$, $X^{1'}$, $X^{1''}$, $R^1$, $R^2$ and $R^3$ are as defined herein, useful as FLAP modulators. The invention also relates to pharmaceutical compositions comprising compounds of Formula (I). Methods of making and using the compounds of Formula (I) are also within the scope of the invention.

20 Claims, No Drawings

(56) References Cited

U.S. PATENT DOCUMENTS

| | | |
|---|---|---|
| 2012/0214762 A1 | 8/2012 | Staben |
| 2014/0275028 A1 | 9/2014 | Chai et al. |
| 2014/0275029 A1 | 9/2014 | Chai et al. |
| 2015/0119382 A1 | 4/2015 | Chai et al. |
| 2015/0246052 A1 | 9/2015 | Chai et al. |
| 2016/0039790 A1 | 2/2016 | Chai et al. |
| 2016/0046600 A1 | 2/2016 | Chai et al. |
| 2016/0108028 A1 | 4/2016 | Chai et al. |

FOREIGN PATENT DOCUMENTS

| | | | |
|---|---|---|---|
| WO | WO 03018061 A1 | 3/2003 | |
| WO | WO 2004108686 A2 | 12/2004 | |
| WO | WO 2005018672 A1 | 3/2005 | |
| WO | WO 2008153129 A1 | 12/2008 | |
| WO | WO 2009000413 A1 | 12/2008 | |
| WO | WO 2010001869 A1 * | 1/2010 | ........... A61K 31/415 |
| WO | WO 2011109254 A1 | 9/2011 | |

OTHER PUBLICATIONS

U.S. Appl. No. 61/799,901, filed Mar. 15, 2013, Chai et al.
Abramovitz et al, "5-lipoxygenase-activating protein stimulates the utilization of arachidonic acid by 5-lipoxygenase," *Eur. J. Biochem.*, 1993, 215:105-111.
Avis et al, editors, *Pharmaceutical Dosage Forms: Parenteral Medications*, $2^{nd}$ Edition, vol. 1, published by Marcel Dekker, Inc., 1992, Table of Contents and Index.
Avis et al, editors, *Pharmaceutical Dosage Forms: Parenteral Medications*, vol. 2, published by Marcel Dekker, Inc., 1993, Table of Contents and Index.
Banoglu, E., et al., "Identification of Novel Benzimidazole Derivatives as Inhibitors of Leukotriene Biosynthesis by Virtual Screening, Targeting 5-Lipoxygenase-Activating Protein (FLAPP")," vol. 20, No. 12, pp. 3728-3741 (2012).
Berge et al, "Pharmaceutical Salts," *Journal of Pharmaceutical Sciences*, 1997, 66(1):1-19.
Bundgaard, editor, *Design of Prodrugs*, published by Elsevier, 1985, Table of Contents.
Chi et al, "Interaction between ALOX5AP and CYP3A5 gene variants significantly increases the risk for cerebral infarctions in Chinese," *NeuroReport.*, 2014, 25(7):452-457.
Chu et al, "Involvement of 5-lipoxygenase activating protein in the amyloidotic phenotype of an Alzheimer's disease mouse model," *Journal of Neuroinflammation*, 2012, 9:127.
Chwieśko-Minarowska et al, "The role of leukotrienes in the pathogenesis of systemic sclerosis," *Folia Histochemica et Cytobiologica*, 2012, 50(2), 180-85.
Gould, "Salt selection for basic drugs," *International Journal of Pharmaceutics*, 1986, 33:201-217.
Greene et al, editors, *Protective Groups in Organic Synthesis*, $3^{rd}$ Edition, published by John Wiley & Sons, 1999, Index.
Griffiths et al, "Collagen-induced Arthritis is Reduced in 5-Lipoxygenase-activating Protein-deficient Mice," *J. Exp. Med.*, 1997, 185(6):1123-29).
Haeggström et al, "Lipoxygenase and Leukotriene Pathways: Biochemistry, Biology, and Roles in Disease," *Chemical Reviews*, 2011, 111(10):5866-98.
Helgadottir et al, "The gene encoding 5-lipoxygenase activating protein confers risk of myocardial infarction, atherosclerosis and stroke," *Nature Genetics*, Mar. 2004, 36(3):233-39.

Holloway et al, "The role of LTA4H and ALOX5AP polymorphism in asthma and allergy susceptibility," *Allergy*, 2008, 63(8):1046-53.
Ji et al, "Genetic Variants in the Promoter Region of the ALOX5AP Gene and Susceptibility of Ischemic Stroke," *Cerebrovascular Diseases*, 2011, 32(3), 261-68.
Krawiec et al, "Leukotriene inhibitors and non-steroidal therapies in the treatment of asthma," *Expert Opinion on Pharmacotherapy*, 2001, 2(1), 47-65.
Lieberman et al, editors, *Pharmaceutical Dosage Forms: Tablets*, Second Edition, vol. 1, published by Marcel Dekker, Inc., 1989, Table of Contents and Index.
Lieberman et al, editors, *Pharmaceutical Dosage Forms: Tablets*, Second Edition, vols. 2-3, published by Marcel Dekker, Inc., 1990, Table of Contents and Index.
Lieberman et al, editors, *Pharmaceutical Dosage Forms: Disperse Systems*, vols. 1-2, published by Marcel Dekker, Inc., 1996, Table of Contents and Index.
Loell et al, "Activated LTB4 pathway in muscle tissue of patients with polymyositis or dermatomyositis," *Ann. Rheum. Dis.*, 2013, 72(2):293-99.
Mcomie, editor, *Protective Groups in Organic Chemistry*, published Plenum Press, 1973, Index and Table of Contents.
Nair et al, "Expression Analysis of Leukotriene-Inflammatory Gene Interaction Network in Patients with Coronary Artery Disease," *Journal of Atherosclerosis and Thrombosis*, 2013, 20:000-000.
Reicin et al, "Montelukast, a Leukotriene Receptor Antagonist, in Combination with Loratadine, a Histamine Receptor Antagonist, in the Treatment of Chronic Asthma," *Arch. Intern. Med.*, 2000, 160(16):2418-88.
Rosnowska et al, "Leukotrienes C4 and B4 in cerebrospinal fluid of patients with multiple sclerosis," *Polski Merkuriusz Lekarski*, 1997, 2:254-55. (English Abstract).
Rowe et al, editors, *The Handbook of Pharmaceutical Excipients*, $5^{th}$ Edition, published by the American Pharmaceutical Association and the Pharmaceutical Society of Great Britain, 2006, Table of Contents and Index.
Samuelsson, "Leukotrienes: Mediators of Immediate Hypersensitivity Reactions and Inflammation," *Science*, 1983, 220:568-75).
Sanada et al, "The effectiveness of montelukast for the treatment of anti-histamine-resistant chronic urticaria," *Arch. Dermatol. Res.*, 2005, 297(3):134-138.
Strid et al, "Distinct parts of leukotriene C(4) synthase interact with 5-lipoxygenase and 5-lipoxygenase activating protein," *Biochemical and Biophysical Research Communications*, 2009, 381(4):518-22.
Tulah et al, "The role of ALOX5AP, LTA4H and LTB4R polymorphisms in determining baseline lung function and COPD susceptibility in UK smokers," *BMC Medical Genetucs*, 2011, 29(12), 173.
Wang et al, "Eicosanoids and cancer," *Nature Reviews—Cancer*, 2010, 10(3), 181-93.
Yu et al, "Disruption of the 5-lipoxygenase pathway attenuates atherogenesis consequent to COX-2 deletion in mice," *Proc. Natl. Acad. Sci.* (*PNAS*), 2012, 109(17):6727-32.
Yu et al, "Myeloid Cell 5-Lipoxygenase Activating Protein Modulates the Response to Vascular Injury," *Circulation Research*, 2013, 112:432-440.
International Search Report mailed Jul. 17, 2014 for Application No. PCT/US2014/025609.
International Search Report mailed Jul. 29, 2014 for Application No. PCT/US2014/025582.

* cited by examiner

1,2,6-SUBSTITUTED BENZIMIDAZOLES AS FLAP MODULATORS

CROSS REFERENCE TO RELATED APPLICATIONS

This application is a 35 U.S.C. 371 nationalization of PCT application PCT/US2014/025609 filed Mar. 13, 2014, which claims priority to Provisional Application 61/799,901, filed Mar. 15, 2013, each of which are incorporated herein by reference in its entirety.

FIELD OF THE INVENTION

The present invention relates to substituted compounds useful as 5-lipoxygenase-activating protein (FLAP) modulators, pharmaceutical compositions of such compounds, methods of preparation and use thereof. More particularly, FLAP modulators are useful for preventing, treating or ameliorating FLAP-mediated diseases and/or disorders, including those inflammation diseases and/or disorders associated with dermatological and respiratory disorders, allergic disorders, autoimmunity, cancer, cardiovascular and metabolic disorders.

BACKGROUND OF THE INVENTION

FLAP is a key initiator of the leukotriene synthesis pathway that binds and then transfers arachidonic acid to 5-lipoxygenase (M. Abramovitz et al., "5-lipoxygenase-activating protein stimulates the utilization of arachidonic acid by 5-lipoxygenase," *Eur. J. Biochem.*, 1993, 215, 105-11). FLAP has been demonstrated to interact with $LTC_4$ synthase, and could putatively modulate the production of $LTC_4$ (T. Strid et al., "Distinct parts of leukotriene C(4) synthase interact with 5-lipoxygenase and 5-lipoxygenase activating protein," *Biochem. Biophys. Res. Comm.*, 2009, 381(4), 518-22). Modulation (including without limitation inhibition) or genetic deletion of FLAP blocks leukotriene production, specifically $LTB_4$, the cysteinyl leukotrienes ($LTC_4$, $LTD_4$ and $LTE_4$) as well as 5-oxo-ETE (J. Z. Haeggström et al., "Lipoxygenase and leukotriene pathways: biochemistry, biology, and roles in disease," *Chem Rev.*, 2011, 111(10), 5866-98).

Leukotrienes are immune-modulating lipids formed from arachidonic acid (reviewed in B. Samuelsson, "Leukotrienes: mediators of immediate hypersensitivity reactions and inflammation," *Science*, 1983, 220, 568-75). They are synthesized primarily by eosinophils, neutrophils, mast cells, basophils, dendritic cells, macrophages and monocytes. Leukotrienes mediate multiple biological effects including, by way of example only, smooth muscle contraction, leukocyte recruitment and activation, cytokine secretion, fibrosis, mucous secretion, and vascular function (J. Z. Haeggström, at 5866-98).

FLAP-deficient mice are healthy and reproduce normally. They do not produce leukotrienes and have decreased susceptibility in mouse models of arthritis (R. J. Griffiths et al., "Collagen-induced arthritis is reduced in 5-lipoxygenase-activating protein-deficient mice," *J. Exp. Med.*, 1997, 185, 1123-29). In humans, FLAP itself has been linked by genetic studies to respiratory disorders and cardiovascular disease, including myocardial infarction, atherosclerosis and stroke (A. Helgadottir et al., "The gene encoding 5-lipoxygenase activating protein confers risk of myocardial infarction, atherosclerosis, cerebral infarctions, coronary artery disease and stroke," *Nat. Genet.*, 2004, 36, 233-39; A. S. Tulah et al., "The role of ALOX5AP, LTA4H and LTB4R polymorphisms in determining baseline lung function and COPD susceptibility in UK smokers," *BMC Med. Genet.*, 2011, 29(12), 173; R. Ji et al., "Genetic variants in the promoter region of the ALOX5AP gene and susceptibility of ischemic stroke," *Cerebrovasc. Dis.*, 2011, 32(3), 261-68; J. W. Holloway et al., "The role of LTA4H and ALOX5AP polymorphism in asthma and allergy susceptibility," *Allergy*, 2008, 63(8), 1046-53; J. Nair et al., "Expression analysis of leukotriene-inflammatory gene interaction network in patients with coronary artery disease," *J Atheroscler. Thromb.*, 2013; L. F. Chi et al., "Interaction between ALOX5AP and CYP3A5 gene variants significantly increases the risk for cerebral infarctions in Chinese," *Neuroreport.*, 2013). In addition, studies using animal models support a causative role for leukotrienes in aortic aneurisms, atherosclerosis, pulmonary arterial hypertension, myocardial infarction, atherosclerosis, and stroke (reviewed in J. Z. Haeggström, at 5866-98).

Leukotrienes also play a role in autoimmune disorders such as rheumatoid arthritis, inflammatory bowel disease, nephritis, spondyloarthritis, polymyositis, dermatomyositis, gouty effusions, systemic lupus erythematosus, systemic sclerosis, Alzheimer's disease and multiple sclerosis (S. Chwieśko-Minarowska et al., "The role of leukotrienes in the pathogenesis of systemic sclerosis," *Folia Histochem. Cytobiol.*, 2012, 50(2), 180-85; M. Rosnowska et al., "Leukotrienes C4 and B4 in cerebrospinal fluid of patients with multiple sclerosis," *Pol. Merkuriusz Lek.*, 1997, 2, 254-55; and reviewed in J. Z. Haeggström, at 5866-98; I. Loell et al., "Activated LTB4 pathway in muscle tissue of patients with polymyositis or dermatomyositis," *Ann. Rheum. Dis.*, 2013, 72(2), 293-99; J. Chu et al., "Involvement of 5-lipoxygenase activating protein in the amyloidotic phenotype of an Alzheimer's disease mouse model," *J. Neuroinflammation*, 2012, 9, 127). Leukotrienes have also been implicated in several aspects of carcinogenesis including tumor cell proliferation, differentiation, apoptosis, tumor-associated angiogenesis, as well as the migration and invasion of carcinoma cells (D. Wang and R. N. Dubois, "Eicosanoids and cancer," *Nat. Rev. Cancer*, 2010, 10(3), 181-93).

Leukotrienes play a key role in allergic disorders such as allergic rhinitis, allergic dermatitis and asthma, aspirin exacerbated respiratory disease, as well as respiratory disorders such as exacerbations, non-allergic asthma, fibrotic lung diseases, acute respiratory distress syndrome and chronic obstructive pulmonary disease (reviewed in J. Z. Haeggström at 5866-98). Approved antagonists of the $LTC_4$ receptor and leukotriene synthesis modulators such as zileuton have shown clinical efficacy in a variety of respiratory disorders (reviewed in M. E. Krawiec and S. E. Wenzel, "Leukotriene modulators and non-steroidal therapies in the treatment of asthma," *Expert. Opin. Pharmacotherapy*, 2001, 2(1), 47-65).

All the above evidence supports a key role of leukotrienes in a variety of human diseases and/or disorders, and FLAP modulation would be effective for the prevention, treatment, or amelioration of these immune-mediated inflammatory diseases and/or disorders. Furthermore, there still remains a need for FLAP modulator compounds that have pharmacokinetic and pharmacodynamic properties suitable for use as human pharmaceuticals.

SUMMARY OF THE INVENTION

In its many embodiments, the present invention provides novel compounds useful as, for example, FLAP modulators (including without limitation novel compounds that inhibit FLAP), methods of preparing such compounds, pharmaceutical compositions comprising one or more such compounds, methods of preparing pharmaceutical compositions comprising one or more such compounds, and methods of prophylaxis, treatment, amelioration, including without limitation inhibition, of one or more diseases and/or disorders associated with FLAP using such compounds or pharmaceutical compositions.

One aspect of the present invention is directed to compounds, methods, and compositions for the treatment or prophylaxis or amelioration of a variety of diseases and/or disorders that are mediated or sustained through the activity of leukotrienes, including pulmonary, allergic, fibrotic, neurological, inflammatory, autoimmune and cardiovascular diseases and cancer or associated symptoms or complications thereof.

More specifically, this invention is directed to a method of treating exacerbations, non-allergic asthma, fibrotic lung diseases, acute respiratory distress syndrome and chronic obstructive pulmonary disease, or associated symptoms or complications thereof, in a subject afflicted with such a disease and/or disorder, wherein the method comprises administering a FLAP modulator.

Another aspect of the present invention is directed to compounds, methods, and compositions for the treatment or prophylaxis or amelioration of cardiac and cardiovascular diseases and/or disorders, or associated symptoms or complications thereof, that include but are not limited to myocardial infarction, atherosclerosis, atherosclerosis and stroke aortic aneurisms, or associated symptoms or complications thereof, in a subject afflicted with such a disease and/or disorder, wherein the method comprises administering a FLAP modulator.

Yet another aspect of the present invention is directed to compounds, methods, and compositions for the prophylaxis, treatment, or amelioration of autoimmune diseases and/or disorders, or associated symptoms or complications thereof, that include but are not limited to rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis or allergic disorders that include but are not limited to allergic rhinitis, allergic dermatitis and asthma, or associated symptoms or complications thereof, in a subject afflicted with such a disease and/or disorder, wherein the method comprises administering a FLAP modulator.

Finally, one aspect of the present invention is directed to compounds, methods, and compositions for the prophylaxis, treatment, or amelioration of carcinogenesis including but not limited to tumor cell proliferation, differentiation, apoptosis, tumor-associated angiogenesis, as well as the migration and invasion of carcinoma cells, or associated symptoms or complications thereof, in a subject afflicted with such a disease and/or disorder, wherein the method comprises administering a FLAP modulator.

Another aspect of the present invention features a compound of Formula (I)

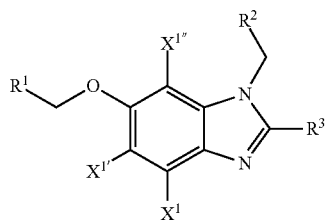

wherein:
$X^1$ is H Cl, or F;
$X^{1'}$ is H, Cl, or F;
$X^{1''}$ is H, or F;
$R^1$ is

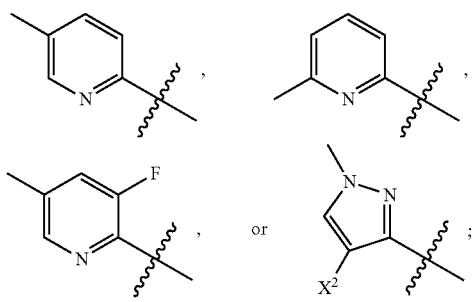

$X^2$ is H, F, or Cl;
$R^2$ is

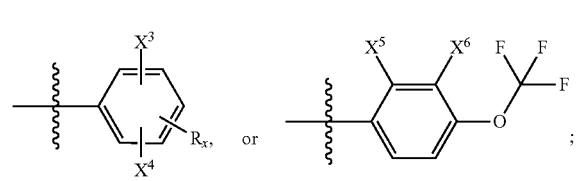

$R_x$ is Br, $CH_3$, —CN, $CF_3$,

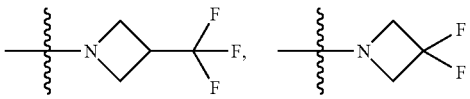

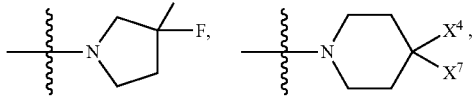

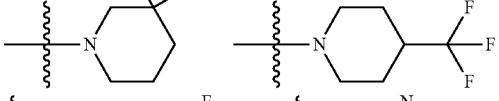

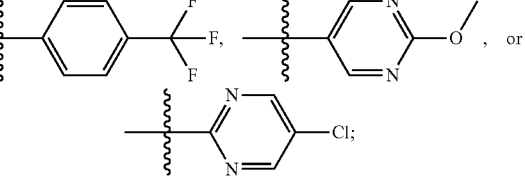

$X^3$ is H, or F;
$X^4$ is H, or F;
$X^5$ is H, Br, Cl, $CH_3$, $OCH_3$, or F;
$X^6$ is H, Cl, $CH_3$, or F;
$X^7$ is H, F, $CH_3$, or $C(CH_3)_3$;
$R^3$ is

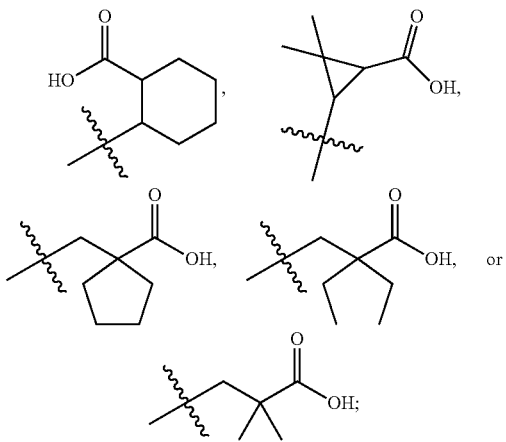

provided that the second eluting isomer of racemic cis-2-{1-(4-Cyanobenzyl)-6-[(5-methylpyridin-2-yl)methoxy]-1H-benzimidazol-2-yl}cyclohexanecarboxylic acid when purified by chiral SFC on (CHIRALCEL OJ-H 5 µm 250×20 mm) mobile phase (65% $CO_2$, 35% EtOH), the second eluting isomer of racemic cis-3-{1-(4-Bromo-2-fluorobenzyl)-6-[(5-methylpyridin-2-yl)methoxy]-1H-benzimidazol-2-yl}-2,2-dimethylcyclopropanecarboxylic acid when purified by chiral SFC on (CHIRALPAK AD-H 5 µm 250×20 mm) mobile phase (60% $CO_2$, 40% MeOH), and the first eluting isomer of racemic cis-2-{1-[2-Fluoro-4-(trifluoromethoxy)benzyl]-6-[(1-methyl-1H-pyrazol-3-yl)methoxy]-1H-benzimidazol-2-yl}cyclohexanecarboxylic acid when purified by chiral SFC (CHIRALCEL OD-H 5 µm 250×20 mm) mobile phase (80% $CO_2$, 20% MeOH) are specifically excluded;
and solvates, hydrates, and pharmaceutically acceptable salts thereof.

Another aspect of the present invention features a pharmaceutical composition comprising a therapeutically effective amount of at least one compound of Formula (I) and at least one pharmaceutically acceptable carrier. The invention is also directed towards providing a process for formulating a pharmaceutical composition, comprising formulating a pharmaceutical composition of a therapeutically effective amount of at least one compound of Formula (I) and at least one pharmaceutically acceptable carrier. The present invention further relates to a process for making a pharmaceutical composition comprising mixing any of the compounds according to Formula (I) and a pharmaceutically acceptable carrier.

The present invention also features a method of treating a subject suffering from or diagnosed with a disease and/or disorder mediated by FLAP activity, comprising administering to the subject a therapeutically effective amount of at least one compound of Formula (I). Such a disease and/or disorder can include, but is not limited to respiratory disorders, cardiac and cardiovascular diseases, autoimmune disorders, carcinogenesis or associated symptoms or complications. More specifically, this invention is directed to a method of treating exacerbations, non-allergic asthma, fibrotic lung diseases, acute respiratory distress syndrome, chronic obstructive pulmonary disease myocardial infarction, atherosclerosis, atherosclerosis and stroke aortic aneurisms, rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis, allergic rhinitis, allergic dermatitis and asthma, tumor cell proliferation, differentiation, apoptosis, tumor-associated angiogenesis, as well as the migration and invasion of carcinoma cells, or associated symptoms or complications thereof, in a subject afflicted with such a disease and/or disorder, or associated symptoms or complications thereof, wherein the method comprises administering a FLAP modulator to a subject in need thereof, a therapeutically effective amount of at least one compound of Formula (I), preferably in a pharmaceutical composition comprising at least one compound of Formula (I).

Additional embodiments and advantages of the invention will become apparent from the detailed discussion, schemes, examples, and claims below.

DETAILED DESCRIPTION OF THE INVENTION

This invention relates to novel FLAP modulators and compositions thereof for the prophylaxis, treatment, or amelioration of numerous diseases and/or disorders, including but not limited to respiratory diseases and/or disorders, cardiac and cardiovascular diseases and/or disorders, autoimmune diseases and/or disorders, carcinogenesis, and associated symptoms or complications thereof.

Another aspect of the present invention features a compound of Formula (I)

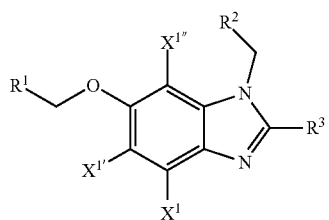

wherein:
$X^1$ is H Cl, or F;
$X^{1'}$ is H, Cl, or F;
$X^{1''}$ is H, or F;
$R^1$ is

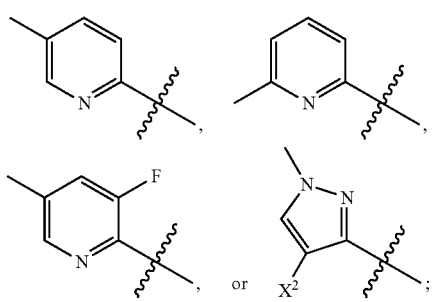

$X^2$ is H, F, or Cl;

$R^2$ is

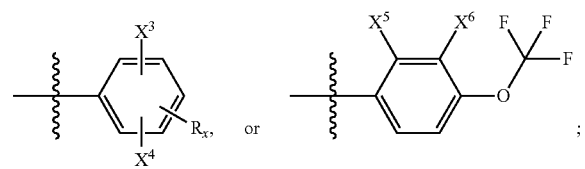

$R_x$ is Br, $CH_3$, —CN, $CF_3$,

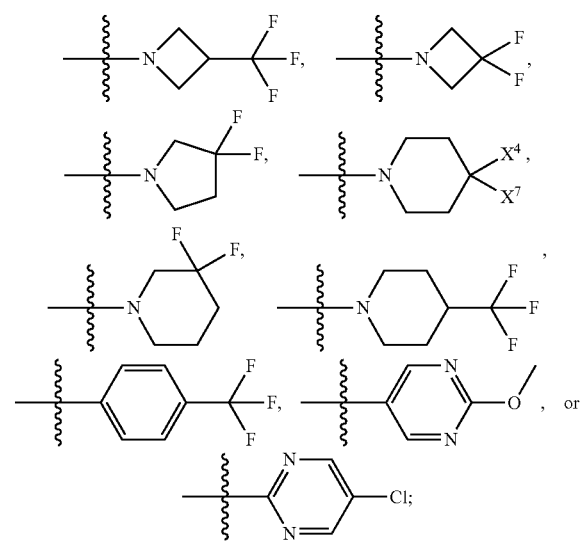

$X^3$ is H, or F;
$X^4$ is H, or F;
$X^5$ is H, Br, Cl, $CH_3$, $OCH_3$, or F;
$X^6$ is H, Cl, $CH_3$, or F;
$X^7$ is H, F, $CH_3$, or $C(CH_3)_3$;
$R^3$ is

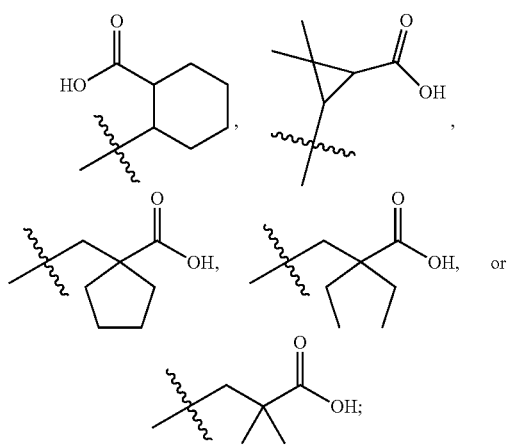

and
provided that the second eluting isomer of racemic cis-2-{1-(4-Cyanobenzyl)-6-[(5-methylpyridin-2-yl)methoxy]-1H-benzimidazol-2-yl}cyclohexanecarboxylic acid when purified by chiral SFC on (CHIRALCEL OJ-H 5 μm 250×20 mm) mobile phase (65% $CO_2$, 35% EtOH), the second eluting isomer of racemic cis-3-{1-(4-Bromo-2-fluorobenzyl)-6-[(5-methylpyridin-2-yl)methoxy]-1H-benzimidazol-2-yl}-2,2-dimethylcyclopropanecarboxylic acid when purified by chiral SFC on (CHIRALPAK AD-H 5 μm 250×20 mm) mobile phase (60% $CO_2$, 40% MeOH), and the first eluting isomer of racemic cis-2-{1-[2-Fluoro-4-(trifluoromethoxy)benzyl]-6-[(1-methyl-1H-pyrazol-3-yl)methoxy]-1H-benzimidazol-2-yl}cyclohexanecarboxylic acid when purified by chiral SFC (CHIRALCEL OD-H 5 μm 250×20 mm) mobile phase (80% $CO_2$, 20% MeOH) are specifically excluded;
and solvates, hydrates, and pharmaceutically acceptable salts thereof.

In another aspect of the present invention:
$X^1$ is H, Cl, or F;
$X^{1'}$ is H, Cl, or F;
$X^{1'''}$ is H, or F;
$R^1$ is

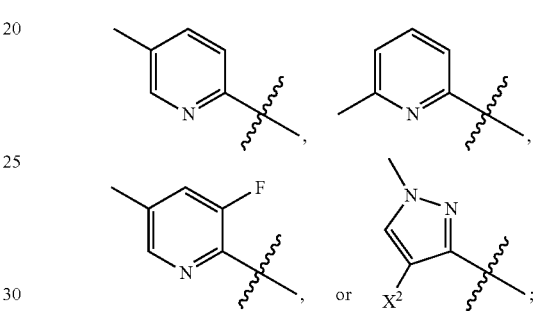

$X^2$ is H, F, or Cl;
$R^2$ is

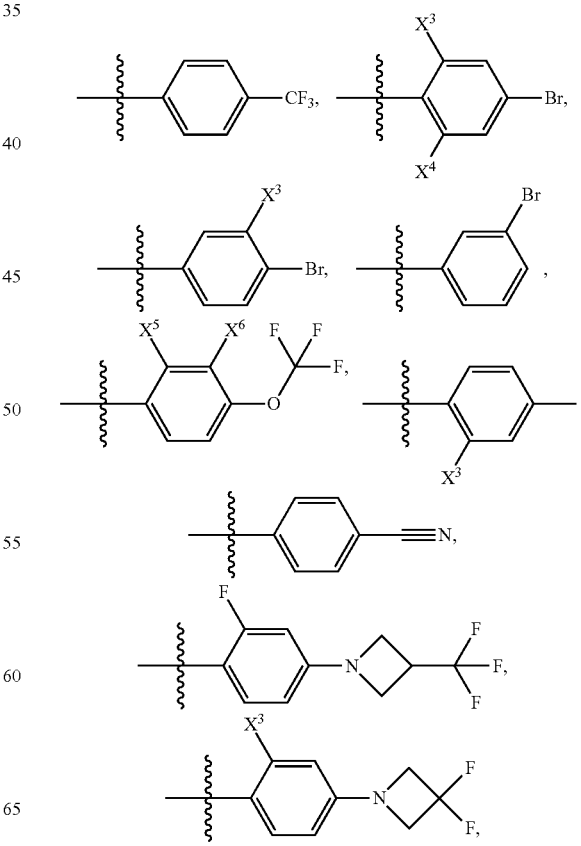

9

-continued

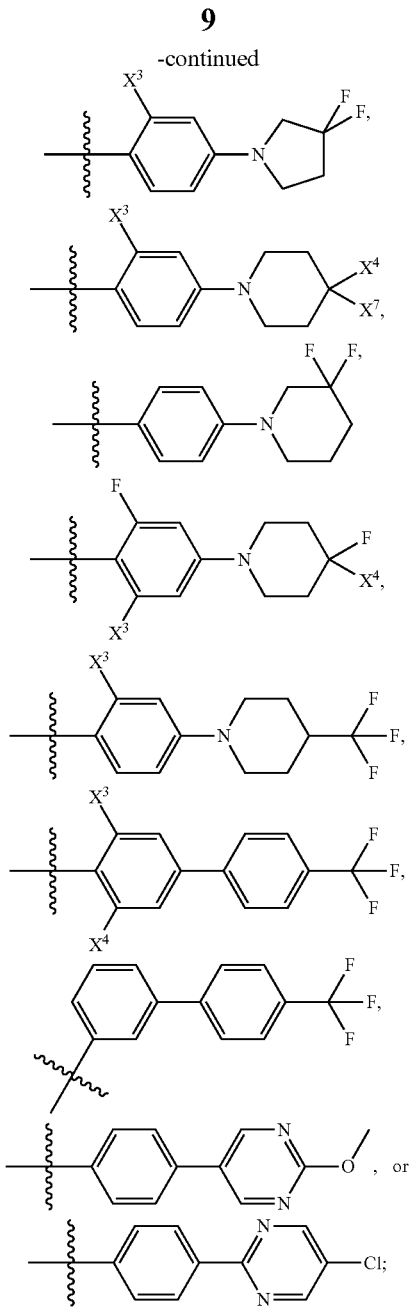

X³ is H, or F;
X⁴ is H, or F;
X⁵ is H, Br, Cl, CH₃, OCH₃, or F;
X⁶ is H, Cl, CH₃, or F;
X⁷ is H, F, CH₃, or C(CH₃)₃;
R³ is

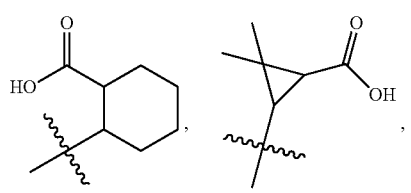

10

-continued

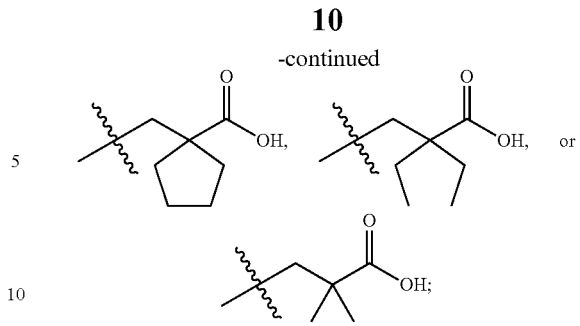

provided that the second eluting isomer of racemic cis-2-{1-(4-Cyanobenzyl)-6-[(5-methylpyridin-2-yl)methoxy]-1H-benzimidazol-2-yl}cyclohexanecarboxylic acid when purified by chiral SFC on (CHIRALCEL OJ-H 5 μm 250×20 mm) mobile phase (65% CO₂, 35% EtOH), the second eluting isomer of racemic cis-3-{1-(4-Bromo-2-fluorobenzyl)-6-[(5-methylpyridin-2-yl)methoxy]-1H-benzimidazol-2-yl}-2,2-dimethylcyclopropanecarboxylic acid when purified by chiral SFC on (CHIRALPAK AD-H 5 μm 250×20 mm) mobile phase (60% CO₂, 40% MeOH), and the first eluting isomer of racemic cis-2-{1-[2-Fluoro-4-(trifluoromethoxy)benzyl]-6-[(1-methyl-1H-pyrazol-3-yl)methoxy]-1H-benzimidazol-2-yl}cyclohexanecarboxylic acid when purified by chiral SFC (CHIRALCEL OD-H 5 μm 250×20 mm) mobile phase (80% CO₂, 20% MeOH) are specifically excluded;

and solvates, hydrates, and pharmaceutically acceptable salts thereof.

In another aspect of the present invention:
X¹ is H Cl, or F;
X¹' is H, Cl, or F;
X¹'' is H, or F;
R¹ is

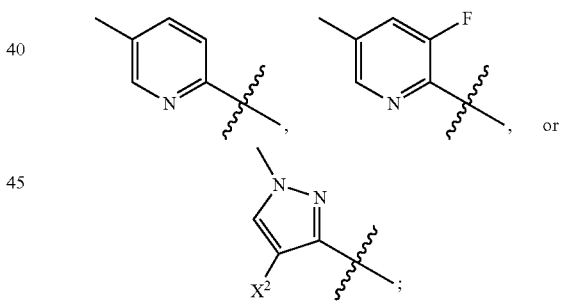

X² is H, F, or Cl;
R² is

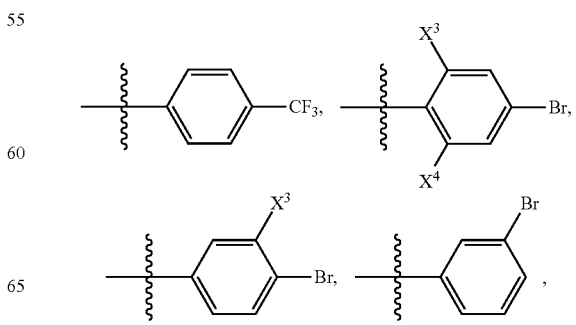

$X^3$ is H, or F;
$X^4$ is H, or F;
$X^5$ is H, Br, Cl, $CH_3$, $OCH_3$, or F;
$X^6$ is H, Cl, $CH_3$, or F;
$X^7$ is H, F, $CH_3$, or $C(CH_3)_3$;
$R^3$ is provided that the second eluting isomer of racemic cis-2-{1-(4-Cyanobenzyl)-6-[(5-methylpyridin-2-yl)methoxy]-1H-benzimidazol-2-yl}cyclohexanecarboxylic acid when purified by chiral SFC on (CHIRALCEL OJ-H 5 μm 250×20 mm) mobile phase (65% $CO_2$, 35% EtOH), and the first eluting isomer of racemic cis-2-{1-[2-Fluoro-4-(trifluoromethoxy)benzyl]-6-[(1-methyl-1H-pyrazol-3-yl)methoxy]-1H-benzimidazol-2-yl}cyclohexanecarboxylic acid when purified by chiral SFC (CHIRALCEL OD-H 5 μm 250×20 mm) mobile phase (80% $CO_2$, 20% MeOH) are specifically excluded;

and solvates, hydrates, and pharmaceutically acceptable salts thereof.

In another aspect of the present invention:

$X^1$ is H Cl, or F
$X^{1'}$ is H, Cl, or F;
$X^{1''}$ is H, or F;
$R^1$ is $X^2$ is H, F, or Cl;

R² is

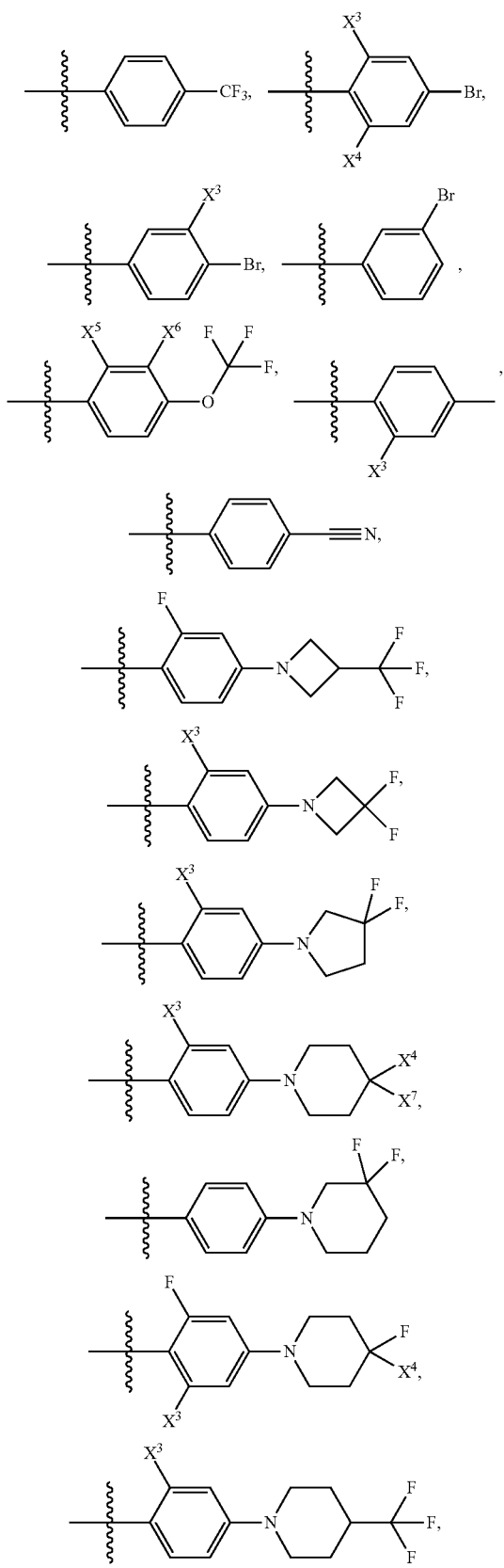

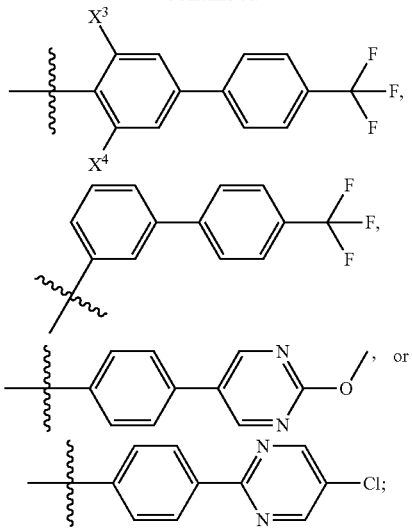

$X^3$ is H, or F;
$X^4$ is H, or F;
$X^5$ is H, Br, Cl, CH₃, OCH₃, or F;
$X^6$ is H, Cl, CH₃, or F;
$X^7$ is H, F, CH₃, or C(CH₃)₃;
R³ is

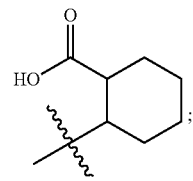 [SMILES: *C1CCCCC1C(=O)O]

provided that the second eluting isomer of racemic cis-2-{1-(4-Cyanobenzyl)-6-[(5-methylpyridin-2-yl)methoxy]-1H-benzimidazol-2-yl}cyclohexanecarboxylic acid when purified by chiral SFC on (CHIRALCEL OJ-H 5 μm 250×20 mm) mobile phase (65% CO₂, 35% EtOH), and the first eluting isomer of racemic cis-2-{1-[2-Fluoro-4-(trifluoromethoxy)benzyl]-6-[(1-methyl-1H-pyrazol-3-yl)methoxy]-1H-benzimidazol-2-yl}cyclohexanecarboxylic acid when purified by chiral SFC (CHIRALCEL OD-H 5 μm 250×20 mm) mobile phase (80% CO₂, 20% MeOH) are specifically excluded;

and solvates, hydrates, and pharmaceutically acceptable salts thereof.

In another aspect of the present invention:
$X^1$ is H Cl, or F
$X^{1'}$ is H, Cl, or F;
$X^{1''}$ is H, or F;
R¹ is

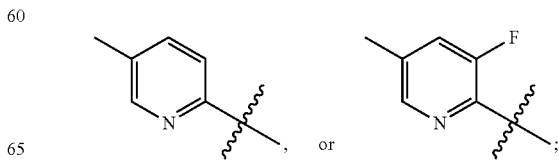

$R^2$ is

[chemical structures shown]

$X^3$ is H, or F;
$X^4$ is H, or F;
$X^5$ is H, Br, Cl, $CH_3$, $OCH_3$, or F;
$X^6$ is H, Cl, $CH_3$, or F;
$X^7$ is H, F, $CH_3$, or $C(CH_3)_3$;
$R^3$ is

[chemical structure shown]

provided that the second eluting isomer of racemic cis-2-{1-(4-Cyanobenzyl)-6-[(5-methylpyridin-2-yl)methoxy]-1H-benzimidazol-2-yl}cyclohexanecarboxylic acid when purified by chiral SFC on (CHIRALCEL OJ-H 5 μm 250×20 mm) mobile phase (65% $CO_2$, 35% EtOH), is specifically excluded;

and solvates, hydrates, and pharmaceutically acceptable salts thereof.

The embodiments of the present invention also include the optical isomers, hydrates, metabolites, enantiomers, diastereomers, cis-trans isomers, racemates, prodrugs or pharmaceutically acceptable salts thereof, provided that the second eluting isomer of racemic cis-2-{1-(4-Cyanobenzyl)-6-[(5-methylpyridin-2-yl)methoxy]-1H-benzimidazol-2-yl}cyclohexanecarboxylic acid when purified by chiral SFC on (CHIRALCEL OJ-H 5 μm 250×20 mm) mobile phase (65% $CO_2$, 35% EtOH), the second eluting isomer of racemic cis-3-{1-(4-Bromo-2-fluorobenzyl)-6-[(5-methylpyridin-2-yl)methoxy]-1H-benzimidazol-2-yl}-2,2-dimethylcyclopropanecarboxylic acid when purified by chiral SFC on (CHIRALPAK AD-H 5 μm 250×20 mm) mobile phase (60% $CO_2$, 40% MeOH), and the first eluting isomer of racemic cis-2-{1-[2-Fluoro-4-(trifluoromethoxy)benzyl]-6-[(1-methyl-1H-pyrazol-3-yl)methoxy]-1H-benzimidazol-2-yl}cyclohexanecarboxylic acid when purified by chiral SFC (CHIRALCEL OD-H 5 μm 250×20 mm) mobile phase (80% $CO_2$, 20% MeOH) are specifically excluded;

In another aspect of the present invention:
$X^1$ is H Cl, or F;
$X^{1'}$ is H, Cl, or F;
$X^{1'''}$ is H, or F;

$R^1$ is

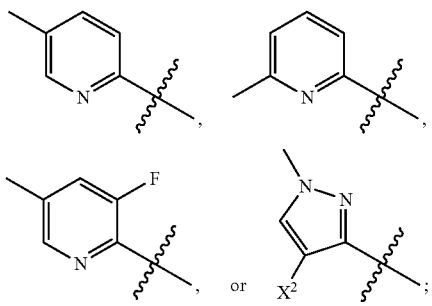

$X^2$ is H, F, or Cl;
$R^2$ is

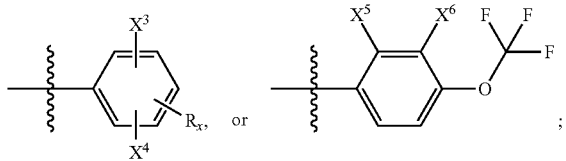

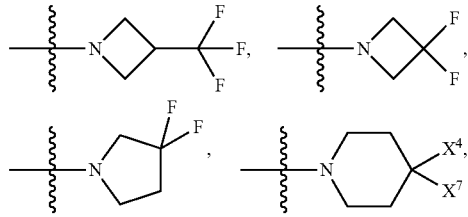

$R_x$ is Br, $CH_3$, $CH_3$,

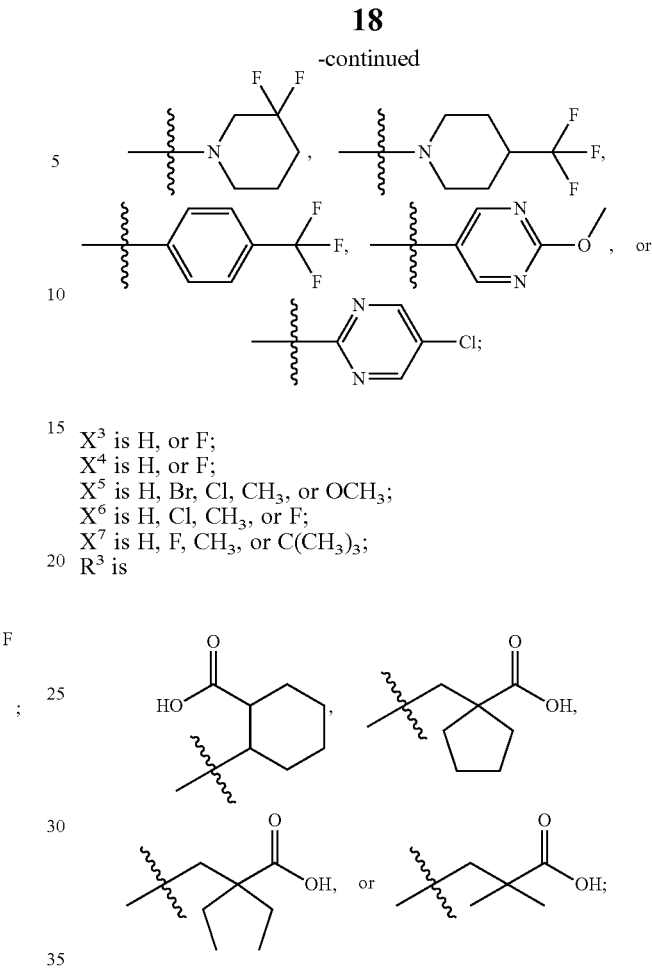

$X^3$ is H, or F;
$X^4$ is H, or F;
$X^5$ is H, Br, Cl, $CH_3$, or $OCH_3$;
$X^6$ is H, Cl, $CH_3$, or F;
$X^7$ is H, F, $CH_3$, or $C(CH_3)_3$;
$R^3$ is and
and solvates, hydrates, and pharmaceutically acceptable salts thereof.

It is an embodiment of the present invention to provide a compound selected from the compounds listed in Table 1.

TABLE 1 racemic cis-2-{1-(4-Bromobenzyl)-6-[(5-methylpyridin-2-yl)methoxy]-1H-benzimidazol-2-yl}cyclohexanecarboxylic acid,
(1S,2R)-2-(1-(4-Bromobenzyl)-6-((5-methylpyridin-2-yl)methoxy)-1H-benzo[d]imidazol-2-yl)cyclohexanecarboxylic acid,
(1R,2S)-2-{1-(4-Bromobenzyl)-6-[(5-methylpyridin-2-yl)methoxy]-1H-benzimidazol-2-yl}cyclohexanecarboxylic acid,
racemic cis-2-{1-(4-Bromo-3-fluorobenzyl)-6-[(5-methylpyridin-2-yl)methoxy]-1H-benzimidazol-2-yl}cyclohexanecarboxylic acid as the TFA salt,
racemic trans-2-{1-(4-Bromobenzyl)-6-[(5-methylpyridin-2-yl)methoxy]-1H-benzimidazol-2-yl}cyclohexanecarboxylic acid as the TFA salt,
(1S*,2S*)-2-{1-(4-Bromobenzyl)-6-[(5-methylpyridin-2-yl)methoxy]-1H-benzimidazol-2-yl}cyclohexanecarboxylic acid,
(1R*,2R*)-2-{1-(4-Bromobenzyl)-6-[(5-methylpyridin-2-yl)methoxy]-1H-benzimidazol-2-yl}cyclohexanecarboxylic acid,
2-({1-(4-Bromobenzyl)-6-[(5-methylpyridin-2-yl)methoxy]-1H-benzimidazol-2-yl}methyl)-2-ethylbutanoic acid as the TFA salt,
1-({1-(4-Bromobenzyl)-6-[(5-methylpyridin-2-yl)methoxy]-1H-benzimidazol-2-yl}methyl)cyclopentanecarboxylic acid as the TFA salt,
racemic cis-2-{1-(4-Bromo-2-fluorobenzyl)-6-[(5-methylpyridin-2-yl)methoxy]-1H-benzimidazol-2-yl}cyclohexanecarboxylic acid,
(1R*,2S*)-2-{1-(4-Bromo-2-fluorobenzyl)-6-[(5-methylpyridin-2-yl)methoxy]-1H-benzimidazol-2-yl}cyclohexanecarboxylic acid,
(1S*,2R*)-2-{1-(4-Bromo-2-fluorobenzyl)-6-[(5-methylpyridin-2-yl)methoxy]-1H-benzimidazol-2-yl}cyclohexanecarboxylic acid,
racemic trans-2-{1-(4-Bromo-2-fluorobenzyl)-6-[(5-methylpyridin-2-yl)methoxy]-1H-benzimidazol-2-yl}cyclohexanecarboxylic acid,
2-({1-(3-Bromobenzyl)-6-[(5-methylpyridin-2-yl)methoxy]-1H-benzimidazol-2-yl}methyl)-2-ethylbutanoic acid, TABLE 1-continued racemic cis-3-{1-(4-Bromo-2-fluorobenzyl)-6-[(5-methylpyridin-2-yl)methoxy]-1H-
benzimidazol-2-yl}-2,2-dimethylcyclopropanecarboxylic acid,
(1S*,3R*)-3-{1-(4-Bromo-2-fluorobenzyl)-6-[(5-methylpyridin-2-yl)methoxy]-1H-
benzimidazol-2-yl}-2,2-dimethylcyclopropanecarboxylic acid,
racemic trans-2-{1-(4-Cyanobenzyl)-6-[(5-methylpyridin-2-yl)methoxy]-1H-
benzimidazol-2-yl}cyclohexanecarboxylic acid as the TFA salt,
2-({1-(4-Cyanobenzyl)-6-[(5-methylpyridin-2-yl)methoxy]-1H-benzimidazol-2-
yl}methyl)-2-ethylbutanoic acid as the TFA salt,
racemic cis-2-{1-[3-Fluoro-4-(trifluoromethoxy)benzyl]-6-[(5-methylpyridin-2-
yl)methoxy]-1H-benzimidazol-2-yl}cyclohexanecarboxylic acid,
racemic trans-2-{1-[2-Fluoro-4-(trifluoromethoxy)benzyl]-6-[(5-methylpyridin-2-
yl)methoxy]-1H-benzimidazol-2-yl}cyclohexanecarboxylic acid,
2-Ethyl-2-({6-[(5-methylpyridin-2-yl)methoxy]-1-[4-(trifluoromethoxy)benzyl]-1H-
benzimidazol-2-yl}methyl)butanoic acid,
2-Ethyl-2-({1-[2-fluoro-4-(trifluoromethoxy)benzyl]-6-[(5-methylpyridin-2-yl)methoxy]-
1H-benzimidazol-2-yl}methyl)butanoic acid,
2-({1-[3-Chloro-4-(trifluoromethoxy)benzyl]-6-[(5-methylpyridin-2-yl)methoxy]-1H-
benzimidazol-2-yl}methyl)-2-ethylbutanoic acid,
racemic cis-2,2-Dimethyl-3-{6-[(5-methylpyridin-2-yl)methoxy]-1-[4-
(trifluoromethoxy)benzyl]-1H-benzimidazol-2-yl}cyclopropanecarboxylic acid,
racemic cis-2-{1-[2-Fluoro-4-(trifluoromethoxy)benzyl]-6-[(5-methylpyridin-2-
yl)methoxy]-1H-benzimidazol-2-yl}cyclohexanecarboxylic acid,
racemic cis-2-{6-[(5-Methylpyridin-2-yl)methoxy]-1-[4-(trifluoromethoxy)benzyl]-1H-
benzimidazol-2-yl}cyclohexanecarboxylic acid,
(1R*,2S*)-2-{6-[(5-Methylpyridin-2-yl)methoxy]-1-[4-(trifluoromethoxy)benzyl]-1H-
benzimidazol-2-yl}cyclohexanecarboxylic acid,
(1S*,2R*)-2-{6-[(5-Methylpyridin-2-yl)methoxy]-1-[4-(trifluoromethoxy)benzyl]-1H-
benzimidazol-2-yl}cyclohexanecarboxylic acid,
2-Ethyl-2-({1-[3-fluoro-4-(trifluoromethoxy)benzyl]-6-[(5-methylpyridin-2-yl)methoxy]-
1H-benzimidazol-2-yl}methyl)butanoic acid,
racemic trans-2-{6-[(5-Methylpyridin-2-yl)methoxy]-1-[4-(trifluoromethoxy)benzyl]-1H-
benzimidazol-2-yl}cyclohexanecarboxylic acid,
racemic cis-2-{1-[3-Chloro-4-(trifluoromethoxy)benzyl]-6-[(5-methylpyridin-2-
yl)methoxy]-1H-benzimidazol-2-yl}cyclohexanecarboxylic acid,
racemic trans-2-(6-[(5-Methylpyridin-2-yl)methoxy]-1-{[4'-(trifluoromethyl)biphenyl-4-
yl]methyl}-1H-benzimidazol-2-yl)cyclohexanecarboxylic acid,
(1R*,2R*)-2-(6-[(5-Methylpyridin-2-yl)methoxy]-1-{[4'-(trifluoromethyl)biphenyl-4-
yl]methyl}-1H-benzimidazol-2-yl)cyclohexanecarboxylic acid,
(1S*,2S*)-2-(6-[(5-Methylpyridin-2-yl)methoxy]-1-{[4'-(trifluoromethyl)biphenyl-4-
yl]methyl}-1H-benzimidazol-2-yl)cyclohexanecarboxylic acid,
(1S*,2R*)-2-{6-[(1-Methyl-1H-pyrazol-3-yl)methoxy]-1-[4-(trifluoromethoxy)benzyl]-
1H-benzimidazol-2-yl}cyclohexanecarboxylic acid,
racemic cis-2-{1-(4-Cyanobenzyl)-6-[(5-methylpyridin-2-yl)methoxy]-1H-
benzimidazol-2-yl}cyclohexanecarboxylic acid as the TFA salt,
(1R*,2S*)-2-{1-(4-Cyanobenzyl)-6-[(5-methylpyridin-2-yl)methoxy]-1H-benzimidazol-
2-yl}cyclohexanecarboxylic acid,
racemic cis-2-{1-(4-Bromobenzyl)-6-[(1-methyl-1H-pyrazol-3-yl)methoxy]-1H-
benzimidazol-2-yl}cyclohexanecarboxylic acid as the TFA salt,
racemic trans-2-{1-(4-Bromobenzyl)-6-[(1-methyl-1H-pyrazol-3-yl)methoxy]-1H-
benzimidazol-2-yl}cyclohexanecarboxylic acid as the TFA salt,
2-({1-(4-Bromobenzyl)-6-[(1-methyl-1H-pyrazol-3-yl)methoxy]-1H-benzimidazol-2-
yl}methyl)-2-ethylbutanoic acid as the TFA salt,
2-Ethyl-2-({6-[(1-methyl-1H-pyrazol-3-yl)methoxy]-1-(4-piperidin-1-ylbenzyl)-1H-
benzimidazol-2-yl}methyl)butanoic acid,
racemic cis-2-{6-[(1-Methyl-1H-pyrazol-3-yl)methoxy]-1-[4-(trifluoromethoxy)benzyl]-
1H-benzimidazol-2-yl}cyclohexanecarboxylic acid,
(1R*,2S*)-2-{6-[(1-Methyl-1H-pyrazol-3-yl)methoxy]-1-[4-(trifluoromethoxy)benzyl]-
1H-benzimidazol-2-yl}cyclohexanecarboxylic acid,
1-({1-(4-Bromobenzyl)-6-[(1-methyl-1H-pyrazol-3-yl)methoxy]-1H-benzimidazol-2-
yl}methyl)cyclopentanecarboxylic acid as the TFA salt,
racemic cis-2-{1-(4-Cyanobenzyl)-6-[(1-methyl-1H-pyrazol-3-yl)methoxy]-1H-
benzimidazol-2-yl}cyclohexanecarboxylic acid -Trifluoroacetic acid salt,
racemic trans-2-{1-(4-Cyanobenzyl)-6-[(1-methyl-1H-pyrazol-3-yl)methoxy]-1H-
benzimidazol-2-yl}cyclohexanecarboxylic acid -Trifluoroacetic acid salt,
2-({1-(4-Cyanobenzyl)-6-[(1-methyl-1H-pyrazol-3-yl)methoxy]-1H-benzimidazol-2-
yl}methyl)-2-ethylbutanoic acid -Trifluoroacetic acid salt,
2-Ethyl-2-({6-[(1-methyl-1H-pyrazol-3-yl)methoxy]-1-[4-(trifluoromethoxy)benzyl]-1H-
benzimidazol-2-yl}methyl)butanoic acid,
racemic cis-2-{1-[2-Fluoro-4-(trifluoromethoxy)benzyl]-6-[(1-methyl-1H-pyrazol-3-
yl)methoxy]-1H-benzimidazol-2-yl}cyclohexanecarboxylic acid,
(1R*,2S*)-2-(1-(2-fluoro-4-(trifluoromethoxy)benzyl)-6-((1-methyl-1H-pyrazol-3-
yl)methoxy)-1H-benzo[d]imidazol-2-yl)cyclohexanecarboxylic acid,
racemic trans-2-{6-[(1-Methyl-1H-pyrazol-3-yl)methoxy]-1-[4-
(trifluoromethoxy)benzyl]-1H-benzimidazol-2-yl}cyclohexanecarboxylic acid,
racemic cis-2-{1-[3-Fluoro-4-(trifluoromethoxy)benzyl]-6-[(1-methyl-1H-pyrazol-3-
yl)methoxy]-1H-benzimidazol-2-yl}cyclohexanecarboxylic acid,
2-Ethyl-2-({1-[2-fluoro-4-(trifluoromethoxy)benzyl]-6-[(1-methyl-1H-pyrazol-3-
yl)methoxy]-1H-benzimidazol-2-yl}methyl)butanoic acid,
2-Ethyl-2-({1-[3-fluoro-4-(trifluoromethoxy)benzyl]-6-[(1-methyl-1H-pyrazol-3-
yl)methoxy]-1H-benzimidazol-2-yl}methyl)butanoic acid, TABLE 1-continued 2-({1-(4-Bromo-2-fluorobenzyl)-6-[(1-methyl-1H-pyrazol-3-yl)methoxy]-1H-benzimidazol-2-yl}methyl)-2-ethylbutanoic acid,
racemic cis-2-{1-(4-Bromobenzyl)-4-fluoro-6-[(5-methylpyridin-2-yl)methoxy]-1H-benzimidazol-2-yl}cyclohexanecarboxylic acid,
3-{1-(4-Bromobenzyl)-4-fluoro-6-[(5-methylpyridin-2-yl)methoxy]-1H-benzimidazol-2-yl}-2,2-dimethylpropanoic acid,
1-({1-(4-Bromobenzyl)-4-fluoro-6-[(5-methylpyridin-2-yl)methoxy]-1H-benzimidazol-2-yl}methyl)cyclopentanecarboxylic acid,
racemic trans-2-{1-(4-Bromobenzyl)-4-fluoro-6-[(5-methylpyridin-2-yl)methoxy]-1H-benzimidazol-2-yl}cyclohexanecarboxylic acid,
racemic cis-3-{1-(4-Bromobenzyl)-4-fluoro-6-[(5-methylpyridin-2-yl)methoxy]-1H-benzimidazol-2-yl}-2,2-dimethylcyclopropanecarboxylic acid,
racemic cis-3-{4-Fluoro-1-(4-methylbenzyl)-6-[(5-methylpyridin-2-yl)methoxy]-1H-benzimidazol-2-yl}-2,2-dimethylcyclopropanecarboxylic acid as the TFA salt,
2-({1-(4-Bromobenzyl)-4-fluoro-6-[(5-methylpyridin-2-yl)methoxy]-1H-benzimidazol-2-yl}methyl)-2-ethylbutanoic acid as the TFA salt,
racemic cis-2-{4-Fluoro-6-[(5-methylpyridin-2-yl)methoxy]-1-[4-(trifluoromethoxy)benzyl]-1H-benzimidazol-2-yl}cyclohexanecarboxylic acid as the TFA salt,
racemic trans-2-{4-Fluoro-6-[(5-methylpyridin-2-yl)methoxy]-1-[4-(trifluoromethoxy)benzyl]-1H-benzimidazol-2-yl}cyclohexanecarboxylic acid as the TFA salt,
racemic cis-2-{4-Fluoro-1-(4-methylbenzyl)-6-[(5-methylpyridin-2-yl)methoxy]-1H-benzimidazol-2-yl}cyclohexanecarboxylic acid as the TFA salt,
2-Ethyl-2-({4-fluoro-6-[(5-methylpyridin-2-yl)methoxy]-1-[4-(trifluoromethoxy)benzyl]-1H-benzimidazol-2-yl}methyl)butanoic acid as the TFA salt,
racemic trans-2-{4-Fluoro-1-(4-methylbenzyl)-6-[(5-methylpyridin-2-yl)methoxy]-1H-benzimidazol-2-yl}cyclohexanecarboxylic acid as the TFA salt,
2-Ethyl-2-({4-fluoro-1-(4-methylbenzyl)-6-[(5-methylpyridin-2-yl)methoxy]-1H-benzimidazol-2-yl}methyl)butanoic acid as the TFA salt,
1-({4-Fluoro-6-[(5-methylpyridin-2-yl)methoxy]-1-[4-(trifluoromethoxy)benzyl]-1H-benzimidazol-2-yl}methyl)cyclopentanecarboxylic acid as the TFA salt,
1-({4-Fluoro-1-(4-methylbenzyl)-6-[(5-methylpyridin-2-yl)methoxy]-1H-benzimidazol-2-yl}methyl)cyclopentanecarboxylic acid as the TFA salt,
racmic cis-3-{4-Fluoro-6-[(5-methylpyridin-2-yl)methoxy]-1-[4-(trifluoromethoxy)benzyl]-1H-benzimidazol-2-yl}-2,2-dimethylcyclopropanecarboxylic acid as the TFA salt,
racemic cis-2-{1-(4-Bromobenzyl)-4-chloro-6-[(5-methylpyridin-2-yl)methoxy]-1H-benzimidazol-2-yl}cyclohexanecarboxylic acid,
racemic cis-3-{1-(4-Bromobenzyl)-4-chloro-6-[(5-methylpyridin-2-yl)methoxy]-1H-benzimidazol-2-yl}-2,2-dimethylcyclopropanecarboxylic acid,
racemic trans-2-{1-(4-Bromobenzyl)-4-chloro-6-[(5-methylpyridin-2-yl)methoxy]-1H-benzimidazol-2-yl}cyclohexanecarboxylic acid,
1-({1-(4-Bromobenzyl)-4-chloro-6-[(5-methylpyridin-2-yl)methoxy]-1H-benzimidazol-2-yl}methyl)cyclopentanecarboxylic acid,
3-{1-(4-Bromobenzyl)-4-chloro-6-[(5-methylpyridin-2-yl)methoxy]-1H-benzimidazol-2-yl}-2,2-dimethylpropanoic acid,
racemic cis-2-{1-[4-(5-Chloropyrimidin-2-yl)benzyl]-6-[(5-methylpyridin-2-yl)methoxy]-1H-benzimidazol-2-yl}cyclohexanecarboxylic acid,
racemic cis-2-{1-(4-Bromobenzyl)-6-[(4-chloro-1-methyl-1H-pyrazol-3-yl)methoxy]-1H-benzimidazol-2-yl}cyclohexanecarboxylic acid,
racemic cis-2-{6-[(4-Chloro-1-methyl-1H-pyrazol-3-yl)methoxy]-1-(4-piperidin-1-ylbenzyl)-1H-benzimidazol-2-yl}cyclohexanecarboxylic acid,
racemic cis-2-{6-[(4-Chloro-1-methyl-1H-pyrazol-3-yl)methoxy]-1-[2-fluoro-4-(trifluoromethoxy)benzyl]-1H-benzimidazol-2-yl}cyclohexanecarboxylic acid,
racemic cis-2-{1-[2-Methoxy-4-(trifluoromethoxy)benzyl]-6-[(1-methyl-1H-pyrazol-3-yl)methoxy]-1H-benzimidazol-2-yl}cyclohexanecarboxylic acid,
racemic cis-2-{6-[(4-Fluoro-1-methyl-1H-pyrazol-3-yl)methoxy]-1-[2-fluoro-4-(trifluoromethoxy)benzyl]-1H-benzimidazol-2-yl}cyclohexanecarboxylic acid,
racemic cis-2-{1-[4-(4,4-Difluoropiperidin-1-yl)benzyl]-6-[(1-methyl-1H-pyrazol-3-yl)methoxy]-1H-benzimidazol-2-yl}cyclohexanecarboxylic acid,
racemic cis-2-{6-[(4-Chloro-1-methyl-1H-pyrazol-3-yl)methoxy]-1-[4-(4-fluoropiperidin-1-yl)benzyl]-1H-benzimidazol-2-yl}cyclohexanecarboxylic acid,
racemic cis-2-{6-[(1-Methyl-1H-pyrazol-3-yl)methoxy]-1-(4-piperidin-1-ylbenzyl)-1H-benzimidazol-2-yl}cyclohexanecarboxylic acid,
racemic cis-2-{1-[4-(3,3-Difluoroazetidin-1-yl)benzyl]-6-[(1-methyl-1H-pyrazol-3-yl)methoxy]-1H-benzimidazol-2-yl}cyclohexanecarboxylic acid,
racemic cis-2-{5-Fluoro-1-[2-fluoro-4-(trifluoromethoxy)benzyl]-6-[(1-methyl-1H-pyrazol-3-yl)methoxy]-1H-benzimidazol-2-yl}cyclohexanecarboxylic acid,
racemic cis-2-{7-Fluoro-1-[2-fluoro-4-(trifluoromethoxy)benzyl]-6-[(1-methyl-1H-pyrazol-3-yl)methoxy]-1H-benzimidazol-2-yl}cyclohexanecarboxylic acid,
2-Ethyl-2-({6-[(1-methyl-1H-pyrazol-3-yl)methoxy]-1-[2-methyl-4-(trifluoromethoxy)benzyl]-1H-benzimidazol-2-yl}methyl)butanoic acid,
racemic cis-2-{1-(4-Bromobenzyl)-4-fluoro-6-[(1-methyl-1H-pyrazol-3-yl)methoxy]-1H-benzimidazol-2-yl}cyclohexanecarboxylic acid,
racemic cis-2-{1-(4-Bromo-2-fluorobenzyl)-4-fluoro-6-[(1-methyl-1H-pyrazol-3-yl)methoxy]-1H-benzimidazol-2-yl}cyclohexanecarboxylic acid,
racemic cis-2-{4-Fluoro-6-[(1-methyl-1H-pyrazol-3-yl)methoxy]-1-[4-(trifluoromethoxy)benzyl]-1H-benzimidazol-2-yl}cyclohexanecarboxylic acid as the HCl salt, TABLE 1-continued racemic cis-2-{4-Fluoro-1-[2-fluoro-4-(trifluoromethoxy)benzyl]-6-[(1-methyl-1H-pyrazol-3-yl)methoxy]-1H-benzimidazol-2-yl}cyclohexanecarboxylic acid as the HCl salt,
racemic cis-2-{4-Fluoro-1-(4-methylbenzyl)-6-[(1-methyl-1H-pyrazol-3-yl)methoxy]-1H-benzimidazol-2-yl}cyclohexanecarboxylic acid as the HCl salt,
racemic cis-2-{1-(4-Cyanobenzyl)-4-fluoro-6-[(1-methyl-1H-pyrazol-3-yl)methoxy]-1H-benzimidazol-2-yl}cyclohexanecarboxylic acid as the HCl salt,
racemic cis-2-{6-[(1-Methyl-1H-pyrazol-3-yl)methoxy]-1-[2-methyl-4-(trifluoromethoxy)benzyl]-1H-benzimidazol-2-yl}cyclohexanecarboxylic acid,
racemic cis-2-{6-[(5-Methylpyridin-2-yl)methoxy]-1-[2-methyl-4-(trifluoromethoxy)benzyl]-1H-benzimidazol-2-yl}cyclohexanecarboxylic acid,
racemic cis-2-{1-[2-Chloro-4-(trifluoromethoxy)benzyl]-6-[(5-methylpyridin-2-yl)methoxy]-1H-benzimidazol-2-yl}cyclohexanecarboxylic acid as the HCl salt,
racemic cis-2-{1-[2-Bromo-4-(trifluoromethoxy)benzyl]-6-[(5-methylpyridin-2-yl)methoxy]-1H-benzimidazol-2-yl}cyclohexanecarboxylic acid as the HCl salt,
racemic cis-2-{1-[2-Chloro-4-(trifluoromethoxy)benzyl]-6-[(1-methyl-1H-pyrazol-3-yl)methoxy]-1H-benzimidazol-2-yl}cyclohexanecarboxylic acid as the HCl salt,
racemic cis-2-{1-[2-Bromo-4-(trifluoromethoxy)benzyl]-6-[(1-methyl-1H-pyrazol-3-yl)methoxy]-1H-benzimidazol-2-yl}cyclohexanecarboxylic acid as the HCl salt,
2-Ethyl-2-({6-[(5-methylpyridin-2-yl)methoxy]-1-[2-methyl-4-(trifluoromethoxy)benzyl]-1H-benzimidazol-2-yl}methyl)butanoic acid,
racemic cis-2-{6-[(1-Methyl-1H-pyrazol-3-yl)methoxy]-1-[3-methyl-4-(trifluoromethoxy)benzyl]-1H-benzimidazol-2-yl}cyclohexanecarboxylic acid as the HCl salt,
3-{1-(4-Bromobenzyl)-6-[(1-methyl-1H-pyrazol-3-yl)methoxy]-1H-benzimidazol-2-yl}-2,2-dimethylpropanoic acid,
3-{1-(4-Bromobenzyl)-6-[(6-methylpyridin-2-yl)methoxy]-1H-benzimidazol-2-yl}-2,2-dimethylpropanoic acid,
racemic cis-2-{6-[(5-Methylpyridin-2-yl)methoxy]-1-[3-methyl-4-(trifluoromethoxy)benzyl]-1H-benzimidazol-2-yl}cyclohexanecarboxylic acid,
racemic cis-2-{5-Chloro-1-[2-fluoro-4-(trifluoromethoxy)benzyl]-6-[(5-methylpyridin-2-yl)methoxy]-1H-benzimidazol-2-yl}cyclohexanecarboxylic acid as the HCl salt,
racemic cis-3-{1-(4-Bromobenzyl)-6-[(5-methylpyridin-2-yl)methoxy]-1H-benzimidazol-2-yl}-2,2-dimethylcyclopropanecarboxylic acid as the TFA salt,
(1S*,3R*)-3-{1-(4-Bromobenzyl)-6-[(5-methylpyridin-2-yl)methoxy]-1H-benzimidazol-2-yl}-2,2-dimethylcyclopropanecarboxylic acid,
(1R*,3S*)-3-{1-(4-Bromobenzyl)-6-[(5-methylpyridin-2-yl)methoxy]-1H-benzimidazol-2-yl}-2,2-dimethylcyclopropanecarboxylic acid,
racemic trans-3-{1-(4-Bromobenzyl)-6-[(5-methylpyridin-2-yl)methoxy]-1H-benzimidazol-2-yl}-2,2-dimethylcyclopropanecarboxylic acid as the TFA salt,
(1R*,3R*)-3-{1-(4-Bromobenzyl)-6-[(5-methylpyridin-2-yl)methoxy]-1H-benzimidazol-2-yl}-2,2-dimethylcyclopropanecarboxylic acid,
(1S*,3S*)-3-{1-(4-Bromobenzyl)-6-[(5-methylpyridin-2-yl)methoxy]-1H-benzimidazol-2-yl}-2,2-dimethylcyclopropanecarboxylic acid,
racemic trans-3-{1-(4-Bromobenzyl)-6-[(1-methyl-1H-pyrazol-3-yl)methoxy]-1H-benzimidazol-2-yl}-2,2-dimethylcyclopropanecarboxylic acid as the TFA salt,
3-{1-(4-Bromobenzyl)-6-[(5-methylpyridin-2-yl)methoxy]-1H-benzimidazol-2-yl}-2,2-dimethylpropanoic acid as the TFA salt,
racemic cis-2-{1-(4-Methylbenzyl)-6-[(5-methylpyridin-2-yl)methoxy]-1H-benzimidazol-2-yl}cyclohexanecarboxylic acid,
racemic trans-2-{1-(4-Methylbenzyl)-6-[(5-methylpyridin-2-yl)methoxy]-1H-benzimidazol-2-yl}cyclohexanecarboxylic acid,
racemic cis-2,2-Dimethyl-3-{1-(4-methylbenzyl)-6-[(5-methylpyridin-2-yl)methoxy]-1H-benzimidazol-2-yl}cyclopropanecarboxylic acid,
racemic cis-2,2-Dimethyl-3-{6-[(1-methyl-1H-pyrazol-3-yl)methoxy]-1-[4-(trifluoromethoxy)benzyl]-1H-benzimidazol-2-yl}cyclopropanecarboxylic acid,
racemic cis-2-{1-(4-Bromo-2,6-difluorobenzyl)-6-[(3-fluoro-5-methylpyridin-2-yl)methoxy]-1H-benzimidazol-2-yl}cyclohexanecarboxylic acid,
racemic trans-2-{1-(4-Bromo-2,6-difluorobenzyl)-6-[(3-fluoro-5-methylpyridin-2-yl)methoxy]-1H-benzimidazol-2-yl}cyclohexanecarboxylic acid,
racemic cis-2-{1-(4-Bromobenzyl)-6-[(3-fluoro-5-methylpyridin-2-yl)methoxy]-1H-benzimidazol-2-yl}cyclohexanecarboxylic acid,
racemic cis-2-{1-(4-Bromo-2,6-difluorobenzyl)-6-[(5-methylpyridin-2-yl)methoxy]-1H-benzimidazol-2-yl}cyclohexanecarboxylic acid,
3-{1-(2-Fluoro-4-methylbenzyl)-6-[(3-fluoro-5-methylpyridin-2-yl)methoxy]-1H-benzimidazol-2-yl}-2,2-dimethylpropanoic acid,
3-{1-(4-Bromobenzyl)-6-[(3-fluoro-5-methylpyridin-2-yl)methoxy]-1H-benzimidazol-2-yl}-2,2-dimethylpropanoic acid,
3-{1-(4-Bromo-2-fluorobenzyl)-6-[(3-fluoro-5-methylpyridin-2-yl)methoxy]-1H-benzimidazol-2-yl}-2,2-dimethylpropanoic acid,
3-{1-(4-Bromo-2,6-difluorobenzyl)-6-[(3-fluoro-5-methylpyridin-2-yl)methoxy]-1H-benzimidazol-2-yl}-2,2-dimethylpropanoic acid,
3-{6-[(3-Fluoro-5-methylpyridin-2-yl)methoxy]-1-[2-fluoro-4-(trifluoromethoxy)benzyl]-1H-benzimidazol-2-yl}-2,2-dimethylpropanoic acid,
racemic cis-3-{1-(4-Bromobenzyl)-6-[(3-fluoro-5-methylpyridin-2-yl)methoxy]-1H-benzimidazol-2-yl}-2,2-dimethylcyclopropanecarboxylic acid,
racemic cis-3-{1-(4-Bromobenzyl)-6-[(6-methylpyridin-2-yl)methoxy]-1H-benzimidazol-2-yl}-2,2-dimethylcyclopropanecarboxylic acid,
racemic cis-3-{1-(4-Bromobenzyl)-6-[(1-methyl-1H-pyrazol-3-yl)methoxy]-1H-benzimidazol-2-yl}-2,2-dimethylcyclopropanecarboxylic acid, TABLE 1-continued 2-({1-(4-Cyanobenzyl)-6-[(3-fluoro-5-methylpyridin-2-yl)methoxy]-1H-benzimidazol-2-yl}methyl)-2-ethylbutanoic acid,
2-({1-(4-Bromobenzyl)-6-[(3-fluoro-5-methylpyridin-2-yl)methoxy]-1H-benzimidazol-2-yl}methyl)-2-ethylbutanoic acid,
racemic cis-2-(1-{[3,5-Difluoro-4'-(trifluoromethyl)biphenyl-4-yl]methyl}-6-[(3-fluoro-5-methylpyridin-2-yl)methoxy]-1H-benzimidazol-2-yl)cyclohexanecarboxylic acid,
racemic cis-2-(1-{[3,5-Difluoro-4'-(trifluoromethyl)biphenyl-4-yl]methyl}-6-[(5-methylpyridin-2-yl)methoxy]-1H-benzimidazol-2-yl)cyclohexanecarboxylic acid,
(1R*,2S*)-2-(6-[(3-Fluoro-5-methylpyridin-2-yl)methoxy]-1-{[4'-(trifluoromethyl)biphenyl-4-yl]methyl}-1H-benzimidazol-2-yl)cyclohexanecarboxylic acid,
racemic trans-2-{1-(4-Bromo-2,6-difluorobenzyl)-6-[(5-methylpyridin-2-yl)methoxy]-1H-benzimidazol-2-yl}cyclohexanecarboxylic acid,
3-(6-[(3-Fluoro-5-methylpyridin-2-yl)methoxy]-1-{[3-fluoro-4'-(trifluoromethyl)biphenyl-4-yl]methyl}-1H-benzimidazol-2-yl)-2,2-dimethylpropanoic acid,
3-(6-[(3-Fluoro-5-methylpyridin-2-yl)methoxy]-1-{[4'-(trifluoromethyl)biphenyl-4-yl]methyl}-1H-benzimidazol-2-yl)-2,2-dimethylpropanoic acid,
3-(6-[(3-Fluoro-5-methylpyridin-2-yl)methoxy]-1-{[4'-(trifluoromethyl)biphenyl-3-yl]methyl}-1H-benzimidazol-2-yl)-2,2-dimethylpropanoic acid,
racemic cis-2-{1-[4-(2-Methoxypyrimidin-5-yl)benzyl]-6-[(5-methylpyridin-2-yl)methoxy]-1H-benzimidazol-2-yl}cyclohexanecarboxylic acid,
racemic cis-2-(6-[(5-Methylpyridin-2-yl)methoxy]-1-{[4'-(trifluoromethyl)biphenyl-3-yl]methyl}-1H-benzimidazol-2-yl)cyclohexanecarboxylic acid,
racemic cis-2-(6-[(5-Methylpyridin-2-yl)methoxy]-1-{[4'-(trifluoromethyl)biphenyl-4-yl]methyl}-1H-benzimidazol-2-yl)cyclohexanecarboxylic acid,
(1S,2R)-2-(6-((5-methylpyridin-2-yl)methoxy)-1-((4'-(trifluoromethyl)-[1,1'-biphenyl]-4-yl)methyl)-1H-benzo[d]imidazol-2-yl)cyclohexanecarboxylic acid,
(1R,2S)-2-(6-[(5-Methylpyridin-2-yl)methoxy]-1-{[4'-(trifluoromethyl)biphenyl-4-yl]methyl}-1H-benzimidazol-2-yl)cyclohexanecarboxylic acid,
2-ethyl-2-((6-((5-methylpyridin-2-yl)methoxy)-1-((4'-(trifluoromethyl)-[1,1'-biphenyl]-3-yl)methyl)-1H-benzo[d]imidazol-2-yl)methyl)butanoic acid,
racemic cis-2-(6-[(1-Methyl-1H-pyrazol-3-yl)methoxy]-1-{[4'-(trifluoromethyl)biphenyl-3-yl]methyl}-1H-benzimidazol-2-yl)cyclohexanecarboxylic acid,
racemic cis-2-(6-[(4-Chloro-1-methyl-1H-pyrazol-3-yl)methoxy]-1-{[4'-(trifluoromethyl)biphenyl-4-yl]methyl}-1H-benzimidazol-2-yl)cyclohexanecarboxylic acid,
racemic cis-2-{1-[4-(3,3-Difluoropyrrolidin-1-yl)benzyl]-6-[(5-methylpyridin-2-yl)methoxy]-1H-benzimidazol-2-yl}cyclohexanecarboxylic acid,:
racemic cis-2-{1-[4-(3,3-Difluoropiperidin-1-yl)benzyl]-6-[(5-methylpyridin-2-yl)methoxy]-1H-benzimidazol-2-yl}cyclohexanecarboxylic acid,
racemic cis-2-{1-[4-(4,4-Difluoropiperidin-1-yl)benzyl]-6-[(5-methylpyridin-2-yl)methoxy]-1H-benzimidazol-2-yl}cyclohexanecarboxylic acid,
2-({1-[4-(3,3-Difluoropiperidin-1-yl)benzyl]-6-[(1-methyl-1H-pyrazol-3-yl)methoxy]-1H-benzimidazol-2-yl}methyl)-2-ethylbutanoic acid,
racemic cis-2-{6-[(5-Methylpyridin-2-yl)methoxy]-1-(4-piperidin-1-ylbenzyl)-1H-benzimidazol-2-yl}cyclohexanecarboxylic acid,
(1S*,2R*)-2-{6-[(5-Methylpyridin-2-yl)methoxy]-1-(4-piperidin-1-ylbenzyl)-1H-benzimidazol-2-yl}cyclohexanecarboxylic acid,
(1R*,2S*)-2-{6-[(5-Methylpyridin-2-yl)methoxy]-1-(4-piperidin-1-ylbenzyl)-1H-benzimidazol-2-yl}cyclohexanecarboxylic acid,
racemic cis-2-{1-[4-(3,3-Difluoroazetidin-1-yl)benzyl]-6-[(5-methylpyridin-2-yl)methoxy]-1H-benzimidazol-2-yl}cyclohexanecarboxylic acid,
(1S*,2R*)-2-{1-[4-(3,3-Difluoroazetidin-1-yl)benzyl]-6-[(5-methylpyridin-2-yl)methoxy]-1H-benzimidazol-2-yl}cyclohexanecarboxylic acid,
racemic cis-2-{1-[4-(4,4-Difluoropiperidin-1-yl)-2-fluorobenzyl]-6-[(5-methylpyridin-2-yl)methoxy]-1H-benzimidazol-2-yl}cyclohexanecarboxylic acid,
racemic cis-2-{1-[4-(3,3-Difluoropyrrolidin-1-yl)-2-fluorobenzyl]-6-[(5-methylpyridin-2-yl)methoxy]-1H-benzimidazol-2-yl}cyclohexanecarboxylic acid,
(1R*,2S*)-2-{1-[4-(3,3-Difluoropyrrolidin-1-yl)-2-fluorobenzyl]-6-[(5-methylpyridin-2-yl)methoxy]-1H-benzimidazol-2-yl}cyclohexanecarboxylic acid,
(1S*,2R*)-2-{1-[4-(3,3-Difluoropyrrolidin-1-yl)-2-fluorobenzyl]-6-[(5-methylpyridin-2-yl)methoxy]-1H-benzimidazol-2-yl}cyclohexanecarboxylic acid,
racemic cis-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid,
(1R*,2S*)-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid,
(1S*,2R*)-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid,
racemic cis-2-{1-[4-(3,3-Difluoroazetidin-1-yl)benzyl]-4-fluoro-6-[(1-methyl-1H-pyrazol-3-yl)methoxy]-1H-benzimidazol-2-yl}cyclohexanecarboxylic acid as the formate salt,
racemic cis-2-{4-Fluoro-6-[(1-methyl-1H-pyrazol-3-yl)methoxy]-1-(4-piperidin-1-ylbenzyl)-1H-benzimidazol-2-yl}cyclohexanecarboxylic acid as the HCl salt,
2-({1-[4-(4,4-Difluoropiperidin-1-yl)benzyl]-6-[(5-methylpyridin-2-yl)methoxy]-1H-benzimidazol-2-yl}methyl)-2-ethylbutanoic acid,
racemic trans-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid,
racemic cis-2-{1-[2,6-Difluoro-4-(4-fluoropiperidin-1-yl)benzyl]-6-[(3-fluoro-5-methylpyridin-2-yl)methoxy]-1H-benzimidazol-2-yl}cyclohexanecarboxylic acid,
racemic cis-2-{1-[2-Fluoro-4-(4-fluoropiperidin-1-yl)benzyl]-6-[(3-fluoro-5-

TABLE 1-continued methylpyridin-2-yl)methoxy]-1H-benzimidazol-2-yl}cyclohexanecarboxylic acid,
(1R*,2S*)-2-{1-[2-Fluoro-4-(4-fluoropiperidin-1-yl)benzyl]-6-[(3-fluoro-5-methylpyridin-2-yl)methoxy]-1H-benzimidazol-2-yl}cyclohexanecarboxylic acid,
(1S*,2R*)-2-{1-[2-Fluoro-4-(4-fluoropiperidin-1-yl)benzyl]-6-[(3-fluoro-5-methylpyridin-2-yl)methoxy]-1H-benzimidazol-2-yl}cyclohexanecarboxylic acid,
(1R*,2S*)-2-{6-[(3-Fluoro-5-methylpyridin-2-yl)methoxy]-1-[4-(4-fluoropiperidin-1-yl)benzyl]-1H-benzimidazol-2-yl}cyclohexanecarboxylic acid,
racemic cis-2-{1-[2-Fluoro-4-(4-methylpiperidin-1-yl)benzyl]-6-[(3-fluoro-5-methylpyridin-2-yl)methoxy]-1H-benzimidazol-2-yl}cyclohexanecarboxylic acid,
racemic cis-2-{6-[(3-Fluoro-5-methylpyridin-2-yl)methoxy]-1-[4-(4-methylpiperidin-1-yl)benzyl]-1H-benzimidazol-2-yl}cyclohexanecarboxylic acid,
racemic cis-2-{6-[(3-Fluoro-5-methylpyridin-2-yl)methoxy]-1-(4-piperidin-1-ylbenzyl)-1H-benzimidazol-2-yl}cyclohexanecarboxylic acid,
2-Ethyl-2-({6-[(3-fluoro-5-methylpyridin-2-yl)methoxy]-1-[4-(4-methylpiperidin-1-yl)benzyl]-1H-benzimidazol-2-yl}methyl)butanoic acid,
2-Ethyl-2-({1-[2-fluoro-4-(4-methylpiperidin-1-yl)benzyl]-6-[(3-fluoro-5-methylpyridin-2-yl)methoxy]-1H-benzimidazol-2-yl}methyl)butanoic acid,
2-Ethyl-2-({6-[(3-fluoro-5-methylpyridin-2-yl)methoxy]-1-[4-(4-fluoropiperidin-1-yl)benzyl]-1H-benzimidazol-2-yl}methyl)butanoic acid,
3-(6-[(3-Fluoro-5-methylpyridin-2-yl)methoxy]-1-{2-fluoro-4-[3-(trifluoromethyl)azetidin-1-yl]benzyl}-1H-benzimidazol-2-yl)-2,2-dimethylpropanoic acid,
3-{1-[4-(4-tert-Butylpiperidin-1-yl)benzyl]-6-[(3-fluoro-5-methylpyridin-2-yl)methoxy]-1H-benzimidazol-2-yl}-2,2-dimethylpropanoic acid,
3-{6-[(3-Fluoro-5-methylpyridin-2-yl)methoxy]-1-[4-(4-methylpiperidin-1-yl)benzyl]-1H-benzimidazol-2-yl}-2,2-dimethylpropanoic acid,
3-{1-[2-Fluoro-4-(4-fluoropiperidin-1-yl)benzyl]-6-[(3-fluoro-5-methylpyridin-2-yl)methoxy]-1H-benzimidazol-2-yl}-2,2-dimethylpropanoic acid,
racemic cis-2-(6-((5-methylpyrimidin-2-yl)methoxy)-1-((4'-(trifluoromethyl)-[1,1'-biphenyl]-4-yl)methyl)-1H-benzo[d]imidazol-2-yl)cyclohexanecarboxylic acid,
racemic cis-2-(6-((5-methylpyrazin-2-yl)methoxy)-1-((4'-(trifluoromethyl)-[1,1'-biphenyl]-4-yl)methyl)-1H-benzo[d]imidazol-2-yl)cyclohexanecarboxylic acid,
2-ethyl-2-((1-((3-fluoro-4'-(trifluoromethyl)-[1,1'-biphenyl]-4-yl)methyl)-6-((1-methyl-1H-pyrazol-3-yl)methoxy)-1H-benzo[d]imidazol-2-yl)methyl)butanoic acid,
2-ethyl-2-((6-((1-methyl-1H-pyrazol-3-yl)methoxy)-1-((4'-(trifluoromethyl)-[1,1'-biphenyl]-4-yl)methyl)-1H-benzo[d]imidazol-2-yl)methyl)butanoic acid,
racemic cis-2-(6-((5-methylpyrazin-2-yl)methoxy)-1-(4-(4-(trifluoromethyl)piperidin-1-yl)benzyl)-1H-benzo[d]imidazol-2-yl)cyclohexanecarboxylic acid,
2-ethyl-2-((1-(2-fluoro-4-(4-(trifluoromethyl)piperidin-1-yl)benzyl)-6-((1-methyl-1H-pyrazol-3-yl)methoxy)-1H-benzo[d]imidazol-2-yl)methyl)butanoic acid,
2-ethyl-2-((6-((1-methyl-1H-pyrazol-3-yl)methoxy)-1-(4-(4-(trifluoromethyl)piperidin-1-yl)benzyl)-1H-benzo[d]imidazol-2-yl)methyl)butanoic acid,
and solvates, hydrates, and pharmaceutically acceptable salts thereof.

Another embodiment of the invention is a compound selected from the group consisting of
racemic cis-2-{1-(4-Bromobenzyl)-6-[(5-methylpyridin-2-yl)methoxy]-1H-benzimidazol-2-yl}cyclohexanecarboxylic acid,
(1S,2R)-2-(1-(4-Bromobenzyl)-6-((5-methylpyridin-2-yl)methoxy)-1H-benzo[d]imidazol-2-yl)cyclohexanecarboxylic acid,
(1R,2S)-2-{1-(4-Bromobenzyl)-6-[(5-methylpyridin-2-yl)methoxy]-1H-benzimidazol-2-yl}cyclohexanecarboxylic acid,
racemic cis-2-{1-(4-Bromo-3-fluorobenzyl)-6-[(5-methylpyridin-2-yl)methoxy]-1H-benzimidazol-2-yl}cyclohexanecarboxylic acid as the TFA salt,
racemic cis-2-{1-(4-Bromo-2-fluorobenzyl)-6-[(5-methylpyridin-2-yl)methoxy]-1H-benzimidazol-2-yl}cyclohexanecarboxylic acid,
(1R*,2S*)-2-{1-(4-Bromo-2-fluorobenzyl)-6-[(5-methylpyridin-2-yl)methoxy]-1H-benzimidazol-2-yl}cyclohexanecarboxylic acid,
(1S*,2R*)-2-{1-(4-Bromo-2-fluorobenzyl)-6-[(5-methylpyridin-2-yl)methoxy]-1H-benzimidazol-2-yl}cyclohexanecarboxylic acid,
racemic cis-3-{1-(4-Bromo-2-fluorobenzyl)-6-[(5-methylpyridin-2-yl)methoxy]-1H-benzimidazol-2-yl}-2,2-dimethylcyclopropanecarboxylic acid,
(1S*,3R*)-3-{1-(4-Bromo-2-fluorobenzyl)-6-[(5-methylpyridin-2-yl)methoxy]-1H-benzimidazol-2-yl}-2,2-dimethylcyclopropanecarboxylic acid,
racemic cis-2-{1-[3-Fluoro-4-(trifluoromethoxy)benzyl]-6-[(5-methylpyridin-2-yl)methoxy]-1H-benzimidazol-2-yl}cyclohexanecarboxylic acid,
racemic cis-2,2-Dimethyl-3-{6-[(5-methylpyridin-2-yl)methoxy]-1-[4-(trifluoromethoxy)benzyl]-1H-benzimidazol-2-yl}cyclopropanecarboxylic acid,
racemic cis-2-{1-[2-Fluoro-4-(trifluoromethoxy)benzyl]-6-[(5-methylpyridin-2-yl)methoxy]-1H-benzimidazol-2-yl}cyclohexanecarboxylic acid,
racemic cis-2-{6-[(5-Methylpyridin-2-yl)methoxy]-1-[4-(trifluoromethoxy)benzyl]-1H-benzimidazol-2-yl}cyclohexanecarboxylic acid,
(1R*,2S*)-2-{6-[(5-Methylpyridin-2-yl)methoxy]-1-[4-(trifluoromethoxy)benzyl]-1H-benzimidazol-2-yl}cyclohexanecarboxylic acid,
(1S*,2R*)-2-{6-[(5-Methylpyridin-2-yl)methoxy]-1-[4-(trifluoromethoxy)benzyl]-1H-benzimidazol-2-yl}cyclohexanecarboxylic acid,
racemic cis-2-{1-[3-Chloro-4-(trifluoromethoxy)benzyl]-6-[(5-methylpyridin-2-yl)methoxy]-1H-benzimidazol-2-yl}cyclohexanecarboxylic acid,
(1S*,2R*)-2-{6-[(1-Methyl-1H-pyrazol-3-yl)methoxy]-1-[4-(trifluoromethoxy)benzyl]-1H-benzimidazol-2-yl}cyclohexanecarboxylic acid,
racemic cis-2-{1-(4-Cyanobenzyl)-6-[(5-methylpyridin-2-yl)methoxy]-1H-benzimidazol-2-yl}cyclohexanecarboxylic acid as the TFA salt, (1R*,2S*)-2-{1-(4-Cyanobenzyl)-6-[(5-methylpyridin-2-yl)methoxy]-1H-benzimidazol-2-yl}cyclohexanecarboxylic acid, racemic cis-2-{1-(4-Bromobenzyl)-6-[(1-methyl-1H-pyrazol-3-yl)methoxy]-1H-benzimidazol-2-yl}cyclohexanecarboxylic acid as the TFA salt, racemic cis-2-{6-[(1-Methyl-1H-pyrazol-3-yl)methoxy]-1-[4-(trifluoromethoxy)benzyl]-1H-benzimidazol-2-yl}cyclohexanecarboxylic acid, (1R*,2S*)-2-{6-[(1-Methyl-1H-pyrazol-3-yl)methoxy]-1-[4-(trifluoromethoxy)benzyl]-1H-benzimidazol-2-yl}cyclohexanecarboxylic acid, racemic cis-2-{1-(4-Cyanobenzyl)-6-[(1-methyl-1H-pyrazol-3-yl)methoxy]-1H-benzimidazol-2-yl}cyclohexanecarboxylic acid as the TFA salt, racemic cis-2-{1-[2-Fluoro-4-(trifluoromethoxy)benzyl]-6-[(1-methyl-1H-pyrazol-3-yl)methoxy]-1H-benzimidazol-2-yl}cyclohexanecarboxylic acid, (1R*,2S*)-2-(1-(2-Fluoro-4-(trifluoromethoxy)benzyl)-6-((1-methyl-1H-pyrazol-3-yl)methoxy)-1H-benzo[d]imidazol-2-yl)cyclohexanecarboxylic acid, racemic cis-2-{1-[3-Fluoro-4-(trifluoromethoxy)benzyl]-6-[(1-methyl-1H-pyrazol-3-yl)methoxy]-1H-benzimidazol-2-yl}cyclohexanecarboxylic acid, racemic cis-2-{1-(4-Bromobenzyl)-4-fluoro-6-[(5-methylpyridin-2-yl)methoxy]-1H-benzimidazol-2-yl}cyclohexanecarboxylic acid, racemic cis-3-{1-(4-Bromobenzyl)-4-fluoro-6-[(5-methylpyridin-2-yl)methoxy]-1H-benzimidazol-2-yl}-2,2-dimethylcyclopropanecarboxylic acid, racemic cis-3-{4-Fluoro-1-(4-methylbenzyl)-6-[(5-methylpyridin-2-yl)methoxy]-1H-benzimidazol-2-yl}-2,2-dimethylcyclopropanecarboxylic acid as the TFA salt, racemic cis-2-{4-Fluoro-6-[(5-methylpyridin-2-yl)methoxy]-1-[4-(trifluoromethoxy)benzyl]-1H-benzimidazol-2-yl}cyclohexanecarboxylic acid as the TFA salt, racemic cis-2-{4-Fluoro-1-(4-methylbenzyl)-6-[(5-methylpyridin-2-yl)methoxy]-1H-benzimidazol-2-yl}cyclohexanecarboxylic acid as the TFA salt, racemic cis-3-{4-Fluoro-6-[(5-methylpyridin-2-yl)methoxy]-1-[4-(trifluoromethoxy)benzyl]-1H-benzimidazol-2-yl}-2,2-dimethylcyclopropanecarboxylic acid as the TFA salt, racemic cis-2-{1-(4-Bromobenzyl)-4-chloro-6-[(5-methylpyridin-2-yl)methoxy]-1H-benzimidazol-2-yl}cyclohexanecarboxylic acid, racemic cis-3-{1-(4-Bromobenzyl)-4-chloro-6-[(5-methylpyridin-2-yl)methoxy]-1H-benzimidazol-2-yl}-2,2-dimethylcyclopropanecarboxylic acid, racemic cis-2-{1-[4-(5-Chloropyrimidin-2-yl)benzyl]-6-[(5-methylpyridin-2-yl)methoxy]-1H-benzimidazol-2-yl}cyclohexanecarboxylic acid, racemic cis-2-{1-(4-Bromobenzyl)-6-[(4-chloro-1-methyl-1H-pyrazol-3-yl)methoxy]-1H-benzimidazol-2-yl}cyclohexanecarboxylic acid, racemic cis-2-{6-[(4-Chloro-1-methyl-1H-pyrazol-3-yl)methoxy]-1-(4-piperidin-1-ylbenzyl)-1H-benzimidazol-2-yl}cyclohexanecarboxylic acid, racemic cis-2-{6-[(4-Chloro-1-methyl-1H-pyrazol-3-yl)methoxy]-1-[2-fluoro-4-(trifluoromethoxy)benzyl]-1H-benzimidazol-2-yl}cyclohexanecarboxylic acid, racemic cis-2-{1-[2-Methoxy-4-(trifluoromethoxy)benzyl]-6-[(1-methyl-1H-pyrazol-3-yl)methoxy]-1H-benzimidazol-2-yl}cyclohexanecarboxylic acid, racemic cis-2-{6-[(4-Fluoro-1-methyl-1H-pyrazol-3-yl)methoxy]-1-[2-fluoro-4-(trifluoromethoxy)benzyl]-1H-benzimidazol-2-yl}cyclohexanecarboxylic acid, racemic cis-2-{1-[4-(4,4-Difluoropiperidin-1-yl)benzyl]-6-[(1-methyl-1H-pyrazol-3-yl)methoxy]-1H-benzimidazol-2-yl}cyclohexanecarboxylic acid, racemic cis-2-{6-[(4-Chloro-1-methyl-1H-pyrazol-3-yl)methoxy]-1-[4-(4-fluoropiperidin-1-yl)benzyl]-1H-benzimidazol-2-yl}cyclohexanecarboxylic acid, racemic cis-2-{6-[(1-Methyl-1H-pyrazol-3-yl)methoxy]-1-(4-piperidin-1-ylbenzyl)-1H-benzimidazol-2-yl}cyclohexanecarboxylic acid, racemic cis-2-{1-[4-(3,3-Difluoroazetidin-1-yl)benzyl]-6-[(1-methyl-1H-pyrazol-3-yl)methoxy]-1H-benzimidazol-2-yl}cyclohexanecarboxylic acid, racemic cis-2-{5-Fluoro-1-[2-fluoro-4-(trifluoromethoxy)benzyl]-6-[(1-methyl-1H-pyrazol-3-yl)methoxy]-1H-benzimidazol-2-yl}cyclohexanecarboxylic acid, racemic cis-2-{7-Fluoro-1-[2-fluoro-4-(trifluoromethoxy)benzyl]-6-[(1-methyl-1H-pyrazol-3-yl)methoxy]-1H-benzimidazol-2-yl}cyclohexanecarboxylic acid, racemic cis-2-{1-(4-Bromobenzyl)-4-fluoro-6-[(1-methyl-1H-pyrazol-3-yl)methoxy]-1H-benzimidazol-2-yl}cyclohexanecarboxylic acid, racemic cis-2-{1-(4-Bromo-2-fluorobenzyl)-4-fluoro-6-[(1-methyl-1H-pyrazol-3-yl)methoxy]-1H-benzimidazol-2-yl}cyclohexanecarboxylic acid, racemic cis-2-{4-Fluoro-6-[(1-methyl-1H-pyrazol-3-yl)methoxy]-1-[4-(trifluoromethoxy)benzyl]-1H-benzimidazol-2-yl}cyclohexanecarboxylic acid as the HCl salt, racemic cis-2-{4-Fluoro-1-[2-fluoro-4-(trifluoromethoxy)benzyl]-6-[(1-methyl-1H-pyrazol-3-yl)methoxy]-1H-benzimidazol-2-yl}cyclohexanecarboxylic acid as the HCl salt, racemic cis-2-{4-Fluoro-1-(4-methylbenzyl)-6-[(1-methyl-1H-pyrazol-3-yl)methoxy]-1H-benzimidazol-2-yl}cyclohexanecarboxylic acid as the HCl salt, racemic cis-2-{1-(4-Cyanobenzyl)-4-fluoro-6-[(1-methyl-1H-pyrazol-3-yl)methoxy]-1H-benzimidazol-2-yl}cyclohexanecarboxylic acid as the HCl salt, racemic cis-2-{6-[(1-Methyl-1H-pyrazol-3-yl)methoxy]-1-[2-methyl-4-(trifluoromethoxy)benzyl]-1H-benzimidazol-2-yl}cyclohexanecarboxylic acid, racemic cis-2-{6-[(5-Methylpyridin-2-yl)methoxy]-1-[2-methyl-4-(trifluoromethoxy)benzyl]-1H-benzimidazol-2-yl}cyclohexanecarboxylic acid, racemic cis-2-{1-[2-Chloro-4-(trifluoromethoxy)benzyl]-6-[(5-methylpyridin-2-yl)methoxy]-1H-benzimidazol-2-yl}cyclohexanecarboxylic acid as the HCl salt, racemic cis-2-{1-[2-Bromo-4-(trifluoromethoxy)benzyl]-6-[(5-methylpyridin-2-yl)methoxy]-1H-benzimidazol-2-yl}cyclohexanecarboxylic acid as the HCl salt, racemic cis-2-{1-[2-Chloro-4-(trifluoromethoxy)benzyl]-6-[(1-methyl-1H-pyrazol-3-yl)methoxy]-1H-benzimidazol-2-yl}cyclohexanecarboxylic acid as the HCl salt, racemic cis-2-{1-[2-Bromo-4-(trifluoromethoxy)benzyl]-6-[(1-methyl-1H-pyrazol-3-yl)methoxy]-1H-benzimidazol-2-yl}cyclohexanecarboxylic acid as the HCl salt, racemic cis-2-{6-[(1-Methyl-1H-pyrazol-3-yl)methoxy]-1-[3-methyl-4-(trifluoromethoxy)benzyl]-1H-benzimidazol-2-yl}cyclohexanecarboxylic acid as the HCl salt, racemic cis-2-{6-[(5-Methylpyridin-2-yl)methoxy]-1-[3-methyl-4-(trifluoromethoxy)benzyl]-1H-benzimidazol-2-yl}cyclohexanecarboxylic acid, racemic cis-2-{5-Chloro-1-[2-fluoro-4-(trifluoromethoxy)benzyl]-6-[(5-methylpyridin-2-yl)methoxy]-1H-benzimidazol-2-yl}cyclohexanecarboxylic acid as the HCl salt, racemic cis-3-{1-(4-Bromobenzyl)-6-[(5-methylpyridin-2-yl)methoxy]-1H-benzimidazol-2-yl}-2,2-dimethylcyclopropanecarboxylic acid as the TFA salt, (1S*,3R*)-3-{1-(4-Bromobenzyl)-6-[(5-methylpyridin-2-yl)methoxy]-1H-benzimidazol-2-yl}-2,2-dimethylcyclopropanecarboxylic acid,
(1R*,3S*)-3-{1-(4-Bromobenzyl)-6-[(5-methylpyridin-2-yl)methoxy]-1H-benzimidazol-2-yl}-2,2-dimethylcyclopropanecarboxylic acid,
racemic cis-2-{1-(4-Methylbenzyl)-6-[(5-methylpyridin-2-yl)methoxy]-1H-benzimidazol-2-yl}cyclohexanecarboxylic acid,
racemic cis-2,2-Dimethyl-3-{1-(4-methylbenzyl)-6-[(5-methylpyridin-2-yl)methoxy]-1H-benzimidazol-2-yl}cyclopropanecarboxylic acid,
racemic cis-2,2-Dimethyl-3-{6-[(1-methyl-1H-pyrazol-3-yl)methoxy]-1-[4-(trifluoromethoxy)benzyl]-1H-benzimidazol-2-yl}cyclopropanecarboxylic acid,
racemic cis-2-{1-(4-Bromo-2,6-difluorobenzyl)-6-[(3-fluoro-5-methylpyridin-2-yl)methoxy]-1H-benzimidazol-2-yl}cyclohexanecarboxylic acid,
racemic cis-2-{1-(4-Bromobenzyl)-6-[(3-fluoro-5-methylpyridin-2-yl)methoxy]-1H-benzimidazol-2-yl}cyclohexanecarboxylic acid,
racemic cis-2-{1-(4-Bromo-2,6-difluorobenzyl)-6-[(5-methylpyridin-2-yl)methoxy]-1H-benzimidazol-2-yl}cyclohexanecarboxylic acid,
racemic cis-3-{1-(4-Bromobenzyl)-6-[(3-fluoro-5-methylpyridin-2-yl)methoxy]-1H-benzimidazol-2-yl}-2,2-dimethylcyclopropanecarboxylic acid,
racemic cis-3-{1-(4-Bromobenzyl)-6-[(6-methylpyridin-2-yl)methoxy]-1H-benzimidazol-2-yl}-2,2-dimethylcyclopropanecarboxylic acid,
racemic cis-3-{1-(4-Bromobenzyl)-6-[(1-methyl-1H-pyrazol-3-yl)methoxy]-1H-benzimidazol-2-yl}-2,2-dimethylcyclopropanecarboxylic acid,
racemic cis-2-(1-((3,5-difluoro-4'-(trifluoromethyl)-[1,1'-biphenyl]-4-yl)methyl)-6-((3-fluoro-5-methylpyridin-2-yl)methoxy)-1H-benzo[d]imidazol-2-yl)cyclohexanecarboxylic acid,
racemic cis-2-(1-{[3,5-Difluoro-4'-(trifluoromethyl)biphenyl-4-yl]methyl}-6-[(5-methylpyridin-2-yl)methoxy]-1H-benzimidazol-2-yl)cyclohexanecarboxylic acid,
(1R*,2S*)-2-(6-[(3-Fluoro-5-methylpyridin-2-yl)methoxy]-1-{[4'-(trifluoromethyl)biphenyl-4-yl]methyl}-1H-benzimidazol-2-yl)cyclohexanecarboxylic acid,
racemic cis-2-{1-[4-(2-Methoxypyrimidin-5-yl)benzyl]-6-[(5-methylpyridin-2-yl)methoxy]-1H-benzimidazol-2-yl}cyclohexanecarboxylic acid,
racemic cis-2-(6-[(5-Methylpyridin-2-yl)methoxy]-1-{[4'-(trifluoromethyl)biphenyl-3-yl]methyl}-1H-benzimidazol-2-yl)cyclohexanecarboxylic acid,
racemic cis-2-(6-[(5-Methylpyridin-2-yl)methoxy]-1-{[4'-(trifluoromethyl)biphenyl-4-yl]methyl}-1H-benzimidazol-2-yl)cyclohexanecarboxylic acid,
(1S,2R)-2-(6-((5-methylpyridin-2-yl)methoxy)-1-((4'-(trifluoromethyl)-[1,1'-biphenyl]-4-yl)methyl)-1H-benzo[d]imidazol-2-yl)cyclohexanecarboxylic acid,
(1R,2S)-2-(6-[(5-Methyl pyridin-2-yl)methoxy]-1-{[4'-(trifluoromethyl)biphenyl-4-yl]methyl}-1H-benzimidazol-2-yl)cyclohexanecarboxylic acid,
racemic cis-2-(6-[(1-Methyl-1H-pyrazol-3-yl)methoxy]-1-{[4'-(trifluoromethyl)biphenyl-3-yl]methyl}-1H-benzimidazol-2-yl)cyclohexanecarboxylic acid,
racemic cis-2-(6-[(4-Chloro-1-methyl-1H-pyrazol-3-yl)methoxy]-1-{[4'-(trifluoromethyl)biphenyl-4-yl]methyl}-1H-benzimidazol-2-yl)cyclohexanecarboxylic acid,
racemic cis-2-{1-[4-(3,3-Difluoropyrrolidin-1-yl)benzyl]-6-[(5-methylpyridin-2-yl)methoxy]-1H-benzimidazol-2-yl}cyclohexanecarboxylic acid,
racemic cis-2-{1-[4-(3,3-Difluoropiperidin-1-yl)benzyl]-6-[(5-methylpyridin-2-yl)methoxy]-1H-benzimidazol-2-yl}cyclohexanecarboxylic acid,
racemic cis-2-{1-[4-(4,4-Difluoropiperidin-1-yl)benzyl]-6-[(5-methylpyridin-2-yl)methoxy]-1H-benzimidazol-2-yl}cyclohexanecarboxylic acid,
racemic cis-2-{6-[(5-Methylpyridin-2-yl)methoxy]-1-(4-piperidin-1-ylbenzyl)-1H-benzimidazol-2-yl}cyclohexanecarboxylic acid,
(1S*,2R*)-2-{6-[(5-Methylpyridin-2-yl)methoxy]-1-(4-piperidin-1-ylbenzyl)-1H-benzimidazol-2-yl}cyclohexanecarboxylic acid,
(1R*,2S*)-2-{6-[(5-Methylpyridin-2-yl)methoxy]-1-(4-piperidin-1-ylbenzyl)-1H-benzimidazol-2-yl}cyclohexanecarboxylic acid,
racemic cis-2-{1-[4-(3,3-Difluoroazetidin-1-yl)benzyl]-6-[(5-methylpyridin-2-yl)methoxy]-1H-benzimidazol-2-yl}cyclohexanecarboxylic acid,
(1S*,2R*)-2-{1-[4-(3,3-Difluoroazetidin-1-yl)benzyl]-6-[(5-methylpyridin-2-yl)methoxy]-1H-benzimidazol-2-yl}cyclohexanecarboxylic acid,
racemic cis-2-{1-[4-(4,4-Difluoropiperidin-1-yl)-2-fluorobenzyl]-6-[(5-methylpyridin-2-yl)methoxy]-1H-benzimidazol-2-yl}cyclohexanecarboxylic acid,
racemic cis-2-{1-[4-(3,3-Difluoropyrrolidin-1-yl)-2-fluorobenzyl]-6-[(5-methylpyridin-2-yl)methoxy]-1H-benzimidazol-2-yl}cyclohexanecarboxylic acid,
(1R*,2S*)-2-{1-[4-(3,3-Difluoropyrrolidin-1-yl)-2-fluorobenzyl]-6-[(5-methylpyridin-2-yl)methoxy]-1H-benzimidazol-2-yl}cyclohexanecarboxylic acid,
(1S*,2R*)-2-{1-[4-(3,3-Difluoropyrrolidin-1-yl)-2-fluorobenzyl]-6-[(5-methylpyridin-2-yl)methoxy]-1H-benzimidazol-2-yl}cyclohexanecarboxylic acid,
racemic cis-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid,
(1R*,2S*)-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid,
(1S*,2R*)-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid,
racemic cis-2-{1-[4-(3,3-Difluoroazetidin-1-yl)benzyl]-4-fluoro-6-[(1-methyl-1H-pyrazol-3-yl)methoxy]-1H-benzimidazol-2-yl}cyclohexanecarboxylic acid as the formate salt,
racemic cis-2-{4-Fluoro-6-[(1-methyl-1H-pyrazol-3-yl)methoxy]-1-(4-piperidin-1-ylbenzyl)-1H-benzimidazol-2-yl}cyclohexanecarboxylic acid as the HCl salt,
racemic cis-2-{1-[2,6-Difluoro-4-(4-fluoropiperidin-1-yl)benzyl]-6-[(3-fluoro-5-methylpyridin-2-yl)methoxy]-1H-benzimidazol-2-yl}cyclohexanecarboxylic acid,
racemic cis-2-{1-[2-Fluoro-4-(4-fluoropiperidin-1-yl)benzyl]-6-[(3-fluoro-5-methylpyridin-2-yl)methoxy]-1H-benzimidazol-2-yl}cyclohexanecarboxylic acid,
(1R*,2S*)-2-{1-[2-Fluoro-4-(4-fluoropiperidin-1-yl)benzyl]-6-[(3-fluoro-5-methylpyridin-2-yl)methoxy]-1H-benzimidazol-2-yl}cyclohexanecarboxylic acid,
(1S*,2R*)-2-{1-[2-Fluoro-4-(4-fluoropiperidin-1-yl)benzyl]-6-[(3-fluoro-5-methylpyridin-2-yl)methoxy]-1H-benzimidazol-2-yl}cyclohexanecarboxylic acid,
(1R*,2S*)-2-{6-[(3-Fluoro-5-methylpyridin-2-yl)methoxy]-1-4-(4-fluoropiperidin-1-yl)benzyl]-1H-benzimidazol-2-yl}cyclohexanecarboxylic acid,
racemic cis-2-{1-[2-Fluoro-4-(4-methylpiperidin-1-yl)benzyl]-6-[(3-fluoro-5-methylpyridin-2-yl)methoxy]-1H-benzimidazol-2-yl}cyclohexanecarboxylic acid, racemic cis-2-{6-[(3-Fluoro-5-methylpyridin-2-yl)methoxy]-1-[4-(4-methylpiperidin-1-yl)benzyl]-1H-benzimidazol-2-yl}cyclohexanecarboxylic acid,
racemic cis-2-{6-[(3-Fluoro-5-methylpyridin-2-yl)methoxy]-1-(4-piperidin-1-ylbenzyl)-1H-benzimidazol-2-yl}cyclohexanecarboxylic acid,
and solvates, hydrates, and pharmaceutically acceptable salts thereof.

Another embodiment of the invention is a compound selected from the group consisting of
3-{1-(3-Bromobenzyl)-6-[(3-fluoro-5-methylpyridin-2-yl)methoxy]-1H-benzimidazol-2-yl}-2,2-dimethylpropanoic acid,
racemic cis-2-(6-[(3-Fluoro-5-methylpyridin-2-yl)methoxy]-1-{2-fluoro-4-[4-(trifluoromethyl)piperidin-1-yl]benzyl}-1H-benzimidazol-2-yl)cyclohexanecarboxylic acid,
3-{1-(5-Bromo-2-fluorobenzyl)-6-[(3-fluoro-5-methylpyridin-2-yl)methoxy]-1H-benzimidazol-2-yl}-2,2-dimethylpropanoic acid,
2-Ethyl-2-[(6-[(3-fluoro-5-methylpyridin-2-yl)methoxy]-1-{4-[4-(trifluoromethyl)piperidin-1-yl]benzyl}-1H-benzimidazol-2-yl)methyl]butanoic acid,
racemic cis-2-{1-[3-(2-Methoxypyrimidin-5-yl)benzyl]-6-[(5-methylpyridin-2-yl)methoxy]-1H-benzimidazol-2-yl}cyclohexanecarboxylic acid,
2-Ethyl-2-({1-[3-(2-methoxypyrimidin-5-yl)benzyl]-6-[(5-methylpyridin-2-yl)methoxy]-1H-benzimidazol-2-yl}methyl)butanoic acid,
(1S*,2R*)-2-{1-(3-Bromobenzyl)-6-[(1-methyl-1H-pyrazol-3-yl)methoxy]-1H-benzimidazol-2-yl}cyclohexanecarboxylic acid,
(1R*,2S*)-2-{1-(3-Bromobenzyl)-6-[(1-methyl-1H-pyrazol-3-yl)methoxy]-1H-benzimidazol-2-yl}cyclohexanecarboxylic acid,
racemic cis-2-{1-(3-Cyanobenzyl)-6-[(1-methyl-1H-pyrazol-3-yl)methoxy]-1H-benzimidazol-2-yl}cyclohexanecarboxylic acid,
racemic trans-2-{1-(3-Methylbenzyl)-6-[(5-methylpyridin-2-yl)methoxy]-1H-benzimidazol-2-yl}cyclohexanecarboxylic acid,
racemic cis-2-{1-(3-Methylbenzyl)-6-[(5-methylpyridin-2-yl)methoxy]-1H-benzimidazol-2-yl}cyclohexanecarboxylic acid,
racemic cis-2,2-Dimethyl-3-{1-(3-methylbenzyl)-6-[(5-methylpyridin-2-yl)methoxy]-1H-benzimidazol-2-yl}cyclopropanecarboxylic acid,
racemic cis-2-{1-[3-(4,4-Difluoropiperidin-1-yl)benzyl]-6-[(1-methyl-1H-pyrazol-3-yl)methoxy]-1H-benzimidazol-2-yl}cyclohexanecarboxylic acid,
racemic cis-2-{6-[(1-Methyl-1H-pyrazol-3-yl)methoxy]-1-(3-piperidin-1-ylbenzyl)-1H-benzimidazol-2-yl}cyclohexanecarboxylic acid,
racemic cis-2-{1-[3-(3,3-Difluoroazetidin-1-yl)benzyl]-6-[(1-methyl-1H-pyrazol-3-yl)methoxy]-1H-benzimidazol-2-yl}cyclohexanecarboxylic acid as the trifluoroacetic acid salt,
racemic trans-2-{1-(2-Methylbenzyl)-6-[(5-methylpyridin-2-yl)methoxy]-1H-benzimidazol-2-yl}cyclohexanecarboxylic acid,
racemic cis-2-{1-(2-Methylbenzyl)-6-[(5-methylpyridin-2-yl)methoxy]-1H-benzimidazol-2-yl}cyclohexanecarboxylic acid,
racemic cis-2-{1-[5-(4,4-Difluoropiperidin-1-yl)-2-fluorobenzyl]-6-[(5-methylpyridin-2-yl)methoxy]-1H-benzimidazol-2-yl}cyclohexanecarboxylic acid,
racemic cis-2-{1-(2-Fluoro-5-piperidin-1-ylbenzyl)-6-[(5-methylpyridin-2-yl)methoxy]-1H-benzimidazol-2-yl}cyclohexanecarboxylic acid,
racemic cis-2,2-Dimethyl-3-{1-(2-methylbenzyl)-6-[(5-methylpyridin-2-yl)methoxy]-1H-benzimidazol-2-yl}cyclopropanecarboxylic acid,
2-({1-[3-(3,3-Difluoropyrrolidin-1-yl)benzyl]-6-[(1-methyl-1H-pyrazol-3-yl)methoxy]-1H-benzimidazol-2-yl}methyl)-2-ethylbutanoic acid,
2-Ethyl-2-({6-[(1-methyl-1H-pyrazol-3-yl)methoxy]-1-(3-piperidin-1-ylbenzyl)-1H-benzimidazol-2-yl}methyl)butanoic acid,
2-Ethyl-2-({1-[3-(2-methoxypyrimidin-5-yl)benzyl]-6-[(1-methyl-1H-pyrazol-3-yl)methoxy]-1H-benzimidazol-2-yl}methyl)butanoic acid,
2-Ethyl-2-({1-[2-fluoro-4-(2-methoxypyrimidin-5-yl)benzyl]-6-[(1-methyl-1H-pyrazol-3-yl)methoxy]-1H-benzimidazol-2-yl}methyl)butanoic acid,
2-({1-(3-Bromobenzyl)-6-[(1-methyl-1H-pyrazol-3-yl)methoxy]-1H-benzimidazol-2-yl}methyl)-2-ethylbutanoic acid,
2-({1-[4-(3,3-Difluoropyrrolidin-1-yl)benzyl]-6-[(1-methyl-1H-pyrazol-3-yl)methoxy]-1H-benzimidazol-2-yl}methyl)-2-ethylbutanoic acid,
racemic trans-2-{1-(3-Bromobenzyl)-6-[(5-methylpyridin-2-yl)methoxy]-1H-benzimidazol-2-yl}cyclohexanecarboxylic acid,
racemic trans-2-{1-(5-Bromo-2-fluorobenzyl)-6-[(5-methylpyridin-2-yl)methoxy]-1H-benzimidazol-2-yl}cyclohexanecarboxylic acid,
racemic cis-2-{1-[3-(3,3-Difluoroazetidin-1-yl)benzyl]-6-[(5-methylpyridin-2-yl)methoxy]-1H-benzimidazol-2-yl}cyclohexanecarboxylic acid,
racemic cis-2-{1-[3-(3,3-Difluoropyrrolidin-1-yl)benzyl]-6-[(5-methylpyridin-2-yl)methoxy]-1H-benzimidazol-2-yl}cyclohexanecarboxylic acid,
racemic cis-2-{1-[3-(4,4-Difluoropiperidin-1-yl)benzyl]-6-[(5-methylpyridin-2-yl)methoxy]-1H-benzimidazol-2-yl}cyclohexanecarboxylic acid,
racemic cis-2-{1-[3-(3,3-Difluoropiperidin-1-yl)benzyl]-6-[(5-methylpyridin-2-yl)methoxy]-1H-benzimidazol-2-yl}cyclohexanecarboxylic acid,
racemic cis-2-{6-[(5-Methylpyridin-2-yl)methoxy]-1-(3-piperidin-1-ylbenzyl)-1H-benzimidazol-2-yl}cyclohexanecarboxylic acid,
racemic trans-2-{6-[(5-Methylpyridin-2-yl)methoxy]-1-(3-piperidin-1-ylbenzyl)-1H-benzimidazol-2-yl}cyclohexanecarboxylic acid,
3-{1-(5-Bromo-2-fluorobenzyl)-6-[(5-methylpyridin-2-yl)methoxy]-1H-benzimidazol-2-yl}-2,2-dimethylpropanoic acid,
2-({1-[4-(3,3-Difluoropyrrolidin-1-yl)benzyl]-6-[(5-methylpyridin-2-yl)methoxy]-1H-benzimidazol-2-yl}methyl)-2-ethylbutanoic acid,
racemic cis-3-{1-(5-Bromo-2-fluorobenzyl)-6-[(5-methylpyridin-2-yl)methoxy]-1H-benzimidazol-2-yl}-2,2-dimethylcyclopropanecarboxylic acid,
racemic cis-2-{1-(3-Bromobenzyl)-6-[(5-methylpyridin-2-yl)methoxy]-1H-benzimidazol-2-yl}cyclohexanecarboxylic acid,
racemic-cis-2-{1-(5-Bromo-2-fluorobenzyl)-6-[(5-methylpyridin-2-yl)methoxy]-1H-benzimidazol-2-yl}cyclohexanecarboxylic acid,
1-({1-(3-Bromobenzyl)-4-fluoro-6-[(5-methylpyridin-2-yl)methoxy]-1H-benzimidazol-2-yl}methyl)cyclopentanecarboxylic acid as the trifluoroacetic salt, 1-({1-(2-Bromobenzyl)-4-fluoro-6-[(5-methylpyridin-2-yl)methoxy]-1H-benzimidazol-2-yl}methyl)cyclopentanecarboxylic acid as the trifluoroacetic salt,
3-{1-(3-Bromobenzyl)-6-[(5-methylpyridin-2-yl)methoxy]-1H-benzimidazol-2-yl}-2,2-dimethylpropanoic acid as the trifluoroacetic acid salt,
racemic cis-2-{1-(5-Bromo-2-fluorobenzyl)-6-[(1-methyl-1H-pyrazol-3-yl)methoxy]-1H-benzimidazol-2-yl}cyclohexanecarboxylic acid,
2-({1-(5-Bromo-2-fluorobenzyl)-6-[(1-methyl-1H-pyrazol-3-yl)methoxy]-1H-benzimidazol-2-yl}methyl)-2-ethylbutanoic acid,
2-({1-(5-Bromo-2-fluorobenzyl)-6-[(5-methylpyridin-2-yl)methoxy]-1H-benzimidazol-2-yl}methyl)-2-ethylbutanoic acid,
racemic cis-2-{1-[4-(3,3-Difluoropyrrolidin-1-yl)benzyl]-4-fluoro-6-[(1-methyl-1H-pyrazol-3-yl)methoxy]-1H-benzimidazol-2-yl}cyclohexanecarboxylic acid,
and solvates, hydrates, and pharmaceutically acceptable salts thereof.

Another embodiment of the invention is a process for making racemic cis-2-(1-(4-bromobenzyl)-6-((5-methylpyridin-2-yl)methoxy)-1H-benzo[d]imidazol-2-yl)cyclohexanecarboxylic acid comprising the following reaction:

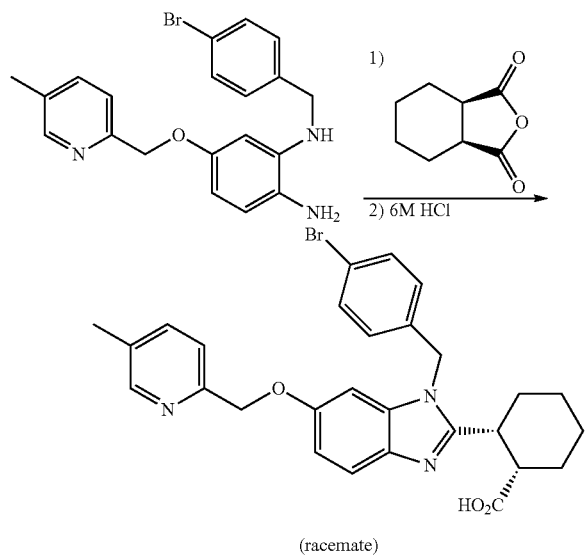

(racemate)

wherein the hexahydroisobenzofuran-1,3-dione is reacted at at temperature between 0° C. and 80° C., and the HCl is reacted at a temperature between 50° C. and 90° C.; wherein the product is formed in at least 75% yield, and the cis:trans ratio is at least 90%

The invention is also directed to a pharmaceutical composition which include, without limitation, one or more of the disclosed compounds, and pharmaceutically acceptable carriers or excipients.

Another embodiment of the present invention is a pharmaceutical composition of the present invention that comprises at least a compound selected from the compounds listed in Table 1.

The present invention also features a method of treating a subject suffering from or diagnosed with a disease and/or disorder mediated by FLAP activity, comprising administering to the subject a therapeutically effective amount of at least one compound of Formula (I).

The present invention also features a method for preventing, treating, ameliorating, including without limitation inhibiting, the progression of an FLAP-mediated disease and/or disorder in a subject in need thereof, comprising administering to said subject a therapeutically effective amount of at least one compound of Formula (I). Such a disease and/or disorder includes, but is not limited to diabetes, respiratory disorders, and associated symptoms or complications thereof. More specifically, this invention is directed to a method of treating, but not limited to, exacerbations, non-allergic asthma, fibrotic lung diseases, acute respiratory distress syndrome and chronic obstructive pulmonary disease, and their associated symptoms or complications, in a subject afflicted with such a disease and/or disorder.

In another embodiment, the compounds of the present invention are useful for the amelioration of symptoms associated with and/or the treatment of the following cardiac and cardiovascular diseases and/or disorders: myocardial infarction, atherosclerosis, atherosclerosis and stroke aortic aneurisms, or associated symptoms or complications thereof, in a subject afflicted with such a disease and/or disorder.

In another embodiment, the compounds of the present invention are useful for the amelioration of symptoms associated with and/or the treatment of autoimmune or allergic diseases and/or disorders, wherein said autoimmune or allergic diseases and/or disorders include, but are not limited to, rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis, allergic rhinitis, allergic dermatitis and asthma, or associated symptoms or complications thereof, in a subject afflicted with such a disease and/or disorder. In a further embodiment, the compounds of the present invention are useful for the amelioration of symptoms associated with and/or the prophylaxis or treatment of carcinogenesis, wherein said carcinogenesis include, but is not limited to, tumor cell proliferation, differentiation, apoptosis, tumor-associated angiogenesis, as well as the migration and invasion of carcinoma cells.

It is a further embodiment of the invention to provide a process for making a pharmaceutical composition comprising admixing any of the compounds according to Formula (I) and a pharmaceutically acceptable carrier.

In a further embodiment of the invention, a method for treating or ameliorating an FLAP-mediated disease and/or disorder in a subject in need thereof comprises administering to the subject a therapeutically effective amount of at least one compound of Formula (I), wherein the therapeutically effective amount of the compound of Formula (I) is from about 0.1 mg/dose to about 5 g/dose. In particular, the therapeutically effective amount of the compound of Formula (I) is from about 0.5 mg/dose to about 1000 mg/dose. More particularly, the therapeutically effective amount of the compound of Formula (I) is from about 1 mg/dose to about 100 mg/dose. In a further embodiment of the invention, the number of doses per day of a compound of Formula (I) is from 1 to 3 doses. In a further embodiment of the invention, the therapeutically effective amount of the compound of Formula (I) is from about 0.001 mg/kg/day to about 30 mg/kg/day. More particularly, the therapeutically effective amount of the compound of Formula (I) is from about 0.01 mg/kg/day to about 2 mg/kg/day.

The invention is further described below.

A) Terms

Some terms are defined below and by their usage throughout this disclosure.

It should also be noted that any atom with unsatisfied valences in the text, schemes, examples, structural formulae and any tables herein is assumed to have the hydrogen atom or atoms to satisfy the valences.

As used herein, the following terms are intended to have the following definitions. The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

The term "aryl" means an unsaturated, aromatic monocyclic or polycyclic hydrocarbon ring system radical. Examples include phenyl and the like, and all that are exemplified in the below examples. An aryl radical may be attached to a core molecule by any ring atom where allowed by available valences.

The term "hetero", when used as a prefix for a ring system, refers to the replacement of at least one carbon atom member in the ring system with a heteroatom selected from N, O, S, S(O), or $SO_2$. A hetero ring may have 1, 2, 3 or 4 carbon atom members replaced by a nitrogen atom. Alternatively, a ring may have 1, 2 or 3 nitrogen atom members and 1 oxygen or sulfur atom member. Alternatively, a ring may have 1 oxygen or sulfur atom member. Alternatively, up to two adjacent ring members may be heteroatoms, wherein one heteroatom is nitrogen and the other heteroatom is selected from N, S or O.

The term "heteroaryl" means an unsaturated monocyclic, polycyclic aromatic "hetero" ring system radical, selected from the group consisting of pyrazolyl, oxadiazolyl, furanyl, imidazolyl, imidazolidinyl, triazolyl, pyridinyl, pyrimidinyl, pyridazinyl, pyrazinyl, benzimidazolyl, benzoxazolyl, quinoxalinyl, quinazolinyl, benzothiazolyl, isoxazolyl, thiazolyl, oxazolyl, and isoindolyl. Examples include 1H-pyrazol-1-yl, 1H-pyrazol-3-yl, 1H-pyrazol-5-yl, 1,2,4-oxadiazol-5-yl, 1,2,4-oxadiazol-3-yl, furan-2-yl, 1H-imidazol-1-yl, 1H-imidazol-2-yl, 1H-imidazol-4-yl, 1H-imidazol-5-yl, imidazolidin-1-yl, 1H-1,2,4-triazol-1-yl, 1H-1,2,4-triazol-2-yl, 1H-1,2,4-triazol-3-yl, 1H-1,2,4-triazol-4-yl, 1H-1,2,3-triazol-1-yl, 2H-1,2,3-triazol-2-yl, pyridin-3-yl, pyrimidin-1-yl, pyrimidin-2-yl, pyrimidin-4-yl, pyrimidin-5-yl, pyridazin-2-yl, pyridazin-3-yl, pyridazin-4-yl, pyrazin-1-yl, pyrazin-2-yl, pyrazin-3-yl, benzimidazol-1-yl, benzoxazol-2-yl, quinoxalin-2-yl, quinazolin-2-yl, benzothiazol-2-yl, isoxazol-3-yl, 1,3-thiazol-4-yl, 1,3-oxazol-2-yl, isoindol-1-yl, and the like, and all that are exemplified in the below examples. A heteroaryl radical may be attached to a core molecule by any ring atom where allowed by available valences.

The term "carboxy" means a radical of the formula: —C(O)OH.

The term "halogen" or "halo" means a radical selected from the group consisting of chloro, bromo, fluoro or iodo.

The term "oxo" means a radical of the formula: =O.

The term "substituted" refers to a radical in which one or more hydrogen atoms are each independently replaced with the same or different substituent(s). In a preferred embodiment, up to three hydrogen atoms are each independently replaced.

With reference to substituents, the term "independently" means that when more than one of such substituent is possible, such substituents may be the same or different from each other.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

In general, IUPAC nomenclature rules are used herein.

The term "about," whether used explicitly or not in reference to a quantitative expression given herein, means that every quantity given herein qualified with the term or otherwise is meant to refer both to the actual given value and the approximation to such given value that would reasonably be inferred based on the ordinary skill in the art, including approximations due to experimental and/or measurement conditions for such given value.

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The term "composition" is intended to encompass a product comprising the specified ingredients in the specified amounts, as well as any product which results, directly or indirectly, from combinations of the specified ingredients in the specified amounts.

The term "subject" as used herein, refers to a patient, such as an animal, a mammal or a human, who has been the object of treatment, observation or experiment and is at risk of (or susceptible to) developing an FLAP-mediated disorder.

The term "administering" further means that the individual ingredients to be combined may be administered at the same time or at different times during the treatment period, either as one preparation or as different preparations. Accordingly, the invention should be so interpreted that it encompasses any and every administration mode at the same time or at different times. The range of the combination of the compound of the invention and the other therapeutic agent useful for the above-mentioned disorders encompasses, in principle, all combinations of the compound of the invention and any and every pharmaceutical agent useful for the above-mentioned disorders.

The term "treating" refers, without limitation, to facilitating the eradication of, preventing, ameliorating or otherwise inhibiting the progression of or promoting stasis of an FLAP-mediated disease and/or disorder, or associated symptoms or complications thereof.

The term "prodrug" means a compound of Formula (I) or a form thereof that is converted in vivo into a functional derivative form that may contribute to therapeutic biological activity, wherein the converted form may be: 1) a relatively active form; 2) a relatively inactive form; 3) a relatively less active form; or, 4) any form which results, directly or indirectly, from such in vivo conversions. Prodrugs are useful when said compound may be either too toxic to administer systemically, absorbed poorly by the digestive tract or broken down by the body before it reaches its target. Conventional procedures for the selection and preparation of suitable prodrug derivatives are described in, for example, "Design of Prodrugs", ed. H. Bundgaard, Elsevier, 1985.

The term "metabolite" means a prodrug form of a compound of Formula (I) or a form thereof converted by in vivo metabolism or a metabolic process to a relatively less active functional derivative of said compound.

The term "medicament" or "medicine" refers to a product containing a compound of Formula (I) or a form thereof. The present invention includes use of such a medicament for treating an FLAP-mediated disorder.

The term "combination form" refers to the use of a combination product comprising a compound of Formula (I) or a form, pharmaceutical composition, medicine or medicament thereof and at least one therapeutic agent for treating an FLAP-mediated disorder.

Methods are known in the art for determining effective doses for therapeutic and prophylactic purposes for the disclosed pharmaceutical compositions or the disclosed drug combinations, whether or not formulated in the same composition.

For therapeutic purposes, the term "therapeutically effective amount" or "effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease and/or disorder being treated. For prophylactic purposes (i.e., inhibiting the progression of a disorder), the term "therapeutically effective amount" refers to that amount of each active compound or pharmaceutical agent, alone or in combination, that treats or inhibits in a subject the progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together. The effective amount of said compound is from about 0.001 mg/kg/day to about 300 mg/kg/day.

Advantageously, the effective amount of a combination product for treating an FLAP-mediated disease and/or disorder, or associated symptoms or complications thereof, may be a reduced amount of either or both, the compound or therapeutic agent, compared to the effective amount of the compound or therapeutic agent otherwise recommended for treating the disease and/or disorder, or associated symptoms or complications thereof. Therefore, it is contemplated that the compound is administered to the subject before, during or after the time the agent is administered.

The term "pharmaceutically acceptable salt" refers to non-toxic pharmaceutically acceptable salts (Ref. Int'l J. Pharm., 1986, 33: 201-217; J. Pharm. Sci., 1997 (January), 66(1): 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, $3^{rd}$ Edition, John Wiley & Sons, 1999. The protecting groups may be removed at a convenient subsequent stage using methods known in the art. The scope of the present invention encompasses all such protected compound forms and mixtures thereof.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (optical isomers).

The term "stereoisomer" refers to isomers that have the same molecular formula and the same sequence of covalently bonded atoms but a different spatial orientation.

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic" means an equimolar mixture of two enantiomeric species, wherein each of the isolated species rotates the plane of polarized light in the opposite direction such that the mixture is devoid of optical activity.

The term "enantiomer" means an isomer having a non-superimposable mirror image. The term "diastereomer" means stereoisomers that are not enantiomers.

The term "chiral" means a molecule that, in a given configuration, cannot be superimposed on its mirror image. This is in contrast to achiral molecules that can be superimposed on their mirror images.

The two distinct mirror image versions of the chiral molecule are also known as levo (left-handed), abbreviated L, or dextro (right-handed), abbreviated D, depending on which way they rotate polarized light. The symbols "R" and "S" represent the configuration of groups around a stereogenic carbon atom(s).

The symbols "R" and "S" are used in compound names and/or compound structures to describe a pure enantiomer, where the absolute stereochemistry of groups around a stereogenic carbon atom(s) is known.

The symbols "R*" and "S*" are used in compound names and/or compound structures to describe a pure enantiomer, where the relative stereochemistry of groups around a stereogenic carbon atom(s) is known, but where the absolute stereochemistry is unknown.

The term "geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration according to the Cahn-Ingold-Prelog priority rules. In the "E" configuration, the substituents having the highest priorities are on opposite sides in relationship to the carbon-carbon double bond. In the "Z" configuration, the substituents having the highest priorities are oriented on the same side in relationship to the carbon-carbon double bond.

Substituent atoms (other than hydrogen) attached to a ring system may be in a "cis" or "trans" configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Furthermore, compounds of the present invention may have one or more polymorph or amorphous crystalline forms and, as such, are intended to be included in the scope of the invention. In addition, some of the compounds may form solvates with water (i.e., hydrates) or common organic solvents (e.g., organic esters such as ethanolate and the like) and, as such, are also intended to be encompassed within the scope of this invention.

B) Synthesis

The invention provides methods of making the disclosed compounds according to traditional organic synthetic methods as well as matrix or combinatorial synthetic methods. Schemes A-D described suggested synthetic routes. Using the schemes, the guidelines below, and the examples, a person of skill in the art may develop analogous or similar methods for a given compound that is within the invention. These methods are representative of the synthetic schemes, but are not to be construed as limiting the scope of the invention.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diasteromers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, geometric isomers, and enantiomers thereof are encompassed within the scope of the present invention, provided that the second eluting isomer of racemic cis-2-{1-(4-Cyanobenzyl)-6-[(5-methylpyridin-2-yl)methoxy]-1H-benzimidazol-2-yl}cyclohexanecarboxylic acid when purified by chiral SFC on (CHIRALCEL OJ-H 5 μm 250×20 mm) mobile phase (65% $CO_2$, 35% EtOH), and the first eluting isomer of racemic cis-2-{1-[2-Fluoro-4-(trifluoromethoxy)benzyl]-6-[(1-methyl-1H-pyrazol-3-yl)methoxy]-1H-benzimidazol-2-yl}cyclohexanecarboxylic acid when purified by chiral SFC (CHIRALCEL OD-H 5 μm 250×20 mm) mobile phase (80% $CO_2$, 20% MeOH) are specifically excluded;

Representative compounds of the present invention can be synthesized in accordance with the general synthetic schemes described below and are illustrated more particularly in the specific synthetic examples that follow. The general schemes are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

General: $^1$H and $^{13}$C NMR spectra were measured on a Bruker AC-300 (300 MHz) spectrometer using tetramethylsilane and the deuterated solvent respectively as internal standards. Elemental analyses were obtained by Quantitative Technologies Inc. (Whitehouse, N.J.) and the results were within 0.4% of the calculated values unless otherwise mentioned. Melting points were determined in open capillary tubes with a Mel-Temp II apparatus (Laboratory Devices Inc.) and were uncorrected. Electrospray mass spectra (MS-ESI) were recorded in the positive mode on a Hewlett Packard 59987A spectrometer. High resolution mass spectra (HRMS) were obtained on a Micromass Autospec. E spectrometer by fast atom bombardment (FAB) technique.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Examples of the described synthetic routes include Schemes A-D, Intermediates A-Q, and Examples 1-190. Compounds analogous to the target compounds of these examples can be made according to similar routes. The disclosed compounds, except the compounds of Examples 17, 38, and 52 are useful as pharmaceutical agents as described herein.

Abbreviations or acronyms useful herein include:

| Abbreviation | Meaning |
| --- | --- |
| ACN | acetonitrile |
| n-BuLi | n-butyl lithium |
| t-Bu | tert-butyl |
| calcd | calculated |
| $CDCl_3$ | deuterated chloroform |
| DCE | dichloroethane |
| DCM | dichloromethane |
| DIPEA | diisopropyl ethyl amine |
| DMA | N,N-dimethylacetamide |
| DMF | N,N-dimethylformamide |
| DMSO | dimethyl sulfoxide |
| ESI | Electrospray Ionization |
| Et | ethyl |
| $Et_2O$ | diethyl ether |
| $Et_3N$ | triethylamine |
| EtOAc | ethyl acetate |
| FCC | flash column chormatography |
| h | hour(s) |
| HPLC | high pressure liquid chromatography |
| iPr | isopropyl |
| IPA | isopropyl alcohol |
| JohnPhos | (2-Biphenyl)di-tert-butylphosphine |
| LiHMDS | lithium hexamethyldisilylazide |
| Me | methyl |
| min | minute(s) |
| Ms | mesyl |
| MS | mass spectroscopy |
| NMP | N-methyl-2-pyrrolidone |
| NMR | nuclear magnetic resonance spectroscopy |
| OAc | acetate |
| $Pd(dppf)Cl_2$ | (1,1'-Bis(diphenylphosphino)ferrocene)palladium(II) dichloride |
| RuPhos | 2-Dicyclohexylphosphino-2',6'-diisopropoxybiphenyl |
| RuPhos precatalyst | Chloro(2-dicyclohexylphosphino-2',6'-diisopropoxy-1,1-biphenyl)[2-(2 -amino-1,1-biphenyl)]palladium(II) |
| RT | room temperature |
| SFC | supercritical fluid chromatography |
| TBAF | tetrabutylammonium fluoride |
| TFA | trifluoroacetic acid |
| THF | tetrahydrofuran |
| TMS | trimethylsilyl |

General Guidance

Representative compounds of the present invention can be synthesized in accordance with the general synthetic methods described below and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art. The substituents for compounds of Formula (I) or a form thereof, represented in the schemes below, are as previously defined herein.

Unless otherwise specified, reaction solutions were stirred at room temperature under a $N_{2(g)}$ or $Ar_{(g)}$ atmosphere. When solutions were "concentrated to dryness", they were concentrated using a rotary evaporator under reduced pressure, when solutions were dried, they are typically dried over a drying agent such as $MgSO_4$ or $Na_2SO_4$.

Normal phase flash column chromatography (FCC) was performed on silica gel with RediSep® silica gel columns using ethyl acetate (EtOAc)/hexanes, $CH_2Cl_2$/MeOH, $CH_2Cl_2$/10% 2 N $NH_3$ in MeOH, $CH_2Cl_2$/i-PrOH, and the like as eluent, unless otherwise indicated.

Reverse phase high performance liquid chromatography (HPLC) was performed under the following conditions: 1) Instrument, Shimadzu; Column, Waters XBridge C18 10 μM (250×50 mm), Phenomenex Gemini column 5 μm C18 (150×21.2 mm) or Waters Xterra RP18 OBD 5 μm (100×30 mm); Gradient, 95:5 to 0:100 water (0.05% trifluoroacetic acid (TFA))/$CH_3CN$ (0.05% TFA); Flow rate, 30-80 mL/min; Detection, UV at λ=220-254 nM; 2) Instrument, Gilson; Column, Phenomenex LUNA column 5 μm C18 (250×50 mm) or Waters XBridge Prep C18 OBD 5 μm (30×150 mm); Gradient, 95:5 to 0:100 water (0.05% TFA)/$CH_3CN$ (0.05% TFA); Flow rate, 30-80 mL/min; Detection, UV at λ=220-254 nM; 3) Instrument, Gilson/Shimadzu: Column, Inertsil ODS-3 column (30×100 mm) or Inertsil ODS-3 (30×50 mm, 5 μm); Gradient, water-acetonitrile with both phases with 0.05% by volume trifluoroacetic acid; 1 min hold at 5% ACN, then 6 min gradient to 99% ACN followed by a hold at that concentration for 3 min. Flow rate, 80 ml/min; heated column at 46° Celsius with detection of UV light at λ=254 nm; and 4) Instrument, Dionex: UVD 170U Diode array detector and ThermoFinnegan Surveyor MSQ plus mass spectrometer for data collection. Waters XBridge C18 5 μM OBD 50×100 mm prep column. All runs utilized water acetonitrile with 20 mM $NH_4OH$ added to the aqueous phase and a flow rate for all gradients was 80 mL/min using four possible gradients: 1) 5-60% MeCN over 12 min, then ramped to 100% MeCN and held for 6.3 min; 2) 30-70% MeCN over 12 min, then ramped to 100% MeCN and held for 6.3 min; 3) 50-80% MeCN over 12 min, then ramped to 100% MeCN and held for 6.3 min; and 4) 60-100% MeCN over 12 min, and then held for 6.3 min. The total run time for all gradient systems was 18.5 min.

Instances where solutions were filtered through a syringe filter, Pall 0.45 μM GHP membrane 13 mm and 25 mm diameter syringe filters were used.

Thin-layer chromatography was performed using Merck silica gel 60 $F_{254}$ 2.5 cm×7.5 cm 250 μm or 5.0 cm×10.0 cm 250 μm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone. Microwave reactions were carried out in either a CEM Discover® or a Biotage Initiator™ or Optimizer™ microwave at specified temperatures. Mass spectra were obtained on an Agilent series 1100 MSD using electrospray ionization (ESI) in positive mode unless otherwise indicated. Calculated mass corresponds to the exact mass. NMR spectra were obtained on either a Bruker model DPX400 (400 MHz), DPX500 (500 MHz), DRX600 (600 MHz) spectrometer. The format of the $^1H$ NMR data below is: chemical shift in ppm down field of the tetramethylsilane reference (multiplicity, coupling constant J in Hz, integration).

Hydrochloride salts were obtained by treating the corresponding free bases with HCl (4 N in dioxane, 2 M in Et$_2$O, or 1.25 N in MeOH) at room temperature with mixtures and then either concentrated to obtain the HCl salt, or the resulting solid being isolated by filtration. Trifluoroacetic acid salts were obtained by purification of the crude reaction product by preparative reverse phase HPLC, whereby the final products were isolated as either mono-, di- or tri trifluoroacetic acid salts.

Chemical names were generated using ChemDraw Ultra 12.0 (CambridgeSoft Corp., Cambridge, Mass.) or ACD/Name Version 10.01 (Advanced Chemistry).

The compounds of Formula (I), wherein $X^1$, $X^{1'}$, $R^1$, $R^2$, and $R^3$ are defined as in Formula (I), may be synthesized as outlined by the general synthetic route illustrated in Scheme A.

treated with the desired halide in the presence of a base, such as K$_2$CO$_3$, S$_2$CO$_3$, or NaOH, with or without the presence of potassium iodide in a suitable polar solvent, such as CH$_3$CN, dimethyl formamide (DMF), dimethyl acetamide (DMA), tetrahydrofuran (THF), or a mixture thereof, at a temperature ranging from about 50° Celsius to about 180° Celsius using conventional heating or microwave irradiation. Nitroethers (III) are converted to compounds of Formulae (IV) via nucleophilic aromatic substitution (S$_N$Ar) with aryl or heteroaryl-substituted methylene amines in the presence of a suitable base, such as (iPr)$_2$NEt, Et$_3$N, or a mixture thereof, in a solvent, such as CH$_3$CN, DMF, DMA, N-methyl-2-pyrrolidone (NMP) or a mixture thereof, at a temperature ranging from about 50° Celsius to about 150° Celsius. Diamines (V) are obtained by reduction of the nitro

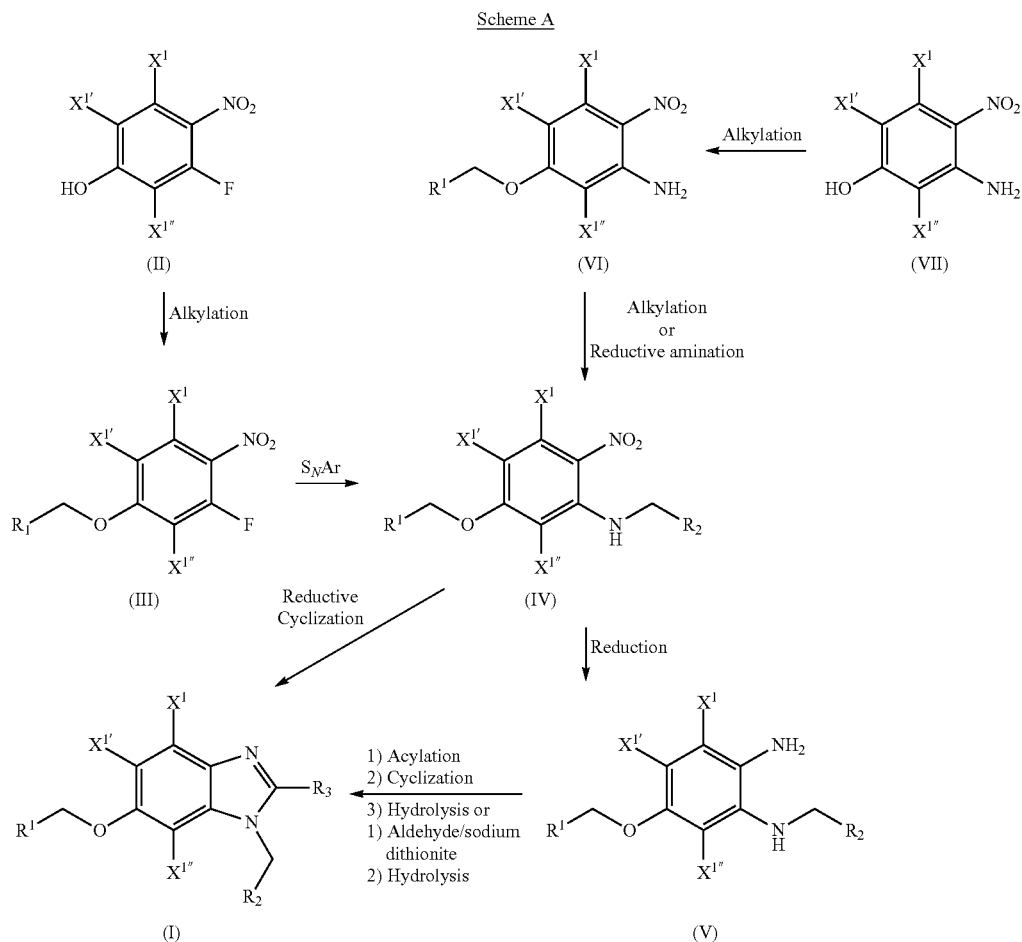

Referring to Scheme A, compounds of Formulae (I) are prepared from cyclization of diamines (V) with anhydrides, di-acids, or aldehyde containing acids where $R^1$ and $R^2$ are aryl or heteroaryl substituents and $R_3$ is an alkyl, cycloalkyl, aryl, or heteroaryl carboxylic acid. $X^1$, $X^{1'}$, and $X^{1''}$ may be hydrogen, halogen, CN or combinations thereof. Various substituted anhydrides and diacids are commercially available or are prepared using known methods. Diamines of formula (V) are obtained via alkylation of the appropriately substituted nitrophenol (II) with aryl or heteroaryl methyl-halides. Preferably, 3-fluoro nitrophenols of formula (II) are group using generally known methods, such as hydrogenation over a Pd or Pt catalyst using H$_2$, in solvents, such as THF, MeOH and EtOH, with or without the presence of a base, such as (iPr)$_2$NEt or Et$_3$N. Alternatively, the nitro group can be reduced through the use of a stoichiometric heterogeneous reductant, such as Zn metal powder, in the presence of an acid, such as NH$_4$Cl or HOAc, in a solvent, such as MeOH, EtOH, acetone, or THF, at temperatures ranging from between 0° Celsius and the reflux temperature of the solvent. Alternatively, reduction of the nitro group can be performed in the presence of a homogeneous stoichiometric reductant, such as SnCl$_2$.2H$_2$O, in solvents, such as EtOH, MeOH, and EtOAc, at temperatures ranging from between 0° Celsius and the reflux temperature of the solvent.

Formation of (I) can also be achieved in a two-step process by first reacting diamine (V) with appropriate anhydrides with or without the use of a base, such as (iPr)$_2$NEt, in a solvent, such as CH$_3$CN, at a temperature ranging from about 50° Celsius to about 90° Celsius. The product thus obtained is converted to (I) by subjecting it to further heating from 0° Celsius to the reflux temperature of the solvent, either conventionally or in a microwave reactor, in the presence of an acid, such as HCl, HOAc, or MsOH. Alternatively, formation of (I) can be achieved by heating diamine (V) and an appropriate organic diacid in the presence of a strong acid catalyst or Lewis acidic dehydrating agent, such as HCl or SnCl$_4$ respectively, at a temperature ranging from about 50° Celsius to about 90° Celsius. In some instances, such as to ease purification, it is desirable to convert (I) to the corresponding alkyl ester by treating (I) with a strong acid, such as HCl, in the presence of an alcoholic solvent, such as EtOH or MeOH, at temperatures ranging from room temperature to 100° Celsius. Methyl esters of (I) can also be obtained using TMSCHN$_2$ in a mixture of toluene and MeOH. Benzimidazole (I) can then be obtained by subsequent hydrolysis using known acidic or basic conditions. Preferably, hydrolysis is conducted using a base, such as LiOH, NaOH or KOH, in solvents such as MeOH, THF, or a mixture thereof, at temperatures ranging from about room temperature to about 80° Celsius. Alternatively, compounds of Formulae (I) can synthesized directly via a reductive cyclization cyclization from compounds of Formulae (IV) using an appropriate aldehyde or hemiacetal and a suitable oxidant, such as sodium dithionite, in a solvent, such as DMA.

Alternatively, compounds of Formulae (IV) could be obtained by alkylating with suitable aryl or heteroaryl methylene halides in the presence of a base, such as (iPr)$_2$NEt or Et$_3$N, in a solvent, such as CH$_3$CN, at a temperature ranging from about 50° Celsius to about 150° Celsius. Additionally, compounds of Formulae (IV) can be obtained via reductive amination of (VI). Reductive aminations are performed using the appropriate aryl or heteroaryl aldehyde in the presence of (VI) and a reductant, such as Na(OAc)$_3$BH or NaB(CN)H$_3$, in a solvent, such as THF, MeOH, EtOH, dichloromethane (DCM), dichloroethane (DCE) or mixtures thereof.

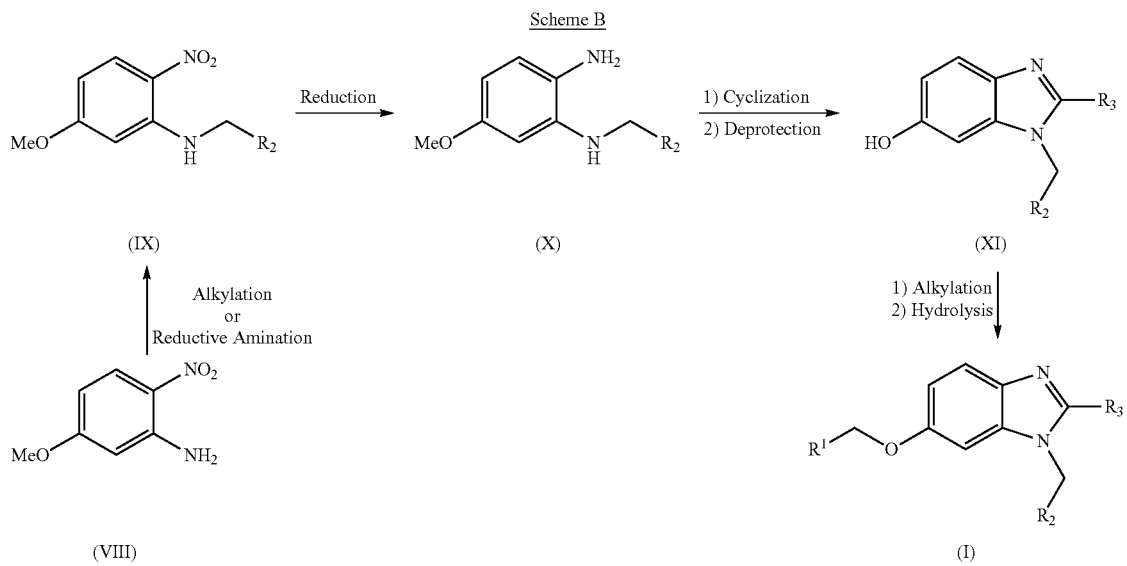

Scheme B

Referring to Scheme B, in alternative embodiments, benzimidazoles of Formulae (I) are obtained by alkylation and hydrolysis of phenol (XI). Phenols (XI) are prepared from an intermediate (VIII), wherein the phenol is protected with an appropriate protecting group, such as methyl, and the amino group alkylated, either by an S$_N$2 process or by reductive amination, using conditions described above to afford (IX). Reduction of the nitro group of (IX) to afford diamines (X) can be performed using conditions described above. Cyclization of (X) to afford (XI) can be performed using methods described above, The protecting group on the phenol of compounds of Formulae (X) may be removed using generally accepted methods. More specifically, when the protecting group is methyl, compounds of Formulae (XI) can be prepared using an appropriate reagent, such as BBr$_3$, in a solvent, such as DCM, at a temperature ranging from −78° Celsius to RT. Alkylation of (XI) and hydrolysis of the ester of R$_3$, if present, are performed using methods described in Scheme A.

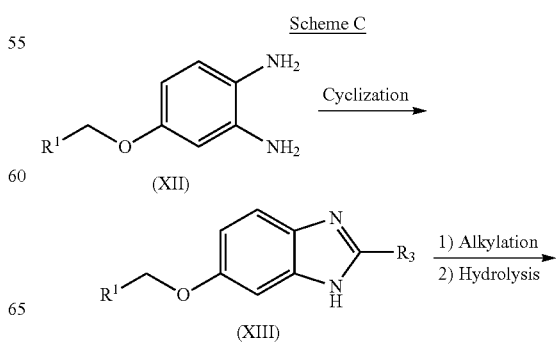

Scheme C

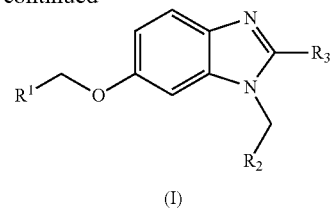

(I)

Referring to Scheme C, compounds of Formulae (I) can be obtained by N-alkylation of one of the benzimidazole (XIII) nitrogens followed by hydrolysis of the ester substituent of $R_3$. Benzimidazole (XIII) can be obtained from diamines XII using known procedures described in Scheme A. Reduction of the nitro group of (VI) using methods described above affords diamine (XII). Cyclization of (XII) to give (XIII) can be performed using conditions described above. Alkylation is performed with the desired aryl- or heteroaryl methylene halide in the presence of a base, such as $K_2CO_3$, $Cs_2CO_3$, or NaOH, a suitable polar solvent, such as $CH_3CN$, DMF, DMA, THF, or a mixture thereof, at a temperature ranging from about room temperature to about 180° Celsius. Hydrolysis of the ester group $R_3$ can be performed using procedures described above.

the solvent. In instances where $R_3$ contains an alkyl ester, hydrolysis using methods described above provides (I).

C) Examples

The following examples are offered by way of illustration; the invention should not be construed as being limited by the chemical reactions and conditions expressed.

Intermediate A: 2-((3-Fluoro-4-nitrophenoxy)methyl)-5-methylpyridine

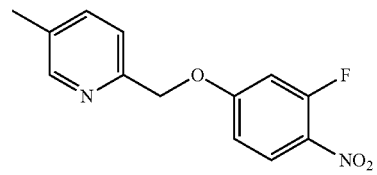 [SMILES: Cc1ccc(COc2ccc([N+](=O)[O-])c(F)c2)nc1]

To a 3-neck, 1 L flask equipped with mechanical stirring, a nitrogen inlet, and temperature probe, 3-fluoro-4-nitrophenol (30 g, 191 mmol) was added to a suspension of 2-(chloromethyl)-5-methylpyridine hydrochloride (33.4 g, Scheme D

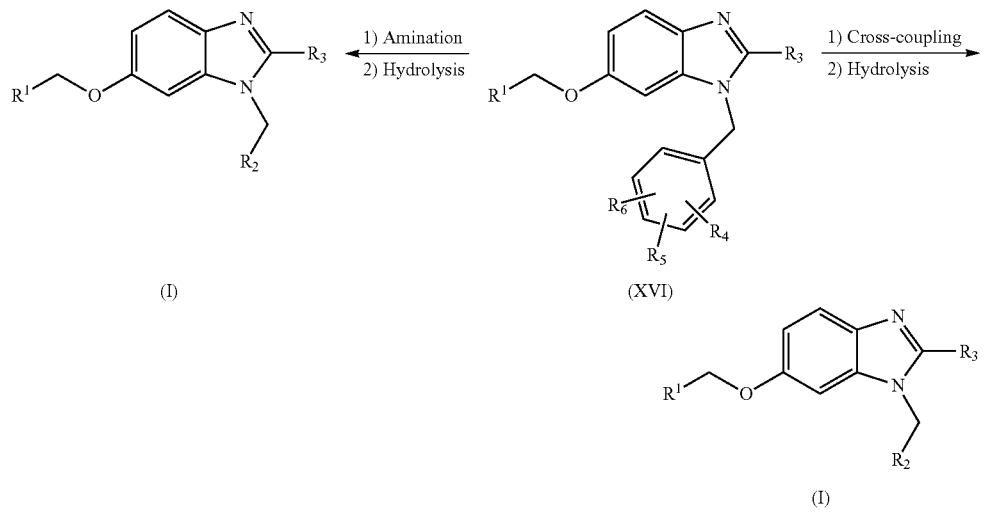

Referring to Scheme D, benzimidazoles (XVI), where $R_4$, $R_5$ or $R_6$ is an appropriate halogen, preferably Br, and substituent $R_3$ is protected as an ester, can be coupled with various amines, aryls, and heteroaryls using known organometallic cross coupling methods. Coupling of the aromatic halides (IXX) with various amines, boronic acids, boronic esters, and stannanes in the presence of a catalyst, such as $Pd(dppf)Cl_2.CH_2Cl_2$, $Pd(OAc)_2$, $Pd(PPh_3)_4$, or RuPHOS/RuPhos pre-catalyst, in a solvent, such as THF, 1,4-dioxane, DMA, DMF, DME, or toluene, in the presence of a base, such as NaOt-Bu, LiHMDS, $Na_2CO_3$, $K_2CO_3$, $Cs_2CO_3$, or $K_3PO_4$, affords esters of benzamidazole (I). Preferred catalysts for amination include $Pd(dppf)Cl_2.CH_2Cl_2$ and RuPHOS/RuPhos pre-catalyst with $K_3PO_4$, NaOt-Bu or LiHMDS in 1,4-dioxane, toluene, or THF at temperatures ranging from about room temperature to the boiling point of 187 mmol), potassium carbonate (57.5 g, 412 mmol), potassium iodide (31.1 g, 187 mmol), and acetonitrile (400 mL) and the mixture was then heated to 60° Celsius. After 3 hours the solvent was evaporated to dryness and the residue was partitioned between EtOAc and water and the organic layer was separated, dried, filtered and concentrated to dryness. To the resulting residue was added IPA (200 mL) and the mixture was heated to 70° Celsius where the suspension became homogeneous. The solution was allowed to cool to RT over 2 hours and placed in the freezer overnight. The solids were collected by filtration and were rinsed with IPA (100 mL) followed by heptanes (2×100 mL) to afford the title compound. $^1$H NMR (400 MHz, DMSO-$d_6$) δ 8.44 (s, 1H), 8.16 (t, J=9.2, 1H), 7.76-7.62 (m, 1H), 7.45 (d, J=7.9, 1H), 7.30 (dd, J=13.7, 2.5, 1H), 7.07 (dd, J=9.3, 1.9, 1H), 5.30 (s, 2H), 2.31 (s, 3H).

Intermediate B: racemic
cis-3-Hydroxyhexahydroisobenzofuran-1(3H)-one

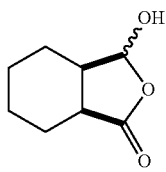

A solution of cis-hexahydroisobenzofuran-1,3-dione (96.5 g, 0.63 mol) and triethylamine (95 mL, 0.69 mol) in THF (2.5 L) was passed through a continuous-flow hydrogenation apparatus (H-Cube Midi®, manufactured by ThalesNano Nanotechnology Inc, Budapest, Hungary) under the following conditions: 10% Pd/C Midi-Cart® cartridge, 20 bar $H_2$ pressure, 50° Celsius, 7.5 mL/min flow rate. The collected product solution was concentrated to dryness. The resulting residue was diluted with water (0.8 L), then the pH was adjusted to 2 using HCl (12 N). The mixture was extracted twice with methyl tert-butyl ether (0.8 L and 0.2 L). The combined organics were washed with saturated NaCl solution, dried over $Na_2SO_4$, filtered and then concentrated to dryness to afford title compound as a white solid (82 g, 84%). $^1$H NMR (400 MHz, $CDCl_3$) δ 5.49 (app br s, 1H), 3.07-2.80 (m, 1H), 2.50-2.31 (m, 1H), 2.21-1.93 (m, 1H), 1.92-1.74 (m, 1H), 1.72-1.35 (m, 3H), 1.32-0.91 (m, 3H).

Intermediate C: Ethyl 3-(5-methoxy-1H-benzo[d]imidazol-2-yl)-2,2-dimethylpropanoate

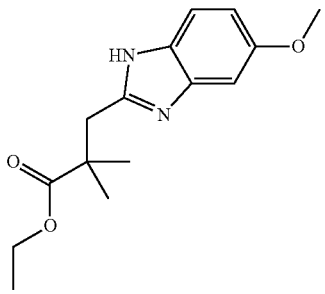 [SMILES: CCOC(=O)C(C)(C)Cc1nc2cc(OC)ccc2[nH]1]

To a 100 mL round-bottomed flask were added a stir bar, 4-methoxy-o-phenylenediamine bis-hydrochloride salt (2 g, 9.5 mmol), acetonitrile (20 mL), triethylamine (2.6 mL, 19 mmol), and 3,3-dimethyldihydrofuran-2,5-dione (1.2 g, 9.5 mmol). After 1 h, the mixture was concentrated to dryness and ethanol (50 mL) followed by HCl (1 mL, 12 N) was added to the residue. The reaction vessel was heated at 80° Celsius for 12 hours before cooling to RT. The reaction mixture was concentrated to dryness. The residue was diluted with water (50 mL) and neutralized with sat. $NaHCO_3$ until pH was 6.8-7. The aqueous was extracted with diethyl ether (3×100 mL), the combined extracts dried over sodium sulfate, filtered and concentrated to dryness. The residue was subjected to FCC to give the title compound (1.5 g, 57%). MS (ESI): mass calcd. for $C_{15}H_{20}N_2O_3$, 276.15; m/z found, 277.1 $[M+H]^+$. A mixture of two tautomer's was observed so peaks are listed for identification purposes only. $^1$H NMR (600 MHz, DMSO-$d_6$) δ 11.99-11.85 (m), 7.39 (d, J=8.7), 7.29 (d, J=8.6), 7.07 (d, J=2.4), 6.92 (d, J=2.4), 6.75 (dd, J=8.6, 2.4), 6.72 (dd, J=8.7, 2.4), 4.13-4.02 (m), 3.78-3.74 (m), 3.00-2.94 (m), 1.24-1.21 (m), 1.13 (t, J=7.1).

Intermediate D: Ethyl 3-(1-(4-bromobenzyl)-6-methoxy-1H-benzo[d]imidazol-2-yl)-2,2-dimethylpropanoate and Intermediate E: Ethyl 3-(1-(4-bromobenzyl)-5-methoxy-1H-benzo[d]imidazol-2-yl)-2,2-dimethylpropanoate

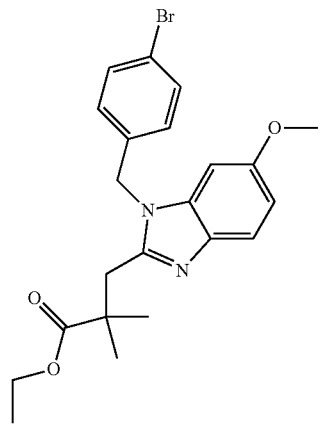

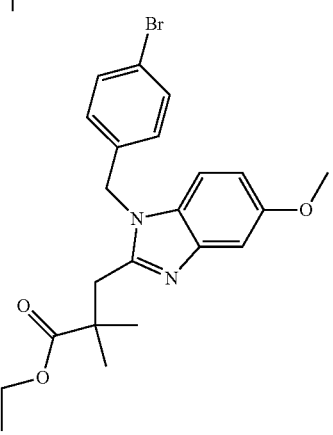

To a 100 mL round-bottomed flask were added a stir bar, ethyl 3-(5-methoxy-1H-benzo[d]imidazol-2-yl)-2,2-dimethylpropanoate (1.5 g, 5.4 mmol), DMF (19 mL), cesium carbonate (3.5 g, 11 mmol), and 4-bromobenzyl bromide (1.4 g, 5.4 mmol). After 12 h, the mixture was partitioned between water (100 mL) and EtOAc (50 mL). The aqueous layer was extracted with EtOAc (50 mL×3). The combined organic layers were dried with sodium sulfate, filtered, and concentrated to dryness. The residue was subjected to FCC to give ethyl 3-(1-(4-bromobenzyl)-6-methoxy-1H-benzo[d]imidazol-2-yl)-2,2-dimethylpropanoate (550 mg, 23%) and ethyl 3-(1-(4-bromobenzyl)-5-methoxy-1H-benzo[d]imidazol-2-yl)-2,2-dimethylpropanoate (620 mg, 26%).

Intermediate D: Ethyl 3-(1-(4-bromobenzyl)-6-methoxy-1H-benzo[d]imidazol-2-yl)-2,2-dimethylpropanoate MS (ESI): mass calcd. for $C_{22}H_{25}BrN_2O_3$, 444.10; m/z found, 445.1 $[M+H]^+$. $^1$H NMR (500 MHz, DMSO-$d_6$) δ 7.55-7.52 (m, 2H), 7.44 (d, J=8.7, 1H), 7.05-7.00 (m, 3H), 6.77 (dd, J=8.7, 2.4, 1H), 5.46 (s, 2H), 4.02 (q, J=7.1, 2H), 3.73 (s, 3H), 3.00 (s, 2H), 1.27 (s, 6H), 1.06 (t, J=7.1, 3H).

Intermediate E: Ethyl 3-(1-(4-bromobenzyl)-5-methoxy-1H-benzo[d]imidazol-2-yl)-2,2-dimethylpropanoate MS (ESI): mass calcd. for $C_{22}H_{25}BrN_2O_3$, 444.10; m/z found, 445.1 [M+H]$^+$. $^1$H NMR (500 MHz, DMSO-d$_6$) δ 7.54-7.50 (m, 2H), 7.29 (d, J=8.8, 1H), 7.10 (d, J=2.4, 1H), 7.00 (d, J=8.1, 2H), 6.79-6.75 (m, 1H), 5.44 (s, 2H), 4.07-4.00 (m, 2H), 3.76 (s, 3H), 3.04 (s, 2H), 1.28 (s, 6H), 1.08 (t, J=7.0, 3H).

Intermediate F: Ethyl 3-(1-(4-bromobenzyl)-6-hydroxy-1H-benzo[d]imidazol-2-yl)-2,2-dimethylpropanoate

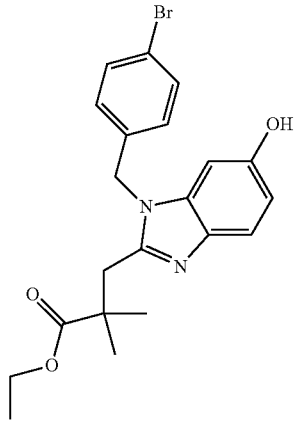 [SMILES: CCOC(=O)C(C)(C)Cc1nc2ccc(O)cc2n1Cc1ccc(Br)cc1]

A solution of boron tribromide (3.1 mL, 1 M in DCM) was added drop-wise to a 100 mL round bottomed flask containing ethyl 3-(1-(4-bromobenzyl)-6-methoxy-1H-benzo[d]imidazol-2-yl)-2,2-dimethylpropanoate (700 mg, 1.6 mmol) and DCM (30 mL) at −78° Celsius. The resulting solution was allowed to warm to 5° Celsius over 3 h and partitioned with sat. NaHCO$_3$ (50 mL). The aqueous layer was extracted with DCM (3×25 mL). The combine organic layers were dried with sodium sulfate, filtered, and concentrated to dryness. The residue was subjected to FCC to give the title compound (410 mg, 60%). MS (ESI): mass calcd. for $C_{21}H_{23}BrN_2O_3$, 430.08; m/z found, 431.0 [M+H].

Intermediate G: Ethyl 3-(1-(4-bromobenzyl)-6-((5-methylpyridin-2-yl)methoxy)-1H-benzo[d]imidazol-2-yl)-2,2-dimethylpropanoate

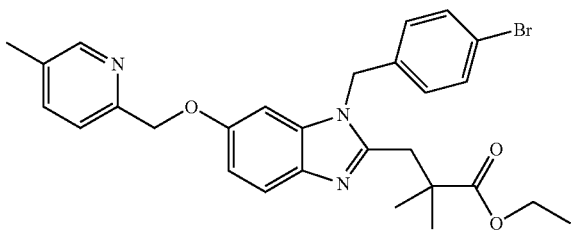 [SMILES: CCOC(=O)C(C)(C)Cc1nc2ccc(OCc3ccc(C)cn3)cc2n1Cc1ccc(Br)cc1]

To a 10 mL round-bottomed flask were added a stir bar, ethyl 3-(1-(4-bromobenzyl)-6-hydroxy-1H-benzo[d]imidazol-2-yl)-2,2-dimethylpropanoate (100 mg, 0.23 mmol), cesium carbonate (227 mg, 0.69 mmol), DMF (2 mL), and 2-(chloromethyl)-5-methylpyridine hydrochloride salt (41 mg, 0.23 mmol). After 12 h, the mixture was partitioned between water (50 mL) and EtOAc (20 mL). The organic layer was separated and the aqueous layer was further extracted with EtOAc (2×20 mL). The combine organic layers were dried with sodium sulfate, filtered, and concentrated to dryness (124 mg, 99%). MS (ESI): mass calcd. for $C_{28}H_{30}BrN_3O_3$, 535.15; m/z found, 536.1 [M+H]$^+$.

Intermediate H: racemic trans-Ethyl 3-(1-(4-bromobenzyl)-6-((5-methylpyridin-2-yl)methoxy)-1H-benzo[d]imidazol-2-yl)-2,2-dimethylcyclopropanecarboxylate as the TFA salt

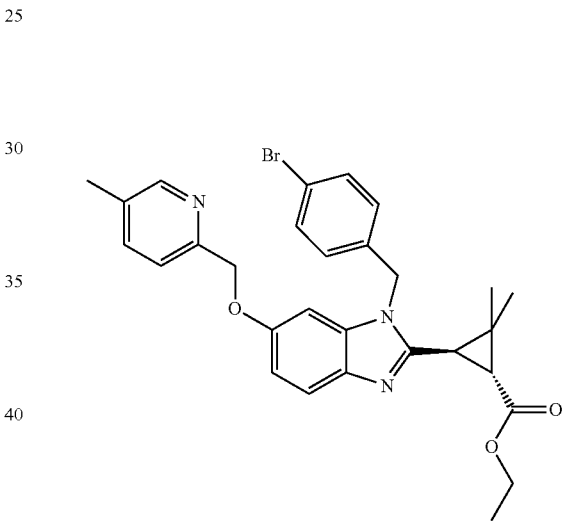

A solution of trimethyl aluminum (0.7 mL, 2M in toluene) was added to 25 mL round-bottom flask containing N-(4-bromobenzyl)-5-((5-methylpyridin-2-yl)methoxy)benzene-1,2-diamine (265 mg, 0.67 mmol), trans-diethyl 3,3-dimethylcyclopropane-1,2-dicarboxylate (142 mg, 0.67 mmol), and DCM (12 mL). After 12 h, the solution was partitioned between sat. NaHCO$_3$ (30 mL) and EtOAc (30 mL). The organic layer was separated and the aqueous layer was extracted with EtOAc (2×30 mL). The combine organic layers were dried with sodium sulfate, filtered, and concentrated to dryness. To the residue was added ethanol (2 mL) and concentrated HCl (0.1 mL, 12 N). The solution was heated to 90° Celsius. After 5 h, the mixture was cooled, concentrated to dryness, and purified by reverse phase HPLC to afford the title compound. MS (ESI): mass calcd. for $C_{29}H_{30}BrN_3O_3$, 547.15; m/z found, 548.1 [M+H]$^+$.

Intermediate I: racemic cis-Ethyl 3-(1-(4-bromobenzyl)-6-((5-methyl pyridin-2-yl)methoxy)-1H-benzo[d]imidazol-2-yl)-2,2-dimethylcyclopropanecarboxylate

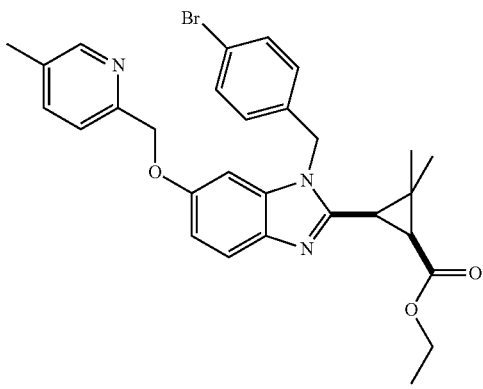

To a 25 mL round-bottomed flask was added N-(4-bromobenzyl)-5-((5-methylpyridin-2-yl)methoxy)benzene-1,2-diamine (109 mg, 0.3 mmol), cis-6,6-dimethyl-3-oxabicyclo[3.1.0]hexane-2,4-dione (38 mg, 0.3 mmol) and acetonitrile (2.5 mL). The resulting solution was heated to 90° Celsius. After 3 h, the solution was cooled and concentrated to dryness. To the resulting residue was added ethanol (4 mL) and concentrated HCl (0.1 mL, 12 N). The solution was heated to 90° Celsius. After 12 h, the mixture was cooled, concentrated to dryness, and purified by reverse phase HPLC to afford the title compound. MS (ESI): mass calcd. for $C_{29}H_{23}BrN_3O_3$, 547.14; m/z found, 548.1 $[M+H]^+$.

Intermediate J: 2-((3,5-difluoro-4-nitrophenoxy)methyl)-5-methylpyridine

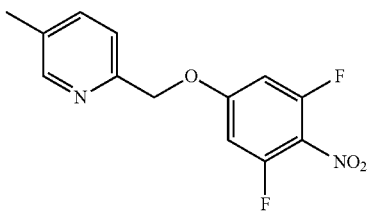 [SMILES: Cc1ccc(COc2cc(F)c([N+](=O)[O-])c(F)c2)nc1]

Step A: 3,5-difluoro-4-nitrophenol

To a solution of 3,5-difluorophenol (10 g, 76.9 mmol) in $CH_2Cl_2$ at 0° Celsius was added 4.9 mL of 70% nitric acid dropwise. After addition was complete, the reaction was allowed to warm to room temperature and stirred for 1 hour. The reaction was poured into a separatory funnel and washed once with 750 mL water. The organic layer was dried with $Na_2SO_4$, filtered and concentrated to dryness. The resulting residue was purified via FCC to afford the title compound. $^1H$ NMR (400 MHz, DMSO-$d_6$) δ 6.81-6.67 (m, 2H), 3.40 (bs, 1H).

Step B: 2-((3,5-Difluoro-4-nitrophenoxy)methyl)-5-methylpyridine

To 3,5-difluoro-4-nitrophenol (7.44 g, 42.5 mmol), $Cs_2CO_3$ (27.7 g, 84.9 mmol), and 2-(chloromethyl)-5-methylpyridine hydrochloride (7.6 g, 42.5 mmol) was added DMF (281 mL) and the reaction was stirred at 75° Celsius for 18 hours. The reaction was allowed to cool to room temperature before being poured into sat. $NaHCO_3$. The aqueous phase was extracted three times with EtOAc, and the combined organic layers were washed four times with brine, dried ($Na_2SO_4$), filtered, and concentrated. The crude material was purified via FCC to afford the title compound. MS (ESI): mass calcd. for $C_{13}H_{10}F_2N_2O_3$, 280.1; m/z found, 281.0 $[M+H]^+$.

Intermediate K: 2-((3-Chloro-5-fluoro-4-nitrophenoxy)methyl)-5-methylpyridine

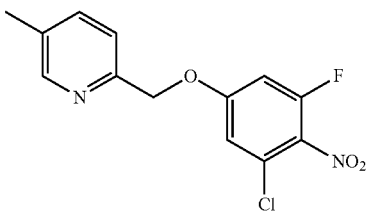 [SMILES: Cc1ccc(COc2cc(F)c([N+](=O)[O-])c(Cl)c2)nc1]

To a mixture of 3-chloro-5-fluoro-4-nitrophenol (2.6 g, 13 mmol), cesium carbonate (8.7 g, 27 mmol), and 2-(chloromethyl)-5-methylpyridine hydrochloride (2.4 g, 13 mmol) was added DMF (88 mL) and the resulting mixture was heated to 75° Celsius for 19 h. The mixture was cooled to RT and then stirred for an additional 20 h. The resulting mixture was then partitioned between sat. $NaHCO_3$ and EtOAc. The organic layer was separated and the aqueous layer was further extracted with EtOAc. The combined organic layers were washed with brine, dried and concentrated to dryness. The resulting residue was purified using FCC to afford the title compound (2.93 g, 74%). MS (ESI): mass calcd. for $C_{13}H_{10}ClFN_2O_3$, 296.04; m/z found, 297.1 $[M+H]^+$. $^1H$ NMR (400 MHz, $CDCl_3$) δ 8.45 (dd, J=1.4, 0.7, 1H), 7.55 (dd, J=7.9, 1.6, 1H), 7.32 (d, J=7.9, 1H), 6.93 (dd, J=2.5, 1.8, 1H), 6.79 (dd, J=11.1, 2.6, 1H), 5.19 (s, 2H), 2.37 (s, 3H).

Intermediate L: 3-((3-Fluoro-4-nitrophenoxy)methyl)-1-methyl-1H-pyrazole

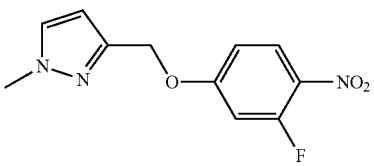 [SMILES: Cn1ccc(COc2ccc([N+](=O)[O-])c(F)c2)n1]

The title compound was prepared using analogous conditions described in Intermediate A using 3-(chloromethyl)-1-methyl-1H-pyrazole. MS (ESI): mass calcd. for $C_{11}H_{10}FN_3O_3$, 251.07; m/z found, 252.1 $[M+H]^+$. $^1H$ NMR (400 MHz, $CDCl_3$) δ 8.13-8.00 (m, 1H), 7.37 (d, J=2.3, 1H), 6.94-6.80 (m, 2H), 6.33 (d, J=2.3, 1H), 5.15 (s, 2H), 3.92 (s, 3H).

Intermediate M: 4-Chloro-3-((3-fluoro-4-nitrophenoxy)methyl)-1-methyl-1H-pyrazole

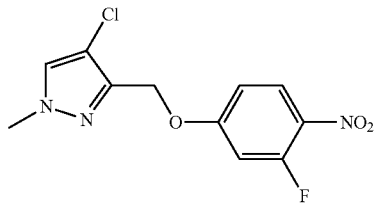 [SMILES: Cn1cc(Cl)c(COc2ccc([N+](=O)[O-])c(F)c2)n1]

The title compound was prepared using analogous conditions described in Intermediate A using 4-chloro-3-(chloromethyl)-1-methyl-1H-pyrazole. MS (ESI): mass calcd. for $C_{11}H_9ClFN_3O_3$, 285.03; m/z found, 286.0 [M+H]$^+$. $^1$H NMR (400 MHz, CDCl$_3$) δ 8.12-8.06 (m, 1H), 7.40 (s, 1H), 6.95-6.88 (m, 2H), 5.11 (d, J=10.0, 2H), 3.90 (s, 3H).

Intermediate N: 4-Fluoro-3-((3-fluoro-4-nitrophenoxy)methyl)-1-methyl-1H-pyrazole

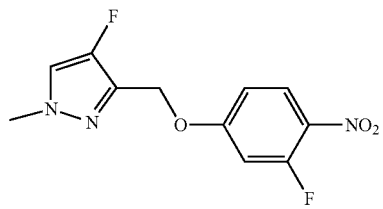 [SMILES: Cn1cc(F)c(COc2ccc([N+](=O)[O-])c(F)c2)n1]

Step A: 4-Fluoro-1-methyl-1H-pyrazole-3-carboxylic acid

To a 200 mL round-bottomed flask equipped with a reflux condenser and stir bar, were added 1-methyl-1H-pyrazole-3-carboxylic acid (1.5 g, 11.9 mmol), dry acetonitrile (60 mL), and Selectfluor® (12.6 g, 35.7 mmol). The reaction vessel was heated to 80° Celsius for 32 h. Additional Selectfluor® (8.5 g, 24.0 mmol) was added to the reaction mixture and it was stirred at 80° Celsius for 5 days. The reaction mixture was cooled to RT and the solids were removed by filtration. The filtrate was concentrated to dryness and subjected to FCC to yield crude title compound (330 mg, 13% yield). The impure material was then recrystallized from hot methanol to give the title compound as long yellow crystals. Additional title compound could be obtained from the mother liquor by filtration of the solid that forms upon concentration (11.53 g total combined yield, 70%). The crystallized title compound contained minor impurities, but was used in subsequent steps without further purification. Analytically pure title compound can be obtained by subjecting it to HPLC purification. MS (ESI): mass calcd. for $C_5H_5FN_2O_2$ 144.03, m/z found 145.0 [M+H]$^+$ (low intensity).

Step B: (4-Fluoro-1-methyl-1H-pyrazol-3-yl)methanol

To a 50 mL round-bottomed flask containing 4-fluoro-1-methyl-1H-pyrazole-3-carboxylic acid (344 mg, 1.7 mmol) in THF (17 mL), was added triethylamine (0.23 mL, 1.7 mmol) and the reaction mixture was cooled to 0° Celsius. Isobutylchloroformate (216 µL, 1.7 mmol) was added and the reaction mixture was stirred at 0° Celsius for 30 minutes. The solids were removed by filtration, the filtrate was collected, transferred to a 25 mL round bottomed flask and sodium borohydride (95 mg, 2.5 mmol) and the reaction mixture was stirred at RT for 10 min. The reaction mixture was concentrated to dryness and purified by FCC without additional work up to provide the title compound (120 mg, 55% yield) as a yellow oil. The compound showed very low UV activity and did not ionize by MS.

Step C: 3-(Chloromethyl)-4-fluoro-1-methyl-1H-pyrazole

To a 25 mL round-bottomed flask containing (4-fluoro-1-methyl-1H-pyrazol-3-yl)methanol (285 g, 2.2 mmol) in dry DCM (10 mL), was added thionyl chloride (0.3 mL, 4.4 mmol). The reaction mixture was stirred at RT for 2 h then concentrated to dryness to provide the title compound, which was carried forward without further purification.

Step D: 4-Fluoro-3-((3-fluoro-4-nitrophenoxy)methyl)-1-methyl-1H-pyrazole

The title compound was prepared using analogous conditions described in Example Intermediate A using 3-(chloromethyl)-4-fluoro-1-methyl-1H-pyrazole. MS (ESI): mass calcd. for $C_{11}H_9F_2N_3O_3$, 269.06; m/z found, 270.1 [M+H]$^+$. $^1$H NMR (400 MHz, CDCl$_3$) δ 8.10 (d, J=9.1, 1H), 7.28 (d, J=4.9, 1H), 6.94-6.85 (m, 2H), 5.13 (s, 2H), 3.86 (s, 3H).

Intermediate O: 3-((2,3-Difluoro-4-nitrophenoxy)methyl)-1-methyl-1H-pyrazole

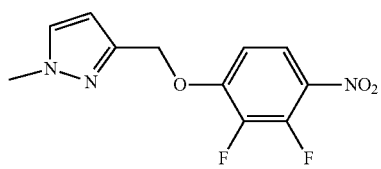 [SMILES: Cn1ccc(COc2ccc([N+](=O)[O-])c(F)c2F)n1]

The title compound was prepared using analogous conditions described in Intermediate A using 2,3-difluoro-4-nitrophenol. MS (ESI): mass calcd. for $C_{11}H_9F_2N_3O_3$, 269.06; m/z found, 270.0 [M+H]$^+$. $^1$H NMR (400 MHz, CDCl$_3$) δ 7.91-7.86 (m, 1H), 7.36 (d, J=2.2, 1H), 7.10-7.02 (m, 1H), 6.35 (d, J=2.3, 1H), 5.27 (s, 2H), 3.91 (s, 3H).

Intermediate P: 3-((2,5-Difluoro-4-nitrophenoxy)methyl)-1-methyl-1H-pyrazole

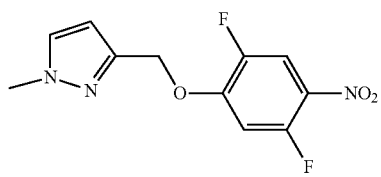 [SMILES: Cn1ccc(COc2cc(F)c([N+](=O)[O-])cc2F)n1]

The title compound was prepared using analogous conditions described in Intermediate A using 2,5-difluoro-4-nitrophenol. MS (ESI): mass calcd. for $C_{11}H_9F_2N_3O_3$, 269.06; m/z found, 270.0 [M+H]$^+$. $^1$H NMR (400 MHz, CDCl$_3$) δ 7.91-7.83 (m, 1H), 7.37 (d, J=2.3, 1H), 7.14-7.05 (m, 1H), 6.36 (d, J=2.2, 1H), 5.23 (s, 2H), 3.92 (s, 3H).

Intermediate Q: 3-((3,5-Difluoro-4-nitrophenoxy)methyl)-1-methyl-1H-pyrazole

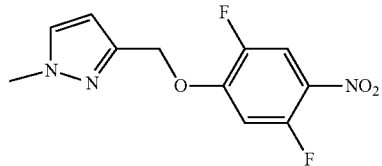 [SMILES: Cn1ccc(COc2cc(F)c([N+](=O)[O-])cc2F)n1]

The title compound was prepared using analogous conditions described in Intermediate A using 3,5-difluoro-4-nitrophenol. MS (ESI): mass calcd. for C$_{11}$H$_9$F$_2$N$_3$O$_3$, 269.06; m/z found, 270.0 [M+H]$^+$.

Example 1 racemic cis-2-{1-(4-Bromobenzyl)-6-[(5-methyl-pyridin-2-yl)methoxy]-1H-benzimidazol-2-yl}cyclohexanecarboxylic acid

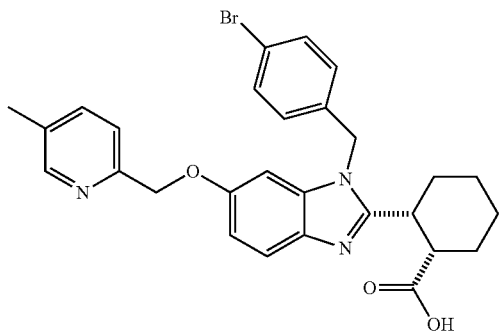

Step A: N-(4-Bromobenzyl)-5-((5-methylpyridin-2-yl)methoxy)-2-nitroaniline

A mixture of 2-((3-fluoro-4-nitrophenoxy)methyl)-5-methylpyridine (2.0 g, 7.6 mmol), 4-bromobenzyl amine (1.6 g, 8.4 mmol), DIPEA (2.63 mL, 15.3 mmol) and acetonitrile (25.4 mL) were sealed in a reaction vessel and heated to 60° Celsius for 24 h. The mixture was cooled to RT, transferred to a round bottomed flask and concentrated to dryness. The crude mixture was heated to 70° Celsius in a minimum amount of i-PrOH until homogeneous and cooled to RT. The resulting mixture was filtered to collect the yellow solids which were dried to afford the title compound (2.82 g, 86%). MS (ESI): mass calcd. for C$_{20}$H$_{18}$BrN$_3$O$_3$, 427.053; m/z found, 428.0 [M+H].

Step B: N$^1$-(4-Bromobenzyl)-5-((5-methylpyridin-2-yl)methoxy)benzene-1,2-diamine To a solution of N-(4-bromobenzyl)-5-((5-methylpyridin-2-yl)methoxy)-2-nitroaniline (4.1 g, 9.6 mmol) in THF (75 mL) was added DIPEA (0.8 mL, 4.8 mmol) followed by 5% platinum on carbon (0.4 g, 2.1 mmol). The reaction vessel was evacuated and then placed under 1 atmosphere of H$_2$ for 6 h. The mixture was then flushed with N$_2$ and filtered through a pad of Celite. The Celite was rinsed with THF. The resulting filtrate was concentrated to dryness to afford the title compound, which was used without further purification. MS (ESI): mass calcd. for C$_{22}$H$_{26}$BrN$_3$O, 397.08; m/z found, 398.0 [M+H]$^+$.

Step C: racemic 2-{1-(4-Bromobenzyl)-6-[(5-methylpyridin-2-yl)methoxy]-1H-benzimidazol-2-yl}cyclohexanecarboxylic acid To a 75 mL sealable tube, were added N-1-(4-bromobenzyl)-5-((5-methylpyridin-2-yl)methoxy)benzene-1,2-diamine (4.6 g, 7.7 mmol) in acetonitrile (26 mL), DIPEA (1.4 mL, 7.9 mmol) and cis-hexahydroisobenzofuran-1,3-dione (1.21 g, 7.86 mmol). The resulting mixture was sealed and heated to 60° Celsius for 1 h. The mixture was cooled to RT and HCl (13 mL, 79 mmol, 6 N) was added. The resulting solution was sealed in the reaction vessel and heated to 60° Celsius overnight. The reaction was cooled to RT and partitioned between 1N NaOH and EtOAc. The organic layer was separated, washed with 1N NaOH and the aqueous layer was acidified to pH ~5 using 1N HCl. The resulting aqueous suspension was extracted with EtOAc. The combined organic layers were dried, filtered and concentrated to dryness to afford the title compound. An analytically pure sample was obtained using preparative reverse phase HPLC. MS (ESI): mass calcd. for C$_{28}$H$_{28}$BrN$_3$O$_3$, 533.13; m/z found, 534.1 [M+H]$^+$. $^1$H NMR (500 MHz, CD$_3$OD) δ 8.30 (d, J=2.0, 1H), 7.62 (dd, J=8.0, 1.6, 1H), 7.56 (d, J=8.8, 1H), 7.46-7.42 (m, 2H), 7.40 (d, J=8.0, 1H), 7.03-6.99 (m, 2H), 6.96 (dd, J=8.8, 2.4, 1H), 6.83 (d, J=2.3, 1H), 5.45 (dd, J=35.9, 17.6, 2H), 5.11 (s, 2H), 3.62-3.54 (m, 1H), 2.89-2.76 (m, 1H), 2.43-2.37 (m, 1H), 2.37 (s, 3H), 2.06-1.96 (m, 1H), 1.94-1.82 (m, 2H), 1.82-1.73 (m, 2H), 1.54-1.40 (m, 2H).

Example 2

(1S,2R)-2-(1-(4-Bromobenzyl)-6-((5-methylpyridin-2-yl)methoxy)-1H-benzo[d]imidazol-2-yl)cyclohexanecarboxylic acid

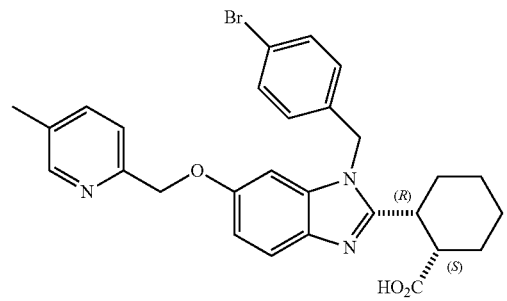

Step A: 2-((3-Fluoro-4-nitrophenoxy)methyl)-5-methylpyridine 3-fluoro-4-nitrophenol (200.0 g, 1.27 mol) was added to a solution of 2-(chloromethyl)-5-methylpyridine hydrochloride (222 g, 1.25 mol), powdered potassium carbonate (383.6 g, 2.75 mol), potassium iodide (207 g, 1.25 mol), and acetonitrile (3.4 L). The resulting mixture was stirred at 60°

Celsius for 2 h. The reaction was cooled to RT, concentrated to dryness and partitioned between H$_2$O (1.5 L) and ethyl acetate (1.5 L). The organic layers were separated and the aqueous layer was extracted with ethyl acetate (1.0 L). The combined organic layers were washed with brine (1 L) then dried over magnesium sulfate, filtered, and concentrated to dryness. The crude solid was recrystallized from i-PrOH (1.5 L) at 70° Celsius. After cooling to 0° Celsius the solid was collected by filtration and rinsed with i-PrOH (2×200 mL) and heptanes (2×200 mL) to yield the title compound as a dark solid (242.0 g, 73.9%). MS (ESI): mass calcd. for C$_{13}$H$_{11}$FN$_2$O$_3$, 262.10; m/z found, 263.1 [M+H]$^+$. $^1$H NMR (400 MHz, DMSO-d$_6$) δ 8.44 (s, 1H), 8.16 (t, J=9.2, 1H), 7.76-7.62 (m, 1H), 7.45 (d, J=7.9, 1H), 7.30 (dd, J=13.7, 2.5, 1H), 7.07 (dd, J=9.3, 1.9, 1H), 5.30 (s, 2H), 2.31 (s, 3H).

Step B: N-(4-Bromobenzyl)-5-((5-methylpyridin-2-yl)methoxy)-2-nitroaniline

To a round-bottomed flask containing 2-((3-fluoro-4-nitrophenoxy)methyl)-5-methylpyridine (68.0 g, 259 mmol) and 4-bromobenzylamine (58 g, 259 mmol) in acetonitrile (680 mL) was added DIPEA (113 mL, 648 mmol). The stirred mixture was then heated to 80° Celsius. After 14.5 h, the mixture was cooled to RT and was concentrated to 261 g. The resulting residue was added to i-PrOH (900 mL) and heated to 70° Celsius until homogeneous. The solution was cooled to RT and the crystalline solids were isolated through filtration. The filter cake was washed with cold i-PrOH (200 mL), the solids were collected and dried in a vacuum oven at 40° Celsius for 3 days to give the title compound (78.4 g, 71%). MS (ESI): mass calcd. for C$_{20}$H$_{18}$BrN$_3$O$_3$, 427.1; m/z found, 428.0 [M+H]$^+$. $^1$H NMR (400 MHz, CDCl$_3$) δ 8.66 (t, J=5.9, 1H), 8.36 (d, J=2.1, 1H), 8.16 (d, J=9.5, 1H), 7.57-7.37 (m, 3H), 7.27-7.23 (d incident with solvent signal, 1H), 7.22-7.13 (m, 2H), 6.34 (dd, J=9.5, 2.6, 1H), 6.18 (d, J=2.6, 1H), 5.12 (s, 2H), 4.44 (d, J=5.8, 2H), 2.35 (s, 3H).

Step C: Preparation of N$^1$-(4-Bromobenzyl)-5-((5-methylpyridin-2-yl)methoxy)benzene-1,2-diamine To a high pressure reactor were added N-(4-bromobenzyl)-5-((5-methylpyridin-2-yl)methoxy)-2-nitroaniline (78.4 g, 183 mmol), 5% Pt/C (35.7 g, 4.6 mmol), zinc iodide (5.84 g, 18.3 mmol) and ethyl acetate (1.5 L). The reactor was flushed with N$_2$ and then stirred under an atmosphere of H$_2$ (60 psi) for 18 h. The mixture was then filtered, washed with water (1 L), dried over magnesium sulfate and concentrated to dryness under reduced pressure to afford the title compound as an oil (60.4 g, 83%). MS (ESI): mass calcd. for C$_{20}$H$_{20}$BrN$_3$O, 397.1; m/z found, 398.0 [M+H]$^+$. $^1$H NMR (400 MHz, CDCl$_3$) δ 8.46-8.32 (m, 1H), 7.52-7.40 (m, 3H), 7.34 (d, J=8.0, 1H), 7.25-7.19 (m, 2H), 6.64 (d, J=8.1, 1H), 6.30-6.21 (m, 2H), 5.06 (s, 2H), 4.24 (s, 2H), 2.75 (bs, 2H), 2.32 (s, 3H).

Step D: Preparation of (1S,2R)-2-(1-(4-Bromobenzyl)-6-((5-methylpyridin-2-yl)methoxy)-1H-benzo[d]imidazol-2-yl)cyclohexanecarboxylic acid A solution of N$^1$-(4-bromobenzyl)-5-((5-methylpyridin-2-yl)methoxy)benzene-1,2-diamine (63.4 g, 152 mmol) in acetonitrile (400 mL) was added to a mixture of cis-1,2-cyclohexanedicarboxylic anhydride (23.4 g, 152 mmol) in acetonitrile (400 mL). After stirring for 30 min at RT, DIPEA (26.1 mL, 152 mmol) was added followed by a second portion of cis-hexahydroisobenzofuran-1,3-dione (1.55 g, 10 mmol). After stirring for 15 min, HCl (253 mL, 1.52 mol, 6 M) was added and the resulting mixture was heated to 80° Celsius for 2.5 h. The solution was then cooled to 10° Celsius and slowly treated with NaOH (983 mL, 2 M). The resulting mixture was partitioned between water (1150 mL) and toluene (850 mL) and the resulting organic layer was separated. The product containing aqueous layer (pH=12.6) was cooled to 10° Celsius and treated with HCl (69 mL, 6 M) to afford a final pH of 5.9. The resulting mixture was partitioned with ethyl acetate (600 mL) and the organic layer was separated. The organic layer was washed with brine (500 mL), dried over sodium sulfate, filtered and concentrated to dryness to afford a tan solid (73 g, 90%). The initial purification was performed using stationary phase 1000 g of lichroprep silicagel 25-40 um (Merck), 80 mm diameter, 20 cm length, 230 nm detection. A gradient of DCM (95%)/MeOH (5%) was held for 25 min and then ramped over 10 min DCM (90%)/MeOH (10%) and then flushed with 100% ethanol to provide the racemic cis-2-(1-(4-bromobenzyl)-6-((5-methylpyridin-2-yl)methoxy)-1H-benzo[d]imidazol-2-yl)cyclohexanecarboxylic acid. The racemic material was separated into its constituent enantiomers through chiral stationary phase chromatography (stationary phase 2000 g of Chiralpak AS 1000 Å 20 μm (daicel), 110 mm diameter, 38 cm length, 230 nm detection. Isocratic 100% methanol at 450 mL/min over 36 injections). The first eluting cis isomer was contaminated with a small quantity of trans isomer, which was removed through FCC (95:5 dichloromethane:MeOH ramping to 90:10 dichloromethane:MeOH). After concentration, the title compound was present as a foam (24.8 g, 72% of theoretical resolution). MS (ESI): mass calcd. for C$_{28}$H$_{28}$BrN$_3$O$_3$, 533.10; m/z found, 534.2 [M+H]$^+$. $^1$H NMR (400 MHz, CD$_3$OD) δ 8.28 (d, J=2.1, 1H), 7.60 (dd, J=8.2, 2.2, 1H), 7.54 (d, J=8.8, 1H), 7.44-7.39 (m, 2H), 7.38 (d, J=8.0, 1H), 7.02-6.96 (m, 2H), 6.94 (dd, J=8.8, 2.4, 1H), 6.81 (d, J=2.3, 1H), 5.52-5.33 (m, 2H), 5.08 (s, 2H), 3.59-3.52 (m, 1H), 2.86-2.77 (m, 1H), 2.42-2.31 (s, 4H), 2.07-1.68 (m, 5H), 1.52-1.36 (m, 2H). The absolute stereochemistry was determined by single crystal x-ray analysis.

Example 3

(1R,2S)-2-{1-(4-Bromobenzyl)-6-[(5-methylpyridin-2-yl)methoxy]-1H-benzimidazol-2-yl}cyclohexanecarboxylic acid

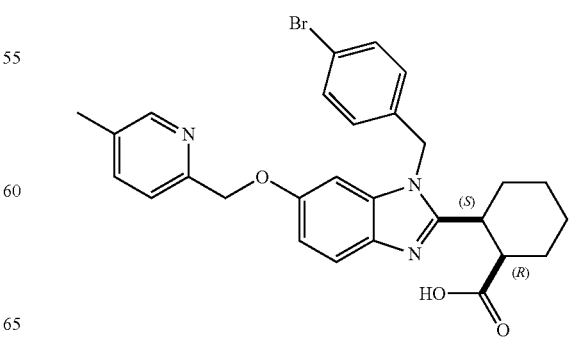

racemic cis-2-{1-(4-Bromobenzyl)-6-[(5-methylpyridin-2-yl)methoxy]-1H-benzimidazol-2-yl}cyclohexanecarboxylic acid was purified by chiral stationary phase chromatography (stationary phase 2000 g of Chiralpak AS 1000 Å 20 μm (daicel), 110 mm diameter, 38 cm length, 230 nm detection. Isocratic 100% methanol at 450 mL/min over 36 injections) as the second eluting isomer. MS (ESI): mass calcd. for $C_{28}H_{28}BrN_3O_3$, 533.13; m/z found, 534.2 [M+H]$^+$. The absolute stereochemistry was determined by single crystal x-ray analysis.

Example 4 racemic cis-2-{1-(4-Bromo-3-fluorobenzyl)-6-[(5-methylpyridin-2-yl)methoxy]-1H-benzimidazol-2-yl}cyclohexanecarboxylic acid as the TFA salt

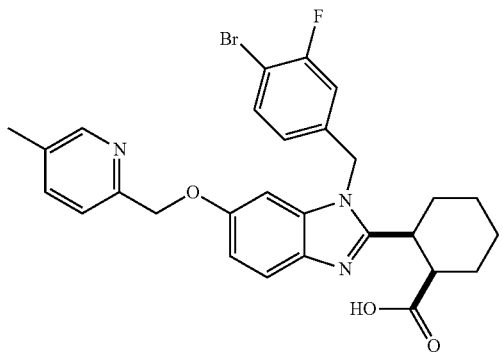

The title compound was prepared using similar methods to those in Example 1 Steps A-B using (4-bromo-3-fluorophenyl)methanamine HCl, DIPEA (2.7 equiv.) and heating the reaction to 80° Celsius for 24 h.

Step C: racemic cis-2-{1-(4-Bromo-3-fluorobenzyl)-6-[(5-methylpyridin-2-yl)methoxy]-1H-benzimidazol-2-yl}cyclohexanecarboxylic acid as the TFA salt To a 15 mL round bottomed flask were added N-1-(4-bromo-3-fluorobenzyl)-5-((5-methylpyridin-2-yl)methoxy)benzene-1,2-diamine (182 mg, 0.44 mmol), cis-3-hydroxyhexahydroisobenzofuran-1(3H)-one (68 mg, 0.44 mmol), sodium metabisulfite (100 mg, 0.52 mmol), DMF (2.9 mL) and water (63 μL, 3.5 mmol). The mixture was left open to the air and heated to 70° Celsius for 3 h. The mixture was cooled to RT and filtered. The filtrate was purified by reverse phase HPLC to afford the title compound. MS (ESI): mass calcd. for $C_{28}H_{27}BrFN_3O_3$, 551.12; m/z found, 552.0 [M+H]$^+$. $^1$H NMR (400 MHz, CDCl$_3$) δ 8.45-8.42 (m, 1H), 8.01-7.96 (m, 1H), 7.74 (d, J=8.2, 1H), 7.62 (d, J=8.9, 1H), 7.49-7.44 (m, 1H), 7.14-7.08 (m, 2H), 6.76-6.66 (m, 2H), 5.63-5.50 (m, 2H), 5.50-5.37 (m, 2H), 3.34-3.28 (m, 1H), 2.91-2.86 (m, 2H), 2.50 (s, 3H), 2.30-2.18 (m, 2H), 1.93-1.83 (m, 2H), 1.65-1.52 (m, 3H), 1.40-1.30 (m, 1H).

Example 5 racemic trans-2-{1-(4-Bromobenzyl)-6-[(5-methylpyridin-2-yl)methoxy]-1H-benzimidazol-2-yl}cyclohexanecarboxylic acid as the TFA salt

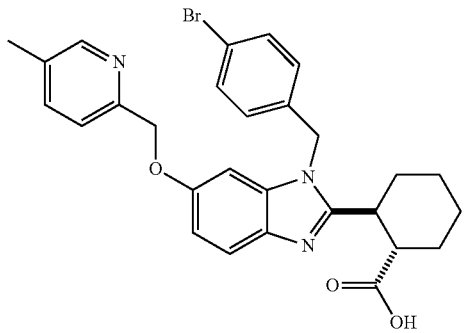

The title compound was prepared in a manner analogous to that in Example 1 substituting trans-hexahydroisobenzofuran-1,3-dione in Step C. MS (ESI): mass calcd. for $C_{28}H_{28}BrN_3O_3$, 533.13; m/z found, 534.1 [M+H]$^+$. $^1$H NMR (600 MHz, CD$_3$OD) δ 8.31 (s, 1H), 7.62 (dd, J=8.0, 1.7, 1H), 7.48 (d, J=8.8, 1H), 7.46-7.42 (m, 2H), 7.40 (d, J=8.0, 1H), 7.06 (d, J=8.5, 2H), 6.95 (dd, J=8.8, 2.4, 1H), 6.89 (d, J=2.3, 1H), 5.45 (s, 2H), 5.11 (s, 2H), 3.14 (td, J=11.8, 3.6, 1H), 3.08-2.99 (m, 1H), 2.35 (s, 3H), 2.21 (d, J=11.2, 1H), 1.86 (d, J=12.1, 1H), 1.75 (d, J=13.7, 1H), 1.62 (dd, J=13.2, 2.9, 1H), 1.55-1.39 (m, 3H), 1.30 (qd, J=12.6, 3.3, 1H).

Example 6

(1S,2S)-2-{1-(4-Bromobenzyl)-6-[(5-methylpyridin-2-yl)methoxy]-1H-benzimidazol-2-yl}cyclohexanecarboxylic acid

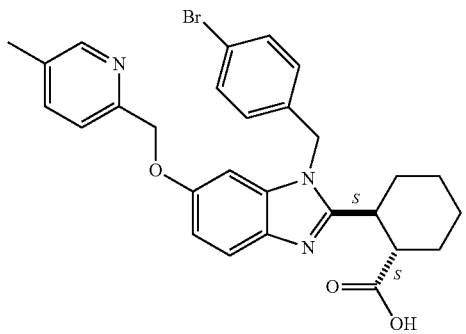

Method 1: racemic trans-2-{1-(4-Bromobenzyl)-6-[(5-methylpyridin-2-yl)methoxy]-1H-benzimidazol-2-yl}cyclohexanecarboxylic acid was purified by chiral SFC on (CHIRALCEL OJ-H 5 μm 250×20 mm) mobile phase (70% CO$_2$, 30% mixture of MeOH/i-PrOH 50/50 v/v) to yield the title compound as the second eluting isomer. MS (ESI): mass calcd. for $C_{28}H_{28}BrN_3O_3$, 533.13; m/z found, 534.1 [M+H]$^+$. Method 2: (1R*,2S*)-2-{1-(4-Bromobenzyl)-6-[(5-methylpyridin-2-yl)methoxy]-1H-benzimidazol-2-yl}cyclohexanecarboxylic acid (100 mg, 0.19 mmol) was dissolved in acetic acid (1.9 mL, 0.19 mmol) and heated to 90° Celsius for 2.5 d. The reaction was allowed to cool to RT and then solvent was removed. The residue was purified by basic HPLC to afford the title compound. MS (ESI): mass calcd. for $C_{28}H_{28}BrN_3O_3$, 533.13; m/z found, 534.1 [M+H]+. 1H NMR (600 MHz, CD3OD) δ 8.31 (s, 1H), 7.62 (dd, J=8.0, 1.7, 1H), 7.48 (d, J=8.8, 1H), 7.46-7.42 (m, 2H), 7.40 (d, J=8.0, 1H), 7.06 (d, J=8.5, 2H), 6.95 (dd, J=8.8, 2.4, 1H), 6.89 (d, J=2.3, 1H), 5.45 (s, 2H), 5.11 (s, 2H), 3.14 (td, J=11.8, 3.6, 1H), 3.08-2.99 (m, 1H), 2.35 (s, 3H), 2.21 (d, J=11.2, 1H), 1.86 (d, J=12.1, 1H), 1.75 (d, J=13.7, 1H), 1.62 (dd, J=13.2, 2.9, 1H), 1.55-1.39 (m, 3H), 1.30 (qd, J=12.6, 3.3, 1 H).

Example 7

(1R,2R)-2-{1-(4-Bromobenzyl)-6-[(5-methylpyridin-2-yl)methoxy]-1H-benzimidazol-2-yl}cyclohexanecarboxylic acid

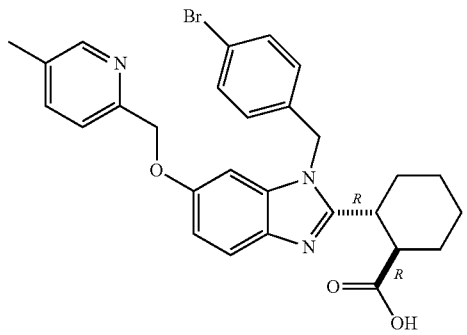

racemic trans-2-{1-(4-Bromobenzyl)-6-[(5-methylpyridin-2-yl)methoxy]-1H-benzimidazol-2-yl}cyclohexanecarboxylic acid was purified by chiral SFC on (CHIRALCEL OJ-H 5 µm 250×20 mm) mobile phase (70% $CO_2$, 30% mixture of MeOH/i-PrOH 50/50 v/v) to yield the title compound as the first eluting isomer.

Example 8

2-({1-(4-Bromobenzyl)-6-[(5-methylpyridin-2-yl)methoxy]-1H-benzimidazol-2-yl}methyl)-2-ethylbutanoic acid as the TFA salt

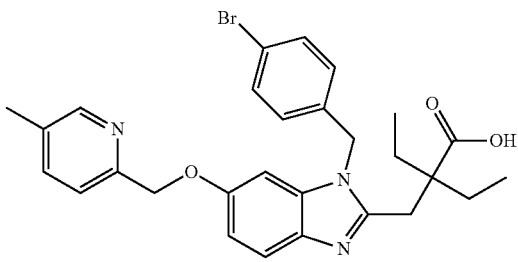 [SMILES: CCC(CC)(Cc1nc2ccc(OCc3ccc(C)cn3)cc2n1Cc1ccc(Br)cc1)C(=O)O]

The title compound was prepared using in a manner analogous to that in Example 1 substituting 3,3-diethyldihydrofuran-2,5-dione in Step C. MS (ESI): mass calcd. for $C_{28}H_{30}BrN_3O_3$, 535.15; m/z found, 536.2 [M+H]+. 1H NMR (500 MHz, CD3OD) δ 8.40 (s, 1H), 7.80 (d, J=8.0, 1H), 7.74 (d, J=9.0, 1H), 7.51 (dd, J=8.3, 4.1, 3H), 7.32 (dd, J=9.0, 2.2, 1H), 7.21 (s, 1H), 7.10 (d, J=8.4, 2H), 5.72 (s, 2H), 5.24 (s, 2H), 3.38 (s, 2H), 2.41 (s, 3H), 1.80 (qq, J=14.8, 7.5, 4H), 0.88 (t, J=7.4, 6H).

Example 9

1-({1-(4-Bromobenzyl)-6-[(5-methylpyridin-2-yl)methoxy]-1H-benzimidazol-2-yl}methyl)cyclopentanecarboxylic acid as the TFA salt

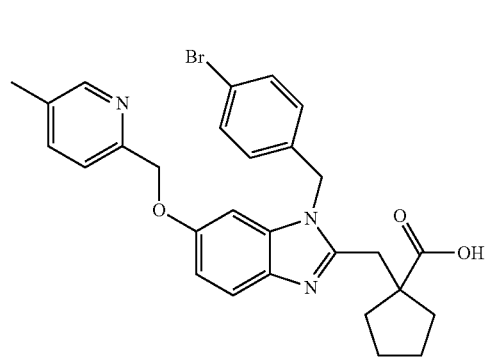 [SMILES: Cc1ccc(COc2ccc3nc(CC4(C(=O)O)CCCC4)n(Cc4ccc(Br)cc4)c3c2)nc1]

The title compound was prepared using in a manner analogous to that in Example 1 substituting 2-oxaspiro[4.4]nonane-1,3-dione in Step C. MS (ESI): mass calcd. for $C_{28}H_{28}BrN_3O_3$, 533.13; m/z found, 534.1 [M+H]+. 1H NMR (600 MHz, CD3OD) δ 8.42 (s, 1H), 7.84 (dd, J=8.1, 1.6, 1H), 7.72 (d, J=9.0, 1H), 7.55 (d, J=8.0, 1H), 7.52-7.49 (m, 2H), 7.31 (dd, J=9.0, 2.3, 1H), 7.19 (d, J=2.2, 1H), 7.10 (d, J=8.5, 2H), 5.71 (s, 2H), 5.25 (s, 2H), 3.49 (s, 2H), 2.42 (s, 3H), 2.33-2.25 (m, 2H), 1.86-1.74 (m, 6H).

Example 10 racemic cis-2-{1-(4-Bromo-2-fluorobenzyl)-6-[(5-methylpyridin-2-yl)methoxy]-1H-benzimidazol-2-yl}cyclohexanecarboxylic acid

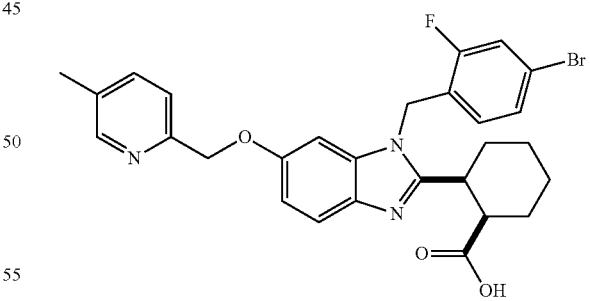

The title compound was prepared in a manner analogous to that in Example 1 substituting 4-bromo-2-fluorobenzylamine in Step A. MS (ESI): mass calcd. for $C_{28}H_{27}BrFN_3O_3$, 551.12; m/z found, 552.1 [M+H]+. 1H NMR (500 MHz, CD3OD) δ 8.44 (s, 1H), 7.89 (dd, J=8.0, 1.5, 1H), 7.73 (d, J=9.0, 1H), 7.59 (d, J=8.1, 1H), 7.50 (dd, J=10.0, 1.9, 1H), 7.35 (dd, J=9.0, 2.3, 1H), 7.28 (dd, J=8.2, 1.6, 1H), 7.21 (d, J=2.2, 1H), 6.87 (t, J=8.2, 1H), 5.80 (s, 2H), 5.27 (s, 2H), 3.69 (dt, J=7.6, 3.6, 1H), 2.97 (dd, J=8.1, 3.9, 1H), 2.44 (s, 3H), 2.41-2.29 (m, 1H), 2.27-2.19 (m, 1H), 2.09-2.02 (m, 1H), 2.01-1.95 (m, 1H), 1.89-1.78 (m, 1H), 1.75-1.65 (m, 1H), 1.63-1.47 (m, 2H).

Example 11

(1R*,2S*)-2-{1-(4-Bromo-2-fluorobenzyl)-6-[(5-methylpyridin-2-yl)methoxy]-1H-benzimidazol-2-yl}cyclohexanecarboxylic acid

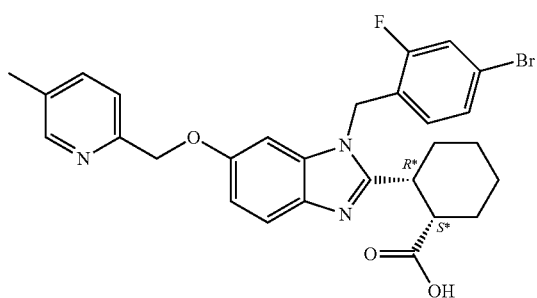 [SMILES: Cc1ccc(COc2ccc3nc([C@@H]4CCCC[C@@H]4C(=O)O)n(Cc4ccc(Br)cc4F)c3c2)nc1]

racemic cis-2-{1-(4-Bromo-2-fluorobenzyl)-6-[(5-methylpyridin-2-yl)methoxy]-1H-benzimidazol-2-yl}cyclohexanecarboxylic acid was purified by chiral SFC on (CHIRALCEL OD-H 5 μm 250×20 mm) mobile phase (70% $CO_2$, 30% MeOH) to yield the title compound as the second eluting isomer. MS (ESI): mass calcd. for $C_{28}H_{27}BrFN_3O_3$, 551.12; m/z found, 552.1 [M+H]$^+$. $^1$H NMR (500 MHz, $CD_3OD$) δ 8.30 (s, 1H), 7.63 (dd, J=8.1, 1.6, 1H), 7.56 (d, J=8.8, 1H), 7.46-7.36 (m, 2H), 7.17 (d, J=8.3, 1.5, 1H), 6.96 (dd, J=8.8, 2.3, 1H), 6.84 (d, J=2.3, 1H), 6.67 (t, J=8.2, 1H), 5.48 (dd, J=41.4, 17.2, 2H), 5.12 (s, 3H), 3.67-3.54 (m, 1H), 2.91-2.72 (m, 1H), 2.44-2.37 (m, 1H), 2.36 (s, 3H), 2.03-1.76 (m, 5H), 1.53-1.40 (m, 2H).

Example 12

(1S*,2R*)-2-{1-(4-Bromo-2-fluorobenzyl)-6-[(5-methylpyridin-2-yl)methoxy]-1H-benzimidazol-2-yl}cyclohexanecarboxylic acid

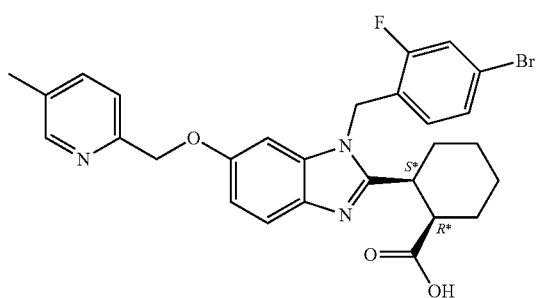 [SMILES: Cc1ccc(COc2ccc3nc([C@H]4CCCC[C@H]4C(=O)O)n(Cc4ccc(Br)cc4F)c3c2)nc1]

racemic cis-2-{1-(4-Bromo-2-fluorobenzyl)-6-[(5-methylpyridin-2-yl)methoxy]-1H-benzimidazol-2-yl}cyclohexanecarboxylic acid was purified by chiral SFC on (CHIRALCEL OD-H 5 μm 250×20 mm) mobile phase (70% $CO_2$, 30% MeOH) to yield the title compound as the first eluting isomer. MS (ESI): mass calcd. for $C_{28}H_{27}BrFN_3O_3$, 551.122; m/z found, 552.1 [M+H]$^+$.

Example 13 racemic trans-2-{1-(4-Bromo-2-fluorobenzyl)-6-[(5-methylpyridin-2-yl)methoxy]-1H-benzimidazol-2-yl}cyclohexanecarboxylic acid

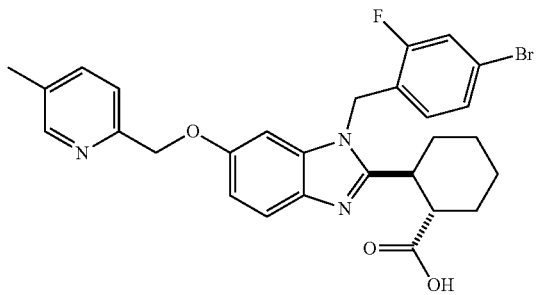

The title compound was prepared in a manner analogous to that in Example 1 substituting 4-bromo-2-fluorobenzylamine in Step A and trans-cyclohexanedicarboxylic anhydride in Step C. MS (ESI): mass calcd. for $C_{28}H_{27}BrFN_3O_3$, 551.12; m/z found, 552.1 [M+H]$^+$. $^1$H NMR (500 MHz, $CD_3OD$) δ 8.47 (s, 1H), 7.90 (d, J=8.1, 1H), 7.68 (d, J=8.9, 1H), 7.62 (d, J=8.0, 1H), 7.48 (dd, J=10.0, 1.9, 1H), 7.38-7.31 (m, 3H), 7.21 (t, J=8.2, 1H), 5.89 (d, J=16.8, 1H), 5.77 (d, J=16.8, 1H), 5.30 (s, 2H), 3.56 (td, J=12.2, 3.4, 1H), 2.96 (td, J=11.7, 3.8, 1H), 2.44 (s, 3H), 2.40-2.34 (m, 1H), 1.98-1.92 (m, 1H), 1.89-1.83 (m, 1H), 1.83-1.76 (m, 1H), 1.65-1.55 (m, 2H), 1.55-1.45 (m, 1H), 1.46-1.35 (m, 1H).

Example 14

2-({1-(3-Bromobenzyl)-6-[(5-methylpyridin-2-yl)methoxy]-1H-benzimidazol-2-yl}methyl)-2-ethylbutanoic acid

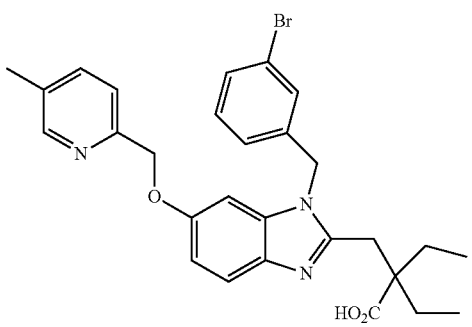 [SMILES: CCC(CC)(Cc1nc2ccc(OCc3ccc(C)cn3)cc2n1Cc1cccc(Br)c1)C(=O)O]

The title compound was prepared using similar methods to those in Example 1 using (3-bromophenyl)methanamine in Step A and 3,3-diethyldihydrofuran-2,5-dione in Step C. MS (ESI): mass calcd. for $C_{28}H_{30}BrN_3O_3$, 535.15; m/z found, 537.1 [M+H]$^+$. $^1$H NMR (500 MHz, $CDCl_3$) δ 8.39-8.35 (d, J=2.1, 1H), 7.65-7.60 (d, J=8.8, 1H), 7.53-7.47 (dd, J=8.0, 1.7, 1H), 7.47-7.41 (d, J=8.8, 1H), 7.41-7.35 (d, J=8.0, 1H), 7.20-7.13 (m, 2H), 7.07-7.01 (dd, J=8.8, 2.3, 1H), 6.91-6.86 (d, J=7.7, 1H), 6.84-6.79 (d, J=2.3, 1H), 5.27-5.23 (s, 2H), 5.20-5.16 (s, 2H), 2.98-2.94 (s, 2H), 2.35-2.31 (s, 3H), 1.76-1.55 (m, 4H), 0.85-0.78 (t, J=7.4, 6H). 537.1 (M+H) m/z

Example 15 racemic cis-3-{1-(4-Bromo-2-fluorobenzyl)-6-[(5-methylpyridin-2-yl)methoxy]-1H-benzimidazol-2-yl}-2,2-dimethylcyclopropanecarboxylic acid

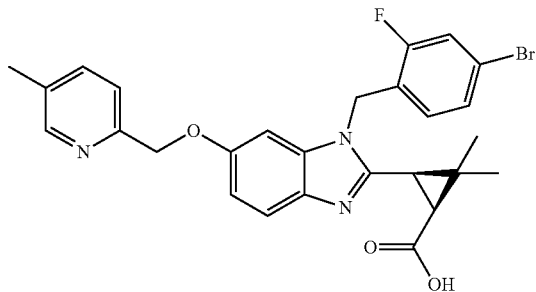 [SMILES: Cc1ccc(COc2ccc3nc([C@@H]4[C@H](C(=O)O)C4(C)C)n(Cc4ccc(Br)cc4F)c3c2)nc1]

The title compound was prepared in a manner analogous to that in Example 1 substituting 4-bromo-2-fluorobenzylamine in Step A and cis-6,6-dimethyl-3-oxabicyclo[3.1.0]hexane-2,4-dione in Step C. MS (ESI): mass calcd. for $C_{27}H_{25}BrFN_3O_3$, 537.11; m/z found, 538.4 [M+H]$^+$. $^1$H NMR (500 MHz, CD$_3$OD) δ 8.34 (s, 1H), 7.65 (dd, J=8.0, 1.5, 1H), 7.57 (d, J=8.7, 1H), 7.46-7.39 (m, 2H), 7.28 (dd, J=8.2, 1.5, 1H), 7.11 (s, 1H), 7.08 (d, J=8.6, 1H), 6.90 (t, J=8.2, 1H), 5.57 (d, J=16.9, 1H), 5.52 (d, J=16.9, 1H), 5.15 (s, 2H), 2.44 (d, J=7.8, 1H), 2.36 (s, 3H), 2.26 (d, J=7.1, 1H), 1.27 (s, 3H), 1.12 (s, 3H).

Example 16

(1S*,3R*)-3-{1-(4-Bromo-2-fluorobenzyl)-6-[(5-methylpyridin-2-yl)methoxy]-1H-benzimidazol-2-yl}-2,2-dimethylcyclopropanecarboxylic acid

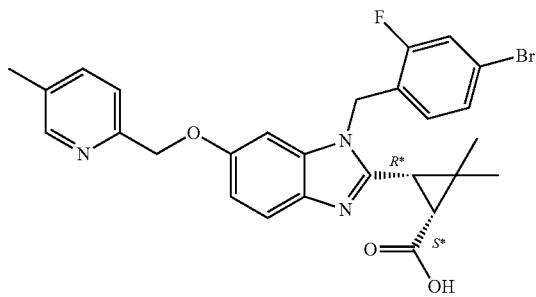 [SMILES: Cc1ccc(COc2ccc3nc([C@H]4[C@@H](C(=O)O)C4(C)C)n(Cc4ccc(Br)cc4F)c3c2)nc1]

racemic cis-3-{1-(4-Bromo-2-fluorobenzyl)-6-[(5-methylpyridin-2-yl)methoxy]-1H-benzimidazol-2-yl}-2,2-dimethylcyclopropanecarboxylic acid was purified by chiral SFC on (CHIRALPAK AD-H 5 μm 250×20 mm) mobile phase (60% CO$_2$, 40% MeOH) to yield the title compound as the first eluting isomer. MS (ESI): mass calcd. for $C_{27}H_{25}BrFN_3O_3$, 537.11; m/z found, 538.0 [M+H]$^+$. $^1$H NMR (400 MHz, DMSO-d$_6$) δ 14.42 (s, 1H), 8.38 (s, 1H), 7.66-7.58 (m, 2H), 7.52 (d, J=8.8, 1H), 7.39 (d, J=8.0, 1H), 7.34 (dd, J=8.3, 1.7, 1H), 7.23 (d, J=2.2, 1H), 6.93 (dd, J=8.8, 2.4, 1H), 6.80 (t, J=8.2, 1H), 5.49 (s, 2H), 5.13 (s, 2H), 2.37 (d, J=8.6, 1H), 2.30 (s, 3H), 2.08 (d, J=8.5, 1H), 1.17 (s, 3H), 1.10 (s, 3H).

Example 17

(1R*,3S*)-3-{1-(4-Bromo-2-fluorobenzyl)-6-[(5-methylpyridin-2-yl)methoxy]-1H-benzimidazol-2-yl}-2,2-dimethylcyclopropanecarboxylic acid

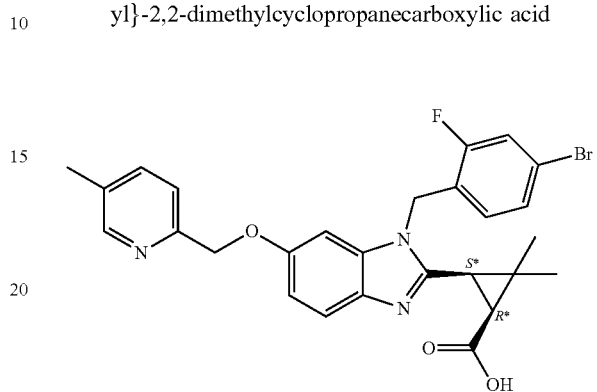

racemic cis-3-{1-(4-Bromo-2-fluorobenzyl)-6-[(5-methylpyridin-2-yl)methoxy]-1H-benzimidazol-2-yl}-2,2-dimethylcyclopropanecarboxylic acid was purified by chiral SFC on (CHIRALPAK AD-H 5 μm 250×20 mm) mobile phase (60% CO$_2$, 40% MeOH) to yield the title compound as the second eluting isomer. MS (ESI): mass calcd. for $C_{27}H_{25}BrFN_3O_3$, 537.11; m/z found, 538.0 [M+H]$^+$.

Example 18 racemic trans-2-{1-(4-Cyanobenzyl)-6-[(5-methylpyridin-2-yl)methoxy]-1H-benzimidazol-2-yl}cyclohexanecarboxylic acid as the TFA salt

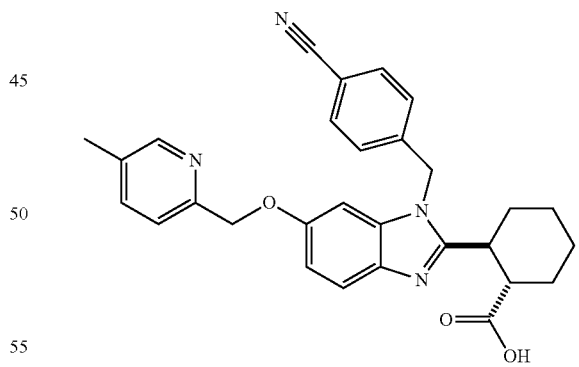

The title compound was prepared in a manner analogous to that in Example 1 substituting 4-(aminomethyl)benzonitrile in Step A and trans-cyclohexanedicarboxylic anhydride in Step C. MS (ESI): mass calcd. for $C_{29}H_{28}N_4O_3$, 480.21; m/z found, 481.2 [M+H]$^+$. $^1$H NMR (400 MHz, CD$_3$OD) δ 8.52-8.39 (d, J=1.9, 2H), 7.94-7.86 (ddd, J=8.1, 2.2, 0.9, 3H), 7.76-7.66 (m, 8H), 7.61-7.56 (d, J=8.1, 3H), 7.49-7.42 (d, J=8.4, 5H), 7.37-7.29 (dd, J=9.0, 2.3, 3H), 7.27-7.20 (d, J=2.3, 3H), 6.02-5.92 (m, 3H), 5.91-5.81 (m, 3H), 5.31-5.24 (s, 5H), 3.59-3.48 (td, J=12.0, 3.1, 3H), 3.07-2.95 (td, J=11.5, 3.7, 3H), 2.12-2.03 (s, 1H), 2.00-1.89 (d, J=12.4, 3H), 1.86-1.74 (d, J=13.5, 8H), 1.69-1.45 (m, 8H), 1.45-1.29 (q, J=9.7, 7.2, 5H).

Example 19

2-({1-(4-Cyanobenzyl)-6-[(5-methylpyridin-2-yl)methoxy]-1H-benzimidazol-2-yl}methyl)-2-ethylbutanoic acid as the TFA salt

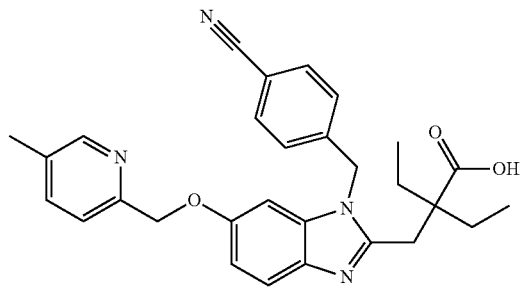 [SMILES: CCC(CC)(Cc1nc2ccc(OCc3ccc(C)cn3)cc2n1Cc1ccc(C#N)cc1)C(=O)O]

The title compound was prepared in a manner analogous to that in Example 1 substituting 4-(aminomethyl)benzonitrile in Step A and 3,3-diethyldihydrofuran-2,5-dione in Step C. MS (ESI): mass calcd. for $C_{29}H_{30}N_4O_3$, 482.23; m/z found, 483.2 [M+H]+. $^1$H NMR (400 MHz, CD$_3$OD) δ 8.62-8.54 (m, 1H), 8.23-8.13 (ddd, J=8.1, 2.1, 0.9, 1H), 7.84-7.77 (dd, J=8.6, 5.8, 2H), 7.76-7.69 (m, 2H), 7.42-7.38 (dd, J=9.1, 2.3, 1H), 7.38-7.34 (m, 2H), 7.28-7.22 (d, J=2.3, 1H), 5.97-5.85 (s, 2H), 5.41-5.35 (s, 2H), 3.46-3.37 (s, 2H), 2.54-2.49 (s, 3H), 1.91-1.73 (tt, J=14.3, 7.1, 4H), 0.94-0.84 (t, J=7.4, 6H).

Example 20 racemic cis-2-{1-[3-Fluoro-4-(trifluoromethoxy)benzyl]-6-[(5-methylpyridin-2-yl)methoxy]-1H-benzimidazol-2-yl}cyclohexanecarboxylic acid

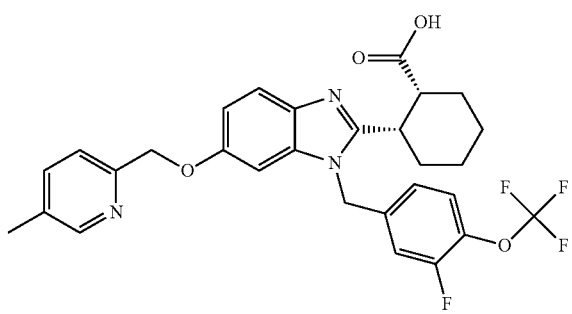 [SMILES: Cc1ccc(COc2ccc3nc([C@H]4CCCC[C@H]4C(=O)O)n(Cc4ccc(OC(F)(F)F)c(F)c4)c3c2)nc1]

The title compound was prepared using analogous conditions described in Example 1 using (2-fluoro-4-(trifluoromethoxy)phenyl)methanamine in Step A. MS (ESI): mass calcd. for $C_{29}H_{27}F_4N_3O_4$, 557.19; m/z found, 558.2 [M+H]+. $^1$H NMR (500 MHz, CD$_3$OD) δ 8.30 (s, 1H), 7.61 (d, J=6.1, 1H), 7.56 (d, J=8.8, 1H), 7.40 (d, J=8.0, 1H), 7.33 (t, J=8.2, 1H), 7.06 (d, J=11.0, 1H), 6.96 (dd, J=8.8, 2.4, 2H), 6.81 (d, J=2.3, 1H), 5.55 (d, J=17.5, 1H), 5.46 (d, J=17.5, 1H), 5.15-5.03 (m, 2H), 3.61-3.55 (m, 1H), 2.87-2.74 (m, 1H), 2.45-2.34 (m, 1H), 2.33 (s, 3H), 2.07-1.96 (m, 1H), 1.96-1.69 (m, 4H), 1.47 (d, J=8.1, 2H).

Example 21 racemic trans-2-{1-[2-Fluoro-4-(trifluoromethoxy)benzyl]-6-[(5-methylpyridin-2-yl)methoxy]-1H-benzimidazol-2-yl}cyclohexanecarboxylic acid

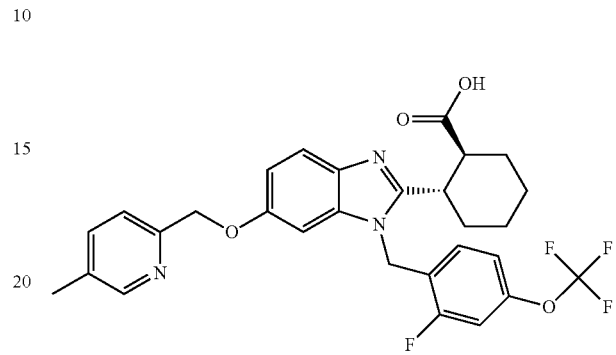

The title compound was prepared using analogous conditions described in Example 1 using (2-fluoro-4-(trifluoromethoxy)phenyl)methanamine in Step A and racemic trans-hexahydroisobenzofuran-1,3-dione in Step C. MS (ESI): mass calcd. for $C_{29}H_{27}F_4N_3O_4$, 557.19; m/z found, 558.2 [M+H]+. $^1$H NMR (500 MHz, CD$_3$OD) δ 8.33 (s, 1H), 7.65 (d, J=6.2, 1H), 7.47 (dd, J=21.4, 8.2, 2H), 7.20 (d, J=9.5, 1H), 7.06-6.93 (m, 4H), 5.67 (d, J=17.1, 1H), 5.48 (d, J=16.9, 1H), 5.13 (s, 2H), 3.17-3.06 (m, 1H), 3.06-2.95 (m, 1H), 2.35 (s, 3H), 2.26-2.11 (m, 1H), 1.91-1.82 (m, 1H), 1.74 (sm, 1H), 1.63-1.43 (m, 4H), 1.39-1.28 (m, 1H).

Example 22

2-Ethyl-2-({6-[(5-methylpyridin-2-yl)methoxy]-1-[4-(trifluoromethoxy)benzyl]-1H-benzimidazol-2-yl}methyl)butanoic acid

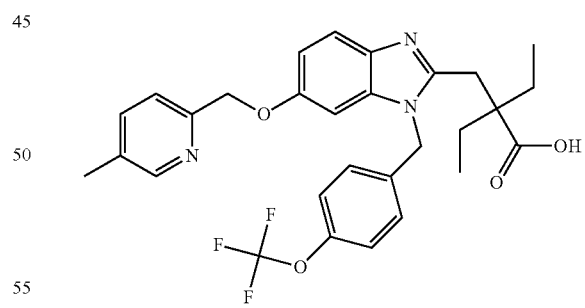

The title compound was prepared using analogous conditions described in Example 1 using (4-(trifluoromethoxy)phenyl)methanamine in Step A and 3,3-diethyldihydrofuran-2,5-dione in Step C. MS (ESI): mass calcd. for $C_{29}H_{30}F_3N_3O_4$, 541.22; m/z found, 542.1 [M+H]+. $^1$H NMR (500 MHz, CD$_3$OD) δ 8.32 (s, 1H), 7.63 (dd, J=8.0, 1.6, 1H), 7.55 (d, J=8.8, 1H), 7.43 (d, J=8.0, 1H), 7.20 (d, J=8.1, 2H), 7.11 (d, J=8.8, 2H), 6.97 (dd, J=8.8, 2.4, 1H), 6.94 (d, J=2.3, 1H), 5.50 (s, 2H), 5.11 (s, 2H), 3.06 (s, 2H), 2.34 (s, 3H), 1.89-1.76 (m, 4H), 0.83 (t, J=7.5, 6H).

Example 23

2-Ethyl-2-({1-[2-fluoro-4-(trifluoromethoxy)benzyl]-6-[(5-methylpyridin-2-yl)methoxy]-1H-benzimidazol-2-yl}methyl)butanoic acid

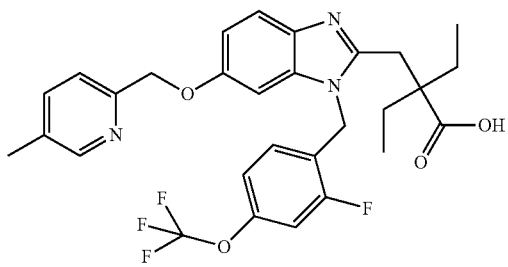 [SMILES: CCC(CC)(Cc1nc2ccc(OCc3ccc(C)cn3)cc2n1Cc1ccc(OC(F)(F)F)cc1F)C(=O)O]

The title compound was prepared using analogous conditions described in Example 1 using (2-fluoro-4-(trifluoromethoxy)phenyl)methanamine in Step A and 3,3-diethyldihydrofuran-2,5-dione in Step C. MS (ESI): mass calcd. for $C_{29}H_{29}F_4N_3O_4$, 559.21; m/z found, 560.1 [M+H]$^+$. $^1$H NMR (500 MHz, CD$_3$OD) δ 8.33 (s, 1H), 7.70-7.37 (m, 3H), 7.18 (d, J=10.4, 1H), 6.96 (dd, J=19.4, 8.6, 3H), 6.82 (t, J=8.4, 1H), 5.54 (s, 2H), 5.12 (s, 2H), 3.12 (d, J=41.8, 2H), 2.34 (s, 3H), 1.91-1.70 (m, 4H), 0.86 (t, J=7.4, 6H).

Example 24

2-({1-[3-Chloro-4-(trifluoromethoxy)benzyl]-6-[(5-methylpyridin-2-yl)methoxy]-1H-benzimidazol-2-yl}methyl)-2-ethylbutanoic acid

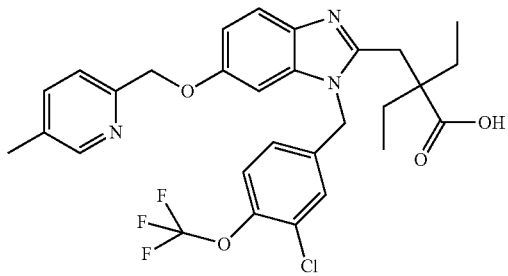 [SMILES: CCC(CC)(Cc1nc2ccc(OCc3ccc(C)cn3)cc2n1Cc1ccc(OC(F)(F)F)c(Cl)c1)C(=O)O]

The title compound was prepared using analogous conditions described in Example 1 using (3-chloro-4-(trifluoromethoxy)phenyl)methanamine in Step A and using 3,3-diethyldihydrofuran-2,5-dione in Step C. MS (ESI): mass calcd. for $C_{29}H_{29}ClF_3N_3O_4$, 575.18; m/z found, 576.2 [M+H]$^+$. $^1$H NMR (500 MHz, CD$_3$OD) δ 8.43 (s, 1H), 7.86 (dd, J=8.0, 1.5, 1H), 7.76 (d, J=9.0, 1H), 7.57 (d, J=8.0, 1H), 7.44 (d, J=2.1, 1H), 7.42 (dd, J=8.6, 1.1, 1H), 7.33 (dd, J=9.0, 2.3, 1H), 7.25-7.12 (m, 2H), 5.79 (s, 2H), 5.26 (s, 2H), 3.36 (d, J=16.9, 2H), 2.41 (s, 3H), 1.88-1.71 (m, 4H), 0.88 (t, J=7.4, 6H).

Example 25 racemic cis-2,2-Dimethyl-3-{6-[(5-methylpyridin-2-yl)methoxy]-1-[4-(trifluoromethoxy)benzyl]-1H-benzimidazol-2-yl}cyclopropanecarboxylic acid

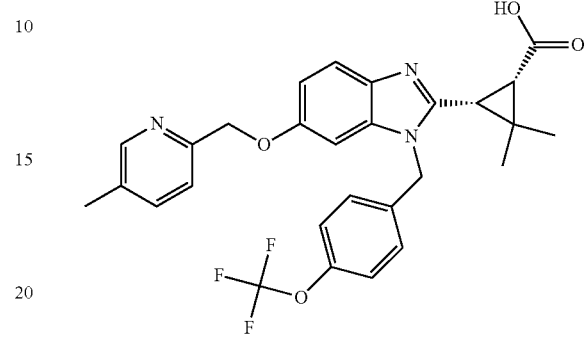

The title compound was prepared using analogous conditions described in Example 1 using (4-(trifluoromethoxy)phenyl)methanamine in Step A and using cis-6-dimethyl-3-oxabicyclo[3.1.0]hexane-2,4-dione in Step C. MS (ESI): mass calcd. for $C_{28}H_{26}F_3N_3O_4$, 525.19; m/z found, 526.2 [M+H]$^+$. $^1$H NMR (500 MHz, CD$_3$OD) δ 8.34 (s, 1H), 7.68-7.62 (m, 1H), 7.58 (d, J=8.9, 1H), 7.46 (d, J=8.0, 1H), 7.24 (dd, J=22.2, 8.6, 4H), 7.16 (d, J=2.1, 1H), 7.09 (dd, J=8.9, 2.3, 1H), 5.63 (d, J=16.9, 1H), 5.52 (d, J=16.9, 1H), 5.16 (s, 2H), 2.40 (d, J=8.2, 1H), 2.35 (s, 3H), 2.22 (d, J=8.2, 1H), 1.17 (s, 3H), 1.03 (s, 3H).

Example 26 racemic cis-2-{1-[2-Fluoro-4-(trifluoromethoxy)benzyl]-6-[(5-methylpyridin-2-yl)methoxy]-1H-benzimidazol-2-yl}cyclohexanecarboxylic acid

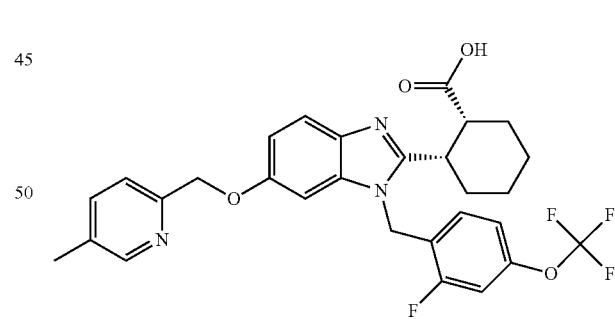

The title compound was prepared using analogous conditions described in Example 1 using (2-fluoro-4-(trifluoromethoxy)phenyl)methanamine in Step A. MS (ESI): mass calcd. for $C_{29}H_{27}F_4N_3O_4$, 557.19; m/z found, 558.2 [M+H]$^+$. $^1$H NMR (500 MHz, CD$_3$OD) δ 8.31 (s, 1H), 7.63 (d, J=6.3, 1H), 7.56 (d, J=8.8, 1H), 7.42 (d, J=7.9, 1H), 7.20 (d, J=10.5, 1H), 6.96 (dd, J=8.8, 2.3, 2H), 6.92-6.82 (m, 2H), 5.57 (d, J=17.4, 1H), 5.51 (d, J=17.3, 1H), 5.11 (s, 2H), 3.60 (s, 1H), 2.85-2.78 (m, 1H), 2.45-2.36 (m, 1H), 2.34 (s, 3H), 2.06-1.95 (m, 1H), 1.95-1.83 (m, 2H), 1.83-1.72 (m, 2H), 1.53-1.38 (m, 2H).

Example 27 racemic cis-2-{6-[(5-Methylpyridin-2-yl)methoxy]-1-[4-(trifluoromethoxy)benzyl]-1H-benzimidazol-2-yl}cyclohexanecarboxylic acid

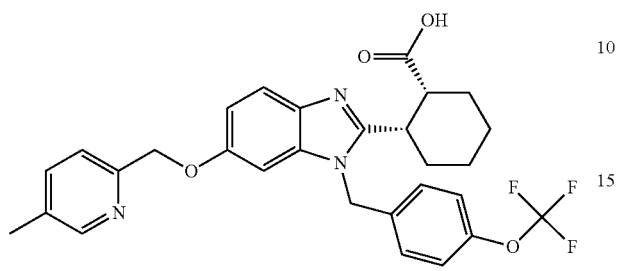

The title compound was prepared using analogous conditions described in Example 1 using (4-(trifluoromethoxy)phenyl)methanamine in Step A. MS (ESI): mass calcd. for $C_{29}H_{28}F_3N_3O_4$, 539.20; m/z found, 540.2 [M+H]$^+$. $^1$H NMR (500 MHz, CD$_3$OD) δ 8.30 (s, 1H), 7.62 (d, J=8.0, 1H), 7.56 (d, J=8.8, 1H), 7.41 (d, J=8.0, 1H), 7.19 (s, 4H), 6.96 (dd, J=8.8, 2.3, 1H), 6.85 (d, J=2.3, 1H), 5.55 (d, J=17.2, 1H), 5.47 (d, J=17.2, 1H), 5.11-5.05 (m, 2H), 3.63-3.52 (m, 1H), 2.92-2.76 (m, 1H), 2.42-2.36 (m, 1H), 2.34 (s, 3H), 2.07-1.95 (m, 1H), 1.95-1.70 (m, 4H), 1.56-1.37 (m, 2H).

Example 28

(1R*,2S*)-2-{6-[(5-Methylpyridin-2-yl)methoxy]-1-[4-(trifluoromethoxy)benzyl]-1H-benzimidazol-2-yl}cyclohexanecarboxylic acid

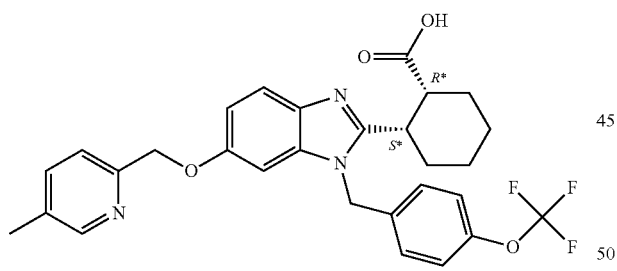

racemic cis-2-{6-[(5-Methylpyridin-2-yl)methoxy]-1-[4-(trifluoromethoxy)benzyl]-1H-benzimidazol-2-yl}cyclohexanecarboxylic acid was purified by chiral SFC on (CHIRALPAK IC 5 μm 250×20 mm) mobile phase (60% CO$_2$, 40% EtOH) to yield the title compound as the second eluting isomer. MS (ESI): mass calcd. for $C_{29}H_{28}F_3N_3O_4$, 539.20; m/z found, 540.2 [M+H]$^+$. $^1$H NMR (500 MHz, CD$_3$OD) δ 8.30 (d, J=2.1, 1H), 7.62 (dd, J=8.1, 2.1, 1H), 7.55 (d, J=8.8, 1H), 7.40 (d, J=8.0, 1H), 7.19 (s, 4H), 6.95 (dd, J=8.8, 2.4, 1H), 6.84 (d, J=2.4, 1H), 5.54 (d, J=17.3, 1H), 5.47 (d, J=17.3, 1H), 5.12-5.04 (m, 2H), 3.61-3.53 (m, 1H), 2.89-2.76 (m, 1H), 2.43-2.35 (m, 1H), 2.34 (s, 3H), 2.05-1.93 (m, 1H), 1.94-1.81 (m, 2H), 1.80-1.69 (m, 2H), 1.53-1.37 (m, 2H).

Example 29

(1S*,2R*)-2-{6-[(5-Methylpyridin-2-yl)methoxy]-1-[4-(trifluoromethoxy)benzyl]-1H-benzimidazol-2-yl}cyclohexanecarboxylic acid

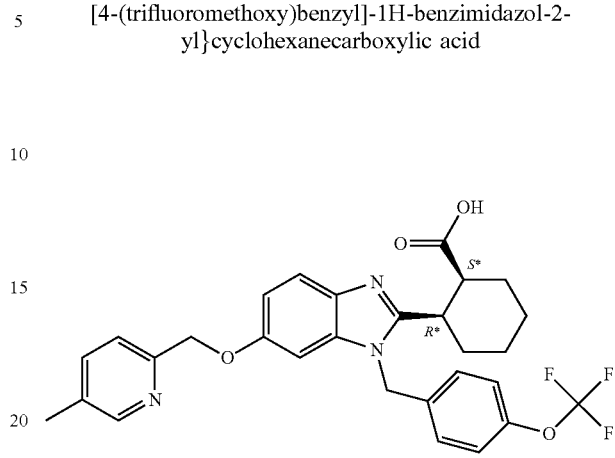

racemic cis-2-{6-[(5-Methylpyridin-2-yl)methoxy]-1-[4-(trifluoromethoxy)benzyl]-1H-benzimidazol-2-yl}cyclohexanecarboxylic acid was purified by chiral SFC on (CHIRALPAK IC 5 μm 250×20 mm) mobile phase (60% CO$_2$, 40% EtOH) to yield the title compound as the first eluting isomer. MS (ESI): mass calcd. for $C_{29}H_{28}F_3N_3O_4$, 539.20; m/z found, 540.2 [M+H]$^+$.

Example 30

2-Ethyl-2-({1-[3-fluoro-4-(trifluoromethoxy)benzyl]-6-[(5-methylpyridin-2-yl)methoxy]-1H-benzimidazol-2-yl}methyl)butanoic acid

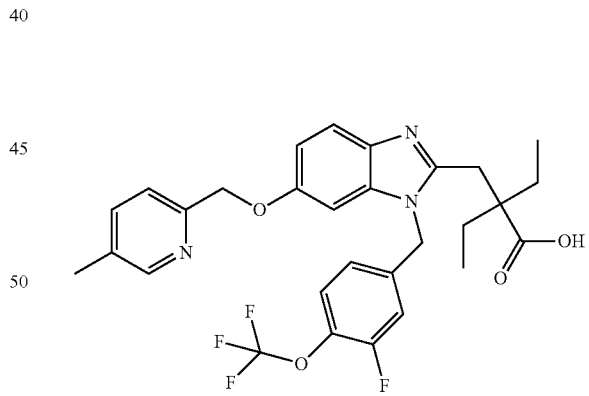

The title compound was prepared using analogous conditions described in Example 1 using (3-fluoro-4-(trifluoromethoxy)phenyl)methanamine in Step A and 3,3-diethyl-dihydrofuran-2,5-dione in Step C. MS (ESI): mass calcd. for $C_{29}H_{29}F_4N_3O_4$, 559.21; m/z found, 560.1 [M+H]$^+$. $^1$H NMR (400 MHz, CD$_3$OD) δ 8.31 (d, J=2.0, 1H), 7.63 (dd, J=8.0, 1.6, 1H), 7.56 (d, J=8.8, 1H), 7.42 (d, J=8.0, 1H), 7.37-7.28 (m, 1H), 7.01-6.93 (m, 2H), 6.90 (d, J=2.3, 1H), 6.86 (d, J=8.5, 1H), 5.51 (s, 2H), 5.12 (s, 2H), 3.05 (s, 2H), 2.36 (s, 3H), 1.91-1.78 (m, 4H), 0.84 (t, J=7.4, 6H).

Example 31 racemic trans-2-{6-[(5-Methylpyridin-2-yl)methoxy]-1-[4-(trifluoromethoxy)benzyl]-1H-benzimidazol-2-yl}cyclohexanecarboxylic acid

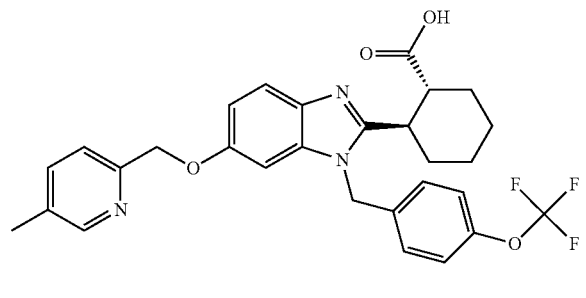 [SMILES: Cc1ccc(COc2ccc3nc([C@@H]4CCCC[C@H]4C(=O)O)n(Cc4ccc(OC(F)(F)F)cc4)c3c2)nc1]

The title compound was prepared using analogous conditions described in Example 1 using (4-(trifluoromethoxy)phenyl)methanamine in Step A and racemic trans-hexahydroisobenzofuran-1,3-dione in Step C. MS (ESI): mass calcd. for $C_{29}H_{28}F_3N_3O_4$, 539.20; m/z found, 540.2 [M+H]$^+$. $^1$H NMR (500 MHz, CD$_3$OD) δ 8.32 (s, 1H), 7.63 (dd, J=8.0, 1.6, 1H), 7.49 (d, J=8.7, 1H), 7.43 (d, J=8.0, 1H), 7.26 (d, J=8.8, 2H), 7.23-7.17 (m, 2H), 6.96 (dd, J=8.7, 2.4, 1H), 6.93 (d, J=2.2, 1H), 5.58-5.45 (m, 2H), 5.11 (s, 2H), 3.18-3.09 (m, 1H), 3.08-2.97 (m, 1H), 2.34 (s, 3H), 2.28-2.13 (m, 1H), 1.89-1.78 (m, 1H), 1.79-1.68 (m, 1H), 1.63-1.38 (m, 4H), 1.35-1.19 (m, 1H).

Example 32 racemic cis-2-{1-[3-Chloro-4-(trifluoromethoxy)benzyl]-6-[(5-methylpyridin-2-yl)methoxy]-1H-benzimidazol-2-yl}cyclohexanecarboxylic acid

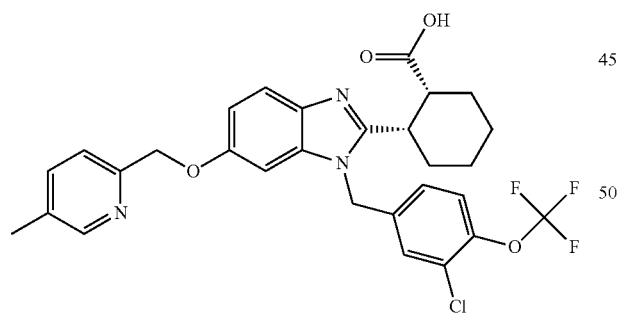

The title compound was prepared using analogous conditions described in Example 1 using (3-chloro-4-(trifluoromethoxy)phenyl)methanamine in Step A. MS (ESI): mass calcd. for $C_{29}H_{27}ClF_3N_3O_4$, 573.16; m/z found, 574.0 [M+H]$^+$. $^1$H NMR (500 MHz, CD$_3$OD) δ 8.29 (s, 1H), 7.61 (dd, J=7.9, 1.6, 1H), 7.56 (d, J=8.8, 1H), 7.39 (d, J=8.0, 1H), 7.33 (d, J=7.2, 2H), 7.08 (dd, J=8.6, 2.0, 1H), 6.96 (dd, J=8.8, 2.4, 1H), 6.81 (d, J=2.3, 1H), 5.55 (d, J=17.5, 1H), 5.46 (d, J=17.5, 1H), 5.17-5.03 (m, 2H), 3.62-3.52 (m, 1H), 2.85-2.76 (m, 1H), 2.43-2.35 (m, 1H), 2.33 (s, 3H), 2.08-1.96 (m, 1H), 1.97-1.69 (m, 4H), 1.56-1.39 (m, 2H).

Example 33 racemic trans-2-(6-[(5-Methylpyridin-2-yl)methoxy]-1-{[4'-(trifluoromethyl)biphenyl-4-yl]methyl}-1H-benzimidazol-2-yl)cyclohexanecarboxylic acid

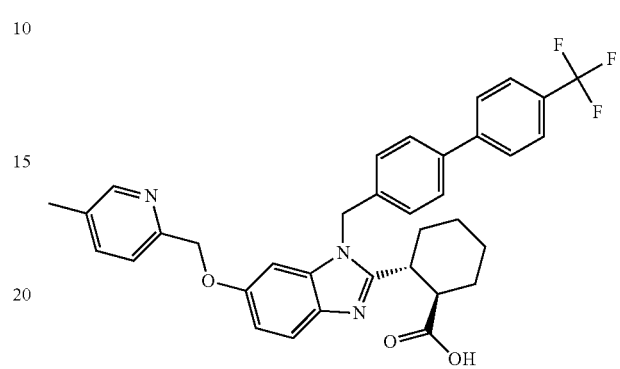

The title compound was prepared using analogous conditions described in Example 1 using 5-((5-methylpyridin-2-yl)methoxy)-N$^1$-((4'-(trifluoromethyl)-[1,1'-biphenyl]-4-yl)methyl)benzene-1,2-diamine and racemic trans-hexahydroisobenzofuran-1,3-dione in Step C. MS (ESI): mass calcd. for $C_{35}H_{32}F_3N_3O_3$, 599.2; m/z found, 600.2 [M+H]$^+$. $^1$H NMR (500 MHz, CD$_3$OD) δ 8.27 (d, J=2.1, 1H), 7.76 (d, J=8.1, 2H), 7.69 (d, J=8.3, 2H), 7.65-7.58 (m, 2H), 7.58-7.46 (m, 2H), 7.42-7.22 (m, 3H), 6.97-6.90 (m, 2H), 5.53 (s, 2H), 5.09 (s, 2H), 3.19 (td, J=11.5, 3.6, 1H), 3.03 (td, J=11.3, 3.5, 1H), 2.23 (s, 3H), 2.21-2.17 (m, 1H), 1.89-1.79 (m, 1H), 1.77-1.59 (m, 2H), 1.58-1.19 (m, 4H).

Example 34

(1R*,2R*)-2-(6-[(5-Methylpyridin-2-yl)methoxy]-1-{[4'-(trifluoromethyl)biphenyl-4-yl]methyl}-1H-benzimidazol-2-yl)cyclohexanecarboxylic acid

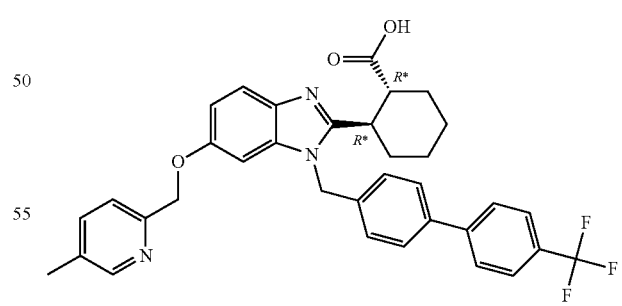

racemic trans-2-(6-[(5-Methylpyridin-2-yl)methoxy]-1-{[4'-(trifluoromethyl)biphenyl-4-yl]methyl}-1H-benzimidazol-2-yl)cyclohexanecarboxylic acid was purified by chiral SFC on (CHIRALPAK AD-H 5 μm 250×20 mm) mobile phase (60% CO$_2$, 40% MeOH) to yield the title compound as the second eluting isomer. MS (ESI): mass calcd. for $C_{35}H_{32}F_3N_3O_3$, 599.24; m/z found, 600.2 [M+H]$^+$.

Example 35

(1S*,2S*)-2-(6-[(5-Methylpyridin-2-yl)methoxy]-1-{[4'-(trifluoromethyl)biphenyl-4-yl]methyl}-1H-benzimidazol-2-yl)cyclohexanecarboxylic acid

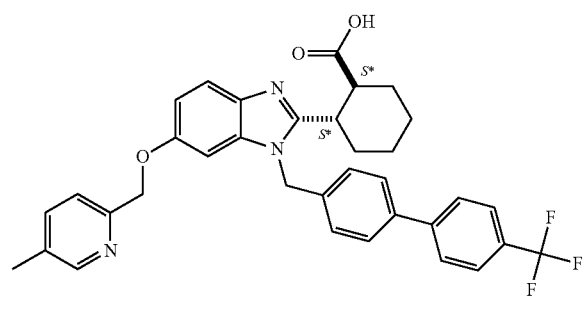

racemic trans-2-(6-[(5-Methylpyridin-2-yl)methoxy]-1-{[4'-(trifluoromethyl)biphenyl-4-yl]methyl}-1H-benzimidazol-2-yl)cyclohexanecarboxylic acid was purified by chiral SFC on (CHIRALPAK AD-H 5 μm 250×20 mm) mobile phase (60% $CO_2$, 40% MeOH) to yield the title compound as the first eluting isomer. MS (ESI): mass calcd. for $C_{35}H_{32}F_3N_3O_3$, 599.24; m/z found, 600.2 $[M+H]^+$. $^1$H NMR (500 MHz, $CD_3OD$) δ 8.29 (s, 1H), 7.81-7.76 (m, 2H), 7.74-7.68 (m, 2H), 7.65-7.61 (m, 2H), 7.60-7.55 (m, 1H), 7.49 (d, J=8.6 Hz, 1H), 7.41 (d, J=8.0 Hz, 1H), 7.27 (d, J=8.1 Hz, 2H), 7.00-6.89 (m, 2H), 5.62-5.51 (m, 2H), 5.11 (s, 2H), 3.24-3.12 (m, 1H), 3.09-2.92 (m, 1H), 2.25 (s, 3H), 2.24-2.18 (m, 1H), 1.89-1.81 (m, 1H), 1.77-1.68 (m, 1H), 1.67-1.58 (m, 1H), 1.58-1.39 (m, 3H), 1.36-1.24 (m, 1H).

Example 36

(1S*,2R*)-2-{6-[(1-Methyl-1H-pyrazol-3-yl)methoxy]-1-[4-(trifluoromethoxy)benzyl]-1H-benzimidazol-2-yl}cyclohexanecarboxylic acid

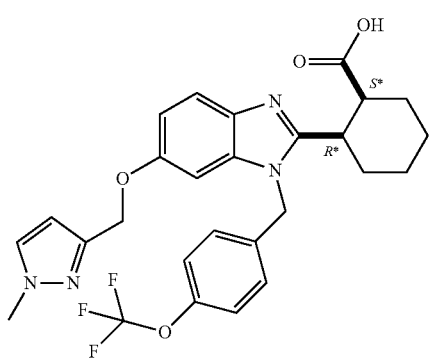

racemic cis-2-{6-[(1-Methyl-1H-pyrazol-3-yl)methoxy]-1-[4-(trifluoromethoxy)benzyl]-1H-benzimidazol-2-yl}cyclohexanecarboxylic acid was purified by chiral SFC on (CHIRALCEL OD-H 5 μm 250×20 mm) mobile phase (75% $CO_2$, 25% MeOH) to yield the title compound as the second eluting isomer. MS (ESI): mass calcd. for $C_{27}H_{27}F_3N_4O_4$, 528.20; m/z found, 529.2 $[M+H]^+$. $^1$H NMR (500 MHz, $CD_3OD$) δ 7.56-7.50 (m, 1H), 7.49 (d, J=2.2, 1H), 7.21 (d, J=9.4, 4H), 6.93-6.88 (m, 2H), 6.25 (d, J=2.3, 1H), 5.56 (d, J=17.3, 1H), 5.50 (d, J=17.2, 1H), 5.04-4.95 (m, 2H), 3.82 (s, 3H), 3.61-3.53 (m, 1H), 2.88-2.77 (m, 1H), 2.46-2.33 (m, 1H), 2.05-1.69 (m, 5H), 1.58-1.37 (m, 2H).

Example 37 racemic cis-2-{1-(4-Cyanobenzyl)-6-[(5-methylpyridin-2-yl)methoxy]-1H-benzimidazol-2-yl}cyclohexanecarboxylic acid as the TFA salt

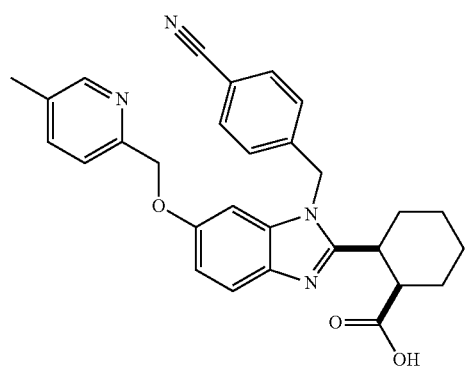

The title compound was prepared using analogous conditions described in Example 1 using 4-(aminomethyl)benzonitrile in Step A. MS (ESI): mass calcd. for $C_{29}H_{28}N_4O_3$, 480.22; m/z found, 481.2 $[M+H]^+$. $^1$H NMR (500 MHz, $CD_3OD$) δ 8.37 (s, 1H), 7.82 (d, J=8.1, 1H), 7.74 (d, J=9.0, 1H), 7.71 (d, J=8.4, 2H), 7.51 (d, J=8.0, 1H), 7.35 (dd, J=9.0, 2.3, 1H), 7.25 (d, J=8.4, 2H), 7.11 (d, J=2.3, 1H), 5.93 (d, J=18.0, 1H), 5.84 (d, J=17.9, 1H), 5.24 (d, J=13.3, 1H), 5.20 (d, J=13.2, 1H), 3.64 (dt, J=12.1, 3.8, 1H), 2.94-2.85 (m, 1H), 2.41 (s, 3H), 2.36-2.25 (m, 1H), 2.23-2.15 (m, 1H), 2.12-2.05 (m, 1H), 2.01-1.94 (m, 1H), 1.87-1.73 (m, 1H), 1.74-1.64 (m, 1H), 1.62-1.47 (m, 2H).

Example 38

(1S*,2R*)-2-{1-(4-Cyanobenzyl)-6-[(5-methylpyridin-2-yl)methoxy]-1H-benzimidazol-2-yl}cyclohexanecarboxylic acid

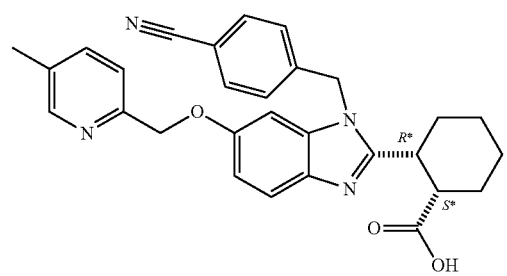

racemic cis-2-{1-(4-Cyanobenzyl)-6-[(5-methylpyridin-2-yl)methoxy]-1H-benzimidazol-2-yl}cyclohexanecarboxylic acid was purified by chiral SFC on (CHIRALCEL OJ-H 5 μm 250×20 mm) mobile phase (65% $CO_2$, 35% EtOH) to yield the title compound as the second eluting isomer. MS (ESI): mass calcd. for C$_{29}$H$_{28}$N$_4$O$_3$, 480.22; m/z found, 481.2 [M+H]$^+$.

Example 39

(1R*,2S*)-2-{1-(4-Cyanobenzyl)-6-[(5-methylpyridin-2-yl)methoxy]-1H-benzimidazol-2-yl}cyclohexanecarboxylic acid

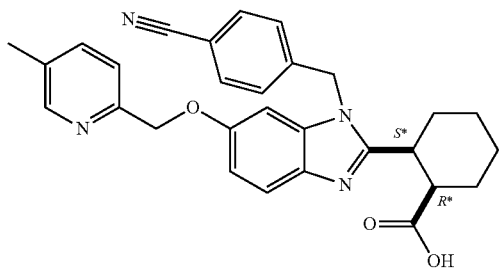

racemic cis-2-{1-(4-Cyanobenzyl)-6-[(5-methylpyridin-2-yl)methoxy]-1H-benzimidazol-2-yl}cyclohexanecarboxylic acid was purified by chiral SFC on (CHIRALCEL OJ-H 5 µm 250×20 mm) mobile phase (65% CO$_2$, 35% EtOH) to yield the title compound as the first eluting isomer. MS (ESI): mass calcd. for C$_{29}$H$_{28}$N$_4$O$_3$, 480.22; m/z found, 481.2 [M+H]$^+$. $^1$H NMR (500 MHz, CD$_3$OD) δ 8.44 (s, 1H), 8.31-8.24 (m, 1H), 7.65-7.58 (m, 3H), 7.55 (d, J=8.8 Hz, 1H), 7.37 (d, J=8.0 Hz, 1H), 7.23 (d, J=8.3 Hz, 2H), 6.95 (dd, J=8.8, 2.4 Hz, 1H), 6.76 (d, J=2.4 Hz, 1H), 5.59 (d, J=17.8 Hz, 1H), 5.52 (d, J=17.8 Hz, 1H), 5.14-5.02 (m, 2H), 3.60-3.54 (m, 1H), 2.83-2.74 (m, 1H), 2.43-2.37 (m, 1H), 2.36-2.31 (m, 3H), 2.05-1.94 (m, 1H), 1.94-1.68 (m, 4H), 1.52-1.38 (m, 2H).

Example 40 racemic cis-2-{1-(4-Bromobenzyl)-6-[(1-methyl-1H-pyrazol-3-yl)methoxy]-1H-benzimidazol-2-yl}cyclohexanecarboxylic acid as the TFA salt

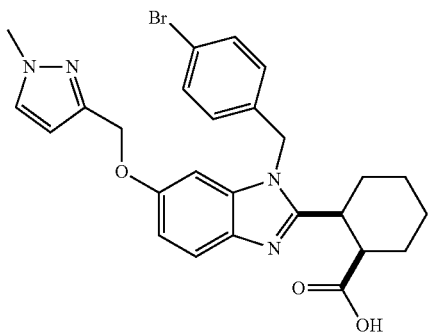

The title compound was prepared in a manner analogous to that in Example 1 substituting Intermediate L in Step A. MS (ESI): mass calcd. for C$_{26}$H$_{27}$BrN$_4$O$_3$, 522.13; m/z found, 523.1 [M+H]$^+$. $^1$H NMR (500 MHz, CD$_3$OD) δ 7.68 (d, J=9.0, 1H), 7.56-7.52 (m, 2H), 7.50 (d, J=2.2, 1H), 7.26 (dd, J=9.0, 2.3, 1H), 7.18 (d, J=2.2, 1H), 7.04 (d, J=8.5, 2H), 6.22 (d, J=2.3, 1H), 5.76 (app q, J=17.3, 2H), 5.12-5.00 (m, 2H), 3.81 (s, 3H), 3.62 (dt, J=12.1, 3.7, 1H), 2.93-2.89 (m, 1H), 2.31 (dt, J=12.3, 8.0, 1H), 2.26-2.11 (m, 1H), 2.10-2.01 (m, 1H), 2.01-1.89 (m, 1H), 1.79 (td, J=13.1, 4.5, 1H), 1.73-1.61 (m, 1H), 1.62-1.38 (m, 2H).

Example 41 racemic trans-2-{1-(4-Bromobenzyl)-6-[(1-methyl-1H-pyrazol-3-yl)methoxy]-1H-benzimidazol-2-yl}cyclohexanecarboxylic acid as the TFA salt

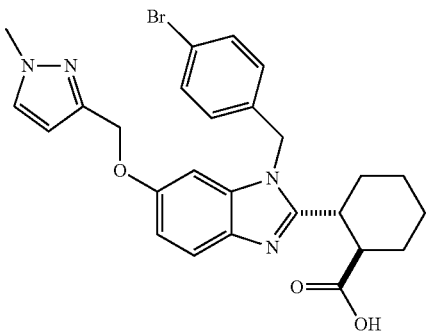

The title compound was prepared in a manner analogous to that in Example 1 substituting Intermediate L in Step A and trans-hexahydroisobenzofuran-1,3-dione in Step C. MS (ESI): mass calcd. for C$_{26}$H$_{27}$BrN$_4$O$_3$, 522.13; m/z found, 523.1 [M+H]$^+$. $^1$H NMR (500 MHz, CD$_3$OD) δ 7.64 (d, J=9.0, 1H), 7.60-7.49 (m, 3H), 7.34 (d, J=2.2, 1H), 7.29-7.17 (m, 3H), 6.28 (d, J=2.2, 1H), 5.86 (d, J=16.6, 1H), 5.73 (d, J=16.7, 1H), 5.09 (s, 2H), 3.84 (s, 3H), 3.54 (td, J=12.1, 3.5, 1H), 2.99 (td, J=11.7, 3.6, 1H), 2.37 (dd, J=13.0, 3.1, 1H), 1.99-1.86 (m, 1H), 1.87-1.77 (m, 1H), 1.77-1.68 (m, 1H), 1.68-1.43 (m, 3H), 1.42-1.24 (m, 1H).

Example 42

2-({1-(4-Bromobenzyl)-6-[(1-methyl-1H-pyrazol-3-yl)methoxy]-1H-benzimidazol-2-yl}methyl)-2-ethylbutanoic acid as the TFA salt

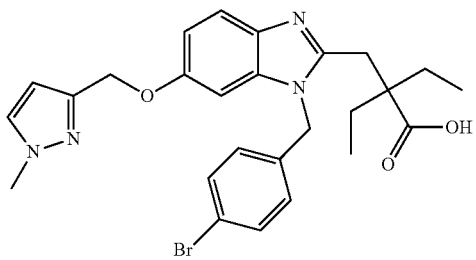 [SMILES: CCC(CC)(Cc1nc2ccc(OCc3ccn(C)n3)cc2n1Cc1ccc(Br)cc1)C(=O)O]

The title compound was prepared in a manner analogous to that in Example 1 substituting Intermediate L in Step A and 3,3-diethyldihydrofuran-2,5-dione in Step C. MS (ESI): mass calcd. for C$_{26}$H$_{29}$BrN$_4$O$_3$, 524.14; m/z found, 525.1 [M+H]$^+$. $^1$H NMR (600 MHz, CD$_3$OD) δ 7.71 (dd, J=8.6, 0.8, 1H), 7.56-7.53 (m, 2H), 7.52 (d, J=2.2, 1H), 7.31-7.24 (m, 2H), 7.14 (d, J=8.5, 2H), 6.25 (d, J=2.3, 1H), 5.75 (s, 2H), 5.07 (s, 2H), 3.83 (s, 3H), 3.39 (s, 2H), 1.88-1.69 (m, 4H), 0.88 (t, J=7.5, 6H).

Example 43

2-Ethyl-2-({6-[(1-methyl-1H-pyrazol-3-yl)methoxy]-1-(4-piperidin-1-ylbenzyl)-1H-benzimidazol-2-yl}methyl)butanoic acid

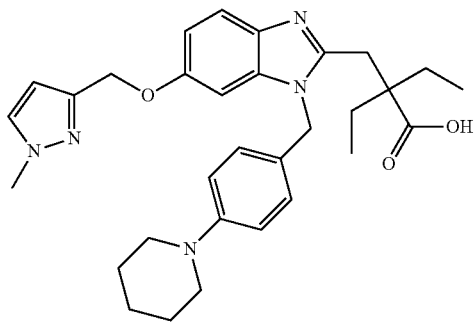 [SMILES: CCC(CC)(Cc1nc2ccc(OCc3ccn(C)n3)cc2n1Cc1ccc(N2CCCCC2)cc1)C(=O)O]

The title compound was prepared from 2-({1-(4-Bromobenzyl)-6-[(1-methyl-1H-pyrazol-3-yl)methoxy]-1H-benzimidazol-2-yl}methyl)-2-ethylbutanoic acid using piperidine in the conditions for Example 152. MS (ESI): mass calcd. for $C_{31}H_{39}N_5O_3$, 529.31; m/z found, 530.3 [M+H]$^+$. $^1$H NMR (500 MHz, CD$_3$OD) δ 7.70 (d, J=9.0, 1H), 7.55 (d, J=2.2, 1H), 7.35-7.27 (m, 5H), 7.25 (dd, J=9.0, 2.3, 1H), 6.31 (d, J=2.3, 1H), 5.75 (s, 2H), 5.05 (s, 2H), 3.86 (s, 3H), 3.45-3.33 (m, 6H), 1.91-1.64 (m, 10H), 0.87 (t, J=7.5, 6H).

Example 44 racemic cis-2-{6-[(1-Methyl-1H-pyrazol-3-yl)methoxy]-1-[4-(trifluoromethoxy)benzyl]-1H-benzimidazol-2-yl}cyclohexanecarboxylic acid

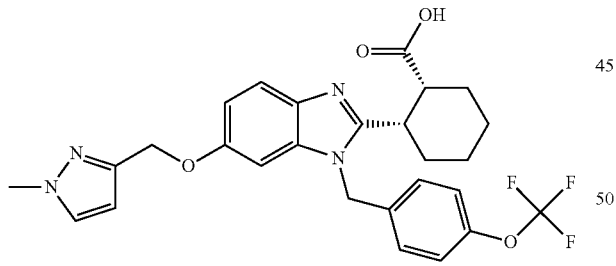

The title compound was prepared using analogous conditions described in Example 1 using Intermediate L and (4-(trifluoromethoxy)phenyl)methanamine in Step A and using 5-((1-methyl-1H-pyrazol-3-yl)methoxy)-N$^1$-(4-(trifluoromethoxy)benzyl)benzene-1,2-diamine in Step C. MS (ESI): mass calcd. for $C_{27}H_{27}F_3N_4O_4$, 528.20; m/z found, 529.2 [M+H]$^+$. $^1$H NMR (400 MHz, CD$_3$OD) δ 7.55-7.51 (m, 1H), 7.48 (d, J=2.2, 1H), 7.25-7.18 (m, 4H), 6.93-6.85 (m, 2H), 6.25 (d, J=2.2, 1H), 5.56 (d, J=17.2 Hz, 1H), 5.50 (d, J=17.2 Hz, 1H), 5.01-4.94 (m, 2H), 3.82 (s, 3H), 3.60-3.47 (m, 1H), 2.85-2.70 (m, 1H), 2.39-2.30 (m, 1H), 2.07-1.96 (m, 1H), 1.96-1.68 (m, 4H), 1.52-1.30 (m, 2H).

Example 45

(1R*,2S*)-2-{6-[(1-Methyl-1H-pyrazol-3-yl)methoxy]-1-[4-(trifluoromethoxy)benzyl]-1H-benzimidazol-2-yl}cyclohexanecarboxylic acid

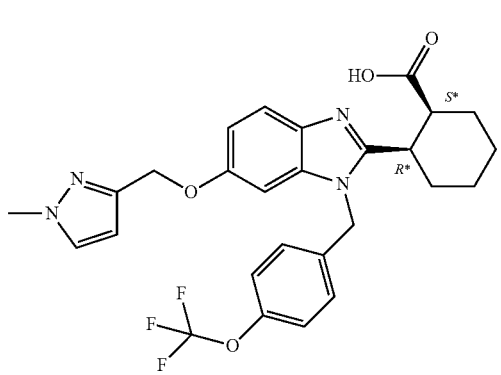 [SMILES: Cn1ccc(COc2ccc3nc([C@@H]4CCCC[C@@H]4C(=O)O)n(Cc4ccc(OC(F)(F)F)cc4)c3c2)n1]

racemic cis-2-{6-[(1-Methyl-1H-pyrazol-3-yl)methoxy]-1-[4-(trifluoromethoxy)benzyl]-1H-benzimidazol-2-yl}cyclohexanecarboxylic acid was purified by chiral SFC (CHIRALCEL OD-H 5 μm 250×20 mm) mobile phase (75% CO$_2$, 25% MeOH) to provide the title compound as the first eluting isomer. MS (ESI): mass calcd. for $C_{27}H_{27}F_3N_4O_4$, 528.2; m/z found, 529.2 [M+H]$^+$.

Example 46

1-({1-(4-Bromobenzyl)-6-[(1-methyl-1H-pyrazol-3-yl)methoxy]-1H-benzimidazol-2-yl}methyl)cyclopentanecarboxylic acid as the TFA salt

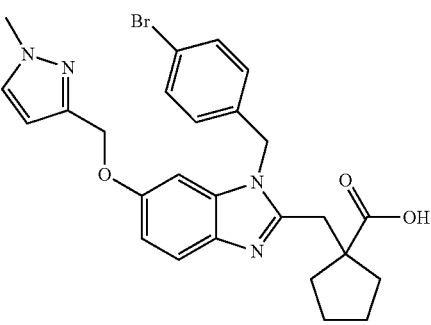 [SMILES: Cn1ccc(COc2ccc3nc(CC4(C(=O)O)CCCC4)n(Cc4ccc(Br)cc4)c3c2)n1]

The title compound was prepared in a manner analogous to that in Example 1 substituting Intermediate L in Step A and 2-oxaspiro[4.4]nonane-1,3-dione in Step C. MS (ESI): mass calcd. for $C_{26}H_{27}BrN_4O_3$, 522.13; m/z found, 523.1 [M+H]. $^1$H NMR (600 MHz, CD$_3$OD) δ 7.68 (d, J=8.9, 1H), 7.57-7.52 (m, 2H), 7.51 (d, J=2.2, 1H), 7.24 (dt, J=6.7, 2.1, 2H), 7.13 (d, J=8.6, 2H), 6.25 (d, J=2.3, 1H), 5.73 (s, 2H), 5.07 (s, 2H), 3.83 (s, 3H), 3.48 (s, 2H), 2.30 (t, J=7.6, 2H), 1.87-1.68 (m, 6H).

Example 47 racemic cis-2-{1-(4-Cyanobenzyl)-6-[(1-methyl-1H-pyrazol-3-yl)methoxy]-1H-benzimidazol-2-yl}cyclohexanecarboxylic acid as the TFA salt

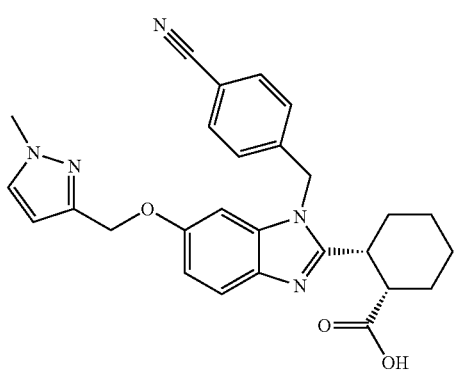 [SMILES: Cn1ccc(COc2ccc3nc([C@@H]4CCCC[C@@H]4C(=O)O)n(Cc4ccc(C#N)cc4)c3c2)n1]

The title compound was prepared in a manner analogous to that in Example 1 substituting Intermediate L and 4-(aminomethyl)benzonitrile in Step A and cis-cyclohexanedicarboxylic anhydride in Step C. MS (ESI): mass calcd. for $C_{27}H_{27}N_5O_3$, 469.21; m/z found, 470.25 [M+H]$^+$. $^1$H NMR (500 MHz, CD$_3$OD) δ7.77-7.72 (m, 2H), 7.72-7.68 (d, J=9.0, 1H), 7.54-7.47 (d, J=2.3, 1H), 7.32-7.25 (m, 3H), 7.20-7.13 (d, J=2.2, 1H), 6.25-6.21 (d, J=2.3, 1H), 5.98-5.91 (d, 1H), 5.89-5.83 (d, 1H), 5.08-4.99 (q, 2H), 3.86-3.78 (s, 3H), 3.67-3.59 (dt, J=12.1, 3.9, 1H), 2.91-2.86 (dd, J=8.2, 3.6, 1H), 2.38-2.26 (m, 1H), 2.23-2.11 (m, 1H), 2.11-2.05 (m, 1H), 2.02-1.94 (m, 1H), 1.85-1.74 (m, 1H), 1.72-1.65 (m, 1H), 1.63-1.48 (m, 2H).

Example 48 racemic trans-2-{1-(4-Cyanobenzyl)-6-[(1-methyl-1H-pyrazol-3-yl)methoxy]-1H-benzimidazol-2-yl}cyclohexanecarboxylic acid as the TFA salt

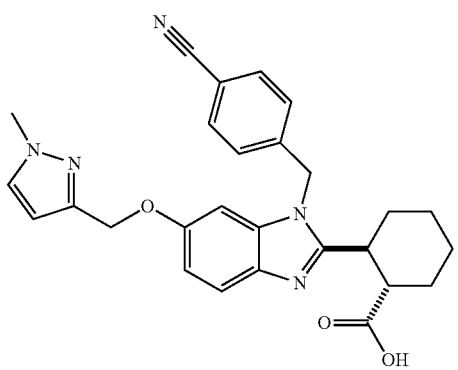

The title compound was prepared in a manner analogous to that in Example 1 substituting Intermediate L and 4-(aminomethyl)benzonitrile in Step A and trans-cyclohexanedicarboxylic anhydride in Step C. MS (ESI): mass calcd. for $C_{27}H_{27}N_5O_3$, 469.21; m/z found, 470.1 [M+H]$^+$. $^1$H NMR (400 MHz, CD$_3$OD) δ 7.80-7.59 (m, 2H), 7.59-7.41 (m, 2H), 7.41-7.24 (m, 2H), 6.96-6.80 (m, 2H), 6.37-6.17 (d, J=2.2, 1H), 5.67-5.53 (s, 2H), 5.04-4.96 (s, 2H), 3.95-3.71 (m, 3H), 3.18-3.06 (td, J=12.0, 11.5, 3.5, 1H), 3.07-2.92 (m, 1H), 2.28-2.15 (d, J=9.6, 1H), 1.90-1.81 (d, J=9.3, 1H), 1.81-1.69 (d, J=13.1, 1H), 1.69-1.59 (d, J=3.2, 1H), 1.58-1.41 (m, 4H).

Example 49

2-({1-(4-Cyanobenzyl)-6-[(1-methyl-1H-pyrazol-3-yl)methoxy]-1H-benzimidazol-2-yl}methyl)-2-ethylbutanoic acid as the TFA salt

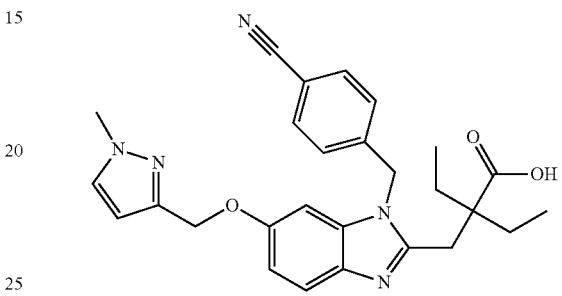

The title compound was prepared in a manner analogous to that in Example 1 Intermediate L and 4-(aminomethyl)benzonitrile in Step A and 3,3-diethyldihydrofuran-2,5-dione in Step C. MS (ESI): mass calcd. for $C_{27}H_{29}N_5O_3$, 471.23; m/z found, 472.2 [M+H]$^+$. $^1$H NMR (400 MHz, CD$_3$OD) δ 7.80-7.69 (m, 3H), 7.57-7.48 (d, J=2.2, 1H), 7.40-7.34 (m, 2H), 7.31-7.25 (dd, J=9.0, 2.3, 1H), 7.23-7.20 (d, J=2.4, 1H), 6.29-6.16 (d, J=2.3, 1H), 5.96-5.74 (s, 2H), 5.13-5.01 (s, 2H), 3.90-3.76 (s, 3H), 3.47-3.36 (s, 2H), 1.88-1.64 (tt, J=14.3, 7.2, 4H), 0.97-0.76 (t, J=7.4, 6H).

Example 50

2-Ethyl-2-({6-[(1-methyl-1H-pyrazol-3-yl)methoxy]-1-[4-(trifluoromethoxy)benzyl]-1H-benzimidazol-2-yl}methyl)butanoic acid

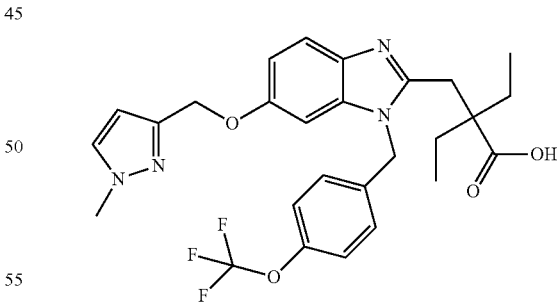

The title compound was prepared using analogous conditions described in Example 1 using Intermediate L and (4-(trifluoromethoxy)phenyl)methanamine in Step A and 3,3-diethyldihydrofuran-2,5-dione in Step C. MS (ESI): mass calcd. for $C_{27}H_{29}F_3N_4O_4$, 530.21; m/z found, 531.2 [M+H]$^+$. $^1$H NMR (400 MHz, CDCl$_3$) δ 7.62 (d, J=8.8, 1H), 7.32 (d, J=2.2, 1H), 7.17 (t, J=9.3, 2H), 7.14-6.99 (m, 3H), 6.91 (d, J=2.2, 1H), 6.30 (d, J=2.2, 1H), 5.32 (s, 2H), 5.08 (s, 2H), 3.86 (s, 3H), 2.97 (s, 2H), 1.74-1.48 (m, 4H), 0.80 (t, J=7.4, 6H).

Example 51 racemic cis-2-{1-[2-Fluoro-4-(trifluoromethoxy)benzyl]-6-[(1-methyl-1H-pyrazol-3-yl)methoxy]-1H-benzimidazol-2-yl}cyclohexanecarboxylic acid

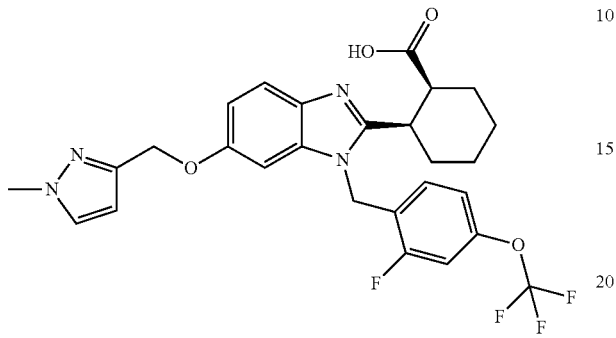

The title compound was prepared using analogous conditions described in Example 1 using Intermediate L and (2-fluoro-4-(trifluoromethoxy)phenyl)methanamine in Step A. MS (ESI): mass calcd. for $C_{27}H_{26}F_4N_4O_4$, 546.20; m/z found, 547.2 [M+H]$^+$. $^1$H NMR (500 MHz, CD$_3$OD) δ 7.54 (d, J=8.7, 1H), 7.50 (d, J=2.2, 1H), 7.22 (d, J=10.5, 1H), 7.01 (d, J=8.6, 1H), 6.97-6.87 (m, 3H), 6.27 (d, J=2.2, 1H), 5.59 (d, J=17.5, 1H), 5.53 (d, J=17.4, 1H), 5.00 (s, 2H), 3.83 (s, 3H), 3.64-3.55 (m, 1H), 2.86-2.77 (m, 1H), 2.46-2.33 (m, 1H), 2.05-1.72 (m, 5H), 1.55-1.39 (m, 2H).

Example 52

(1S*,2R*)-2-{1-[2-Fluoro-4-(trifluoromethoxy)benzyl]-6-[(1-methyl-1H-pyrazol-3-yl)methoxy]-1H-benzimidazol-2-yl}cyclohexanecarboxylic acid

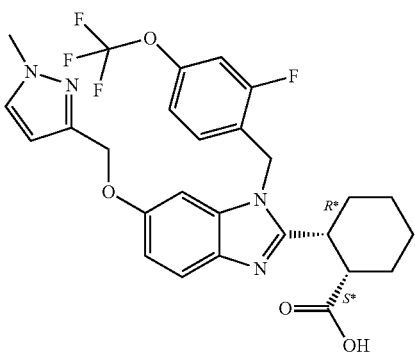 [SMILES: Cn1ccc(COc2ccc3nc([C@@H]4CCCC[C@@H]4C(=O)O)n(Cc4ccc(OC(F)(F)F)cc4F)c3c2)n1]

racemic cis-2-{1-[2-Fluoro-4-(trifluoromethoxy)benzyl]-6-[(1-methyl-1H-pyrazol-3-yl)methoxy]-1H-benzimidazol-2-yl}cyclohexanecarboxylic acid was purified by chiral SFC (CHIRALCEL OD-H 5 μm 250×20 mm) mobile phase (80% CO$_2$, 20% MeOH) to provide the title compound as the first eluting isomer. MS (ESI): mass calcd. for $C_{27}H_{26}F_4N_4O_4$, 546.19; m/z found, 576.2 [M+H]$^+$.

Example 53

(1R*,2S*)-2-(1-(2-Fluoro-4-(trifluoromethoxy)benzyl)-6-((1-methyl-1H-pyrazol-3-yl)methoxy)-1H-benzo[d]imidazol-2-yl)cyclohexanecarboxylic acid Method 1:

racemic cis-2-{1-[2-Fluoro-4-(trifluoromethoxy)benzyl]-6-[(1-methyl-1H-pyrazol-3-yl)methoxy]-1H-benzimidazol-2-yl}cyclohexanecarboxylic acid was purified by chiral SFC (CHIRALCEL OD-H 5 μm 250×20 mm) mobile phase (80% CO$_2$, 20% MeOH) to provide the title compound as the second eluting isomer. MS (ESI): mass calcd. for $C_{27}H_{26}F_4N_4O_4$, 546.19; m/z found, 547.2 [M+H]$^+$. $^1$H NMR (500 MHz, CD$_3$OD) δ 7.54 (d, J=8.7, 1H), 7.50 (d, J=2.2, 1H), 7.22 (d, J=10.5, 1H), 7.01 (d, J=8.8, 1H), 6.97-6.88 (m, 3H), 6.27 (d, J=2.2, 1H), 5.60 (d, J=17.4, 1H), 5.53 (d, J=17.5, 1H), 5.00 (s, 2H), 3.83 (s, 3H), 3.64-3.54 (m, 1H), 2.89-2.78 (m, 1H), 2.45-2.31 (m, 1H), 2.05-1.72 (m, 5H), 1.55-1.39 (m, 2H).

Method 2:

Step A: 3-((3-Fluoro-4-nitrophenoxy)methyl)-1-methyl-1H-pyrazole

A solution of 3-fluoro-4-nitrophenol (50.0 g, 0.31 mol), 3-(chloromethyl)-1-methyl-1H-pyrazole hydrochloride (52.1 g, 0.31 mol), powdered potassium carbonate (53.3 g, 0.38 mol), potassium iodide (52.8 g, 0.32 mol), and acetonitrile (900 mL) was stirred at 60° Celsius for 8 h. The reaction was cooled to RT and concentrated to dryness. The residue was partitioned between H$_2$O (500 mL), sat. NaHCO$_3$ (200 mL), and ethyl acetate (900 mL). The organic layer was separated, dried with MgSO$_4$, filtered and concentrated to dryness. The resulting residue was recrystallized from ethanol (250 mL) and H$_2$O (250 mL). The solid was collected by filtration and rinsed with a H$_2$O/ethanol (2:1, 225 mL) followed by hexanes (250 mL) yielding the title compound as a tan solid (70.7 g, 90.2%). MS (ESI): mass calcd. for $C_{11}H_{10}FN_3O_3$, 251.1; m/z found, 252.0 [M+H]$^+$. $^1$H NMR (400 MHz, CDCl$_3$) δ 8.13-8.03 (m, 1H), 7.42-7.32 (d, J=2.2, 1H), 6.93-6.87 (m, 1H), 6.87-6.84 (d, J=1.6, 1H), 6.36-6.29 (d, J=2.2, 1H), 5.18-5.10 (s, 2H), 4.00-3.87 (s, 3H).

Step B: N-(2-Fluoro-4-(trifluoromethoxy)benzyl)-5-((1-methyl-1H-pyrazol-3-yl)methoxy)-2-nitroaniline A solution of 3-((3-fluoro-4-nitrophenoxy)methyl)-1-methyl-1H-pyrazole (70.0 g, 0.28 mol), (2-fluoro-4-(trifluoromethoxy)phenyl)methanamine (58.3 g, 0.28 mol), DIPEA (63.1 mL, 0.36 mol) and acetonitrile (350 mL) was stirred at 80° Celsius for 16 h. The reaction was cooled to RT, concentrated to dryness, and the resulting residue was recrystallized from ethanol (350 mL) and H$_2$O (350 mL). The solid was collected by filtration and rinsed with a mixture of H$_2$O/ethanol (3:1, 200 mL) followed by hexanes (2×300 mL) yielding the title compound as a yellow solid (116.3 g, 94.7%). MS (ESI): mass calcd. for C$_{19}$H$_{16}$F$_4$N$_4$O$_4$, 440.1; m/z found, 441.0 [M+H]$^+$. $^1$H NMR (600 MHz, CDCl$_3$) δ 8.68-8.52 (m, 1H), 8.20-8.14 (d, J=9.5, 1H), 7.39-7.34 (m, 1H), 7.34-7.31 (d, J=2.2, 1H), 7.06-6.97 (d, J=9.8, 2H), 6.42-6.33 (dd, J=9.5, 2.5, 1H), 6.33-6.24 (m, 2H), 5.09-5.01 (s, 2H), 4.60-4.52 (d, J=5.9, 2H), 3.93-3.85 (s, 3H).

Step C: N$^1$-(2-Fluoro-4-(trifluoromethoxy)benzyl)-5-((1-methyl-1H-pyrazol-3-yl)methoxy)benzene-1,2-diamine In a high pressure reactor a solution of N-(2-fluoro-4-(trifluoromethoxy)benzyl)-5-((1-methyl-1H-pyrazol-3-yl)methoxy)-2-nitroaniline (80.0 g, 0.18 mol), 5% Pt/C (50% H$_2$O, Johnson Matthey B102022-5) (7.1 g, 0.91 mmol) and ethyl acetate (800 mL) was filled twice with N$_2$ (60 psi) then twice with H$_2$ (60 psi). The flask was then filled with H$_2$ (60 psi) and let stir at RT 15 h. The reaction mixture was filtered (zapcap brand filter), the solid was rinsed with EtOAc (2×200 mL). The filtrate was concentrated to dryness to afford the title compound as a brown oil (74.5 g, 99.5%). This material was used without further purification. MS (ESI): mass calcd. for C$_{19}$H$_{18}$F$_4$N$_4$O$_2$, 410.1; m/z found, 411.1 [M+H]$^+$. $^1$H NMR (600 MHz, CDCl$_3$) δ 7.42-7.35 (m, 1H), 7.33-7.29 (d, J=2.2, 1H), 7.01-6.94 (d, J=9.2, 1H), 6.71-6.66 (d, J=8.3, 1H), 6.37-6.31 (dd, J=8.3, 2.7, 1H), 6.31-6.26 (m, 1H), 4.98-4.94 (s, 1H), 4.41-4.33 (s, 1H), 3.93-3.85 (s, 2H), 3.35-2.72 (s, 1H).

Step D: (1R*,2S*)-2-(1-(2-Fluoro-4-(trifluoromethoxy)benzyl)-6-((1-methyl-1H-pyrazol-3-yl)methoxy)-1H-benzo[d]imidazol-2-yl)cyclohexanecarboxylic acid To a solution of N$^1$-(2-fluoro-4-(trifluoromethoxy)benzyl)-5-((1-methyl-1H-pyrazol-3-yl)methoxy)benzene-1,2-diamine (74.5 g, 0.18 mol) in ethanol (750 mL) was added a solution of racemic cis-3-hydroxyhexahydroisobenzofuran-1(3H)-one (28.4 g, 0.18 mol) and sodium sulfite (46.7 g, 0.36 mol) in H$_2$O (750 mL). The reaction mixture was left open to air and stirred vigorously at RT. After 65 h, saturated sodium bicarbonate (600 mL) was added and the organic solvents were concentrated to dryness. The resulting suspension was partitioned between TBME (1.5 L) and H$_2$O (1.5 L). The aqueous layer was partitioned between EtOAc (1.5 L) and HCl was added (160 mL, 6 M). The organic layer was separated and the aqueous was further extracted with ethyl acetate (500 mL). The combined organic layers were dried with MgSO$_4$, filtered and concentrated to dryness. The resulting residue was dissolved in ethanol (450 mL) and H$_2$O (100 mL), seeded (500 mg, 0.9 mmol) and stirred at room temperature for 1 h. H$_2$O (300 mL) was then added portion wise over 30 min. The precipitate was filtered, rinsed with H$_2$O/ethanol (2:1, 2×120 mL) and hexanes (2×200 mL) yielding the title compound as a light pink solid (59.8 g, 60.2%). The racemic material was separated into its constituent enantiomers through chiral stationary phase chromatography (stationary phase 600 g of Chiralpak IC, diameter: 110 mm, detector: Knauer superpreparative cell (0.5 mm), temperature: 35° Celsius, eluent: 0-20 min 40% heptane, 40% ethanol, 20% DCM (500 ml/min) (there was 0.10 v/v % acetic acid added to the eluents) to provide the title compound. MS (ESI): mass calcd. for C$_{27}$H$_{26}$F$_4$N$_4$O$_4$, 546.2; m/z found, 547.0 [M+H]$^+$. $^1$H NMR (600 MHz, CDCl$_3$) δ 7.63-7.59 (d, J=8.9, 1H), 7.34-7.30 (d, J=2.2, 1H), 7.11-7.06 (m, 1H), 7.06-7.02 (dd, J=8.9, 2.3, 1H), 6.95-6.90 (d, J=8.6, 1H), 6.88-6.84 (d, J=2.3, 1H), 6.81-6.74 (m, 1H), 6.31-6.28 (d, J=2.2, 1H), 5.38-5.28 (s, 2H), 5.09-5.04 (s, 2H), 3.89-3.84 (s, 3H), 3.24-3.14 (d, J=11.5, 1H), 3.08-3.02 (d, J=3.0, 1H), 2.65-2.51 (m, 1H), 1.90-1.78 (m, 2H), 1.78-1.70 (m, 1H), 1.69-1.58 (d, J=14.2, 2H), 1.56-1.39 (m, 2H).

Example 54 racemic trans-2-{6-[(1-Methyl-1H-pyrazol-3-yl)methoxy]-1-[4-(trifluoromethoxy)benzyl]-1H-benzimidazol-2-yl}cyclohexanecarboxylic acid

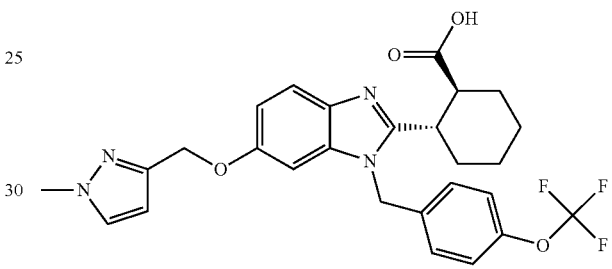

The title compound was prepared using analogous conditions described in Example 1 using Intermediate L and (4-(trifluoromethoxy)phenyl)methanamine in Step A and racemic trans-hexahydroisobenzofuran-1,3-dione in Step C. MS (ESI): mass calcd. for C$_{27}$H$_{27}$F$_3$N$_4$O$_4$, 528.20; m/z found, 529.2 [M+H]$^+$. $^1$H NMR (400 MHz, CDCl$_3$) δ 7.51 (d, J=8.8, 1H), 7.28 (d, J=2.2, 1H), 7.13 (s, 4H), 6.91 (dd, J=8.8, 2.2, 1H), 6.77 (d, J=2.2, 1H), 6.25 (d, J=2.2, 1H), 5.49 (d, J=17.0, 1H), 5.35-5.26 (m, 1H), 5.01 (s, 2H), 3.84 (d, 3H), 3.11-2.96 (m, 2H), 2.18-2.08 (m, 1H), 1.77-1.38 (m, 5H), 1.25-1.10 (m, 2H).

Example 55 racemic cis-2-{1-[3-Fluoro-4-(trifluoromethoxy)benzyl]-6-[(1-methyl-1H-pyrazol-3-yl)methoxy]-1H-benzimidazol-2-yl}cyclohexanecarboxylic acid

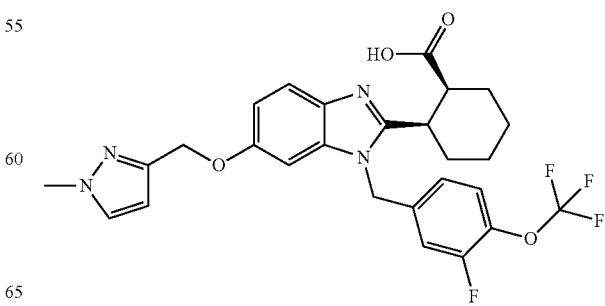

The title compound was prepared using analogous conditions described in Example 1 using Intermediate L and (3-fluoro-4-(trifluoromethoxy)phenyl)methanamine in Step A. MS (ESI): mass calcd. for C<sub>27</sub>H<sub>26</sub>F<sub>4</sub>N<sub>4</sub>O<sub>4</sub>, 546.20; m/z found, 547.3 [M+H]$^+$. $^1$H NMR (400 MHz, CD$_3$OD) δ 7.54 (d, J=8.7, 1H), 7.48 (d, J=2.1, 1H), 7.36 (t, J=8.0, 1H), 7.11 (d, J=10.9, 1H), 7.00 (d, J=8.4, 1H), 6.95-6.86 (m, 2H), 6.25 (d, J=2.2, 1H), 5.58 (d, J=17.6, 1H), 5.49 (d, J=17.5, 1H), 4.99 (s, 2H), 3.82 (s, 3H), 3.64-3.55 (m, 1H), 2.85-2.75 (m, 1H), 2.44-2.33 (m, 1H), 2.07-1.69 (m, 5H), 1.53-1.39 (m, 2H).

Example 56

2-Ethyl-2-({1-[2-fluoro-4-(trifluoromethoxy)benzyl]-6-[(1-methyl-1H-pyrazol-3-yl)methoxy]-1H-benzimidazol-2-yl}methyl)butanoic acid

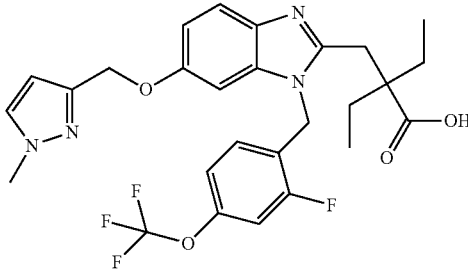 [SMILES: CCC(CC)(Cc1nc2ccc(OCc3ccn(C)n3)cc2n1Cc1ccc(OC(F)(F)F)cc1F)C(=O)O]

The title compound was prepared using analogous conditions described in Example 1 using Intermediate L and (2-fluoro-4-(trifluoromethoxy)phenyl)methanamine in Step A and 3,3-diethyldihydrofuran-2,5-dione in Step C. MS (ESI): mass calcd. for C<sub>27</sub>H<sub>28</sub>F<sub>4</sub>N<sub>4</sub>O<sub>4</sub>, 548.21; m/z found, 549.2 [M+H]$^+$. $^1$H NMR (500 MHz, CD$_3$OD) δ 7.52 (d, J=8.8, 1H), 7.50 (d, J=2.1, 1H), 7.20 (d, J=10.4, 1H), 7.03 (d, J=8.7, 1H), 6.98 (d, J=2.2, 1H), 6.92 (dd, J=8.8, 2.3, 1H), 6.85 (t, J=8.5, 1H), 6.28 (d, J=2.2, 1H), 5.57 (s, 2H), 5.01 (s, 2H), 3.84 (s, 3H), 3.07 (s, 2H), 1.89-1.72 (m, 4H), 0.86 (t, J=7.4, 6H).

Example 57

2-Ethyl-2-({1-[3-fluoro-4-(trifluoromethoxy)benzyl]-6-[(1-methyl-1H-pyrazol-3-yl)methoxy]-1H-benzimidazol-2-yl}methyl)butanoic acid

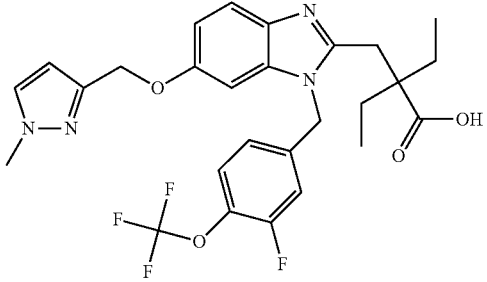 [SMILES: CCC(CC)(Cc1nc2ccc(OCc3ccn(C)n3)cc2n1Cc1ccc(OC(F)(F)F)c(F)c1)C(=O)O]

The title compound was prepared using analogous conditions described in Example 1 using Intermediate L and (3-fluoro-4-(trifluoromethoxy)phenyl)methanamine in Step A and 3,3-diethyldihydrofuran-2,5-dione in Step C. MS (ESI): mass calcd. for C<sub>27</sub>H<sub>28</sub>F<sub>4</sub>N<sub>4</sub>O<sub>4</sub>, 548.21; m/z found, 549.1 [M+H]$^+$. $^1$H NMR (500 MHz, CD$_3$OD) δ 7.53 (d, J=8.8, 1H), 7.49 (d, J=2.2, 1H), 7.36 (t, J=7.7, 1H), 7.00 (dd, J=10.9, 2.0, 1H), 6.96 (d, J=2.2, 1H), 6.92 (dd, J=8.6, 2.2, 1H), 6.89 (d, J=8.5, 1H), 6.27 (d, J=2.3, 1H), 5.56 (s, 2H), 5.01 (s, 2H), 3.83 (s, 3H), 3.04 (s, 2H), 1.87-1.71 (m, 4H), 0.85 (t, J=7.5, 6H).

Example 58

2-({1-(4-Bromo-2-fluorobenzyl)-6-[(1-methyl-1H-pyrazol-3-yl)methoxy]-1H-benzimidazol-2-yl}methyl)-2-ethylbutanoic acid

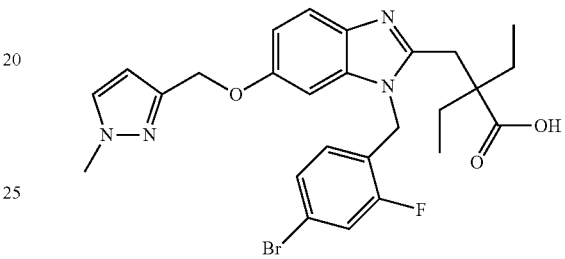

The title compound was prepared using analogous conditions described in Example 1 using Intermediate L and (4-bromo-2-fluorophenyl)methanamine in Step A and 3,3-diethyldihydrofuran-2,5-dione in Step C. MS (ESI): mass calcd. for C<sub>26</sub>H<sub>28</sub>BrFN<sub>4</sub>O<sub>3</sub>, 542.13; m/z found, 543.2 [M+H]$^+$. $^1$H NMR (600 MHz, CD$_3$OD) δ 7.52 (d, J=8.9, 1H), 7.51 (d, J=2.3, 1H), 7.42 (dd, J=9.8, 1.9, 1H), 7.24 (dd, J=8.3, 1.6, 1H), 6.96 (d, J=2.3, 1H), 6.92 (dd, J=8.8, 2.4, 1H), 6.66 (t, J=8.2, 1H), 6.27 (d, J=2.3, 1H), 5.50 (s, 2H), 5.01 (s, 2H), 3.88-3.77 (m, 3H), 3.09 (d, J=20.2, 2H), 1.82 (q, J=7.3, 4H), 0.86 (t, J=7.5, 6H).

Example 59 racemic cis-2-{1-(4-Bromobenzyl)-4-fluoro-6-[(5-methylpyridin-2-yl)methoxy]-1H-benzimidazol-2-yl}cyclohexanecarboxylic acid

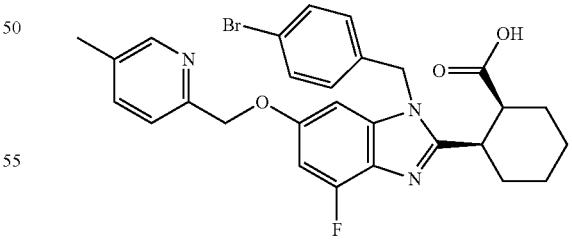

The title compound was prepared in a manner analogous to that in Example 1 using 2-((3,5-difluoro-4-nitrophenoxy)methyl)-5-methylpyridine in Step A and cis-hexahydroisobenzofuran-1,3-dione in Step C. MS (ESI): mass calcd. for C<sub>28</sub>H<sub>27</sub>BrFN<sub>3</sub>O<sub>3</sub>, 551.12; m/z found, 552 [M+H]$^+$. $^1$H NMR (600 MHz, CDCl$_3$) δ 8.24 (s, 1H), 7.45 (dd, J=8.0, 1.5, 1H), 7.32 (d, J=8.4, 2H), 7.29-7.26 (m, 1H), 6.80 (d, J=8.4, 2H), 6.60 (dd, J=11.5, 1.7, 1H), 6.35 (d, J=1.2, 1H), 5.17 (q, J=17.0, 2H), 5.04 (dd, J=38.8, 13.5, 2H), 3.33 (s, 1H), 2.88 (s, 1H), 2.61 (d, J=7.0, 1H), 2.32 (s, 3H), 1.87 (dd, J=8.8, 3.9, 1H), 1.80-1.59 (m, 4H), 1.45 (d, J=23.7, 1H), 1.37 (td, J=9.1, 4.3, 1H).

Example 60

3-{1-(4-Bromobenzyl)-4-fluoro-6-[(5-methylpyridin-2-yl)methoxy]-1H-benzimidazol-2-yl}-2,2-dimethylpropanoic acid

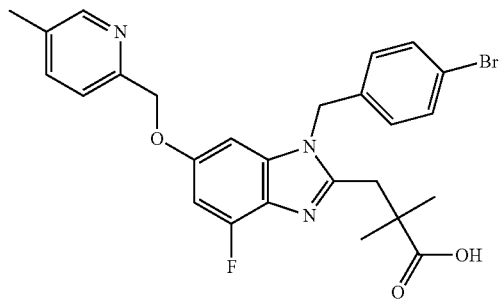 [SMILES: Cc1ccc(COc2cc(F)c3nc(CC(C)(C)C(=O)O)n(Cc4ccc(Br)cc4)c3c2)nc1]

The title compound was prepared in a manner analogous to that in Example 1 using 2-((3,5-difluoro-4-nitrophenoxy)methyl)-5-methylpyridine in Step A and 3,3-dimethyldihydrofuran-2,5-dione in Step C. MS (ESI): mass calcd. for $C_{26}H_{25}BrFN_3O_3$, 525.11; m/z found, 526.1 [M+H]$^+$. $^1$H NMR (600 MHz, CDCl$_3$) δ 8.34 (d, J=19.0, 1H), 7.49 (dd, J=8.0, 1.6, 1H), 7.33 (dd, J=10.5, 8.2, 3H), 6.78 (d, J=8.4, 2H), 6.65 (dd, J=11.6, 1.9, 1H), 6.45 (d, J=2.0, 1H), 5.19 (s, 2H), 5.11 (s, 2H), 3.02 (s, 2H), 2.32 (d, J=6.9, 3H), 1.33 (s, 6H).

Example 61

1-({1-(4-Bromobenzyl)-4-fluoro-6-[(5-methylpyridin-2-yl)methoxy]-1H-benzimidazol-2-yl}methyl)cyclopentanecarboxylic acid

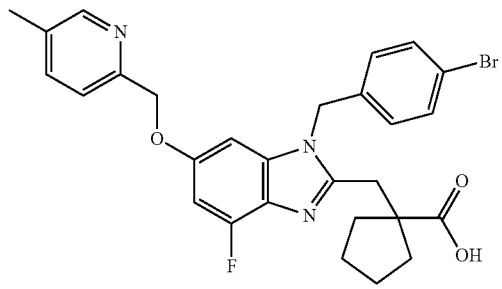 [SMILES: Cc1ccc(COc2cc(F)c3nc(CC4(C(=O)O)CCCC4)n(Cc4ccc(Br)cc4)c3c2)nc1]

The title compound was prepared in a manner analogous to that in Example 1 using 2-((3,5-difluoro-4-nitrophenoxy)methyl)-5-methylpyridine in Step A and 2-oxaspiro[4.4]nonane-1,3-dione in Step C. MS (ESI): mass calcd. for $C_{28}H_{27}BrFN_3O_3$, 551.12; m/z found, 552 [M+H]$^+$. $^1$H NMR (600 MHz, CDCl$_3$) δ 8.32 (s, 1H), 7.48 (dd, J=8.0, 1.6, 1H), 7.37-7.29 (m, 3H), 6.78 (d, J=8.5, 2H), 6.62 (dd, J=11.6, 2.0, 1H), 6.43 (d, J=2.0, 1H), 5.16 (s, 2H), 5.10 (s, 2H), 3.06 (s, 2H), 2.37-2.28 (m, 5H), 1.78-1.52 (m, 6H).

Example 62 racemic trans-2-{1-(4-Bromobenzyl)-4-fluoro-6-[(5-methylpyridin-2-yl)methoxy]-1H-benzimidazol-2-yl}cyclohexanecarboxylic acid

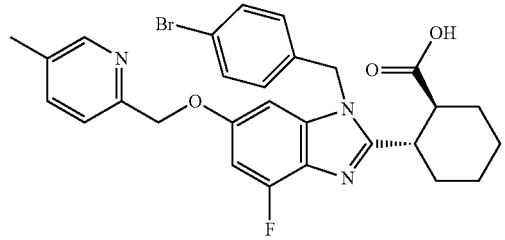 [SMILES: Cc1ccc(COc2cc(F)c3nc([C@H]4CCCC[C@@H]4C(=O)O)n(Cc4ccc(Br)cc4)c3c2)nc1]

The title compound was prepared in a manner analogous to that in Example 1 using 2-((3,5-difluoro-4-nitrophenoxy)methyl)-5-methylpyridine in Step A trans-hexahydroisobenzofuran-1,3-dione in Step C. MS (ESI): mass calcd. for $C_{28}H_{27}BrFN_3O_3$, 551.12; m/z found, 552 [M+H]$^+$. $^1$H NMR (600 MHz, CDCl$_3$) δ 8.22 (s, 1H), 7.42 (dd, J=8.0, 1.6, 1H), 7.27 (s, 1H), 7.25 (s, 1H), 7.23 (d, J=8.0, 1H), 6.80 (d, J=8.4, 2H), 6.52 (dd, J=11.7, 1.9, 1H), 6.14 (d, J=1.4, 1H), 5.22 (dd, J=79.8, 16.8, 2H), 5.10-4.90 (m, 2H), 3.17 (dd, J=16.3, 6.9, 1H), 3.01 (td, J=11.3, 4.2, 1H), 2.30 (s, 3H), 2.15 (d, J=11.4, 1H), 1.70 (dd, J=33.4, 12.9, 2H), 1.59-1.37 (m, 3H), 1.28 (dd, J=25.5, 12.8, 1H), 1.18 (dd, J=25.7, 12.8, 1H).

Example 63 racemic cis-3-{1-(4-Bromobenzyl)-4-fluoro-6-[(5-methylpyridin-2-yl)methoxy]-1H-benzimidazol-2-yl}-2,2-dimethylcyclopropanecarboxylic acid

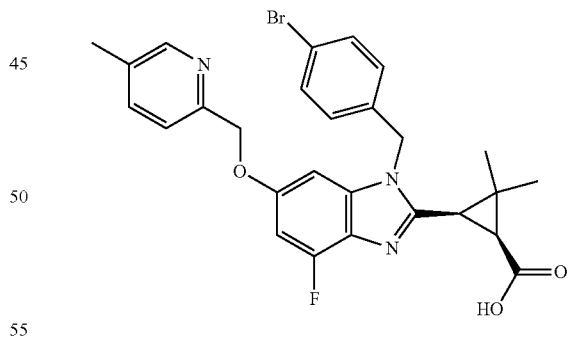

The title compound was prepared in a manner analogous to that in Example 1 using 2-((3,5-difluoro-4-nitrophenoxy)methyl)-5-methylpyridine in Step A and 6,6-dimethyl-3-oxabicyclo[3.1.0]hexane-2,4-dione in Step C. MS (ESI): mass calcd. for $C_{27}H_{25}BrFN_3O_3$, 537.11; m/z found, 538 [M+H]$^+$. $^1$H NMR (600 MHz, CDCl$_3$) δ 8.36 (d, J=2.1, 1H), 7.51 (dd, J=7.9, 1.6, 1H), 7.49-7.44 (m, 2H), 7.35 (d, J=7.9, 1H), 6.89 (d, J=8.5, 2H), 6.79 (dd, J=11.3, 1.9, 1H), 6.64 (d, J=2.0, 1H), 5.25 (q, J=16.9, 2H), 5.16 (s, 2H), 2.35 (s, 3H), 2.30 (d, J=8.3, 1H), 2.04 (d, J=8.3, 1H), 1.24 (s, 3H), 1.01 (s, 3H).

Example 64 racemic cis-3-{4-Fluoro-1-(4-methylbenzyl)-6-[(5-methyl pyridin-2-yl)methoxy]-1H-benzimidazol-2-yl}-2,2-dimethylcyclopropanecarboxylic acid as the TFA salt

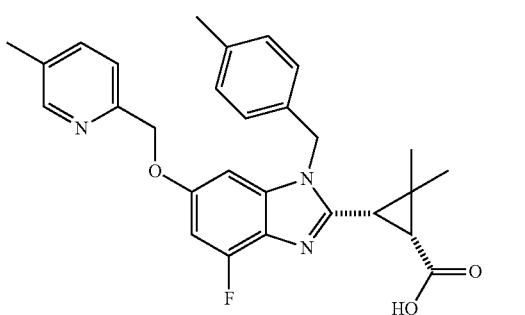

The title compound was prepared in a manner analogous to that in Example 1 using 2-((3,5-difluoro-4-nitrophenoxy)methyl)-5-methylpyridine in Step A, p-tolylmethanamine in Step B, and 6,6-dimethyl-3-oxabicyclo[3.1.0]hexane-2,4-dione in Step C. MS (ESI): mass calcd. for $C_{28}H_{28}FN_3O_3$, 473.21; m/z found, 474.2 [M+H]$^+$. $^1$H NMR (600 MHz, CD$_3$OD) δ 8.51 (s, 1H), 8.01 (dd, J=8.1, 1.6, 1H), 7.69 (d, J=8.1, 1H), 7.17 (d, J=8.0, 2H), 7.07 (d, J=8.1, 2H), 7.04-6.99 (m, 2H), 5.56-5.42 (m, 2H), 5.32-5.25 (m, 2H), 2.51 (d, J=8.2, 1H), 2.46 (s, 3H), 2.34 (t, J=7.0, 1H), 2.32 (s, 3H), 1.33 (s, 3H), 1.26 (s, 3H).

Example 65

2-({1-(4-Bromobenzyl)-4-fluoro-6-[(5-methylpyridin-2-yl)methoxy]-1H-benzimidazol-2-yl}methyl)-2-ethylbutanoic acid as the TFA salt

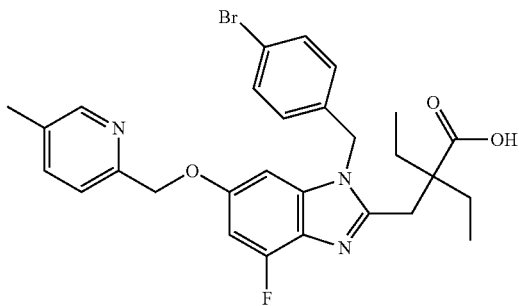 [SMILES: CCC(CC)(Cc1nc2c(F)cc(OCc3ccc(C)cn3)cc2n1Cc1ccc(Br)cc1)C(=O)O]

The title compound was prepared in a manner analogous to that in Example 1 using 2-((3,5-difluoro-4-nitrophenoxy)methyl)-5-methylpyridine in Step A and 3,3-diethyldihydrofuran-2,5-dione in Step C. MS (ESI): mass calcd. for $C_{28}H_{29}BrFN_3O_3$, 553.14; m/z found, 554.1 [M+H]$^+$. $^1$H NMR (600 MHz, CD$_3$OD) δ 8.59-8.53 (m, 1H), 8.16 (dd, J=8.2, 1.4, 1H), 7.78 (d, J=8.2, 1H), 7.52-7.44 (m, 2H), 6.99 (d, J=8.6, 2H), 6.92 (dd, J=11.7, 2.1, 1H), 6.89 (d, J=2.1, 1H), 5.54 (s, 2H), 5.34 (s, 2H), 3.15 (s, 2H), 2.50 (s, 3H), 1.84 (q, J=7.5, 4H), 0.86 (t, J=7.5, 6H).

Example 66 racemic cis-2-{4-Fluoro-6-[(5-methylpyridin-2-yl)methoxy]-1-[4-(trifluoromethoxy)benzyl]-1H-benzimidazol-2-yl}cyclohexanecarboxylic acid as the TFA salt

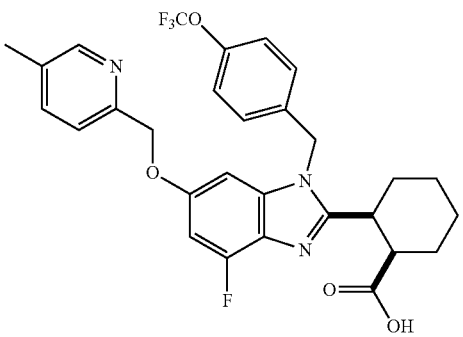

The title compound was prepared in a manner analogous to that in Example 1 using 2-((3,5-difluoro-4-nitrophenoxy)methyl)-5-methylpyridine in Step A and (4-(trifluoromethoxy)phenyl)methanamine in Step B. MS (ESI): mass calcd. for $C_{29}H_{27}F_4N_3O_4$, 557.19; m/z found, 558.2 [M+H]$^+$. $^1$H NMR (500 MHz, CD$_3$OD) δ 8.51-8.42 (m, 1H), 7.99 (dd, J=8.1, 1.5, 1H), 7.66 (d, J=8.1, 1H), 7.25 (d, J=8.4, 2H), 7.21 (d, J=8.9, 2H), 7.07 (dd, J=11.7, 2.0, 1H), 6.96 (d, J=2.0, 1H), 5.81-5.66 (m, 2H), 5.32-5.22 (m, 2H), 3.63 (dt, J=10.4, 3.9, 1H), 2.87 (q, J=4.6, 1H), 2.44 (s, 3H), 2.33-2.19 (m, 2H), 2.02-1.95 (m, 1H), 1.95-1.84 (m, 1H), 1.84-1.70 (m, 1H), 1.70-1.44 (m, 3H).

Example 67 racemic trans-2-{4-Fluoro-6-[(5-methylpyridin-2-yl)methoxy]-1-[4-(trifluoromethoxy)benzyl]-1H-benzimidazol-2-yl}cyclohexanecarboxylic acid as the TFA salt

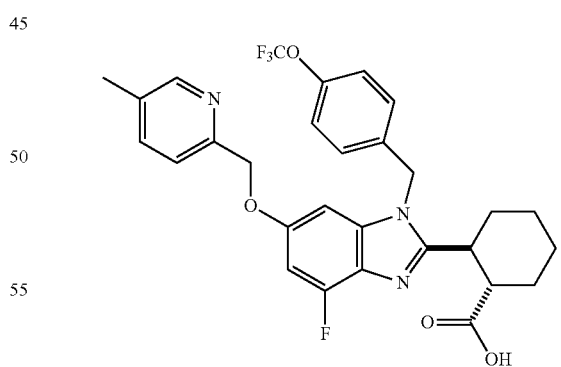

The title compound was prepared in a manner analogous to that in Example 1 using 2-((3,5-difluoro-4-nitrophenoxy)methyl)-5-methylpyridine in Step A, (4-(trifluoromethoxy)phenyl)methanamine in Step B, and trans-hexahydroisobenzofuran-1,3-dione in Step C. MS (ESI): mass calcd. for $C_{29}H_{27}F_4N_3O_4$, 557.19; m/z found, 558.2 [M+H]$^+$. 2:1 mixture of trans to cis; trans reported $^1$H NMR (500 MHz, CD$_3$OD) δ 8.53 (d, J=2.0 Hz, 1H), 8.07 (dd, J=8.1, 2.1 Hz, 1H), 7.73 (d, J=8.1 Hz, 1H), 7.36-7.30 (m, 2H), 7.28-7.19 (m, 2H), 6.99 (d, J=2.1 Hz, 1H), 6.93 (dd, J=11.7, 2.1 Hz, 1H), 5.68 (d, J=10.7 Hz, 1H), 5.63 (d, J=16.9 Hz, 1H), 5.32 (s, 2H), 3.29-3.23 (m, 1H), 3.12-3.01 (m, 1H), 2.47 (s, 3H), 2.34-2.16 (m, 2H), 1.92-1.84 (m, 1H), 1.80-1.71 (m, 1H), 1.64-1.44 (m, 3H), 1.36-1.23 (m, 1H).

Example 68 racemic cis-2-{4-Fluoro-1-(4-methylbenzyl)-6-[(5-methylpyridin-2-yl)methoxy]-1H-benzimidazol-2-yl}cyclohexanecarboxylic acid as the TFA salt

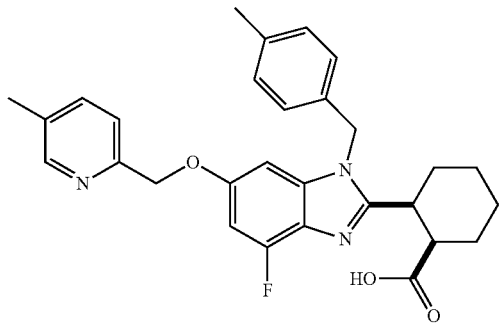

The title compound was prepared in a manner analogous to that in Example 1 using 2-((3,5-difluoro-4-nitrophenoxy)methyl)-5-methylpyridine in Step A and p-tolylmethanamine in Step B. MS (ESI): mass calcd. for $C_{29}H_{30}FN_3O_3$, 487.23; m/z found, 488.2 [M+H]$^+$. $^1$H NMR (600 MHz, CD$_3$OD) δ8.41 (d, J=2.0, 1H), 7.85 (d, J=8.0, 1H), 7.56 (d, J=8.1, 1H), 7.16 (d, J=7.9, 2H), 7.07 (dd, J=11.7, 2.0, 1H), 6.99 (d, J=8.1, 2H), 6.98 (d, J=2.0, 1H), 5.68 (d, J=16.8, 1H), 5.61 (d, J=16.9, 1H), 5.26-5.17 (m, 2H), 3.61 (dt, J=7.9, 3.7, 1H), 2.89 (q, J=4.2, 1H), 2.41 (s, 3H), 2.33 (s, 3H), 2.28-2.23 (m, 2H), 2.01-1.87 (m, 2H), 1.83-1.69 (m, 1H), 1.68-1.44 (m, 3H).

Example 69

2-Ethyl-2-({4-fluoro-6-[(5-methylpyridin-2-yl)methoxy]-1-[4-(trifluoromethoxy)benzyl]-1H-benzimidazol-2-yl}methyl)butanoic acid as the TFA salt

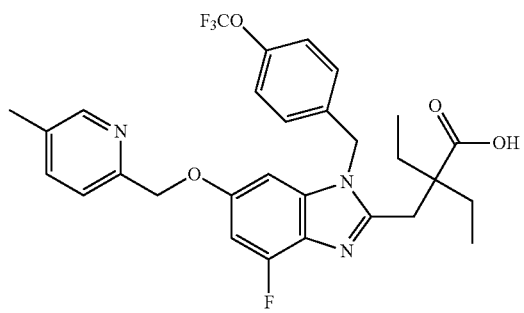 [SMILES: CCC(CC)(Cc1nc2c(F)cc(OCc3ccc(C)cn3)cc2n1Cc1ccc(OC(F)(F)F)cc1)C(=O)O]

The title compound was prepared in a manner analogous to that in Example 1 using 2-((3,5-difluoro-4-nitrophenoxy)methyl)-5-methylpyridine in Step A, (4-(trifluoromethoxy)phenyl)methanamine in Step B, and 3,3-diethyldihydrofuran-2,5-dione in Step C. MS (ESI): mass calcd. for $C_{29}H_{29}F_4N_3O_4$, 559.21; m/z found, 560.2 [M+H]$^+$. $^1$H NMR (600 MHz, CD$_3$OD) δ8.55-8.47 (m, 1H), 8.04 (dd, J=8.1, 1.5, 1H), 7.70 (d, J=8.1, 1H), 7.23 (d, J=8.1, 2H), 7.16 (t, J=5.7, 2H), 6.90-6.79 (m, 2H), 5.56 (s, 2H), 5.28 (s, 2H), 3.12 (s, 2H), 2.46 (s, 3H), 1.91-1.76 (m, 4H), 0.85 (t, J=7.5, 6H).

Example 70 racemic trans-2-{4-Fluoro-1-(4-methylbenzyl)-6-[(5-methylpyridin-2-yl)methoxy]-1H-benzimidazol-2-yl}cyclohexanecarboxylic acid as the TFA salt

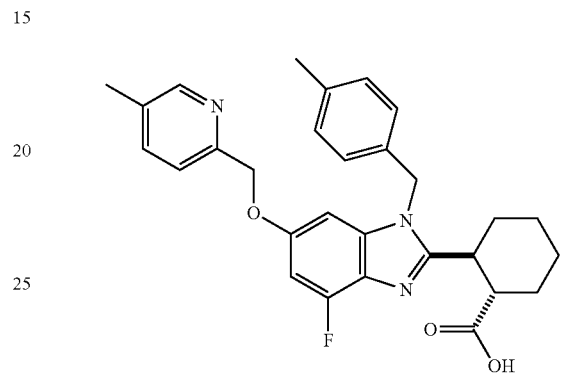

The title compound was prepared in a manner analogous to that in Example 1 using 2-((3,5-difluoro-4-nitrophenoxy)methyl)-5-methylpyridine in Step A, p-tolylmethanamine in Step B, trans-hexahydroisobenzofuran-1,3-dione in Step C. MS (ESI): mass calcd. for $C_{29}H_{30}FN_3O_3$, 487.23; m/z found, 488.2 [M+H]$^+$. $^1$H NMR (600 MHz, CD$_3$OD) δ8.57 (s, 1H), 8.12 (dd, J=8.1, 1.5, 1H), 7.78 (d, J=8.1, 1H), 7.25-7.11 (m, 5H), 7.04 (dd, J=11.7, 2.0, 1H), 5.68 (t, J=15.9, 1H), 5.61 (d, J=16.4, 1H), 5.36 (s, 2H), 3.48-3.34 (m, 1H), 3.06 (td, J=11.7, 3.6, 1H), 2.50 (s, 3H), 2.34 (s, 3H), 2.33-2.30 (m, 1H), 1.91 (d, J=12.9, 1H), 1.76 (d, J=13.2, 1H), 1.60-1.43 (m, 4H), 1.34-1.24 (m, 1H).

Example 71

2-Ethyl-2-({4-fluoro-1-(4-methylbenzyl)-6-[(5-methylpyridin-2-yl)methoxy]-1H-benzimidazol-2-yl}methyl)butanoic acid as the TFA salt

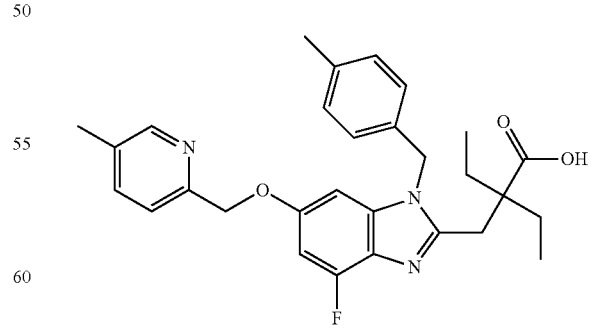

The title compound was prepared in a manner analogous to that in Example 1 using 2-((3,5-difluoro-4-nitrophenoxy)methyl)-5-methylpyridine in Step A, p-tolylmethanamine in Step B, and 3,3-diethyldihydrofuran-2,5-dione in Step C.

MS (ESI): mass calcd. for $C_{29}H_{32}FN_3O_3$, 489.24; m/z found, 490.2 $[M+H]^+$. $^1$H NMR (600 MHz, CD$_3$OD) δ 8.57-8.52 (m, 1H), 8.14 (dd, J=8.1, 1.4, 1H), 7.78 (d, J=8.2, 1H), 7.14 (d, J=7.9, 2H), 7.02-6.94 (m, 4H), 5.53 (s, 2H), 5.33 (s, 2H), 3.19 (s, 2H), 2.49 (s, 3H), 2.31 (s, 3H), 1.83 (q, J=7.5, 4H), 0.87 (t, J=7.5, 6H).

Example 72

1-({4-Fluoro-6-[(5-methylpyridin-2-yl)methoxy]-1-[4-(trifluoromethoxy)benzyl]-1H-benzimidazol-2-yl}methyl)cyclopentanecarboxylic acid as the TFA salt

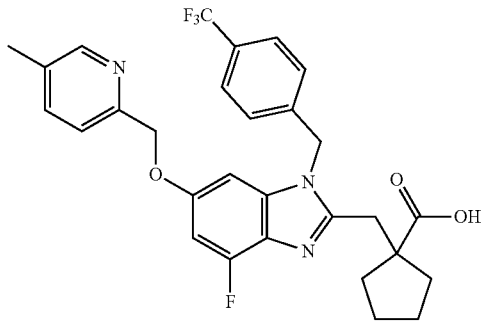 [SMILES: Cc1ccc(COc2cc(F)c3nc(CC4(C(=O)O)CCCC4)n(Cc4ccc(C(F)(F)F)cc4)c3c2)nc1]

The title compound was prepared in a manner analogous to that in Example 1 using 2-((3,5-difluoro-4-nitrophenoxy)methyl)-5-methylpyridine in Step A, (4-(trifluoromethyl)phenyl)methanamine in Step B, and 2-oxaspiro[4.4]nonane-1,3-dione in Step C. MS (ESI): mass calcd. for $C_{29}H_{27}F_4N_3O_4$, 557.19; m/z found, 558.2 $[M+H]^+$. $^1$H NMR (500 MHz, CD$_3$OD) δ8.47 (s, 1H), 7.96 (dd, J=8.1, 1.7, 1H), 7.65 (d, J=8.1, 1H), 7.24 (d, J=8.3, 2H), 7.16 (d, J=8.7, 2H), 6.85 (td, J=6.3, 2.0, 2H), 5.57 (s, 2H), 5.25 (s, 2H), 3.24 (s, 2H), 2.45 (s, 3H), 2.31-2.21 (m, 2H), 1.86-1.64 (m, 6H).

Example 73

1-({4-Fluoro-1-(4-methylbenzyl)-6-[(5-methylpyridin-2-yl)methoxy]-1H-benzimidazol-2-yl}methyl)cyclopentanecarboxylic acid as the TFA salt

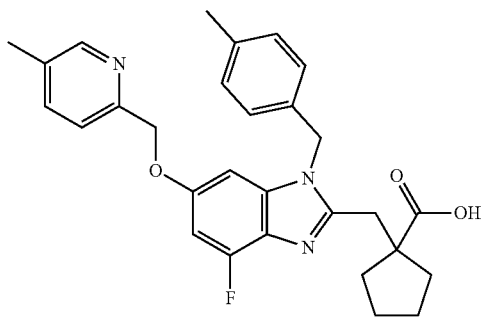 [SMILES: Cc1ccc(Cn2c(CC3(C(=O)O)CCCC3)nc3c(F)cc(OCc4ccc(C)cn4)cc32)cc1]

The title compound was prepared in a manner analogous to that in Example 1 using 2-((3,5-difluoro-4-nitrophenoxy)methyl)-5-methylpyridine in Step A, p-tolylmethanamine in Step B, and 2-oxaspiro[4.4]nonane-1,3-dione in Step C. MS (ESI): mass calcd. for $C_{29}H_{30}FN_3O_3$, 487.23; m/z found, 488.2 $[M+H]^+$. $^1$H NMR (600 MHz, CD$_3$OD) δ 8.44 (s, 1H), 7.88 (d, J=7.8, 1H), 7.60 (d, J=8.1, 1H), 7.13 (d, J=8.0, 2H), 6.95 (d, J=8.0, 2H), 6.86 (s, 1H), 5.47 (s, 2H), 5.21 (s, 2H), 3.24 (s, 2H), 2.42 (s, 3H), 2.31 (s, 3H), 2.24 (dt, J=23.8, 11.8, 2H), 1.82-1.64 (m, 7H).

Example 74 racemic cis-3-{4-Fluoro-6-[(5-methylpyridin-2-yl)methoxy]-1-[4-(trifluoromethoxy)benzyl]-1H-benzimidazol-2-yl}-2,2-dimethylcyclopropanecarboxylic acid as the TFA salt

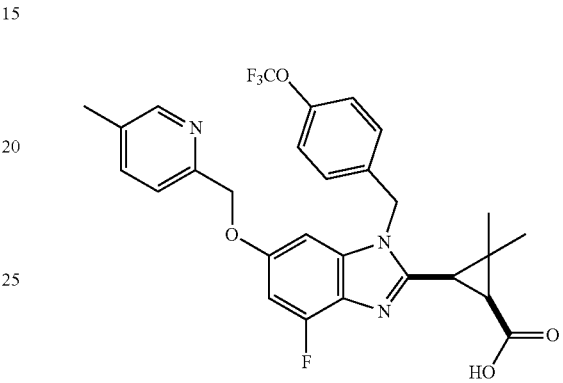

The title compound was prepared in a manner analogous to that in Example 1 using 2-((3,5-difluoro-4-nitrophenoxy)methyl)-5-methylpyridine in Step A, (4-(trifluoromethoxy)phenyl)methanamine in Step B, and 6,6-dimethyl-3-oxabicyclo[3.1.0]hexane-2,4-dione in Step C. MS (ESI): mass calcd. for $C_{28}H_{25}F_4N_3O_4$, 543.18; m/z found, 544.1 $[M+H]^+$. $^1$H NMR (500 MHz, CD$_3$OD) δ 8.53 (s, 1H), 8.06 (d, J=8.1, 1H), 7.72 (d, J=8.1, 1H), 7.33-7.20 (m, 4H), 7.06-6.94 (m, 2H), 5.63-5.51 (m, 2H), 5.31 (s, 2H), 2.50 (d, J=8.2, 1H), 2.47 (s, 3H), 2.32 (d, J=8.2, 1H), 1.32 (d, J=5.5, 3H), 1.30 (s, 3H).

Example 75 racemic cis-2-{1-(4-Bromobenzyl)-4-chloro-6-[(5-methylpyridin-2-yl)methoxy]-1H-benzimidazol-2-yl}cyclohexanecarboxylic acid

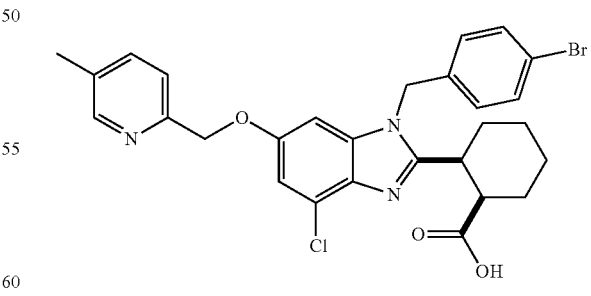

The title compound was prepared in a manner analogous to that in Example 1 using 2-((3-chloro-5-fluoro-4-nitrophenoxy)methyl)-5-methylpyridine in Step A. MS (ESI): mass calcd. for $C_{28}H_{27}BrClN_3O_3$, 567.09; m/z found, 568.4 $[M+H]^+$. $^1$H NMR (500 MHz, CD$_3$OD) δ 8.50 (s, 1H), 8.01 (d, J=8.1, 1H), 7.69 (d, J=7.0, 1H), 7.48 (d, J=8.5, 2H), 7.29

(d, J=1.8, 1H), 7.06 (d, J=1.8, 1H), 7.02 (d, J=8.4, 2H), 5.71 (d, J=17.3, 1H), 5.62 (d, J=17.4, 1H), 5.35-5.25 (m, 2H), 3.65 (dt, J=8.0, 3.8, 1H), 2.89 (dd, J=8.8, 4.3, 1H), 2.36 (d, J=9.4, 1H), 2.30-2.18 (m, 1H), 1.97-1.86 (m, 2H), 1.81 (dd, J=13.8, 10.8, 1H), 1.64 (td, J=13.5, 6.1, 2H), 1.49 (t, J=11.9, 1 H).

Example 76 racemic cis-3-{1-(4-Bromobenzyl)-4-chloro-6-[(5-methylpyridin-2-yl)methoxy]-1H-benzimidazol-2-yl}-2,2-dimethylcyclopropanecarboxylic acid

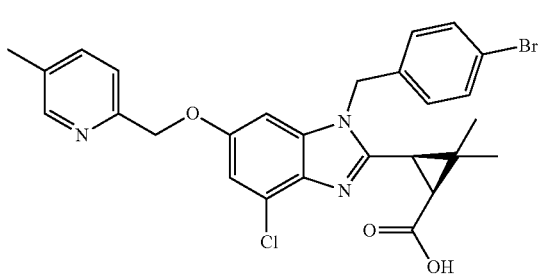 [SMILES: Cc1ccc(COc2cc(Cl)c3nc([C@@H]4[C@H](C(=O)O)C4(C)C)n(Cc4ccc(Br)cc4)c3c2)nc1]

The title compound was prepared in a manner analogous to that in Example 1 using 2-((3-chloro-5-fluoro-4-nitrophenoxy)methyl)-5-methylpyridine in Step A and cis-6,6-dimethyl-3-oxabicyclo[3.1.0]hexane-2,4-dione in Step C. MS (ESI): mass calcd. for $C_{27}H_{25}BrClN_3O_3$, 553.08; m/z found, 554.0 [M+H]$^+$. $^1$H NMR (500 MHz, CD$_3$OD) δ 8.43 (s, 1H), 7.85 (d, J=7.9, 1H), 7.58 (d, J=7.8, 1H), 7.53-7.45 (m, 2H), 7.17 (d, J=2.1, 1H), 7.09 (d, J=2.1, 1H), 7.07-7.02 (m, 2H), 5.53 (d, J=16.8, 1H), 5.47 (d, J=16.8, 1H), 5.23 (s, 2H), 2.48 (d, J=8.2, 1H), 2.42 (s, 3H), 2.27 (d, J=8.2, 1H), 1.26 (s, 3H), 1.14 (s, 3H).

Example 77 racemic trans-2-{1-(4-Bromobenzyl)-4-chloro-6-[(5-methylpyridin-2-yl)methoxy]-1H-benzimidazol-2-yl}cyclohexanecarboxylic acid

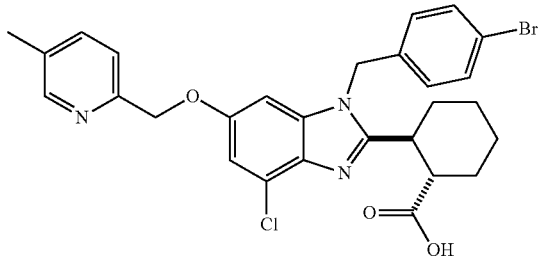

The title compound was prepared in a manner analogous to that in Example 1 using 2-((3-chloro-5-fluoro-4-nitrophenoxy)methyl)-5-methylpyridine in Step A and trans-hexahydroisobenzofuran-1,3-dione in Step C. MS (ESI): mass calcd. for $C_{28}H_{27}BrClN_3O_3$, 567.09; m/z found, 568.1 [M+H]$^+$. $^1$H NMR (500 MHz, CD$_3$OD) δ 8.59 (s, 1H), 8.12 (d, J=8.1, 1H), 7.78 (d, J=6.5, 1H), 7.54-7.47 (m, 2H), 7.27 (d, J=2.0, 1H), 7.19-7.13 (m, 3H), 5.69 (d, J=16.9, 1H), 5.63 (d, J=16.9, 1H), 5.36 (s, 2H), 3.38-3.32 (m, 1H), 3.22-3.14 (m, 1H), 2.49 (s, 3H), 2.34-2.29 (m, 1H), 1.92-1.85 (m, 1H), 1.82-1.75 (m, 1H), 1.68-1.44 (m, 4H), 1.36-1.25 (m, 1H).

Example 78

1-({1-(4-Bromobenzyl)-4-chloro-6-[(5-methylpyridin-2-yl)methoxy]-1H-benzimidazol-2-yl}methyl)cyclopentanecarboxylic acid

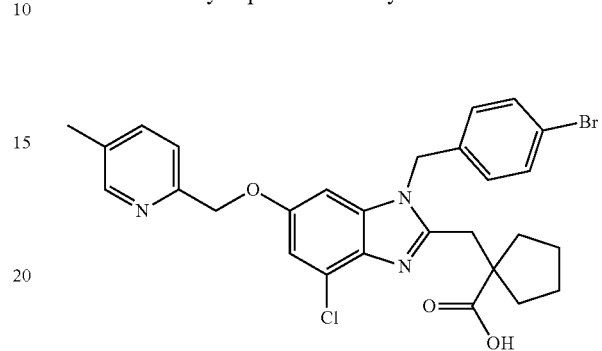

The title compound was prepared in a manner analogous to that in Example 1 using 2-((3-chloro-5-fluoro-4-nitrophenoxy)methyl)-5-methylpyridine in Step A and 2-oxaspiro[4.4]nonane-1,3-dione in Step C. MS (ESI): mass calcd. for $C_{28}H_{27}BrClN_3O_3$, 567.09; m/z found, 568.4 [M+H]$^+$. $^1$H NMR (500 MHz, CDCl$_3$) δ 8.52 (s, 1H), 8.09 (d, J=8.1, 1H), 7.72 (d, J=8.2, 1H), 7.47 (d, J=8.3, 2H), 7.19 (d, J=1.6, 1H), 6.99 (dd, J=5.2, 2.9, 3H), 5.55 (s, 2H), 5.31 (s, 2H), 3.30-3.29 (m, 2H), 2.48 (s, 3H), 2.30-2.17 (m, 2H), 1.88-1.76 (m, 2H), 1.76-1.69 (m, 4H).

Example 79

3-{1-(4-Bromobenzyl)-4-chloro-6-[(5-methylpyridin-2-yl)methoxy]-1H-benzimidazol-2-yl}-2,2-dimethylpropanoic acid

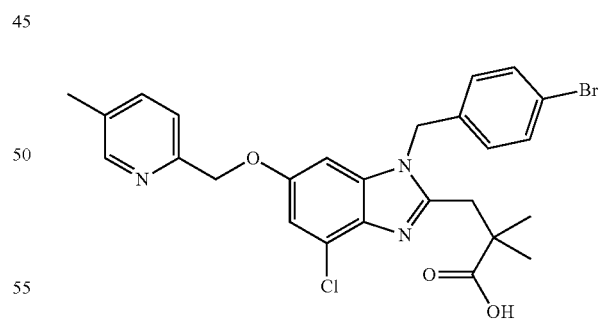

The title compound was prepared in a manner analogous to that in Example 1 using 2-((3-chloro-5-fluoro-4-nitrophenoxy)methyl)-5-methylpyridine in Step A and 2,3-dimethylsuccinic anhydride in Step C. MS (ESI): mass calcd. for $C_{26}H_{25}BrClN_3O_3$, 541.08; m/z found, 542.0 [M+H]$^+$. $^1$H NMR (500 MHz, CD$_3$OD) δ 8.50 (s, 1H), 8.03 (d, J=8.1, 1H), 7.68 (d, J=8.2, 1H), 7.50-7.42 (m, 2H), 7.20 (d, J=2.1, 1H), 7.01-6.93 (m, 3H), 5.58 (s, 2H), 5.29 (s, 2H), 3.25 (s, 2H), 2.47 (s, 3H), 1.36 (s, 6H).

Example 80 racemic cis-2-{1-[4-(5-Chloropyrimidin-2-yl)benzyl]-6-[(5-methylpyridin-2-yl)methoxy]-1H-benzimidazol-2-yl}cyclohexanecarboxylic acid

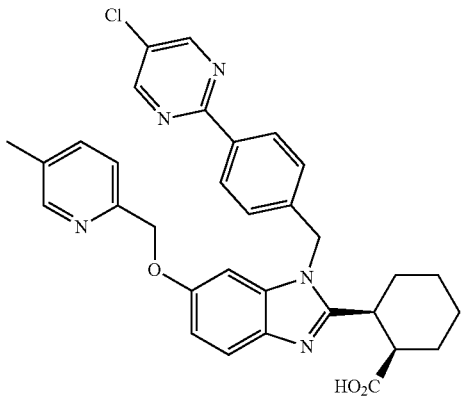 [SMILES: Cc1ccc(COc2ccc3nc([C@H]4CCCC[C@H]4C(=O)O)n(Cc4ccc(-c5ncc(Cl)cn5)cc4)c3c2)nc1]

Step A. tert-butyl-4-(5-Chloropyrimidin-2-yl)benzylcarbamate

To a 10 mL microwave vial were added 2,5-dichloropyrimidine (285 mg, 1.8 mmol), Pd(dppf)Cl$_2$.DCM (45 mg, 0.05 mmol), (4-(((tert-butoxycarbonyl)amino)methyl)phenyl)boronic acid (419 mg, 1.67 mmol), Na$_2$CO$_3$ (2 mL, 2M) and 1,4-dioxane (7 mL). The vial was flushed with N$_2$ then capped and placed in a heating block and heated at 80° Celsius. After 6 h, the resulting mixture cooled to RT and transferred to a round-bottomed flask and concentrated to dryness. The residue was purified using FCC to provide 376 mg of the title compound. MS (ESI): mass calcd. for C$_{16}$H$_{18}$ClN$_3$O$_2$, 319.11; m/z found 320.1 [M+H]$^+$.

Step B. N-(4-(5-Chloropyrimidin-2-yl)benzyl)-5-((5-methylpyridin-2-yl)methoxy)-2-nitroaniline To a solution of tert-butyl 4-(5-chloropyrimidin-2-yl)benzylcarbamate (355 mg, 1.11 mmol) in DCM (10 mL) was added TFA (1 mL). The reaction mixture was stirred for 5 h at RT and concentrated to dryness. To the resulting residue was added DMA (3 mL), DIPEA (0.57 mL) and 2-((3-fluoro-4-nitrophenoxy)methyl)-5-methylpyridine (0.29 g, 1.11 mmol). The mixture and heated to 80° Celsius for 6 h. The mixture was then poured into water and the solids were collected by filtration to provide of the title compound (475 mg). $^1$H NMR (400 MHz, CDCl$_3$) δ 8.77-8.72 (s, 2H), 8.41-8.32 (m, 2H), 8.21-8.13 (d, J=9.5, 1H), 7.49-7.39 (m, 3H), 7.26-7.21 (m, 3H), 6.38-6.30 (dd, J=9.5, 2.5, 1H), 6.27-6.21 (d, J=2.5, 1H), 5.14-5.09 (s, 2H), 4.60-4.53 (d, J=5.8, 2H), 2.30-2.25 (s, 3H).

Step C. racemic cis-2-{1-[4-(5-Chloropyrimidin-2-yl)benzyl]-6-[(5-methylpyridin-2-yl)methoxy]-1H-benzimidazol-2-yl}cyclohexanecarboxylic acid In a 5 mL microwave vial were added N-(4-(5-chloropyrimidin-2-yl)benzyl)-5-((5-methylpyridin-2-yl)methoxy)-2-nitroaniline (59 mg, 0.13 mmol), cis-hexahydroisobenzofuran-1,3-dione (33 mg, 0.21 mmol), sodium dithionite (69 mg, 0.39 mmol), DMA (1 mL) and water (0.2 mL). The resulting mixture was heated to 50° Celsius for 16 h. The mixture was cooled to RT, diluted with water (10 mL) and pH adjusted to ~1 with HCl (1M). To the mixture was added DCM (1 mL) and the pH was adjusted to ~3 with saturated NaHCO$_3$ (10 mL). The organic layer was separated, concentrated to dryness and the residue was purified using FCC to provide 20.7 mg of the title compound. MS (ESI): mass calcd. for C$_{32}$H$_{30}$ClN$_5$O$_3$, 567.20; m/z found, 569.1 [M+H]$^+$. $^1$H NMR (400 MHz, CDCl$_3$) δ 8.76-8.71 (s, 2H), 8.39-8.31 (m, 3H), 7.66-7.59 (d, J=8.9, 1H), 7.50-7.43 (dd, J=8.0, 1.7, 1H), 7.39-7.32 (d, J=8.0, 1H), 7.15-7.08 (m, 2H), 7.07-7.00 (dd, J=8.9, 2.3, 1H), 6.85-6.79 (d, J=2.3, 1H), 5.41-5.27 (m, 2H), 5.18-5.13 (s, 2H), 3.22-3.14 (m, 1H), 3.07-3.03 (m, 1H), 2.61-2.51 (m, 1H), 2.30-2.25 (s, 3H), 1.89-1.55 (m, 5H), 1.49-1.35 (m, 2H).

Example 81 racemic cis-2-{1-(4-Bromobenzyl)-6-[(4-chloro-1-methyl-1H-pyrazol-3-yl)methoxy]-1H-benzimidazol-2-yl}cyclohexanecarboxylic acid

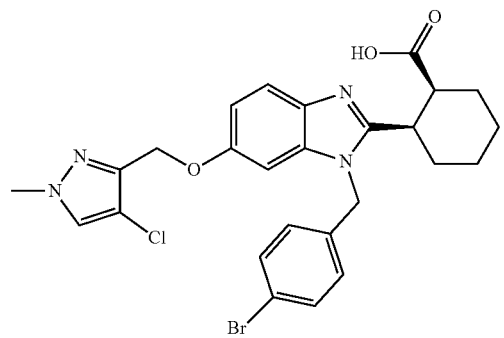 [SMILES: Cn1cc(Cl)c(COc2ccc3nc([C@@H]4CCCC[C@@H]4C(=O)O)n(Cc4ccc(Br)cc4)c3c2)n1]

The title compound was prepared using analogous conditions described in Step A of Example 1 using Intermediate M and (4-bromophenyl)methanamine and as described in Step C of Example 80 using N-(4-bromobenzyl)-5-((4-chloro-1-methyl-1H-pyrazol-3-yl)methoxy)-2-nitroaniline. MS (ESI): mass calcd. for C$_{26}$H$_{26}$BrClN$_4$O$_3$, 557.88; m/z found, 557.0; 559.0 [M+H]$^+$. $^1$H NMR (400 MHz, CD$_3$OD) δ 7.63 (s, 1H), 7.56-7.51 (m, 1H), 7.47 (d, J=8.5, 2H), 7.04 (d, J=8.5, 2H), 6.94 (d, J=8.2, 2H), 5.53 (d, J=17.2, 1H), 5.45 (d, J=17.3, 1H), 4.98 (s, 2H), 3.79 (s, 3H), 3.61-3.53 (m, 1H), 2.90-2.77 (m, 1H), 2.42-2.28 (m, 1H), 2.07-1.95 (m, 1H), 1.91-1.70 (m, 4H), 1.55-1.39 (m, 2H).

Example 82 racemic cis-2-{6-[(4-Chloro-1-methyl-1H-pyrazol-3-yl)methoxy]-1-(4-piperidin-1-ylbenzyl)-1H-benzimidazol-2-yl}cyclohexanecarboxylic acid

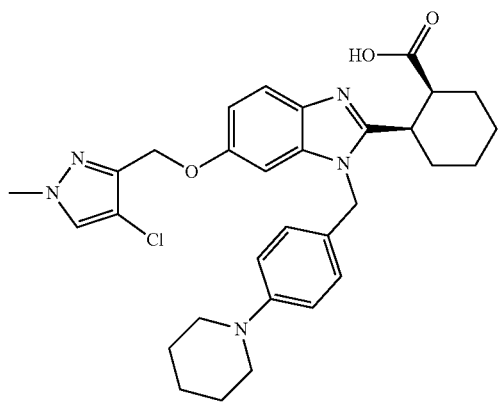 [SMILES: Cn1cc(Cl)c(COc2ccc3nc([C@@H]4CCCC[C@@H]4C(=O)O)n(Cc4ccc(N5CCCCC5)cc4)c3c2)n1]

The title compound was prepared from racemic cis-2-(1-(4-bromobenzyl)-6-((4-chloro-1-methyl-1H-pyrazol-3-yl)methoxy)-1H-benzo[d]imidazol-2-yl)cyclohexanecarboxylic acid using analogous conditions described in Example 152 using piperidine. MS (ESI): mass calcd. for $C_{31}H_{36}ClN_5O_3$, 562.12; m/z found, 562.2 [M+H]$^+$. $^1$H NMR (400 MHz, CD$_3$OD) δ 7.65 (s, 1H), 7.53 (d, J=8.8, 1H), 7.03 (d, J=8.9, 3H), 6.92 (d, J=8.8, 3H), 5.44 (d, J=16.6, 1H), 5.37 (d, J=16.4, 1H), 4.98 (s, 2H), 3.81 (s, 3H), 3.60-3.49 (m, 1H), 3.14-3.09 (m, 4H), 2.91-2.79 (m, 1H), 2.40-2.28 (m, 1H), 2.03-1.93 (m, 1H), 1.91-1.63 (m, 8H), 1.62-1.53 (m, 2H), 1.53-1.37 (m, 2H).

Example 83 racemic cis-2-{6-[(4-Chloro-1-methyl-1H-pyrazol-3-yl)methoxy]-1-[2-fluoro-4-(trifluoromethoxy)benzyl]-1H-benzimidazol-2-yl}cyclohexanecarboxylic acid

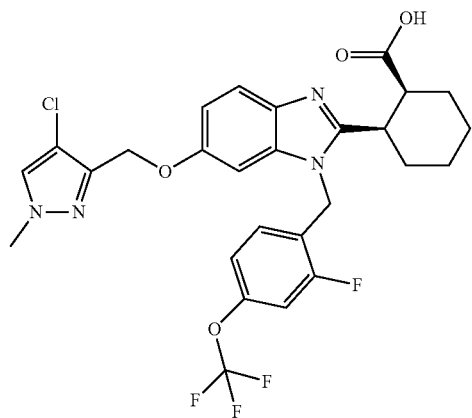 [SMILES: Cn1cc(Cl)c(COc2ccc3nc([C@@H]4CCCC[C@@H]4C(=O)O)n(Cc4ccc(OC(F)(F)F)cc4F)c3c2)n1]

The title compound was prepared using analogous conditions described in Example 1 using Intermediate M and (2-fluoro-4-(trifluoromethoxy)phenyl)methanamine in Step A and as described in Step C of Example 80 using N-(2-methoxy-4-(trifluoromethoxy)benzyl)-5-((1-methyl-1H-pyrazol-3-yl)methoxy)-2-nitroaniline. MS (ESI): mass calcd. for $C_{27}H_{25}ClF_4N_4O_4$, 580.97; m/z found, 581.0 [M+H]$^+$. $^1$H NMR (400 MHz, CD$_3$OD) δ 7.63 (s, 1H), 7.54 (d, J=8.8, 1H), 7.22 (d, J=10.5, 1H), 7.01 (d, J=8.6, 1H), 6.98 (d, J=2.2, 1H), 6.95-6.86 (m, 2H), 5.57 (q, J=17.5, 2H), 4.97 (s, 2H), 3.80 (s, 3H), 3.67-3.55 (m, 1H), 2.87-2.76 (m, 1H), 2.46-2.31 (m, 1H), 2.08-1.69 (m, 5H), 1.56-1.37 (m, 2H).

Example 84 racemic cis-2-{1-[2-Methoxy-4-(trifluoromethoxy)benzyl]-6-[(1-methyl-1H-pyrazol-3-yl)methoxy]-1H-benzimidazol-2-yl}cyclohexanecarboxylic acid

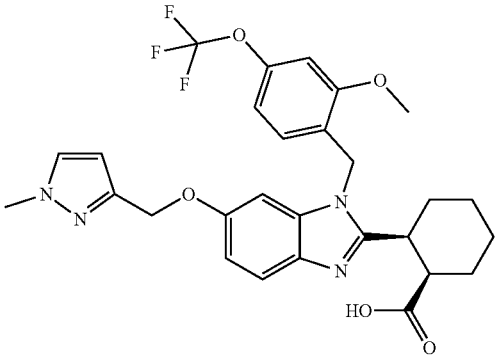 [SMILES: COc1cc(OC(F)(F)F)ccc1Cn1c([C@H]2CCCC[C@H]2C(=O)O)nc2ccc(OCc3ccn(C)n3)cc21]

The title compound was prepared using analogous conditions described in Example 1 using Intermediate M and (2-methoxy-4-(trifluoromethoxy)phenyl)methanamine in Step A and as described in Step C of Example 80 using N-(2-methoxy-4-(trifluoromethoxy)benzyl)-5-((1-methyl-1H-pyrazol-3-yl)methoxy)-2-nitroaniline. MS (ESI): mass calcd. for $C_{28}H_{29}F_3N_4O_5$, 558.56; m/z found, 559.2 [M+H]$^+$. $^1$H NMR (500 MHz, CD$_3$OD) δ 7.55-7.51 (m, 1H), 7.49 (d, J=2.2, 1H), 6.96 (s, 1H), 6.91 (dd, J=4.6, 2.3, 2H), 6.74 (s, 2H), 6.26 (d, J=2.3, 1H), 5.49 (d, J=17.4, 1H), 5.39 (d, J=17.3, 1H), 4.99 (s, 2H), 3.92 (s, 3H), 3.83 (s, 3H), 3.59-3.50 (m, 1H), 2.84-2.75 (m, 1H), 2.43-2.30 (m, 1H), 2.08-1.96 (m, 1H), 1.94-1.70 (m, 4H), 1.56-1.38 (m, 2H).

Example 85 racemic cis-2-{6-[(4-Fluoro-1-methyl-1H-pyrazol-3-yl)methoxy]-1-[2-fluoro-4-(trifluoromethoxy)benzyl]-1H-benzimidazol-2-yl}cyclohexanecarboxylic acid

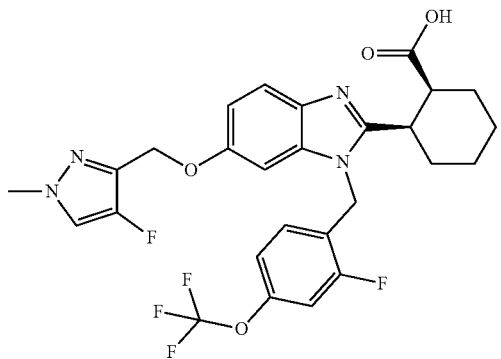 [SMILES: Cn1cc(F)c(COc2ccc3nc([C@@H]4CCCC[C@@H]4C(=O)O)n(Cc4ccc(OC(F)(F)F)cc4F)c3c2)n1]

The title compound was prepared using analogous conditions described in Step B of Example 1 using 4-fluoro-3-((3-fluoro-4-nitrophenoxy)methyl)-1-methyl-1H-pyrazole and (2-fluoro-4-(trifluoromethoxy)phenyl)methanamine and as described in Step C of Example 80 using 5-((4-fluoro-1-methyl-1H-pyrazol-3-yl)methoxy)-N-(2-fluoro-4-(trifluoromethoxy)benzyl)-2-nitroaniline. MS (ESI): mass calcd. for $C_{27}H_{25}F_5N_4O_4$, 564.52; m/z found, 565.0 [M+H]$^+$. $^1$H NMR (600 MHz, CD$_3$OD) δ 7.69 (d, J=9.0, 1H), 7.56 (d, J=4.6, 1H), 7.31 (dd, J=6.0, 3.8, 2H), 7.27 (dd, J=9.0, 2.3, 1H), 7.15-7.08 (m, 2H), 5.87 (s, 2H), 5.06 (d, J=19.6, 2H), 3.78 (s, 3H), 3.71-3.66 (m, 1H), 2.98-2.87 (m, 1H), 2.40-2.29 (m, 1H), 2.28-2.15 (m, 1H), 2.09-1.95 (m, 2H), 1.88-1.77 (m, 1H), 1.74-1.65 (m, 1H), 1.63-1.48 (m, 2H).

Example 86 racemic cis-2-{1-[4-(4,4-Difluoropiperidin-1-yl)benzyl]-6-[(1-methyl-1H-pyrazol-3-yl)methoxy]-1H-benzimidazol-2-yl}cyclohexanecarboxylic acid

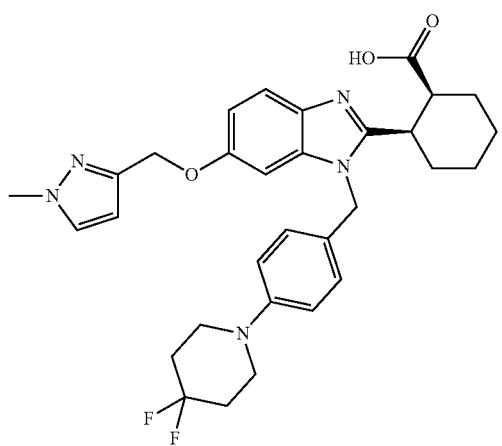 [SMILES: Cn1ccc(COc2ccc3nc([C@@H]4CCCC[C@@H]4C(=O)O)n(Cc4ccc(N5CCC(F)(F)CC5)cc4)c3c2)n1]

The title compound was prepared from racemic cis-2-(1-(4-bromobenzyl)-6-((1-methyl-1H-pyrazol-3-yl)methoxy)-1H-benzo[d]imidazol-2-yl)cyclohexanecarboxylic acid using analogous conditions to Example 152 using 4,4-difluoropiperidine. MS (ESI): mass calcd. for $C_{31}H_{35}F_2N_5O_3$, 563.65; m/z found, 564.3 [M+H]$^+$. $^1$H NMR (500 MHz, CD$_3$OD) δ7.55-7.48 (m, 2H), 7.04 (d, J=8.7, 2H), 6.96 (dd, J=10.0, 5.5, 3H), 6.93-6.88 (m, 1H), 6.27 (d, J=2.2, 1H), 5.43 (d, J=16.7, 1H), 5.38 (d, J=16.7, 1H), 4.99 (s, 2H), 3.83 (s, 3H), 3.61-3.52 (m, 1H), 3.34-3.32 (m, 4H), 2.88-2.79 (m, 1H), 2.43-2.29 (m, 1H), 2.12-1.93 (m, 5H), 1.93-1.66 (m, 4H), 1.57-1.37 (m, 2H).

Example 87 racemic cis-2-{6-[(4-Chloro-1-methyl-1H-pyrazol-3-yl)methoxy]-1-[4-(4-fluoropiperidin-1-yl)benzyl]-1H-benzimidazol-2-yl}cyclohexanecarboxylic acid

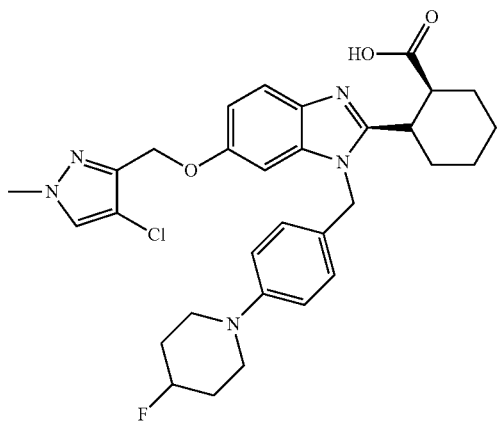

The title compound was prepared from racemic cis-2-(1-(4-bromobenzyl)-6-((4-chloro-1-methyl-1H-pyrazol-3-yl)methoxy)-1H-benzo[d]imidazol-2-yl)cyclohexanecarboxylic acid using analogous conditions described in Example 152 using 4-fluoropiperidine. MS (ESI): mass calcd. for $C_{31}H_{35}ClFN_5O_3$, 580.11; m/z found, 581.0 [M+H]$^+$. $^1$H NMR (400 MHz, CD$_3$OD) δ7.68 (t, J=4.5, 2H), 7.31 (d, J=2.1, 1H), 7.26 (dd, J=9.0, 2.3, 1H), 7.14-7.02 (m, 4H), 5.70 (s, 2H), 5.03 (s, 2H), 4.79-4.68 (m, 1H), 3.81 (s, 3H), 3.66-3.53 (m, 1H), 3.51-3.36 (m, 2H), 3.28-3.17 (m, 2H), 2.88 (s, 1H), 2.40-2.13 (m, 2H), 2.12-1.84 (m, 6H), 1.84-1.63 (m, 2H), 1.61-1.46 (m, 2H).

Example 88 racemic cis-2-{6-[(1-Methyl-1H-pyrazol-3-yl)methoxy]-1-(4-piperidin-1-ylbenzyl)-1H-benzimidazol-2-yl}cyclohexanecarboxylic acid

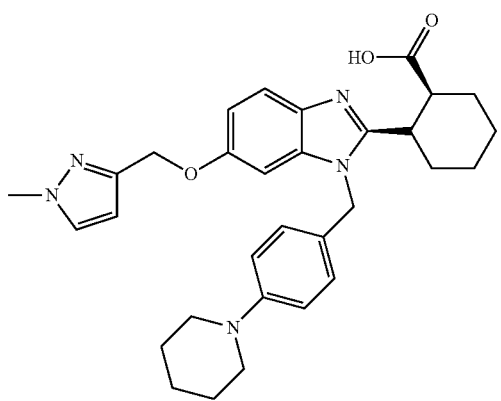

The title compound was prepared from racemic cis-2-(1-(4-bromobenzyl)-6-((1-methyl-1H-pyrazol-3-yl)methoxy)-1H-benzo[d]imidazol-2-yl)cyclohexanecarboxylic acid using analogous conditions to Example 152 using piperidine. MS (ESI): mass calcd. for $C_{31}H_{37}N_5O_3$, 527.67; m/z found, 528.3 [M+H]. $^1$H NMR (500 MHz, CD$_3$OD) δ 7.51 (dd, J=8.2, 5.5, 2H), 7.01 (d, J=8.7, 2H), 6.97 (d, J=2.3, 1H), 6.94-6.87 (m, 3H), 6.27 (d, J=2.3, 1H), 5.45-5.34 (m, 2H), 4.99 (s, 2H), 3.83 (s, 3H), 3.63-3.53 (m, 1H), 3.15-3.06 (m, 4H), 2.85-2.76 (m, 1H), 2.43-2.25 (m, 1H), 1.99-1.75 (m, 4H), 1.74-1.63 (m, 5H), 1.63-1.52 (m, 2H), 1.53-1.34 (m, 2H).

Example 89 racemic cis-2-{1-[4-(3,3-Difluoroazetidin-1-yl)benzyl]-6-[(1-methyl-1H-pyrazol-3-yl)methoxy]-1H-benzimidazol-2-yl}cyclohexanecarboxylic acid

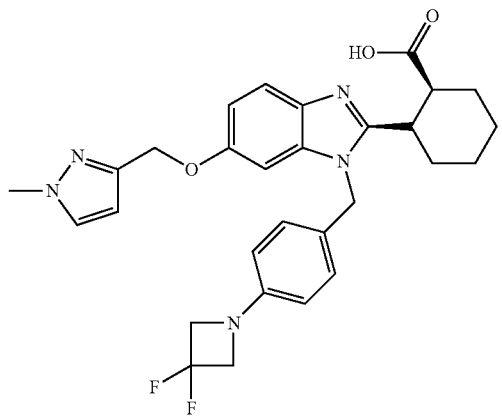

The title compound was prepared from racemic cis-2-(1-(4-bromobenzyl)-6-((1-methyl-1H-pyrazol-3-yl)methoxy)-1H-benzo[d]imidazol-2-yl)cyclohexanecarboxylic acid using analogous conditions to Example 152 using 3,3-difluoroazetidine. MS (ESI): mass calcd. for $C_{29}H_{31}F_2N_5O_3$, 535.24; m/z found, 536.3 [M+H]$^+$. $^1$H NMR (500 MHz, CD$_3$OD) δ 7.52 (d, J=9.6, 2H), 7.04 (d, J=8.2, 2H), 6.96 (s, 1H), 6.91 (d, J=8.8, 1H), 6.52 (d, J=8.3, 2H), 6.26 (s, 1H), 5.44 (d, J=16.5, 1H), 5.38 (d, J=16.4, 1H), 4.99 (s, 2H), 4.17 (t, J=11.9, 4H), 3.83 (s, 3H), 3.59-3.53 (m, 1H), 2.88-2.78 (m, 1H), 2.41-2.29 (m, 1H), 1.98 (s, 1H), 1.79 (t, J=27.9, 5H), 1.53-1.38 (m, 1H).

Example 90 racemic cis-2-{5-Fluoro-1-[2-fluoro-4-(trifluoromethoxy)benzyl]-6-[(1-methyl-1H-pyrazol-3-yl)methoxy]-1H-benzimidazol-2-yl}cyclohexanecarboxylic acid

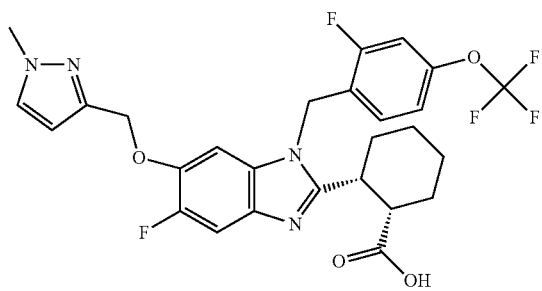 [SMILES: Cn1ccc(COc2cc3c(cc2F)nc([C@@H]2CCCC[C@@H]2C(=O)O)n3Cc2ccc(OC(F)(F)F)cc2F)n1]

The title compound was prepared using analogous conditions described in Step B of Example 1 using Intermediate P and (2-fluoro-4-(trifluoromethoxy)phenyl)methanamine and as described in Step C of Example 80 using 4-fluoro-N-(2-fluoro-4-(trifluoromethoxy)benzyl)-5-((1-methyl-1H-pyrazol-3-yl)methoxy)-2-nitroaniline. MS (ESI): mass calcd. for $C_{27}H_{25}F_5N_4O_4$, 564.18; m/z found, 565.0 [M+H]$^+$. $^1$H NMR (500 MHz, CD$_3$OD) δ7.48 (d, J=2.3, 1H), 7.37 (d, J=11.3, 1H), 7.26-7.19 (m, 1H), 7.11 (d, J=7.3, 1H), 7.05-6.98 (m, 1H), 6.88 (t, J=8.5, 1H), 6.27 (d, J=2.3, 1H), 5.59 (d, J=17.5, 1H), 5.52 (d, J=17.5, 1H), 5.05 (s, 2H), 3.81 (s, 3H), 3.63-3.56 (m, 1H), 2.87-2.75 (m, 1H), 2.49-2.32 (m, 1H), 2.05-1.70 (m, 5H), 1.50-1.40 (m, 2H).

Example 91 racemic cis-2-{7-Fluoro-1-[2-fluoro-4-(trifluoromethoxy)benzyl]-6-[(1-methyl-1H-pyrazol-3-yl)methoxy]-1H-benzimidazol-2-yl}cyclohexanecarboxylic acid

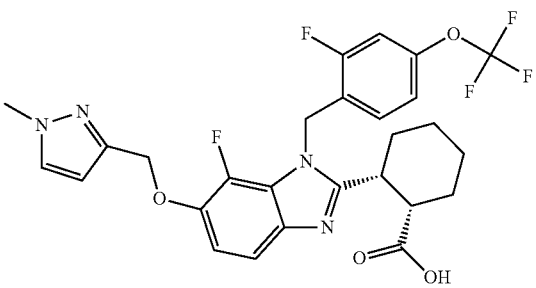 [SMILES: Cn1ccc(COc2ccc3nc([C@@H]4CCCC[C@@H]4C(=O)O)n(Cc4ccc(OC(F)(F)F)cc4F)c3c2F)n1]

The title compound was prepared using analogous conditions described in Step B of Example 1 using 3-((2,3-difluoro-4-nitrophenoxy)methyl)-1-methyl-1H-pyrazole and (2-fluoro-4-(trifluoromethoxy)phenyl)methanamine and as described in Step C of Example 80 using 2-fluoro-N-(2-fluoro-4-(trifluoromethoxy)benzyl)-3-((1-methyl-1H-pyrazol-3-yl)methoxy)-6-nitroaniline. MS (ESI): mass calcd. for $C_{27}H_{25}F_5N_4O_4$, 564.18; m/z found, 565.0 [M+H]$^+$. $^1$H NMR (500 MHz, CD$_3$OD) δ 7.50 (d, J=2.3, 1H), 7.36 (dd, J=8.8, 1.0, 1H), 7.22-7.16 (m, 1H), 7.10-7.04 (m, 1H), 7.04-6.99 (m, 1H), 6.93 (t, J=8.5, 1H), 6.29 (d, J=2.3, 1H), 5.71 (d, J=17.6, 1H), 5.62 (d, J=17.5, 1H), 5.07 (s, 2H), 3.85 (s, 3H), 3.63 (q, J=5.0, 1H), 3.32 (p, J=1.7, OH), 2.83 (dt, J=8.8, 4.3, 1H), 2.47 (q, J=9.0, 1H), 2.02-1.96 (m, 1H), 1.96-1.67 (m, 4H), 1.53-1.38 (m, 2H).

Example 92

2-Ethyl-2-({6-[(1-methyl-1H-pyrazol-3-yl)methoxy]-1-[2-methyl-4-(trifluoromethoxy)benzyl]-1H-benzimidazol-2-yl}methyl)butanoic acid

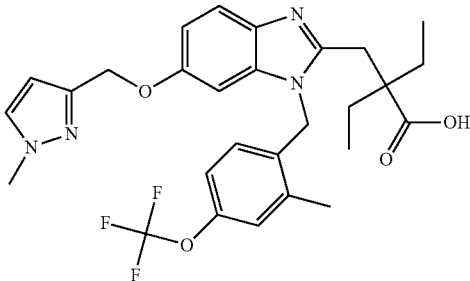 [SMILES: CCC(CC)(Cc1nc2ccc(OCc3ccn(C)n3)cc2n1Cc1ccc(OC(F)(F)F)cc1C)C(=O)O]

Step A: 3-((3-Fluoro-4-nitrophenoxy)methyl)-1-methyl-1H-pyrazole

To a solution of 3-(chloromethyl)-1-methyl-1H-pyrazole (15.6 g, 0.12 mol) in acetonitrile (200 mL) was added $K_2CO_3$ (67 g, 0.48 mol) followed by 3-fluoro-4-nitrophenol (19 g, 0.12 mol). The mixture was stirred at 90° Celsius overnight. When the reaction was complete, it was cooled to RT and the solvent was concentrated to dryness. The resulting residue was dissolved in DCM (500 mL) and then washed with water (500 mL). The organic phase was separated, concentrated to dryness and purified by recrystallization from ethyl acetate (100 mL) to give the title compound. MS (ESI): mass calcd. for $C_{11}H_{10}FN_3O_3$, 251.07; m/z found, 252.2 [M+H]$^+$. $^1$H NMR (300 MHz, CDCl$_3$) δ 8.05-7.99 (t, 1H), 7.33 (d, J=3, 1H), 6.86-6.84 (m, 1H), 6.81-6.78 (m, 1H), 6.29 (d, J=3, 1H), 5.11 (s, 2H), 3.88 (s, 3H).

Step B: 5-((1-Methyl-1H-pyrazol-3-yl)methoxy)-N-(2-methyl-4-(trifluoromethoxy)benzyl)-2-nitroaniline To a solution of 3-((3-fluoro-4-nitrophenoxy)methyl)-1-methyl-1H-pyrazole (143 mg, 0.573 mmol) in acetonitrile (10 mL) was added $K_2CO_3$ (317 mg, 2.3 mmol) followed by (2-methyl-4-(trifluoromethoxy)phenyl)methanamine (117 mg, 0.573 mmol). The mixture was stirred at 90° Celsius overnight. The reaction was cooled to RT and concentrated to dryness. The resulting residue was dissolved in DCM (50 mL) and washed with water (50 mL). The organic phase was concentrated to give the title compound. MS (ESI): mass calcd. for $C_{20}H_{19}F_3N_4O_4$, 436.14; m/z found, 437 [M+H]$^+$.

Step C: 5-((1-Methyl-1H-pyrazol-3-yl)methoxy)-N$^1$-(2-methyl-4-(trifluoromethoxy)benzyl)benzene-1,2-diamine To a suspension of 5-((1-methyl-1H-pyrazol-3-yl)methoxy)-N-(2-methyl-4-(trifluoromethoxy)benzyl)-2-nitroaniline (187 mg, 0.43 mmol) in ethanol (30 mL) was added SnCl$_2$.2H$_2$O (482 mg, 2.21 mmol). The resulting mixture was heated at 90° Celsius. After overnight, the mixture was cooled to RT and diluted with saturated NaHCO$_3$ (40 mL). The resulting mixture was extracted with DCM (3×50 mL). The combined organics were concentrated to dryness to provide the title compound, which was used without further purification. MS (ESI): mass calcd. for $C_{20}H_{21}F_3N_4O_2$, 406.16; m/z found, 407 [M+H]$^+$.

Step D: racemic cis-2-{7-Fluoro-1-[2-fluoro-4-(trifluoromethoxy)benzyl]-6-[(1-methyl-1H-pyrazol-3-yl)methoxy]-1H-benzimidazol-2-yl}cyclohexanecarboxylic acid A mixture of 5-((1-methyl-1H-pyrazol-3-yl)methoxy)-N$^1$-(2-methyl-4-(trifluoromethoxy)benzyl)benzene-1,2-diamine (138 mg, 0.34 mmol) and 3,3-diethyldihydrofuran-2,5-dione (82 mg, 0.53 mmol) in acetonitrile (20 mL) was stirred at 80° Celsius for 8 h. The mixture was cooled to 60° Celsius and HCl (4 mL, 6 N) was added. The reaction was stirred at 60° Celsius for 18 h. When the reaction was judged to be complete by LCMS, the reaction mixture was cooled to RT and concentrated to dryness. The resulting residue was dissolved in THF (9 mL), MeOH (9 mL) and NaOH (2 mL, 5%). The mixture was stirred at 40° Celsius. After 16 h the reaction was concentrated to dryness and the residue was dissolved in water (30 mL) and washed with EtOAc (20 mL). The aqueous layer was separated and acidified to pH ~6 with HCl (6 N) then extracted with DCM (2×30 mL). The combined organic layers were dried over Na$_2$SO$_4$, filtered, concentrated to dryness and purified by reverse phase HPLC to give the title compound. MS (ESI): mass calcd. for $C_{28}H_{31}F_3N_4O_4$, 544.32; m/z found, 545.3 [M+H]$^+$. $^1$H NMR (300 MHz, DMSO-d$_6$) δ 12.23 (s, 1H), 7.59 (d, J=1.9, 1H), 7.46 (d, J=8.6, 1H), 7.29 (s, 1H), 7.09 (d, J=2.3, 1H), 7.03 (d, J=9.5, 1H), 6.81 (dd, J=8.7, 2.3, 1H), 6.22 (d, J=2.2, 1H), 6.18 (d, J=8.8, 1H), 5.44 (s, 2H), 4.91 (s, 2H), 3.77 (s, 3H), 2.85 (s, 2H), 2.47 (s, 3H), 1.77 (q, J=7.3, 4H), 0.69 (t, J=7.3, 6H).

Example 93 racemic cis-2-{1-(4-Bromobenzyl)-4-fluoro-6-[(1-methyl-H-pyrazol-3-yl)methoxy]-1H-benzimidazol-2-yl}cyclohexanecarboxylic acid

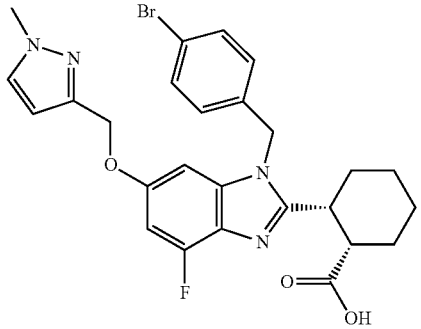 [SMILES: Cn1ccc(COc2cc(F)c3nc([C@@H]4CCCC[C@@H]4C(=O)O)n(Cc4ccc(Br)cc4)c3c2)n1]

The title compound was prepared using analogous conditions described in Steps A-C of Example 92 using 3,5-difluoro-4-nitrophenol in Step A and (4-bromophenyl)methanamine in Step B and as described in Step C of Example 1 using N-(4-bromobenzyl)-3-fluoro-5-((1-methyl-1H-pyrazol-3-yl)methoxy)benzene-1,2-diamine. MS (ESI): mass calcd. for $C_{26}H_{26}BrFN_4O_3$, 540.10; m/z found, 540.9 [M+H]$^+$. $^1$H NMR (300 MHz, DMSO-d$_6$) δ 12.01 (s, 1H), 7.63 (s, 1H), 7.51 (d, J=8.1, 2H), 7.10 (d, J=8.1, 2H), 6.94 (s, 1H), 6.71 (d, J=14.2, 1H), 6.24 (s, 1H), 5.51 (d, J=17.1, 1H), 5.43 (d, J=17.1, 1H), 4.95 (s, 2H), 3.74-3.57 (m, 1H), 2.80-2.63 (m, 1H), 2.51 (s, 3H), 1.91-1.76 (m, 2H), 1.76-1.41 (m, 3H), 1.40-1.18 (m, 2H).

Example 94 racemic cis-2-{1-(4-Bromo-2-fluorobenzyl)-4-fluoro-6-[(1-methyl-1H-pyrazol-3-yl)methoxy]-1H-benzimidazol-2-yl}cyclohexanecarboxylic acid

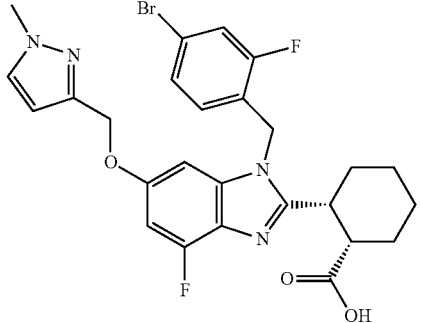 [SMILES: Cn1ccc(COc2cc(F)c3nc([C@@H]4CCCC[C@@H]4C(=O)O)n(Cc4ccc(Br)cc4F)c3c2)n1]

The title compound was prepared using analogous conditions described in Steps A-C of Example 92 using 3,5- difluoro-4-nitrophenol in Step A and (4-bromo-2-fluorophenyl)methanamine in Step B and as described in Step C of Example 1 using N¹-(4-bromo-2-fluorobenzyl)-3-fluoro-5-((1-methyl-1H-pyrazol-3-yl)methoxy)benzene-1,2-diamine. MS (ESI): mass calcd. for $C_{26}H_{25}BrF_2N_4O_3$, 558.11; m/z found, 558.9 [M+H]⁺. ¹H NMR (300 MHz, DMSO-d₆) δ 7.64 (dd, J=9.0, 2.0, 2H), 7.29 (dd, J=8.3, 1.9, 1H), 6.98 (d, J=2.1, 1H), 6.77-6.61 (m, 2H), 6.25 (d, J=2.2, 1H), 5.60-5.31 (m, 2H), 4.94 (s, 2H), 3.80 (s, 3H), 3.66-3.53 (m, 1H), 2.76-2.59 (m, 1H), 1.88-1.76 (m, 2H), 1.76-1.48 (m, 3H), 1.43-1.23 (m, 2H).

Example 95 racemic cis-2-{4-Fluoro-6-[(1-methyl-1H-pyrazol-3-yl)methoxy]-1-[4-(trifluoromethoxy)benzyl]-1H-benzimidazol-2-yl}cyclohexanecarboxylic acid as the HCl salt

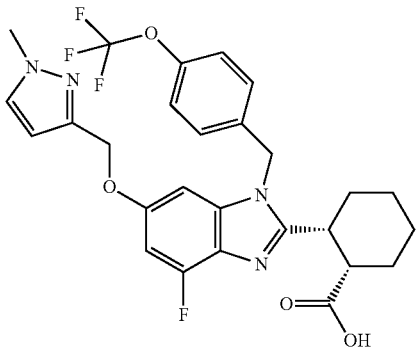 [SMILES: Cn1ccc(COc2cc(F)c3nc([C@@H]4CCCC[C@@H]4C(=O)O)n(Cc4ccc(OC(F)(F)F)cc4)c3c2)n1]

The title compound was prepared using analogous conditions described in Steps A-C of Example 92 using 3,5-difluoro-4-nitrophenol in Step A and (4-(trifluoromethoxy)phenyl)methanamine in Step B and as described in Step C of Example 1 using 3-fluoro-5-((1-methyl-1H-pyrazol-3-yl)methoxy)-N¹-(4-(trifluoromethoxy)benzyl)benzene-1,2-diamine. MS (ESI): mass calcd. for $C_{27}H_{26}F_4N_4O_4$, 546.19; m/z found, 547.0 [M+H]⁺. ¹H NMR (300 MHz, DMSO-d₆) δ 7.62 (d, J=2.2, 1H), 7.40-7.27 (m, 4H), 7.05 (s, 1H), 6.88 (d, J=12.3, 1H), 6.23 (d, J=2.2, 1H), 5.68 (d, J=17.1, 1H), 5.59 (d, J=17.3, 1H), 4.97 (s, 2H), 3.79 (s, 3H), 3.72-3.58 (m, 1H), 2.81-2.68 (m, 1H), 2.34 (d, J=12.1, 1H), 1.93-1.58 (m, 5H), 1.47-1.22 (m, 2H).

Example 96 racemic cis-2-{4-Fluoro-1-[2-fluoro-4-(trifluoromethoxy)benzyl]-6-[(1-methyl-1H-pyrazol-3-yl)methoxy]-1H-benzimidazol-2-yl}cyclohexanecarboxylic acid as the HCl salt

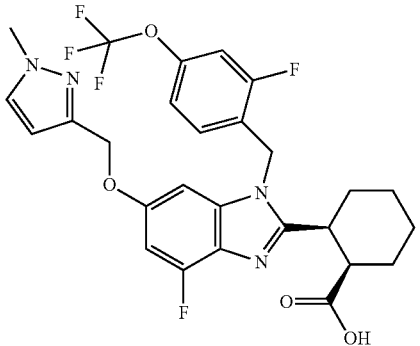 [SMILES: Cn1ccc(COc2cc(F)c3nc([C@H]4CCCC[C@H]4C(=O)O)n(Cc4ccc(OC(F)(F)F)cc4F)c3c2)n1]

The title compound was prepared using analogous conditions described in Steps A-C of Example 92 using 3,5-difluoro-4-nitrophenol in Step A and (2-fluoro-4-(trifluoromethoxy)phenyl)methanamine in Step B and as described in Step C of Example 1 using 3-fluoro-N-(2-fluoro-4-(trifluoromethoxy)benzyl)-5-((1-methyl-1H-pyrazol-3-yl)methoxy)benzene-1,2-diamine. MS (ESI): mass calcd. for $C_{27}H_{25}F_5N_4O_4$, 564.18; m/z found, 565 [M+H]⁺. ¹H NMR (300 MHz, DMSO-d₆) δ 7.63 (d, J=2.2, 1H), 7.51 (d, J=10.4, 1H), 7.14 (d, J=7.9, 1H), 7.09-7.03 (m, 1H), 6.98-6.88 (m, 1H), 6.84 (d, J=12.3, 1H), 6.25 (d, J=2.2, 1H), 5.63 (s, 2H), 4.97 (s, 2H), 3.87-3.72 (m, 3H), 3.69-3.59 (m, 1H), 2.80-2.68 (m, 1H), 2.46-2.29 (m, 1H), 1.92-1.57 (m, 5H), 1.48-1.27 (m, 2H).

Example 97 racemic cis-2-{4-Fluoro-1-(4-methylbenzyl)-6-[(1-methyl-1H-pyrazol-3-yl)methoxy]-1H-benzimidazol-2-yl}cyclohexanecarboxylic acid as the HCl salt

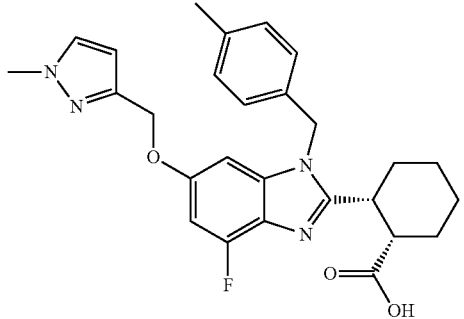 [SMILES: Cc1ccc(Cn2c([C@@H]3CCCC[C@@H]3C(=O)O)nc3c(F)cc(OCc4ccn(C)n4)cc32)cc1]

The title compound was prepared using analogous conditions described in Steps A-C of Example 92 using 3,5-difluoro-4-nitrophenol in Step A and p-tolylmethanamine in Step B and as described in Step C of Example 1 using 3-fluoro-5-((1-methyl-1H-pyrazol-3-yl)methoxy)-N¹-(4-methylbenzyl)benzene-1,2-diamine. MS (ESI): mass calcd. for $C_{27}H_{29}FN_4O_3$, 476.22; m/z found, 477.0 [M+H]⁺. ¹H NMR (300 MHz, DMSO-d₆) δ 7.63 (d, J=2.2, 1H), 7.19-6.95 (m, 6H), 6.22 (d, J=2.2, 1H), 5.68 (d, J=16.7, 1H), 5.57 (d, J=16.8, 1H), 4.98 (s, 2H), 3.79 (s, 3H), 3.76-3.57 (m, 1H), 2.88-2.70 (m, 1H), 2.28 (s, 3H), 2.26-2.11 (m, 1H), 2.08-1.66 (m, 4H), 1.65-1.27 (m, 3H).

Example 98 racemic cis-2-{1-(4-Cyanobenzyl)-4-fluoro-6-[(1-methyl-1H-pyrazol-3-yl)methoxy]-1H-benzimidazol-2-yl}cyclohexanecarboxylic acid as the HCl salt

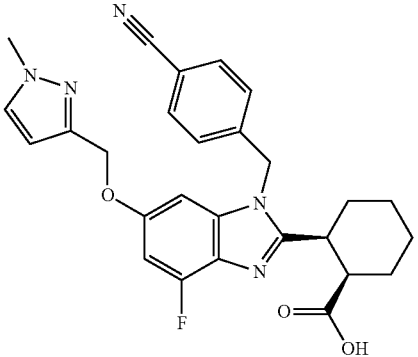 [SMILES: Cn1ccc(COc2cc(F)c3nc([C@H]4CCCC[C@H]4C(=O)O)n(Cc4ccc(C#N)cc4)c3c2)n1]

The title compound was prepared using analogous conditions described in Steps A-C of Example 92 using 3,5-difluoro-4-nitrophenol in Step A and 4-(aminomethyl)benzonitrile in Step B and as described in Step C of Example 1 using 4-(((2-amino-3-fluoro-5-((1-methyl-1H-pyrazol-3-yl)methoxy)phenyl)amino)methyl)benzonitrile. MS (ESI): mass calcd. for $C_{27}H_{26}FN_5O_3$, 487.20; m/z found, 488.2 [M+H]+. 1H NMR (300 MHz, DMSO-$d_6$) δ 7.91-7.76 (m, 2H), 7.71-7.54 (m, 1H), 7.31 (d, J=8.3, 2H), 7.04-6.98 (m, 1H), 6.91-6.81 (m, 1H), 6.22 (d, J=2.2, 1H), 5.85-5.47 (m, 2H), 4.95 (s, 2H), 3.79 (s, 3H), 3.75-3.56 (m, 1H), 2.83-2.63 (m, 1H), 2.38 (s, 1H), 1.98-1.54 (m, 5H), 1.52-1.24 (m, 2H).

Example 99 racemic cis-2-{6-[(1-Methyl-1H-pyrazol-3-yl)methoxy]-1-[2-methyl-4-(trifluoromethoxy)benzyl]-1H-benzimidazol-2-yl}cyclohexanecarboxylic acid

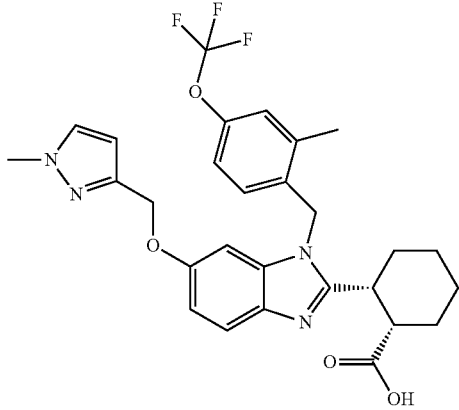 [SMILES: Cc1cc(OC(F)(F)F)ccc1Cn1c([C@@H]2CCCC[C@@H]2C(=O)O)nc2ccc(OCc3ccn(C)n3)cc21]

The title compound was prepared using analogous conditions described in Example 92 using 5-((1-methyl-1H-pyrazol-3-yl)methoxy)-N1-(2-methyl-4-(trifluoromethoxy)benzyl)benzene-1,2-diamine and cis-hexahydroisobenzofuran-1,3-dione in Step D. MS (ESI): mass calcd. for $C_{28}H_{29}F_3N_4O_4$, 542.20; m/z found, 543.2 [M+H]+. 1H NMR (300 MHz, DMSO-$d_6$) δ 7.71 (d, J=7.7, 1H), 7.58 (d, J=2.2, 1H), 7.35 (s, 1H), 7.24 (s, 1H), 7.15 (s, 1H), 7.01 (d, J=10.0, 1H), 6.42 (d, J=8.8, 1H), 6.18 (d, J=2.2, 1H), 5.72-5.60 (m, 2H), 4.96 (s, 2H), 3.76 (s, 3H), 3.65 (s, 1H), 2.72 (s, 1H), 2.51 (s, 3H), 2.22-1.66 (m, 5H), 1.62-1.33 (m, 3H).

Example 100 racemic cis-2-{6-[(5-Methyl pyridin-2-yl)methoxy]-1-[2-methyl-4-(trifluoromethoxy)benzyl]-1H-benzimidazol-2-yl}cyclohexanecarboxylic acid

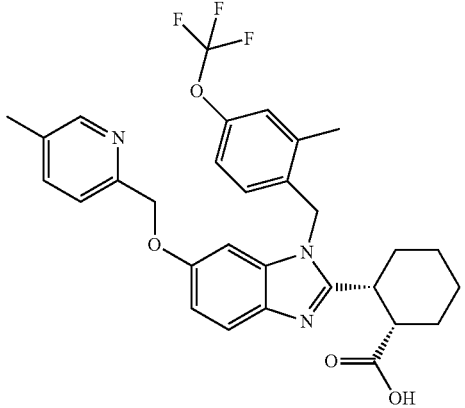 [SMILES: Cc1ccc(COc2ccc3nc([C@@H]4CCCC[C@@H]4C(=O)O)n(Cc4ccc(OC(F)(F)F)cc4C)c3c2)nc1]

The title compound was prepared using analogous conditions described in Example 92 using 2-((3-fluoro-4-nitrophenoxy)methyl)-5-methylpyridine in Step B and N1-(2-methyl-4-(trifluoromethoxy)benzyl)-5-((5-methylpyridin-2-yl)methoxy)benzene-1,2-diamine and cis-hexahydroisobenzofuran-1,3-dione in Step D. MS (ESI): mass calcd. for $C_{30}H_{30}F_3N_3O_4$, 553.20; m/z found, 553.9 [M+H]+. 1H NMR (300 MHz, DMSO-$d_6$) δ 8.34 (s, 1H), 7.66 (s, 1H), 7.60 (d, J=7.3, 1H), 7.37 (d, J=8.2, 1H), 7.32 (s, 1H), 7.15 (s, 2H), 6.95 (d, J=7.9, 1H), 6.36 (d, J=8.3, 1H), 5.60 (s, 2H), 5.11 (s, 2H), 3.59 (s, 1H), 2.71 (s, 1H), 2.50 (s, 3H), 2.28 (s, 3H), 1.75 (brs, 4H), 1.60-1.30 (m, 4H).

Example 101 racemic cis-2-{1-[2-Chloro-4-(trifluoromethoxy)benzyl]-6-[(5-methylpyridin-2-yl)methoxy]-1H-benzimidazol-2-yl}cyclohexanecarboxylic acid as the HCl salt

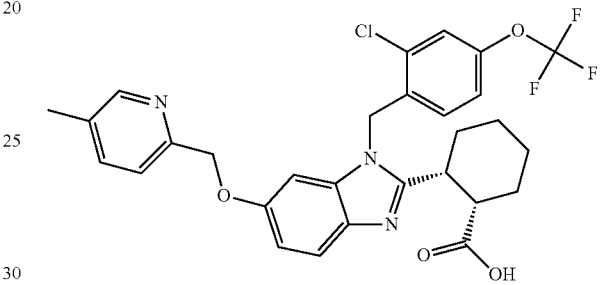

The title compound was prepared using analogous conditions described in Example 92 using (2-chloro-4-(trifluoromethoxy)phenyl)methanamine and 2-((3-fluoro-4-nitrophenoxy)methyl)-5-methylpyridine in Step B and N-(2-chloro-4-(trifluoromethoxy)benzyl)-5-((5-methylpyridin-2-yl)methoxy)benzene-1,2-diamine and cis-hexahydroisobenzofuran-1,3-dione in Step D. MS (ESI): mass calcd. for $C_{29}H_{27}ClF_3N_3O_4$, 573.16; m/z found, 573.9 [M+H]+. 1H NMR (300 MHz, DMSO-$d_6$) δ 8.52 (s, 1H), 7.92 (d, J=8.2, 1H), 7.79 (d, J=8.9, 1H), 7.76 (d, J=1.8, 1H), 7.62 (d, J=7.7, 1H), 7.31-7.23 (m, 3H), 6.80 (d, J=8.6, 1H), 5.89-5.74 (m, 2H), 5.28 (s, 2H), 3.75-3.62 (m, 1H), 2.81-2.68 (m, 1H), 2.36 (s, 3H), 2.21-1.69 (m, 5H), 1.64-1.30 (m, 3H).

Example 102 racemic cis-2-{1-[2-Bromo-4-(trifluoromethoxy)benzyl]-6-[(5-methylpyridin-2-yl)methoxy]-1H-benzimidazol-2-yl}cyclohexanecarboxylic acid as the HCl salt

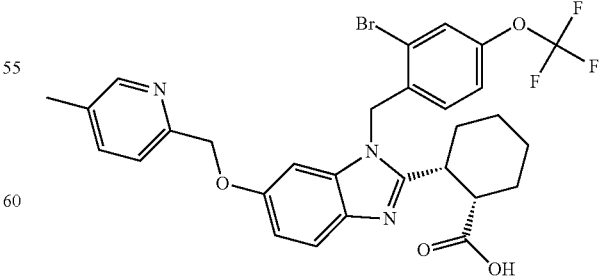

The title compound was prepared using analogous conditions described in Example 92 using (2-bromo-4-(trifluoromethoxy)phenyl)methanamine and 2-((3-fluoro-4-nitrophenoxy)methyl)-5-methylpyridine in Step B and N¹-(2-bromo-4-(trifluoromethoxy)benzyl)-5-((5-methylpyridin-2-yl)methoxy)benzene-1,2-diamine and cis-hexahydroisobenzofuran-1,3-dione in Step D. MS (ESI): mass calcd. for $C_{29}H_{27}BrF_3N_3O_4$, 617.11; m/z found, 617.8 [M+H]⁺. ¹H NMR (300 MHz, DMSO-$d_6$) δ 8.57 (s, 1H), 8.00 (d, J=8.4, 1H), 7.89 (s, 1H), 7.82 (d, J=8.8, 1H), 7.68 (d, J=8.1, 1H), 7.42-7.22 (m, 3H), 6.78 (d, J=8.6, 1H), 5.85-5.71 (m, 2H), 5.33 (s, 2H), 3.70 (s, 1H), 2.76 (s, 1H), 2.38 (s, 3H), 2.25-1.70 (m, 5H), 1.62-1.32 (m, 3H).

Example 103 racemic cis-2-{1-[2-Chloro-4-(trifluoromethoxy)benzyl]-6-[(1-methyl-1H-pyrazol-3-yl)methoxy]-1H-benzimidazol-2-yl}cyclohexanecarboxylic acid as the HCl salt

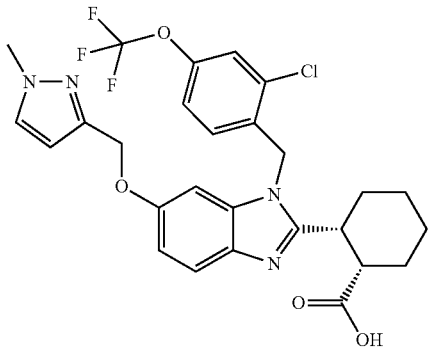 [SMILES: Cn1ccc(COc2ccc3nc([C@@H]4CCCC[C@@H]4C(=O)O)n(Cc4ccc(OC(F)(F)F)cc4Cl)c3c2)n1]

The title compound was prepared using analogous conditions described in Example 92 using (2-chloro-4-(trifluoromethoxy)phenyl)methanamine in Step B and N¹-(2-chloro-4-(trifluoromethoxy)benzyl)-5-((1-methyl-1H-pyrazol-3-yl)methoxy)benzene-1,2-diamine and cis-hexahydroisobenzofuran-1,3-dione in Step D. MS (ESI): mass calcd. for $C_{27}H_{26}ClF_3N_4O_4$, 562.16; m/z found, 562.9 [M+H]⁺. ¹H NMR (300 MHz, DMSO-$d_6$) δ 7.79-7.76 (s, 2H), 7.60 (d, J=2.1, 1H), 7.32-7.28 (m, 2H), 7.20 (dd, J=9.0, 2.1, 1H), 6.87 (d, J=8.6, 1H), 6.20 (d, J=2.2, 1H), 5.92-5.76 (m, 2H), 4.97 (s, 2H), 3.77 (s, 3H), 3.72-3.68 (m, 1H), 2.78-2.77 (m, 1H), 2.28-1.67 (m, 5H), 1.64-1.32 (m, 3H).

Example 104 racemic cis-2-{1-[2-Bromo-4-(trifluoromethoxy)benzyl]-6-[(1-methyl-1H-pyrazol-3-yl)methoxy]-1H-benzimidazol-2-yl}cyclohexanecarboxylic acid as the HCl salt

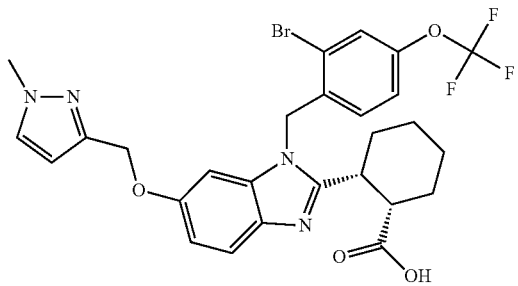 [SMILES: Cn1ccc(COc2ccc3nc([C@@H]4CCCC[C@@H]4C(=O)O)n(Cc4ccc(OC(F)(F)F)cc4Br)c3c2)n1]

The title compound was prepared using analogous conditions described in Example 92 using (2-bromo-4-(trifluoromethoxy)phenyl)methanamine in Step B and N¹-(2-bromo-4-(trifluoromethoxy)benzyl)-5-((5-methylpyridin-2-yl)methoxy)benzene-1,2-diamine and cis-hexahydroisobenzofuran-1,3-dione in Step D. MS (ESI): mass calcd. for $C_{27}H_{26}BrF_3N_4O_4$, 606.11; m/z found, 606.9 [M+H]⁺. ¹H NMR (300 MHz, DMSO-$d_6$) δ 7.91 (s, 1H), 7.80 (d, J=8.9, 1H), 7.61 (d, J=1.9, 1H), 7.42-7.28 (m, 2H), 7.22 (d, J=8.9, 1H), 6.85 (d, J=8.6, 1H), 6.21 (d, J=2.1, 1H), 5.88-5.73 (m, 2H), 4.98 (s, 2H), 3.78 (s, 3H), 3.75-3.64 (m, 1H), 2.78 (s, 1H), 2.34-1.70 (m, 5H), 1.68-1.25 (m, 3H).

Example 105

2-Ethyl-2-({6-[(5-methylpyridin-2-yl)methoxy]-1-[2-methyl-4-(trifluoromethoxy)benzyl]-1H-benzimidazol-2-yl}methyl)butanoic acid

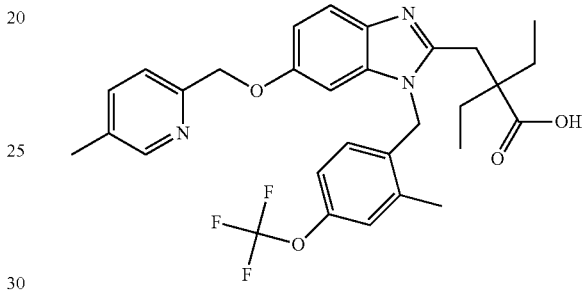

The title compound was prepared using analogous conditions described in Example 92 using 2-((3-fluoro-4-nitrophenoxy)methyl)-5-methylpyridine in Step B and N¹-(2-methyl-4-(trifluoromethoxy)benzyl)-5-((5-methylpyridin-2-yl)methoxy)benzene-1,2-diamine. MS (ESI): mass calcd. for $C_{30}H_{32}F_3N_3O_4$, 555.23; m/z found, 556.0 [M+H]⁺. ¹H NMR (300 MHz, DMSO-$d_6$) δ 12.23 (s, 1H), 8.33 (s, 1H), 7.58 (d, J=7.9, 1H), 7.48 (d, J=8.7, 1H), 7.36 (d, J=7.8, 1H), 7.28 (s, 1H), 7.08 (d, J=2.1, 1H), 7.00 (d, J=7.9, 1H), 6.86 (dd, J=8.7, 2.3, 1H), 6.16 (d, J=8.4, 1H), 5.43 (s, 2H), 5.06 (s, 2H), 2.85 (s, 2H), 2.46 (s, 3H), 2.27 (s, 3H), 1.81-1.73 (m, 4H), 0.69 (t, J=7.4, 6H).

Example 106 racemic cis-2-{6-[(1-Methyl-1H-pyrazol-3-yl)methoxy]-1-[3-methyl-4-(trifluoromethoxy)benzyl]-1H-benzimidazol-2-yl}cyclohexanecarboxylic acid as the HCl salt

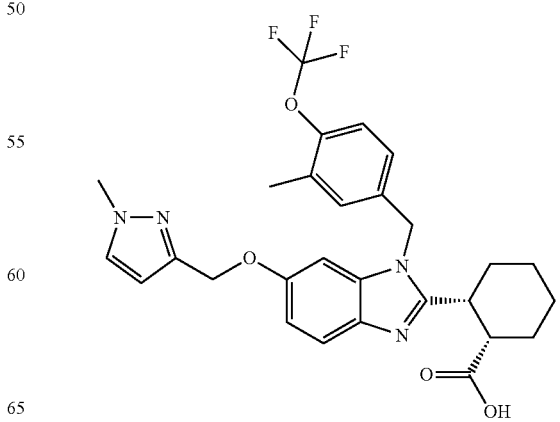

The title compound was prepared using analogous conditions described in Example 92 using (3-methyl-4-(trifluoromethoxy)phenyl)methanamine in Step B and 5-((1-methyl-1H-pyrazol-3-yl)methoxy)-N$^1$-(3-methyl-4-(trifluoromethoxy)benzyl)benzene-1,2-diamine and cis-hexahydroisobenzofuran-1,3-dione in Step D. MS (ESI): mass calcd. for $C_{28}H_{29}F_3N_4O_4$, 542.21; m/z found, 543.0 [M+H]$^+$. $^1$H NMR (300 MHz, DMSO-d$_6$) δ 7.71 (d, J=8.8, 1H), 7.60 (d, J=2.1, 1H), 7.34-7.31 (m, 2H), 7.18 (s, 2H), 7.12 (d, J=8.6, 1H), 6.19 (d, J=2.2, 1H), 5.84-5.70 (m, 2H), 4.99 (s, 2H), 3.78 (s, 3H), 3.68 (s, 1H), 2.83 (s, 1H), 2.22 (s, 3H), 2.00 (s, 3H), 1.81 (s, 2H), 1.57 (s, 1H), 1.42 (s, 2H).

Example 107

3-{1-(4-Bromobenzyl)-6-[(1-methyl-1H-pyrazol-3-yl)methoxy]-1H-benzimidazol-2-yl}-2,2-dimethyl-propanoic acid

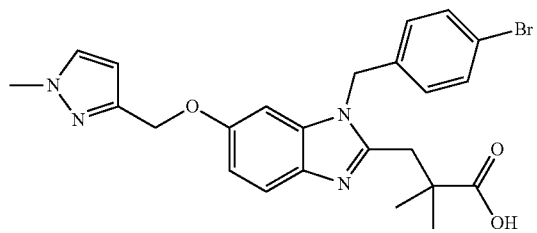 [SMILES: Cn1ccc(COc2ccc3nc(CC(C)(C)C(=O)O)n(Cc4ccc(Br)cc4)c3c2)n1]

Step A: Ethyl 3-(1-(4-bromobenzyl)-6-hydroxy-1H-benzo[d]imidazol-2-yl)-2,2-dimethylpropanoate To a solution of ethyl 3-(1-(4-bromobenzyl)-6-methoxy-1H-benzo[d]imidazol-2-yl)-2,2-dimethylpropanoate (12 g, 27 mmol) in DCM (200 mL) was added BBr$_3$ (20 g, 81 mmol) in DCM (100 mL) drop wise at −78° Celsius. The solution was gradually warmed to 5° Celsius and stirred for 3 h. The reaction mixture was slowly added to saturated NaHCO$_3$ with rapid stirring for 1 h. The organic phase was separated and aqueous phase was extracted with DCM (200 mL). The combined organic phases were dried over Na$_2$SO$_4$, filtered, concentrated to dryness and purified by FCC to provide the title compound. MS (ESI): mass calcd. for $C_{21}H_{23}BrN_2O_3$, 430.09; m/z found, 438 [M+H]+.

Step B: 3-{1-(4-Bromobenzyl)-6-[(1-methyl-1H-pyrazol-3-yl)methoxy]-1H-benzimidazol-2-yl}-2,2-dimethylpropanoic acid A mixture of ethyl 3-(1-(4-bromobenzyl)-6-hydroxy-1H-benzo[d]imidazol-2-yl)-2,2-dimethylpropanoate (322 mg, 0.75 mmol), 3-(chloromethyl)-1-methyl-1H-pyrazole (97.5 mg, 0.75 mmol) and K$_2$CO$_3$ (310 mg, 2.25 mmol) in DMF (20 mL) was stirred at 50° Celsius for 18 h. The resulting residue was dissolved in THF (9 mL), MeOH (9 mL) and NaOH (2 mL, 5%). The mixture was stirred at 40° Celsius. After 16 h the reaction was concentrated to dryness and the residue was dissolved in water (30 mL), washed with EtOAc (20 mL). The aqueous layer was separated and acidified to pH ~6 with HCl (6 N) then extracted with DCM (2×30 mL). The combined organic layers were dried over Na$_2$SO$_4$, filtered, concentrated to dryness and purified by reverse phase HPLC to give the title compound (63 mg, 19%). MS (ESI): mass calcd. for $C_{24}H_{25}BrN_4O_3$, 496.11; m/z found, 497.1 [M+H]$^+$. $^1$H NMR (300 MHz, CD$_3$OD) δ 7.84 (d, J=2.4, 1H), 7.76 (d, J=9.0, 1H), 7.54 (d, J=8.5, 2H), 7.32 (dd, J=9.0, 2.3, 1H), 7.27 (d, J=2.1, 1H), 7.16 (d, J=8.4, 2H), 6.49 (d, J=2.4, 1H), 5.83 (s, 2H), 5.21 (s, 2H), 3.98 (s, 3H), 3.51 (s, 2H), 1.41 (s, 6H).

Example 108

3-{1-(4-Bromobenzyl)-6-[(6-methylpyridin-2-yl)methoxy]-1H-benzimidazol-2-yl}-2,2-dimethylpropanoic acid

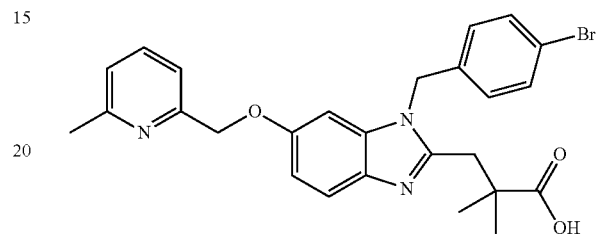

The title compound was prepared using analogous conditions described in Example 107 using 2-(chloromethyl)-6-methylpyridine in Step B. MS (ESI): mass calcd. for $C_{26}H_{26}BrN_3O_3$, 507.12; m/z found, 508.0 [M+H]$^+$. $^1$H NMR (300 MHz, CD$_3$OD) δ 8.47 (app t, J=8.0, 1H), 7.97 (d, J=7.9, 1H), 7.90 (d, J=8.0, 1H), 7.83 (d, J=8.9, 1H), 7.52 (d, J=8.4, 2H), 7.47-7.37 (m, 2H), 7.18 (d, J=8.4, 2H), 5.89 (s, 2H), 5.53 (s, 2H), 3.53 (s, 2H), 2.85 (s, 3H), 1.42 (s, 6H).

Example 109 racemic cis-2-{6-[(5-Methylpyridin-2-yl)methoxy]-1-[3-methyl-4-(trifluoromethoxy)benzyl]-1H-benzimidazol-2-yl}cyclohexanecarboxylic acid

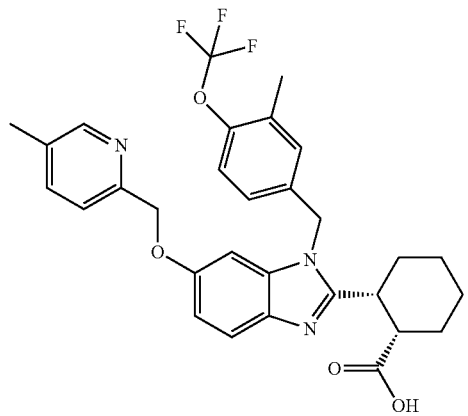 [SMILES: Cc1ccc(COc2ccc3nc([C@@H]4CCCC[C@@H]4C(=O)O)n(Cc4ccc(OC(F)(F)F)c(C)c4)c3c2)nc1]

The title compound was prepared using analogous conditions described in Example 92 using (3-methyl-4-(trifluoromethoxy)phenyl)methanamine and 2-((3-fluoro-4-nitrophenoxy)methyl)-5-methylpyridine in Step B and N$^1$-(3-methyl-4-(trifluoromethoxy)benzyl)-5-((5-methylpyridin-2-yl)methoxy)benzene-1,2-diamine and cis-hexahydroisobenzofuran-1,3-dione in Step D. MS (ESI): mass calcd. for $C_{30}H_{30}F_3N_3O_4$, 553.22; m/z found, 554.0 [M+H]$^+$. $^1$H NMR (300 MHz, DMSO-d$_6$) δ 12.04 (s, 1H), 8.34 (d, J=1.9, 1H), 7.56 (dd, J=7.8, 2.0, 1H), 7.45 (d, J=8.7, 1H), 7.33 (d, J=7.9, 1H), 7.21-7.19 (m, 2H), 7.08-6.97 (m, 2H), 6.83 (dd, J=8.7, 2.3, 1H), 5.49-5.33 (m, 2H), 5.08 (s, 2H), 3.73-3.64 (m, 1H), 2.75-2.64 (m, 1H), 2.27 (s, 3H), 2.19 (s, 3H), 1.90-1.41 (m, 6H), 1.33 (s, 2H).

Example 110 racemic cis-2-{5-Chloro-1-[2-fluoro-4-(trifluoromethoxy)benzyl]-6-[(5-methylpyridin-2-yl)methoxy]-1H-benzimidazol-2-yl}cyclohexanecarboxylic acid as the HCl salt

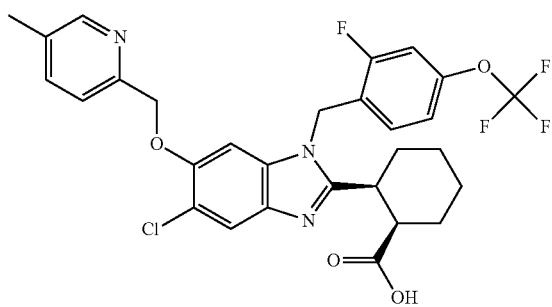 [SMILES: Cc1ccc(COc2cc3c(cc2Cl)nc([C@H]2CCCC[C@H]2C(=O)O)n3Cc2ccc(OC(F)(F)F)cc2F)nc1]

The title compound was prepared using analogous conditions described in Steps A-C of Example Example 92 using 2-chloro-4-fluoro-5-nitrophenol and 2-(chloromethyl)-5-methyl pyridine in Step A and (2-fluoro-4-(trifluoromethoxy)phenyl)methanamine in Step B and as described in Step C of Example 1 using 4-chloro-N$^1$-(2-fluoro-4-(trifluoromethoxy)benzyl)-5-((5-methylpyridin-2-yl)methoxy)benzene-1,2-diamine. MS (ESI): mass calcd. for $C_{29}H_{26}ClF_4N_3O_4$, 591.20; m/z found, 592.1 [M+H]$^+$. $^1$H NMR (300 MHz, DMSO-d$_6$) δ 8.54 (s, 1H), 8.01-7.91 (m, 2H), 7.79-7.60 (m, 2H), 7.51 (d, J=11.3, 1H), 7.12 (d, J=8.6, 1H), 7.08-6.95 (m, 1H), 5.80 (s, 2H), 5.36 (s, 2H), 3.67 (s, 1H), 2.81-2.79 (m, 1H), 2.37 (s, 3H), 2.17 (s, 1H), 2.01 (s, 1H), 1.80 (s, 3H), 1.51 (s, 2H), 1.39 (s, 1H).

Example 111 racemic cis-3-{1-(4-Bromobenzyl)-6-[(5-methylpyridin-2-yl)methoxy]-1H-benzimidazol-2-yl}-2,2-dimethylcyclopropanecarboxylic acid as the TFA salt

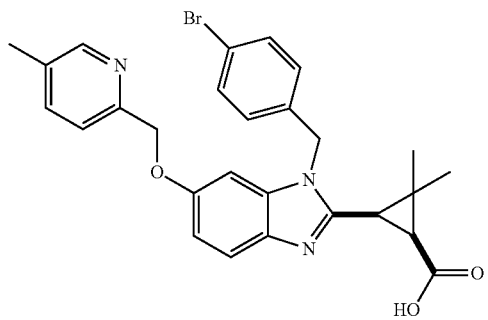

A solution of LiOH (78 mg, 0.19 mmol) in water (2 mL) was added to a 20 mL round-bottomed flask containing cis-ethyl 3-(1-(4-bromobenzyl)-6-((5-methylpyridin-2-yl)methoxy)-1H-benzo[d]imidazol-2-yl)-2,2-dimethylcyclopropanecarboxylate (110 mg, 0.19 mmol), THF (6 mL), MeOH (6 mL), and water (4 mL). The resulting solution was heated to 80° Celsius. After 2 h, the solution was concentrated to dryness and the residue was treated with sat. NH$_4$Cl (20 mL) and EtOAc (20 mL). The organic layer was separated and the aqueous layer was further extracted with EtOAc (2×20 mL). The combine organic layers were dried with sodium sulfate, filtered, and concentrated to dryness. The residue was subjected to FCC to give the title compound (84 mg, 83%). MS (ESI): mass calcd. for $C_{27}H_{26}BrN_3O_3$, 519.11; m/z found, 520.1 [M+H]$^+$.

Example 112

(1S*,3R*)-3-{1-(4-Bromobenzyl)-6-[(5-methylpyridin-2-yl)methoxy]-1H-benzimidazol-2-yl}-2,2-dimethylcyclopropanecarboxylic acid

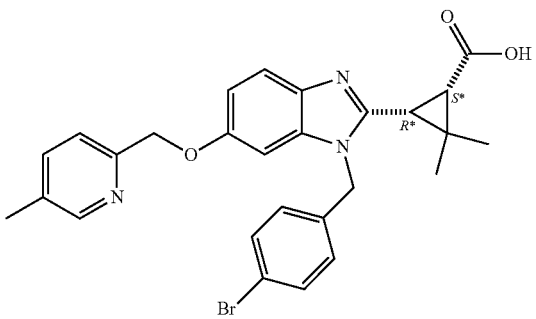

racemic cis-3-{1-(4-Bromobenzyl)-6-[(5-methylpyridin-2-yl)methoxy]-1H-benzimidazol-2-yl}-2,2-dimethylcyclopropanecarboxylic acid was purified by SFC (CHIRALPAK AD-H 5 μm 250×20 mm) mobile phase (65% CO$_2$, 35% MeOH) as the first eluting isomer. MS (ESI): mass calcd. for $C_{27}H_{26}BrN_3O_3$, 519.12; m/z found, 520.0 [M+H]$^+$. $^1$H NMR (400 MHz, DMSO-d$_6$) δ 14.86 (s, 1H), 8.41 (d, J=2.1, 1H), 7.65 (dd, J=7.9, 1.6, 1H), 7.56 (dd, J=8.6, 3.3, 3H), 7.43 (d, J=7.9, 1H), 7.30 (d, J=2.3, 1H), 7.10 (d, J=8.5, 2H), 6.98 (dd, J=8.8, 2.4, 1H), 5.54 (d, J=16.9, 1H), 5.47 (d, J=16.7, 1H), 5.18 (s, 2H), 2.44 (d, J=8.5, 1H), 2.33 (s, 3H), 2.13 (d, J=8.5, 1H), 1.18 (s, 3H), 1.07 (s, 3H).

Example 113

(1R*,3S*)-3-{1-(4-Bromobenzyl)-6-[(5-methylpyridin-2-yl)methoxy]-1H-benzimidazol-2-yl}-2,2-dimethylcyclopropanecarboxylic acid

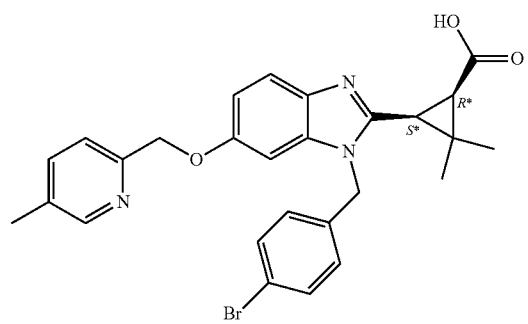 [SMILES: Cc1ccc(COc2ccc3nc([C@H]4[C@@H](C(=O)O)C4(C)C)n(Cc4ccc(Br)cc4)c3c2)nc1]

racemic cis-3-{1-(4-Bromobenzyl)-6-[(5-methylpyridin-2-yl)methoxy]-1H-benzimidazol-2-yl}-2,2-dimethylcyclopropanecarboxylic acid was purified by SFC (CHIRALPAK AD-H 5 μm 250×20 mm) mobile phase (65% CO$_2$, 35% MeOH) as the second eluting isomer. MS (ESI): mass calcd. for C$_{27}$H$_{26}$BrN$_3$O$_3$, 519.12; m/z found, 520.0 [M+H]$^+$.

Example 114 racemic trans-3-{1-(4-Bromobenzyl)-6-[(5-methylpyridin-2-yl)methoxy]-1H-benzimidazol-2-yl}-2,2-dimethylcyclopropanecarboxylic acid as the TFA salt

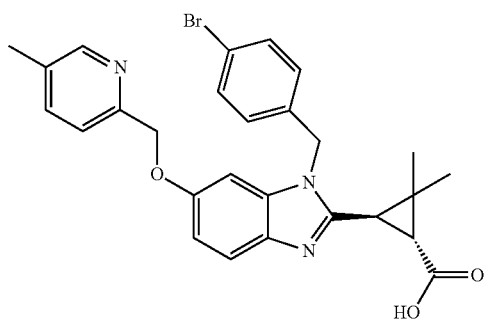 [SMILES: Cc1ccc(COc2ccc3nc([C@@H]4[C@@H](C(=O)O)C4(C)C)n(Cc4ccc(Br)cc4)c3c2)nc1]

The title compound was prepared using in a manner analogous to that in Example 111 using racemic trans-ethyl 3-(1-(4-bromobenzyl)-6-((5-methylpyridin-2-yl)methoxy)-1H-benzo[d]imidazol-2-yl)-2,2-dimethylcyclopropanecarboxylate. MS (ESI): mass calcd. for C$_{27}$H$_{26}$BrN$_3$O$_3$, 519.12; m/z found, 520.1 [M+H]$^+$. $^1$H NMR (600 MHz, CD$_3$OD) δ 8.54 (s, 1H), 8.07 (dd, J=8.1, 1.4, 1H), 7.75 (d, J=8.1, 1H), 7.72 (d, J=9.0, 1H), 7.58-7.53 (m, 2H), 7.45 (d, J=2.3, 1H), 7.37 (dd, J=9.0, 2.3, 1H), 7.15 (d, J=8.5, 2H), 5.72 (app q, J=16.8, 2H), 5.39 (s, 2H), 2.86 (d, J=5.9, 1H), 2.69-2.58 (m, 1H), 2.48 (s, 3H), 1.26 (s, 3H), 0.92 (s, 3H).

Example 115

(1R*,3R*)-3-{1-(4-Bromobenzyl)-6-[(5-methylpyridin-2-yl)methoxy]-1H-benzimidazol-2-yl}-2,2-dimethylcyclopropanecarboxylic acid

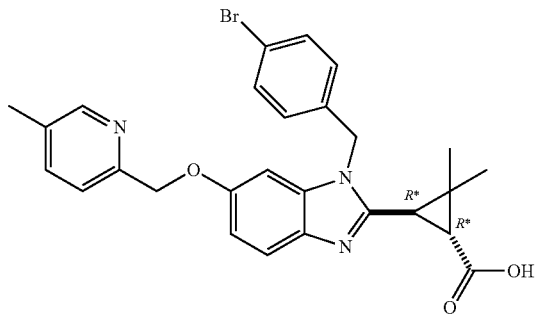

racemic trans-3-{1-(4-Bromobenzyl)-6-[(5-methylpyridin-2-yl)methoxy]-1H-benzimidazol-2-yl}-2,2-dimethylcyclopropanecarboxylic acid was purified by chiral SFC (CHIRALPAK IC 5 μm 250×20 mm) mobile phase (58% CO$_2$, 42% iPrOH) to provide the title compound as the first eluting isomer. MS (ESI): mass calcd. for C$_{27}$H$_{26}$BrN$_3$O$_3$, 519.12; m/z found, 520.1 [M+H]$^+$.

Example 116

(1S*,3S*)-3-{1-(4-Bromobenzyl)-6-[(5-methylpyridin-2-yl)methoxy]-1H-benzimidazol-2-yl}-2,2-dimethylcyclopropanecarboxylic acid

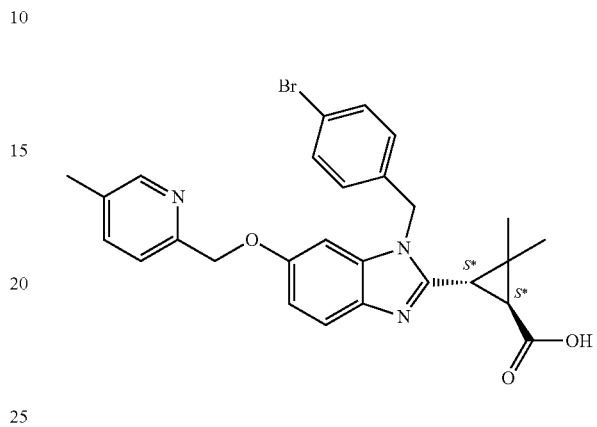

racemic trans-3-{1-(4-Bromobenzyl)-6-[(5-methylpyridin-2-yl)methoxy]-1H-benzimidazol-2-yl}-2,2-dimethylcyclopropanecarboxylic acid was purified by chiral SFC (CHIRALPAK IC 5 μm 250×20 mm) mobile phase (58% CO$_2$, 42% iPrOH) to provide the title compound as the second eluting isomer. MS (ESI): mass calcd. for C$_{27}$H$_{26}$BrN$_3$O$_3$, 519.12; m/z found, 520.1 [M+H]$^+$. $^1$H NMR (600 MHz, CD$_3$OD) δ 8.54 (s, 1H), 8.07 (dd, J=8.1, 1.4, 1H), 7.75 (d, J=8.1, 1H), 7.72 (d, J=9.0, 1H), 7.58-7.53 (m, 2H), 7.45 (d, J=2.3, 1H), 7.37 (dd, J=9.0, 2.3, 1H), 7.15 (d, J=8.5, 2H), 5.72 (app q, J=16.8, 2H), 5.39 (s, 2H), 2.86 (d, J=5.9, 1H), 2.69-2.58 (m, 1H), 2.48 (s, 3H), 1.26 (s, 3H), 0.92 (s, 3H).

Example 117 racemic trans-3-{1-(4-Bromobenzyl)-6-[(1-methyl-1H-pyrazol-3-yl)methoxy]-1H-benzimidazol-2-yl}-2,2-dimethylcyclopropanecarboxylic acid as the TFA salt

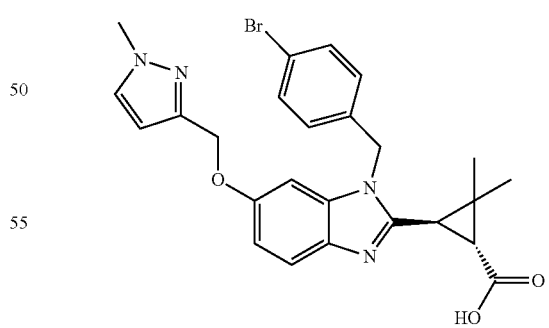

The title compound was prepared using in a manner analogous to that in Intermediate H using N-(4-bromobenzyl)-5-((1-methyl-1H-pyrazol-3-yl)methoxy)benzene-1,2-diamine and Example 111. MS (ESI): mass calcd. for C$_{25}$H$_{25}$BrN$_4$O$_3$, 508.11; m/z found, 509.2 [M+H]$^+$. $^1$H NMR (500 MHz, CD$_3$OD) δ 7.64 (d, J=9.0, 1H), 7.59-7.55 (m, 2H), 7.54 (d, J=2.2, 1H), 7.43 (d, J=2.2, 1H), 7.24 (dd, J=9.0, 2.3, 1H), 7.16 (d, J=8.5, 2H), 6.31 (d, J=2.3, 1H), 5.72 (q, J=16.7, 2H), 5.12 (s, 2H), 3.84 (s, 3H), 2.83 (d, J=5.9, 1H), 2.63 (d, J=5.9, 1H), 1.25 (s, 3H), 0.89 (s, 3H).

Example 118

3-{1-(4-Bromobenzyl)-6-[(5-methylpyridin-2-yl)methoxy]-1H-benzimidazol-2-yl}-2,2-dimethylpropanoic acid as the TFA salt

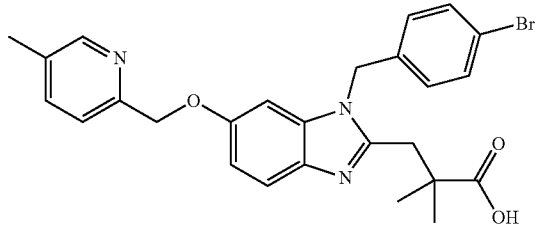 [SMILES: Cc1ccc(COc2ccc3nc(CC(C)(C)C(=O)O)n(Cc4ccc(Br)cc4)c3c2)nc1]

The title compound was prepared using in a manner analogous to that in Example 111 using ethyl 3-(1-(4-bromobenzyl)-6-((5-methylpyridin-2-yl)methoxy)-1H-benzo[d]imidazol-2-yl)-2,2-dimethylpropanoate. MS (ESI): mass calcd. for $C_{26}H_{26}BrN_3O_3$, 507.12; m/z found, 508.1 [M+H]$^+$. $^1$H NMR (600 MHz, DMSO-$d_6$) δ 8.41 (s, 1H), 7.68 (d, J=8.0, 1H), 7.64 (d, J=8.8, 1H), 7.52 (d, J=8.5, 2H), 7.42 (d, J=7.9, 1H), 7.26 (d, J=1.9, 1H), 7.11 (d, J=8.3, 3H), 5.63 (s, 2H), 5.18 (s, 2H), 3.27 (s, 2H), 2.32 (s, 3H), 1.27 (s, 6H).

Example 119 racemic cis-2-{1-(4-Methylbenzyl)-6-[(5-methylpyridin-2-yl)methoxy]-1H-benzimidazol-2-yl}cyclohexanecarboxylic acid

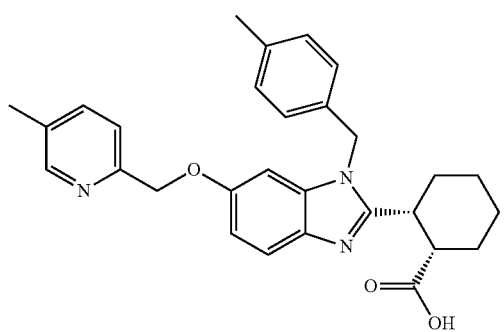 [SMILES: Cc1ccc(Cn2c([C@@H]3CCCC[C@@H]3C(=O)O)nc3ccc(OCc4ccc(C)cn4)cc32)cc1]

The title compound was prepared using analogous conditions described for Example 1 using p-tolylmethanamine in Step A then for Intermediate I using N$^1$-(4-methylbenzyl)-5-((5-methylpyridin-2-yl)methoxy)benzene-1,2-diamine and racemic cis-hexahydroisobenzofuran-1,3-dione followed by the hydrolysis according to Example Example 111. MS (ESI): mass calcd. for $C_{29}H_{31}N_3O_3$, 469.24; m/z found, 470.3 [M+H]$^+$. $^1$H NMR (500 MHz, CD$_3$OD) δ 8.50 (s, 1H), 8.02 (d, J=8.1, 1H), 7.74 (d, J=9.0, 1H), 7.69 (d, J=8.1, 1H), 7.36 (dd, J=9.0, 2.3, 1H), 7.25 (d, J=2.2, 1H), 7.17 (d, J=8.0, 2H), 7.00 (d, J=8.1, 2H), 5.77 (d, J=16.9, 1H), 5.71 (d, J=17.0, 1H), 5.36-5.19 (m, 2H), 3.63 (dt, J=12.1, 3.7, 1H), 2.90 (d, J=3.7, 1H), 2.45 (s, 3H), 2.37-2.25 (m, 4H), 2.19 (d, J=14.2, 1H), 2.05 (d, J=12.9, 1H), 1.96 (t, J=12.1, 1H), 1.82-1.72 (m, 1H), 1.72-1.63 (m, 1H), 1.59-1.35 (m, 2H).

Example 120 racemic trans-2-{1-(4-Methylbenzyl)-6-[(5-methylpyridin-2-yl)methoxy]-1H-benzimidazol-2-yl}cyclohexanecarboxylic acid

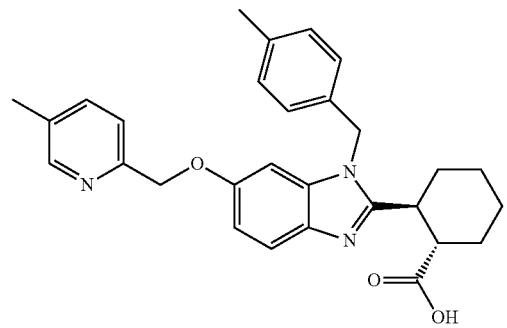

The title compound was prepared using analogous conditions described for Example 1 using p-tolylmethanamine in Step A then for Intermediate I using N$^1$-(4-methylbenzyl)-5-((5-methylpyridin-2-yl)methoxy)benzene-1,2-diamine and racemic trans-hexahydroisobenzofuran-1,3-dione followed by the hydrolysis according to Example Example 111. MS (ESI): mass calcd. for $C_{29}H_{31}N_3O_3$, 469.24; m/z found, 470.3 [M+H]$^+$. $^1$H NMR (500 MHz, CD$_3$OD) 8.33 (s, 1H), 7.65 (d, J=8.0, 1H), 7.47 (d, J=8.7, 1H), 7.44 (s, 1H), 7.11 (d, J=7.9, 2H), 7.03 (d, J=8.1, 2H), 6.98 (d, J=2.2, 1H), 6.95 (dd, J=8.7, 2.3, 1H), 5.44 (s, 2H), 5.12 (s, 2H), 3.15 (td, J=11.2, 4.9, 1H), 3.02-2.94 (m, 1H), 2.35 (s, 3H), 2.30 (s, 3H), 2.21 (d, J=12.2, 1H), 1.85 (d, J=11.5, 1H), 1.70 (d, J=13.3, 1H), 1.46 (dt, J=28.3, 14.0, 4H), 1.31-1.16 (m, 1H).

Example 121 racemic cis-2,2-Dimethyl-3-{1-(4-methylbenzyl)-6-[(5-methylpyridin-2-yl)methoxy]-1H-benzimidazol-2-yl}cyclopropanecarboxylic acid

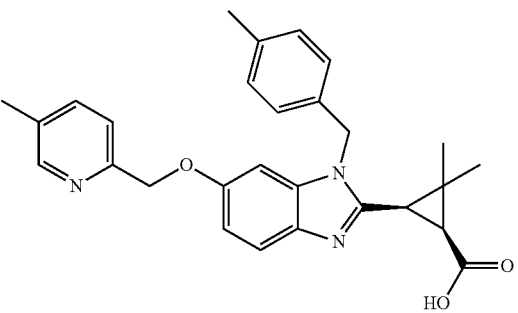 [SMILES: Cc1ccc(Cn2c([C@@H]3[C@H](C(=O)O)C3(C)C)nc3ccc(OCc4ccc(C)cn4)cc32)cc1]

The title compound was prepared using analogous conditions described for Example 1 using p-tolylmethanamine in Step A then for Intermediate I using N$^1$-(4-methylbenzyl)-5-((5-methylpyridin-2-yl)methoxy)benzene-1,2-diamine and cis-6,6-dimethyl-3-oxabicyclo[3.1.0]hexane-2,4-dione followed by the hydrolysis according to Example Example 111. MS (ESI): mass calcd. for $C_{28}H_{29}N_3O_3$, 455.22; m/z found, 456.1 [M+H]+. 1H NMR (400 MHz, CDCl3) δ 8.39 (s, 1H), 7.58 (d, J=8.9, 1H), 7.54-7.48 (m, 1H), 7.40 (d, J=7.9, 1H), 7.13 (d, J=7.9, 2H), 7.04 (dd, J=8.8, 2.3, 1H), 6.98-6.87 (m, 3H), 5.31 (d, J=16.5, 1H), 5.24 (d, J=16.6, 1H), 5.18 (s, 2H), 2.34 (s, 6H), 2.28 (d, J=8.2, 1H), 2.07 (d, J=8.2, 1H), 1.21 (s, 3H), 0.98 (s, 3H).

Example 122 racemic cis-2,2-Dimethyl-3-{6-[(1-methyl-1H-pyrazol-3-yl)methoxy]-1-[4-(trifluoromethoxy)benzyl]-1H-benzimidazol-2-yl}cyclopropanecarboxylic acid

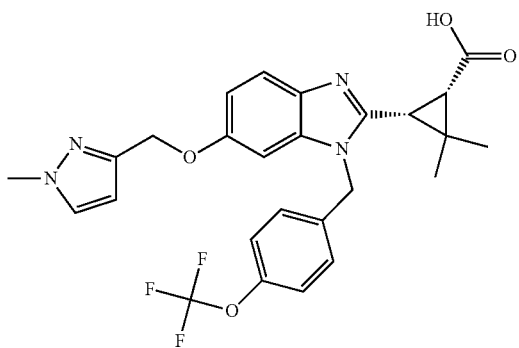 [SMILES: Cn1ccc(COc2ccc3nc([C@@H]4[C@H](C(=O)O)C4(C)C)n(Cc4ccc(OC(F)(F)F)cc4)c3c2)n1]

The title compound was prepared using analogous conditions described for Example 1 using (4-(trifluoromethoxy)phenyl)methanamine and 3-((3-fluoro-4-nitrophenoxy)methyl)-1-methyl-1H-pyrazole in Step A then for Intermediate I using 5-((1-methyl-1H-pyrazol-3-yl)methoxy)-$N^1$-(4-(trifluoromethoxy)benzyl)benzene-1,2-diamine and cis-6,6-dimethyl-3-oxabicyclo[3.1.0]hexane-2,4-dione followed by the hydrolysis according to Example Example 111. MS (ESI): mass calcd. for $C_{26}H_{25}F_3N_4O_4$, 514.18; m/z found, 515.1 [M+H]+. 1H NMR (400 MHz, CDCl3) δ 7.60 (d, J=8.9, 1H), 7.33 (d, J=2.2, 1H), 7.21 (d, J=8.1, 2H), 7.09 (d, J=8.8, 2H), 7.06 (dd, J=8.9, 2.3, 1H), 6.94 (d, J=2.2, 1H), 6.31 (d, J=2.2, 1H), 5.39 (d, J=16.9, 1H), 5.31 (d, J=16.9, 1H), 5.09 (s, 2H), 3.86 (s, 3H), 2.31 (d, J=8.2, 1H), 2.04 (d, J=8.3, 1H), 1.20 (s, 3H), 0.97 (s, 3H).

Example 123 racemic cis-2-{1-(4-Bromo-2,6-difluorobenzyl)-6-[(3-fluoro-5-methylpyridin-2-yl)methoxy]-1H-benzimidazol-2-yl}cyclohexanecarboxylic acid

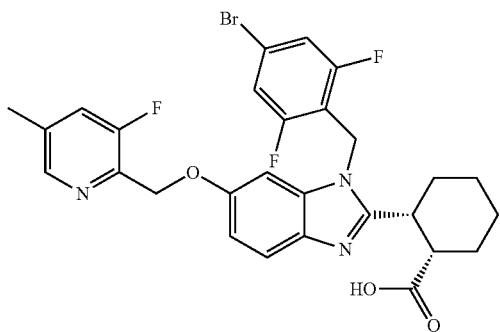 [SMILES: Cc1cnc(COc2ccc3nc([C@@H]4CCCC[C@@H]4C(=O)O)n(Cc4c(F)cc(Br)cc4F)c3c2)c(F)c1]

Step A: N-(4-Bromo-2,6-difluorobenzyl)-5-methoxy-2-nitroaniline

A mixture of 5-methoxy-2-nitroaniline (513 mg, 3 mmol), 4-bromo-2,6-difluorobenzyl amine (616 g, 3 mmol), DIPEA (1.55 mL, 9 mmol) and acetonitrile (10 mL) was heated to 130-150° Celsius for 16 h. The mixture was then cooled to RT and concentrated to dryness. To the residue was added H2O (100 mL) and the resulting solid was collected by filtration and dried to afford the title compound (900 mg, 80.1%).

Step B: $N^1$-(4-Bromo-2,6-difluorobenzyl)-5-methoxybenzene-1,2-diamine

To a solution of N-(4-bromo-2,6-difluorobenzyl)-5-methoxy-2-nitroaniline (600 mg, 1.61 mmol) in EtOH (100 mL) was added SnCl2*2H2O (1.8 g, 8.1 mmol). The mixture was heated at 100° Celsius for 16 h. The mixture was cooled to RT and NaHCO3 (200 mL) was added. The mixture was filtered through celite and the filtrate extracted with EtOAc (3×200 mL). The combine organics were concentrated to dryness to provide the title compound which was used in the next step without further purification. MS (ESI): mass calcd. for $C_{14}H_{13}BrF_2N_2O$, 342.02; m/z found, 343.1 [M+H]+.

Step C: racemic cis-Ethyl 2-(1-(4-bromo-2,6-difluorobenzyl)-6-methoxy-1H-benzo[d]imidazol-2-yl)cyclohexanecarboxylate To a solution of N-1-(4-bromo-2,6-difluorobenzyl)-5-methoxybenzene-1,2-diamine (160 mg, 0.466 mmol) in acetonitrile (5 mL) was added cis-hexahydroisobenzofuran-1,3-dione (80 mg, 0.519 mmol) and the resulting mixture was heated to 100° Celsius for 5 h. The mixture was cooled to RT and concentrated to dryness. The residue was dissolved in EtOH (20 mL) and HCl (1 mL, 12 N). The resulting solution was heated to 100° Celsius for 8 h. The reaction was cooled to RT and concentrated to dryness. The residue was purified by FCC to provide the title compound. MS (ESI): mass calcd. for $C_{24}H_{25}BrF_2N_2O_3$, 506.10; m/z found, 507.2 [M+H]+.

Step D: racemic cis-ethyl 2-(1-(4-bromo-2,6-difluorobenzyl)-6-hydroxy-1H-benzo[d]imidazol-2-yl)cyclohexanecarboxylate A solution of BBr3 (5 mL, 1 M in DCM) was added to a mixture of racemic_cis-ethyl 2-(1-(4-bromo-2,6-difluorobenzyl)-6-methoxy-1H-benzo[d]imidazol-2-yl)cyclohexanecarboxylate (1.5 g, 3.2 mmol) in CH2Cl2 (50 mL) at RT. The reaction mixture was stirred 1 h was and partitioned with H2O (50 mL). The organic layer was separated and concentrated to dryness. The resulting residue was purified by FCC to provide the title compound (110 mg, 87%). MS (ESI): mass calcd. for $C_{23}H_{23}BrF_2N_2O_3$, 492.09; m/z found, 493.2 [M+H]+.

Step E: racemic cis-2-{1-(4-Bromobenzyl)-6-[(1,3-dimethyl-1H-pyrazol-5-yl)methoxy]-1H-benzimidazol-2-yl}cyclohexanecarboxylic acid To a mixture of racemic cis-ethyl 2-(1-(4-bromo-2,6-difluorobenzyl)-6-hydroxy-1H-benzo[d]imidazol-2-yl)cyclohexanecarboxylate (110 mg, 0.22 mmol), 2-(chloromethyl)-3-fluoro-5-methylpyridine (35 mg, 0.22 mmol) in acetonitrile (5 mL) was added Cs2CO3 (79 mg, 0.24 mmol)

and heated at 100° Celsius. After 1 hr the mixture was concentrated to dryness and the residue was purified by FCC to provide racemic cis-ethyl 2-(1-(4-bromo-2,6-difluorobenzyl)-6-((3-fluoro-5-methylpyridin-2-yl)methoxy)-1H-benzo[d]imidazol-2-yl)cyclohexanecarboxylate. To the resulting ethyl ester was added MeOH (2 mL), and NaOH (1 mL, 1 N). The mixture was heated to 110° Celsius. After 1 h the mixture was concentrated to dryness and purified by FCC to provide the title compound and the trans-isomer see Example 124. MS (ESI): mass calcd. for $C_{28}H_{25}BrF_3N_3O_3$, 587.10; m/z found, 588.2 [M+H]$^+$. $^1$H NMR (500 MHz, CD$_3$OD) δ 8.22 (s, 1H), 7.52-7.45 (m, 2H), 7.28 (d, J=7.6, 2H), 6.99 (d, J=2.0, 1H), 6.88 (dd, J=8.7, 2.3, 1H), 5.54 (two d, J=16.4, 2H), 5.18 (s, 2H), 3.79 (d, J=4.6, 1H), 2.78-2.63 (m, 1H), 2.40 (s, 3H), 2.36-2.20 (m, 1H), 2.12-1.86 (m, 3H), 1.86-1.67 (m, 2H), 1.51-1.39 (m, 2H).

Example 124 racemic trans-2-{1-(4-Bromo-2,6-difluorobenzyl)-6-[(3-fluoro-5-methylpyridin-2-yl)methoxy]-1H-benzimidazol-2-yl}cyclohexanecarboxylic acid

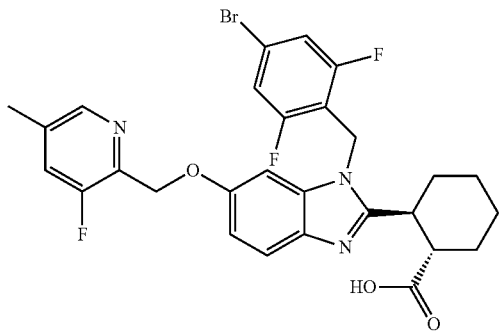 [SMILES: Cc1cnc(COc2ccc3nc([C@H]4CCCC[C@@H]4C(=O)O)n(Cc4c(F)cc(Br)cc4F)c3c2)c(F)c1]

The title compound was isolated from Step E of Example 123. MS (ESI): mass calcd. for $C_{28}H_{25}BrF_3N_3O_3$, 587.10; m/z found, 588.2 [M+H]$^+$. $^1$H NMR (500 MHz, CD$_3$OD) δ 8.23 (s, 1H), 7.51 (d, J=10.5, 1H), 7.40 (d, J=8.7, 1H), 7.30 (d, J=7.5, 2H), 7.06 (d, J=2.1, 1H), 6.89 (dd, J=8.7, 2.3, 1H), 5.62 (two d, J=16.2, 2H), 5.19 (s, 2H), 3.30-3.24 (m, 1H), 2.72 (t, J=9.7, 1H), 2.40 (s, 3H), 2.28-2.14 (m, 1H), 1.93-1.65 (m, 3H), 1.59-1.42 (m, 3H), 1.39-1.27 (m, 1H).

Example 125 racemic cis-2-{1-(4-Bromobenzyl)-6-[(3-fluoro-5-methylpyridin-2-yl)methoxy]-1H-benzimidazol-2-yl}cyclohexanecarboxylic acid

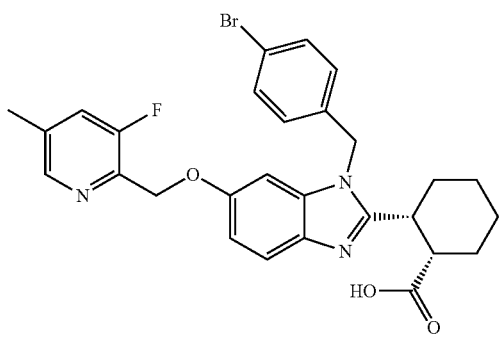 [SMILES: Cc1cnc(COc2ccc3nc([C@@H]4CCCC[C@@H]4C(=O)O)n(Cc4ccc(Br)cc4)c3c2)c(F)c1]

The title compound was prepared using methods similar to those in Example 123 using 4-bromobenzyl amine in Step A. MS (ESI): mass calcd. for $C_{28}H_{27}BrFN_3O_3$, 551.10; m/z found, 552.1 [M+H]$^+$. $^1$H NMR (500 MHz, CD$_3$OD) δ 8.12 (s, 1H), 7.53 (d, J=8.7, 1H), 7.45-7.35 (m, 3H), 7.01 (d, J=8.4, 2H), 6.95-6.81 (m, 2H), 5.46 (two d, J=17.3, 2H), 5.14 (d, J=1.3, 2H), 3.61 (d, J=4.4, 1H), 2.70-2.62 (m, 1H), 2.44-2.29 (m, 4H), 1.96-1.77 (m, 4H), 1.71-1.65 (m, 1H), 1.45-1.32 (m, 2H).

Example 126 racemic cis-2-{1-(4-Bromo-2,6-difluorobenzyl)-6-[(5-methylpyridin-2-yl)methoxy]-1H-benzimidazol-2-yl}cyclohexanecarboxylic acid

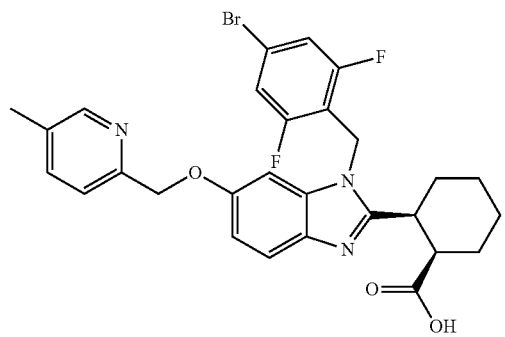 [SMILES: Cc1ccc(COc2ccc3nc([C@H]4CCCC[C@H]4C(=O)O)n(Cc4c(F)cc(Br)cc4F)c3c2)nc1]

The title compound was prepared using methods similar to those in Example 123 using 2-(chloromethyl)-5-methylpyridine in Step E. MS (ESI): mass calcd. for $C_{28}H_{26}BrF_2N_3O_3$, 569.11; m/z found, 570.2 [M+H]$^+$. $^1$H NMR (500 MHz, CD$_3$OD) δ 8.38 (dd, J=1.4, 0.7, 1H), 7.64 (dd, J=8.0, 1.6, 1H), 7.50 (d, J=9.4, 1H), 7.41 (d, J=8.0, 1H), 7.24 (d, J=7.6, 2H), 6.96-6.85 (m, 2H), 5.50 (two d, J=16.3, 2H), 5.14 (s, 2H), 3.81-3.70 (m, 1H), 2.77-2.63 (m, 1H), 2.37 (s, 3H), 2.32-2.22 (m, 1H), 2.08-1.89 (m, 3H), 1.83-1.71 (m, 2H), 1.49-1.40 (m, 2H).

Example 127

3-{1-(2-Fluoro-4-methylbenzyl)-6-[(3-fluoro-5-methylpyridin-2-yl)methoxy]-1H-benzimidazol-2-yl}-2,2-dimethylpropanoic acid

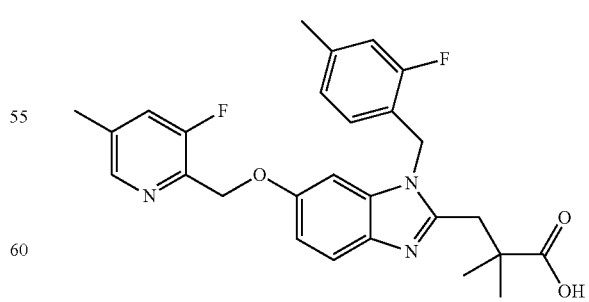

The title compound was prepared using methods similar to those in Example 123 using (2-fluoro-4-methylphenyl)methanamine in Step A and 3,3-dimethyldihydrofuran-2,5-dione in Step C. MS (ESI): mass calcd. for $C_{27}H_{27}F_2N_3O_3$, 479.20; m/z found, 480.3 [M+H]+. 1H NMR (500 MHz, CD3OD) δ 8.18 (s, 1H), 7.51-7.42 (m, 2H), 6.98-6.82 (m, 4H), 6.65 (t, J=7.9, 1H), 5.58 (s, 2H), 5.13 (d, J=1.5, 2H), 3.14 (s, 2H), 2.38 (s, 3H), 2.30 (s, 3H), 1.25 (s, 6H).

Example 128

3-{1-(4-Bromobenzyl)-6-[(3-fluoro-5-methylpyridin-2-yl)methoxy]-1H-benzimidazol-2-yl}-2,2-dimethylpropanoic acid

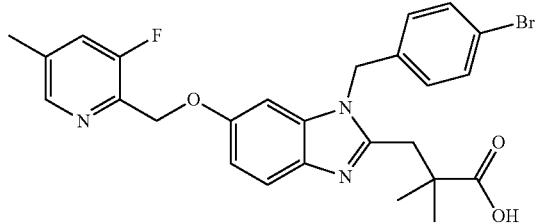 [SMILES: Cc1cnc(COc2ccc3nc(CC(C)(C)C(=O)O)n(Cc4ccc(Br)cc4)c3c2)c(F)c1]

The title compound was prepared using methods similar to those in Example 123 using 4-bromobenzyl amine in Step A and 3,3-dimethyldihydrofuran-2,5-dione in Step C. MS (ESI): mass calcd. for $C_{26}H_{25}BrFN_3O_3$, 525.1; m/z found, 526.2 [M+H]+. 1H NMR (400 MHz, CD3OD) δ 8.04 (s, 1H), 7.45-7.23 (m, 4H), 6.90-6.70 (m, 4H), 5.44 (s, 2H), 5.05 (d, J=1.6, 2H), 2.98 (s, 2H), 2.27 (s, 3H), 1.15 (s, 6H).

Example 129

3-{1-(4-Bromo-2-fluorobenzyl)-6-[(3-fluoro-5-methylpyridin-2-yl)methoxy]-1H-benzimidazol-2-yl}-2,2-dimethylpropanoic acid

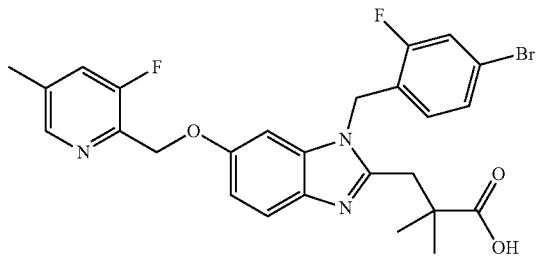 [SMILES: Cc1cnc(COc2ccc3nc(CC(C)(C)C(=O)O)n(Cc4ccc(Br)cc4F)c3c2)c(F)c1]

The title compound was prepared using methods similar to those in Example 123 using 4-bromo-2-fluorobenzyl amine in Step A and 3,3-dimethyldihydrofuran-2,5-dione in Step C. MS (ESI): mass calcd. for $C_{26}H_{24}BrF_2N_3O_3$, 543.10; m/z found, 544.2 [M+H]+. 1H NMR (400 MHz, CD3OD) δ 8.16 (s, 1H), 7.56-7.34 (m, 3H), 7.20 (d, J=8.2, 1H), 6.97-6.86 (m, 2H), 6.63 (t, J=8.1, 1H), 5.61 (s, 2H), 5.16 (s, 2H), 3.12 (s, 2H), 2.39 (s, 3H), 1.25 (s, 6H).

Example 130

3-{1-(4-Bromo-2,6-difluorobenzyl)-6-[(3-fluoro-5-methylpyridin-2-yl)methoxy]-1H-benzimidazol-2-yl}-2,2-dimethylpropanoic acid

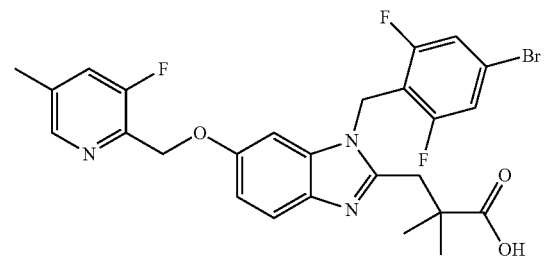 [SMILES: Cc1cnc(COc2ccc3nc(CC(C)(C)C(=O)O)n(Cc4c(F)cc(Br)cc4F)c3c2)c(F)c1]

The title compound was prepared using methods similar to those in Example 123 using 3,3-dimethyldihydrofuran-2,5-dione in Step C. MS (ESI): mass calcd. for $C_{26}H_{23}BrF_3N_3O_3$, 561.09; m/z found, 562.2 [M+H]+. 1H NMR (500 MHz, CD3OD) δ 8.51 (s, 1H), 8.11 (d, J=9.8, 1H), 7.80 (d, J=9.6, 1H), 7.46-7.35 (m, 4H), 5.93 (s, 2H), 5.50 (s, 2H), 3.58 (s, 2H), 2.56 (s, 3H), 1.45 (s, 6H).

Example 131

3-{6-[(3-Fluoro-5-methylpyridin-2-yl)methoxy]-1-[2-fluoro-4-(trifluoromethoxy)benzyl]-1H-benzimidazol-2-yl}-2,2-dimethylpropanoic acid

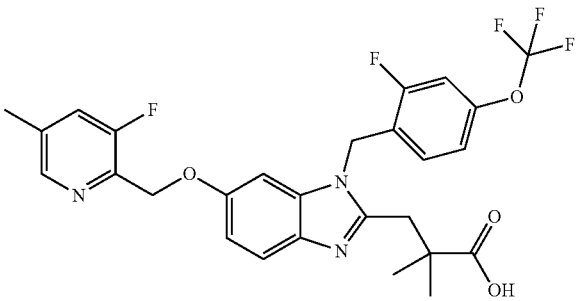 [SMILES: Cc1cnc(COc2ccc3nc(CC(C)(C)C(=O)O)n(Cc4ccc(OC(F)(F)F)cc4F)c3c2)c(F)c1]

The title compound was prepared using methods similar to those in Example 123 using (2-fluoro-4-(trifluoromethoxy)phenyl)methanamine in Step A and 3,3-dimethyldihydrofuran-2,5-dione in Step C. MS (ESI): mass calcd. for $C_{27}H_{24}F_5N_3O_4$, 549.17; m/z found, 550.3 [M+H]+. 1H NMR (500 MHz, CD3OD) δ 8.18 (s, 1H), 7.53-7.41 (m, 2H), 7.18 (d, J=10.5, 1H), 7.05-6.89 (m, 3H), 6.83 (t, J=8.5, 1H), 5.65 (s, 2H), 5.15 (d, J=1.8, 2H), 3.12 (s, 2H), 2.37 (s, 3H), 1.28 (s, 6H).

Example 132 racemic cis-3-{1-(4-Bromobenzyl)-6-[(3-fluoro-5-methylpyridin-2-yl)methoxy]-1H-benzimidazol-2-yl}-2,2-dimethylcyclopropanecarboxylic acid

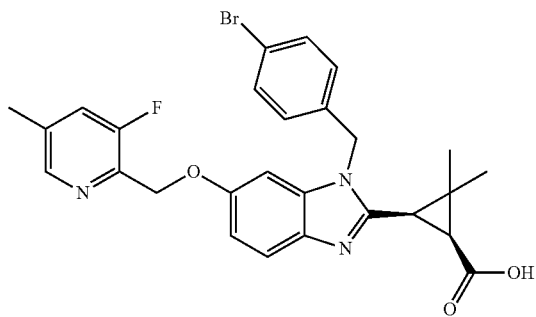 [SMILES: Cc1cnc(COc2ccc3nc([C@@H]4[C@H](C(=O)O)C4(C)C)n(Cc4ccc(Br)cc4)c3c2)c(F)c1]

The title compound was prepared using a method similar to those in Example 123 using 4-bromobenzyl amine in Step A and 6,6-dimethyl-3-oxabicyclo[3.1.0]hexane-2,4-dione in Step C. MS (ESI): mass calcd. for $C_{27}H_{25}BrFN_3O_3$, 537.1; m/z found, 538.2 [M+H]+. 1H NMR (500 MHz, CD3OD) δ 8.07 (s, 1H), 7.44-7.32 (m, 4H), 7.00-6.92 (m, 3H), 6.89-6.82 (m, 1H), 5.34 (m, 2H), 5.08 (s, 2H), 2.29 (s, 3H), 1.98-1.91 (m, 2H), 1.21 (s, 3H), 1.16 (s, 3H).

Example 133 racemic cis-3-{1-(4-Bromobenzyl)-6-[(6-methyl-pyridin-2-yl)methoxy]-1H-benzimidazol-2-yl}-2,2-dimethylcyclopropanecarboxylic acid

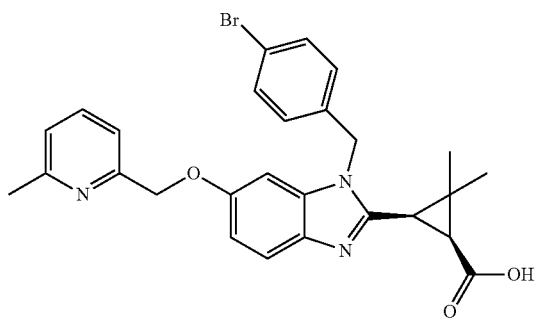 [SMILES: Cc1cccc(COc2ccc3nc([C@@H]4[C@H](C(=O)O)C4(C)C)n(Cc4ccc(Br)cc4)c3c2)n1]

The title compound was prepared using methods similar to those in Example 123 using 4-bromo-benzylamine in Step A, cis-6,6-dimethyl-3-oxabicyclo[3.1.0]hexane-2,4-dione in Step C and 2-(chloromethyl)-6-methylpyridine in Step E. MS (ESI): mass calcd. for $C_{27}H_{26}BrN_3O_3$, 519.12; m/z found, 520.1.1 [M+H]+. 1H NMR (500 MHz, CD3OD) δ 7.67 (t, J=7.7, 1H), 7.55 (d, J=8.6, 1H), 7.46 (d, J=8.4, 2H), 7.32 (d, J=7.7, 1H), 7.19 (d, J=7.7, 1H), 7.10-6.97 (m, 4H), 5.55-5.37 (m, 2H), 5.12 (s, 2H), 2.50 (s, 3H), 2.24 (d, J=8.2, 1H), 2.15 (d, J=8.2, 1H), 1.22 (s, 3H), 1.16 (s, 3H).

Example 134 racemic cis-3-{1-(4-Bromobenzyl)-6-[(1-methyl-1H-pyrazol-3-yl)methoxy]-1H-benzimidazol-2-yl}-2,2-dimethylcyclopropanecarboxylic acid

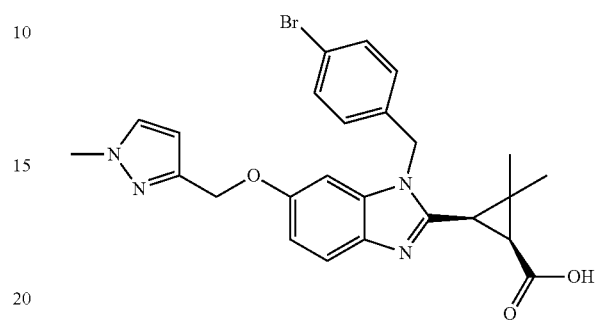

The title compound was prepared using methods similar to those in Example 123 using 4-bromobenzyl amine in Step A, cis-6,6-dimethyl-3-oxabicyclo[3.1.0]hexane-2,4-dione in Step C and 3-(chloromethyl)-1-methyl-1H-pyrazole in E. MS (ESI): mass calcd. for $C_{25}H_{25}BrN_4O_3$, 508.11; m/z found, 509.1 [M+H]+. 1H NMR (600 MHz, CD3OD) δ 7.54-7.44 (m, 4H), 7.07 (d, J=8.4, 2H), 7.00 (d, J=2.1, 1H), 6.94 (dd, J=8.8, 2.3, 1H), 6.26 (d, J=2.2, 1H), 5.52-5.32 (m, 2H), 5.02 (s, 2H), 3.83 (s, 3H), 2.10-1.98 (m, 2H), 1.31 (s, 3H), 1.26 (s, 3H).

Example 135

2-({1-(4-Cyanobenzyl)-6-[(3-fluoro-5-methylpyridin-2-yl)methoxy]-1H-benzimidazol-2-yl}methyl)-2-ethylbutanoic acid

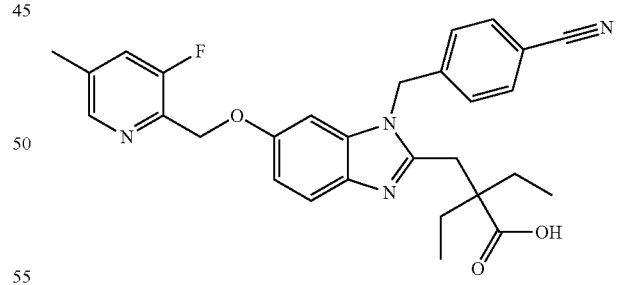

The title compound was prepared using methods similar to those in Example 123 using 4-(aminomethyl)benzonitrile in Step A and 3,3-diethyldihydrofuran-2,5-dione in Step C. MS (ESI): mass calcd. for $C_{29}H_{29}FN_4O_3$, 500.22; m/z found, 501.3 [M+H]+. 1H NMR (500 MHz, CD3OD) δ 8.15 (s, 1H), 7.64 (d, J=8.4, 2H), 7.57-7.36 (m, 2H), 7.15 (d, J=8.4, 2H), 6.93-6.84 (m, 2H), 5.70 (s, 2H), 5.14 (d, J=1.8, 2H), 2.99 (s, 2H), 2.37 (s, 3H), 1.83-1.54 (m, 4H), 0.87 (t, J=7.4, 6H).

Example 136

2-({1-(4-Bromobenzyl)-6-[(3-fluoro-5-methylpyridin-2-yl)methoxy]-1H-benzimidazol-2-yl}methyl)-2-ethylbutanoic acid

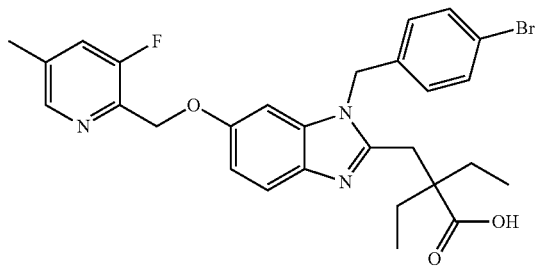 [SMILES: CCC(CC)(Cc1nc2ccc(OCc3ncc(C)cc3F)cc2n1Cc1ccc(Br)cc1)C(=O)O]

The title compound was prepared using methods similar to those in Example 123 using 4-bromobenzyl amine in Step A and 3,3-diethyldihydrofuran-2,5-dione in Step C. MS (ESI): mass calcd. for $C_{28}H_{29}BrFN_3O_3$, 553.1; m/z found, 554.2 [M+H]$^+$. $^1$H NMR (500 MHz, CD$_3$OD) 8.15 (s, 1H), 7.52 (d, J=8.6, 1H), 7.46-7.39 (m, 3H), 6.93 (d, J=8.3, 4H), 5.53 (s, 2H), 5.16 (d, J=0.9, 2H), 3.05 (s, 2H), 2.38 (s, 3H), 1.86-1.65 (m, 4H), 0.87 (t, J=7.2, 6H).

Example 137 racemic cis-2-(1-((3,5-difluoro-4'-(trifluoromethyl)-[1,1'-biphenyl]-4-yl)methyl)-6-((3-fluoro-5-methylpyridin-2-yl)methoxy)-1H-benzo[d]imidazol-2-yl)cyclohexanecarboxylic acid

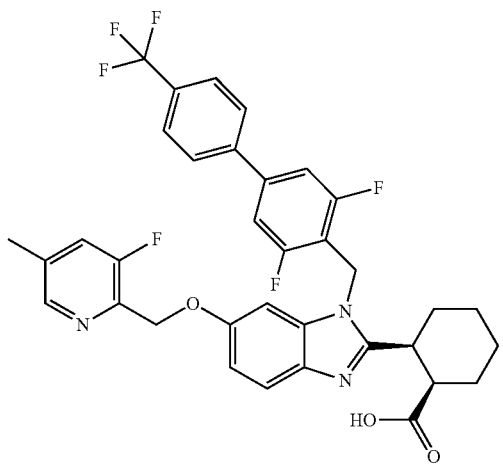 [SMILES: Cc1cnc(COc2ccc3nc([C@H]4CCCC[C@H]4C(=O)O)n(Cc4c(F)cc(-c5ccc(C(F)(F)F)cc5)cc4F)c3c2)c(F)c1]

To a 5 mL microwave vial were added racemic cis-2-{1-(4-bromo-2,6-difluorobenzyl)-6-[(3-fluoro-5-methylpyridin-2-yl)methoxy]-1H-benzimidazol-2-yl}cyclohexanecarboxylic acid (40 mg, 0.07 mmol), Pd(dppf)Cl$_2$.DCM (5.0 mg, 0.007 mmol), (4-(trifluoromethyl)phenyl)boronic acid (18 mg, 0.010 mmol), K$_2$CO$_3$ (0.2 mL, 1M in H$_2$O), EtOH (0.67 mL) and toluene (0.3 mL). The mixture was heated at 110° Celsius for 1 h, cooled to RT, concentrated to dryness and purified using FCC to provide the title compound. MS (ESI): mass calcd. for $C_{35}H_{29}F_6N_3O_3$, 653.21; m/z found, 654.3 [M+H]$^+$. $^1$H NMR (500 MHz, CD$_3$OD) δ 8.19 (s, 1H), 7.78 (dd, J=40.8, 8.3, 4H), 7.56-7.33 (m, 4H), 7.04 (d, J=2.2, 1H), 6.87 (dd, J=8.8, 2.3, 1H), 5.63 (two d, J=16.3, 2H), 5.23-5.11 (m, 2H), 3.90 (d, J=4.6, 1H), 2.78-2.67 (m, 1H), 2.40-2.23 (m, 4H), 2.16-2.06 (m, 1H), 2.05-1.89 (m, 2H), 1.87-1.68 (m, 2H), 1.51-1.37 (m, 2H).

Example 138 racemic cis-2-(1-{[3,5-Difluoro-4'-(trifluoromethyl)biphenyl-4-yl]methyl}-6-[(5-methylpyridin-2-yl)methoxy]-1H-benzimidazol-2-yl)cyclohexanecarboxylic acid

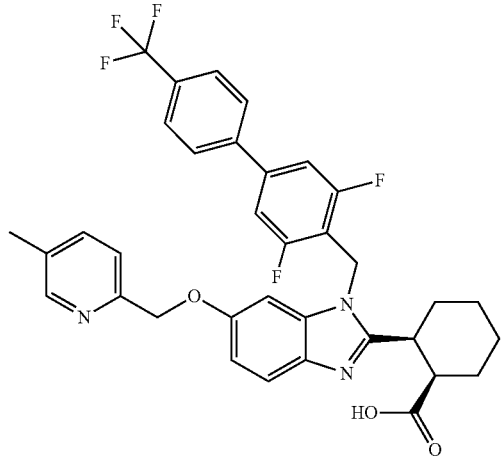 [SMILES: Cc1ccc(COc2ccc3nc([C@H]4CCCC[C@H]4C(=O)O)n(Cc4c(F)cc(-c5ccc(C(F)(F)F)cc5)cc4F)c3c2)nc1]

The title compound was prepared using methods similar to those in Example 123 using 2-(chloromethyl)-5-methylpyridine in step E and Example 137. MS (ESI): mass calcd. for $C_{35}H_{30}F_5N_3O_3$, 635.22; m/z found, 636.3 [M+H]$^+$. $^1$H NMR (400 MHz, CD$_3$OD) δ 8.33 (s, 1H), 7.80 (dd, J=32.2, 8.4, 4H), 7.66-7.47 (m, 2H), 7.45-7.28 (m, 3H), 6.98-6.77 (m, 1H), 5.62 (two d, J=16.3, 2H), 5.13 (s, 2H), 4.03-3.88 (m, 1H), 2.63 (d, J=19.7, 1H), 2.35-2.11 (m, 5H), 2.14-1.89 (m, 2H), 1.85-1.71 (m, 2H), 1.54-1.36 (m, 2H).

Example 139

(1R*,2S*)-2-(6-[(3-Fluoro-5-methylpyridin-2-yl)methoxy]-1-{[4'-(trifluoromethyl)biphenyl-4-yl]methyl}-1H-benzimidazol-2-yl)cyclohexanecarboxylic acid

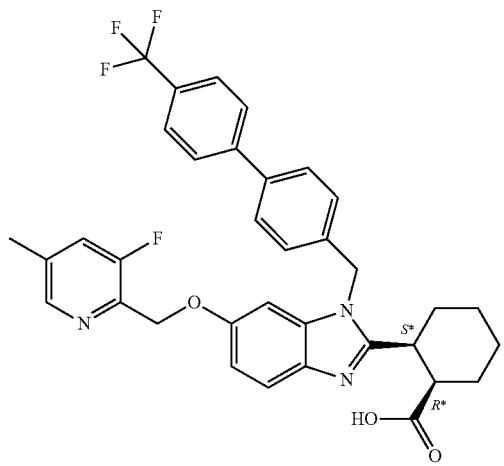 [SMILES: Cc1cnc(COc2ccc3nc([C@H]4CCCC[C@H]4C(=O)O)n(Cc4ccc(-c5ccc(C(F)(F)F)cc5)cc4)c3c2)c(F)c1]

The title compound was prepared using methods similar to those in Example 137 using racemic cis-ethyl 2-(1-(4-bromobenzyl)-6-((3-fluoro-5-methylpyridin-2-yl)methoxy)-1H-benzo[d]imidazol-2-yl)cyclohexanecarboxylate followed by SFC chiral separation (CHIRALCEL OD-H 5 μm 250×20 mm) mobile phase (80% $CO_2$, 20% MeOH). MS (ESI): mass calcd. for $C_{35}H_{31}F_4N_3O_3$, 617.23; m/z found, 618.3 [M+H]. $^1$H NMR (500 MHz, $CD_3OD$) δ 8.14 (s, 1H), 7.79 (d, J=8.2, 2H), 7.71 (d, J=8.4, 2H), 7.63 (d, J=8.3, 2H), 7.54 (d, J=8.8, 1H), 7.41 (d, J=10.4, 1H), 7.21 (d, J=8.2, 2H), 6.97 (d, J=2.2, 1H), 6.88 (dd, J=8.7, 2.2, 1H), 5.59 (two d, J=17.3, 2H), 5.15 (d, J=1.6, 2H), 3.72 (d, J=4.2, 1H), 2.72-2.60 (m, 1H), 2.42-2.33 (m, 1H), 2.29 (s, 3H), 2.06-1.55 (m, 5H), 1.42-1.34 (m, 2H).

Example 140 racemic trans-2-{1-(4-Bromo-2,6-difluorobenzyl)-6-[(5-methylpyridin-2-yl)methoxy]-1H-benzimidazol-2-yl}cyclohexanecarboxylic acid

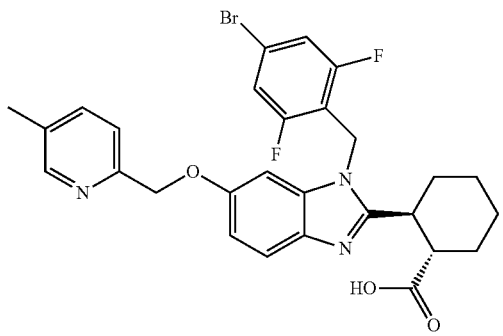 [SMILES: Cc1ccc(COc2ccc3nc([C@H]4CCCC[C@@H]4C(=O)O)n(Cc4c(F)cc(Br)cc4F)c3c2)nc1]

The title compound was prepared using a method similar to those in Example 137 using 2-(chloromethyl)-5-methylpyridine in Step E. MS (ESI): mass calcd. for $C_{28}H_{26}BrF_2N_3O_3$, 569.11; m/z found, 570.2 [M+H]$^+$. $^1$H NMR (500 MHz, $CD_3OD$) δ 8.41-8.35 (m, 1H), 7.74-7.56 (m, 1H), 7.47-7.37 (m, 2H), 7.34-7.21 (m, 2H), 6.98-6.85 (m, 2H), 5.59 (two d, J=16.2, 2H), 5.20-5.10 (m, 2H), 3.29-3.26 (m, 1H), 2.78-2.60 (m, 1H), 2.37 (s, 3H), 2.27-2.11 (m, 1H), 1.90-1.65 (m, 3H), 1.62-1.44 (m, 3H), 1.38-1.24 (m, 1H).

Example 141

3-(6-[(3-Fluoro-5-methylpyridin-2-yl)methoxy]-1-{[3-fluoro-4'-(trifluoromethyl)biphenyl-4-yl]methyl}-1H-benzimidazol-2-yl)-2,2-dimethylpropanoic acid

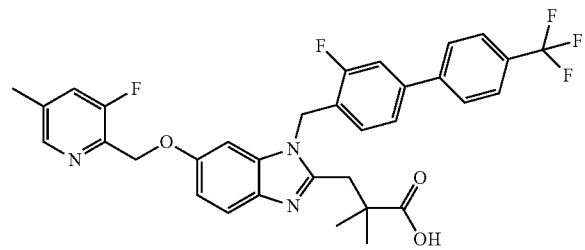 [SMILES: Cc1cnc(COc2ccc3nc(CC(C)(C)C(=O)O)n(Cc4ccc(-c5ccc(C(F)(F)F)cc5)cc4F)c3c2)c(F)c1]

The title compound was prepared using methods similar to those in Example 123 using 4-bromo-2-fluorobenzyl amine in Step A and 3,3-dimethyldihydrofuran-2,5-dione in Step C and Example 137. MS (ESI): mass calcd. for $C_{33}H_{28}F_5N_3O_3$, 609.21; m/z found, 610.3 [M+H]$^+$. $^1$H NMR (400 MHz, $CDCl_3$) δ 8.14 (s, 1H), 7.75 (dd, J=27.6, 8.2, 4H), 7.57-7.26 (m, 4H), 7.05-6.78 (m, 3H), 5.67 (s, 2H), 5.14 (s, 2H), 3.18 (s, 2H), 2.28 (s, 3H), 1.30 (s, 6H).

Example 142

3-(6-[(3-Fluoro-5-methylpyridin-2-yl)methoxy]-1-{[4'-(trifluoromethyl)biphenyl-4-yl]methyl}-1H-benzimidazol-2-yl)-2,2-dimethylpropanoic acid

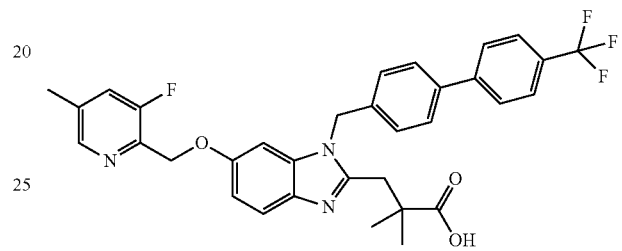

The title compound was prepared using methods similar to those in Example 123 using 4-bromobenzyl amine in Step A and 3,3-dimethyldihydrofuran-2,5-dione in Step C and Example 137. MS (ESI): mass calcd. for $C_{33}H_{29}F_4N_3O_3$, 591.21; m/z found, 592.3 [M+H]$^+$. $^1$H NMR (500 MHz, $CD_3OD$) 8.15 (s, 1H), 7.79 (d, J=8.3, 2H), 7.71 (d, J=8.3, 2H), 7.62 (d, J=8.3, 2H), 7.52 (d, J=8.8, 1H), 7.42 (d, J=10.5, 1H), 7.15 (d, J=8.3, 2H), 7.01 (d, J=2.3, 1H), 6.93 (dd, J=8.8, 2.3, 1H), 5.64 (s, 2H), 5.16 (d, J=1.6, 2H), 3.14 (s, 2H), 2.29 (s, 3H), 1.29 (s, 6H).

Example 143

3-(6-[(3-Fluoro-5-methylpyridin-2-yl)methoxy]-1-{[4'-(trifluoromethyl)biphenyl-3-yl]methyl}-1H-benzimidazol-2-yl)-2,2-dimethylpropanoic acid

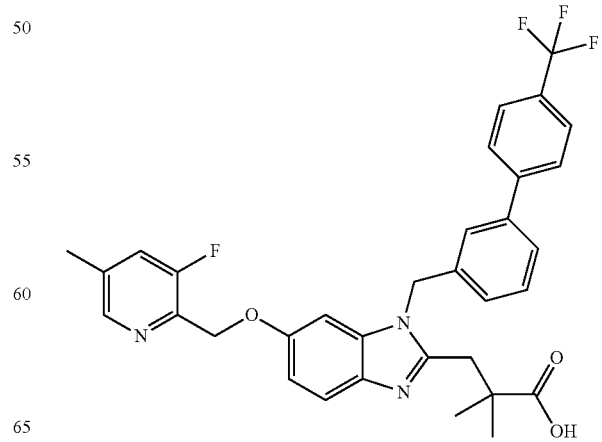

The title compound was prepared using methods similar to those in Example 123 using 3-bromobenzyl amine in Step A and 3,3-dimethyldihydrofuran-2,5-dione in Step C and Example 137. MS (ESI): mass calcd. for $C_{33}H_{29}F_4N_3O_3$, 591.21; m/z found, 592.3 [M+H]$^+$. $^1$H NMR (500 MHz, CD$_3$OD) δ 8.10 (s, 1H), 7.68 (s, 4H), 7.56 (d, J=7.7 Hz, 1H), 7.52 (d, J=8.8 Hz, 1H), 7.43-7.30 (m, 3H), 7.06-6.97 (m, 2H), 6.93 (dd, J=8.6, 2.4 Hz, 1H), 5.66 (s, 2H), 5.14 (d, J=1.9 Hz, 2H), 3.14 (s, 2H), 2.29 (s, 3H), 1.28 (s, 6H).

Example 144 racemic cis-2-{1-[4-(2-Methoxypyrimidin-5-yl)benzyl]-6-[(5-methylpyridin-2-yl)methoxy]-1H-benzimidazol-2-yl}cyclohexanecarboxylic acid

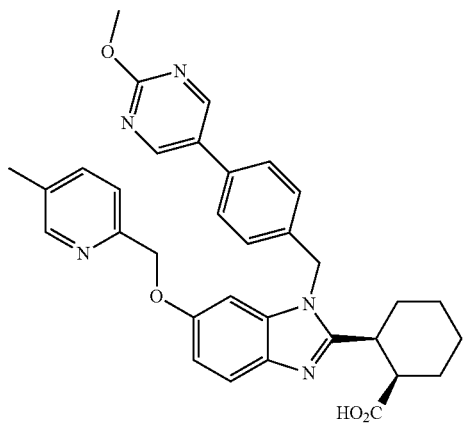 [SMILES: COc1ncc(-c2ccc(Cn3c([C@H]4CCCC[C@H]4C(=O)O)nc4ccc(OCc5ccc(C)cn5)cc43)cc2)cn1]

To a 5 mL vial were added racemic cis-2-(1-(4-bromobenzyl)-6-((5-methylpyridin-2-yl)methoxy)-1H-benzo[d]imidazol-2-yl)cyclohexanecarboxylic acid (77.2 mg, 0.14 mmol), Pd(dppf)Cl$_2$.DCM (14 mg, 0.017 mmol), (2-methoxypyrimidin-5-yl)boronic acid (73 mg, 0.47 mmol), Na$_2$CO$_3$ (0.3 mL, 2M) and 1,4-dioxane (2 mL). The vial was flushed with N$_2$ then capped and placed in a heating block and heated at 80° Celsius. After 6 h the mixture was cooled to RT and transferred to a round-bottomed flask and concentrated to dryness. The resulting residue was then partitioned between water (10 mL, ~pH 3) and DCM (10 mL) with stirring for 1 h at RT. The organic layer was separated, concentrated to dryness and purified by FCC to provide 65.3 mg of the title compound. MS (ESI): mass calcd. for $C_{33}H_{33}N_5O_4$, 563.25; m/z found, 564.2 [M+H]$^+$. (500 MHz; CDCl$_3$) δ 8.70 (s, 2H), 8.37 (d, J=2.2 Hz, 1H), 7.63 (d, J=8.8 Hz, 1H), 7.51-7.45 (m, 3H), 7.38 (d, J=8.0 Hz, 1H), 7.13 (d, J=8.1 Hz, 2H), 7.05 (dd, J=8.8, 2.3 Hz, 1H), 6.82 (d, J=2.3 Hz, 1H), 5.39-5.29 (m, 2H), 5.14 (s, 2H), 4.07 (s, 3H), 3.20 (d, J=11.3 Hz, 1H), 3.07 (s, 1H), 2.58 (d, J=10.9 Hz, 1H), 2.30 (s, 3H), 1.91-1.59 (m, 5H), 1.45 (q, J=12.4, 11.7 Hz, 2H).

Example 145 racemic cis-2-(6-[(5-Methylpyridin-2-yl)methoxy]-1-{[4'-(trifluoromethyl)biphenyl-3-yl]methyl}-1H-benzimidazol-2-yl)cyclohexanecarboxylic acid

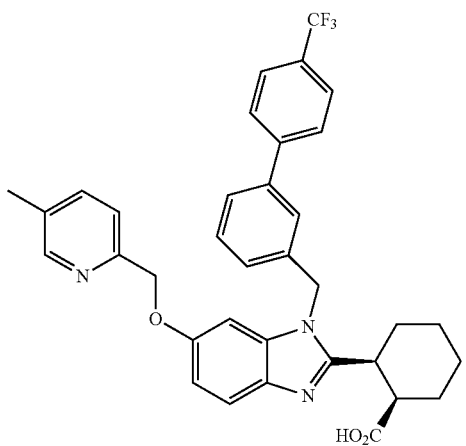 [SMILES: Cc1ccc(COc2ccc3nc([C@H]4CCCC[C@H]4C(=O)O)n(Cc4cccc(-c5ccc(C(F)(F)F)cc5)c4)c3c2)nc1]

The title compound was prepared using similar methods to those in Example 144 using (4-(trifluoromethyl)phenyl) boronic acid and racemic cis-2-{1-(3-bromobenzyl)-6-[(5-methylpyridin-2-yl)methoxy]-1H-benzimidazol-2-yl}cyclohexanecarboxylic acid. MS (ESI): mass calcd. for $C_{35}H_{32}F_3N_3O_3$, 599.24; m/z found, 600.2 [M+H]. $^1$H NMR (500 MHz, CDCl$_3$) δ 8.32 (d, J=2.0 Hz, 1H), 7.68 (d, J=8.1 Hz, 2H), 7.62 (d, J=8.8 Hz, 1H), 7.57 (d, J=8.1 Hz, 2H), 7.54 (d, J=7.8 Hz, 1H), 7.45 (dd, J=8.1, 2.2 Hz, 1H), 7.43-7.38 (m, 2H), 7.35 (d, J=8.0 Hz, 1H), 7.04 (dd, J=8.8, 2.3 Hz, 1H), 6.97 (d, J=7.8 Hz, 1H), 6.82 (d, J=2.3 Hz, 1H), 5.36 (s, 2H), 5.14 (s, 2H), 3.25-3.09 (m, 1H), 3.09-2.97 (m, 1H), 2.65-2.53 (m, 1H), 2.28 (s, 3H), 1.87-1.71 (m, 3H), 1.70-1.58 (m, 2H), 1.51-1.31 (m, 2H).

Example 146 racemic cis-2-(6-[(5-Methylpyridin-2-yl)methoxy]-1-{[4'-(trifluoromethyl)biphenyl-4-yl]methyl}-1H-benzimidazol-2-yl)cyclohexanecarboxylic acid

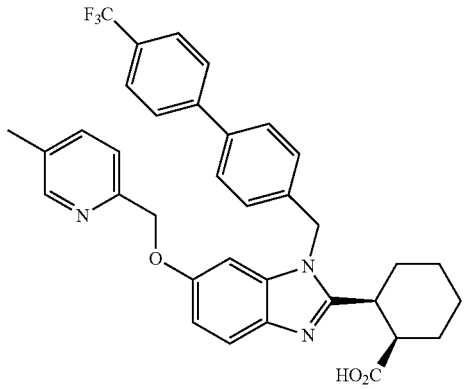 [SMILES: Cc1ccc(COc2ccc3nc([C@H]4CCCC[C@H]4C(=O)O)n(Cc4ccc(-c5ccc(C(F)(F)F)cc5)cc4)c3c2)nc1]

The title compound was prepared using similar methods to those in Example 144 using (4-(trifluoromethyl)phenyl)

boronic acid. MS (ESI): mass calcd. for $C_{35}H_{32}F_3N_3O_3$, 599.24; m/z found, 600.3 [M+H]+. $^1$H NMR (500 MHz; CDCl$_3$) δ 8.36-8.34 (m, 1H), 7.72-7.68 (m, 2H), 7.67-7.60 (m, 3H), 7.56-7.51 (m, 2H), 7.49-7.46 (m, 1H), 7.37 (d, J=8.0, 1H), 7.14-7.10 (m, 2H), 7.04 (dd, J=8.8, 2.2, 1H), 6.83 (d, J=2.2, 1H), 5.38-5.30 (m, 2H), 5.14 (s, 2H), 3.25-3.19 (m, 1H), 3.07-3.03 (m, 1H), 2.61-2.54 (m, 1H), 2.27 (s, 3H), 1.89-1.58 (m, 5H), 1.52-1.37 (m, 2H).

Example 147

(1S,2R)-2-(6-((5-methylpyridin-2-yl)methoxy)-1-((4'-(trifluoromethyl)-[1,1'-biphenyl]-4-yl)methyl)-1H-benzo[d]imidazol-2-yl)cyclohexanecarboxylic acid

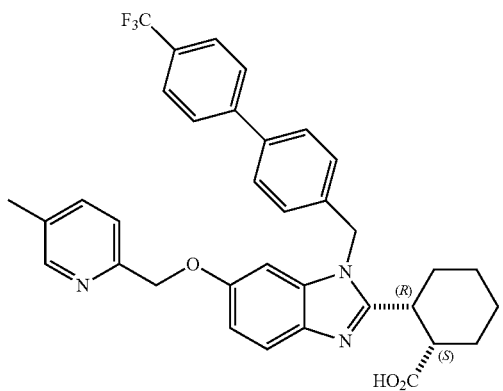

Step A: Preparation of (4'-(Trifluoromethyl)-[1,1'-biphenyl]-4-yl)methanamine

To a nitrogen purged flask containing 4-trifluoromethylphenyl boronic acid (76.6 g, 403 mmol), [1,1'-bis(di-tert-butylphosphino)ferrocene]dichloropalladium(II) (6.07 g, 9.31 mmol), and potassium carbonate (83.6 g, 605 mmol) were added 4-bromobenzylamine (75.0 g, 403 mmol), N$_2$ sparged 2-methyltetrahydrofuran (750 mL) and N$_2$ sparged water (750 mL). The mixture was then warmed to 80° Celsius for 15 h. The mixture was cooled to RT, the layers were separated and the organic layer was washed with brine, dried over magnesium sulfate and filtered through celite. The filtrate was concentrated to dryness to afford the title compound (114.37 g, 85% purity, 96%). MS (ESI): mass calcd. for $C_{14}H_{12}F_3N$, 251.10; m/z found, 252.1 [M+H]+. $^1$H NMR (400 MHz, CDCl$_3$) 7.68 (s, 4H), 7.58 (d, J=7.9, 2H), 7.42 (d, J=7.9, 2H) 3.94 (s, 2H). Absolute stereochemistry was determined by alternative synthesis starting with the product of Example 2.

Step B: Preparation of 5-((5-Methylpyridin-2-yl)methoxy)-2-nitro-N-((4'-(trifluoromethyl)-[1,1'-biphenyl]-4-yl)methyl)aniline To a flask containing (4'-(trifluoromethyl)-[1,1'-biphenyl]-4-yl)methanamine (107 g, 406 mmol) and 2-((3-fluoro-4-nitrophenoxy)methyl)-5-methylpyridine (114 g, 406 mmol) in acetonitrile (900 mL) was added DIPEA (106 mL, 610 mmol). The stirred mixture was then warmed to 80° Celsius and held for 7 h. After cooling to RT, the resulting slurry was diluted with acetonitrile (300 mL), filtered and the resulting solids were washed with acetonitrile (200 mL). The solids were dried in a vacuum oven at 75° Celsius for 3 h to give the title compound (147.5 g, 73%). MS (ESI): mass calcd. for $C_{27}H_{22}F_3N_3O_3$, 493.2; m/z found, 494.1 [M+H]+. $^1$H NMR (400 MHz, CDCl$_3$) δ 8.71 (bs, 1H), 8.38 (s, 1H), 8.17 (d, J=9.5, 1H), 7.69 (s, 4H), 7.58 (d, J=7.8, 2H), 7.49 (d, J=7.8, 1H), 7.43 (d, J=7.8, 2H), 7.29 (d, J=8.0, 1H), 6.35 (d, J=9.6, 1H), 6.29 (s, 1H), 5.13 (s, 2H), 4.54 (d, J=5.7, 2H), 2.30 (s, 3H).

Step C: Preparation of 5-((5-Methylpyridin-2-yl)methoxy)-N$^1$-((4'-(trifluoromethyl)-[1,1'-biphenyl]-4-yl)methyl)benzene-1,2-diamine To a high pressure reactor were added 5-((5-methylpyridin-2-yl)methoxy)-2-nitro-N-((4'-(trifluoromethyl)-[1,1'-biphenyl]-4-yl)methyl)aniline (147 g, 297 mmol), 5% Pt/C (23.2 g, 2.97 mmol), and THF (2.5 L). The reactor was flushed with nitrogen and then stirred under an atmosphere of H$_2$ (135 psi) for 24 h. The mixture was then filtered through celite and the filtrate was concentrated to dryness to afford the title compound as a tan solid (134 g, 97%). MS (ESI): mass calcd. for $C_{27}H_{24}F_3N_3O$, 463.2; m/z found, 464.1 [M+H]+. $^1$H NMR (400 MHz, CDCl$_3$) δ 8.42-8.35 (m, 1H), 7.69 (s, 4H), 7.60-7.53 (m, 2H), 7.50-7.44 (m, 3H), 7.37 (d, J=8.0, 1H), 6.66 (d, J=8.3, 1H), 6.38 (d, J=2.7, 1H), 6.27 (dd, J=8.3, 2.7, 1H), 5.08 (s, 2H), 4.36 (s, 2H), 4.13 (bs, 1H), 3.05 (bs, 2H), 2.30 (s, 3H).

Step D: Preparation of (1S,2R)-2-(6-((5-Methyl pyridin-2-yl)methoxy)-1-((4'-(trifluoromethyl)-[1,1'-biphenyl]-4-yl)methyl)-1H-benzo[d]imidazol-2-yl) cyclohexanecarboxylic acid To a slurry of 5-((5-methylpyridin-2-yl)methoxy)-N$^1$-((4'-(trifluoromethyl)-[1,1'-biphenyl]-4-yl)methyl)benzene-1,2-diamine (131 g, 283 mmol) in acetonitrile (1.3 L) at 30° Celsius were added DIPEA (48.7 mL, 283 mmol) followed by cis-1,2-cyclohexanedicarboxylic anhydride (44.7 g, 290 mmol). The mixture was stirred at 35° Celsius for 1 h and then HCl (471 mL, 2.83 mol, 6 M) was added. The resulting solution was warmed to 80° Celsius for 3 h and then cooled to RT. The reaction mixture was treated with NaOH (1.2 L, 2 M) and the resulting biphasic mixture was separated. The organic layer was concentrated to a mass of 231.3 g and then partitioned between dichloromethane (1 L) and water (800 mL). The layers were separated, and the aqueous was washed with dichloromethane (200 mL). The combined organics were dried over magnesium sulfate, filtered, and concentrated to dryness to a brown foam (183 g, 80% purity, 86%). A portion of the material (179 g) was purified by silica gel chromatography (Lichroprep silica gel, 100% ethyl acetate ramping to 100% of 1:1 dichloromethane:methanol) and then separated into its constituent isomers through chiral stationary phase chromatography (Chiralpak AD, 1:1 acetonitrile:methanol). The fractions containing the first eluting isomer were concentrated to a foam (58 g, 96% purity, 78% of theoretical for resolution). A portion of the foam (45 g, 72 mmol) was dissolved in ethanol (800 mL) and treated at room temperature with sodium ethoxide (4.92 g, 72 mmol) in ethanol (100 mL). The resulting suspension was stirred for 1.5 h, diluted with heptane (750 mL), filtered, washed with 3:1 heptane:ethanol (500 mL), and dried for 18 h in a vacuum oven at 60° Celsius to provide the corresponding sodium salt (36 g, 80% of theoretical for salt formation). The dried sodium salt (36 g, 58 mmol) was taken up in water (700 mL) at RT and remaining solids were removed by polish filtration. The filtrate was then treated with 1 N HCl$_{(aq)}$ (58 mL, 58 mmol) over 30 min. The resulting suspension was stirred for 2 h, filtered, washed with water (250 mL), dried for 18 h in a vacuum oven at 75° Celsius to provide the title compound (34 g, 99% of theoretical from sodium salt). MS (ESI): mass calcd. for $C_{35}H_{32}F_3N_3O_3$, 599.2; m/z found, 600.1 [M+H]$^+$. $^1$H NMR (400 MHz, CDCl$_3$) δ 8.36-8.31 (m, 1H), 7.72-7.59 (m, 5H), 7.55-7.50 (m, 2H), 7.50-7.45 (m, 1H), 7.37 (d, J=8.0, 1H), 7.13-7.09 (m, 2H), 7.02 (dd, J=8.9, 2.3, 1H), 6.83 (d, J=2.3, 1H), 5.34 (s, 2H), 5.14 (s, 2H), 3.23 (dt, J=10.9, 3.1, 1H), 3.03 (q, J=3.9, 1H), 2.63-2.51 (m, 1H), 2.26 (s, 3H), 1.91-1.25 (m, 7H).

Example 148

(1R,2S)-2-(6-[(5-Methylpyridin-2-yl)methoxy]-1-{[4'-(trifluoromethyl)biphenyl-4-yl]methyl}-1H-benzimidazol-2-yl)cyclohexanecarboxylic acid

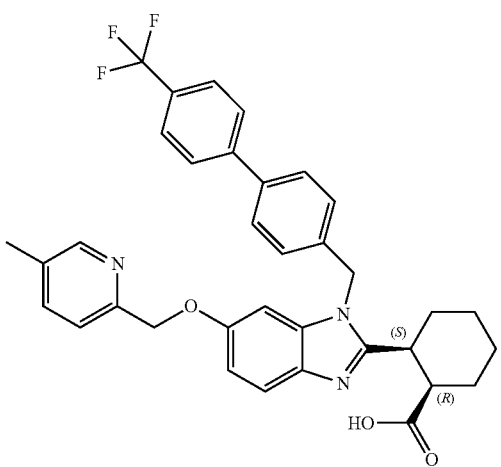

racemic cis-2-(6-[(5-Methylpyridin-2-yl)methoxy]-1-{[4'-(trifluoromethyl)biphenyl-4-yl]methyl}-1H-benzimidazol-2-yl)cyclohexanecarboxylic acid was purified using chiral stationary phase chromatography (Chiralpak AD, 1:1 acetonitrile:methanol) as the 15 second eluting isomer. (ESI): mass calcd. for $C_{35}H_{32}F_3N_3O_3$, 599.2; m/z found, 600.1 [M+H]$^+$. $^1$H NMR (400 MHz, CDCl$_3$) δ 8.36-8.31 (m, 1H), 7.72-7.59 (m, 5H), 7.55-7.50 (m, 2H), 7.50-7.45 (m, 1H), 7.37 (d, J=8.0, 1H), 7.13-7.09 (m, 2H), 7.02 (dd, J=8.9, 2.3, 1H), 6.83 (d, J=2.3, 1H), 5.34 (s, 2H), 5.14 (s, 2H), 3.23 (dt, J=10.9, 3.1, 1H), 3.03 (q, J=3.9, 1H), 2.63-2.51 (m, 1H), 2.26 (s, 3H), 1.91-1.25 (m, 7H).

Example 149

2-ethyl-2-((6-((5-methylpyridin-2-yl)methoxy)-1-((4'-(trifluoromethyl)-[1,1'-biphenyl]-3-yl)methyl)-1H-benzo[d]imidazol-2-yl)methyl)butanoic acid

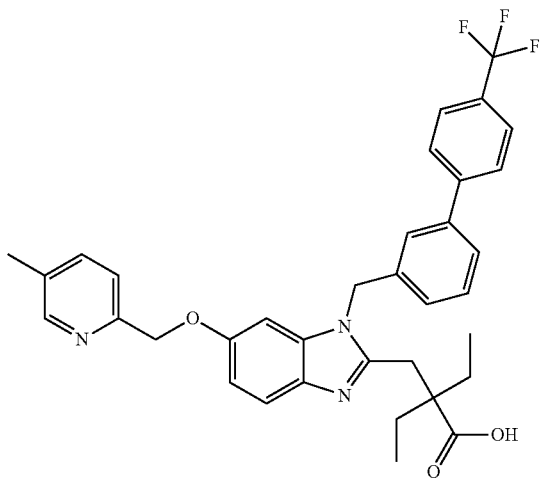 [SMILES: CCC(CC)(Cc1nc2ccc(OCc3ccc(C)cn3)cc2n1Cc1cccc(-c2ccc(C(F)(F)F)cc2)c1)C(=O)O]

The title compound was prepared using similar methods to those in Example 144 using (4-(trifluoromethyl)phenyl)boronic acid and 2-((1-(3-bromobenzyl)-6-((5-methylpyridin-2-yl)methoxy)-1H-benzo[d]imidazol-2-yl)methyl)-2-ethylbutanoic acid. MS (ESI): mass calcd. for $C_{35}H_{34}F_3N_3O_3$, 602.26; m/z found, 603.2 [M+H]$^+$. $^1$H NMR (400 MHz, CDCl$_3$) δ 8.37-8.32 (m, 1H), 7.70-7.65 (m, 2H), 7.65-7.61 (d, J=8.8, 1H), 7.58-7.50 (m, 3H), 7.49-7.44 (m, 1H), 7.43-7.35 (m, 2H), 7.06-7.02 (dd, J=8.9, 2.4, 1H), 7.02-6.97 (d, J=8.1, 1H), 6.90-6.86 (d, J=2.3, 1H), 5.39-5.32 (s, 2H), 5.19-5.14 (s, 2H), 3.04-2.98 (s, 2H), 2.32-2.27 (s, 3H), 1.73-1.54 (m, 4H), 0.84-0.74 (t, J=7.4, 6H), 7.26-7.24 (s, 1H).

Example 150 racemic cis-2-(6-[(1-Methyl-1H-pyrazol-3-yl)methoxy]-1-{[4'-(trifluoromethyl)biphenyl-3-yl]methyl}-1H-benzimidazol-2-yl)cyclohexanecarboxylic acid

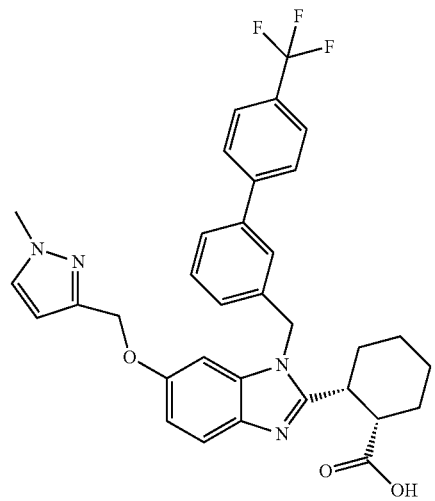 [SMILES: Cn1ccc(COc2ccc3nc([C@@H]4CCCC[C@@H]4C(=O)O)n(Cc4cccc(-c5ccc(C(F)(F)F)cc5)c4)c3c2)n1]

The title compound was prepared using analogous conditions described in Example 144 using 3-((2,5-difluoro-4-nitrophenoxy)methyl)-1-methyl-1H-pyrazole and (4-(trifluoromethyl)phenyl)boronic acid. MS (ESI): mass calcd. for C$_{33}$H$_{31}$F$_3$N$_4$O$_3$. C$_2$HF$_3$O$_2$, 588.2; m/z found, 589 [M+H]$^+$. $^1$H NMR (400 MHz, CD$_3$OD) δ 7.76-7.64 (m, 6H), 7.53 (t, J=7.8, 1H), 7.44-7.35 (m, 2H), 7.28-7.17 (m, 3H), 6.19 (d, J=2.3, 1H), 5.93 (d, J=17.2, 1H), 5.84 (d, J=17.2, 1H), 5.09-4.98 (m, 2H), 3.74 (s, 3H), 3.74-3.65 (m, 1H), 2.96-2.88 (m, 1H), 2.39-2.25 (m, 1H), 2.23-1.95 (m, 3H), 1.84-1.46 (m, 4H).

Example 151 racemic cis-2-(6-[(4-Chloro-1-methyl-1H-pyrazol-3-yl)methoxy]-1-{[4'-(trifluoromethyl)biphenyl-4-yl]methyl}-1H-benzimidazol-2-yl)cyclohexanecarboxylic acid

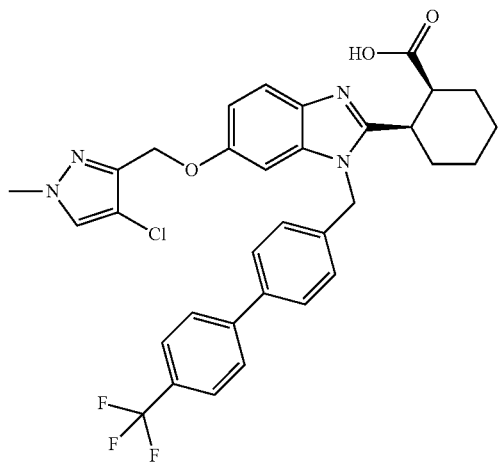 [SMILES: Cn1cc(Cl)c(COc2ccc3nc([C@@H]4CCCC[C@@H]4C(=O)O)n(Cc4ccc(-c5ccc(C(F)(F)F)cc5)cc4)c3c2)n1]

The title compound was prepared using analogous conditions described in Example 144 using (1S,2R)-2-(1-(4-bromobenzyl)-6-((4-chloro-1-methyl-1H-pyrazol-3-yl)methoxy)-1H-benzo[d]imidazol-2-yl)cyclohexanecarboxylic acid and (4-(trifluoromethyl)phenyl) boronic acid. MS (ESI): mass calcd. for C$_{33}$H$_{30}$ClF$_3$N$_4$O$_3$, 623.08; m/z found, 623.0 [M+H]$^+$. $^1$H NMR (500 MHz, CD$_3$OD) δ 7.81 (d, J=8.3, 2H), 7.76-7.67 (m, 5H), 7.63 (s, 1H), 7.34-7.23 (m, 4H), 5.90 (d, J=17.4, 1H), 5.84 (d, J=17.4, 1H), 5.09-4.99 (m, 2H), 3.75 (s, 3H), 3.70-3.61 (m, 1H), 3.00-2.89 (m, 1H), 2.42-2.28 (m, 1H), 2.25-2.17 (m, 1H), 2.14-2.05 (m, 1H), 2.05-1.94 (m, 1H), 1.88-1.63 (m, 2H), 1.64-1.43 (m, 2H).

Example 152 racemic cis-2-{1-[4-(3,3-Difluoropyrrolidin-1-yl)benzyl]-6-[(5-methylpyridin-2-yl)methoxy]-1H-benzimidazol-2-yl}cyclohexanecarboxylic acid

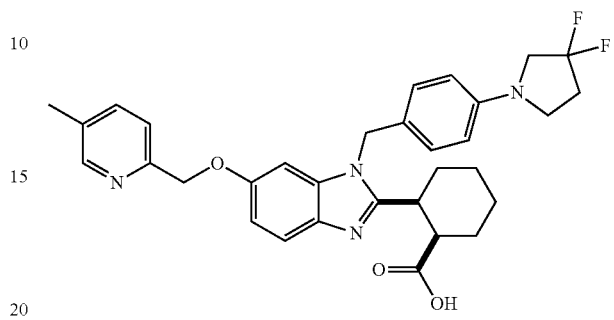

To a sealable vial was added racemic cis-2-{1-(4-bromobenzyl)-6-[(5-methylpyridin-2-yl)methoxy]-1H-benzimidazol-2-yl}cyclohexanecarboxylic acid (320 mg, 0.56 mmol) RuPhos precatalyst (45 mg, 0.060 mmol), RuPhos (28.5 mg, 0.060 mmol) and 3,3-difluoropyrrolidine hydrochloride (172 mg, 1.20 mmol) and N$_2$ sparged THF (6.0 mL) followed by LiHMDS (3.0 mL, 1.0 M in THF). The resulting reddish mixture was heated to 500 Celsius for 2 h. The reaction mixture was cooled to RT and treated with HCl (3 mL, 0.5 N) and MeOH until homogeneous. The mixture was purified using reverse phase HPLC to afford the title compound (128 mg, 38%). MS (ESI): mass calcd. for C$_{32}$H$_{34}$F$_2$N$_4$O$_3$, 560.26; m/z found, 561.2 [M+H]$^+$. $^1$H NMR (400 MHz, CD$_3$OD) δ 8.32 (s, 1H), 7.64 (dd, J=8.0, 1.6, 1H), 7.54 (d, J=8.9, 1H), 7.43 (d, J=8.0, 1H), 7.03-6.92 (m, 4H), 6.54 (d, J=8.7, 2H), 5.42 (d, J=16.5, 1H), 5.33 (d, J=16.5, 1H), 5.10 (s, 2H), 3.62 (t, J=13.3, 2H), 3.58-3.52 (m, 1H), 3.47 (t, J=7.2, 2H), 2.92-2.82 (m, 1H), 2.48 (m, 2H), 2.38-2.27 (m, 4H), 2.07-1.95 (m, 1H), 1.88-1.69 (m, 4H), 1.56-1.37 (m, 2H).

Example 153 racemic cis-2-{1-[4-(3,3-Difluoropiperidin-1-yl)benzyl]-6-[(5-methylpyridin-2-yl)methoxy]-1H-benzimidazol-2-yl}cyclohexanecarboxylic acid

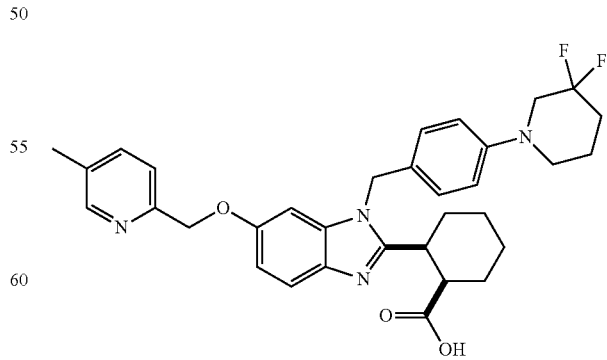

The title compound was prepared in a manner analogous to that in Example 152 substituting 3,3-difluoropiperidine hydrochloride. MS (ESI): mass calcd. for C$_{33}$H$_{36}$F$_2$N$_4$O$_3$, 574.28; m/z found, 575.3 [M+H]⁺. ¹H NMR (400 MHz, CD₃OD) δ 8.32 (s, 1H), 7.63 (dd, J=7.9, 1.7 Hz, 1H), 7.54 (d, J=8.8 Hz, 1H), 7.42 (d, J=8.0 Hz, 1H), 7.00 (d, J=8.7 Hz, 2H), 6.95 (dd, J=8.8, 2.4 Hz, 1H), 6.92 (d, J=2.3 Hz, 1H), 6.89 (d, J=8.8 Hz, 2H), 5.41 (d, J=16.7 Hz, 1H), 5.34 (d, J=16.7 Hz, 1H), 5.10 (s, 2H), 3.59-3.53 (m, 1H), 3.35 (t, J=11.7 Hz, 2H), 3.21-3.17 (m, 2H), 2.85 (dd, J=11.4, 4.6 Hz, 1H), 2.40-2.26 (m, 4H), 2.06-1.94 (m, 3H), 1.91-1.68 (m, 6H), 1.53-1.38 (m, 2H).

Example 154 racemic cis-2-{1-[4-(4,4-Difluoropiperidin-1-yl)benzyl]-6-[(5-methylpyridin-2-yl)methoxy]-1H-benzimidazol-2-yl}cyclohexanecarboxylic acid

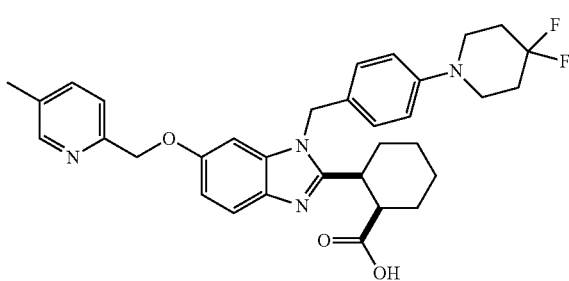

The title compound was prepared in a manner analogous to that in Example 152 substituting 4,4-difluoropiperidine hydrochloride. MS (ESI): mass calcd. for C₃₃H₃₆F₂N₄O₃, 574.28; m/z found, 575.3 [M+H]⁺. ¹H NMR (500 MHz, CD₃OD) δ 8.33 (s, 1H), 7.65 (dd, J=8.0, 1.5 Hz, 1H), 7.55 (d, J=8.8 Hz, 1H), 7.44 (d, J=8.0 Hz, 1H), 7.04-6.96 (m, 4H), 6.96-6.91 (m, 2H), 5.44 (d, J=16.6 Hz, 1H), 5.37 (d, J=16.8 Hz, 1H), 5.10 (s, 2H), 3.59-3.51 (m, 1H), 3.34-3.31 (m, 4H), 2.90-2.82 (m, 1H), 2.35 (s, 3H), 2.32-2.28 (m, 1H), 2.09-1.97 (m, 5H), 1.88-1.72 (m, 4H), 1.56-1.47 (m, 1H), 1.47-1.39 (m, 1H).

Example 155

2-({1-[4-(3,3-Difluoropiperidin-1-yl)benzyl]-6-[(1-methyl-1H-pyrazol-3-yl)methoxy]-1H-benzimidazol-2-yl}methyl)-2-ethylbutanoic acid

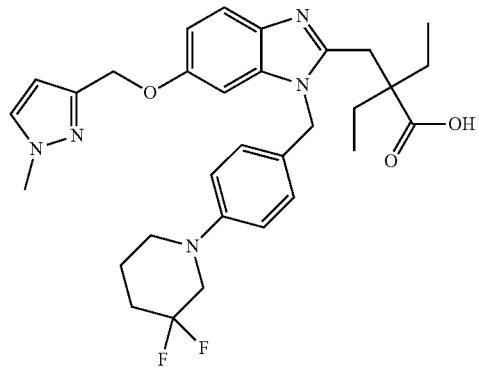 [SMILES: CCC(CC)(Cc1nc2ccc(OCc3ccn(C)n3)cc2n1Cc1ccc(N2CCCC(F)(F)C2)cc1)C(=O)O]

The title compound was prepared using analogous conditions described in Example 152 using 2-((1-(4-bromobenzyl)-6-((1-methyl-1H-pyrazol-3-yl)methoxy)-1H-benzo[d]imidazol-2-yl)methyl)-2-ethylbutanoic acid and 3,3-difluoropiperidine. MS (ESI): mass calcd. for C₃₁H₃₇F₂N₅O₃, 565.2; m/z found, 566.3 [M+H]⁺. ¹H NMR (500 MHz, CD₃OD) δ 7.69 (d, J=9.0, 1H), 7.57-7.51 (m, 1H), 7.34 (d, J=2.1, 1H), 7.25 (dd, J=9.1, 2.3, 1H), 7.13 (d, J=8.7, 2H), 6.96 (d, J=8.8, 2H), 6.28 (d, J=2.2, 1H), 6.25 (d, J=2.2, OH), 5.65 (s, 2H), 5.07 (s, 2H), 3.84 (s, 3H), 3.40 (t, J=5.7, 4H), 3.27-3.23 (m, 2H), 2.08-1.96 (m, 2H), 1.89-1.68 (m, 6H), 0.90-0.83 (m, 6H).

Example 156 racemic cis-2-{6-[(5-Methylpyridin-2-yl)methoxy]-1-(4-piperidin-1-ylbenzyl)-1H-benzimidazol-2-yl}cyclohexanecarboxylic acid

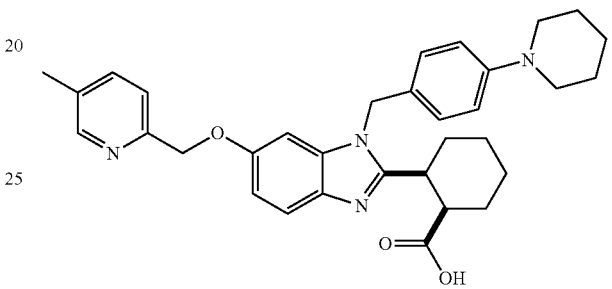

The title compound was prepared in a manner analogous to that in Example 152 substituting piperidine. MS (ESI): mass calcd. for C₃₃H₃₈N₄O₃, 538.29; m/z found, 539.3 [M+H]⁺. ¹H NMR (500 MHz, CD₃OD) δ 8.32 (d, J=2.0, 1H), 7.64 (dd, J=8.0, 1.6, 1H), 7.54 (d, J=9.0, 1H), 7.43 (d, J=8.0, 1H), 7.01-6.92 (m, 4H), 6.91-6.86 (m, 2H), 5.40 (d, J=16.6, 1H), 5.33 (d, J=16.6, 1H), 5.10 (s, 2H), 3.55 (dt, J=7.9, 4.1, 1H), 3.13-3.07 (m, 4H), 2.89-2.79 (m, 1H), 2.39-2.28 (m, 4H), 2.03-1.93 (m, 1H), 1.90-1.71 (m, 4H), 1.71-1.64 (m, 4H), 1.60-1.53 (m, 2H), 1.53-1.36 (m, 2H).

Example 157

(1S*,2R*)-2-{6-[(5-Methylpyridin-2-yl)methoxy]-1-(4-piperidin-1-ylbenzyl)-1H-benzimidazol-2-yl}cyclohexanecarboxylic acid

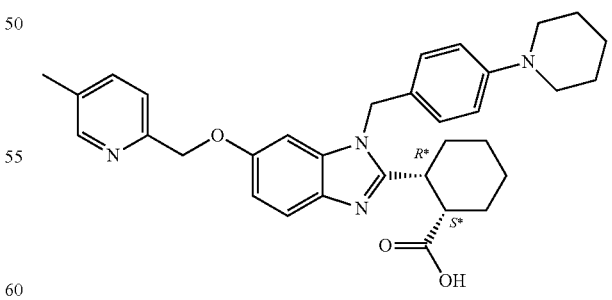

racemic cis-2-{6-[(5-Methylpyridin-2-yl)methoxy]-1-(4-piperidin-1-ylbenzyl)-1H-benzimidazol-2-yl}cyclohexanecarboxylic acid was purified by chiral SFC on (CHIRALPAK AD-H 5 μm 250×20 mm) mobile phase (60% CO₂, 40% MeOH) to yield the title compound as the first eluting isomer. MS (ESI): mass calcd. for C₃₃H₃₈N₄O₃, 538.29; m/z found, 539.3 [M+H]+. 1H NMR (500 MHz, CD3OD) δ 8.32 (s, 1H), 7.64 (dd, J=8.2, 1.9, 1H), 7.54 (d, J=8.6, 1H), 7.43 (d, J=8.0, 1H), 6.98 (d, J=8.7, 2H), 6.96-6.92 (m, 2H), 6.89 (d, J=8.8, 2H), 5.37 (q, J=16.6, 2H), 5.10 (s, 2H), 3.61-3.53 (m, 1H), 3.14-3.06 (m, 4H), 2.86-2.79 (m, 1H), 2.35 (s, 4H), 2.02-1.92 (m, 1H), 1.91-1.75 (m, 3H), 1.75-1.65 (m, 5H), 1.60-1.53 (m, 2H), 1.53-1.36 (m, 2H).

Example 158

(1R*,2S*)-2-{6-[(5-Methylpyridin-2-yl)methoxy]-1-(4-piperidin-1-ylbenzyl)-1H-benzimidazol-2-yl}cyclohexanecarboxylic acid

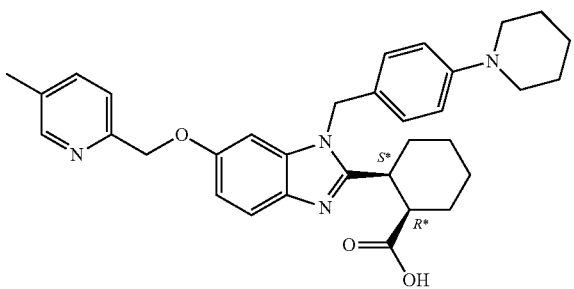 [SMILES: Cc1ccc(COc2ccc3nc([C@H]4CCCC[C@H]4C(=O)O)n(Cc4ccc(N5CCCCC5)cc4)c3c2)nc1]

racemic cis-2-{6-[(5-Methylpyridin-2-yl)methoxy]-1-(4-piperidin-1-ylbenzyl)-1H-benzimidazol-2-yl}cyclohexanecarboxylic acid was purified by chiral SFC on (CHIRALPAK AD-H 5 μm 250×20 mm) mobile phase (60% CO2, 40% MeOH) to yield the title compound as the second eluting isomer. MS (ESI): mass calcd. for C33H38N4O3, 538.29; m/z found, 539.3 [M+H]+.

Example 159 racemic cis-2-{1-[4-(3,3-Difluoroazetidin-1-yl)benzyl]-6-[(5-methylpyridin-2-yl)methoxy]-1H-benzimidazol-2-yl}cyclohexanecarboxylic acid

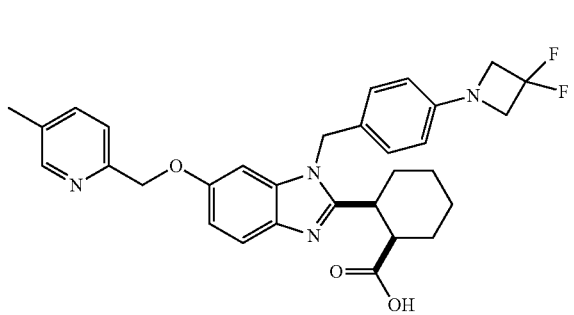

The title compound was prepared in a manner analogous to that in Example 152 substituting 3,3-difluoroazetidine hydrochloride. MS (ESI): mass calcd. for C31H32F2N4O3, 546.24; m/z found, 547.2 [M+H]+. 1H NMR (500 MHz, CD3OD) δ 8.32 (s, 1H), 7.64 (dd, J=8.0, 1.6, 1H), 7.54 (d, J=8.8, 1H), 7.42 (d, J=8.0, 1H), 7.01 (d, J=8.5, 2H), 6.98 (dd, J=8.8, 2.3, 1H), 6.93 (d, J=2.3, 1H), 6.52-6.47 (m, 2H), 5.43 (d, J=16.6, 1H), 5.36 (d, J=16.6, 1H), 5.10 (s, 2H), 4.17 (t, J=12.0, 4H), 3.58-3.52 (m, 1H), 2.89-2.81 (m, 1H), 2.35 (s, 3H), 2.33-2.29 (m, 1H), 2.09-2.02 (m, 1H), 1.86-1.72 (m, 4H), 1.53-1.48 (m, 1H), 1.46-1.39 (m, 1H).

Example 160

(1S*,2R*)-2-{1-[4-(3,3-Difluoroazetidin-1-yl)benzyl]-6-[(5-methylpyridin-2-yl)methoxy]-1H-benzimidazol-2-yl}cyclohexanecarboxylic acid

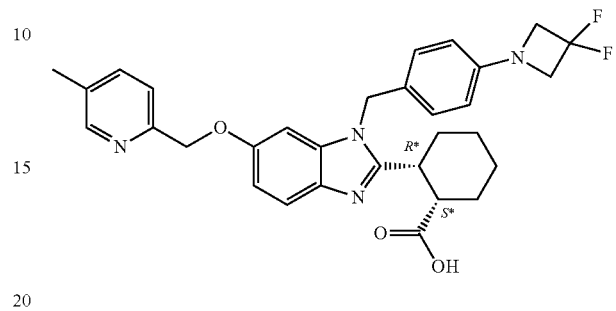

The title compound was prepared in a manner analogous to that in Example 152 substituting (1R*,2S*)-2-(1-(4-bromobenzyl)-6-((5-methylpyridin-2-yl)methoxy)-1H-benzo[d]imidazol-2-yl)cyclohexanecarboxylic acid, 3,3-difluoroazetidine hydrochloride (4 eq), and 5 eq LiHMDS. MS (ESI): mass calcd. for C31H32F2N4O3, 546.24; m/z found, 547.2 [M+H]+. 1H NMR (500 MHz, DMSO-d6) δ 7.51 (s, 1H), 6.82 (d, J=7.9, 1H), 6.73 (d, J=8.8, 1H), 6.61 (d, J=7.9, 1H), 6.23-6.03 (m, 4H), 5.68 (d, J=8.4, 2H), 4.57 (q, J=16.7, 2H), 4.29 (s, 2H), 3.36 (t, J=11.9, 4H), 2.80-2.70 (m, 1H), 2.10-2.00 (m, 1H), 1.61-1.46 (m, 4H), 1.21-1.13 (m, 1H), 1.12-0.86 (m, 4H), 0.75-0.55 (m, 2H).

Example 161 racemic cis-2-{1-[4-(4,4-Difluoropiperidin-1-yl)-2-fluorobenzyl]-6-[(5-methylpyridin-2-yl)methoxy]-1H-benzimidazol-2-yl}cyclohexanecarboxylic acid

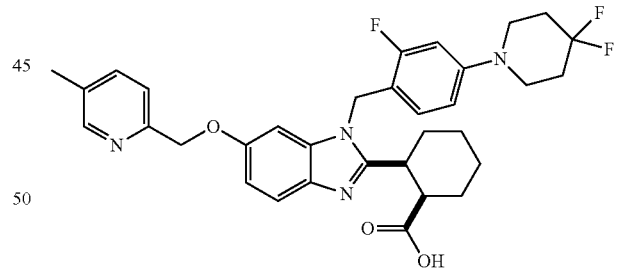

The title compound was prepared in a manner analogous to that in Example 152 substituting racemic cis-2-{1-(4-bromo-2-fluorobenzyl)-6-[(5-methylpyridin-2-yl)methoxy]-1H-benzimidazol-2-yl}cyclohexanecarboxylic acid and 4,4-difluoropiperidine hydrochloride. MS (ESI): mass calcd. for C33H35F3N4O3, 592.27; m/z found, 593.3 [M+H]+. 1H NMR (500 MHz, CDCl3) δ 8.34 (s, 1H), 7.65 (d, J=8.3, 1H), 7.55 (d, J=8.6, 1H), 7.46 (d, J=8.0, 1H), 7.03-6.98 (m, 2H), 6.85-6.76 (m, 2H), 6.67 (dd, J=8.6, 2.3, 1H), 5.47 (d, J=16.7, 1H), 5.41 (d, J=16.7, 1H), 5.12 (s, 2H), 3.64-3.53 (m, 1H), 3.41-3.35 (m, 4H), 2.91-2.81 (m, 1H), 2.35 (s, 4H), 2.34-2.29 (m, 1H), 2.11-1.95 (m, 5H), 1.86-1.72 (m, 4H), 1.56-1.49 (m, 1H), 1.49-1.41 (m, 1H).

Example 162 racemic cis-2-{1-[4-(3,3-Difluoropyrrolidin-1-yl)-2-fluorobenzyl]-6-[(5-methylpyridin-2-yl)methoxy]-1H-benzimidazol-2-yl}cyclohexanecarboxylic acid

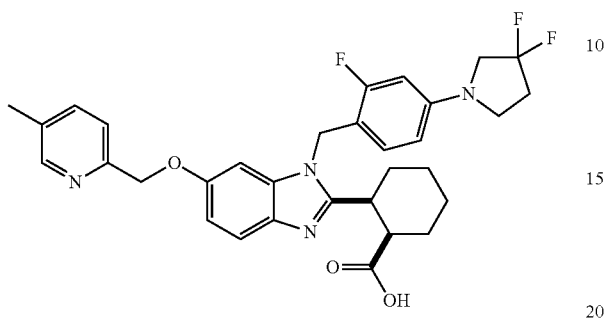

The title compound was prepared in a manner analogous to that in Example 152 substituting racemic cis-2-2-{1-(4-bromo-2-fluorobenzyl)-6-[(5-methylpyridin-2-yl)methoxy]-1H-benzimidazol-2-yl}cyclohexanecarboxylic acid. MS (ESI): mass calcd. for $C_{32}H_{33}F_3N_4O_3$, 578.25; m/z found, 579.2 [M+H]$^+$. $^1$H NMR (500 MHz, CD$_3$OD) δ 8.34 (s, 1H), 7.66 (d, J=6.2, 1H), 7.55 (d, J=8.6, 1H), 7.46 (d, J=7.9, 1H), 7.03-6.98 (m, 2H), 6.84 (t, J=8.6, 1H), 6.40 (dd, J=13.4, 2.3, 1H), 6.30 (dd, J=8.6, 2.3, 1H), 5.47 (d, J=16.5, 1H), 5.40 (d, J=16.4, 1H), 5.12 (s, 2H), 3.69-3.57 (m, 3H), 3.49 (t, J=7.2, 2H), 2.89 (s, 1H), 2.55-2.43 (m, 2H), 2.35 (s, 3H), 2.34-2.28 (m, 1H), 2.16-2.03 (m, 1H), 1.88-1.73 (m, 4H), 1.59-1.43 (m, 2H).

Example 163

(1R*,2S*)-2-{1-[4-(3,3-Difluoropyrrolidin-1-yl)-2-fluorobenzyl]-6-[(5-methylpyridin-2-yl)methoxy]-1H-benzimidazol-2-yl}cyclohexanecarboxylic acid

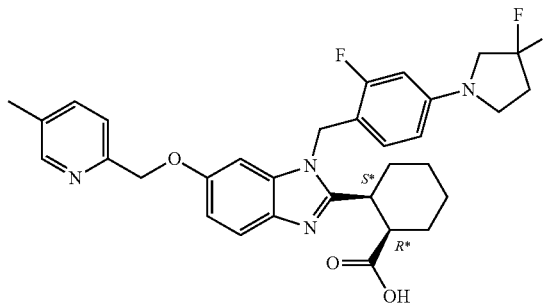

racemic cis-2-{1-[4-(3,3-Difluoropyrrolidin-1-yl)-2-fluorobenzyl]-6-[(5-methylpyridin-2-yl)methoxy]-1H-benzimidazol-2-yl}cyclohexanecarboxylic acid was purified by chiral SFC on (CHIRALPAK AD-H 5 µm 250×20 mm) mobile phase (60% CO$_2$, 40% MeOH) to yield the title compound as the second eluting isomer. MS (ESI): mass calcd. for $C_{32}H_{33}F_3N_4O_3$, 578.25; m/z found, 579.2 [M+H]$^+$. $^1$H NMR (500 MHz, DMSO-d$_6$) δ 12.08 (s, 1H), 8.38 (d, J=2.2, 1H), 7.61 (dd, J=7.9, 1.7, 1H), 7.45 (d, J=8.7, 1H), 7.39 (d, J=8.0, 1H), 7.07 (d, J=2.4, 1H), 6.84 (dd, J=8.7, 2.4, 1H), 6.76 (t, J=8.8, 1H), 6.47 (dd, J=13.4, 2.3, 1H), 6.28 (dd, J=8.6, 2.3, 1H), 5.41-5.28 (m, 2H), 5.10 (s, 2H), 3.72-3.59 (m, 3H), 3.43 (t, J=7.2, 2H), 2.77-2.66 (m, 1H), 2.29 (s, 3H), 1.87-1.51 (m, 6H), 1.38-1.25 (m, 2H).

Example 164

(1S*,2R*)-2-{1-[4-(3,3-Difluoropyrrolidin-1-yl)-2-fluorobenzyl]-6-[(5-methylpyridin-2-yl)methoxy]-1H-benzimidazol-2-yl}cyclohexanecarboxylic acid

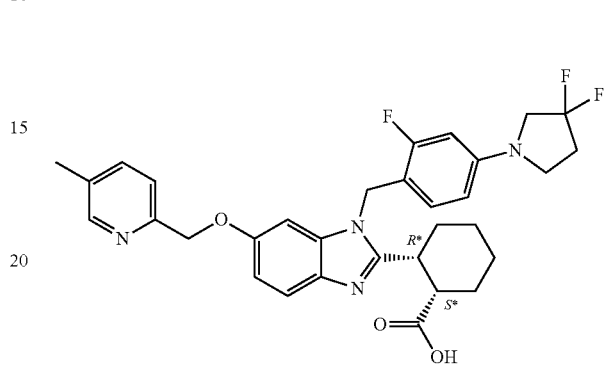

racemic cis-2-{1-[4-(3,3-Difluoropyrrolidin-1-yl)-2-fluorobenzyl]-6-[(5-methylpyridin-2-yl)methoxy]-1H-benzimidazol-2-yl}cyclohexanecarboxylic acid was purified by chiral SFC on (CHIRALPAK AD-H 5 µm 250×20 mm) mobile phase (60% CO$_2$, 40% MeOH) to yield the title compound as the first eluting isomer. MS (ESI): mass calcd. for $C_{32}H_{33}F_3N_4O_3$, 578.25; m/z found, 579.2 [M+H]$^+$.

Example 165 racemic cis-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid

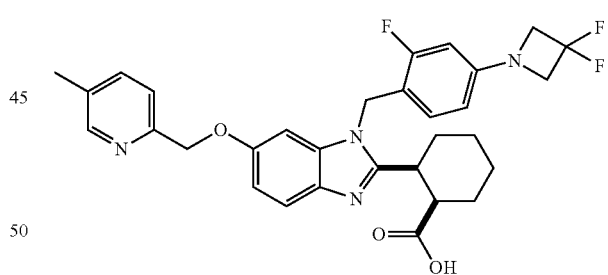

The title compound was prepared in a manner analogous to that in Example 152 substituting (1S,2R)-2-{1-(4-bromo-2-fluorobenzyl)-6-[(5-methylpyridin-2-yl)methoxy]-1H-benzimidazol-2-yl}cyclohexanecarboxylic acid and 3,3-difluoroazetidine hydrochloride. MS (ESI): mass calcd. for $C_{31}H_{31}F_3N_4O_3$, 564.23; m/z found, 565.2 [M+H]$^+$. $^1$H NMR (500 MHz, CD$_3$OD) δ 8.34 (s, 1H), 7.67-7.63 (m, 1H), 7.55 (d, J=8.6, 1H), 7.45 (d, J=8.0, 1H), 7.02-6.98 (m, 2H), 6.81 (t, J=8.5, 1H), 6.39 (dd, J=12.3, 2.3, 1H), 6.24 (dd, J=8.4, 2.3, 1H), 5.47 (d, J=16.6, 1H), 5.41 (d, J=16.6, 1H), 5.12 (s, 2H), 4.21 (t, J=12.0, 4H), 3.68-3.54 (m, 1H), 2.91-2.82 (m, 1H), 2.35 (s, 3H), 2.34-2.26 (m, 1H), 2.12-2.02 (m, 1H), 1.90-1.75 (m, 4H), 1.56-1.49 (m, 1H), 1.49-1.42 (m, 1H).

Example 166

(1R*,2S*)-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid

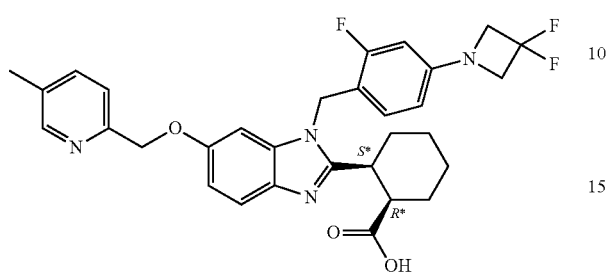

racemic cis-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid was purified by chiral SFC on (CHIRALPAK AD-H 5 μm 250×20 mm) mobile phase (60% $CO_2$, 40% MeOH) to yield the title compound as the second eluting isomer. MS (ESI): mass calcd. for $C_{31}H_{31}F_3N_4O_3$, 564.23; m/z found, 565.3 [M+H]$^+$. $^1$H NMR (500 MHz, DMSO-$d_6$) δ 12.06 (s, 1H), 8.38 (s, 1H), 7.61 (d, J=8.0, 1H), 7.46 (d, J=8.7, 1H), 7.39 (d, J=7.9, 1H), 7.06 (d, J=2.3, 1H), 6.84 (dd, J=8.7, 2.4, 1H), 6.77 (t, J=8.6, 1H), 6.46 (dd, J=12.3, 2.3, 1H), 6.23 (dd, J=8.4, 2.3, 1H), 5.40-5.29 (m, 2H), 5.10 (s, 2H), 4.25 (t, J=12.3, 4H), 3.71-3.64 (m, 1H), 2.73-2.67 (m, 1H), 2.29 (s, 3H), 1.85-1.75 (m, 2H), 1.74-1.57 (m, 4H), 1.33 (s, 2H).

Example 167

(1S*,2R*)-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid

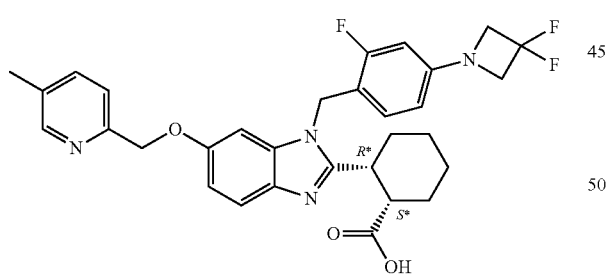

racemic cis-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid was purified by chiral SFC on (CHIRALPAK AD-H 5 μm 250×20 mm) mobile phase (60% $CO_2$, 40% MeOH) to yield the title compound as the first eluting isomer. MS (ESI): mass calcd. for $C_{31}H_{31}F_3N_4O_3$, 564.23; m/z found, 565.3 [M+H]$^+$. $^1$H NMR (500 MHz, DMSO-$d_6$) δ 12.06 (s, 1H), 8.38 (s, 1H), 7.61 (d, J=7.9, 1H), 7.46 (d, J=8.7, 1H), 7.39 (d, J=7.9, 1H), 7.06 (d, J=2.3, 1H), 6.84 (dd, J=8.7, 2.4, 1H), 6.77 (t, J=8.5, 1H), 6.46 (dd, J=12.4, 2.2, 1H), 6.23 (dd, J=8.4, 2.1, 1H), 5.41-5.28 (m, 2H), 5.10 (s, 2H), 4.25 (t, J=12.3, 4H), 3.71-3.65 (m, 1H), 2.75-2.65 (m, 1H), 2.29 (s, 3H), 1.87-1.53 (m, 6H), 1.39-1.26 (m, 2H).

Example 168 racemic cis-2-{1-[4-(3,3-Difluoroazetidin-1-yl)benzyl]-4-fluoro-6-[(1-methyl-1H-pyrazol-3-yl)methoxy]-1H-benzimidazol-2-yl}cyclohexanecarboxylic acid as the formate salt

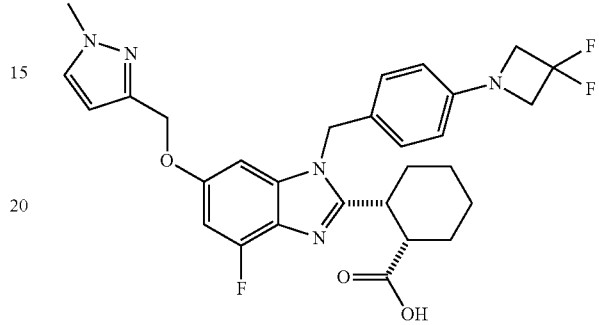

The title compound was prepared using analogous conditions described in Example 152 using cis-2-{1-(4-Bromobenzyl)-4-fluoro-6-[(1-methyl-1H-pyrazol-3-yl)methoxy]-1H-benzimidazol-2-yl}cyclohexanecarboxylic acid and 3,3-difluoroazetidine. MS (ESI): mass calcd. for $C_{29}H_{30}F_3N_5O_3$, 553.20; m/z found, 554.0 [M+H]$^+$. $^1$H NMR (300 MHz, DMSO-$d_6$) δ 7.64 (d, J=2.2, 1H), 7.06-7.01 (m, 1H), 6.98 (d, J=8.3, 2H), 6.89-6.73 (m, 1H), 6.65 (d, J=8.3, 2H), 6.26 (d, J=2.2, 1H), 5.43 (d, J=16.4, 1H), 5.31 (d, J=16.4, 1H), 4.98 (s, 2H), 4.06 (t, J=14.2, 2H), 3.81 (s, 3H), 3.74-3.68 (m, 1H), 3.63 (t, J=14.2, 2H), 2.83-2.73 (m, 1H), 2.42-2.28 (m, 1H), 1.94-1.55 (m, 6H), 1.45-1.28 (m, 1H).

Example 169 racemic cis-2-{4-Fluoro-6-[(1-methyl-1H-pyrazol-3-yl)methoxy]-1-(4-piperidin-1-ylbenzyl)-1H-benzimidazol-2-yl}cyclohexanecarboxylic acid as the HCl salt

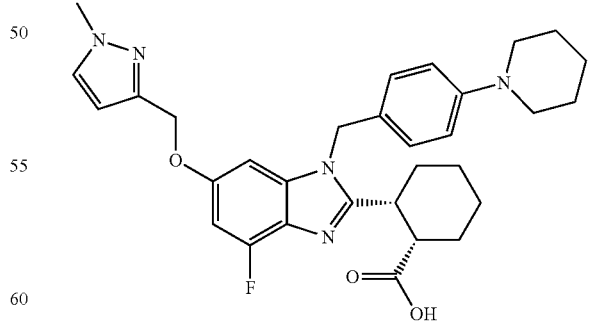

The title compound was prepared using analogous conditions described in Example 152 using cis-2-{1-(4-Bromobenzyl)-4-fluoro-6-[(1-methyl-1H-pyrazol-3-yl)methoxy]-1H-benzimidazol-2-yl}cyclohexanecarboxylic acid and piperidine. MS (ESI): mass calcd. for $C_{31}H_{36}FN_5O_3$, 545.3; m/z found, 546 [M+H]$^+$. 1H NMR (300 MHz, DMSO-d$_6$) δ 7.93-7.68 (m, 2H), 7.66 (d, J=2.2, 1H), 7.43-7.28 (m, 2H), 7.06-6.93 (m, 1H), 6.84 (d, J=12.9, 1H), 6.24 (d, J=2.2, 1H), 5.63 (d, J=17.3, 1H), 5.55 (d, J=17.1, 1H), 4.95 (s, 2H), 3.80 (s, 3H), 3.76-3.62 (m, 1H), 3.56-3.26 (m, 4H), 2.83-2.70 (m, 1H), 2.17-1.26 (m, 14H).

Example 170

2-({1-[4-(4,4-Difluoropiperidin-1-yl)benzyl]-6-[(5-methylpyridin-2-yl)methoxy]-1H-benzimidazol-2-yl}methyl)-2-ethylbutanoic acid

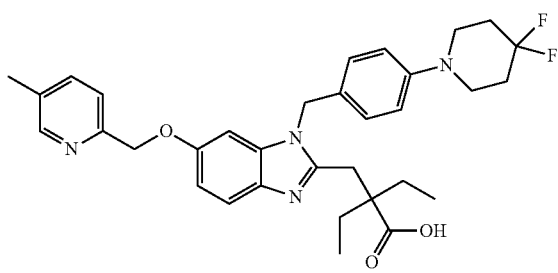 [SMILES: CCC(CC)(Cc1nc2ccc(OCc3ccc(C)cn3)cc2n1Cc1ccc(N2CCC(F)(F)CC2)cc1)C(=O)O]

To a mixture of 2-((1-(4-(4,4-difluoropiperidin-1-yl)benzyl)-6-((5-methylpyridin-2-yl)methoxy)-1H-benzo[d]imidazol-2-yl)methyl)-2-ethylbutanoic acid (90 mg, 0.17 mmol), RuPhos precatalyst (12.5 mg, 0.017 mmol), RuPhos (8.0 mg, 0.017 mmol), and 4,4-difluoropiperdine hydrochloride (79 mg, 0.50 mmol) in a sealed microwave vial is added degassed THF (1.7 mL) followed by and LiHMDS (1.01 mL, 1.0 M in THF) in that order. The resulting reddish mixture is stirred at RT for 3 h. The reaction was then partitioned between NH$_4$Cl and EtOAc and the organic layer is then dried and concentrated. Purification using high pressure liquid chromatography then afforded the title compound (52 mg, 54%). MS (ESI): mass calcd. for $C_{33}H_{38}F_2N_4O_3$, 576.29; m/z found, 577.3 [M+H]$^+$. $^1$H NMR (500 MHz, CD$_3$OD) δ 8.34 (s, 1H), 7.65 (dd, J=8.0, 1.6, 1H), 7.53 (d, J=8.7, 1H), 7.45 (d, J=8.0, 1H), 7.01-6.82 (m, 6H), 5.36 (s, 2H), 5.11 (s, 2H), 3.30-3.27 (m, 4H), 3.07 (s, 2H), 2.34 (s, 3H), 2.06-1.97 (m, 4H), 1.82-1.69 (m, 4H), 0.82 (t, J=7.4, 6H).

Example 171 racemic trans-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid

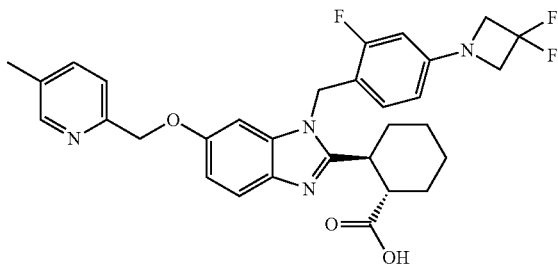 [SMILES: Cc1ccc(COc2ccc3nc([C@H]4CCCC[C@@H]4C(=O)O)n(Cc4ccc(N5CC(F)(F)C5)cc4F)c3c2)nc1]

Step A: N-(4-Bromo-2-fluorobenzyl)-5-((5-methylpyridin-2-yl)methoxy)-2-nitroaniline A mixture of 2-((3-fluoro-4-nitrophenoxy)methyl)-5-methylpyridine (1.50 g, 5.72 mmol), 4-bromo-2-fluorobenzylamine hydrochloride (1.51 g, 6.29 mmol), DIPEA (2.96 mL, 17.2 mmol) and acetonitrile (19.1 mL) was sealed in reaction vessel and heated to 75° Celsius for 18 h. The mixture was then cooled to RT, transferred to a round bottomed flask and concentrated to dryness. The resulting residue was then heated in a minimum amount of i-PrOH to 70° Celsius until homogeneous. The resulting solution was then cooled to RT where yellow solids precipitated, which were collected by filtration. (2.40 g, 94%). MS (ESI): mass calcd. for $C_{20}H_{17}BrFN_3O_3$, 445.04; m/z found, 446.0 [M+H]$^+$.

Step B: N-(4-(3,3-Difluoroazetidin-1-yl)-2-fluorobenzyl)-5-((5-methylpyridin-2-yl)methoxy)-2-nitroaniline To a sealable vial was added N-(4-bromo-2-fluorobenzyl)-5-((5-methylpyridin-2-yl)methoxy)-2-nitroaniline (700 mg, 1.57 mmol) RuPhos precatalyst (234 mg, 0.314 mmol) and RuPhos (149 mg, 0.314 mmol), 3,3-difluoroazetidine hydrochloride (610 mg, 4.71 mmol) and N$_2$ sparged THF (7.84 mL) followed by LiHMDS (6.27 mL, 1.0 N in THF). The resulting mixture is stirred at RT for 3 min. The resulting mixture was partitioned between NH$_4$Cl and EtOAc, the organic layer was separated, dried and concentrated to dryness. The residue was purified by FCC to provide the title compound (440 mg, 61%). MS (ESI): mass calcd. for $C_{23}H_{21}F_3N_4O_3$, 458.16; m/z found, 459.1 [M+H]$^+$.

Step C: racemic trans-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid The title compound was prepared in a manner analogous to that in Example 80 using N-(4-(3,3-difluoroazetidin-1-yl)-2-fluorobenzyl)-5-((5-methylpyridin-2-yl)methoxy)-2-nitroaniline and trans-3-hydroxyhexahydroisobenzofuran-1(3H)-one in Step C. MS (ESI): mass calcd. for $C_{31}H_{31}F_3N_4O_3$, 564.23; m/z found, 565.2 [M+H]. $^1$H NMR (500 MHz, CD$_3$OD) δ 8.36 (s, 1H), 7.67 (dd, J=8.0, 1.6, 1H), 7.47 (dd, J=8.4, 3.0, 2H), 7.04 (d, J=2.3, 1H), 6.95 (dd, J=8.8, 2.4, 1H), 6.92 (t, J=8.5, 1H), 6.38 (dd, J=12.2, 2.3, 1H), 6.27 (dd, J=8.4, 2.3, 1H), 5.53 (d, J=16.4, 1H), 5.32 (d, J=16.4, 1H), 5.14 (s, 2H), 4.21 (t, J=12.0, 4H), 3.21 (td, J=11.3, 3.8, 1H), 2.98 (td, J=11.5, 3.5, 1H), 2.36 (s, 3H), 2.22 (d, J=10.5, 1H), 1.89-1.85 (m, 1H), 1.75 (d, J=13.3, 1H), 1.60-1.45 (m, 4H), 1.37-1.21 (m, 1H).

Example 172 racemic cis-2-{1-[2,6-Difluoro-4-(4-fluoropiperidin-1-yl)benzyl]-6-[(3-fluoro-5-methylpyridin-2-yl)methoxy]-1H-benzimidazol-2-yl}cyclohexanecarboxylic acid

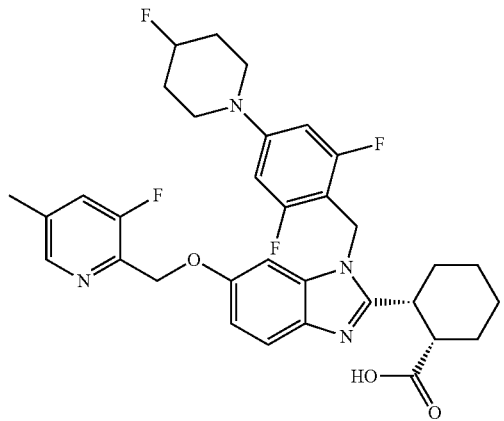 [SMILES: Cc1cnc(COc2ccc3nc([C@@H]4CCCC[C@@H]4C(=O)O)n(Cc4c(F)cc(N5CCC(F)CC5)cc4F)c3c2)c(F)c1]

To a 5 mL vial were added racemic cis-ethyl 2-(1-(4-bromo-2,6-difluorobenzyl)-6-((3-fluoro-5-methylpyridin-2-yl)methoxy)-1H-benzo[d]imidazol-2-yl)cyclohexanecarboxylate (150 mg, 0.24 mmol), Pd(t-Bu$_3$P)$_2$ (12 mg, 0.024 mmol), 4-fluoropiperidine (28 mg, 0.27 mmol), Cs$_2$CO$_3$ (238 mg, 0.73 mmol) and toluene (1 mL). The mixture was heated at 110° Celsius for 1 h. The mixture was cooled to RT, concentrated to dryness and purified by FCC to afford racemic cis-ethyl 2-(1-(2,6-difluoro-4-(4-fluoropiperidin-1-yl)benzyl)-6-((3-fluoro-5-methylpyridin-2-yl)methoxy)-1H-benzo[d]imidazol-2-yl)cyclohexanecarboxylate. To the resulting ethyl ester, in a 5 mL vial, was added HCl (5 mL, 6 N). The mixture was heated at 100° Celsius for 16 h. The mixture was cooled to RT then concentrated to dryness. The residue was purified using FCC to provide the title compound. MS (ESI): mass calcd. for C$_{33}$H$_{34}$F$_4$N$_4$O$_3$, 610.26; m/z found, 611.3 [M+H]$^+$. $^1$H NMR (500 MHz, CD$_3$OD) δ 6.71 (s, 1H), 6.00-5.97 (m, 1H), 5.95 (d, J=8.8 Hz, 1H), 5.59 (d, J=2.3 Hz, 1H), 5.38 (dd, J=8.8, 2.3 Hz, 1H), 5.07-4.97 (m, 2H), 3.96 (d, J=15.9 Hz, 1H), 3.80 (d, J=15.9 Hz, 1H), 3.68-3.59 (m, 2H), 3.22-3.16 (m, 1H), 2.21-2.15 (m, 1H), 1.93-1.83 (m, 2H), 1.74-1.66 (m, 2H), 1.35-1.28 (m, 1H), 0.87 (s, 3H), 0.83-0.72 (m, 1H), 0.50-0.35 (m, 5H), 0.32-0.14 (m, 4H), 0.01-0.14 (m, 2H).

Example 173 racemic cis-2-{1-[2-Fluoro-4-(4-fluoropiperidin-1-yl)benzyl]-6-[(3-fluoro-5-methylpyridin-2-yl)methoxy]-1H-benzimidazol-2-yl}cyclohexanecarboxylic acid

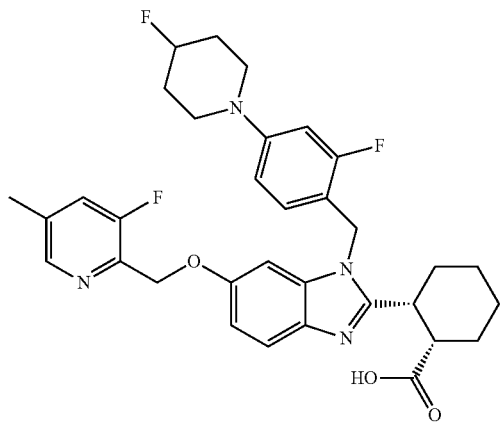 [SMILES: Cc1cnc(COc2ccc3nc([C@@H]4CCCC[C@@H]4C(=O)O)n(Cc4ccc(N5CCC(F)CC5)cc4F)c3c2)c(F)c1]

The title compound was prepared using methods similar to those in Example 123 using 4-bromo-2-fluorobenzyl amine in Step A and Example 172. MS (ESI): mass calcd. for C$_{33}$H$_{35}$F$_3$N$_4$O$_3$, 592.27; m/z found, 593.3 [M+H]$^+$. $^1$H NMR (400 MHz, CD$_3$OD) δ 8.14 (s, 1H), 7.69 (d, J=8.4, 2H), 7.59 (d, J=8.3, 2H), 7.54-7.36 (m, 4H), 7.12 (d, J=8.2, 2H), 7.00 (d, J=2.2, 1H), 6.92 (dd, J=8.8, 2.4, 1H), 5.64 (s, 2H), 5.15 (d, J=1.6, 2H), 3.20-3.01 (m, 8H), 2.28 (s, 3H), 1.28 (s, 6H).

Example 174

(1R*,2S*)-2-{1-[2-Fluoro-4-(4-fluoropiperidin-1-yl)benzyl]-6-[(3-fluoro-5-methylpyridin-2-yl)methoxy]-1H-benzimidazol-2-yl}cyclohexanecarboxylic acid

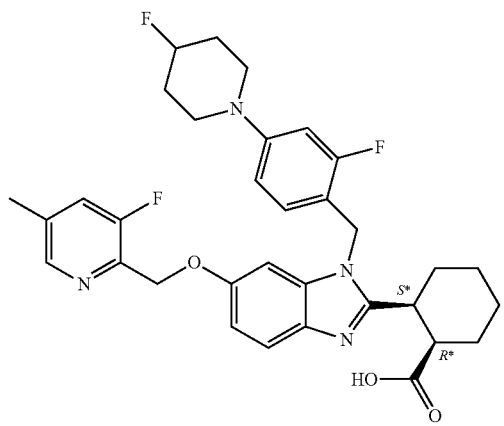 [SMILES: Cc1cnc(COc2ccc3nc([C@H]4CCCC[C@H]4C(=O)O)n(Cc4ccc(N5CCC(F)CC5)cc4F)c3c2)c(F)c1]

racemic cis-2-{1-[2-Fluoro-4-(4-fluoropiperidin-1-yl)benzyl]-6-[(3-fluoro-5-methylpyridin-2-yl)methoxy]-1H-benzimidazol-2-yl}cyclohexanecarboxylic acid was purified using chiral SFC (CHIRALCEL OJ 5 μm 250×4.6 mm) mobile phase (70% CO$_2$, 20% MeOH) to provide the title compound as the second eluting isomer. MS (ESI): mass calcd. for C$_{33}$H$_{35}$F$_3$N$_4$O$_3$, 592.27; m/z found, 593.3 [M+H]$^+$. $^1$H NMR (400 MHz, CD$_3$OD) δ 8.14 (s, 1H), 7.69 (d, J=8.4, 2H), 7.59 (d, J=8.3, 2H), 7.54-7.36 (m, 4H), 7.12 (d, J=8.2, 2H), 7.00 (d, J=2.2, 1H), 6.92 (dd, J=8.8, 2.4, 1H), 5.64 (s, 2H), 5.15 (d, J=1.6, 2H), 3.20-3.01 (m, 8H), 2.28 (s, 3H), 1.28 (s, 6H).

Example 175

(1S*,2R*)-2-{1-[2-Fluoro-4-(4-fluoropiperidin-1-yl)benzyl]-6-[(3-fluoro-5-methylpyridin-2-yl)methoxy]-1H-benzimidazol-2-yl}cyclohexanecarboxylic acid

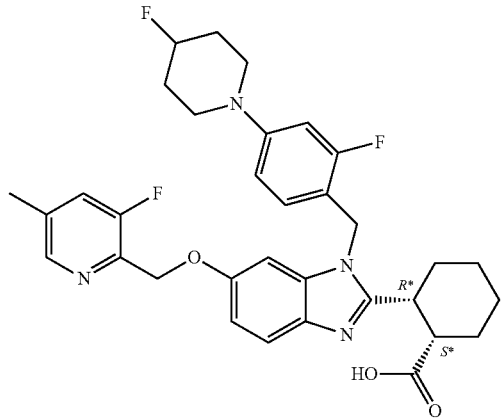 [SMILES: Cc1cnc(COc2ccc3nc([C@@H]4CCCC[C@@H]4C(=O)O)n(Cc4ccc(N5CCC(F)CC5)cc4F)c3c2)c(F)c1]

racemic cis-2-{1-[2-Fluoro-4-(4-fluoropiperidin-1-yl)benzyl]-6-[(3-fluoro-5-methylpyridin-2-yl)methoxy]-1H-benzimidazol-2-yl}cyclohexanecarboxylic acid was purified using chiral SFC (CHIRALCEL OJ 5 μm 250×4.6 mm) mobile phase (70% CO$_2$, 20% MeOH) to provide the title compound as the first eluting isomer. MS (ESI): mass calcd. for C$_{33}$H$_{35}$F$_3$N$_4$O$_3$, 592.27; m/z found, 593.3 [M+H]$^+$.

Example 176

(1R*,2S*)-2-{6-[(3-Fluoro-5-methylpyridin-2-yl)methoxy]-1-[4-(4-fluoropiperidin-1-yl)benzyl]-1H-benzimidazol-2-yl}cyclohexanecarboxylic acid

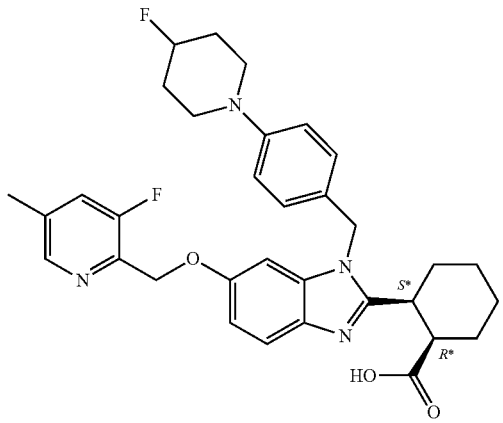 [SMILES: Cc1cnc(COc2ccc3nc([C@H]4CCCC[C@H]4C(=O)O)n(Cc4ccc(N5CCC(F)CC5)cc4)c3c2)c(F)c1]

The title compound was prepared using methods similar to those in Example 172 using (1R*,2S*)-ethyl 2-(1-(4-bromobenzyl)-6-((3-fluoro-5-methylpyridin-2-yl)methoxy)-1H-benzo[d]imidazol-2-yl)cyclohexanecarboxylate. MS (ESI): mass calcd. for C$_{33}$H$_{36}$F$_2$N$_4$O$_3$, 574.28; m/z found, 575.4 [M+H]$^+$. $^1$H NMR (500 MHz, CD$_3$OD) δ 8.18 (s, 1H), 7.57-7.40 (m, 2H), 7.09-6.86 (m, 6H), 5.39 (s, 2H), 5.14 (d, J=1.7, 2H), 4.80-4.64 (m, 1H), 3.60 (s, 1H), 3.36-3.31 (m, 2H), 3.15-3.07 (m, 2H), 2.80-2.70 (m, 1H), 2.40-2.32 (m, 4H), 2.03-1.73 (m, 8H), 1.71-1.63 (m, 1H), 1.51-1.35 (m, 2H).

Example 177 racemic cis-2-{1-[2-Fluoro-4-(4-methylpiperidin-1-yl)benzyl]-6-[(3-fluoro-5-methylpyridin-2-yl)methoxy]-1H-benzimidazol-2-yl}cyclohexanecarboxylic acid

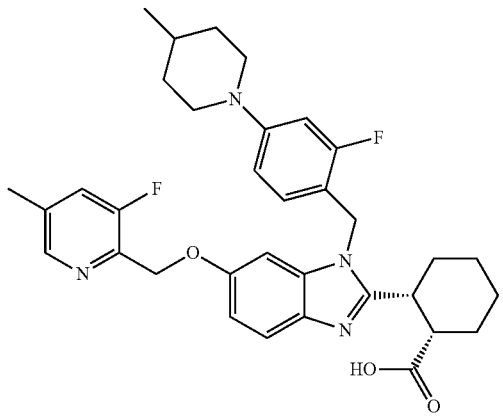 [SMILES: Cc1cnc(COc2ccc3nc([C@@H]4CCCC[C@@H]4C(=O)O)n(Cc4ccc(N5CCC(C)CC5)cc4F)c3c2)c(F)c1]

The title compound was prepared using methods similar to those in Example 123 using 4-bromo-2-fluorobenzyl amine in Step A and Example 172 using 4-methylpiperidine. MS (ESI): mass calcd. for C$_{34}$H$_{38}$F$_2$N$_4$O$_3$, 588.29; m/z found, 589.4 [M+H]$^+$. $^1$H NMR (500 MHz, CD$_3$OD) δ 8.18 (s, 1H), 7.55-7.41 (m, 2H), 6.95 (d, J=2.1, 1H), 6.85 (dd, J=8.6, 2.2, 1H), 6.73-6.56 (m, 3H), 5.67-5.22 (m, 2H), 5.15 (s, 2H), 3.82-3.57 (m, 3H), 2.73-2.54 (m, 3H), 2.44-2.30 (m, 4H), 2.12-1.78 (m, 4H), 1.73-1.65 (m, 3H), 1.59-1.44 (m, 1H), 1.44-1.34 (m, 2H), 1.33-1.19 (m, 2H), 0.95 (d, J=6.5, 3H).

Example 178 racemic cis-2-{6-[(3-Fluoro-5-methylpyridin-2-yl)methoxy]-1-[4-(4-methylpiperidin-1-yl)benzyl]-1H-benzimidazol-2-yl}cyclohexanecarboxylic acid

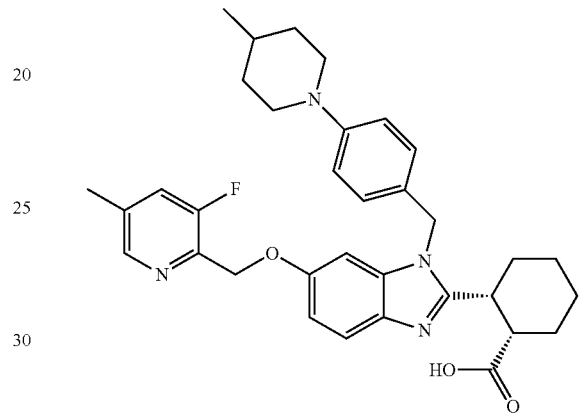

The title compound was prepared using methods similar to those in Example 123 using 4-bromo-benzyl amine in Step A and Example 172 using 4-methylpiperidine. MS (ESI): mass calcd. for C$_{34}$H$_{39}$FN$_4$O$_3$, 570.30; m/z found, 571.4 [M+H]$^+$. $^1$H NMR (500 MHz, CD$_3$OD) δ 8.18 (s, 1H), 7.60-7.35 (m, 2H), 7.04-6.80 (m, 6H), 5.56-5.22 (m, 2H), 5.14 (d, J=1.5, 2H), 3.74-3.53 (m, 3H), 2.62 (td, J=12.2, 2.3, 3H), 2.37 (s, 4H), 2.02-1.66 (m, 6H), 1.65-1.44 (m, 2H), 1.40-1.25 (m, 4H), 0.95 (d, J=6.5, 3H).

Example 179 racemic cis-2-{6-[(3-Fluoro-5-methylpyridin-2-yl)methoxy]-1-(4-piperidin-1-ylbenzyl)-1H-benzimidazol-2-yl}cyclohexanecarboxylic acid

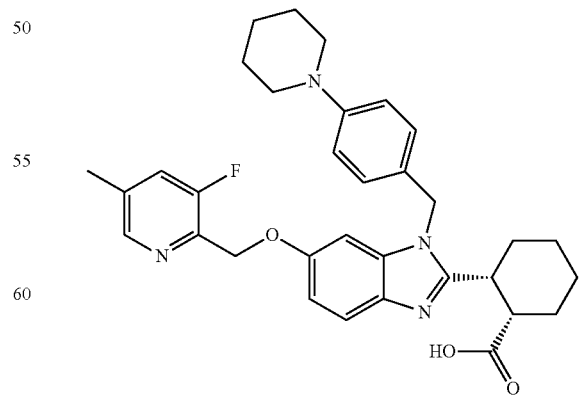

The title compound was prepared using methods similar to those in Example 123 using 4-bromobenzyl amine in Step A and Example 172 using piperidine. MS (ESI): mass calcd. for $C_{33}H_{37}FN_4O_3$, 556.29; m/z found, 557.3 [M+H]$^+$. $^1$H NMR (500 MHz, CD$_3$OD) δ 8.09 (s, 1H), 7.42 (d, J=8.8, 1H), 7.36 (d, J=9.7, 1H), 6.92-6.84 (m, 3H), 6.83-6.71 (m, 3H), 5.32 (two d, J=16.8, 2H), 5.05 (d, J=1.7, 2H), 3.62 (d, J=4.3, 1H), 3.03-2.95 (m, 4H), 2.57-2.43 (m, 1H), 2.34-2.18 (m, 4H), 1.97-1.75 (m, 2H), 1.74-1.61 (m, 2H), 1.61-1.49 (m, 5H), 1.51-1.42 (m, 2H), 1.31-1.22 (m, 2H).

Example 180

2-Ethyl-2-({6-[(3-fluoro-5-methyl pyridin-2-yl)methoxy]-1-[4-(4-methylpiperidin-1-yl)benzyl]-1H-benzimidazol-2-yl}methyl)butanoic acid

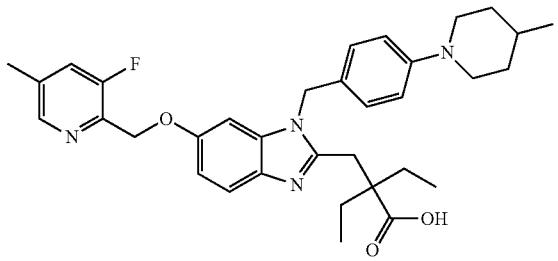

The title compound was prepared using methods similar to those in Example 123 using 4-bromobenzyl amine in Step A, 3,3-diethyldihydrofuran-2,5-dione in Step C and Example 172 using 4-methylpiperdine. MS (ESI): mass calcd. for $C_{34}H_{41}FN_4O_3$, 572.3; m/z found, 573.3 [M+H]$^+$. $^1$H NMR (400 MHz, CD$_3$OD) δ 8.09 (s, 1H), 7.41-7.31 (m, 2H), 6.90-6.72 (m, 6H), 5.36 (s, 2H), 5.04 (d, J=1.7, 2H), 3.48 (d, J=12.3, 2H), 2.97 (s, 2H), 2.52 (td, J=12.2, 2.4, 2H), 1.76-1.50 (m, 6H), 1.48-1.31 (m, 1H), 1.27-1.11 (m, 2H), 0.85 (d, J=6.5, 3H), 0.78 (t, J=7.4, 6H).

Example 181

2-Ethyl-2-({1-[2-fluoro-4-(4-methylpiperidin-1-yl)benzyl]-6-[(3-fluoro-5-methylpyridin-2-yl)methoxy]-1H-benzimidazol-2-yl}methyl)butanoic acid

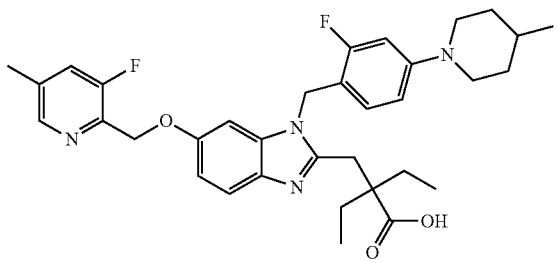

The title compound was prepared using methods similar to those in Example 123 using 4-bromo-2-fluorobenzyl amine in Step A and 3,3-diethyldihydrofuran-2,5-dione in Step C and Example 172 using 4-methylpiperidine. MS (ESI): mass calcd. for $C_{34}H_{40}F_2N_4O_3$, 590.3; m/z found, 591.4 [M+H]$^+$. $^1$H NMR (500 MHz, CD$_3$OD) δ 8.19 (s, 1H), 7.51-7.40 (m, 2H), 7.01-6.81 (m, 2H), 6.71-6.55 (m, 3H), 5.48 (s, 2H), 5.13 (d, J=1.5, 2H), 3.63 (d, J=12.5, 2H), 3.12 (s, 2H), 2.65 (td, J=12.4, 2.5, 2H), 2.37 (s, 3H), 1.82-1.62 (m, 6H), 1.51-1.42 (m, 1H), 1.30-1.16 (m, 2H), 0.98-0.82 (m, 9H).

Example 182

2-Ethyl-2-({6-[(3-fluoro-5-methyl pyridin-2-yl)methoxy]-1-[4-(4-fluoropiperidin-1-yl)benzyl]-1H-benzimidazol-2-yl}methyl)butanoic acid

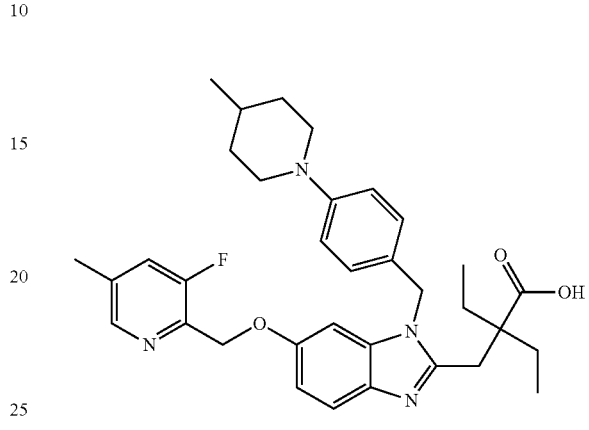

The title compound was prepared using methods similar to those in Example 123 using 4-bromobenzyl amine in Step A and 3,3-diethyldihydrofuran-2,5-dione in Step C and Example 172 using 4-methylpiperidine. MS (ESI): mass calcd. for $C_{33}H_{38}F_2N_4O_3$, 576.29; m/z found, 577.4 [M+H]$^-$ $^1$H NMR (400 MHz, CD$_3$OD) δ 8.20 (s, 1H), 7.49 (t, J=10.0, 2H), 7.12-6.85 (m, 6H), 5.39 (s, 2H), 5.17 (s, 2H), 3.17-3.01 (m, 4H), 2.09-1.63 (m, 8H), 1.40-1.19 (m, 1H), 0.84 (t, J=7.1, 6H).

Example 183

3-(6-[(3-Fluoro-5-methylpyridin-2-yl)methoxy]-1-{2-fluoro-4-[3-(trifluoromethyl)azetidin-1-yl]benzyl}-1H-benzimidazol-2-yl)-2,2-dimethylpropanoic acid

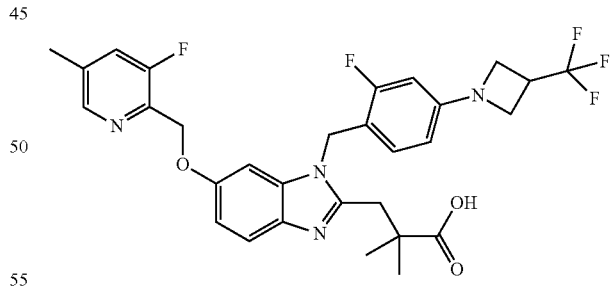

The title compound was prepared using methods similar to those in Example 123 using 4-bromo-2-fluorobenzyl amine in Step A and 3,3-dimethyldihydrofuran-2,5-dione in Step C and Example 172 using 3-(trifluoromethyl)azetidine. MS (ESI): mass calcd. for $C_{30}H_{29}F_5N_4O_3$, 588.22; m/z found, 589.3 [M+H]$^+$. $^1$H NMR (500 MHz, CD$_3$OD) δ 8.18 (s, 1H), 7.47 (dd, J=13.1, 9.8, 2H), 6.92 (dd, J=12.0, 10.1, 2H), 6.78 (t, J=8.4, 1H), 6.27-6.13 (m, 2H), 5.43 (s, 2H), 5.15 (d, J=1.0, 2H), 4.02 (t, J=8.3, 2H), 3.87 (dd, J=8.1, 5.4, 2H), 3.56-3.46 (m, 1H), 3.17 (s, 2H), 2.37 (s, 3H), 1.25 (s, 6H).

Example 184

3-{1-[4-(4-tert-Butylpiperidin-1-yl)benzyl]-6-[(3-fluoro-5-methylpyridin-2-yl)methoxy]-1H-benzimidazol-2-yl}-2,2-dimethylpropanoic acid

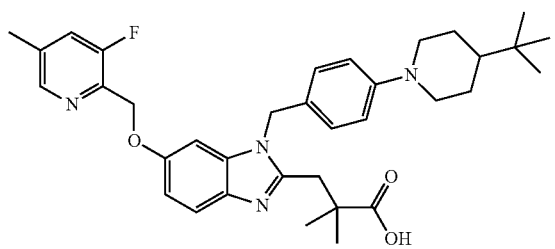 [SMILES: Cc1cnc(COc2ccc3nc(CC(C)(C)C(=O)O)n(Cc4ccc(N5CCC(C(C)(C)C)CC5)cc4)c3c2)c(F)c1]

The title compound was prepared using methods similar to those in Example 123 using 4-bromobenzyl amine in Step A, 3,3-dimethyldihydrofuran-2,5-dione in Step C and Example 172 using 4-(tert-butyl)piperidine. MS (ESI): mass calcd. for $C_{35}H_{43}FN_4O_3$, 586.33; m/z found, 587.4 $[M+H]^+$. $^1$H NMR (500 MHz, CD$_3$OD) δ 8.19 (s, 1H), 7.56-7.35 (m, 2H), 7.02-6.74 (m, 6H), 5.46 (s, 2H), 5.14 (d, J=1.7, 2H), 3.68 (d, J=12.1, 2H), 3.12 (s, 2H), 2.54 (td, J=12.2, 2.2, 2H), 2.37 (s, 3H), 1.77 (d, J=13.0, 2H), 1.44-1.31 (m, 2H), 1.24 (s, 6H), 1.14-1.07 (m, 1H), 0.88 (s, 9H).

Example 185

3-{6-[(3-Fluoro-5-methylpyridin-2-yl)methoxy]-1-[4-(4-methylpiperidin-1-yl)benzyl]-1H-benzimidazol-2-yl}-2,2-dimethylpropanoic acid

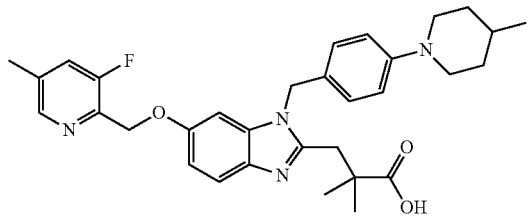

The title compound was prepared using methods similar to those in Example 123 using 4-bromobenzyl amine in Step A and 3,3-dimethyldihydrofuran-2,5-dione in Step C and Example 172 using 4-methylpiperidine. MS (ESI): mass calcd. for $C_{32}H_{37}FN_4O_3$, 544.29; m/z found, 545.4 $[M+H]^+$. $^1$H NMR (500 MHz, CD$_3$OD) δ 8.08 (s, 1H), 7.41-7.27 (m, 2H), 6.95-6.68 (m, 6H), 5.36 (s, 2H), 5.03 (d, J=1.8, 2H), 3.48 (d, J=12.4, 2H), 3.02 (s, 2H), 2.51 (td, J=12.2, 2.5, 2H), 2.26 (s, 3H), 1.60 (d, J=12.8, 2H), 1.43-1.28 (m, 1H), 1.24-1.09 (m, 8H), 0.85 (d, J=6.5, 3H).

Example 186

3-{1-[2-Fluoro-4-(4-fluoropiperidin-1-yl)benzyl]-6-[(3-fluoro-5-methylpyridin-2-yl)methoxy]-1H-benzimidazol-2-yl}-2,2-dimethylpropanoic acid

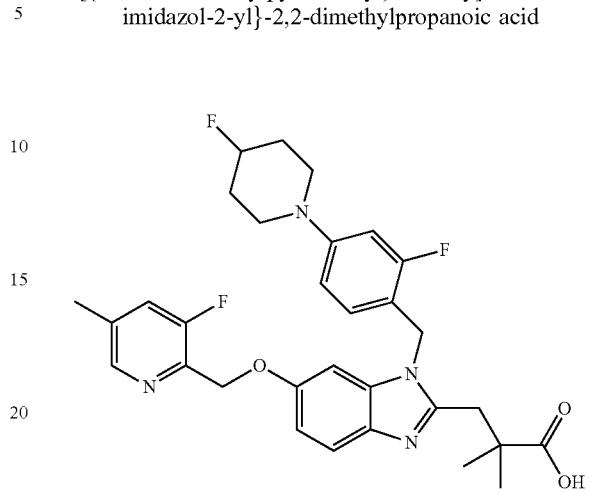

The title compound was prepared using methods similar to those in Example 123 using 4-bromo-2-fluorobenzyl amine in Step A and 3,3-dimethyldihydrofuran-2,5-dione in Step C and Example 172 using 4-fluoropiperidine. MS (ESI): mass calcd. for $C_{31}H_{33}F_3N_4O_3$, 566.25; m/z found, 567.3 $[M+H]^+$. $^1$H NMR (500 MHz, CD$_3$OD) δ 8.20 (s, 1H), 7.53-7.37 (m, 2H), 6.98-6.85 (m, 2H), 6.79-6.58 (m, 3H), 5.49 (s, 2H), 5.14 (d, J=1.6, 2H), 4.81-4.67 (m, 1H), 3.41-3.32 (m, 2H), 3.24-3.10 (m, 4H), 2.38 (s, 3H), 2.04-1.90 (m, 2H), 1.88-1.75 (m, 2H), 1.25 (s, 6H).

Example 187

2-ethyl-2-((1-((3-fluoro-4'-(trifluoromethyl)-[1,1'-biphenyl]-4-yl)methyl)-6-((1-methyl-1H-pyrazol-3-yl)methoxy)-1H-benzo[d]imidazol-2-yl)methyl)butanoic acid

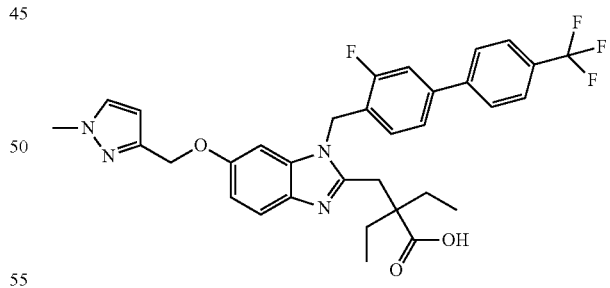

The title compound was prepared in a manner analogous to that in Example 144 using (4-(trifluoromethyl)phenyl)boronic acid and 2-((1-(4-bromo-2-fluorobenzyl)-6-((1-methyl-1H-pyrazol-3-yl)methoxy)-1H-benzo[d]imidazol-2-yl)methyl)-2-ethylbutanoic acid and (4-(trifluoromethyl)phenyl)boronic acid. MS (ESI): mass calcd. for $C_{33}H_{32}F_4N_4O_3$, 608.24; m/z found, 609.2 $[M+H]^+$. $^1$H NMR (400 MHz, CD$_3$OD) δ 7.81 (d, J=8.3, 2H), 7.73 (d, J=8.4, 2H), 7.57-7.54 (m, 1H), 7.54-7.52 (m, 1H), 7.49 (d, J=2.3, 1H), 7.41 (dd, J=8.0, 1.8, 1H), 7.03 (d, J=2.3, 1H), 6.93 (dd, J=8.8, 2.3, 1H), 6.88 (t, J=7.9, 1H), 6.28 (d, J=2.3, 1H), 5.61 (s, 2H), 5.01 (s, 2H), 3.81 (s, 3H), 3.12 (s, 2H), 1.90-1.73 (m, 4H), 0.88 (t, J=7.5, 6H).

Example 188

2-ethyl-2-((6-((1-methyl-1H-pyrazol-3-yl)methoxy)-1-((4'-(trifluoromethyl)-[1,1'-biphenyl]-4-yl)methyl)-1H-benzo[d]imidazol-2-yl)methyl)butanoic acid

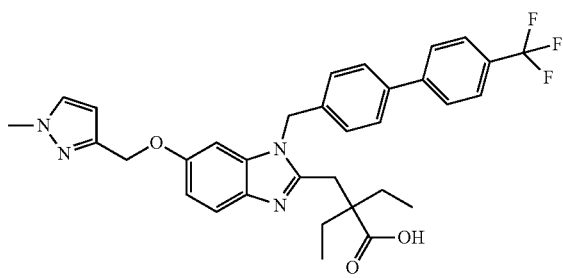 [SMILES: CCC(CC)(Cc1nc2ccc(OCc3ccn(C)n3)cc2n1Cc1ccc(-c2ccc(C(F)(F)F)cc2)cc1)C(=O)O]

The title compound was prepared using analogous conditions described in Example 144 using (4-(trifluoromethyl)phenyl)boronic acid 2-((1-(4-bromo-2-fluorobenzyl)-6-((1-methyl-1H-pyrazol-3-yl)methoxy)-1H-benzo[d]imidazol-2-yl)methyl)-2-ethylbutanoic acid and (4-(trifluoromethyl)phenyl)boronic acid. MS (ESI): mass calcd. for $C_{33}H_{32}F_4N_4O_3$, 608.24; m/z found, 609.2 [M+H]$^+$. $^1$H NMR (400 MHz, CD$_3$OD) δ 7.81 (d, J=8.3, 2H), 7.73 (d, J=8.4, 2H), 7.57-7.54 (m, 1H), 7.54-7.52 (m, 1H), 7.49 (d, J=2.3, 1H), 7.41 (dd, J=8.0, 1.8, 1H), 7.03 (d, J=2.3, 1H), 6.93 (dd, J=8.8, 2.3, 1H), 6.88 (t, J=7.9, 1H), 6.28 (d, J=2.3, 1H), 5.61 (s, 2H), 5.01 (s, 2H), 3.81 (s, 3H), 3.12 (s, 2H), 1.90-1.73 (m, 4H), 0.88 (t, J=7.5, 6H).

Example 189

2-ethyl-2-((1-(2-fluoro-4-(4-(trifluoromethyl)piperidin-1-yl)benzyl)-6-((1-methyl-1H-pyrazol-3-yl)methoxy)-1H-benzo[d]imidazol-2-yl)methyl)butanoic acid

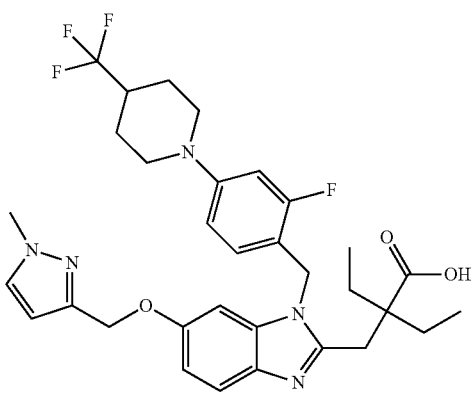 [SMILES: CCC(CC)(Cc1nc2ccc(OCc3ccn(C)n3)cc2n1Cc1ccc(N2CCC(C(F)(F)F)CC2)cc1F)C(=O)O]

The title compound was prepared in a manner analogous to that in Example 152 substituting 4-(trifluoromethyl)piperidine hydrochloride and 2-((1-(4-bromo-2-fluorobenzyl)-6-((1-methyl-1H-pyrazol-3-yl)methoxy)-1H-benzo[d]imidazol-2-yl)methyl)-2-ethylbutanoic acid and 4-(trifluoromethyl)piperidine. MS (ESI): mass calcd. for $C_{32}H_{37}F_4N_5O_3$, 615.28; m/z found, 615.2 [M+H]$^+$. $^1$H NMR (400 MHz, CD$_3$OD) δ 7.68 (d, J=9.0, 1H), 7.56 (d, J=2.3, 1H), 7.40 (d, J=2.3, 1H), 7.26 (dd, J=9.0, 2.3, 1H), 7.24-7.18 (m, 1H), 6.80-6.73 (m, 2H), 6.33 (d, J=2.3, 1H), 5.68 (s, 2H), 5.09 (s, 2H), 3.88 (s, 3H), 3.87-3.84 (m, 2H), 3.46 (s, 2H), 2.80 (td, J=12.7, 2.6, 2H), 2.43-2.30 (m, 1H), 1.97-1.88 (m, 2H), 1.87-1.68 (m, 4H), 1.68-1.53 (m, 2H), 0.88 (t, J=7.4, 6H).

Example 190

2-ethyl-2-((6-((1-methyl-1H-pyrazol-3-yl)methoxy)-1-(4-(4-(trifluoromethyl)piperidin-1-yl)benzyl)-1H-benzo[d]imidazol-2-yl)methyl)butanoic acid

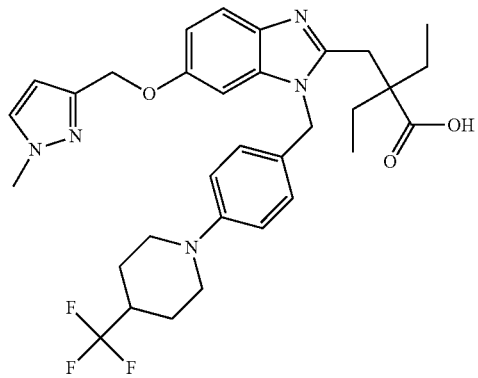 [SMILES: CCC(CC)(Cc1nc2ccc(OCc3ccn(C)n3)cc2n1Cc1ccc(N2CCC(C(F)(F)F)CC2)cc1)C(=O)O]

The title compound was prepared in a manner analogous to that in Example 152 substituting 4-(trifluoromethyl)piperidine hydrochloride and 2-((1-(4-bromobenzyl)-6-((1-methyl-1H-pyrazol-3-yl)methoxy)-1H-benzo[d]imidazol-2-yl)methyl)-2-ethylbutanoic acid and 4-(trifluoromethyl)piperidine. MS (ESI): mass calcd. for $C_{32}H_{38}F_3N_5O_3$, 597.29; m/z found, 598.2 [M+H]$^+$. $^1$H NMR (500 MHz, CD$_3$OD) δ 7.70 (d, J=9.1, 1H), 7.55 (d, J=2.3, 1H), 7.35 (d, J=2.3, 1H), 7.26 (dd, J=9.0, 2.3, 1H), 7.20-7.15 (m, 2H), 7.10-7.02 (m, 2H), 6.31 (d, J=2.3, 1H), 5.68 (s, 2H), 5.07 (s, 2H), 3.85 (s, 3H), 3.83-3.77 (m, 2H), 3.41 (s, 2H), 2.85 (td, J=12.6, 2.6, 2H), 2.46-2.29 (m, 1H), 2.00-1.95 (m, 2H), 1.86-1.60 (m, 6H), 0.87 (t, J=7.4, 6H).

Example 191

3-{1-(3-Bromobenzyl)-6-[(3-fluoro-5-methylpyridin-2-yl)methoxy]-1H-benzimidazol-2-yl}-2,2-dimethylpropanoic acid

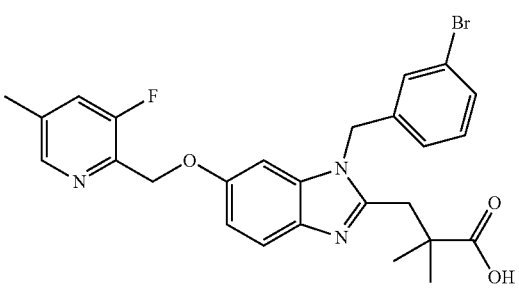 [SMILES: Cc1cnc(COc2ccc3nc(CC(C)(C)C(=O)O)n(Cc4cccc(Br)c4)c3c2)c(F)c1]

The title compound was prepared using methods similar to those in Example 123 using (3-bromophenyl)methanamine in Step A and 3,3-dimethyldihydrofuran-2,5-dione in Step C. MS (ESI): mass calcd. for $C_{26}H_{25}BrFN_3O_3$, 525.11; m/z found, 526.2 [M+H]$^+$. $^1$H NMR (500 MHz, CD$_3$OD) 8.15 (s, 1H), 7.52 (d, J=8.7 Hz, 1H), 7.44-7.35 (m, 2H), 7.23-7.12 (m, 2H), 7.02-6.86 (m, 3H), 5.59 (s, 2H), 5.16 (d, J=1.6 Hz, 2H), 3.09 (s, 2H), 2.36 (s, 3H), 1.31-1.23 (m, 6H).

Example 192 racemic cis-2-(6-[(3-Fluoro-5-methylpyridin-2-yl)methoxy]-1-{2-fluoro-4-[4-(trifluoromethyl)piperidin-1-yl]benzyl}-1H-benzimidazol-2-yl)cyclohexanecarboxylic acid

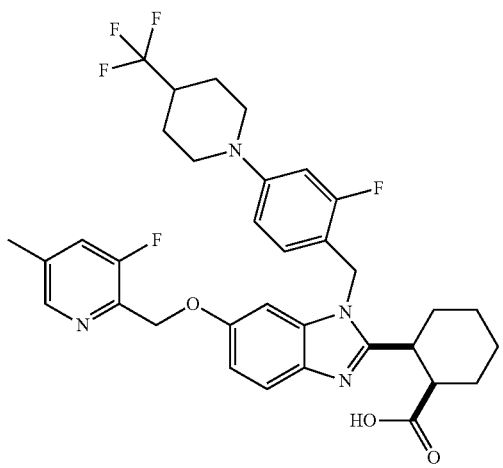

The title compound was prepared using methods similar to those in Example 123 using 4-bromo-2-fluorobenzyl amine in Step A and Example 172 using 4-(trifluoromethyl)piperidine. MS (ESI): mass calcd. for $C_{34}H_{35}F_5N_4O_3$, 642.27; m/z found, 643.3 [M+H]$^+$. $^1$H NMR (500 MHz, CD$_3$OD) δ 8.19 (s, 1H), 7.54-7.42 (m, 2H), 6.97 (d, J=2.3 Hz, 1H), 6.86 (dd, J=8.8, 2.4 Hz, 1H), 6.78-6.59 (m, 3H), 5.59 (d, J=16.9 Hz, 1H), 5.31 (d, J=16.9 Hz, 1H), 5.15 (s, 2H), 3.83-3.66 (m, 3H), 2.79-2.60 (m, 3H), 2.43-2.20 (m, 5H), 2.06-1.56 (m, 9H), 1.48-1.33 (m, 2H).

Example 193

3-{1-(5-Bromo-2-fluorobenzyl)-6-[(3-fluoro-5-methylpyridin-2-yl)methoxy]-1H-benzimidazol-2-yl}-2,2-dimethylpropanoic acid

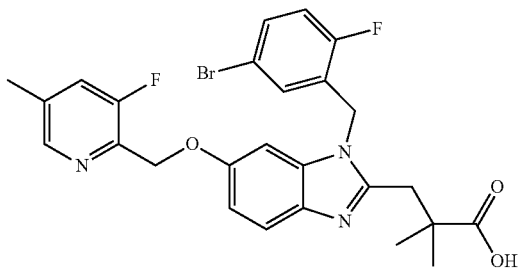 [SMILES: Cc1cnc(COc2ccc3nc(CC(C)(C)C(=O)O)n(Cc4cc(Br)ccc4F)c3c2)c(F)c1]

The title compound was prepared using methods similar to those in Example 123 using (5-bromo-2-fluorophenyl)methanamine in Step A and 3,3-dimethyldihydrofuran-2,5-dione in Step C. MS (ESI): mass calcd. for $C_{26}H_{24}BrF_2N_3O_3$, 543.10; m/z found, 544.2 [M+H]$^+$. $^1$H NMR (500 MHz, CD$_3$OD) δ 8.16 (s, 1H), 7.53-7.39 (m, 3H), 7.10 (dd, J=9.8, 8.8 Hz, 1H), 6.98-6.87 (m, 2H), 6.76 (dd, J=6.5, 2.5 Hz, 1H), 5.66 (s, 2H), 5.16 (d, J=1.8 Hz, 2H), 3.11 (s, 2H), 2.37 (s, 3H), 1.26 (s, 6H).

Example 194

2-Ethyl-2-[(6-[(3-fluoro-5-methylpyridin-2-yl)methoxy]-1-{4-[4-(trifluoromethyl)piperidin-1-yl]benzyl}-1H-benzimidazol-2-yl)methyl]butanoic acid

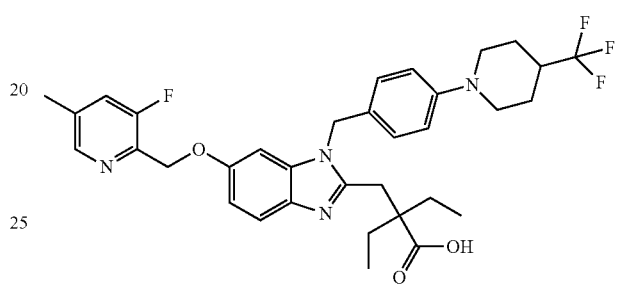

The title compound was prepared using methods similar to those in Example 123 using 3,3-ethyldihydrofuran-2,5-dione in Step C and Example 172 using 4-(trifluoromethyl)piperidine. MS (ESI): mass calcd. for $C_{34}H_{38}F_4N_4O_3$, 626.29; m/z found, 627.3 [M+H]$^+$. $^1$H NMR (500 MHz, CD$_3$OD) δ 8.09 (s, 1H), 7.41-7.30 (m, 2H), 6.91-6.70 (m, 6H), 5.37 (s, 2H), 5.04 (d, J=1.8 Hz, 2H), 3.65-3.56 (m, 2H), 2.97 (s, 2H), 2.56 (td, J=12.5, 2.3 Hz, 2H), 2.28 (s, 3H), 2.22-2.08 (m, 1H), 1.88-1.75 (m, 2H), 1.71-1.49 (m, 6H), 0.78 (t, J=7.4 Hz, 6H).

Example 195 racemic cis-2-{1-[3-(2-Methoxypyrimidin-5-yl)benzyl]-6-[(5-methylpyridin-2-yl)methoxy]-1H-benzimidazol-2-yl}cyclohexanecarboxylic acid

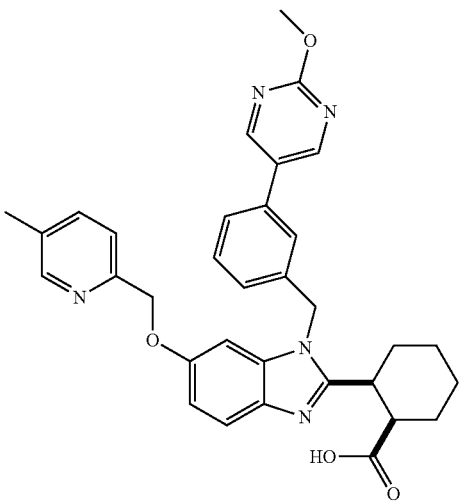

The title compound prepared using similar methods to those in Example 144 using (2-methoxypyrimidin-5-yl)boronic acid and racemic cis-2-{1-(3-bromobenzyl)-6-[(5-methylpyridin-2-yl)methoxy]-1H-benzimidazol-2-yl}cyclohexanecarboxylic acid. MS (ESI): mass calcd. for $C_{33}H_{33}N_5O_4$, 563.25; m/z found, 564.3 [M+H]$^+$. $^1$H NMR (500 MHz, CDCl$_3$) δ 8.65-8.57 (s, 2H), 8.35-8.29 (s, 1H), 7.65-7.60 (d, J=8.9 Hz, 1H), 7.49-7.45 (m, 2H), 7.44-7.40 (m, 1H), 7.38-7.34 (d, J=7.9 Hz, 1H), 7.20-7.15 (s, 1H), 7.06-7.01 (dd, J=8.9, 2.3 Hz, 1H), 7.01-6.96 (d, J=7.6 Hz, 1H), 6.81-6.77 (d, J=2.3 Hz, 1H), 5.38-5.33 (s, 2H), 5.16-5.09 (s, 2H), 4.07-4.03 (s, 3H), 3.23-3.16 (m, 1H), 3.06-3.00 (m, 1H), 2.62-2.53 (dt, J=15.4, 5.3 Hz, 1H), 2.31-2.25 (s, 3H), 1.91-1.70 (m, 3H), 1.70-1.57 (m, 2H), 1.43-1.33 (m, 2H).

Example 196

2-Ethyl-2-({1-[3-(2-methoxypyrimidin-5-yl)benzyl]-6-[(5-methylpyridin-2-yl)methoxy]-1H-benzimidazol-2-yl}methyl)butanoic acid

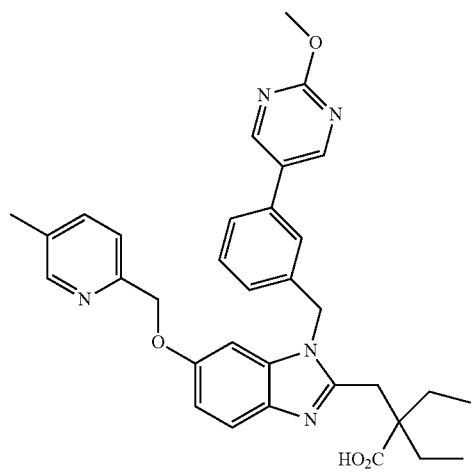 [SMILES: CCC(CC)(Cc1nc2ccc(OCc3ccc(C)cn3)cc2n1Cc1cccc(-c2cnc(OC)nc2)c1)C(=O)O]

The title compound prepared using similar methods to those in Example 144 using (2-methoxypyrimidin-5-yl)boronic acid and 2-({1-(3-Bromobenzyl)-6-[(5-methylpyridin-2-yl)methoxy]-1H-benzimidazol-2-yl}methyl)-2-ethylbutanoic acid. MS (ESI): mass calcd. for $C_{33}H_{35}N_5O_4$, 565.27; m/z found, 566.3 [M+H]$^+$. $^1$H NMR (500 MHz, CDCl$_3$) δ 8.62-8.58 (s, 2H), 8.37-8.33 (s, 1H), 7.66-7.61 (d, J=8.8 Hz, 1H), 7.52-7.36 (ddd, J=33.1, 18.2, 7.2 Hz, 4H), 7.18-7.14 (s, 1H), 7.07-6.97 (m, 2H), 6.89-6.84 (d, J=1.8 Hz, 1H), 5.38-5.34 (s, 2H), 5.18-5.14 (s, 2H), 4.07-4.03 (s, 3H), 3.02-2.98 (s, 2H), 2.32-2.28 (s, 3H), 1.73-1.56 (m, 4H), 0.84-0.77 (t, J=7.3 Hz, 6H).

Example 197

(1S*,2R*)-2-{1-(3-Bromobenzyl)-6-[(1-methyl-1H-pyrazol-3-yl)methoxy]-1H-benzimidazol-2-yl}cyclohexanecarboxylic acid

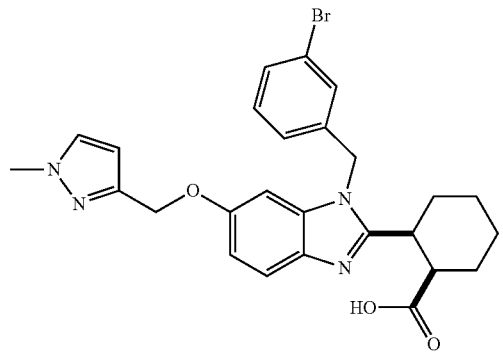

The title compound was prepared using analogous conditions described in Step A of Example 1 using Intermediate L and (3-bromophenyl)methanamine and as described in Step C of Example 80 using N-(3-bromobenzyl)-5-((1-methyl-1H-pyrazol-3-yl)methoxy)-2-nitroaniline. Method 1: racemic cis-2-{1-(3-bromobenzyl)-6-[(1-methyl-1H-pyrazol-3-yl)methoxy]-1H-benzimidazol-2-yl}cyclohexanecarboxylic acid was purified by chiral SFC on (CHIRALCEL AD-H 5 μm 250×20 mm) mobile phase (60% CO$_2$, 40% MeOH) to yield the title compound as the first eluting isomer. MS (ESI): mass calcd. for $C_{26}H_{27}BrN_4O_3$, 523.43; m/z found, 524.1 [M+H]$^+$. $^1$H NMR (500 MHz, CD$_3$OD) δ 7.54 (dd, J=8.2, 1.0, 1H), 7.49 (d, J=2.2, 1H), 7.44 (d, J=8.0, 1H), 7.33 (s, 1H), 7.22 (t, J=7.9, 1H), 7.05 (d, J=8.2, 1H), 6.94-6.89 (m, 2H), 6.24 (d, J=2.3, 1H), 5.54 (d, J=17.3, 1H), 5.46 (d, J=17.4, 1H), 5.05-4.96 (m, 2H), 3.82 (s, 3H), 3.55 (d, J=4.0, 1H), 2.86-2.78 (m, 1H), 2.40-2.31 (m, 1H), 2.06-1.95 (m, 1H), 1.93-1.68 (m, 4H), 1.56-1.35 (m, 2H).

Example 198

(1R*,2S*)-2-{1-(3-Bromobenzyl)-6-[(1-methyl-1H-pyrazol-3-yl)methoxy]-1H-benzimidazol-2-yl}cyclohexanecarboxylic acid

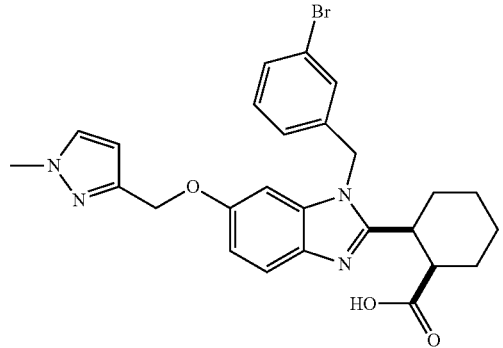

The title compound was prepared using analogous conditions described in (1S*,2R*)-2-{1-(3-bromobenzyl)-6-[(1-methyl-1H-pyrazol-3-yl)methoxy]-1H-benzimidazol-2-yl}cyclohexanecarboxylic acid. Method 1: racemic cis-2-{1-(3-Bromobenzyl)-6-[(1-methyl-1H-pyrazol-3-yl)methoxy]-1H-benzimidazol-2-yl}cyclohexanecarboxylic acid was purified by chiral SFC on (CHIRALCEL AD-H 5 µm 250×20 mm) mobile phase (60% CO$_2$, 40% MeOH) to yield the title compound as the second eluting isomer. MS (ESI): mass calcd. for C$_{26}$H$_{27}$BrN$_4$O$_3$, 523.43; m/z found, 524.1 [M+H]$^+$. $^1$H NMR (500 MHz, CD$_3$OD) 7.54 (d, J=9.2, 1H), 7.49 (d, J=2.2, 1H), 7.44 (d, J=7.9, 1H), 7.33 (s, 1H), 7.22 (t, J=7.9, 1H), 7.05 (d, J=7.8, 1H), 6.93-6.88 (m, 2H), 6.24 (d, J=2.2, 1H), 5.54 (d, J=17.3, 1H), 5.46 (d, J=17.3, 1H), 5.06-4.93 (m, 2H), 3.82 (s, 3H), 3.59-3.45 (m, 1H), 2.85-2.78 (m, 1H), 2.42-2.28 (m, 1H), 2.06-1.70 (m, 5H), 1.54-1.39 (m, 2H).

Example 199 racemic cis-2-{1-(3-Cyanobenzyl)-6-[(1-methyl-1H-pyrazol-3-yl)methoxy]-1H-benzimidazol-2-yl}cyclohexanecarboxylic acid

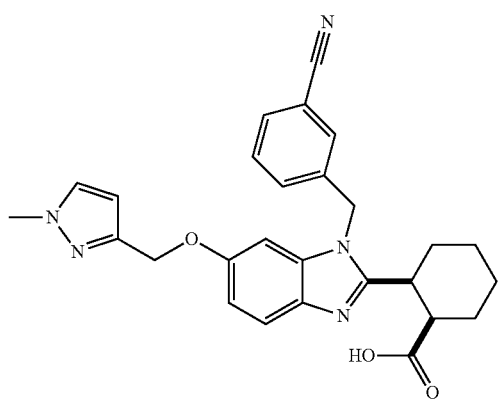

The title compound was prepared using analogous conditions described in Step A and B of Example 1 using Intermediate L and 3-(aminomethyl)benzonitrile and as described in Step C of Example 80 using 3-(((5-((1-methyl-1H-pyrazol-3-yl)methoxy)-2-nitrophenyl)amino)methyl)benzonitrile. MS (ESI): mass calcd. for C$_{27}$H$_{27}$N$_5$O$_3$, 469.55; m/z found, 470.1 [M+H]$^+$. $^1$H NMR (500 MHz, CD$_3$OD) δ 7.65 (d, J=7.7, 1H), 7.55 (d, J=8.8, 1H), 7.53-7.46 (m, 3H), 7.39 (d, J=7.9, 1H), 6.92 (dd, J=8.8, 2.4, 1H), 6.87 (d, J=2.3, 1H), 6.23 (d, J=2.3, 1H), 5.60 (d, J=17.5, 1H), 5.52 (d, J=17.5, 1H), 5.05-4.93 (m, 2H), 3.82 (s, 3H), 3.62-3.50 (m, 1H), 2.85-2.74 (m, 1H), 2.47-2.28 (m, 1H), 2.05-1.94 (m, 1H), 1.96-1.70 (m, 4H), 1.56-1.34 (m, 2H).

Example 200 racemic trans-2-{1-(3-Methylbenzyl)-6-[(5-methylpyridin-2-yl)methoxy]-1H-benzimidazol-2-yl}cyclohexanecarboxylic acid

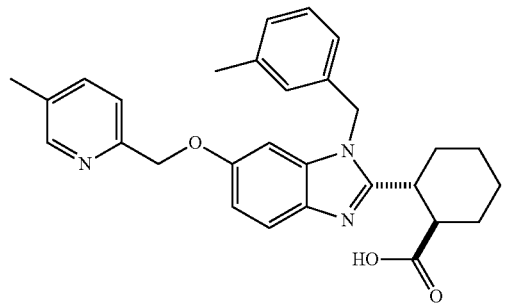

The title compound was prepared using analogous conditions described in Step A of Example 1 using m-tolylmethanamine and trans-hexahydroisobenzofuran-1,3-dione in Step C. MS (ESI): mass calcd. for C$_{29}$H$_{31}$N$_3$O$_3$, 469.24; m/z found, 470.3 [M+H]. $^1$H NMR (500 MHz, CD$_3$OD) δ 8.32 (s, 1H), 7.63 (d, J=8.3, 1H), 7.48 (d, J=9.4, 1H), 7.43 (d, J=8.0, 1H), 7.17 (t, J=7.6, 1H), 7.08 (d, J=7.7, 1H), 6.97 (d, J=13.8, 2H), 6.95-6.88 (m, 2H), 5.50-5.40 (m, 2H), 5.12 (s, 2H), 3.21-3.09 (m, 1H), 3.03-2.92 (m, 1H), 2.34 (s, 3H), 2.26 (s, 3H), 2.24-2.18 (m, 1H), 1.90-1.76 (m, 1H), 1.75-1.63 (m, 1H), 1.56-1.39 (m, 4H), 1.34-1.16 (m, 1H).

Example 201 racemic cis-2-{1-(3-Methylbenzyl)-6-[(5-methylpyridin-2-yl)methoxy]-1H-benzimidazol-2-yl}cyclohexanecarboxylic acid

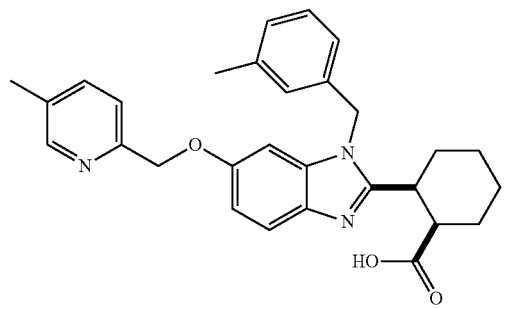

The title compound was prepared using analogous conditions described in Step A of Example 1 using m-tolylmethanamine. MS (ESI): mass calcd. for C$_{29}$H$_{31}$N$_3$O$_3$, 469.24; m/z found, 470.3 [M+H]$^+$. $^1$H NMR (500 MHz, CD$_3$OD) δ 8.29 (s, 1H), 7.61 (dd, J=8.0, 2.0, 1H), 7.55 (d, J=8.8, 1H), 7.40 (d, J=8.0, 1H), 7.15 (m, 1H), 7.07 (d, J=7.5, 1H), 6.95 (dd, J=8.8, 2.4, 1H), 6.92-6.89 (m, 1H), 6.88-6.83 (m, 2H), 5.46 (d, J=17.0, 1H), 5.39 (d, J=17.0, 1H), 5.12-5.02 (m, 2H), 3.58-3.49 (m, 1H), 2.88-2.74 (m, 1H), 2.39-2.31 (m, 1H), 2.33 (s, 3H), 2.24 (s, 3H), 2.04-1.95 (m, 1H), 1.94-1.66 (m, 4H), 1.55-1.33 (m, 2H).

Example 202 racemic cis-2,2-Dimethyl-3-{1-(3-methylbenzyl)-6-[(5-methylpyridin-2-yl)methoxy]-1H-benzimidazol-2-yl}cyclopropanecarboxylic acid

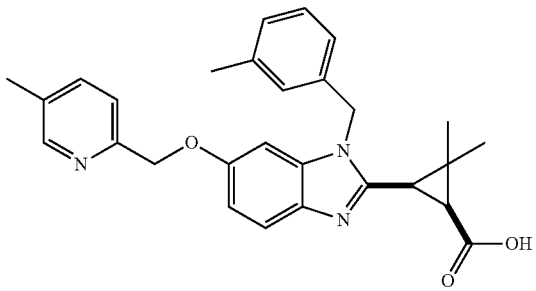

The title compound was prepared using analogous conditions described in Step A of Example 1 using m-tolylmethanamine and cis-6-dimethyl-3-oxabicyclo[3.1.0]hexane-2,4-dione in step C. MS (ESI): mass calcd. for $C_{28}H_{29}N_3O_3$, 455.22; m/z found, 456.1 [M+H]$^+$. $^1$H NMR (500 MHz, CD$_3$OD) δ 8.34 (s, 1H), 7.65 (dd, J=8.0, 1.6, 1H), 7.59 (d, J=8.9, 1H), 7.47 (d, J=8.0, 1H), 7.21 (dd, J=12.7, 5.0, 2H), 7.16-7.06 (m, 2H), 6.93 (s, 1H), 6.88 (d, J=7.6, 1H), 5.58 (d, J=16.6, 1H), 5.44 (d, J=16.6, 1H), 5.17 (s, 2H), 2.39 (t, J=7.1, 1H), 2.35 (s, 3H), 2.27 (s, 3H), 2.22 (d, J=8.2, 1H), 1.13 (s, 3H), 0.98 (s, 3H).

Example 203 racemic cis-2-{1-[3-(4,4-Difluoropiperidin-1-yl)benzyl]-6-[(1-methyl-1H-pyrazol-3-yl)methoxy]-1H-benzimidazol-2-yl}cyclohexanecarboxylic acid

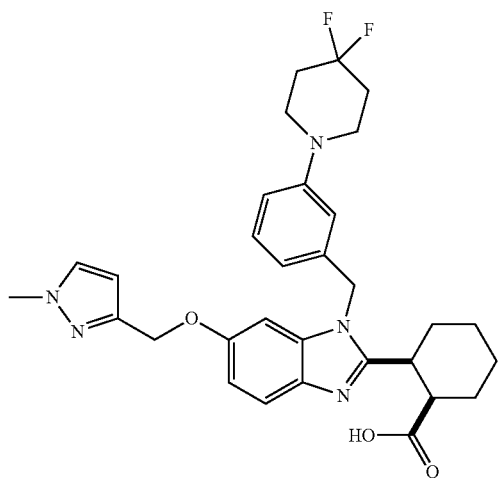

The title compound was prepared using analogous conditions to Example 152 using racemic cis-2-(1-(3-bromobenzyl)-6-((1-methyl-1H-pyrazol-3-yl)methoxy)-1H-benzo[d]imidazol-2-yl)cyclohexanecarboxylic acid and 4,4-difluoropiperidine. MS (ESI): mass calcd. for $C_{31}H_{35}F_2N_5O_3$, 563.65; m/z found, 564.2 [M+H]$^+$. $^1$H NMR (500 MHz, CD$_3$OD) δ 7.53 (d, J=9.3, 1H), 7.49 (d, J=2.1, 1H), 7.20 (t, J=7.9, 1H), 6.97-6.89 (m, 3H), 6.76 (s, 1H), 6.61 (d, J=7.6, 1H), 6.23 (d, J=2.2, 1H), 5.51 (d, J=17.0, 1H), 5.39 (d, J=16.8, 1H), 5.04-4.93 (m, 2H), 3.82 (s, 3H), 3.62-3.52 (m, 1H), 3.29-3.21 (m, 4H), 2.91-2.81 (m, 1H), 2.40-2.28 (m, 1H), 2.11-1.65 (m, 9H), 1.56-1.41 (m, 2H).

Example 204 racemic cis-2-{6-[(1-Methyl-1H-pyrazol-3-yl)methoxy]-1-(3-piperidin-1-ylbenzyl)-1H-benzimidazol-2-yl}cyclohexanecarboxylic acid

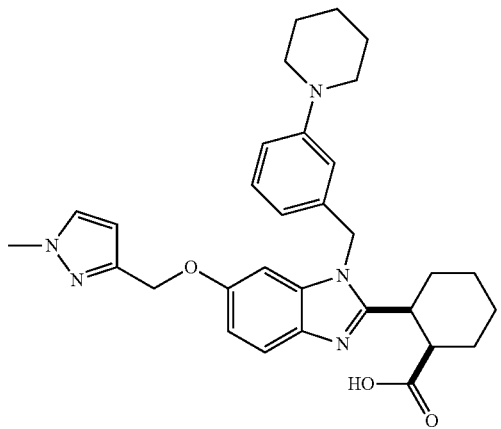

The title compound was prepared using analogous conditions to Example 152 using racemic cis-2-(1-(3-bromobenzyl)-6-((1-methyl-1H-pyrazol-3-yl)methoxy)-1H-benzo[d]imidazol-2-yl)cyclohexanecarboxylic acid and piperidine. MS (ESI): mass calcd. for $C_{31}H_{37}N_5O_3$, 527.67; m/z found, 528.3 [M+H]$^+$. $^1$H NMR (500 MHz, CD$_3$OD) δ 7.53 (d, J=8.9, 1H), 7.49 (d, J=2.2, 1H), 7.17 (m, 1H), 6.96 (d, J=2.2, 1H), 6.94-6.86 (m, 2H), 6.73 (s, 1H), 6.56 (d, J=7.4, 1H), 6.25 (d, J=2.3, 1H), 5.49 (d, J=16.7, 1H), 5.40 (d, J=17.1, 1H), 4.98 (s, 2H), 3.82 (s, 3H), 3.57-3.49 (m, 1H), 3.09-3.00 (m, 4H), 2.89-2.82 (m, 1H), 2.38-2.26 (m, 1H), 2.01 (s, 1H), 1.93-1.67 (m, 4H), 1.68-1.39 (m, 8H).

Example 205 racemic cis-2-{1-[3-(3,3-Difluoroazetidin-1-yl)benzyl]-6-[(1-methyl-1H-pyrazol-3-yl)methoxy]-1H-benzimidazol-2-yl}cyclohexanecarboxylic acid as the trifluoroacetic acid salt

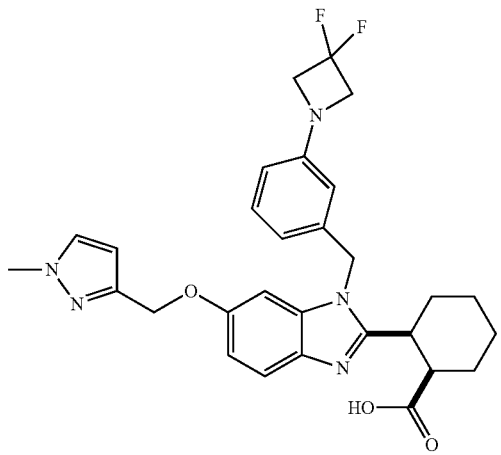

The title compound was prepared using analogous conditions to Example 152 using racemic cis-2-(1-(3-bromobenzyl)-6-((1-methyl-1H-pyrazol-3-yl)methoxy)-1H-benzo[d]imidazol-2-yl)cyclohexanecarboxylic acid and 3,3-difluoroazetidine. MS (ESI): mass calcd. for $C_{29}H_{31}F_2N_5O_3$, 535.24; m/z found, 536.1 [M+H]$^+$. $^1$H NMR (500 MHz, CD$_3$OD) δ 7.67 (d, J=9.0, 1H), 7.49 (d, J=2.2, 1H), 7.28-7.21 (m, 2H), 7.18 (t, J=4.7, 1H), 6.64-6.49 (m, 2H), 6.28-6.19 (m, 2H), 5.77 (d, J=17.1, 1H), 5.66 (d, J=17.1, 1H), 5.09-4.99 (m, 2H), 4.19-4.00 (m, 4H), 3.80 (s, 3H), 3.65 (dt, J=12.2, 3.6, 1H), 2.91 (d, J=3.7, 1H), 2.39-2.25 (m, 1H), 2.23-2.14 (m, 1H), 2.12-2.03 (m, 1H), 2.03-1.92 (m, 1H), 1.84-1.66 (m, 2H), 1.61-1.46 (m, 2H).

Example 206 racemic trans-2-{1-(2-Methylbenzyl)-6-[(5-methyl-pyridin-2-yl)methoxy]-1H-benzimidazol-2-yl}cyclohexanecarboxylic acid

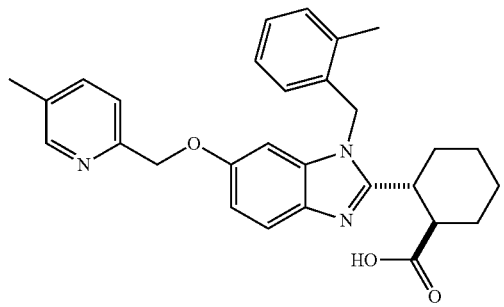

The title compound was prepared using analogous conditions described in Step A of Example 1 using o-tolylmethanamine and trans-hexahydroisobenzofuran-1,3-dione in step C. MS (ESI): mass calcd. for $C_{29}H_{31}N_3O_3$, 469.23; m/z found, 470.3 [M+H]$^+$. $^1$H NMR (500 MHz, CD$_3$OD) δ 8.29 (s, 1H), 7.62 (dd, J=8.0, 1.6, 1H), 7.50 (d, J=8.8, 1H), 7.42 (d, J=8.0, 1H), 7.23 (d, J=7.5, 1H), 7.17 (m, 1H), 7.00 (t, J=7.4, 1H), 6.96 (dd, J=8.8, 2.4, 1H), 6.86 (d, J=2.3, 1H), 6.50 (d, J=7.7, 1H), 5.59 (d, J=17.2, 1H), 5.40 (d, J=17.2, 1H), 5.12-5.05 (m, 2H), 3.09-2.89 (m, 2H), 2.41 (s, 3H), 2.33 (s, 3H), 2.17 (s, 1H), 1.82 (d, J=7.2, 1H), 1.73-1.60 (m, 1H), 1.56-1.39 (m, 4H), 1.22-1.07 (m, 1H).

Example 207 racemic cis-2-{1-(2-Methylbenzyl)-6-[(5-methyl-pyridin-2-yl)methoxy]-1H-benzimidazol-2-yl}cyclohexanecarboxylic acid

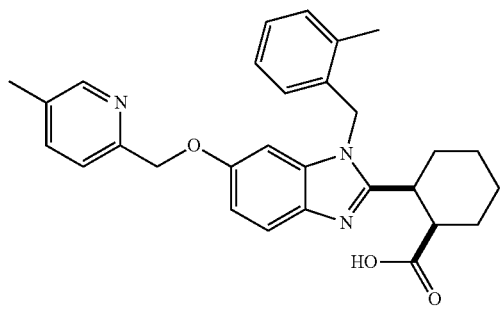

The title compound was prepared using analogous conditions described in Step A of Example 1 using o-tolylmethanamine. MS (ESI): mass calcd. for $C_{29}H_{31}N_3O_3$, 469.24; m/z found, 470.3 [M+H]$^+$. $^1$H NMR (500 MHz, CD$_3$OD) δ 8.26 (s, 1H), 7.59 (dd, J=8.1, 1.7, 1H), 7.57 (d, J=8.9, 1H), 7.38 (d, J=8.0, 1H), 7.22 (d, J=7.5, 1H), 7.15 (m, 1H), 6.96 (m, 1H), 6.94 (d, J=2.3, 1H), 6.75 (d, J=2.3, 1H), 6.40 (d, J=7.7, 1H), 5.47 (d, J=17.5, 1H), 5.40 (d, J=17.5, 1H), 5.06 (s, 2H), 3.50-3.41 (m, 1H), 2.84-2.71 (m, 1H), 2.40 (s, 3H), 2.38-2.33 (m, 1H), 2.31 (s, 3H), 2.03-1.94 (m, 1H), 1.91-1.65 (m, 4H), 1.51-1.31 (m, 2H).

Example 208 racemic cis-2-{1-[5-(4,4-Difluoropiperidin-1-yl)-2-fluorobenzyl]-6-[(5-methylpyridin-2-yl)methoxy]-1H-benzimidazol-2-yl}cyclohexanecarboxylic acid

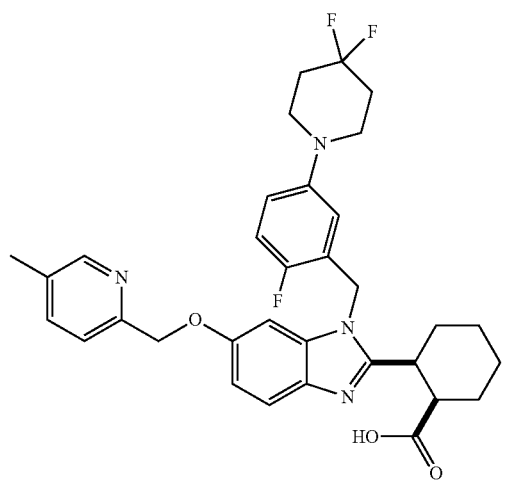

The title compound was prepared using analogous conditions to Example 152 using racemic cis-2-(1-(5-bromo-2-fluorobenzyl)-6-((5-methylpyridin-2-yl)methoxy)-1H-benzo[d]imidazol-2-yl)cyclohexanecarboxylic acid and 4,4-difluoropiperidine. MS (ESI): mass calcd. for $C_{33}H_{35}F_3N_4O_3$, 592.67; m/z found, 593.3 [M+H]$^+$. $^1$H NMR (500 MHz, CD$_3$OD) 8.53 (s, 1H), 8.08 (d, J=8.1, 1H), 7.75 (d, J=9.0, 1H), 7.73 (d, J=8.2, 1H), 7.38 (dd, J=9.0, 2.3, 1H), 7.24 (d, J=2.2, 1H), 7.12 (m, 1H), 7.07-7.01 (m, 1H), 6.59-6.51 (m, 1H), 5.79 (s, 2H), 5.40-5.26 (m, 2H), 3.79-3.66 (m, 1H), 3.17-3.08 (m, 4H), 2.96-2.88 (m, 1H), 2.48 (s, 3H), 2.38-2.18 (m, 2H), 2.11-1.91 (m, 6H), 1.85-1.51 (m, 4H).

Example 209 racemic cis-2-{1-(2-Fluoro-5-piperidin-1-ylbenzyl)-6-[(5-methylpyridin-2-yl)methoxy]-1H-benzimidazol-2-yl}cyclohexanecarboxylic acid

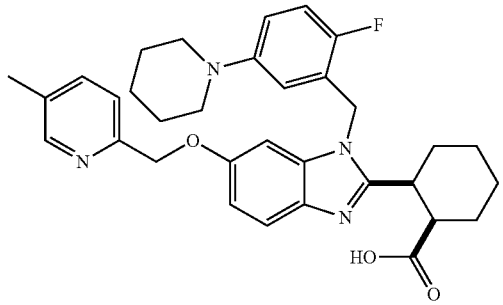

The title compound was prepared using analogous conditions to Example 152 using racemic cis-2-(1-(5-bromo-2-fluorobenzyl)-6-((5-methylpyridin-2-yl)methoxy)-1H-benzo[d]imidazol-2-yl)cyclohexanecarboxylic acid and piperidine. MS (ESI): mass calcd. for $C_{33}H_{37}FN_4O_3$, 556.69; m/z found, 557.3 [M+H]$^+$. $^1$H NMR (400 MHz, CD$_3$OD) δ 8.32-8.28 (m, 1H), 7.62 (dd, J=8.0, 1.6, 1H), 7.55 (d, J=8.8, 1H), 7.42 (d, J=8.0, 1H), 7.07-6.99 (m, 1H), 6.96 (dd, J=8.8, 2.4, 1H), 6.93-6.87 (m, 2H), 6.38 (dd, J=6.4, 3.0, 1H), 5.47 (s, 2H), 5.09 (s, 2H), 3.62-3.52 (m, 1H), 2.85-2.80 (m, 4H), 2.34 (s, 3H), 2.34-2.25 (m, 1H), 2.05 (d, J=8.6, 1H), 1.95-1.68 (m, 4H), 1.62-1.36 (m, 9H).

Example 210 racemic cis-2,2-Dimethyl-3-{1-(2-methylbenzyl)-6-[(5-methylpyridin-2-yl)methoxy]-1H-benzimidazol-2-yl}cyclopropanecarboxylic acid

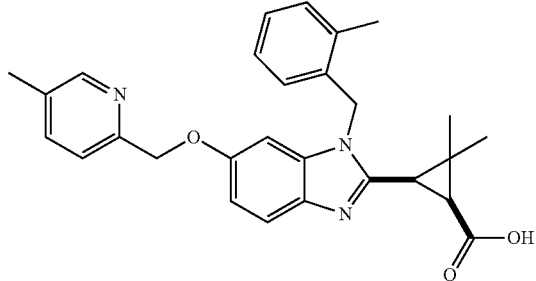

The title compound was prepared using analogous conditions described in Step A of Example 1 using o-tolylmethanamine and cis-6-dimethyl-3-oxabicyclo[3.1.0]hexane-2,4-dione in step C. MS (ESI): mass calcd. for $C_{28}H_{29}N_3O_3$, 455.22; m/z found, 456.1 [M+H]$^+$. $^1$H NMR (400 MHz, CD$_3$OD) δ 8.31 (s, 1H), 7.64 (dd, J=8.0, 1.6, 1H), 7.63 (s, 1H), 7.45 (d, J=8.0, 1H), 7.27 (d, J=7.4, 1H), 7.21 (m, 1H), 7.14-7.01 (m, 3H), 6.46 (d, J=7.7, 1H), 5.55 (s, 2H), 5.13 (s, 2H), 2.39 (s, 3H), 2.34 (s, 3H), 2.27 (d, J=8.2, 1H), 2.18 (d, J=8.2, 1H), 1.07 (s, 3H), 1.06 (s, 3H).

Example 211

2-({1-[3-(3,3-Difluoropyrrolidin-1-yl)benzyl]-6-[(1-methyl-1H-pyrazol-3-yl)methoxy]-1H-benzimidazol-2-yl}methyl)-2-ethylbutanoic acid

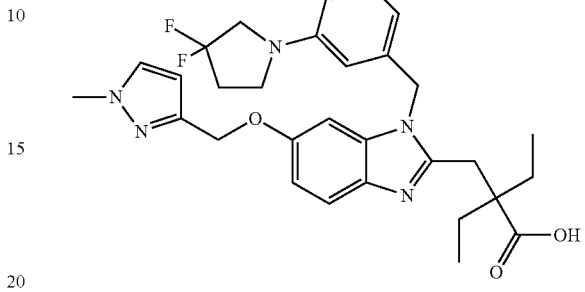

The title compound was prepared using analogous conditions to Example 152 using 2-((1-(3-bromobenzyl)-6-((1-methyl-1H-pyrazol-3-yl)methoxy)-1H-benzo[d]imidazol-2-yl)methyl)-2-ethylbutanoic acid and 3,3-difluoropyrrolidine. MS (ESI): mass calcd. for $C_{30}H_{35}F_2N_5O_3$, 551.27; m/z found, 552.0 [M+H]$^+$. $^1$H NMR (400 MHz, CD$_3$OD) δ 7.52 (d, J=8.8, 1H), 7.48 (d, J=2.2, 1H), 7.14 (m, 1H), 7.01 (d, J=2.3, 1H), 6.91 (dd, J=8.8, 2.4, 1H), 6.51 (dd, J=8.2, 2.0, 1H), 6.36 (d, J=7.8, 1H), 6.29-6.27 (m, 1H), 6.26 (d, J=2.3, 1H), 5.44 (s, 2H), 5.01 (s, 2H), 3.81 (s, 3H), 3.54 (t, J=13.3, 2H), 3.37 (t, J=7.2, 2H), 3.07 (s, 2H), 2.52-2.36 (m, 2H), 1.84-1.68 (m, 4H), 0.84 (t, J=7.5, 6H).

Example 212

2-Ethyl-2-({6-[(1-methyl-1H-pyrazol-3-yl)methoxy]-1-(3-piperidin-1-ylbenzyl)-1H-benzimidazol-2-yl}methyl)butanoic acid

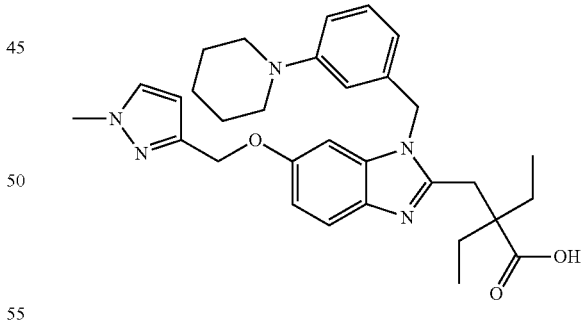

The title compound was prepared using analogous conditions to Example 152 using 2-((1-(3-bromobenzyl)-6-((1-methyl-1H-pyrazol-3-yl)methoxy)-1H-benzo[d]imidazol-2-yl)methyl)-2-ethylbutanoic acid and piperidine. MS (ESI): mass calcd. for $C_{31}H_{39}N_5O_3$, 529.31; m/z found, 530.3 [M+H]$^+$. $^1$H NMR (400 MHz, CD$_3$OD) δ 7.55-7.48 (m, 2H), 7.17-7.12 (m, 1H), 7.02 (d, J=2.3, 1H), 6.91 (dd, J=8.6, 2.1, 1H), 6.87 (dd, J=8.2, 2.1, 1H), 6.64 (s, 1H), 6.46 (d, J=7.3, 1H), 6.27 (d, J=2.3, 1H), 5.44 (s, 2H), 5.00 (s, 2H), 3.82 (s, 3H), 3.08-3.00 (m, 6H), 1.86-1.70 (m, 4H), 1.68-1.50 (m, 6H), 0.83 (t, J=7.5, 6H).

Example 213

2-Ethyl-2-({1-[3-(2-methoxypyrimidin-5-yl)benzyl]-6-[(1-methyl-1H-pyrazol-3-yl)methoxy]-1H-benzimidazol-2-yl}methyl)butanoic acid

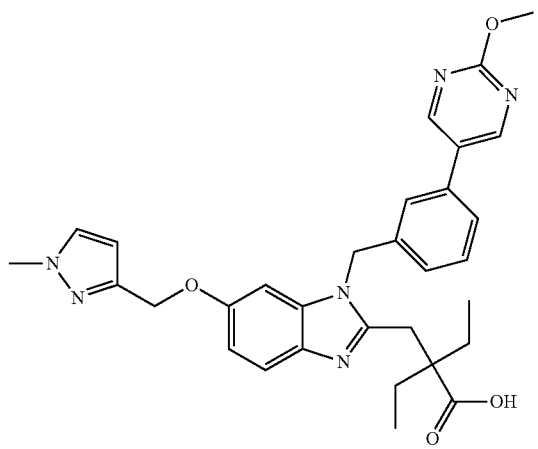

The title compound was prepared using analogous conditions to Example 144 using 2-((1-(3-bromobenzyl)-6-((1-methyl-1H-pyrazol-3-yl)methoxy)-1H-benzo[d]imidazol-2-yl)methyl)-2-ethylbutanoic acid. MS (ESI): mass calcd. for $C_{31}H_{34}N_6O_4$, 554.26; m/z found, 555.2 [M+H]$^+$. $^1$H NMR (500 MHz, CD$_3$OD) δ 8.77 (s, 2H), 7.72 (d, J=9.0, 1H), 7.67 (d, J=7.8, 1H), 7.59-7.50 (m, 2H), 7.48 (d, J=2.2, 1H), 7.31 (d, J=2.1, 1H), 7.29-7.22 (m, 2H), 6.24 (d, J=2.2, 1H), 5.86 (s, 2H), 5.05 (s, 2H), 4.04 (s, 3H), 3.81 (s, 3H), 3.46 (s, 2H), 1.88-1.70 (m, 4H), 0.89 (t, J=7.4, 6H).

Example 214

2-Ethyl-2-({1-[2-fluoro-4-(2-methoxypyrimidin-5-yl)benzyl]-6-[(1-methyl-1H-pyrazol-3-yl)methoxy]-1H-benzimidazol-2-yl}methyl)butanoic acid

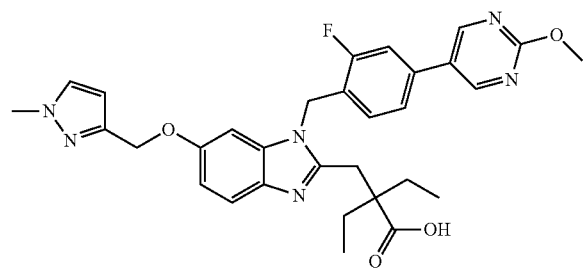

The title compound was prepared using analogous conditions to Example 144 using 2-((1-(4-bromo-2-fluorobenzyl)-6-((1-methyl-1H-pyrazol-3-yl)methoxy)-1H-benzo[d]imidazol-2-yl)methyl)-2-ethylbutanoic acid. MS (ESI): mass calcd. for $C_{31}H_{33}FN_6O_4$, 572.25; m/z found, 573.3 [M+H]$^+$. $^1$H NMR (500 MHz, CD$_3$OD) δ 8.82 (s, 2H), 7.57-7.48 (m, 3H), 7.37 (d, J=8.0, 1H), 7.02 (s, 1H), 6.96-6.84 (m, 2H), 6.29 (d, J=2.0, 1H), 5.60 (s, 2H), 5.00 (s, 2H), 4.04 (s, 3H), 3.83 (s, 3H), 3.12 (s, 2H), 1.84 (q, J=7.4, 4H), 0.88 (t, J=7.4, 6H).

Example 215

2-({1-(3-Bromobenzyl)-6-[(1-methyl-1H-pyrazol-3-yl)methoxy]-1H-benzimidazol-2-yl}methyl)-2-ethylbutanoic acid

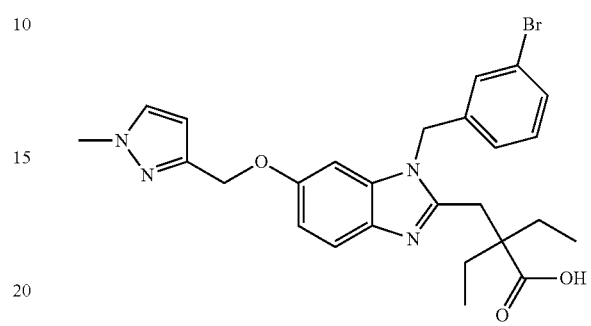

The title compound was prepared using analogous conditions described in Step A and B of Example 1 using Intermediate L and (3-bromophenyl)methanamine and as described in Step C using 3,3-diethyldihydrofuran-2,5-dione. MS (ESI): mass calcd. for $C_{26}H_{29}BrN_4O_3$, 524.14; m/z found, [M+H]$^+$. $^1$H NMR (600 MHz, CD$_3$OD) δ 7.53 (d, J=8.8, 1H), 7.50 (d, J=2.2, 1H), 7.45-7.41 (m, 1H), 7.22 (m, 1H), 7.19 (s, 1H), 7.00-6.96 (m, 2H), 6.93 (dd, J=8.8, 2.4, 1H), 6.27 (d, J=2.3, 1H), 5.50 (s, 2H), 5.01 (s, 2H), 3.84-3.80 (m, 3H), 3.04 (s, 2H), 1.85-1.77 (m, 4H), 0.84 (t, J=7.5, 6H).

Example 216

2-({1-[4-(3,3-Difluoropyrrolidin-1-yl)benzyl]-6-[(1-methyl-1H-pyrazol-3-yl)methoxy]-1H-benzimidazol-2-yl}methyl)-2-ethylbutanoic acid

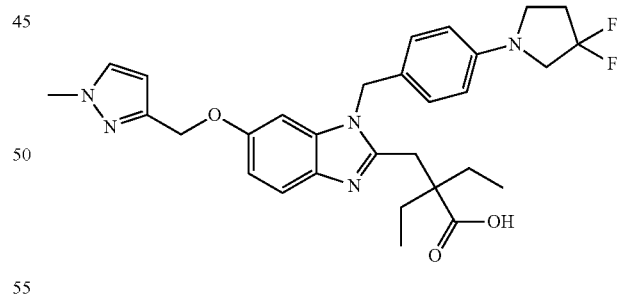

The title compound was prepared using analogous conditions to Example 152 using 2-((1-(4-bromobenzyl)-6-((1-methyl-1H-pyrazol-3-yl)methoxy)-1H-benzo[d]imidazol-2-yl)methyl)-2-ethylbutanoic acid and 3,3-difluoropyrrolidine. MS (ESI): mass calcd. for $C_{30}H_{35}F_2N_5O_3$, 551.27; m/z found, 552.2 [M+H]$^+$. $^1$H NMR (500 MHz, CD$_3$OD) δ 7.68 (d, J=9.1, 1H), 7.54 (d, J=2.2, 1H), 7.34 (d, J=2.2, 1H), 7.24 (dd, J=9.0, 2.3, 1H), 7.14 (d, J=8.6, 2H), 6.61 (d, J=8.7, 2H), 6.30 (d, J=2.2, 1H), 5.64 (s, 2H), 5.07 (s, 2H), 3.85 (s, 3H), 3.64 (t, J=13.2, 2H), 3.50 (t, J=7.2, 2H), 3.41 (s, 2H), 2.58-2.43 (m, 2H), 1.87-1.67 (m, 4H), 0.87 (t, J=7.5, 6H).

Example 217 racemic trans-2-{1-(3-Bromobenzyl)-6-[(5-methyl-pyridin-2-yl)methoxy]-1H-benzimidazol-2-yl}cyclohexanecarboxylic acid

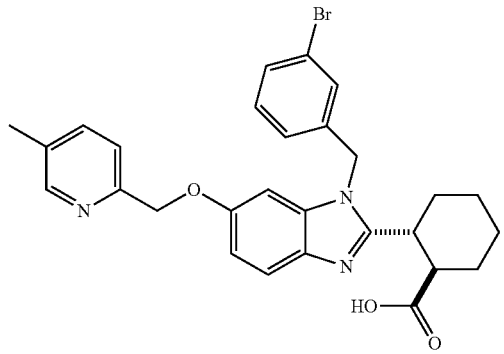

The title compound was prepared using similar methods to those in Example 1 substituting 3-bromobenzyl amine in Step A and trans-hexahydroisobenzofuran-1,3-dione in Step C. MS (ESI): mass calcd. for $C_{28}H_{28}BrN_3O_3$, 533.13; m/z found, 534.1 [M+H]$^+$. $^1$H NMR (500 MHz, CD$_3$OD) 8.33-8.29 (m, 1H), 7.62 (dd, J=8.0, 1.6 Hz, 1H), 7.49 (d, J=8.8 Hz, 1H), 7.44-7.39 (m, 2H), 7.35-7.32 (m, 1H), 7.20 (m, 1H), 7.10-7.06 (m, 1H), 6.96 (dd, 1H), 6.91 (d, J=2.3 Hz, 1H), 5.52 (d, J=17.0 Hz, 1H), 5.48-5.42 (m, 1H), 5.12 (s, 2H), 3.17-3.08 (m, 1H), 3.05-2.95 (m, 1H), 2.34 (s, 3H), 2.25-2.19 (m, 1H), 1.89-1.82 (m, 1H), 1.77-1.68 (m, 1H), 1.60-1.40 (m, 4H), 1.36-1.26 (m, 1H).

Example 218 racemic trans-2-{1-(5-Bromo-2-fluorobenzyl)-6-[(5-methylpyridin-2-yl)methoxy]-1H-benzimidazol-2-yl}cyclohexanecarboxylic acid

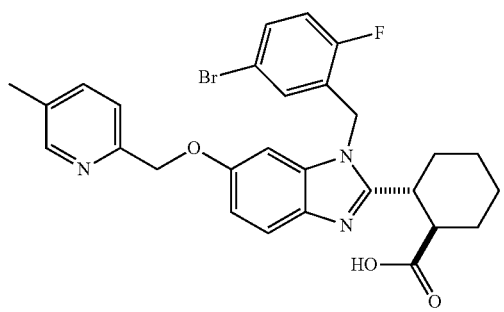

The title compound was prepared using similar methods to those in Example 1 substituting 2-fluoro-5-bromobenzyl amine in Step A and trans-hexahydroisobenzofuran-1,3-dione in Step C. MS (ESI): mass calcd. for $C_{28}H_{27}BrFN_3O_3$, 551.12; m/z found, 552.2 [M+H]. $^1$H NMR (500 MHz, CD$_3$OD) δ 8.34-8.29 (m, 1H), 7.64 (dd, J=8.0, 1.5 Hz, 1H), 7.53-7.49 (m, 1H), 7.49-7.45 (m, 1H), 7.43 (d, J=8.0 Hz, 1H), 7.12 (dd, J=9.8, 8.8 Hz, 1H), 7.06 (dd, J=6.6, 2.4 Hz, 1H), 7.00-6.96 (m, 2H), 5.63 (d, J=17.1 Hz, 1H), 5.47 (d, J=17.1 Hz, 1H), 5.14 (s, 2H), 3.18-3.10 (m, 1H), 3.03-2.94 (m, 1H), 2.34 (s, 3H), 2.25-2.20 (m, 1H), 1.90-1.83 (m, 1H), 1.79-1.71 (m, 1H), 1.60-1.43 (m, 4H), 1.36-1.26 (m, 1H).

Example 219 racemic cis-2-{1-[3-(3,3-Difluoroazetidin-1-yl)benzyl]-6-[(5-methylpyridin-2-yl)methoxy]-1H-benzimidazol-2-yl}cyclohexanecarboxylic acid

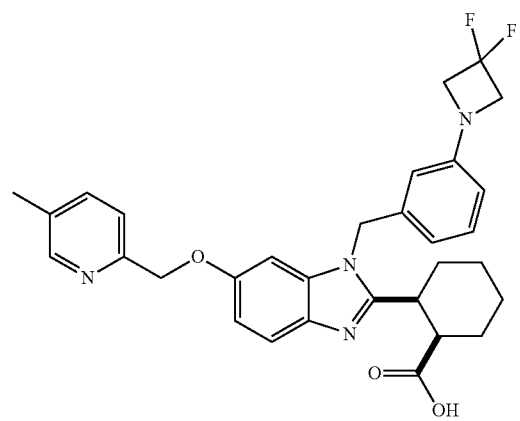

The title compound was prepared in a manner analogous to that in Example 152 substituting racemic cis-2-{1-(3-bromobenzyl)-6-[(5-methylpyridin-2-yl)methoxy]-1H-benzimidazol-2-yl}cyclohexanecarboxylic acid and 3,3-difluoroazetidine hydrochloride. MS (ESI): mass calcd. for $C_{31}H_{32}F_2N_4O_3$, 546.24; m/z found, 547.2 [M+H]$^+$. $^1$H NMR (500 MHz, CD$_3$OD) δ 8.33-8.25 (m, 1H), 7.64-7.59 (m, 1H), 7.54 (d, J=8.8 Hz, 1H), 7.39 (d, J=7.9 Hz, 1H), 7.16 (t, J=7.9 Hz, 1H), 6.96 (dd, J=8.8, 2.4 Hz, 1H), 6.83 (d, J=2.3 Hz, 1H), 6.55 (d, J=7.5 Hz, 1H), 6.47 (dd, J=8.1, 2.0 Hz, 1H), 6.34-6.29 (m, 1H), 5.48 (d, J=17.0 Hz, 1H), 5.35 (d, J=17.1 Hz, 1H), 5.14-5.03 (m, 2H), 4.16-4.02 (m, 4H), 3.60-3.50 (m, 1H), 2.87-2.81 (m, 1H), 2.39-2.29 (m, 4H), 2.12-2.03 (m, 1H), 1.93-1.84 (m, 1H), 1.84-1.71 (m, 3H), 1.55-1.40 (m, 2H).

Example 220 racemic cis-2-{1-[3-(3,3-Difluoropyrrolidin-1-yl)benzyl]-6-[(5-methylpyridin-2-yl)methoxy]-1H-benzimidazol-2-yl}cyclohexanecarboxylic acid

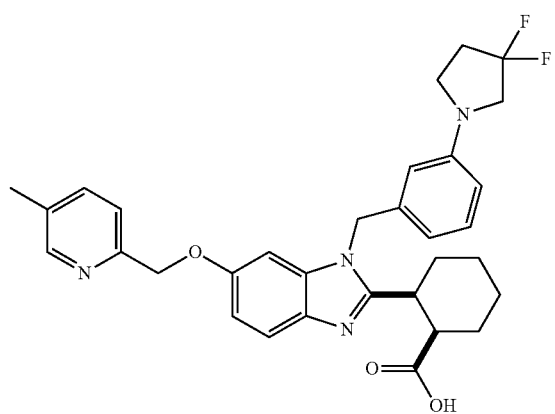

The title compound was prepared in a manner analogous to that in Example 152 substituting racemic cis-2-{1-(3-bromobenzyl)-6-[(5-methylpyridin-2-yl)methoxy]-1H-benzimidazol-2-yl}cyclohexanecarboxylic acid. MS (ESI): mass calcd. for $C_{32}H_{34}F_2N_4O_3$, 560.26; m/z found, 561.3 [M+H]$^+$. $^1$H NMR (500 MHz, CD$_3$OD) δ 8.31-8.26 (m, 1H), 7.62-7.58 (m, 1H), 7.54 (d, J=8.8 Hz, 1H), 7.39 (d, J=8.0 Hz, 1H), 7.13 (t, J=7.9 Hz, 1H), 6.95 (dd, J=8.8, 2.4 Hz, 1H), 6.86 (d, J=2.3 Hz, 1H), 6.51 (dd, J=8.1, 2.2 Hz, 1H), 6.44 (d, J=7.6 Hz, 1H), 6.35-6.31 (m, 1H), 5.47 (d, J=16.7 Hz, 1H), 5.36 (d, J=16.9 Hz, 1H), 5.11-5.03 (m, 2H), 3.61-3.46 (m, 3H), 3.42-3.33 (m, 2H), 2.88-2.82 (m, 1H), 2.49-2.39 (m, 2H), 2.37-2.28 (m, 4H), 2.11-2.03 (m, 1H), 1.94-1.84 (m, 1H), 1.84-1.73 (m, 3H), 1.54-1.38 (m, 2H).

Example 221 racemic cis-2-{1-[3-(4,4-Difluoropiperidin-1-yl)benzyl]-6-[(5-methylpyridin-2-yl)methoxy]-1H-benzimidazol-2-yl}cyclohexanecarboxylic acid

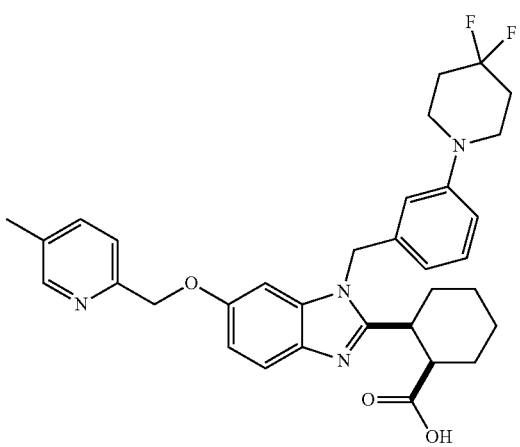

The title compound was prepared in a manner analogous to that in Example 152 substituting racemic cis-2-{1-(3-bromobenzyl)-6-[(5-methylpyridin-2-yl)methoxy]-1H-benzimidazol-2-yl}cyclohexanecarboxylic acid and 4,4-difluoropiperidine hydrochloride. MS (ESI): mass calcd. for $C_{33}H_{36}F_2N_4O_3$, 574.28; m/z found, 575.2 [M+H]$^+$. $^1$H NMR (500 MHz, CD$_3$OD) δ 8.29 (s, 1H), 7.63-7.59 (m, 1H), 7.54 (d, J=8.8 Hz, 1H), 7.39 (d, J=8.0 Hz, 1H), 7.16 (t, J=7.9 Hz, 1H), 6.95 (dd, J=8.8, 2.4 Hz, 1H), 6.90 (dd, J=8.2, 2.2 Hz, 1H), 6.84 (d, J=2.3 Hz, 1H), 6.74-6.72 (m, 1H), 6.57 (d, J=7.5 Hz, 1H), 5.48 (d, J=16.9 Hz, 1H), 5.35 (d, J=16.9 Hz, 1H), 5.10-5.02 (m, 2H), 3.60-3.50 (m, 1H), 3.27-3.20 (m, 4H), 2.90-2.76 (m, 1H), 2.37-2.28 (m, 4H), 2.08-2.01 (m, 1H), 2.01-1.91 (m, 4H), 1.91-1.83 (m, 1H), 1.83-1.71 (m, 3H), 1.53-1.37 (m, 2H).

Example 222 racemic cis-2-{1-[3-(3,3-Difluoropiperidin-1-yl)benzyl]-6-[(5-methylpyridin-2-yl)methoxy]-1H-benzimidazol-2-yl}cyclohexanecarboxylic acid

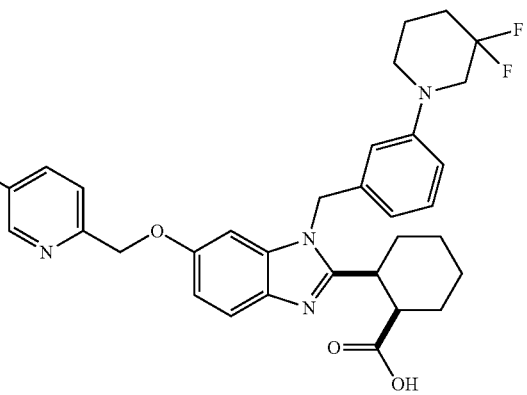

The title compound was prepared in a manner analogous to that in Example 152 substituting racemic-cis-2-{1-(3-bromobenzyl)-6-[(5-methylpyridin-2-yl)methoxy]-1H-benzimidazol-2-yl}cyclohexanecarboxylic acid and 3,3-difluoropiperidine hydrochloride. MS (ESI): mass calcd. for $C_{33}H_{36}F_2N_4O_3$, 574.28; m/z found, 575.2 [M+H]$^+$. $^1$H NMR (500 MHz, CD$_3$OD) δ 8.29 (s, 1H), 7.62-7.58 (m, 1H), 7.55 (d, J=8.8 Hz, 1H), 7.39 (d, J=8.0 Hz, 1H), 7.14 (m, 1H), 6.95 (dd, J=8.8, 2.3 Hz, 1H), 6.89-6.84 (m, 2H), 6.72-6.69 (m, 1H), 6.52 (d, J=7.5 Hz, 1H), 5.46 (d, J=17.2 Hz, 1H), 5.37 (d, J=17.0 Hz, 1H), 5.13-5.01 (m, 2H), 3.58-3.50 (m, 1H), 3.33-3.25 (m, 2H), 3.18-3.05 (m, 2H), 2.89-2.81 (m, 1H), 2.38-2.26 (m, 4H), 2.08-2.01 (m, 1H), 2.01-1.92 (m, 2H), 1.92-1.83 (m, 1H), 1.83-1.70 (m, 5H), 1.54-1.38 (m, 2H).

Example 223 racemic cis-2-{6-[(5-Methylpyridin-2-yl)methoxy]-1-(3-piperidin-1-ylbenzyl)-1H-benzimidazol-2-yl}cyclohexanecarboxylic acid

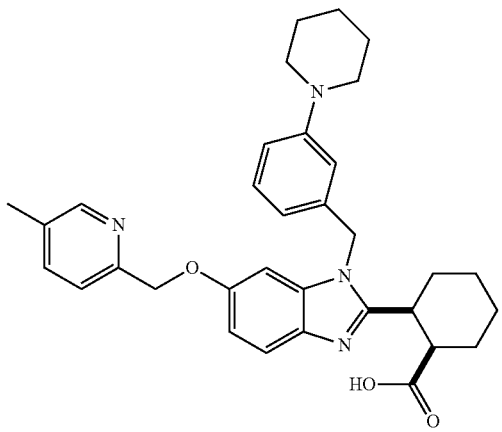

The title compound was prepared using similar methods to those in Example 1 substituting (3-(piperidin-1-yl)phenyl)methanamine in Step A. MS (ESI): mass calcd. for $C_{33}H_{38}N_4O_3$, 538.29; m/z found, 539.3 [M+H]$^+$. $^1$H NMR (500 MHz, CD$_3$OD) δ 8.32-8.27 (m, 1H), 7.63-7.59 (m, 1H), 7.54 (d, J=8.8 Hz, 1H), 7.40 (d, J=8.0 Hz, 1H), 7.16-7.09 (m, 1H), 6.96 (dd, J=8.8, 2.4 Hz, 1H), 6.89 (d, J=2.3 Hz, 1H), 6.87 (dd, J=8.2, 2.2 Hz, 1H), 6.71-6.65 (m, 1H), 6.52 (d, J=7.5 Hz, 1H), 5.46 (d, J=16.9 Hz, 1H), 5.37 (d, J=16.9 Hz, 1H), 5.08 (s, 2H), 3.55-3.49 (m, 1H), 3.07-3.00 (m, 4H), 2.88-2.80 (m, 1H), 2.33 (s, 3H), 2.32-2.26 (m, 1H), 2.12-2.01 (m, 1H), 1.91-1.82 (m, 1H), 1.82-1.69 (m, 3H), 1.67-1.59 (m, 4H), 1.57-1.45 (m, 3H), 1.45-1.35 (m, 1H).

Example 224 racemic trans-2-{6-[(5-Methylpyridin-2-yl)methoxy]-1-(3-piperidin-1-ylbenzyl)-1H-benzimidazol-2-yl}cyclohexanecarboxylic acid

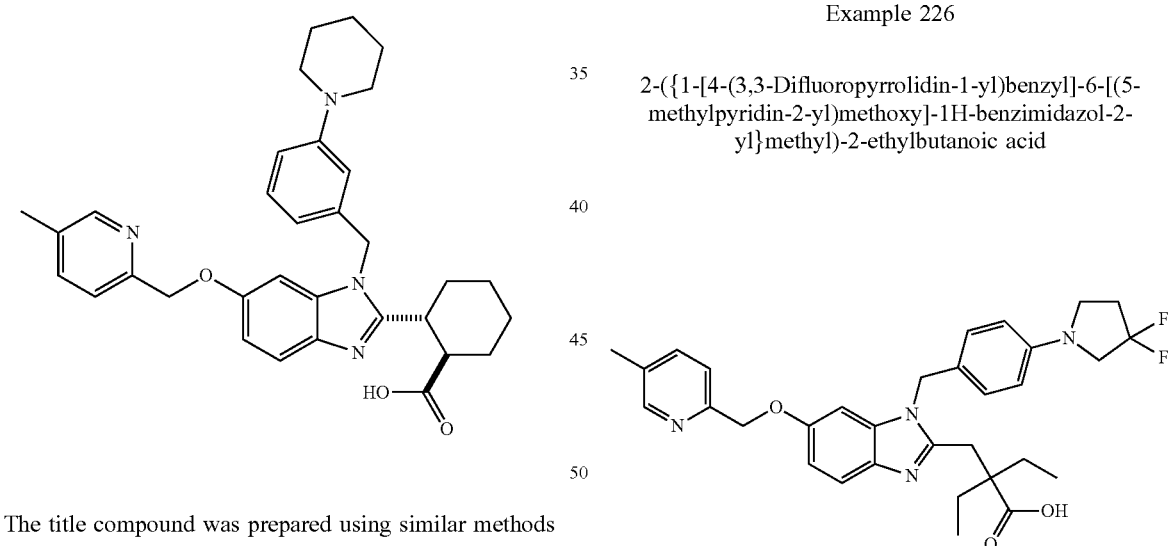

The title compound was prepared using similar methods to those in Example 1 substituting (3-(piperidin-1-yl)phenyl)methanamine in Step A and trans-hexahydroisobenzofuran-1,3-dione in Step C. MS (ESI): mass calcd. for $C_{33}H_{38}N_4O_3$, 538.29; m/z found, 539.2 [M+H]$^+$. $^1$H NMR (500 MHz, CD$_3$OD) δ 8.35-8.31 (m, 1H), 7.67-7.62 (m, 1H), 7.48 (d, J=8.8 Hz, 1H), 7.44 (d, J=8.0 Hz, 1H), 7.14 (m, 1H), 6.99 (d, J=2.3 Hz, 1H), 6.95 (dd, J=8.8, 2.4 Hz, 1H), 6.88 (dd, J=8.2, 2.1 Hz, 1H), 6.79-6.77 (m, 1H), 6.57 (d, J=7.5 Hz, 1H), 5.48-5.38 (m, 2H), 5.11 (s, 2H), 3.22-3.14 (m, 1H), 3.09-3.04 (m, 4H), 3.04-2.93 (m, 1H), 2.34 (s, 3H), 2.26-2.16 (m, 1H), 1.87-1.82 (m, 1H), 1.75-1.68 (m, 1H), 1.68-1.61 (m, 4H), 1.60-1.42 (m, 6H), 1.31-1.21 (m, 1H).

Example 225

3-{1-(5-Bromo-2-fluorobenzyl)-6-[(5-methylpyridin-2-yl)methoxy]-1H-benzimidazol-2-yl}-2,2-dimethylpropanoic acid

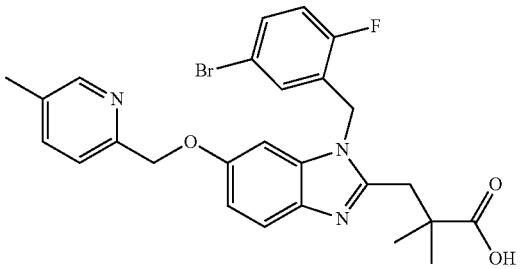 [SMILES: Cc1ccc(COc2ccc3nc(CC(C)(C)C(=O)O)n(Cc4cc(Br)ccc4F)c3c2)nc1]

The title compound was prepared using similar methods to those in Example 1 substituting 2-fluoro-5-bromobenzyl amine in Step A and 3,3-dimethyldihydrofuran-2,5-dione in Step C. MS (ESI): mass calcd. for $C_{26}H_{25}BrFN_3O_3$, 525.11; m/z found, 526.4 [M+H]$^+$. $^1$H NMR (500 MHz, CD$_3$OD) δ 8.30 (s, 1H), 7.65-7.59 (m, 1H), 7.47-7.35 (m, 2H), 7.14-7.05 (m, 1H), 7.04-6.94 (m, 1H), 6.94-6.83 (m, 1H), 6.80-6.59 (m, 1H), 5.54 (s, 2H), 5.11 (s, 2H), 3.09 (s, 2H), 2.34 (s, 3H), 1.23 (s, 6H).

Example 226

2-({1-[4-(3,3-Difluoropyrrolidin-1-yl)benzyl]-6-[(5-methylpyridin-2-yl)methoxy]-1H-benzimidazol-2-yl}methyl)-2-ethylbutanoic acid The title compound was prepared in a manner analogous to that in Example 152 substituting 2-({1-(4-bromobenzyl)-6-[(5-methylpyridin-2-yl)methoxy]-1H-benzimidazol-2-yl}methyl)-2-ethylbutanoic acid. MS (ESI): mass calcd. for $C_{32}H_{36}F_2N_4O_3$, 562.28; m/z found, 563.3 [M+H]$^+$. $^1$H NMR (500 MHz, CD$_3$OD) δ 8.33 (s, 1H), 7.65-7.62 (m, 1H), 7.52 (d, J=8.7 Hz, 1H), 7.44 (d, J=8.0 Hz, 1H), 6.99-6.90 (m, 4H), 6.51 (d, J=8.3 Hz, 2H), 5.34 (s, 2H), 5.11 (s, 2H), 3.59 (t, J=13.3 Hz, 2H), 3.44 (t, J=7.2 Hz, 2H), 3.09 (s, 2H), 2.51-2.40 (m, 2H), 2.34 (s, 3H), 1.85-1.72 (m, 4H), 0.84 (t, J=7.4 Hz, 6H).

Example 227 racemic cis-3-{1-(5-Bromo-2-fluorobenzyl)-6-[(5-methylpyridin-2-yl)methoxy]-1H-benzimidazol-2-yl}-2,2-dimethylcyclopropanecarboxylic acid

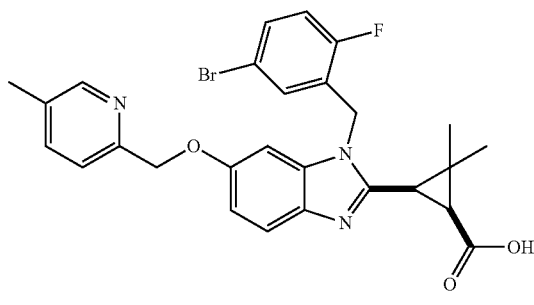

The title compound was prepared using similar methods to those in Example 1 substituting 2-fluoro-5-bromobenzyl amine in Step A and cis-6,6-dimethyl-3-oxabicyclo[3.1.0]hexane-2,4-dione in Step C. MS (ESI): mass calcd. for $C_{27}H_{25}BrFN_3O_3$, 537.11; m/z found, 538.4 [M+H]$^+$. $^1$H NMR (500 MHz, CDCl$_3$) δ 8.40-8.34 (m, 1H), 7.64-7.60 (m, 1H), 7.60-7.55 (m, 1H), 7.53 (d, J=8.8 Hz, 1H), 7.40 (d, J=7.9 Hz, 1H), 7.31-7.23 (m, 2H), 7.05 (dd, J=6.5, 2.4 Hz, 1H), 6.95 (dd, J=8.8, 2.4 Hz, 1H), 5.58 (d, J=17.1 Hz, 1H), 5.53 (d, J=17.0 Hz, 1H), 5.14 (s, 2H), 2.45 (d, J=8.5 Hz, 1H), 2.29 (s, 3H), 2.10 (d, J=8.5 Hz, 1H), 1.13 (s, 3H), 1.07 (s, 3H).

Example 228 racemic cis-2-{1-(3-Bromobenzyl)-6-[(5-methyl-pyridin-2-yl)methoxy]-1H-benzimidazol-2-yl}cyclohexanecarboxylic acid

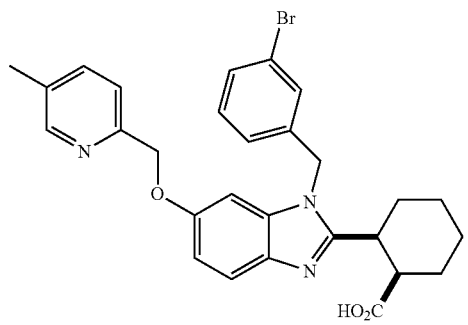

The title compound was prepared using similar methods to those in Example 1 substituting 3-bromobenzyl amine in Step A and N-(4-bromobenzyl)-5-((5-methylpyridin-2-yl)methoxy)benzene-1,2-diamine 4-methylbenzenesulfonate in Step C. MS (ESI): mass calcd. for $C_{28}H_{28}BrN_3O_3$, 533.13; m/z found, 534.2 [M+H]$^+$. $^1$H NMR (500 MHz, DMSO-d$_6$) δ 12.00 (s, 1H), 8.36-8.33 (m, 1H), 7.59-7.55 (m, 1H), 7.50-7.42 (m, 2H), 7.40-7.37 (m, 1H), 7.34 (d, J=8.0 Hz, 1H), 7.23 (m, 1H), 7.07-7.03 (m, 1H), 7.01 (d, J=2.2 Hz, 1H), 6.88-6.82 (m, 1H), 5.51 (d, J=17.2 Hz, 1H), 5.41 (d, J=17.1 Hz, 1H), 5.13-5.03 (m, 2H), 3.71-3.63 (m, 1H), 2.74-2.66 (m, 1H), 2.59-2.52 (m, 1H), 2.28 (s, 3H), 1.88-1.75 (m, 2H), 1.75-1.67 (m, 1H), 1.67-1.57 (m, 1H), 1.56-1.46 (m, 1H), 1.38-1.28 (m, 2H).

Example 229 racemic-cis-2-{1-(5-Bromo-2-fluorobenzyl)-6-[(5-methylpyridin-2-yl)methoxy]-1H-benzimidazol-2-yl}cyclohexanecarboxylic acid

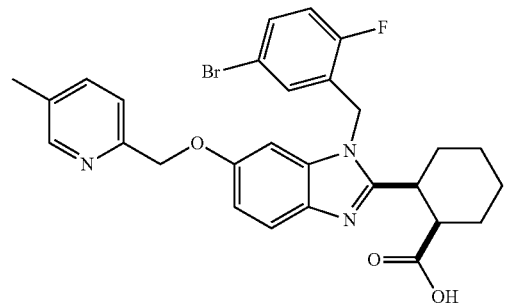

The title compound was prepared using similar methods to those in Example 1 substituting 2-fluoro-5-bromobenzyl amine in Step A and cis-hexahydroisobenzofuran-1,3-dione in Step C. MS (ESI): mass calcd. for $C_{28}H_{27}BrFN_3O_3$, 551.12; m/z found, 552.2 [M+H]$^+$. $^1$H NMR (500 MHz, DMSO-d$_6$) δ 12.06 (s, 1H), 8.36-8.33 (m, 1H), 7.60-7.56 (m, 1H), 7.56-7.51 (m, 1H), 7.49 (d, J=8.7 Hz, 1H), 7.35 (d, J=7.9 Hz, 1H), 7.30-7.24 (m, 1H), 7.03 (d, J=2.2 Hz, 1H), 6.96 (dd, J=6.5, 2.3 Hz, 1H), 6.87 (dd, J=8.7, 2.0 Hz, 1H), 5.49 (s, 2H), 5.10 (s, 2H), 3.67-3.60 (m, 1H), 2.73-2.66 (m, 1H), 2.28 (s, 3H), 1.90-1.43 (m, 6H), 1.39-1.26 (m, 2H).

Example 230

1-({1-(3-Bromobenzyl)-4-fluoro-6-[(5-methylpyridin-2-yl)methoxy]-1H-benzimidazol-2-yl}methyl)cyclopentanecarboxylic acid as the trifluoroacetic salt

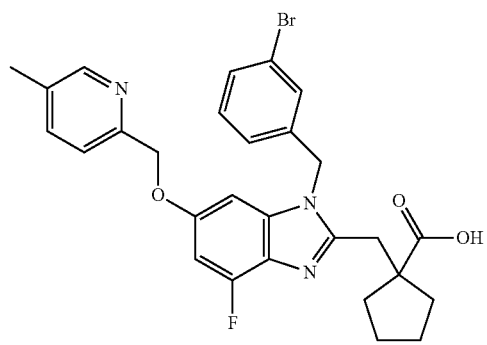 [SMILES: Cc1ccc(COc2cc(F)c3nc(CC4(C(=O)O)CCCC4)n(Cc4cccc(Br)c4)c3c2)nc1]

The title compound was prepared in a manner analogous to that in Example 1 using 2-((3,5-difluoro-4-nitrophenoxy)methyl)-5-methylpyridine in Step A, (3-bromophenyl)methanamine in Step B, and 2-oxaspiro[4.4]nonane-1,3-dione in Step C. MS (ESI): mass calcd. for $C_{28}H_{27}BrFN_3O_3$, 551.12; m/z found, 552.1 [M+H]. $^1$H NMR (600 MHz, CD$_3$OD) δ 8.56 (s, 1H), 8.19-8.14 (m, 1H), 7.78 (d, J=8.2 Hz, 1H), 7.47 (d, J=8.8 Hz, 1H), 7.27-7.21 (m, 2H), 7.02 (d, J=8.2 Hz, 1H), 6.94 (dd, J=11.7, 2.0 Hz, 1H), 6.87 (d, J=2.1 Hz, 1H), 5.58 (s, 2H), 5.35 (s, 2H), 3.28 (s, 2H), 2.51 (s, 3H), 2.27 (dd, J=12.2, 5.3 Hz, 2H), 1.84-1.66 (m, 6H).

Example 231

1-({1-(2-Bromobenzyl)-4-fluoro-6-[(5-methylpyridin-2-yl)methoxy]-1H-benzimidazol-2-yl}methyl)cyclopentanecarboxylic acid as the trifluoroacetic salt

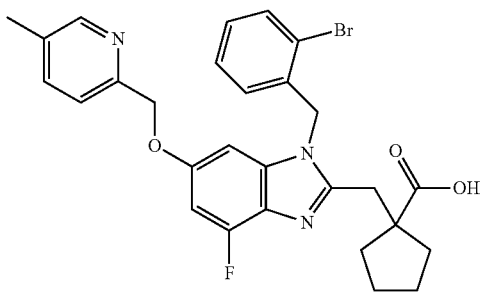 [SMILES: Cc1ccc(COc2cc(F)c3nc(CC4(C(=O)O)CCCC4)n(Cc4ccccc4Br)c3c2)nc1]

The title compound was prepared in a manner analogous to that in Example 1 using 2-((3,5-difluoro-4-nitrophenoxy)methyl)-5-methylpyridine in Step A, (2-bromophenyl)methanamine in Step B, and 2-oxaspiro[4.4]nonane-1,3-dione in Step C. MS (ESI): mass calcd. for $C_{28}H_{27}BrFN_3O_3$, 551.12; m/z found, 552.1 [M+H]. $^1$H NMR (600 MHz, CD$_3$OD) δ 8.45 (s, 1H), 7.94 (d, J=7.6 Hz, 1H), 7.73-7.66 (m, 1H), 7.63 (d, J=8.1 Hz, 1H), 7.28-7.16 (m, 2H), 6.84 (dd, J=11.8, 2.0 Hz, 1H), 6.73 (d, J=2.1 Hz, 1H), 6.47-6.40 (m, 1H), 5.58 (s, 1H), 5.23 (s, 2H), 3.18 (s, 2H), 2.44 (s, 3H), 2.25 (dt, J=9.7, 4.7 Hz, 2H), 1.85 (dd, J=44.9, 38.1 Hz, 2H), 1.81-1.59 (m, 5H).

Example 232

3-{1-(3-Bromobenzyl)-6-[(5-methylpyridin-2-yl)methoxy]-1H-benzimidazol-2-yl}-2,2-dimethylpropanoic acid as the trifluoroacetic acid salt

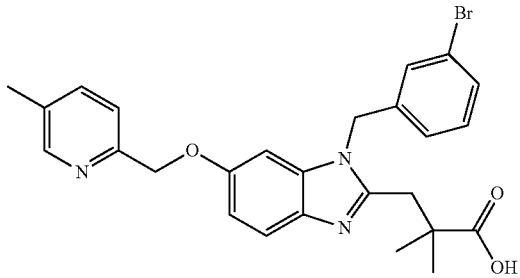 [SMILES: Cc1ccc(COc2ccc3nc(CC(C)(C)C(=O)O)n(Cc4cccc(Br)c4)c3c2)nc1]

The title compound was prepared using similar methods to those in Example 1 using (3-bromophenyl)methanamine in Step A and 3,3-dimethyldihydrofuran-2,5-dione in Step C. MS (ESI): mass calcd. for $C_{26}H_{26}BrN_3O_3$, 507.12; m/z found, 507.9 [M+H]$^+$. $^1$H NMR (500 MHz, DMSO-d$_6$) δ 8.41 (s, 1H), 7.68 (d, J=6.5 Hz, 1H), 7.65 (d, J=8.8 Hz, 1H), 7.51 (d, J=7.9 Hz, 1H), 7.45-7.39 (m, 2H), 7.31-7.23 (m, 2H), 7.13 (d, J=7.6 Hz, 1H), 7.09 (d, J=7.8 Hz, 1H), 5.66 (s, 2H), 5.17 (s, 2H), 3.28 (s, 2H), 2.31 (s, 3H), 1.27 (s, 6H).

Example 233 racemic cis-2-{1-(5-Bromo-2-fluorobenzyl)-6-[(1-methyl-H-pyrazol-3-yl)methoxy]-1H-benzimidazol-2-yl}cyclohexanecarboxylic acid

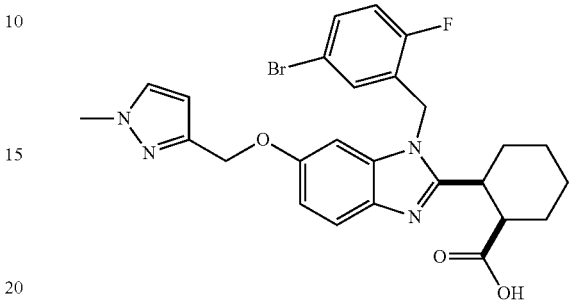

The title compound was prepared using analogous conditions described in Example 92 using (5-bromo-2-fluorophenyl)methanamine in Step B and cis-hexahydroisobenzofuran-1,3-dione in Step D. MS (ESI): mass calcd. for $C_{26}H_{26}BrFN_4O_3$, 540.12; m/z found, 541.2 [M+H]$^+$. $^1$H NMR (300 MHz, DMSO-d$_6$) δ 12.07 (s, 1H), 7.61 (d, J=2.2 Hz, 1H), 7.58-7.49 (m, 1H), 7.46 (d, J=8.7 Hz, 1H), 7.27 (dd, J=9.9, 8.8 Hz, 1H), 7.08 (d, J=2.4 Hz, 1H), 7.00 (dd, J=6.6, 2.6 Hz, 1H), 6.81 (dd, J=8.7, 2.3 Hz, 1H), 6.23 (d, J=2.2 Hz, 1H), 5.50 (s, 2H), 4.93 (s, 2H), 3.79 (s, 3H), 3.67-3.61 (m, 1H), 2.74-2.65 (m, 1H), 1.88-1.54 (m, 6H), 1.44-1.26 (m, 2H).

Example 234

2-({1-(5-Bromo-2-fluorobenzyl)-6-[(1-methyl-1H-pyrazol-3-yl)methoxy]-1H-benzimidazol-2-yl}methyl)-2-ethylbutanoic acid

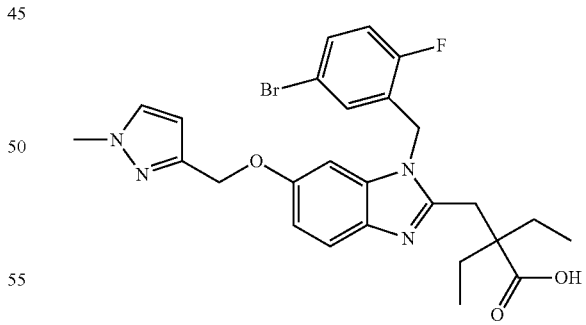

The title compound was prepared using analogous conditions described in Example 92 using (5-bromo-2-fluorophenyl)methanamine in Step B. MS (ESI): mass calcd. for $C_{26}H_{28}BrFN_4O_3$, 542.13; m/z found, M/Z=543.2 [M+H]$^+$. $^1$H NMR (300 MHz, DMSO-d$_6$) δ 7.62 (d, J=2.1 Hz, 1H), 7.59-7.47 (m, 2H), 7.29 (d, J=9.5 Hz, 1H), 7.25 (d, J=2.9 Hz, 1H), 6.95-6.84 (m, 2H), 6.26-6.22 (m, 1H), 5.57 (s, 2H), 4.96 (s, 2H), 3.79 (s, 3H), 3.04 (s, 2H), 1.83-1.72 (m, 4H), 0.74 (t, 6H).

Example 235

2-({1-(5-Bromo-2-fluorobenzyl)-6-[(5-methylpyridin-2-yl)methoxy]-1H-benzimidazol-2-yl}methyl)-2-ethylbutanoic acid

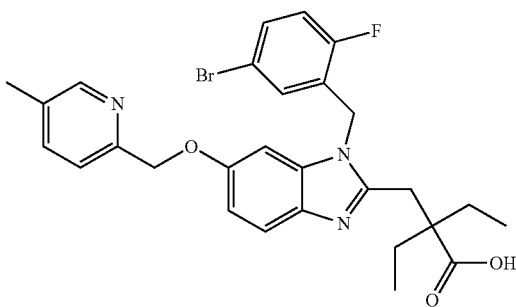 [SMILES: CCC(CC)(Cc1nc2ccc(OCc3ccc(C)cn3)cc2n1Cc1cc(Br)ccc1F)C(=O)O]

The title compound was prepared using analogous conditions described in Example 92 using 2-((3-fluoro-4-nitrophenoxy)methyl)-5-methylpyridine and (5-bromo-2-fluorophenyl)methanamine in Step B. MS (ESI): mass calcd. for $C_{28}H_{29}BrFN_3O_3$, 553.14; m/z found, 554.1 [M+H]$^+$. $^1$H NMR (300 MHz, DMSO-d$_6$) δ 12.24 (s, 1H), 8.35 (s, 1H), 7.62-7.49 (m, 2H), 7.46 (d, J=8.7 Hz, 1H), 7.37 (d, J=7.9 Hz, 1H), 7.26 (dd, J=10.0, 8.7 Hz, 1H), 7.17 (d, J=2.4 Hz, 1H), 6.90-6.77 (m, 2H), 5.51 (s, 2H), 5.10 (s, 2H), 2.95 (s, 2H), 2.28 (s, 3H), 1.88-1.65 (m, 4H), 0.83-0.59 (m, 6H).

Example 236 racemic cis-2-{1-[4-(3,3-Difluoropyrrolidin-1-yl)benzyl]-4-fluoro-6-[(1-methyl-1H-pyrazol-3-yl)methoxy]-1H-benzimidazol-2-yl}cyclohexanecarboxylic acid

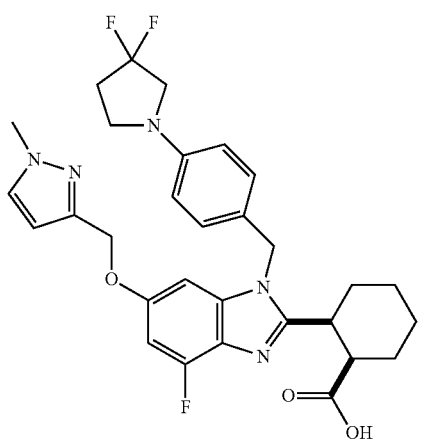

The title compound was prepared using analogous conditions described in Example 152 using cis-2-{1-(4-bromobenzyl)-4-fluoro-6-[(1-methyl-1H-pyrazol-3-yl)methoxy]-1H-benzimidazol-2-yl}cyclohexanecarboxylic acid and 3,3-difluoropyrrolidine. MS (ESI): mass calcd. for $C_{30}H_{32}F_3N_5O_3$, 567.25; m/z found, 568.0 [M+H]$^+$. $^1$H NMR (400 MHz, DMSO-d$_6$) δ 7.63 (d, J=2.2 Hz, 1H), 7.07 (d, J=8.4 Hz, 2H), 6.92 (d, J=2.2 Hz, 1H), 6.68 (dd, J=12.4, 2.1 Hz, 1H), 6.62-6.47 (m, 2H), 6.26 (d, J=2.2 Hz, 1H), 5.39 (d, J=16.2 Hz, 1H), 5.28 (d, J=16.1 Hz, 1H), 4.94 (s, 2H), 3.80 (s, 3H), 3.78-3.70 (m, 1H), 3.64 (t, J=13.4 Hz, 2H), 3.42 (t, J=7.2 Hz, 2H), 3.36-3.28 (m, 2H), 2.69 (d, J=13.1 Hz, 1H), 1.82 (d, J=10.8 Hz, 2H), 1.74-1.46 (m, 4H), 1.32 (d, J=10.4 Hz, 2H).

D) General Administration, Formulation, and Dosages

The present invention provides substituted heteroaryl ketone compounds which are useful as FLAP modulators.

The invention features a method for treating a subject in need thereof with an FLAP-mediated disease and/or disorder, said method comprising administering to the subject a therapeutically effective amount of a compound of the invention. In particular, the invention also provides a method for treating or inhibiting the progression of an FLAP-mediated disease and/or disorder, or associated symptoms or complications thereof in a subject afflicted with such a disease and/or disorder, wherein the method comprises administering to the subject a therapeutically effective amount of a compound of the invention.

Embodiments of the present invention include a method wherein the compound of Formula (I) is a FLAP modulator.

Embodiments of the present invention include a use of the compound of Formula (I) in the manufacture of a medicament for treating an FLAP-mediated disease and/or disorder.

Embodiments of the present invention include a use of the compound of Formula (I) as a medicine.

The compounds of Formula (I) have an FLAP-modulating effect and are useful as therapeutic agents for various FLAP-mediated disorders and/or disorders, or associated symptoms or complications, for example, respiratory disorders, cardiac and cardiovascular diseases, autoimmune disorders, carcinogenesis, and associated symptoms or complications thereof.

The compounds of Formula (I) may be administered orally or parenterally, and after formulation into preparations suitable for the intended administration route, they can be used as therapeutic agents for treating an FLAP-mediated disease and/or disorder. FLAP-mediated diseases and/or disorders include, but are not limited, diseases and/or disorders that are related to leukotriene synthesis pathway, and therefore may be treated, controlled or in some cases prevented, by treatment with the compounds of this invention.

One aspect of the present invention provides a method for the treatment of diseases and/or disorders, or associated symptoms or complications thereof, responsive to the modulation of FLAP in a subject in need thereof which comprises administering to the subject a therapeutically or prophylactically effective amount of a compound of Formula (I) or a form thereof.

Another aspect of the present invention provides a method for the treatment of a disease and/or disorder selected from the group consisting of respiratory diseases and/or disorders, cardiac and cardiovascular diseases and/or disorders, autoimmune diseases and/or disorders, carcinogenesis, and associated symptoms or complications thereof, in a subject in need thereof which comprises administering to the subject a therapeutically or prophylactically effective amount of a compound of Formula (I) or a form thereof.

More specifically, this invention is directed to a method of treating exacerbations, non-allergic asthma, aspirin exacerbated respiratory disease, pulmonary arterial hypertension, fibrotic lung diseases, acute respiratory distress syndrome, obstructive sleep apnea and chronic obstructive pulmonary disease, or associated symptoms or complications thereof, in a subject afflicted with such a disease and/or disorder, wherein the method comprises administering to the subject a therapeutically or prophylactically effective amount of a compound of Formula (I) or a form thereof.

Furthermore, this invention is directed to a method of treating myocardial infarction, atherosclerosis and coronary artery disease, and stroke, aortic aneurisms, atherosclerosis, or associated symptoms or complications thereof, in a subject afflicted with such a disease and/or disorder, wherein the method comprises administering to the subject a therapeutically or prophylactically effective amount of a compound of Formula (I) or a form thereof.

Yet, this invention is also directed to a method of treating rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis, allergic rhinitis, chronic sinusitis, allergic dermatitis and asthma, wherein the method comprises administering to the subject a therapeutically or prophylactically effective amount of a compound of Formula (I) or a form thereof.

Finally, this invention is also directed to a method of treating tumor cell proliferation, differentiation, apoptosis, tumor-associated angiogenesis, as well as the migration and invasion of carcinoma cells, wherein the method comprises administering to the subject a therapeutically or prophylactically effective amount of a compound of Formula (I) or a form thereof.

Another aspect of the present invention provides a pharmaceutical composition comprising at least one compound of Formula (I) or a form thereof, and a pharmaceutically acceptable carrier.

The invention also features a method for treating a subject in need thereof with an FLAP-mediated disease and/or disorder, said method comprising administering to the subject a therapeutically effective amount of a pharmaceutical composition comprising at least one compound of the invention.

Yet another aspect of the present invention relates to the use of a compound of Formula (I) or a form thereof, for the manufacture of a medicament useful for the treatment of an FLAP-mediated disease and/or disorder in a subject in need thereof.

In a clinical use of the compounds of the invention, pharmaceutically-acceptable additives may be added thereto to formulate various preparations in accordance with the intended administration route thereof, and the preparations may be administered.

Various additives generally used in the field of pharmaceutical compositions may be used herein, including, for example, gelatin, lactose, sucrose, titanium oxide, starch, crystalline cellulose, methyl cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, palmitoleic acid, light silicic acid anhydride, talc, vegetable oil, benzyl alcohol, gum arabic, propylene glycol, polyalkylene glycol, cyclodextrin, and hydroxypropylcyclodextrin.

Combined with such additives, the compound of the invention may be formulated into various forms of preparations, for example, solid preparations such as tablets, capsules, granules, powders and suppositories; and liquid preparations such as syrups, elixirs and injections. These preparations can be produced in any method known in the field of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto.

The compounds of the invention are effective for animals, including humans and other mammals. Any ordinary physician, veterinarian or clinician may readily determine the necessity, if any, of treatment with an instant compound.

Those of skill in the treatment of diseases and/or disorders, or associated symptoms or complications thereof, mediated by FLAP can determine the effective daily amount from the test results presented hereinafter and other information. The exact dosage and frequency of administration depends on the particular compound of invention used, the particular disease and/or disorder, or associated symptoms or complications thereof, being treated, the severity of the disease and/or disorder, or associated symptoms or complications thereof, being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines in practicing the present invention.

Preferably, the method for the treatment of the FLAP diseases and/or disorders described in the present invention using any of the compounds as defined herein, the dosage form will contain a pharmaceutically acceptable carrier containing between from about 1 mg to about 1000 mg; particularly from about 0.5 mg to about 500 mg of the compound, and may be constituted into any form suitable for the mode of administration selected. The dosages, however, may be varied depending upon the requirement of the subjects, the severity of the disease and/or disorder, or associated symptoms or complications thereof, being treated and the compound being employed. The use of either daily administration or post-periodic dosing may be employed.

When the compound of the invention is, for example, put into clinical use, then its dose and its administration frequency may vary depending on the sex, the age, the body weight and the condition of the patient and on the type and the range of the necessary treatment with the compound. For oral administration, in general, the dose of the compound may be in a range of from about 0.01 mg/kg/day to about 100 mg/kg of body weight/day or in a range of from about 0.03 mg/kg/day to about 1 mg/kg/day. The oral administration frequency is preferably from one to a few times per day. For parenteral administration, the dose may be in a range of from about 0.001 mg/kg/day to about 10 mg/kg/day, in a range of from about 0.001 mg/kg/day to about 0.1 mg/kg/day or, in a range of from about 0.01 mg/kg/day to about 0.1 mg/kg/day. The parenteral administration frequency is preferably from one to a few times per day. For oral administration, the compositions are preferably provided in the form of tablets containing from about 1.0 mg to about 1000 mg of the active ingredient, particularly 1 mg, 5 mg, 10 mg, 15 mg, 20 mg, 25 mg, 50 mg, 75 mg, 100 mg, 150 mg, 200 mg, 250 mg, 300 mg, 400 mg, 500 mg, 600 mg, 750 mg, 800 mg, 900 mg, and 1000 mg of the active ingredient for the symptomatic adjustment of the dosage to the patient to be treated. The compounds may be administered on a regimen of 1 to 4 times per day, preferably once or twice per day.

Ordinary physicians, veterinarians and clinicians may readily determine the effective dose of the pharmaceutical compound necessary to treat, prevent, inhibit, retard or stop the intended disease, and may readily treat the diseased patient with the compound.

The pharmaceutical compositions herein will contain, per unit dosage unit, e.g., tablet, capsule, powder, injection, suppository, teaspoonful and the like, of from about 0.001 mg/kg/day to about 10 mg/kg/day (particularly from about 0.01 mg/kg/day to about 1 mg/kg/day; and, more particularly, from about 0.1 mg/kg/day to about 0.5 mg/kg/day) and may be given at a dosage of from about 0.001 mg/kg/day to about 30 mg/kg/day (particularly from about 0.01 mg/kg/day to about 2 mg/kg/day, more particularly from about 0.1 mg/kg/day to about 1 mg/kg/day and even more particularly from about 0.5 mg/kg/day to about 1 mg/kg/day).

Preferably these compositions are in unit dosage forms from such as tablets, pills, capsules, dry powders for reconstitution or inhalation, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, dry powder inhaler or other inhalation or insufflation means. Alternatively, the composition may be presented in a form suitable for 1 to 4 times per day, preferably once or twice per day administration; for example, an insoluble salt of the active compound, such as the decanoate salt, may be adapted to provide a depot preparation for intramuscular injection.

The preparation may contain the compound of the invention in an amount in a range of from about 1.0 to about 100% by weight or, in a range of from about 1.0 to about 60% by weight of the preparation. The preparation may contain any other therapeutically-effective compound.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

Some of the crystalline forms for the compounds may exist as polymorphs and as such are intended to be included in the present invention. In addition, some of the compounds may form solvates with water (i.e., hydrates) or common organic solvents, and such solvates are intended to be encompassed within the scope of this invention.

Where the processes for the preparation of the compounds according to the invention give rise to mixtures of stereoisomers, these isomers may be separated by conventional techniques such as preparative chromatography. The compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, cis-trans isomers, and enantiomers thereof are encompassed within the scope of the present invention.

D) Use

Dosages

For preparing pharmaceutical compositions such as tablets, the principal active ingredient is mixed with a pharmaceutical carrier, e.g. conventional tableting ingredients such as diluents, binders, adhesives, disintegrants, lubricants, antiadherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), crosslinked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W.R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active form of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimellitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agents include pharmaceutical grade lecithins. Suitable flocculating agents include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms; however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

The daily dose of a pharmaceutical composition of the present invention may be varied over a wide range from about 0.1 mg to about 5000 mg; preferably, the dose will be in the range of from about 1 mg to about 100 mg per day for an average human. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 or 500 milligrams of the active ingredient for the symptomatic adjustment of the dosage to the subject to be treated. Advantageously, a compound of the present invention may be administered in a single daily dose or the total daily dosage may be administered in divided doses of two, three or four times daily.

It is also apparent to one skilled in the art that the therapeutically effective dose for active compounds of the invention or a pharmaceutical composition thereof will vary according to the desired effect. Therefore, optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as FLAP modulators is required for a subject in need thereof.

In their use, the compounds of the invention may be combined with any other therapeutic agents that are useful for the treatment of an FLAP-mediated disorder.

The combination includes not only the composition of compounds of the invention and one other active substance but also the composition of compounds of the invention and two or more other active substances or non-drug therapy. The scope of possible combinations of a compound of the invention and one, two or more active substances are within the knowledge of one skilled in the art for the treatment of an FLAP-mediated disorder.

Specifically, the combination of a FLAP modulator with prostaglandin modulators, cyclooxygenase-1 modulators, or cyclooxygenase-2 modulators might be used to treat inflammatory and autoimmune diseases and/or disorders as well as cardiovascular diseases and/or disorders, or vascular injury (Z. Yu et al., "Disruption of the 5-lipoxygenase pathway attenuates atherogenesis consequent to COX-2 deletion in mice," *Proc. Natl. Acad. Sci. USA*, 2012, 109(17), 6727-32; Z. Yu et al., "Myeloid Cell 5-Lipoxygenase Activating Protein Modulates the Response to Vascular Injury," *Circ. Res.*, 2012, Epub December 18). Due to the synergy of histamine and leukotrienes, the combination of a FLAP modulator and a histamine receptor 1 or 4 antagonist might have utility in treating respiratory, allergic, dermatological and autoimmune disorders (A. Reicin et al., "Montelukast, a leukotriene receptor antagonist, in combination with loratadine, a histamine receptor antagonist, in the treatment of chronic asthma," *Arch. Intern. Med.*, 2000, 160(16), 2418-88; S. Sanada et al., "The effectiveness of montelukast for the treatment of anti-histamine-resistant chronic urticaria," *Arch. Dermatol. Res.*, 2005, 297(3), 134-38).

Formulations

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

The compounds of the present invention may be formulated into various pharmaceutical forms for administration purposes. Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

E) Biological Examples

The ability of the compounds of the present invention to treat a FLAP-mediated disease and/or disorder, or associated symptoms or complications thereof, was determined using the following procedures. Binding assay data represent the average value obtained from two different assay plates, with samples run in duplicate on each plate. Human whole blood assay data represent a single replicate on an assay plate using whole blood from at least one healthy donor. Certain FLAP binding and human whole blood assay data is presented in Table 2.

FLAP Binding Assay

The assay below is used to test the modulatory activity of compounds against FLAP. Human and mouse FLAP-encoding DNA was amplified by polymerase chain reaction and cloned into pFastBac1 (Invitrogen) with a NH2-terminal 6-His tag for expression in *Spodoptera frugiperda* (Sf-9) cells. FLAP-containing membranes were prepared as was a FITC-labeled FLAP modulator (3-(3-(tert-butylthio)-1-(4-chlorobenzyl)-5-(quinolin-2-ylmethoxy)-1H-indol-2-yl)-2, 2-dimethylpropanoic acid). The FLAP binding assay is performed in HTRF format (homogeneous time resolved fluorescence). FLAP-containing membranes (1 μg/well final for human) are incubated in the presence of the HTRF ligand, [5-[({[2-(2-{3-[3-(tert-butylsulfanyl)-1-(4-chlorobenzyl)-5-(quinolin-2-ylmethoxy)-1H-indol-2-yl]-2,2-dimethylpropanoyl}hydrazino)-2-oxoethyl]sulfanyl}acetyl) amino]-2-(6-hydroxy-3-oxo-3H-xanthen-9-yl)benzoic acid] (25 nM final), a terbium labeled anti-His tag antibody (0.5 ng/well final, from Cisbio) and compounds. The reaction is allowed to proceed for two hours after which the plate is read on an Envision plate reader in HTRF mode. Data are expressed as a HTRF ratio.

For human FLAP binding assays, data are analyzed with 3DX Explorer software. A ratio is calculated with the relative light units at 520 nm over the relative light units at 495 nm. For analysis, data from multiple runs are averaged and each compound may be tested in 2 to 20 runs. Each run comprises two plates and each plate includes duplicates. Data from each plate is averaged and data are imported into 3DX. The data from multiple runs are aggregated as the average of duplicates of the calculated ratios in order to calculate $K_i$ and $IC_{50}$ values. Numbers in parentheses are the number of runs for the assay.

Human Whole Blood Assay

An in vitro cellular assay was performed using human whole blood collected in heparin-containing tubes, which was used to test the ability of compounds to modulate the leukotriene pathway in human whole blood. The blood was diluted 1:1 in RPMI medium, pre-incubated for 15 min at 37° Celsius with test compounds at various concentrations, and then stimulated with calcium ionophore, A23187 (7 μg/mL), for 30 min at 37° Celsius. The samples were then centrifuged and plasma was removed. The plasma was diluted in assay buffer and $LTB_4$ levels were measured using a commercial kit (Enzo Life Sciences). The concentration of each compound that was required for half-maximal inhibition (modulation) of recombinant enzyme activity ($IC_{50}$) was calculated by a 4-parameter equation using the program GraphPad Prism (GraphPad software). For analysis, data are imported into 3DX and aggregated as the average of duplicates of the calculated ratios in order to calculate $K_i$ and $IC_{50}$ values. Numbers in parentheses are the number of runs for the assay.

TABLE 2

FLAP binding and Human Whole Blood assay data

| Cmp No. | FLAP Binding wild type HTRF $K_i$ (μM) | Human Whole Blood $LTB_4$ $IC_{50}$ (μM) |
|---|---|---|
| 1 | 0.0038 (8) | 0.4 (3) |
| 2 | 0.0014 (10) | 0.22 (10) |
| 3 | ~0.83 (8) | >30 (2) |
| 4 | 0.0025 (2) | 1.02 (1) |
| 5 | 0.0064 (6) | 1.39 (5) |
| 6 | 0.39 (4) | ~12 (1) |
| 7 | 0.0022 (4) | 0.71 (2) |
| 8 | 0.01 (6) | 2.32 (2) |
| 9 | 0.018 (4) | ~14 (1) |
| 10 | 0.0045 (3) | 0.38 (2) |
| 11 | 0.00074 (3) | 0.059 (2) |
| 12 | ~2 (2) | nt |
| 13 | 0.0096 (3) | 1.19 (2) |
| 14 | 0.056 (2) | >10 (1) |
| 15 | 0.049 (4) | 1 (2) |
| 16 | 0.023 (2) | 0.41 (2) |
| 17 | >10 (2) | nt |
| 18 | 0.053 (3) | >10 (1) |
| 19 | ~0.75 (2) | nt |
| 20 | 0.008 (2) | 0.75 (2) |
| 21 | 0.009 (6) | 0.74 (4) |
| 22 | 0.024 (3) | 1.66 (4) |
| 23 | 0.018 (4) | 0.91 (2) |
| 24 | 0.011 (2) | >10 (2) |
| 25 | 0.061 (2) | 3.12 (1) |
| 26 | 0.0043 (4) | 0.56 (4) |
| 27 | 0.0045 (4) | 0.62 (4) |
| 28 | 0.0014 (3) | 0.19 (1) |
| 29 | ~2.5 (2) | nt |
| 30 | ~0.08 (4) | 2.66 (2) |
| 31 | 0.0041 (3) | 1.97 (2) |
| 32 | 0.0056 (2) | 0.21 (2) |
| 33 | 0.0066 (3) | 0.74 (1) |
| 34 | 0.71 (4) | >10 (2) |
| 35 | 0.0019 (3) | 1.59 (1) |
| 36 | 0.0022 (8) | 0.59 (10) |
| 37 | 0.026 (4) | 0.68 (3) |
| 38 | >10 (2) | nt |
| 39 | 0.01 (4) | 1.07 (1) |
| 40 | 0.0039 (4) | 0.47 (2) |
| 41 | 0.011 (4) | 6.76 (2) |
| 42 | 0.032 (5) | 1.03 (3) |
| 43 | ~0.94 (4) | nt |
| 44 | 0.0073 (2) | 1.01 (2) |
| 45 | ~2.5 (2) | >10 (2) |
| 46 | 0.11 (3) | 6.19 (2) |
| 47 | ~0.49 (2) | nt |
| 48 | ~0.75 (2) | nt |
| 49 | ~1.88 (2) | nt |
| 50 | ~0.1 (2) | nt |
| 51 | 0.008 (2) | 0.34 (4) |
| 52 | >10 (2) | >10 (1) |
| 53 | 0.003 (8) | 0.27 (6) |
| 54 | 0.0097 (2) | 2.91 (2) |
| 55 | 0.012 (2) | 3.33 (1) |
| 56 | 0.046 (2) | ~2 (1) |
| 57 | 0.045 (2) | ~8 (1) |
| 58 | 0.058 (4) | 1.36 (2) |
| 59 | 0.0029 (4) | 0.19 (2) |
| 60 | 0.051 (3) | 2.64 (2) |
| 61 | 0.006 (3) | 2.28 (2) |
| 62 | 0.0081 (3) | 0.97 (2) |
| 63 | 0.023 (4) | 1.08 (2) |
| 64 | 0.29 (2) | 3.28 (1) |
| 65 | 0.006 (4) | 1.12 (2) |
| 66 | 0.0077 (2) | 0.59 (2) |
| 67 | 0.011 (2) | 1.08 (2) |
| 68 | 0.014 (2) | 0.43 (2) |
| 69 | 0.017 (2) | 1.03 (2) |
| 70 | 0.047 (2) | 0.93 (2) |
| 71 | 0.049 (2) | 3.35 (1) |
| 72 | 0.06 (5) | 1.93 (2) |
| 73 | 0.052 (2) | 3.25 (1) |
| 74 | 0.075 (2) | 2.11 (2) |
| 75 | 0.0058 (2) | 0.44 (2) |
| 76 | 0.021 (3) | 5.71 (1) |
| 77 | 0.019 (4) | 3.95 (1) |
| 78 | 0.024 (4) | 14.05 (1) |
| 79 | 0.085 (4) | ~20 (1) |
| 80 | 0.0033 (2) | 0.3 (2) |
| 81 | 0.0029 (3) | 0.2 (1) |
| 82 | 0.0079 (2) | 0.17 (1) |
| 83 | 0.0042 (2) | 0.35 (1) |
| 84 | 0.0059 (2) | 0.19 (2) |
| 85 | 0.0014 (4) | 0.68 (2) |
| 86 | 0.0097 (2) | 1.75 (2) |
| 87 | 0.015 (2) | 1.78 (2) |
| 88 | 0.032 (2) | 0.82 (2) |
| 89 | 0.032 (2) | 3.61 (1) |
| 90 | 0.027 (2) | 0.85 (1) |
| 91 | 0.0066 (2) | 0.17 (2) |
| 92 | ~0.25 (4) | 1.44 (1) |
| 93 | 0.0011 (2) | 0.55 (2) |
| 94 | 0.0024 (2) | 0.34 (1) |
| 95 | 0.0036 (2) | 1.35 (2) |
| 96 | 0.007 (4) | 0.81 (3) |
| 97 | 0.0075 (2) | 0.3 (2) |
| 98 | 0.058 (4) | 5.72 (1) |
| 99 | 0.018 (2) | 1.06 (1) |
| 100 | 0.019 (2) | 2.54 (1) |
| 101 | 0.021 (2) | 0.9 (2) |
| 102 | 0.024 (2) | 1.03 (2) |
| 103 | 0.03 (2) | 1.01 (2) |
| 104 | 0.03 (2) | 0.69 (2) |
| 105 | 0.04 (2) | 6.25 (1) |
| 106 | 0.0054 (2) | 1.16 (1) |
| 107 | 0.43 (3) | nt |
| 108 | 2.24 (2) | nt |
| 109 | 0.0026 (2) | 0.36 (1) |
| 110 | 0.92 (2) | nt |
| 111 | 0.03 (4) | 0.8 (4) |
| 112 | 0.019 (6) | 0.5 (4) |
| 113 | ~1.79 (6) | nt |
| 114 | 0.77 (3) | nt |
| 115 | 1.1 (3) | nt |
| 116 | ~0.4 (4) | nt |
| 117 | ~1.88 (2) | nt |
| 118 | 0.13 (4) | ~30 (1) |
| 119 | 0.0066 (4) | 0.32 (2) |
| 120 | 0.013 (3) | 0.64 (2) |
| 121 | 0.15 (2) | 2.11 (2) |
| 122 | ~0.83 (2) | 3.4 (1) |
| 123 | 0.00061 (4) | 0.11 (2) |
| 124 | 0.00052 (2) | 0.59 (2) |
| 125 | 0.0011 (3) | 0.3 (2) |
| 126 | 0.0011 (2) | 0.11 (2) |
| 127 | 0.16 (2) | 2.12 (1) |
| 128 | 0.0085 (2) | 1.32 (1) |
| 129 | 0.014 (2) | 0.66 (3) |
| 130 | 0.015 (4) | 0.84 (2) |
| 131 | 0.024 (2) | 3.93 (1) |
| 132 | 0.0029 (2) | 0.27 (2) |
| 133 | ~1.5 (2) | nt |
| 134 | ~0.5 (6) | 0.86 (4) |
| 135 | 0.012 (2) | 1.14 (2) |
| 136 | 0.00064 (2) | 0.48 (2) |
| 137 | 0.00066 (2) | 0.091 (2) |
| 138 | 0.0025 (2) | 0.097 (3) |
| 139 | 0.00047 (2) | 0.14 (1) |
| 140 | 0.003 (2) | 0.43 (2) |
| 141 | 0.0051 (2) | 0.76 (2) |
| 142 | 0.0074 (2) | 0.98 (1) |
| 143 | 0.013 (2) | 1.82 (1) |
| 144 | 0.064 (3) | 0.96 (2) |
| 145 | 0.0072 (3) | 0.92 (2) |
| 146 | 0.011 (3) | 0.88 (2) |
| 147 | 0.0013 (16) | 0.12 (12) |
| 148 | 0.33 (4) | 6.13 (1) |
| 149 | 0.036 (2) | 3.88 (1) |
| 150 | 0.0014 (4) | 0.14 (1) |

TABLE 2-continued

FLAP binding and Human Whole Blood assay data

| Cmp No. | FLAP Binding wild type HTRF $K_i$ (µM) | Human Whole Blood LTB$_4$ IC$_{50}$ (µM) |
|---|---|---|
| 151 | 0.013 (2) | 0.91 (2) |
| 152 | 0.0024 (3) | 0.4 (3) |
| 153 | 0.0044 (3) | 0.4 (3) |
| 154 | 0.0037 (3) | 0.21 (2) |
| 155 | ~0.62 (2) | nt |
| 156 | 0.0068 (6) | 0.29 (2) |
| 157 | 0.003 (2) | 0.42 (2) |
| 158 | 0.27 (3) | >10 (1) |
| 159 | 0.0072 (3) | 0.39 (2) |
| 160 | 0.0038 (3) | 0.31 (3) |
| 161 | 0.004 (3) | 0.3 (2) |
| 162 | 0.0048 (3) | 0.31 (2) |
| 163 | 0.00096 (4) | 0.051 (3) |
| 164 | ~0.75 (2) | nt |
| 165 | 0.011 (3) | 0.26 (4) |
| 166 | 0.37 (3) | 6.4 (1) |
| 167 | 0.0022 (4) | 0.071 (2) |
| 168 | 0.0078 (2) | 3.57 (1) |
| 169 | 0.012 (2) | 1.22 (1) |
| 170 | ~0.1 (2) | 2.75 (3) |
| 171 | 0.013 (3) | 0.79 (1) |
| 172 | 0.00084 (2) | 0.09 (2) |
| 173 | 0.00082 (2) | 0.068 (2) |
| 174 | 0.00034 (2) | 0.12 (2) |
| 175 | 0.07 (2) | 4.86 (1) |
| 176 | 0.00042 (2) | 0.11 (2) |
| 177 | 0.0011 (4) | 0.029 (3) |
| 178 | 0.0012 (2) | 0.047 (1) |
| 179 | 0.0013 (2) | 0.15 (2) |
| 180 | 0.003 (2) | 0.56 (1) |
| 181 | 0.0052 (2) | 0.048 (2) |
| 182 | 0.011 (2) | 0.48 (4) |
| 183 | 0.013 (2) | 0.88 (2) |
| 184 | 0.015 (2) | 0.8 (2) |
| 185 | 0.025 (2) | 0.91 (3) |
| 186 | 0.03 (2) | 0.71 (2) |
| 187 | 0.0073 (3) | 0.36 (2) |
| 188 | 0.012 (3) | 0.55 (2) |
| 189 | 0.029 (3) | 1.48 (1) |
| 190 | 0.21 (2) | 0.93 (2) |
| 191 | 0.07 (2) | >10 (1) |
| 192 | 0.00095 (4) | 0.11 (1) |
| 193 | 0.12 (4) | 5.55 (1) |
| 194 | 0.0057 (2) | 0.58 (2) |
| 195 | 0.019 (2) | 1.43 (1) |
| 196 | ~0.5 (4) | nt |
| 197 | 0.0066 (2) | 1.81 (2) |
| 198 | >10 (2) | nt |
| 199 | ~2.5 (2) | nt |
| 200 | 0.03 (3) | 3.14 (1) |
| 201 | 0.012 (4) | 1.68 (2) |
| 202 | ~0.75 (2) | nt |
| 203 | 0.018 (2) | 0.73 (2) |
| 204 | 0.031 (2) | 0.24 (2) |
| 205 | 0.021 (2) | 1.67 (2) |
| 206 | 0.045 (2) | 1.27 (2) |
| 207 | 0.031 (3) | 1.81 (2) |
| 208 | 0.0095 (2) | 0.37 (1) |
| 209 | 0.0038 (2) | 0.15 (1) |
| 210 | ~1.75 (2) | nt |
| 211 | 0.035 (2) | 0.84 (1) |
| 212 | 0.09 (2) | 1.08 (1) |
| 213 | ~0.94 (4) | nt |
| 214 | ~2.5 (2) | nt |
| 215 | ~0.32 (4) | nt |
| 216 | ~0.18 (2) | nt |
| 217 | 0.06 (2) | nt |
| 218 | 0.024 (2) | 4.17 (1) |
| 219 | 0.0091 (6) | 1.6 (2) |
| 220 | 0.0042 (4) | 0.65 (3) |
| 221 | 0.0066 (4) | 0.5 (2) |
| 222 | 0.0038 (4) | 0.31 (2) |
| 223 | 0.0068 (3) | 0.32 (2) |
| 224 | 0.017 (3) | 2.17 (2) |
| 225 | ~0.87 (2) | nt |
| 226 | 0.017 (2) | ~3.2 (1) |
| 227 | 0.18 (2) | 4.52 (1) |
| 228 | 0.0068 (3) | 4.01 (1) |
| 229 | 0.011 (2) | 6.64 (1) |
| 230 | 0.073 (2) | >30 (1) |
| 231 | 0.18 (2) | >30 (1) |
| 232 | ~0.75 (2) | nt |
| 233 | 0.035 (2) | 2.26 (1) |
| 234 | >10 (2) | nt |
| 235 | nt | nt |
| 236 | 0.0024 (2) | 1.65 (1) |

Numbers in parentheses are the number of runs for the assay
nt means not tested

Throughout this application, various publications are cited. The disclosure of these publications is hereby incorporated by reference into this application to describe more fully the state of the art to which this invention pertains.

While the foregoing specification teaches the principles of the present invention, with examples provided for the purpose of illustration, it will be understood that the practice of the invention encompasses all of the usual variations, adaptations and modifications as come within the scope of the following claims and their equivalents.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of Formula (I)

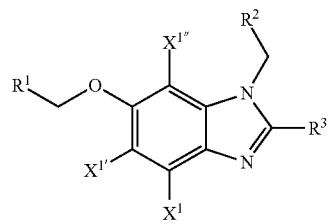

wherein:
$X^1$ is H Cl, or F;
$X^{1'}$ is H, Cl, or F;
$X^{1''}$ is H, or F;
$R^1$ is

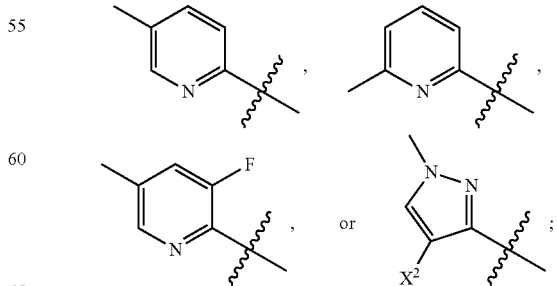

$X^2$ is H, F, or Cl;

R² is

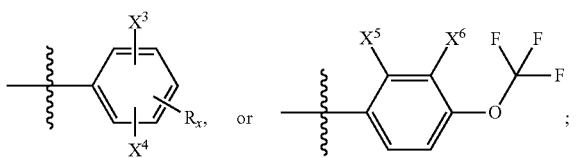

R_x is Br, CH₃, —CN, CF₃,

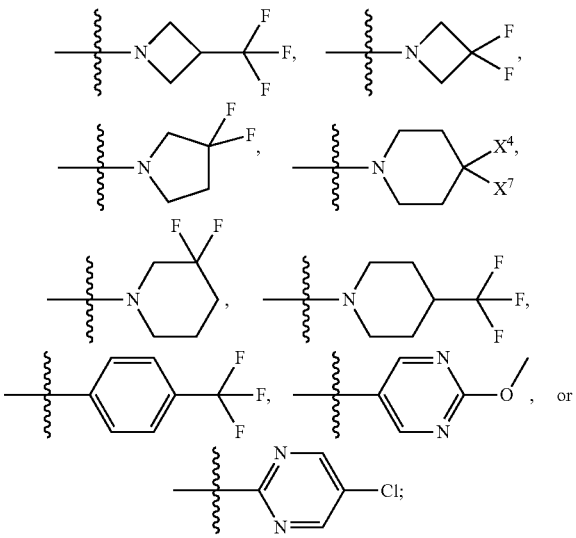

X³ is H, or F;
X⁴ is H, or F;
X⁵ is H, Br, Cl, CH₃, OCH₃, or F;
X⁶ is H, Cl, CH₃, or F;
X⁷ is H, F, CH₃, or C(CH₃)₃; and
R³ is

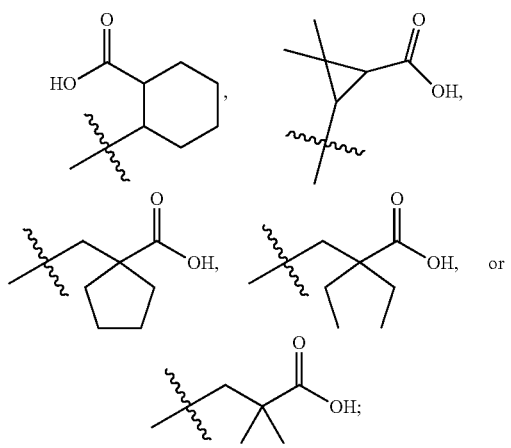

provided that the second eluting isomer of racemic cis-2-{1-(4-Cyanobenzyl)-6-[(5-methylpyridin-2-yl)methoxy]-1H-benzimidazol-2-yl}cyclohexanecarboxylic acid when purified by chiral SFC on (CHIRALCEL OJ-H 5 μm 250×20 mm) mobile phase (65% CO₂, 35% EtOH), the second eluting isomer of racemic cis-3-{1-(4-Bromo-2-fluorobenzyl)-6-[(5-methylpyridin-2-yl)methoxy]-1H-benzimidazol-2-yl}-2,2-dimethylcyclopropanecarboxylic acid when purified by chiral SFC on (CHIRALPAK AD-H 5 μm 250×20 mm) mobile phase (60% CO₂, 40% MeOH), and the first eluting isomer of racemic cis-2-{1-[2-Fluoro-4-(trifluoromethoxy)benzyl]-6-[(1-methyl-1H-pyrazol-3-yl)methoxy]-1H-benzimidazol-2-yl}cyclohexanecarboxylic acid when purified by chiral SFC (CHIRALCEL OD-H 5 μm 250×20 mm) mobile phase (80% CO₂, 20% MeOH) are specifically disclaimed;

and solvates, hydrates, and pharmaceutically acceptable salts thereof.

2. The compound of claim 1 wherein
R² is

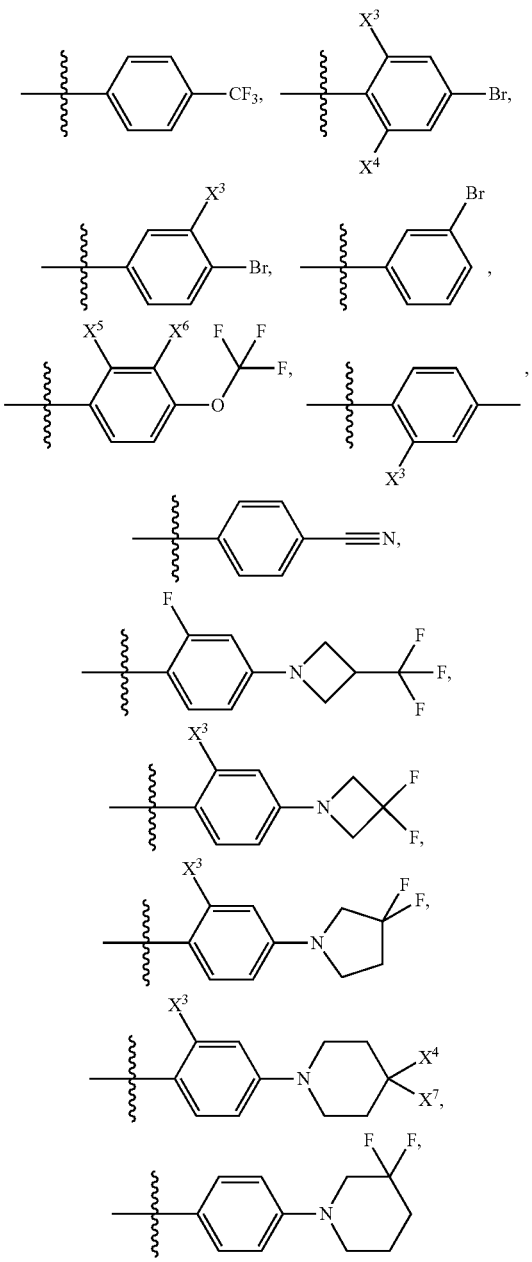

-continued

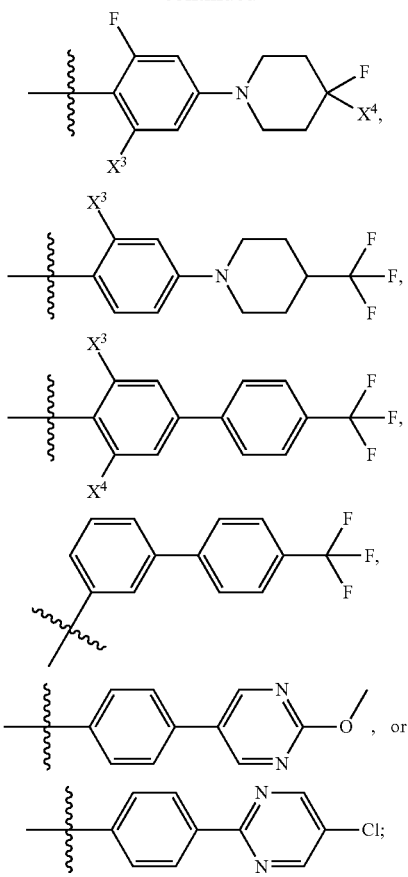

provided that the second eluting isomer of racemic cis-2-{1-(4-Cyanobenzyl)-6-[(5-methylpyridin-2-yl)methoxy]-1H-benzimidazol-2-yl}cyclohexanecarboxylic acid when purified by chiral SFC on (CHIRALCEL OJ-H 5 μm 250×20 mm) mobile phase (65% $CO_2$, 35% EtOH), the second eluting isomer of racemic cis-3-{1-(4-Bromo-2-fluorobenzyl)-6-[(5-methylpyridin-2-yl)methoxy]-1H-benzimidazol-2-yl}-2,2-dimethylcyclopropanecarboxylic acid when purified by chiral SFC on (CHIRALPAK AD-H 5 μm 250×20 mm) mobile phase (60% $CO_2$, 40% MeOH), and the first eluting isomer of racemic cis-2-{1-[2-Fluoro-4-(trifluoromethoxy)benzyl]-6-[(1-methyl-1H-pyrazol-3-yl)methoxy]-1H-benzimidazol-2-yl}cyclohexanecarboxylic acid when purified by chiral SFC (CHIRALCEL OD-H 5 μm 250×20 mm) mobile phase (80% $CO_2$, 20% MeOH) are specifically disclaimed;

and solvates, hydrates, and pharmaceutically acceptable salts thereof.

3. The compound of claim 1 wherein
$R^1$ is

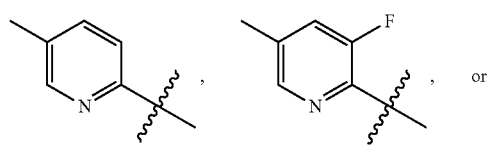

-continued

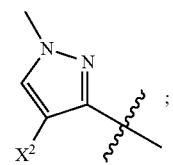

$R^3$ is

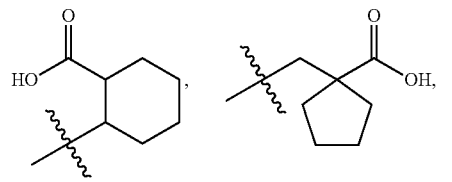

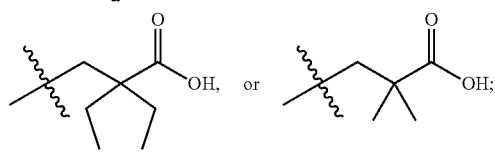

provided that the second eluting isomer of racemic cis-2-{1-(4-Cyanobenzyl)-6-[(5-methylpyridin-2-yl)methoxy]-1H-benzimidazol-2-yl}cyclohexanecarboxylic acid when purified by chiral SFC on (CHIRALCEL OJ-H 5 μm 250×20 mm) mobile phase (65% $CO_2$, 35% EtOH), and the first eluting isomer of racemic cis-2-{1-[2-Fluoro-4-(trifluoromethoxy)benzyl]-6-[(1-methyl-1H-pyrazol-3-yl)methoxy]-1H-benzimidazol-2-yl}cyclohexanecarboxylic acid when purified by chiral SFC (CHIRALCEL OD-H 5 μm 250×20 mm) mobile phase (80% $CO_2$, 20% MeOH) are specifically disclaimed;

and solvates, hydrates, and pharmaceutically acceptable salts thereof.

4. The compound of claim 1, wherein
$R^3$ is

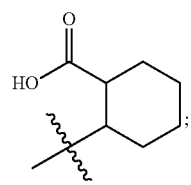 [SMILES: *C1CCCCC1C(=O)O]

and solvates, hydrates, and pharmaceutically acceptable salts thereof.

5. The compound of claim 1, wherein
$R^1$ is

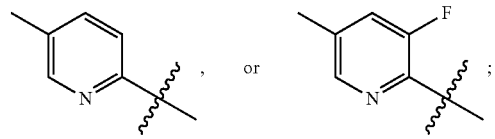

$R^2$ is

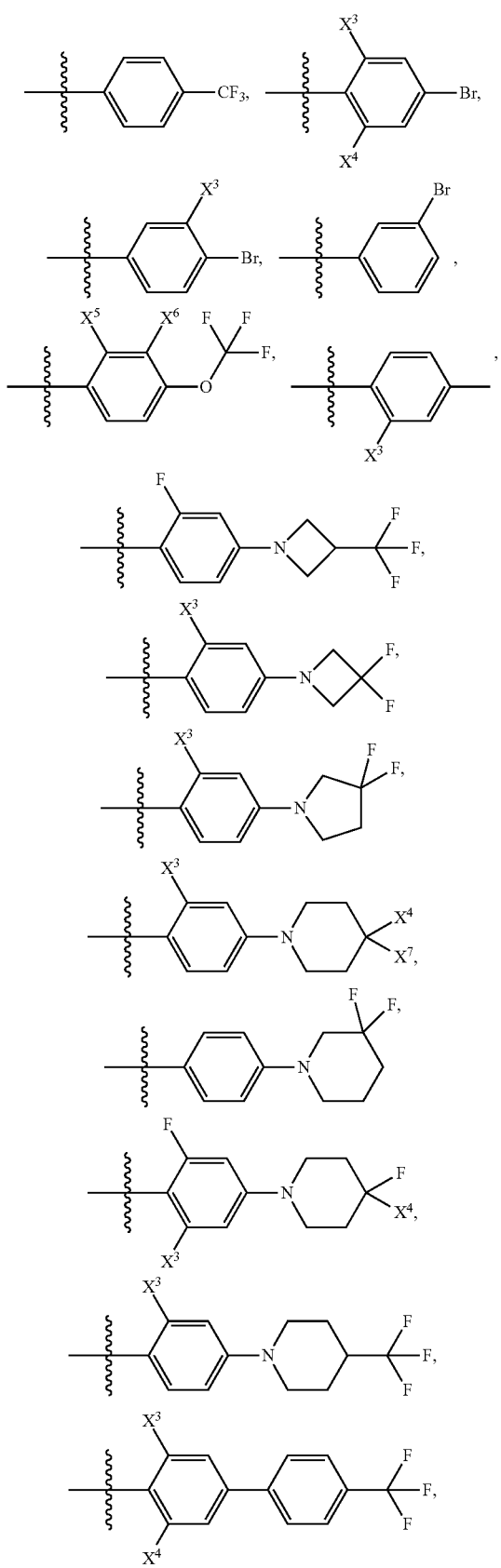
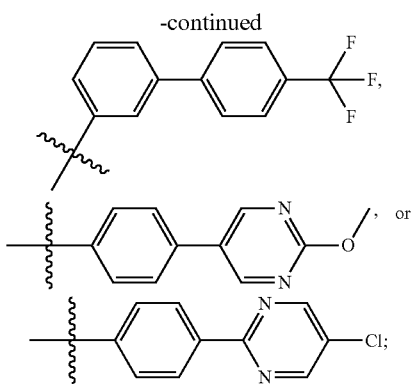

provided that the second eluting isomer of racemic cis-2-{1-(4-Cyanobenzyl)-6-[(5-methylpyridin-2-yl)methoxy]-1H-benzimidazol-2-yl}cyclohexanecarboxylic acid when purified by chiral SFC on (CHIRALCEL OJ-H 5 μm 250×20 mm) mobile phase (65% $CO_2$, 35% EtOH), is specifically disclaimed;

and solvates, hydrates, and pharmaceutically acceptable salts thereof.

6. The compound of claim 1, selected from the group consisting of
   racemic cis-2-{1-(4-Bromobenzyl)-6-[(5-methylpyridin-2-yl)methoxy]-1H-benzimidazol-2-yl}cyclohexanecarboxylic acid,
   (1S,2R)-2-(1-(4-Bromobenzyl)-6-((5-methylpyridin-2-yl)methoxy)-1H-benzo[d]imidazol-2-yl)cyclohexanecarboxylic acid,
   (1R,2S)-2-{1-(4-Bromobenzyl)-6-[(5-methylpyridin-2-yl)methoxy]-1H-benzimidazol-2-yl}cyclohexanecarboxylic acid,
   racemic cis-2-{1-(4-Bromo-3-fluorobenzyl)-6-[(5-methylpyridin-2-yl)methoxy]-1H-benzimidazol-2-yl}cyclohexanecarboxylic acid as the TFA salt,
   racemic trans-2-{1-(4-Bromobenzyl)-6-[(5-methylpyridin-2-yl)methoxy]-1H-benzimidazol-2-yl}cyclohexanecarboxylic acid as the TFA salt,
   (1S*,2S*)-2-{1-(4-Bromobenzyl)-6-[(5-methylpyridin-2-yl)methoxy]-1H-benzimidazol-2-yl}cyclohexanecarboxylic acid,
   (1R*,2R*)-2-{1-(4-Bromobenzyl)-6-[(5-methylpyridin-2-yl)methoxy]-1H-benzimidazol-2-yl}cyclohexanecarboxylic acid,
   2-({1-(4-Bromobenzyl)-6-[(5-methylpyridin-2-yl)methoxy]-1H-benzimidazol-2-yl}methyl)-2-ethylbutanoic acid as the TFA salt,
   1-({1-(4-Bromobenzyl)-6-[(5-methylpyridin-2-yl)methoxy]-1H-benzimidazol-2-yl}methyl)cyclopentanecarboxylic acid as the TFA salt,
   racemic cis-2-{1-(4-Bromo-2-fluorobenzyl)-6-[(5-methylpyridin-2-yl)methoxy]-1H-benzimidazol-2-yl}cyclohexanecarboxylic acid,
   (1R*,2S*)-2-{1-(4-Bromo-2-fluorobenzyl)-6-[(5-methylpyridin-2-yl)methoxy]-1H-benzimidazol-2-yl}cyclohexanecarboxylic acid,
   (1S*,2R*)-2-{1-(4-Bromo-2-fluorobenzyl)-6-[(5-methylpyridin-2-yl)methoxy]-1H-benzimidazol-2-yl}cyclohexanecarboxylic acid,
   racemic trans-2-{1-(4-Bromo-2-fluorobenzyl)-6-[(5-methylpyridin-2-yl)methoxy]-1H-benzimidazol-2-yl}cyclohexanecarboxylic acid, 2-({1-(3-Bromobenzyl)-6-[(5-methylpyridin-2-yl)
methoxy]-1H-benzimidazol-2-yl}methyl)-2-ethylbu-
tanoic acid,
racemic cis-3-{1-(4-Bromo-2-fluorobenzyl)-6-[(5-meth-
ylpyridin-2-yl)methoxy]-1H-benzimidazol-2-yl}-2,2-
dimethylcyclopropanecarboxylic acid,
(1S*,3R*)-3-{1-(4-Bromo-2-fluorobenzyl)-6-[(5-methyl-
pyridin-2-yl)methoxy]-1H-benzimidazol-2-yl}-2,2-di-
methylcyclopropanecarboxylic acid,
(1R*,3S*)-3-{4-Bromo-2-fluorobenzyl)-6-[(5-methyl-
pyridin-2-yl)methoxy]-1H -benzimidazol-2-yl}-2,2-di-
methylcyclopropanecarboxylic acid,
racemic trans-2-{1-(4-Cyanobenzyl)-6-[(5-methylpyri-
din-2-yl)methoxy]-1H-benzimidazol-2-
yl}cyclohexanecarboxylic acid as the TFA salt,
2-({1-(4-Cyanobenzyl)-6-[(5-methylpyridin-2-yl)
methoxy]-1H-benzimidazol-2-yl}methyl)-2-ethylbu-
tanoic acid as the TFA salt,
racemic cis-2-{1-[3-Fluoro-4-(trifluoromethoxy)benzyl]-
6-[(5-methylpyridin-2-yl)methoxy]-1H-benzimidazol-
2-yl}cyclohexanecarboxylic acid,
racemic trans-2-{1-[2-Fluoro-4-(trifluoromethoxy)ben-
zyl]-6-[(5-methylpyridin-2-yl)methoxy]-1H-benzimi-
dazol-2-yl}cyclohexanecarboxylic acid,
2-Ethyl-2-({6-[(5-methylpyridin-2-yl)methoxy]-1-[4-(tri-
fluoromethoxy)benzyl]-1H-benzimidazol-2-
yl}methyl)butanoic acid,
2-Ethyl-2-({1-[2-fluoro-4-(trifluoromethoxy)benzyl]-6-
[(5-methylpyridin-2-yl)methoxy]-1H-benzimidazol-2-
yl}methyl)butanoic acid,
2-({1-[3-Chloro-4-(trifluoromethoxy)benzyl]-6-[(5-
methylpyridin-2-yl)methoxy]-1H-benzimidazol-2-
yl}methyl)-2-ethylbutanoic acid,
racemic cis-2,2-Dimethyl-3-{6-[(5-methylpyridin-2-yl)
methoxy]-1-[4-(trifluoromethoxy)benzyl]-1H-benz-
imidazol-2-yl}cyclopropanecarboxylic acid,
racemic cis-2-{1-[2-Fluoro-4-(trifluoromethoxy)benzyl]-
6-[(5-methylpyridin-2-yl)methoxy]-1H-benzimidazol-
2-yl}cyclohexanecarboxylic acid,
racemic cis-2-{6-[(5-Methylpyridin-2-yl)methoxy]-1-[4-
(trifluoromethoxy)benzyl]-1H-benzimidazol-2-
yl}cyclohexanecarboxylic acid,
(1R*,2S*)-2-{6-[(5-Methylpyridin-2-yl)methoxy]-1-[4-
(trifluoromethoxy)benzyl]-1H-benzimidazol-2-
yl}cyclohexanecarboxylic acid,
(1S*,2R*)-2-{6-[(5-Methylpyridin-2-yl)methoxy]-1-[4-
(trifluoromethoxy)benzyl]-1H-benzimidazol-2-
yl}cyclohexanecarboxylic acid,
2-Ethyl-2-({1-[3-fluoro-4-(trifluoromethoxy)benzyl]-6-
[(5-methylpyridin-2-yl)methoxy]-1H-benzimidazol-2-
yl}methyl)butanoic acid,
racemic trans-2-{6-[(5-Methylpyridin-2-yl)methoxy]-1-
[4-(trifluoromethoxy)benzyl]-1H-benzimidazol-2-
yl}cyclohexanecarboxylic acid,
racemic cis-2-{1-[3-Chloro-4-(trifluoromethoxy)benzyl]-
6-[(5-methylpyridin-2-yl)methoxy]-1H-benzimidazol-
2-yl}cyclohexanecarboxylic acid,
racemic trans-2-(6-[(5-Methylpyridin-2-yl)methoxy]-1-
{[4'-(trifluoromethyl)biphenyl-4-yl]methyl}-1H-benz-
imidazol-2-yl)cyclohexanecarboxylic acid,
(1R*,2R*)-2-(6-[(5-Methylpyridin-2-yl)methoxy]-1-{[4'-
(trifluoromethyl)biphenyl-4-yl]methyl}-1H-benzimi-
dazol-2-yl)cyclohexanecarboxylic acid,
(1S*,2S*)-2-(6-[(5-Methylpyridin-2-yl)methoxy]-1-{[4'-
(trifluoromethyl)biphenyl-4-yl]methyl}-1H-benzimi-
dazol-2-yl)cyclohexanecarboxylic acid,
(1S*,2R*)-2-{6-[(1-Methyl-1H-pyrazol-3-yl)methoxy]-
1-[4-(trifluoromethoxy)benzyl]-1H-benzimidazol-2-
yl}cyclohexanecarboxylic acid,
racemic cis-2-{1-(4-Cyanobenzyl)-6-[(5-methylpyridin-
2-yl)methoxy]-1H-benzimidazol-2-
yl}cyclohexanecarboxylic acid as the TFA salt,
(1S*,2R*)-2-{1-(4-Cyanobenzyl)-6-[(5-methylpyridin-
2yl) methoxy]-1H-benzimidazol-2-
yl}cyclohexanecarboxylic acid,
(1R*,2S*)-2-{1-(4-Cyanobenzyl)-6-[(5-methylpyridin-2-
yl)methoxy]-1H-benzimidazol-2-
yl}cyclohexanecarboxylic acid,
racemic cis-2-{1-(4-Bromobenzyl)-6-[(1-methyl-1H-
pyrazol-3-yl)methoxy]-1H-benzimidazol-2-
yl}cyclohexanecarboxylic acid as the TFA salt,
racemic trans-2-{1-(4-Bromobenzyl)-6-[(1-methyl-1H-
pyrazol-3-yl)methoxy]-1H-benzimidazol-2-
yl}cyclohexanecarboxylic acid as the TFA salt,
2-({1-(4-Bromobenzyl)-6-[(1-methyl-1H-pyrazol-3-yl)
methoxy]-1H-benzimidazol-2-yl}methyl)-2-ethylbu-
tanoic acid as the TFA salt,
2-Ethyl-2-({6-[(1-Methyl-1H-pyrazol-3-yl)methoxy]-1-
(4-piperidin-1-ylbenzyl)-1H-benzimidazol-2-
yl}methyl)butanoic acid,
racemic cis-2-{6-[(1-Methyl-1H-pyrazol-3-yl)methoxy]-
1-[4-(trifluoromethoxy)benzyl]-1H-benzimidazol-2-
yl}cyclohexanecarboxylic acid,
(1R*,2S*)-2-{6-[(1-Methyl-1H-pyrazol-3-yl)methoxy]-
1-[4-(trifluoromethoxy)benzyl]-1H-benzimidazol-2-
yl}cyclohexanecarboxylic acid,
1-({1-(4-Bromobenzyl)-6-[(1-methyl-1H-pyrazol-3-yl)
methoxy]-1H-benzimidazol-2-yl}methyl)cyclopentan-
ecarboxylic acid as the TFA salt,
racemic cis-2-{1-(4-Cyanobenzyl)-6-[(1-methyl-1H-
pyrazol-3-yl)methoxy]-1H-benzimidazol-2-
yl}cyclohexanecarboxylic acid as the Trifluoroacetic
acid salt,
racemic trans-2-{1-(4-Cyanobenzyl)-6-[(1-methyl-1H-
pyrazol-3-yl)methoxy]-1H-benzimidazol-2-
yl}cyclohexanecarboxylic acid as the Trifluoroacetic
acid salt,
2-({1-(4-Cyanobenzyl)-6-[(1-methyl-1H-pyrazol-3-yl)
methoxy]-1H-benzimidazol-2-yl}methyl)-2-ethylbu-
tanoic acid as the Trifluoroacetic acid salt,
2-Ethyl-2-({6-[(1-methyl-1H-pyrazol-3-yl)methoxy]-1-
[4-(trifluoromethoxy)benzyl]-1H-benzimidazol-2-
yl}methyl)butanoic acid,
racemic cis-2-{1-[2-Fluoro-4-(trifluoromethoxy)benzyl]-
6-[(1-methyl-1H-pyrazol-3-yl)methoxy]-1H-benzimi-
dazol-2-yl}cyclohexanecarboxylic acid,
(1S*,2R*)-2-{1-[2-Fluoro-4-(trifluoromethoxy)benzyl]-
6-[(1-methyl-1H-pyrazol-3-yl) methoxy]-1H-benzimi-
dazol-2-yl}cyclohexanecarboxylic acid,
(1R*,2S*)-2-(1-(2-Fluoro-4-(trifluoromethoxy)benzyl)-
6-((1-methyl-1H-pyrazol-3-yl)methoxy)-1H-benzo[d]
imidazol-2-yl)cyclohexanecarboxylic acid,
racemic trans-2-{6-[(1-Methyl-1H-pyrazol-3-yl)
methoxy]-1-[4-(trifluoromethoxy)benzyl]-1H-benz-
imidazol-2-yl}cyclohexanecarboxylic acid,
racemic cis-2-{1-[3-Fluoro-4-(trifluoromethoxy)benzyl]-
6-[(1-methyl-1H-pyrazol-3-yl)methoxy]-1H-benzimi-
dazol-2-yl}cyclohexanecarboxylic acid,
2-Ethyl-2-({1-[2-fluoro-4-(trifluoromethoxy)benzyl]-6-
[(1-methyl-1H-pyrazol-3-yl)methoxy]-1H-benzimida-
zol-2-yl}methyl)butanoic acid, 2-Ethyl-2-({1-[3-fluoro-4-(trifluoromethoxy)benzyl]-6-[(1-methyl-1H-pyrazol-3-yl)methoxy]-1H-benzimidazol-2-yl}methyl)butanoic acid, 2-({1-(4-Bromo-2-fluorobenzyl)-6-[(1-methyl-1H-pyrazol-3-yl)methoxy]-1H-benzimidazol-2-yl}methyl)-2-ethylbutanoic acid, racemic cis-2-{1-(4-Bromobenzyl)-4-fluoro-6-[(5-methylpyridin-2-yl)methoxy]-1H-benzimidazol-2-yl}cyclohexanecarboxylic acid, 3-{1-(4-Bromobenzyl)-4-fluoro-6-[(5-methylpyridin-2-yl)methoxy]-1H-benzimidazol-2-yl}-2,2-dimethylpropanoic acid, 1-({1-(4-Bromobenzyl)-4-fluoro-6-[(5-methylpyridin-2-yl)methoxy]-1H-benzimidazol-2-yl}methyl)cyclopentanecarboxylic acid, racemic trans-2-{1-(4-Bromobenzyl)-4-fluoro-6-[(5-methylpyridin-2-yl)methoxy]-1H-benzimidazol-2-yl}cyclohexanecarboxylic acid, racemic cis-3-{1-(4-Bromobenzyl)-4-fluoro-6-[(5-methylpyridin-2-yl)methoxy]-1H-benzimidazol-2-yl}-2,2-dimethylcyclopropanecarboxylic acid, racemic cis-3-{4-Fluoro-1-(4-methylbenzyl)-6-[(5-methylpyridin-2-yl)methoxy]-1H-benzimidazol-2-yl}-2,2-dimethylcyclopropanecarboxylic acid as the TFA salt, 2-({1-(4-Bromobenzyl)-4-fluoro-6-[(5-methylpyridin-2-yl)methoxy]-1H-benzimidazol-2-yl}methyl)-2-ethylbutanoic acid as the TFA salt, racemic cis-2-{4-Fluoro-6-[(5-methylpyridin-2-yl)methoxy]-1-[4-(trifluoromethoxy)benzyl]-1H-benzimidazol-2-yl}cyclohexanecarboxylic acid as the TFA salt, racemic trans-2-{4-Fluoro-6-[(5-methylpyridin-2-yl)methoxy]-1-[4-(trifluoromethoxy)benzyl]-1H-benzimidazol-2-yl}cyclohexanecarboxylic acid as the TFA salt, racemic cis-2-{4-Fluoro-1-(4-methylbenzyl)-6-[(5-methylpyridin-2-yl)methoxy]-1H-benzimidazol-2-yl}cyclohexanecarboxylic acid as the TFA salt, 2-Ethyl-2-({4-fluoro-6-[(5-methylpyridin-2-yl)methoxy]-1-[4-(trifluoromethoxy)benzyl]-1H-benzimidazol-2-yl}methyl)butanoic acid as the TFA salt, racemic trans-2-{4-Fluoro-1-(4-methylbenzyl)-6-[(5-methylpyridin-2-yl)methoxy]-1H-benzimidazol-2-yl}cyclohexanecarboxylic acid as the TFA salt, 2-Ethyl-2-({4-fluoro-1-(4-methylbenzyl)-6-[(5-methylpyridin-2-yl)methoxy]-1H-benzimidazol-2-yl}methyl)butanoic acid as the TFA salt, 1-({4-Fluoro-6-[(5-methylpyridin-2-yl)methoxy]-1-[4-(trifluoromethoxy)benzyl]-1H-benzimidazol-2-yl}methyl)cyclopentanecarboxylic acid as the TFA salt, 1-({4-Fluoro-1-(4-methylbenzyl)-6-[(5-methylpyridin-2-yl)methoxy]-1H-benzimidazol-2-yl}methyl)cyclopentanecarboxylic acid as the TFA salt, racemic cis-3-{4-Fluoro-6-[(5-methylpyridin-2-yl)methoxy]-1-[4-(trifluoromethoxy)benzyl]-1H-benzimidazol-2-yl}-2,2-dimethylcyclopropanecarboxylic acid as the TFA salt, racemic cis-2-{1-(4-Bromobenzyl)-4-chloro-6-[(5-methylpyridin-2-yl)methoxy]-1H-benzimidazol-2-yl}cyclohexanecarboxylic acid, racemic cis-3-{1-(4-Bromobenzyl)-4-chloro-6-[(5-methylpyridin-2-yl)methoxy]-1H-benzimidazol-2-yl}-2,2-dimethylcyclopropanecarboxylic acid, racemic trans-2-{1-(4-Bromobenzyl)-4-chloro-6-[(5-methylpyridin-2-yl)methoxy]-1H-benzimidazol-2-yl}cyclohexanecarboxylic acid, 1-({1-(4-Bromobenzyl)-4-chloro-6-[(5-methylpyridin-2-yl)methoxy]-1H-benzimidazol-2-yl}methyl)cyclopentanecarboxylic acid, 3-{1-(4-Bromobenzyl)-4-chloro-6-[(5-methylpyridin-2-yl)methoxy]-1H-benzimidazol-2-yl}-2,2-dimethylpropanoic acid, racemic cis-2-{1-[4-(5-Chloropyrimidin-2-yl)benzyl]-6-[(5-methylpyridin-2-yl)methoxy]-1H-benzimidazol-2-yl}cyclohexanecarboxylic acid, racemic cis-2-{1-(4-Bromobenzyl)-6-[(4-chloro-1-methyl-1H-pyrazol-3-yl)methoxy]-1H-benzimidazol-2-yl}cyclohexanecarboxylic acid, racemic cis-2-{6-[(4-Chloro-1-methyl-1H-pyrazol-3-yl)methoxy]-1-(4-piperidin-1-ylbenzyl)-1H-benzimidazol-2-yl}cyclohexanecarboxylic acid, racemic cis-2-{6-[(4-Chloro-1-methyl-1H-pyrazol-3-yl)methoxy]-1-[2-fluoro-4-(trifluoromethoxy)benzyl]-1H-benzimidazol-2-yl}cyclohexanecarboxylic acid, racemic cis-2-{1-[2-Methoxy-4-(trifluoromethoxy)benzyl]-6-[(1-methyl-1H-pyrazol-3-yl)methoxy]-1H-benzimidazol-2-yl}cyclohexanecarboxylic acid, racemic cis-2-{6-[(4-Fluoro-1-methyl-1H-pyrazol-3-yl)methoxy]-1-[2-fluoro-4-(trifluoromethoxy)benzyl]-1H-benzimidazol-2-yl}cyclohexanecarboxylic acid, racemic cis-2-{1-[4-(4,4-Difluoropiperidin-1-yl)benzyl]-6-[(1-methyl-1H-pyrazol-3-yl)methoxy]-1H-benzimidazol-2-yl}cyclohexanecarboxylic acid, racemic cis-2-{6-[(4-Chloro-1-methyl-1H-pyrazol-3-yl)methoxy]-1-[4-(4-fluoropiperidin-1-yl)benzyl]-1H-benzimidazol-2-yl}cyclohexanecarboxylic acid, racemic cis-2-{6-[(1-Methyl-1H-pyrazol-3-yl)methoxy]-1-(4-piperidin-1-ylbenzyl)-1H-benzimidazol-2-yl}cyclohexanecarboxylic acid, racemic cis-2-{1-[4-(3,3-Difluoroazetidin-1-yl)benzyl]-6-[(1-methyl-1H-pyrazol-3-yl)methoxy]-1H-benzimidazol-2-yl}cyclohexanecarboxylic acid, racemic cis-2-{5-Fluoro-1-[2-fluoro-4-(trifluoromethoxy)benzyl]-6-[(1-methyl-1H-pyrazol-3-yl)methoxy]-1H-benzimidazol-2-yl}cyclohexanecarboxylic acid, racemic cis-2-{7-Fluoro-1-[2-fluoro-4-(trifluoromethoxy)benzyl]-6-[(1-methyl-1H-pyrazol-3-yl)methoxy]-1H-benzimidazol-2-yl}cyclohexanecarboxylic acid, 2-Ethyl-2-({6-[(1-methyl-1H-pyrazol-3-yl)methoxy]-1-[2-methyl-4-(trifluoromethoxy)benzyl]-1H-benzimidazol-2-yl}methyl)butanoic acid, racemic cis-2-{1-(4-Bromobenzyl)-4-fluoro-6-[(1-methyl-1H-pyrazol-3-yl)methoxy]-1H-benzimidazol-2-yl}cyclohexanecarboxylic acid, racemic cis-2-{1-(4-Bromo-2-fluorobenzyl)-4-fluoro-6-[(1-methyl-1H-pyrazol-3-yl)methoxy]-1H-benzimidazol-2-yl}cyclohexanecarboxylic acid, racemic cis-2-{4-Fluoro-6-[(1-methyl-1H-pyrazol-3-yl)methoxy]-1-[4-(trifluoromethoxy)benzyl]-1H-benzimidazol-2-yl}cyclohexanecarboxylic acid as the HCl salt, racemic cis-2-{4-Fluoro-1-[2-fluoro-4-(trifluoromethoxy)benzyl]-6-[(1-methyl-1H-pyrazol-3-yl)methoxy]-1H-benzimidazol-2-yl}cyclohexanecarboxylic acid as the HCl salt, racemic cis-2-{4-Fluoro-1-(4-methylbenzyl)-6-[(1-methyl-1H-pyrazol-3-yl)methoxy]-1H-benzimidazol-2-yl}cyclohexanecarboxylic acid as the HCl salt, racemic cis-2-{1-(4-Cyanobenzyl)-4-fluoro-6-[(1-methyl-1H-pyrazol-3-yl)methoxy]-1H-benzimidazol-2-yl}cyclohexanecarboxylic acid as the HCl salt, racemic cis-2-{6-[(1-Methyl-1H-pyrazol-3-yl)methoxy]-1-[2-methyl-4-(trifluoromethoxy)benzyl]-1H-benzimidazol-2-yl}cyclohexanecarboxylic acid,
racemic cis-2-{6-[(5-Methylpyridin-2-yl)methoxy]-1-[2-methyl-4-(trifluoromethoxy)benzyl]-1H-benzimidazol-2-yl}cyclohexanecarboxylic acid,
racemic cis-2-{1-[2-Chloro-4-(trifluoromethoxy)benzyl]-6-[(5-methylpyridin-2-yl)methoxy]-1H-benzimidazol-2-yl}cyclohexanecarboxylic acid as the HCl salt,
racemic cis-2-{1-[2-Bromo-4-(trifluoromethoxy)benzyl]-6-[(5-methylpyridin-2-yl)methoxy]-1H-benzimidazol-2-yl}cyclohexanecarboxylic acid as the HCl salt,
racemic cis-2-{1-[2-Chloro-4-(trifluoromethoxy)benzyl]-6-[(1-methyl-1H-pyrazol-3-yl)methoxy]-1H-benzimidazol-2-yl}cyclohexanecarboxylic acid as the HCl salt,
racemic cis-2-{1-[2-Bromo-4-(trifluoromethoxy)benzyl]-6-[(1-methyl-1H-pyrazol-3-yl)methoxy]-1H-benzimidazol-2-yl}cyclohexanecarboxylic acid as the HCl salt,
2-Ethyl-2-({6-[(5-methylpyridin-2-yl)methoxy]-1-[2-methyl-4-(trifluoromethoxy)benzyl]-1H-benzimidazol-2-yl}methyl)butanoic acid,
racemic cis-2-{6-[(1-Methyl-1H-pyrazol-3-yl)methoxy]-1-[3-methyl-4-(trifluoromethoxy)benzyl]-1H-benzimidazol-2-yl}cyclohexanecarboxylic acid as the HCl salt,
3-{1-(4-Bromobenzyl)-6-[(1-methyl-1H-pyrazol-3-yl)methoxy]-1H-benzimidazol-2-yl}-2,2-dimethylpropanoic acid,
3-{1-(4-Bromobenzyl)-6-[(6-methylpyridin-2-yl)methoxy]-1H-benzimidazol-2-yl}-2,2-dimethylpropanoic acid,
racemic cis-2-{6-[(5-Methylpyridin-2-yl)methoxy]-1-[3-methyl-4-(trifluoromethoxy)benzyl]-1H-benzimidazol-2-yl}cyclohexanecarboxylic acid,
racemic cis-2-{5-Chloro-1-[2-fluoro-4-(trifluoromethoxy)benzyl]-6-[(5-methylpyridin-2-yl)methoxy]-1H-benzimidazol-2-yl}cyclohexanecarboxylic acid as the HCl salt,
racemic cis-3-{1-(4-Bromobenzyl)-6-[(5-methylpyridin-2-yl)methoxy]-1H-benzimidazol-2-yl}-2,2-dimethylcyclopropanecarboxylic acid as the TFA salt,
(1S*,3R*)-3-{1-(4-Bromobenzyl)-6-[(5-methylpyridin-2-yl)methoxy]-1H-benzimidazol-2-yl}-2,2-dimethylcyclopropanecarboxylic acid,
(1R*,3S*)-3-{1-(4-Bromobenzyl)-6-[(5-methylpyridin-2-yl)methoxy]-1H-benzimidazol-2-yl}-2,2-dimethylcyclopropanecarboxylic acid,
racemic trans-3-{1-(4-Bromobenzyl)-6-[(5-methylpyridin-2-yl)methoxy]-1H-benzimidazol-2-yl}-2,2-dimethylcyclopropanecarboxylic acid as the TFA salt,
(1R*,3R*)-3-{1-(4-Bromobenzyl)-6-[(5-methylpyridin-2-yl)methoxy]-1H-benzimidazol-2-yl}-2,2-dimethylcyclopropanecarboxylic acid,
(1S*,3S*)-3-{1-(4-Bromobenzyl)-6-[(5-methylpyridin-2-yl)methoxy]-1H-benzimidazol-2-yl}-2,2-dimethylcyclopropanecarboxylic acid,
racemic trans-3-{1-(4-Bromobenzyl)-6-[(1-methyl-1H-pyrazol-3-yl)methoxy]-1H-benzimidazol-2-yl}-2,2-dimethylcyclopropanecarboxylic acid as the TFA salt,
3-{1-(4-Bromobenzyl)-6-[(5-methylpyridin-2-yl)methoxy]-1H-benzimidazol-2-yl}-2,2-dimethylpropanoic acid as the TFA salt,
racemic cis-2-{1-(4-Methylbenzyl)-6-[(5-methylpyridin-2-yl)methoxy]-1H-benzimidazol-2-yl}cyclohexanecarboxylic acid,
racemic trans-2-{1-(4-Methylbenzyl)-6-[(5-methylpyridin-2-yl)methoxy]-1H-benzimidazol-2-yl}cyclohexanecarboxylic acid,
racemic cis-2,2-Dimethyl-3-{1-(4-methylbenzyl)-6-[(5-methylpyridin-2-yl)methoxy]-1H-benzimidazol-2-yl}cyclopropanecarboxylic acid,
racemic cis-2,2-Dimethyl-3-{6-[(1-methyl-1H-pyrazol-3-yl)methoxy]-1-[4-(trifluoromethoxy)benzyl]-1H-benzimidazol-2-yl}cyclopropanecarboxylic acid,
racemic cis-2-{1-(4-Bromo-2,6-difluorobenzyl)-6-[(3-fluoro-5-methylpyridin-2-yl)methoxy]-1H-benzimidazol-2-yl}cyclohexanecarboxylic acid,
racemic trans-2-{1-(4-Bromo-2,6-difluorobenzyl)-6-[(3-fluoro-5-methylpyridin-2-yl)methoxy]-1H-benzimidazol-2-yl}cyclohexanecarboxylic acid,
racemic cis-2-{1-(4-Bromobenzyl)-6-[(3-fluoro-5-methylpyridin-2-yl)methoxy]-1H-benzimidazol-2-yl}cyclohexanecarboxylic acid,
racemic cis-2-{1-(4-Bromo-2,6-difluorobenzyl)-6-[(5-methylpyridin-2-yl)methoxy]-1H-benzimidazol-2-yl}cyclohexanecarboxylic acid,
3-{1-(2-Fluoro-4-methylbenzyl)-6-[(3-fluoro-5-methylpyridin-2-yl)methoxy]-1H-benzimidazol-2-yl}-2,2-dimethylpropanoic acid,
3-{1-(4-Bromobenzyl)-6-[(3-fluoro-5-methylpyridin-2-yl)methoxy]-1H-benzimidazol-2-yl}-2,2-dimethylpropanoic acid,
3-{1-(4-Bromo-2-fluorobenzyl)-6-[(3-fluoro-5-methylpyridin-2-yl)methoxy]-1H-benzimidazol-2-yl}-2,2-dimethylpropanoic acid,
3-{1-(4-Bromo-2,6-difluorobenzyl)-6-[(3-fluoro-5-methylpyridin-2-yl)methoxy]-1H-benzimidazol-2-yl}-2,2-dimethylpropanoic acid,
3-{6-[(3-Fluoro-5-methylpyridin-2-yl)methoxy]-1-[2-fluoro-4-(trifluoromethoxy)benzyl]-1H-benzimidazol-2-yl}-2,2-dimethylpropanoic acid,
racemic cis-3-{1-(4-Bromobenzyl)-6-[(3-fluoro-5-methylpyridin-2-yl)methoxy]-1H-benzimidazol-2-yl}-2,2-dimethylcyclopropanecarboxylic acid,
racemic cis-3-{1-(4-Bromobenzyl)-6-[(6-methylpyridin-2-yl)methoxy]-1H-benzimidazol-2-yl}-2,2-dimethylcyclopropanecarboxylic acid,
racemic cis-3-{1-(4-Bromobenzyl)-6-[(1-methyl-1H-pyrazol-3-yl)methoxy]-1H-benzimidazol-2-yl}-2,2-dimethylcyclopropanecarboxylic acid,
2-({1-(4-Cyanobenzyl)-6-[(3-fluoro-5-methylpyridin-2-yl)methoxy]-1H-benzimidazol-2-yl}methyl)-2-ethylbutanoic acid,
2-({1-(4-Bromobenzyl)-6-[(3-fluoro-5-methylpyridin-2-yl)methoxy]-1H-benzimidazol-2-yl}methyl)-2-ethylbutanoic acid,
racemic cis-2-(1-{[3,5-Difluoro-4'-(trifluoromethyl)biphenyl-4-yl]methyl}-6-[(3-fluoro-5-methylpyridin-2-yl)methoxy]-1H-benzimidazol-2-yl)cyclohexanecarboxylic acid,
racemic cis-2-(1-{[3,5-Difluoro-4'-(trifluoromethyl)biphenyl-4-yl]methyl}-6-[(5-methylpyridin-2-yl)methoxy]-1H-benzimidazol-2-yl)cyclohexanecarboxylic acid,
(1R*,2S*)-2-(6-[(3-Fluoro-5-methylpyridin-2-yl)methoxy]-1-{[4'-(trifluoromethyl)biphenyl-4-yl]methyl}-1H-benzimidazol-2-yl)cyclohexanecarboxylic acid,
racemic trans-2-{1-(4-Bromo-2,6-difluorobenzyl)-6-[(5-methylpyridin-2-yl)methoxy]-1H-benzimidazol-2-yl}cyclohexanecarboxylic acid,
3-(6-[(3-Fluoro-5-methylpyridin-2-yl)methoxy]-1-{[3-fluoro-4'-(trifluoromethyl)biphenyl-4-yl]methyl}-1H-benzimidazol-2-yl)-2,2-dimethylpropanoic acid, 3-(6-[(3-Fluoro-5-methylpyridin-2-yl)methoxy]-1-{[4'-(trifluoromethyl)biphenyl-4-yl]methyl}-1H-benzimidazol-2-yl)-2,2-dimethylpropanoic acid, 3-(6-[(3-Fluoro-5-methylpyridin-2-yl)methoxy]-1-{[4'-(trifluoromethyl)biphenyl-3-yl]methyl}-1H-benzimidazol-2-yl)-2,2-dimethylpropanoic acid, racemic cis-2-{1-[4-(2-Methoxypyrimidin-5-yl)benzyl]-6-[(5-methylpyridin-2-yl)methoxy]-1H-benzimidazol-2-yl}cyclohexanecarboxylic acid, racemic cis-2-(6-[(5-Methylpyridin-2-yl)methoxy]-1-{[4'-(trifluoromethyl)biphenyl-3-yl]methyl}-1H-benzimidazol-2-yl)cyclohexanecarboxylic acid, racemic cis-2-(6-[(5-Methylpyridin-2-yl)methoxy]-1-{[4'-(trifluoromethyl)biphenyl-4-yl]methyl}-1H-benzimidazol-2-yl)cyclohexanecarboxylic acid, (1S,2R)-2-(6-((5-Methylpyridin-2-yl)methoxy)-1-((4'-(trifluoromethyl)-[1,1'-biphenyl]-4-yl)methyl)-1H-benzo[d]imidazol-2-yl)cyclohexanecarboxylic acid, (1R,2S)-2-(6-[(5-Methylpyridin-2-yl)methoxy]-1-{[4'-(trifluoromethyl)biphenyl-4-yl]methyl}-1H-benzimidazol-2-yl)cyclohexanecarboxylic acid, 2-Ethyl-2-((6-((5-methylpyridin-2-yl)methoxy)-1-{[4'-(trifluoromethyl)-[1,1'-biphenyl]-3-yl]methyl}-1H-benzo[d]imidazol-2-yl)methyl)butanoic acid, racemic cis-2-(6-[(1-Methyl-1H-pyrazol-3-yl)methoxy]-1-{[4'-(trifluoromethyl)biphenyl-3-yl]methyl}-1H-benzimidazol-2-yl)cyclohexanecarboxylic acid, racemic cis-2-(6-[(4-Chloro-1-methyl-1H-pyrazol-3-yl)methoxy]-1-{[4'-(trifluoromethyl)biphenyl-4-yl]methyl}-1H-benzimidazol-2-yl)cyclohexanecarboxylic acid, racemic cis-2-{1-[4-(3,3-Difluoropyrrolidin-1-yl)benzyl]-6-[(5-methylpyridin-2-yl)methoxy]-1H-benzimidazol-2-yl}cyclohexanecarboxylic acid, racemic cis-2-{1-[4-(3,3-Difluoropiperidin-1-yl)benzyl]-6-[(5-methylpyridin-2-yl)methoxy]-1H-benzimidazol-2-yl}cyclohexanecarboxylic acid, racemic cis-2-{1-[4-(4,4-Difluoropiperidin-1-yl)benzyl]-6-[(5-methylpyridin-2-yl)methoxy]-1H-benzimidazol-2-yl}cyclohexanecarboxylic acid, 2-({1-[4-(3,3-Difluoropiperidin-1-yl)benzyl]-6-[(1-methyl-1H-pyrazol-3-yl)methoxy]-1H-benzimidazol-2-yl}methyl)-2-ethylbutanoic acid, racemic cis-2-{6-[(5-Methylpyridin-2-yl)methoxy]-1-(4-piperidin-1-ylbenzyl)-1H-benzimidazol-2-yl}cyclohexanecarboxylic acid, (1S*,2R*)-2-{6-[(5-Methylpyridin-2-yl)methoxy]-1-(4-piperidin-1-ylbenzyl)-1H-benzimidazol-2-yl}cyclohexanecarboxylic acid, (1R*,2S*)-2-{6-[(5-Methylpyridin-2-yl)methoxy]-1-(4-piperidin-1-ylbenzyl)-1H-benzimidazol-2-yl}cyclohexanecarboxylic acid, racemic cis-2-{1-[4-(3,3-Difluoroazetidin-1-yl)benzyl]-6-[(5-methylpyridin-2-yl)methoxy]-1H-benzimidazol-2-yl}cyclohexanecarboxylic acid, (1S*,2R*)-2-{1-[4-(3,3-Difluoroazetidin-1-yl)benzyl]-6-[(5-methylpyridin-2-yl)methoxy]-1H-benzimidazol-2-yl}cyclohexanecarboxylic acid, racemic cis-2-{1-[4-(4,4-Difluoropiperidin-1-yl)-2-fluorobenzyl]-6-[(5-methylpyridin-2-yl)methoxy]-1H-benzimidazol-2-yl}cyclohexanecarboxylic acid, racemic cis-2-{1-[4-(3,3-Difluoropyrrolidin-1-yl)-2-fluorobenzyl]-6-[(5-methylpyridin-2-yl)methoxy]-1H-benzimidazol-2-yl}cyclohexanecarboxylic acid, (1R*,2S*)-2-{1-[4-(3,3-Difluoropyrrolidin-1-yl)-2-fluorobenzyl]-6-[(5-methylpyridin-2-yl)methoxy]-1H-benzimidazol-2-yl}cyclohexanecarboxylic acid, (1S*,2R*)-2-{1-[4-(3,3-Difluoropyrrolidin-1-yl)-2-fluorobenzyl]-6-[(5-methylpyridin-2-yl)methoxy]-1H-benzimidazol-2-yl}cyclohexanecarboxylic acid, racemic cis-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid, (1R*,2S*)-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid, (1S*,2R*)-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid, racemic cis-2-{1-[4-(3,3-Difluoroazetidin-1-yl)benzyl]-4-fluoro-6-[(1-methyl-1H-pyrazol-3-yl)methoxy]-1H-benzimidazol-2-yl}cyclohexanecarboxylic acid as the formate salt, racemic cis-2-{4-Fluoro-6-[(1-methyl-1H-pyrazol-3-yl)methoxy]-1-(4-piperidin-1-ylbenzyl)-1H-benzimidazol-2-yl}cyclohexanecarboxylic acid as the HCl salt, 2-({1-[4-(4,4-Difluoropiperidin-1-yl)benzyl]-6-[(5-methylpyridin-2-yl)methoxy]-1H-benzimidazol-2-yl}methyl)-2-ethylbutanoic acid, racemic trans-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid, racemic cis-2-{1-[2,6-Difluoro-4-(4-fluoropiperidin-1-yl)benzyl]-6-[(3-fluoro-5-methylpyridin-2-yl)methoxy]-1H-benzimidazol-2-yl}cyclohexanecarboxylic acid, racemic cis-2-{1-[2-Fluoro-4-(4-fluoropiperidin-1-yl)benzyl]-6-[(3-fluoro-5-methylpyridin-2-yl)methoxy]-1H-benzimidazol-2-yl}cyclohexanecarboxylic acid, (1R*,2S*)-2-{1-[2-Fluoro-4-(4-fluoropiperidin-1-yl)benzyl]-6-[(3-fluoro-5-methylpyridin-2-yl)methoxy]-1H-benzimidazol-2-yl}cyclohexanecarboxylic acid, (1S*,2R*)-2-{1-[2-Fluoro-4-(4-fluoropiperidin-1-yl)benzyl]-6-[(3-fluoro-5-methylpyridin-2-yl)methoxy]-1H-benzimidazol-2-yl}cyclohexanecarboxylic acid, (1R*,2S*)-2-{6-[(3-Fluoro-5-methylpyridin-2-yl)methoxy]-1-[4-(4-fluoropiperidin-1-yl)benzyl]-1H-benzimidazol-2-yl}cyclohexanecarboxylic acid, racemic cis-2-{1-[2-Fluoro-4-(4-methylpiperidin-1-yl)benzyl]-6-[(3-fluoro-5-methylpyridin-2-yl)methoxy]-1H-benzimidazol-2-yl}cyclohexanecarboxylic acid, racemic cis-2-{6-[(3-Fluoro-5-methylpyridin-2-yl)methoxy]-1-[4-(4-methylpiperidin-1-yl)benzyl]-1H-benzimidazol-2-yl}cyclohexanecarboxylic acid, racemic cis-2-{6-[(3-Fluoro-5-methylpyridin-2-yl)methoxy]-1-(4-piperidin-1-ylbenzyl)-1H-benzimidazol-2-yl}cyclohexanecarboxylic acid, 2-Ethyl-2-({6-[(3-fluoro-5-methylpyridin-2-yl)methoxy]-1-[4-(4-methylpiperidin-1-yl)benzyl]-1H-benzimidazol-2-yl}methyl)butanoic acid, 2-Ethyl-2-({1-[2-fluoro-4-(4-methylpiperidin-1-yl)benzyl]-6-[(3-fluoro-5-methylpyridin-2-yl)methoxy]-1H-benzimidazol-2-yl}methyl)butanoic acid, 2-Ethyl-2-({6-[(3-fluoro-5-methylpyridin-2-yl)methoxy]-1-[4-(4-fluoropiperidin-1-yl)benzyl]-1H-benzimidazol-2-yl}methyl)butanoic acid, 3-(6-[(3-Fluoro-5-methylpyridin-2-yl)methoxy]-1-{2-fluoro-4-[3-(trifluoromethyl)azetidin-1-yl]benzyl}-1H-benzimidazol-2-yl)-2,2-dimethylpropanoic acid, 3-{1-[4-(4-tert-Butylpiperidin-1-yl)benzyl]-6-[(3-fluoro-5-methylpyridin-2-yl)methoxy]-1H-benzimidazol-2-yl}-2,2-dimethylpropanoic acid, 3-{6-[(3-Fluoro-5-methylpyridin-2-yl)methoxy]-1-[4-(4-methylpiperidin-1-yl)benzyl]-1H-benzimidazol-2-yl}-2,2-dimethylpropanoic acid, 3-{1-[2-Fluoro-4-(4-fluoropiperidin-1-yl)benzyl]-6-[(3-fluoro-5-methylpyridin-2-yl)methoxy]-1H-benzimidazol-2-yl}-2,2-dimethylpropanoic acid, 2-Ethyl-2-((1-((3-fluoro-4'-(trifluoromethyl)-[1,1'-biphenyl]-4-yl)methyl)-6-((1-methyl-1H-pyrazol-3-yl)methoxy)-1H-benzo[d]imidazol-2-yl)methyl)butanoic acid, 2-Ethyl-2-((6-((1-methyl-1H-pyrazol-3-yl)methoxy)-1-(4-(4-(trifluoromethyl)-[1,1'-biphenyl]-4-yl)methyl)-1H-benzo[d]imidazol-2-yl)methyl)butanoic acid, 2-Ethyl-2-((1-(2-fluoro-4-(4-(trifluoromethyl)piperidin-1-yl)benzyl)-6-((1-methyl-1H-pyrazol-3-yl)methoxy)-1H-benzo[d]imidazol-2-yl)methyl)butanoic acid, 2-Ethyl-2-((6-((1-methyl-1H-pyrazol-3-yl)methoxy)-1-(4-(4-(trifluoromethyl)piperidin-1-yl)benzyl)-1H-benzo[d]imidazol-2-yl)methyl) acid.

7. The compound of claim 6, selected from the group consisting of racemic cis-2-{1-(4-Bromobenzyl)-6-[(5-methylpyridin-2-yl)methoxy]-1H-benzimidazol-2-yl}cyclohexanecarboxylic acid, (1S,2R)-2-(1-(4-Bromobenzyl)-6-((5-methylpyridin-2-yl)methoxy)-1H-benzo[d]imidazol-2-yl)cyclohexanecarboxylic acid, (1R,2S)-2-{1-(4-Bromobenzyl)-6-[(5-methylpyridin-2-yl)methoxy]-1H-benzimidazol-2-yl}cyclohexanecarboxylic acid, racemic cis-2-{1-(4-Bromo-3-fluorobenzyl)-6-[(5-methylpyridin-2-yl)methoxy]-1H-benzimidazol-2-yl}cyclohexanecarboxylic acid as the TFA salt, racemic cis-2-{1-(4-Bromo-2-fluorobenzyl)-6-[(5-methylpyridin-2-yl)methoxy]-1H-benzimidazol-2-yl}cyclohexanecarboxylic acid, (1R*,2S*)-2-{1-(4-Bromo-2-fluorobenzyl)-6-[(5-methylpyridin-2-yl)methoxy]-1H-benzimidazol-2-yl}cyclohexanecarboxylic acid, (1S*,2R*)-2-{1-(4-Bromo-2-fluorobenzyl)-6-[(5-methylpyridin-2-yl)methoxy]-1H-benzimidazol-2-yl}cyclohexanecarboxylic acid, racemic cis-3-{1-(4-Bromo-2-fluorobenzyl)-6-[(5-methylpyridin-2-yl)methoxy]-1H-benzimidazol-2-yl}-2,2-dimethylcyclopropanecarboxylic acid, (1S*,3R*)-3-{1-(4-Bromo-2-fluorobenzyl)-6-[(5-methylpyridin-2-yl)methoxy]-1H-benzimidazol-2-yl}-2,2-dimethylcyclopropanecarboxylic acid, racemic cis-2-{1-[3-Fluoro-4-(trifluoromethoxy)benzyl]-6-[(5-methylpyridin-2-yl)methoxy]-1H-benzimidazol-2-yl}cyclohexanecarboxylic acid, racemic cis-2,2-Dimethyl-3-{6-[(5-methylpyridin-2-yl)methoxy]-1-[4-(trifluoromethoxy)benzyl]-1H-benzimidazol-2-yl}cyclopropanecarboxylic acid, racemic cis-2-{1-[2-Fluoro-4-(trifluoromethoxy)benzyl]-6-[(5-methylpyridin-2-yl)methoxy]-1H-benzimidazol-2-yl}cyclohexanecarboxylic acid, racemic cis-2-{6-[(5-Methylpyridin-2-yl)methoxy]-1-[4-(trifluoromethoxy)benzyl]-1H-benzimidazol-2-yl}cyclohexanecarboxylic acid, (1R*,2S*)-2-{6-[(5-Methylpyridin-2-yl)methoxy]-1-[4-(trifluoromethoxy)benzyl]-1H-benzimidazol-2-yl}cyclohexanecarboxylic acid, (1S*,2R*)-2-{6-[(5-Methylpyridin-2-yl)methoxy]-1-[4-(trifluoromethoxy)benzyl]-1H-benzimidazol-2-yl}cyclohexanecarboxylic acid, racemic cis-2-{1-[3-Chloro-4-(trifluoromethoxy)benzyl]-6-[(5-methylpyridin-2-yl)methoxy]-1H-benzimidazol-2-yl}cyclohexanecarboxylic acid, (1S*,2R*)-2-{6-[(1-Methyl-1H-pyrazol-3-yl)methoxy]-1-[4-(trifluoromethoxy)benzyl]-1H-benzimidazol-2-yl}cyclohexanecarboxylic acid, racemic cis-2-{1-(4-Cyanobenzyl)-6-[(5-methylpyridin-2-yl)methoxy]-1H-benzimidazol-2-yl}cyclohexanecarboxylic acid as the TFA salt, (1R*,2S*)-2-{1-(4-Cyanobenzyl)-6-[(5-methylpyridin-2-yl)methoxy]-1H-benzimidazol-2-yl}cyclohexanecarboxylic acid, racemic cis-2-{1-(4-Bromobenzyl)-6-[(1-methyl-1H-pyrazol-3-yl)methoxy]-1H-benzimidazol-2-yl}cyclohexanecarboxylic acid as the TFA salt, racemic cis-2-{6-[(1-Methyl-1H-pyrazol-3-yl)methoxy]-1-[4-(trifluoromethoxy)benzyl]-1H-benzimidazol-2-yl}cyclohexanecarboxylic acid, (1R*,2S*)-2-{6-[(1-Methyl-1H-pyrazol-3-yl)methoxy]-1-[4-(trifluoromethoxy)benzyl]-1H-benzimidazol-2-yl}cyclohexanecarboxylic acid, racemic cis-2-{1-(4-Cyanobenzyl)-6-[(1-methyl-1H-pyrazol-3-yl)methoxy]-1H-benzimidazol-2-yl}cyclohexanecarboxylic acid as the TFA salt, racemic cis-2-{1-[2-Fluoro-4-(trifluoromethoxy)benzyl]-6-[(1-methyl-1H-pyrazol-3-yl)methoxy]-1H-benzimidazol-2-yl}cyclohexanecarboxylic acid, (1R*,2S*)-2-(1-(2-Fluoro-4-(trifluoromethoxy)benzyl)-6-((1-methyl-1H-pyrazol-3-yl)methoxy)-1H-benzo[d]imidazol-2-yl)cyclohexanecarboxylic acid, racemic cis-2-{1-[3-Fluoro-4-(trifluoromethoxy)benzyl]-6-[(1-methyl-1H-pyrazol-3-yl)methoxy]-1H-benzimidazol-2-yl}cyclohexanecarboxylic acid, racemic cis-2-{1-(4-Bromobenzyl)-4-fluoro-6-[(5-methylpyridin-2-yl)methoxy]-1H-benzimidazol-2-yl}cyclohexanecarboxylic acid, racemic cis-3-{1-(4-Bromobenzyl)-4-fluoro-6-[(5-methylpyridin-2-yl)methoxy]-1H-benzimidazol-2-yl}-2,2-dimethylcyclopropanecarboxylic acid, racemic cis-3-{4-Fluoro-1-(4-methylbenzyl)-6-[(5-methylpyridin-2-yl)methoxy]-1H-benzimidazol-2-yl}-2,2-dimethylcyclopropanecarboxylic acid as the TFA salt, racemic cis-2-{4-Fluoro-6-[(5-methylpyridin-2-yl)methoxy]-1-[4-(trifluoromethoxy)benzyl]-1H-benzimidazol-2-yl}cyclohexanecarboxylic acid as the TFA salt, racemic cis-2-{4-Fluoro-1-(4-methylbenzyl)-6-[(5-methylpyridin-2-yl)methoxy]-1H-benzimidazol-2-yl}cyclohexanecarboxylic acid as the TFA salt, racemic cis-3-{4-Fluoro-6-[(5-methylpyridin-2-yl)methoxy]-1-[4-(trifluoromethoxy)benzyl]-1H-benzimidazol-2-yl}-2,2-dimethylcyclopropanecarboxylic acid as the TFA salt, racemic cis-2-{1-(4-Bromobenzyl)-4-chloro-6-[(5-methylpyridin-2-yl)methoxy]-1H-benzimidazol-2-yl}cyclohexanecarboxylic acid, racemic cis-3-{1-(4-Bromobenzyl)-4-chloro-6-[(5-methylpyridin-2-yl)methoxy]-1H-benzimidazol-2-yl}-2,2-dimethylcyclopropanecarboxylic acid, racemic cis-2-{1-[4-(5-Chloropyrimidin-2-yl)benzyl]-6-[(5-methylpyridin-2-yl)methoxy]-1H-benzimidazol-2-yl}cyclohexanecarboxylic acid, racemic cis-2-{1-(4-Bromobenzyl)-6-[(4-chloro-1-methyl-1H-pyrazol-3-yl)methoxy]-1H-benzimidazol-2-yl}cyclohexanecarboxylic acid, racemic cis-2-{6-[(4-Chloro-1-methyl-1H-pyrazol-3-yl)methoxy]-1-(4-piperidin-1-ylbenzyl)-1H-benzimidazol-2-yl}cyclohexanecarboxylic acid, racemic cis-2-{6-[(4-Chloro-1-methyl-1H-pyrazol-3-yl)methoxy]-1-[2-fluoro-4-(trifluoromethoxy)benzyl]-1H-benzimidazol-2-yl}cyclohexanecarboxylic acid, racemic cis-2-{1-[2-Methoxy-4-(trifluoromethoxy)benzyl]-6-[(1-methyl-1H-pyrazol-3-yl)methoxy]-1H-benzimidazol-2-yl}cyclohexanecarboxylic acid, racemic cis-2-{6-[(4-Fluoro-1-methyl-1H-pyrazol-3-yl)methoxy]-1-[2-fluoro-4-(trifluoromethoxy)benzyl]-1H-benzimidazol-2-yl}cyclohexanecarboxylic acid, racemic cis-2-{1-[4-(4,4-Difluoropiperidin-1-yl)benzyl]-6-[(1-methyl-1H-pyrazol-3-yl)methoxy]-1H-benzimidazol-2-yl}cyclohexanecarboxylic acid, racemic cis-2-{6-[(4-Chloro-1-methyl-1H-pyrazol-3-yl)methoxy]-1-[4-(4-fluoropiperidin-1-yl)benzyl]-1H-benzimidazol-2-yl}cyclohexanecarboxylic acid, racemic cis-2-{6-[(1-Methyl-1H-pyrazol-3-yl)methoxy]-1-(4-piperidin-1-ylbenzyl)-1H-benzimidazol-2-yl}cyclohexanecarboxylic acid, racemic cis-2-{1-[4-(3,3-Difluoroazetidin-1-yl)benzyl]-6-[(1-methyl-1H-pyrazol-3-yl)methoxy]-1H-benzimidazol-2-yl}cyclohexanecarboxylic acid, racemic cis-2-{5-Fluoro-1-[2-fluoro-4-(trifluoromethoxy)benzyl]-6-[(1-methyl-1H-pyrazol-3-yl)methoxy]-1H-benzimidazol-2-yl}cyclohexanecarboxylic acid, racemic cis-2-{7-Fluoro-1-[2-fluoro-4-(trifluoromethoxy)benzyl]-6-[(1-methyl-1H-pyrazol-3-yl)methoxy]-1H-benzimidazol-2-yl}cyclohexanecarboxylic acid, racemic cis-2-{1-(4-Bromobenzyl)-4-fluoro-6-[(1-methyl-1H-pyrazol-3-yl)methoxy]-1H-benzimidazol-2-yl}cyclohexanecarboxylic acid, racemic cis-2-{1-(4-Bromo-2-fluorobenzyl)-4-fluoro-6-[(1-methyl-1H-pyrazol-3-yl)methoxy]-1H-benzimidazol-2-yl}cyclohexanecarboxylic acid, racemic cis-2-{4-Fluoro-6-[(1-methyl-1H-pyrazol-3-yl)methoxy]-1-[4-(trifluoromethoxy)benzyl]-1H-benzimidazol-2-yl}cyclohexanecarboxylic acid as the HCl salt, racemic cis-2-{4-Fluoro-1-[2-fluoro-4-(trifluoromethoxy)benzyl]-6-[(1-methyl-1H-pyrazol-3-yl)methoxy]-1H-benzimidazol-2-yl}cyclohexanecarboxylic acid as the HCl salt, racemic cis-2-{4-Fluoro-1-(4-methylbenzyl)-6-[(1-methyl-1H-pyrazol-3-yl)methoxy]-1H-benzimidazol-2-yl}cyclohexanecarboxylic acid as the HCl salt, racemic cis-2-{1-(4-Cyanobenzyl)-4-fluoro-6-[(1-methyl-1H-pyrazol-3-yl)methoxy]-1H-benzimidazol-2-yl}cyclohexanecarboxylic acid as the HCl salt, racemic cis-2-{6-[(1-Methyl-1H-pyrazol-3-yl)methoxy]-1-[2-methyl-4-(trifluoromethoxy)benzyl]-1H-benzimidazol-2-yl}cyclohexanecarboxylic acid, racemic cis-2-{6-[(5-Methylpyridin-2-yl)methoxy]-1-[2-methyl-4-(trifluoromethoxy)benzyl]-1H-benzimidazol-2-yl}cyclohexanecarboxylic acid, racemic cis-2-{1-[2-Chloro-4-(trifluoromethoxy)benzyl]-6-[(5-methylpyridin-2-yl)methoxy]-1H-benzimidazol-2-yl}cyclohexanecarboxylic acid as the HCl salt, racemic cis-2-{1-[2-Bromo-4-(trifluoromethoxy)benzyl]-6-[(5-methylpyridin-2-yl)methoxy]-1H-benzimidazol-2-yl}cyclohexanecarboxylic acid as the HCl salt, racemic cis-2-{1-[2-Chloro-4-(trifluoromethoxy)benzyl]-6-[(1-methyl-1H-pyrazol-3-yl)methoxy]-1H-benzimidazol-2-yl}cyclohexanecarboxylic acid as the HCl salt, racemic cis-2-{1-[2-Bromo-4-(trifluoromethoxy)benzyl]-6-[(1-methyl-1H-pyrazol-3-yl)methoxy]-1H-benzimidazol-2-yl}cyclohexanecarboxylic acid as the HCl salt, racemic cis-2-{6-[(1-Methyl-1H-pyrazol-3-yl)methoxy]-1-[3-methyl-4-(trifluoromethoxy)benzyl]-1H-benzimidazol-2-yl}cyclohexanecarboxylic acid as the HCl salt, racemic cis-2-{6-[(5-Methylpyridin-2-yl)methoxy]-1-[3-methyl-4-(trifluoromethoxy)benzyl]-1H-benzimidazol-2-yl}cyclohexanecarboxylic acid, racemic cis-2-{5-Chloro-1-[2-fluoro-4-(trifluoromethoxy)benzyl]-6-[(5-methylpyridin-2-yl)methoxy]-1H-benzimidazol-2-yl}cyclohexanecarboxylic acid as the HCl salt, racemic cis-3-{1-(4-Bromobenzyl)-6-[(5-methylpyridin-2-yl)methoxy]-1H-benzimidazol-2-yl}-2,2-dimethylcyclopropanecarboxylic acid as the TFA salt, (1S*,3R*)-3-{1-(4-Bromobenzyl)-6-[(5-methylpyridin-2-yl)methoxy]-1H-benzimidazol-2-yl}-2,2-dimethylcyclopropanecarboxylic acid, (1R*,3S*)-3-{1-(4-Bromobenzyl)-6-[(5-methylpyridin-2-yl)methoxy]-1H-benzimidazol-2-yl}-2,2-dimethylcyclopropanecarboxylic acid, racemic cis-2-{1-(4-Methylbenzyl)-6-[(5-methylpyridin-2-yl)methoxy]-1H-benzimidazol-2-yl}cyclohexanecarboxylic acid, racemic cis-2,2-Dimethyl-3-{1-(4-methylbenzyl)-6-[(5-methylpyridin-2-yl)methoxy]-1H-benzimidazol-2-yl}cyclopropanecarboxylic acid, racemic cis-2,2-Dimethyl-3-{6-[(1-methyl-1H-pyrazol-3-yl)methoxy]-1-[4-(trifluoromethoxy)benzyl]-1H-benzimidazol-2-yl}cyclopropanecarboxylic acid, racemic cis-2-{1-(4-Bromo-2,6-difluorobenzyl)-6-[(3-fluoro-5-methylpyridin-2-yl)methoxy]-1H-benzimidazol-2-yl}cyclohexanecarboxylic acid, racemic cis-2-{1-(4-Bromobenzyl)-6-[(3-fluoro-5-methylpyridin-2-yl)methoxy]-1H-benzimidazol-2-yl}cyclohexanecarboxylic acid, racemic cis-2-{1-(4-Bromo-2,6-difluorobenzyl)-6-[(5-methylpyridin-2-yl)methoxy]-1H-benzimidazol-2-yl}cyclohexanecarboxylic acid, racemic cis-3-{1-(4-Bromobenzyl)-6-[(3-fluoro-5-methylpyridin-2-yl)methoxy]-1H-benzimidazol-2-yl}-2,2-dimethylcyclopropanecarboxylic acid, racemic cis-3-{1-(4-Bromobenzyl)-6-[(6-methylpyridin-2-yl)methoxy]-1H-benzimidazol-2-yl}-2,2-dimethylcyclopropanecarboxylic acid, racemic cis-3-{1-(4-Bromobenzyl)-6-[(1-methyl-1H-pyrazol-3-yl)methoxy]-1H-benzimidazol-2-yl}-2,2-dimethylcyclopropanecarboxylic acid, racemic cis-2-(1-((3,5-Difluoro-4'-(trifluoromethyl)-[1,1'-biphenyl]-4-yl)methyl)-6-((3-fluoro-5-methylpyridin-2-yl)methoxy)-1H-benzo[d]imidazol-2-yl)cyclohexanecarboxylic acid, racemic cis-2-(1-{[3,5-Difluoro-4'-(trifluoromethyl)biphenyl-4-yl]methyl}-6-[(5-methylpyridin-2-yl)methoxy]-1H-benzimidazol-2-yl)cyclohexanecarboxylic acid, (1R*,2S*)-2-(6-[(3-Fluoro-5-methylpyridin-2-yl)methoxy]-1-{[4'-(trifluoromethyl)biphenyl-4-yl]methyl}-1H-benzimidazol-2-yl)cyclohexanecarboxylic acid, racemic cis-2-{1-[4-(2-Methoxypyrimidin-5-yl)benzyl]-6-[(5-methylpyridin-2-yl)methoxy]-1H-benzimidazol-2-yl}cyclohexanecarboxylic acid, racemic cis-2-(6-[(5-Methylpyridin-2-yl)methoxy]-1-{[4'-(trifluoromethyl)biphenyl-3-yl]methyl}-1H-benzimidazol-2-yl)cyclohexanecarboxylic acid, racemic cis-2-(6-[(5-Methylpyridin-2-yl)methoxy]-1-{[4'-(trifluoromethyl)biphenyl-4-yl]methyl}-1H-benzimidazol-2-yl)cyclohexanecarboxylic acid, (1S,2R)-2-(6-((5-Methylpyridin-2-yl)methoxy)-1-((4'-(trifluoromethyl)-[1,1'-biphenyl]-4-yl)methyl)-1H-benzo[d]imidazol-2-yl)cyclohexanecarboxylic acid, (1R,2S)-2-(6-[(5-Methylpyridin-2-yl)methoxy)-1-{[4'-(trifluoromethyl)biphenyl-4-yl]methyl}-1H-benzimidazol-2-yl)cyclohexanecarboxylic acid, racemic cis-2-(6-[(1-Methyl-1H-pyrazol-3-yl)methoxy]-1-{[4'-(trifluoromethyl)biphenyl-3-yl]methyl}-1H-benzimidazol-2-yl)cyclohexanecarboxylic acid, racemic cis-2-(6-[(4-Chloro-1-methyl-1H-pyrazol-3-yl)methoxy]-1-{[4'-(trifluoromethyl)biphenyl-4-yl]methyl}-1H-benzimidazol-2-yl)cyclohexanecarboxylic acid, racemic cis-2-{1-[4-(3,3-Difluoropyrrolidin-1-yl)benzyl]-6-[(5-methylpyridin-2-yl)methoxy]-1H-benzimidazol-2-yl}cyclohexanecarboxylic acid, racemic cis-2-{1-[4-(3,3-Difluoropiperidin-1-yl)benzyl]-6-[(5-methylpyridin-2-yl)methoxy]-1H-benzimidazol-2-yl}cyclohexanecarboxylic acid, racemic cis-2-{1-[4-(4,4-Difluoropiperidin-1-yl)benzyl]-6-[(5-methylpyridin-2-yl)methoxy]-1H-benzimidazol-2-yl}cyclohexanecarboxylic acid, racemic cis-2-{6-[(5-Methylpyridin-2-yl)methoxy]-1-(4-piperidin-1-ylbenzyl)-1H-benzimidazol-2-yl}cyclohexanecarboxylic acid, (1S*,2R*)-2-{6-[(5-Methylpyridin-2-yl)methoxy]-1-(4-piperidin-1-ylbenzyl)-1H-benzimidazol-2-yl}cyclohexanecarboxylic acid, (1R*,2S*)-2-{6-[(5-Methylpyridin-2-yl)methoxy]-1-(4-piperidin-1-ylbenzyl)-1H-benzimidazol-2-yl}cyclohexanecarboxylic acid, racemic cis-2-{1-[4-(3,3-Difluoroazetidin-1-yl)benzyl]-6-[(5-methylpyridin-2-yl)methoxy]-1H-benzimidazol-2-yl}cyclohexanecarboxylic acid, (1S*,2R*)-2-{1-[4-(3,3-Difluoroazetidin-1-yl)benzyl]-6-[(5-methylpyridin-2-yl)methoxy]-1H-benzimidazol-2-yl}cyclohexanecarboxylic acid, racemic cis-2-{1-[4-(4,4-Difluoropiperidin-1-yl)-2-fluorobenzyl]-6-[(5-methylpyridin-2-yl)methoxy]-1H-benzimidazol-2-yl}cyclohexanecarboxylic acid, racemic cis-2-{1-[4-(3,3-Difluoropyrrolidin-1-yl)-2-fluorobenzyl]-6-[(5-methylpyridin-2-yl)methoxy]-1H-benzimidazol-2-yl}cyclohexanecarboxylic acid, (1R*,2S*)-2-{1-[4-(3,3-Difluoropyrrolidin-1-yl)-2-fluorobenzyl]-6-[(5-methylpyridin-2-yl)methoxy]-1H-benzimidazol-2-yl}cyclohexanecarboxylic acid, (1S*,2R*)-2-{1-[4-(3,3-Difluoropyrrolidin-1-yl)-2-fluorobenzyl]-6-[(5-methylpyridin-2-yl)methoxy]-1H-benzimidazol-2-yl}cyclohexanecarboxylic acid, racemic cis-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid, (1R*,2S*)-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid, (1S*,2R*)-2-{1-[4-(3,3-Difluoroazetidin-1-yl)-2-fluorobenzyl]-6-[(5-methylpyridin-2-yl)methoxy]-1H-benzimidazol-2-yl}cyclohexanecarboxylic acid, racemic cis-2-{1-[4-(3,3-Difluoroazetidin-1-yl)benzyl]-4-fluoro-6-[(1-methyl-1H-pyrazol-3-yl)methoxy]-1H-benzimidazol-2-yl}cyclohexanecarboxylic acid as the formate salt, racemic cis-2-{4-Fluoro-6-[(1-methyl-1H-pyrazol-3-yl)methoxy]-1-(4-piperidin-1-ylbenzyl)-1H-benzimidazol-2-yl}cyclohexanecarboxylic acid as the HCl salt, racemic cis-2-{1-[2,6-Difluoro-4-(4-fluoropiperidin-1-yl)benzyl]-6-[(3-fluoro-5-methylpyridin-2-yl)methoxy]-1H-benzimidazol-2-yl}cyclohexanecarboxylic acid, racemic cis-2-{1-[2-Fluoro-4-(4-fluoropiperidin-1-yl)benzyl]-6-[(3-fluoro-5-methylpyridin-2-yl)methoxy]-1H-benzimidazol-2-yl}cyclohexanecarboxylic acid, (1R*,2S*)-2-{1-[2-Fluoro-4-(4-fluoropiperidin-1-yl)benzyl]-6-[(3-fluoro-5-methylpyridin-2-yl)methoxy]-1H-benzimidazol-2-yl}cyclohexanecarboxylic acid, (1S*,2R*)-2-{1-[2-Fluoro-4-(4-fluoropiperidin-1-yl)benzyl]-6-[(3-fluoro-5-methylpyridin-2-yl)methoxy]-1H-benzimidazol-2-yl}cyclohexanecarboxylic acid, (1R*,2S*)-2-{6-[(3-Fluoro-5-methylpyridin-2-yl)methoxy]-1-[4-(4-fluoropiperidin-1-yl)benzyl]-1H-benzimidazol-2-yl}cyclohexanecarboxylic acid, racemic cis-2-{1-[2-Fluoro-4-(4-methylpiperidin-1-yl)benzyl]-6-[(3-fluoro-5-methylpyridin-2-yl)methoxy]-1H-benzimidazol-2-yl}cyclohexanecarboxylic acid, and racemic cis-2-{6-[(3-Fluoro-5-methylpyridin-2-yl)methoxy]-1-[4-(4-methylpiperidin-1-yl)benzyl]-1H-benzimidazol-2-yl}cyclohexanecarboxylic acid, racemic cis-2-{6-[(3-Fluoro-5-methylpyridin-2-yl)methoxy]-1-(4-piperidin-1-ylbenzyl)-1H-benzimidazol-2-yl}cyclohexanecarboxylic acid.

8. The compound of claim 1 selected from the group consisting of:

3-{1-(3-Bromobenzyl)-6-[(3-fluoro-5-methylpyridin-2-yl)methoxy]-1H-benzimidazol-2-yl}-2,2-dimethylpropanoic acid, racemic cis-2-(6-[(3-Fluoro-5-methylpyridin-2-yl)methoxy]-1-{2-fluoro-4-[4-(trifluoromethyl)piperidin-1-yl]benzyl}-1H-benzimidazol-2-yl)cyclohexanecarboxylic acid, 3-{1-(5-Bromo-2-fluorobenzyl)-6-[(3-fluoro-5-methylpyridin-2-yl)methoxy]-1H-benzimidazol-2-yl}-2,2-dimethylpropanoic acid, 2-Ethyl-2-[(6-[(3-fluoro-5-methylpyridin-2-yl)methoxy]-1-{4-[4-(trifluoromethyl)piperidin-1-yl]benzyl}-1H-benzimidazol-2-yl)methyl]butanoic acid, racemic cis-2-{1-[3-(2-Methoxypyrimidin-5-yl)benzyl]-6-[(5-methylpyridin-2-yl)methoxy]-1H-benzimidazol-2-yl}cyclohexanecarboxylic acid, 2-Ethyl-2-({1-[3-(2-methoxypyrimidin-5-yl)benzyl]-6-[(5-methylpyridin-2-yl)methoxy]-1H-benzimidazol-2-yl}methyl)butanoic acid, (1S*,2R*)-2-{1-(3-Bromobenzyl)-6-[(1-methyl-1H-pyrazol-3-yl)methoxy]-1H-benzimidazol-2-yl}cyclohexanecarboxylic acid, (1R*,2S*)-2-{1-(3-Bromobenzyl)-6-[(1-methyl-1H-pyrazol-3-yl)methoxy]-1H-benzimidazol-2-yl}cyclohexanecarboxylic acid, racemic cis-2-{1-(3-Cyanobenzyl)-6-[(1-methyl-1H-pyrazol-3-yl)methoxy]-1H-benzimidazol-2-yl}cyclohexanecarboxylic acid, racemic trans-2-{1-(3-Methylbenzyl)-6-[(5-methylpyridin-2-yl)methoxy]-1H-benzimidazol-2-yl}cyclohexanecarboxylic acid, racemic cis-2-{1-(3-Methylbenzyl)-6-[(5-methylpyridin-2-yl)methoxy]-1H-benzimidazol-2-yl}cyclohexanecarboxylic acid, racemic cis-2,2-Dimethyl-3-{1-(3-methylbenzyl)-6-[(5-methylpyridin-2-yl)methoxy]-1H-benzimidazol-2-yl}cyclopropanecarboxylic acid, racemic cis-2-{1-[3-(4,4-Difluoropiperidin-1-yl)benzyl]-6-[(1-methyl-1H-pyrazol-3-yl)methoxy]-1H-benzimidazol-2-yl}cyclohexanecarboxylic acid, racemic cis-2-{6-[(1-Methyl-1H-pyrazol-3-yl)methoxy]-1-(3-piperidin-1-ylbenzyl)-1H-benzimidazol-2-yl}cyclohexanecarboxylic acid, racemic cis-2-{1-[3-(3,3-Difluoroazetidin-1-yl)benzyl]-6-[(1-methyl-1H-pyrazol-3-yl)methoxy]-1H-benzimidazol-2-yl}cyclohexanecarboxylic acid as the trifluoroacetic acid salt, racemic trans-2-{1-(2-Methylbenzyl)-6-[(5-methylpyridin-2-yl)methoxy]-1H-benzimidazol-2-yl}cyclohexanecarboxylic acid, racemic cis-2-{1-(2-Methylbenzyl)-6-[(5-methylpyridin-2-yl)methoxy]-1H-benzimidazol-2-yl}cyclohexanecarboxylic acid, racemic cis-2-{1-[5-(4,4-Difluoropiperidin-1-yl)-2-fluorobenzyl]-6-[(5-methylpyridin-2-yl)methoxy]-1H-benzimidazol-2-yl}cyclohexanecarboxylic acid, racemic cis-2-{1-(2-Fluoro-5-piperidin-1-ylbenzyl)-6-[(5-methylpyridin-2-yl)methoxy]-1H-benzimidazol-2-yl}cyclohexanecarboxylic acid, racemic cis-2,2-Dimethyl-3-{1-(2-methylbenzyl)-6-[(5-methylpyridin-2-yl)methoxy]-1H-benzimidazol-2-yl}cyclopropanecarboxylic acid, 2-({1-[3-(3,3-Difluoropyrrolidin-1-yl)benzyl]-6-[(1-methyl-1H-pyrazol-3-yl)methoxy]-1H-benzimidazol-2-yl}methyl)-2-ethylbutanoic acid, 2-Ethyl-2-({6-[(1-methyl-1H-pyrazol-3-yl)methoxy]-1-(3-piperidin-1-ylbenzyl)-1H-benzimidazol-2-yl}methyl)butanoic acid, 2-Ethyl-2-({1-[3-(2-methoxypyrimidin-5-yl)benzyl]-6-[(1-methyl-1H-pyrazol-3-yl)methoxy]-1H-benzimidazol-2-yl}methyl)butanoic acid, 2-Ethyl-2-({1-[2-fluoro-4-(2-methoxypyrimidin-5-yl)benzyl]-6-[(1-methyl-1H-pyrazol-3-yl)methoxy]-1H-benzimidazol-2-yl}methyl)butanoic acid, 2-({1-(3-Bromobenzyl)-6-[(1-methyl-1H-pyrazol-3-yl)methoxy]-1H-benzimidazol-2-yl}methyl)-2-ethylbutanoic acid, 2-({1-[4-(3,3-Difluoropyrrolidin-1-yl)benzyl]-6-[(1-methyl-1H-pyrazol-3-yl)methoxy]-1H-benzimidazol-2-yl}methyl)-2-ethylbutanoic acid, racemic trans-2-{1-(3-Bromobenzyl)-6-[(5-methylpyridin-2-yl)methoxy]-1H-benzimidazol-2-yl}cyclohexanecarboxylic acid, racemic trans-2-{1-(5-Bromo-2-fluorobenzyl)-6-[(5-methylpyridin-2-yl)methoxy]-1H-benzimidazol-2-yl}cyclohexanecarboxylic acid, racemic cis-2-{1-[3-(3,3-Difluoroazetidin-1-yl)benzyl]-6-[(5-methylpyridin-2-yl)methoxy]-1H-benzimidazol-2-yl}cyclohexanecarboxylic acid, racemic cis-2-{1-[3-(3,3-Difluoropyrrolidin-1-yl)benzyl]-6-[(5-methylpyridin-2-yl)methoxy]-1H-benzimidazol-2-yl}cyclohexanecarboxylic acid, racemic cis-2-{1-[3-(4,4-Difluoropiperidin-1-yl)benzyl]-6-[(5-methylpyridin-2-yl)methoxy]-1H-benzimidazol-2-yl}cyclohexanecarboxylic acid, racemic cis-2-{1-[3-(3,3-Difluoropiperidin-1-yl)benzyl]-6-[(5-methylpyridin-2-yl)methoxy]-1H-benzimidazol-2-yl}cyclohexanecarboxylic acid, racemic cis-2-{6-[(5-Methylpyridin-2-yl)methoxy]-1-(3-piperidin-1-ylbenzyl)-1H-benzimidazol-2-yl}cyclohexanecarboxylic acid, racemic trans-2-{6-[(5-Methylpyridin-2-yl)methoxy]-1-(3-piperidin-1-ylbenzyl)-1H-benzimidazol-2-yl}cyclohexanecarboxylic acid, 3-{1-(5-Bromo-2-fluorobenzyl)-6-[(5-methylpyridin-2-yl)methoxy]-1H-benzimidazol-2-yl}-2,2-dimethylpropanoic acid, 2-({1-[4-(3,3-Difluoropyrrolidin-1-yl)benzyl]-6-[(5-methylpyridin-2-yl)methoxy]-1H-benzimidazol-2-yl}methyl)-2-ethylbutanoic acid, racemic cis-3-{1-(5-Bromo-2-fluorobenzyl)-6-[(5-methylpyridin-2-yl)methoxy]-1H-benzimidazol-2-yl}-2,2-dimethylcyclopropanecarboxylic acid, racemic cis-2-{1-(3-Bromobenzyl)-6-[(5-methylpyridin-2-yl)methoxy]-1H-benzimidazol-2-yl}cyclohexanecarboxylic acid, racemic-cis-2-{1-(5-Bromo-2-fluorobenzyl)-6-[(5-methylpyridin-2-yl)methoxy]-1H-benzimidazol-2-yl}cyclohexanecarboxylic acid, 1-({1-(3-Bromobenzyl)-4-fluoro-6-[(5-methylpyridin-2-yl)methoxy]-1H-benzimidazol-2-yl}methyl)cyclopentanecarboxylic acid as the trifluoroacetic salt, 1-({1-(2-Bromobenzyl)-4-fluoro-6-[(5-methylpyridin-2-yl)methoxy]-1H-benzimidazol-2-yl}methyl)cyclopentanecarboxylic acid as the trifluoroacetic salt, 3-{1-(3-Bromobenzyl)-6-[(5-methylpyridin-2-yl)methoxy]-1H-benzimidazol-2-yl}-2,2-dimethylpropanoic acid as the trifluoroacetic acid salt, racemic cis-2-{1-(5-Bromo-2-fluorobenzyl)-6-[(1-methyl-1H-pyrazol-3-yl)methoxy]-1H-benzimidazol-2-yl}cyclohexanecarboxylic acid, 2-({1-(5-Bromo-2-fluorobenzyl)-6-[(1-methyl-1H-pyrazol-3-yl)methoxy]-1H-benzimidazol-2-yl}methyl)-2-ethylbutanoic acid, 2-({1-(5-Bromo-2-fluorobenzyl)-6-[(5-methylpyridin-2-yl)methoxy]-1H-benzimidazol-2-yl}methyl)-2-ethylbutanoic acid, and racemic cis-2-{1-[4-(3,3-Difluoropyrrolidin-1-yl)benzyl]-4-fluoro-6-[(1-methyl-1H-pyrazol-3-yl)methoxy]-1H-benzimidazol-2-yl}cyclohexanecarboxylic acid.

9. A pharmaceutical composition comprising a therapeutically effective amount of at least one compound of claim 1 and at least one pharmaceutically acceptable carrier.

10. A pharmaceutical composition comprising a therapeutically effective amount of at least one compound of claim 6 and at least one pharmaceutically acceptable carrier.

11. A pharmaceutical composition comprising a therapeutically effective amount of at least one compound of claim 8 and at least one pharmaceutically acceptable carrier.

12. A method of treating a subject suffering from or diagnosed with a disease and/or disorder mediated by FLAP activity, wherein the disease and/or disorder is selected from the group consisting of respiratory, cardiac and cardiovascular, autoimmune and allergic, carcinogenesis disease and/or disorder, and associated symptoms or complications thereof, comprising administering to the subject a therapeutically effective amount of at least one compound of claim 1.

13. The method according to claim 12, wherein the respiratory disease and/or disorder is selected from the group consisting of exacerbations, non-allergic asthma, fibrotic lung diseases, acute respiratory distress syndrome and chronic obstructive pulmonary disease, or associated symptoms or complications thereof.

14. The method according to claim 12, wherein the cardiac and cardiovascular disease and/or disorder is selected from the group consisting of myocardial infarction, atherosclerosis, atherosclerosis and stroke aortic aneurisms, or associated symptoms or complications thereof.

15. The method according to claim 12, wherein the autoimmune and allergic disease and/or disorder is selected from the group consisting of rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis, allergic rhinitis, allergic dermatitis and asthma, or associated symptoms or complications thereof.

16. The method according to claim 12, wherein the carcinogenesis disease and/or disorder is selected from the group consisting of tumor cell proliferation, differentiation, apoptosis, tumor-associated angiogenesis, and the migration or invasion of carcinoma cells.

17. The method according to claim 12, wherein the therapeutically effective amount of the compound of Formula (I) is from about 0.1 mg/dose to about 5 g/dose.

18. A process for making a pharmaceutical composition comprising admixing a therapeutically effective amount of any of the compounds according to claim 1 and a pharmaceutically acceptable carrier.

19. A process for making racemic cis-2-(1-(4-bromobenzyl)-6-((5-methylpyridin-2-yl)methoxy)-1H-benzo[d]imidazol-2-yl)cyclohexanecarboxylic acid comprising the following reaction:

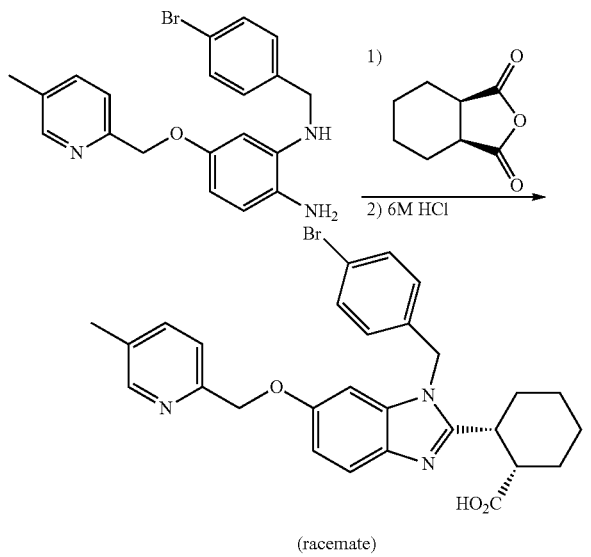

(racemate)

wherein the hexahydroisobenzofuran-1,3-dione is reacted at a temperature between 0° C. and 80° C., and the HCl is reacted at a temperature between 50° C. and 90° C.; wherein the product is formed in at least 75% yield, and the cis:trans ratio is at least 90%.

20. The compound of claim 1, selected from the group consisting of:
racemic cis-2-{1-(4-Bromobenzyl)-6-[(5-methylpyridin-2-yl) methoxy]-1H-benzimidazol-2-yl}cyclohexanecarboxylic acid,
(1S,2R)-2-(1-(4-Bromobenzyl)-6-((5-methylpyridin-2-yl) methoxy)-1H-benzo[d]imidazol-2-yl)cyclohexanecarboxylic acid,
(1R,2S)-2-{1-(4-Bromobenzyl)-6-[(5-methylpyridin-2-yl) methoxy]-1H-benzimidazol-2-yl}cyclohexanecarboxylic acid,
racemic cis-2-{1-(4-Bromo-3-fluorobenzyl)-6-[(5-methylpyridin-2-yl) methoxy]-1H-benzimidazol-2-yl}cyclohexanecarboxylic acid,
racemic trans-2-{1-(4-Bromobenzyl)-6-[(5-methylpyridin-2-yl) methoxy]-1H-benzimidazol-2-yl}cyclohexanecarboxylic acid,
(1S*,2S*)-2-{1-(4-Bromobenzyl)-6-[(methylpyridin-2-yl) methoxy]-1H-benzimidazol-2-yl}cyclohexanecarboxylic acid,
(1R*,2R*)-2-{1-(4-Bromobenzyl)-6-[(5-methylpyridin-2-yl) methoxy]-1H-benzimidazol-2-yl}cyclohexanecarboxylic acid,
2-({1-(4-Bromobenzyl)-6-[(5-methylpyridin-2-yl) methoxy]-1H-benzimidazol-2-yl}methyl)-2-ethylbutanoic acid,
racemic cis-2-{1-(4-Bromo-3-fluorobenzyl)-6-[(5-methylpyridin-2-yl) methoxy]-1H-benzimidazol-2-yl}cyclohexanecarboxylic acid,
racemic trans-2-{1-(4-Bromobenzyl)-6-[(5-methylpyridin-2-yl) methoxy]-1H-benzimidazol-2-yl}cyclohexanecarboxylic acid,
(1S*,2S*)-2-{1-(4-Bromobenzyl)-6-[(methylpyridin-2-yl) methoxy]-1H-benzimidazol-2-yl}cyclohexanecarboxylic acid,
(1R*,2R*)-2-{1-(4-Bromobenzyl)-6-[(5-methylpyridin-2-yl) methoxy]-1H-benzimidazol-2-yl}cyclohexanecarboxylic acid,
2-({1-(4-Bromobenzyl)-6-[(5-methylpyridin-2-yl) methoxy]-1H-benzimidazol-2-yl}methyl)-2-ethylbutanoic acid,
racemic cis-3-{1-(4-Bromo-2-fluorobenzyl)-6-[(5-methylpyridin-2-yl) methoxy]-1H-benzimidazol-2-yl}-2,2-dimethylcyclopropanecarboxylic acid,
(1S*,3R*)-3-{1-(4-Bromo-2-fluorobenzyl)-6-[(5-methylpyridin-2-yl) methoxy]-1H-benzimidazol-2-yl}-2,2-dimethylcyclopropanecarboxylic acid,
(1R*,3S*)-3-{1-(4-Bromo-2-fluorobenzyl)-6-[(5-methylpyridin-2-yl) methoxy]-1H-benzimidazol-2-yl}-2,2-dimethylcyclopropanecarboxylic acid,
racemic trans-2-{1-(4-Cyanobenzyl)-6-[(5-methylpyridin-2-yl) methoxy]-1H-benzimidazol-2-yl}cyclohexanecarboxylic acid,
2-({1-(4-Cyanobenzyl)-6-[(5-methylpyridin-2-yl) methoxy]-1H-benzimidazol-2-yl}methyl)-2-ethylbutanoic acid,
racemic cis-2-{1-[3-Fluoro-4-(trifluoromethoxy)benzyl]-6-[(5-methylpyridin-2-yl) methoxy]-1H-benzimidazol-2-yl}cyclohexanecarboxylic acid,
racemic trans-2-{1[2-Fluoro-4-(trifluoromethoxy)benzyl]-6-[(5-methylpyridin-2-yl) methoxy]-1H-benzimidazol-2-yl}cyclohexanecarboxylic acid,
2-Ethyl-2-({6-[(5-methylpyridin-2-yl)methoxy]-1-[4-(trifluoromethoxy) benzyl]-1H-benzimidazol-2-yl}methyl)butanoic acid,
2-Ethyl-2-({1-[2-fluoro-4-(trifluoromethoxy)benzyl]-6-[(5-methylpyridin-2-yl) methoxy]-1H-benzimidazol-2-yl}methyl)butanoic acid,
2-({1-[3-Chloro-4-(trifluoromethoxy)benzyl]-6-[(5-methylpyridin-2-yl) methoxy]-1H-benzimidazol-2-yl}methyl)-2-ethylbutanoic acid,
racemic cis-2,2-Dimethyl-3-{6-[(5-methylpyridin-2-yl) methoxy]-1-[4-(trifluoromethoxy) benzyl]-1H-benzimidazol-2-yl}cyclopropanecarboxylic acid,
racemic cis-2-{1-[2-Fluoro-4-(trifluoromethoxy)benzyl]-6-[(5-methylpyridin-2-yl) methoxy]-1H-benzimidazol-2-yl}cyclohexanecarboxylic acid,
racemic cis-2-{6-[(5-Methylpyridin-2-yl)methoxy]-1-[4-(trifluoromethoxy) benzyl]-1H-benzimidazol-2-yl}cyclohexanecarboxylic acid,
(1R*,2S*)-2-{6-[(5-Methylpyridin-2-yl)methoxy]-1-[4-(trifluoromethoxy) benzyl]-1H-benzimidazol-2-yl}cyclohexanecarboxylic acid, (1S*,2R*)-2-{6-[(5-Methylpyridin-2-yl)methoxy]-1-[4-(trifluoromethoxy) benzyl]-1H-benzimidazol-2-yl}cyclohexanecarboxylic acid, 2-Ethyl-2-({1-[3-fluoro-4-(trifluoromethoxy)benzyl]-6-[(5-methylpyridin-2-yl) methoxy]-1H-benzimidazol-2-yl}methyl)butanoic acid, racemic trans-2-{6-[(5-Methylpyridin-2-yl)methoxy]-1-[4-(trifluoromethoxy) benzyl]-1H-benzimidazol-2-yl}cyclohexanecarboxylic acid, racemic cis-2-{1-[3-Chloro-4-(trifluoromethoxy)benzyl]-6-[(5-methylpyridin-2-yl) methoxy]-1H-benzimidazol-2-yl}cyclohexanecarboxylic acid, racemic trans-2-(6-[(5-Methylpyridin-2-yl)methoxy]-1-{[4'-(trifluoromethyl) biphenyl-4-yl]methyl}-1H-benzimidazol-2-yl)cyclohexanecarboxylic acid, (1R*,2R*)-2-(6-[(5-Methylpyridin-2-yl)methoxy]-1-{[4'-(trifluoromethyl) biphenyl-4-yl]methyl}1H-benzimidazol-2-yl)cyclohexanecarboxylic acid, (1S*,2S*)-2-(6-[(5-Methylpyridin-2-yl)methoxy]-1-{[4'-(trifluoromethyl) biphenyl-4-yl]methyl}-1H-benzimidazol-2-yl)cyclohexanecarboxylic acid, (1S*,2R*)-2-{6-[(1-Methyl-1H-pyrazol-3-yl)methoxy]-1-[4-(trifluoromethoxy) benzyl]-1H-benzimidazol-2-yl}cyclohexanecarboxylic acid, racemic cis-2-{1-(4-Cyanobenzyl)-6-[(5-methylpyridin-2-yl) methoxy]-1H-benzimidazol-2-yl}cyclohexanecarboxylic acid, (1S*,2R*)-2-{1-(4-Cyanobenzyl)-6-[(5-methylpyridin-2-yl) methoxy]-1H-benzimidazol-2-yl}cyclohexanecarboxylic acid, (1R*,2S*)-2-{1-(4-Cyanobenzyl)-6-[(5-methylpyridin-2-yl) methoxy]-1H-benzimidazol-2-yl}clohexanecarboxylic acid, racemic cis-2-{1-(4-Bromobenzyl)-6-[(1-methyl-1H-pyrazol-3-yl) methoxy]-1H-benzimidazol-2-yl}cyclohexanecarboxylic acid, racemic trans-2-{1-(4-Bromobenzyl)-6-[(1-methyl-1H-pyrazol-3-yl) methoxy]-1H-benzimidazol-2-yl}cyclohexanecarboxylic acid, 2-({1-(4-Bromobenzyl)-6-[(1-methyl-1H-pyrazol-3-yl) methoxy]-1H-benzimidazol-2-yl}methyl)-2-ethylbutanoic acid, 2-Ethyl-2-({6-[(1-Methyl-1H-pyrazol-3-yl) methoxy]-1-(4-piperidin-1-ylbenzyl)-1H-benzimidazol-2-yl}methyl)butanoic acid, racemic cis-2-{6-[(1-Methyl-1H-pyrazol-3-yl)methoxy]-1-[4-(trifluoromethoxy) benzyl]-1H-benzimidazol-2-yl}cyclohexanecarboxylic acid, (1R*,2S*)-2-{6-[(1-Methyl-1H-pyrazol-3-yl)methoxy]-1-]4-(trifluoromethoxy) benzyl]-1H-benzimidazol-2-yl}cyclohexanecarboxylic acid, 1-({1-(4-Bromobenzyl)-6-[(1-methyl-1H-pyrazol-3-yl) methoxy]-1H-benzimidazol-2-yl}methyl)cyclopentanecarboxylic acid, racemic cis-2-{1-(4-Cyanobenzyl)-6-[(1-methyl-1H-pyrazol-3-yl) methoxy]-1H-benzimidazol-2-yl}cyclohexanecarboxylic acid, racemic trans-2-{1-(4-Cyanobenzyl)-6-[(1-methyl-1H-pyrazol-3-yl) methoxy]-1H-benzimidazol-2-yl}cyclohexanecarboxylic acid, 2-({1-(4-Cyanobenzyl)-6-[(1-methyl-1H-pyrazol-3-yl) methoxy]-1H-benzimidazol-2-yl}methyl)-2-ethylbutanoic acid, 2-Ethyl-2-({6-[(1-methyl-1H-pyrazol-3-yl)methoxy]-1-[4-(trifluoromethoxy) benzyl]-1H-benzimidazol-2-yl}methyl)butanoic acid, racemic cis-2-{1-[2-Fluoro-4-(trifluoromethoxy) benzyl]-6-[(1-methyl-1H-pyrazol-3-y1) methoxy]-1H-benzimidazol-2-yl}cyclohexanecarboxylic acid, (1S*,2R*)-2-{1-[2-Fluoro-4-(trifluoromethoxy) benzyl]-6-[(1-methyl-1H-pyrazol-3-yl)methoxy]-1H-benzimidazol-2-yl}cyclohexanecarboxylic acid, (1R*,2S*)-2-(1-(2-Fluoro-4-(trifluoromethoxy)benzyl)-6-((1-methyl-1H-pyrazol-3-yl) methoxy)-1H-benzo[d]imidazol-2-yl)cyclohexanecarboxylic acid, racemic trans-2-{6-[(1-Methyl-1H-pyrazol-3-yl) methoxy]-1-[4-(trifluoromethoxy) benzyl]-1H-benzimidazol-2-yl}cyclohexanecarboxylic acid, racemic cis-2-{1-[3-Fluoro-4-(trifluoromethoxy) benzyl]-6-(1-methyl-1H-pyrazol-3-yl)methoxy]-1H-benzimidazol-2-yl}cyclohexanecarboxylic acid, 2-Ethyl-2-({1-[2-fluoro-4-(trifluoromethoxy)benzyl]-6-[(1-methyl-1H-pyrazol-3-yl) methoxy]-1H-benzimidazol-2-yl}methyl)butanoic acid, 2-Ethyl-2-({1-[3-fluoro-4-(trifluoromethoxy)benzyl]-6-[(1-methyl-1H-pyrazol-3-yl) methoxy]-1H-benzimidazol-2-yl}methyl)butanoic acid, 2-({1-(4-Bromo-2-fluorobenzyl)-6-[(1-methyl-1H-pyrazol-3-yl) methoxy]-1H-benzimidazol-2-yl}methyl)-2-ethylbutanoic acid, racemic cis-2-{1-(4-Bromobenzyl)-4-fluoro-6-[(5-methylpyridin-2-yl) methoxy]-1H-benzimidazol-2-yl}cyclohexanecarboxylic acid, 3-{1-(4-Bromobenzyl)-4-fluoro-6-[(5-methylpyridin-2-yl) methoxy]-1H-benzimidazol-2-yl}-2,2-dimethylpropanoic acid, 1-({1-(4-Bromobenzyl)-4-fluoro-6-[(5-methylpyridin-2-yl) methoxy]-1H-benzimidazol-2-yl}methyl)cyclopentanecarboxylic acid, racemic trans-2-{1-(4-Bromobenzyl)-4-fluoro-6-[(5-methylpyridin-2-yl) methoxy]-1H-benzimidazol-2-yl}cyclohexanecarboxylic acid, racemic cis-3-{1-(4-Bromobenzyl)-4-fluoro-6-[(5-methylpyridin-2-yl) methoxy]-1H-benzimidazol-2-yl}-2,2-dimethylcyclopropanecarboxylic acid, racemic cis-3-{4-Fluoro-1-(4-methylbenzyl)-6-[(5-methylpyridin-2-yl) methoxy]-1H-benzimidazol-2-yl}-2,2-dimethylcyclopropanecarboxylic acid, 2-({1-(4-Bromobenzyl)-4-fluoro-6-[(5-methylpyridin-2-yl) methoxy]-1H-benzimidazol-2-yl}methyl)-2-ethylbutanoic acid, racemic cis-2-{4-Fluoro-6-[(5-methylpyridin-2-yl) methoxy]-1-[4-(trifluoromethoxy) benzyl]-1H-benzimidazol-2-yl}cyclohexanecarboxylic acid, racemic trans-2-{4-Fluoro-6-[(5-methylpyridin-2-yl) methoxy]-1-[4-(trifluoromethoxy) benzyl]-1H-benzimidazol-2-yl}cyclohexanecarboxylic acid, racemic cis-2-{4-Fluoro-1-(4-methylbenzyl)-6-[(5-methylpyridin-2-yl) methoxy]-1H-benzimidazol-2-yl}cyclohexanecarboxylic acid, 2-Ethyl-2-({4-fluoro-6-[(5-methylpyridin-2-yl) methoxy]-1-[4-(trifluoromethoxy) benzyl]-1H-benzimidazol-2-yl}methyl)butanoic acid, racemic trans-2-{4-Fluoro-1-(4-methylbenzyl)-6-[(5-methylpyridin-2-yl) methoxy]-1H-benzimidazol-2-yl}cyclohexanecarboxylic acid, 2-Ethyl-2-({4-fluoro-1-(4-methylbenzyl)-6-[(5-methylpyridin-2-yl) methoxy]-1H-benzimidazol-2-yl}methyl)butanoic acid, 1-({4-Fluoro-6-[(5-methylpyridin-2-yl)methoxy]-1-[4-(trifluoromethoxy) benzyl]-1H-benzimidazol-2-yl}methyl)cyclopentanecarboxylic acid, 1-({4-Fluoro-1-(4-methylbenzyl)-6-[(5-methylpyridin-2-yl) methoxy]-1H-benzimidazol-2-yl}methyl)cyclopentanecarboxylic acid, racmic cis-3-{4-Fluoro-6-[(5-methylpyridin-2-yl) methoxy]-1-[4-(trifluoromethoxy) benzyl]-1H-benzimidazol-2-yl}-2,2-dimethylcyclopropanecarboxylic acid, racemic cis-2-{1-(4-Bromobenzyl)-4-chloro-6-[(5-methylpyridin-2-yl) methoxy]-1H-benzimidazol-2-yl}cyclohexanecarboxylic acid, racemic cis-3-{1-(4-Bromobenzyl)-4-chloro-6-[(5-methylpyridin-2-yl) methoxy]-1H-benzimidazol-2-yl}-2,2-dimethylcyclopropanecarboxylic acid, racemic trans-2-{1-(4-Bromobenzyl)-4-chloro-6-[(5-methylpyridin-2-yl) methoxy]-1H-benzimidazol-2-yl}cyclohexanecarboxylic acid, 1-({1-(4-Bromobenzyl)-4-chloro-6-[(5-methylpyridin-2-yl) methoxy]-1H-benzimidazol-2-yl}methyl)cyclopentanecarboxylic acid, 3-{1-(4-Bromobenzyl)-4-chloro-6-[(5-methylpyridin-2-yl) methoxy]-1H-benzimidazol-2-yl}-2,2-dimethylpropanoic acid, racemic cis-2-{1-[4-(5-Chloropyrimidin-2-yl)benzyl]-6-[(5-methylpyridin-2-yl) methoxy]-1H-benzimidazol-2-yl}cyclohexanecarboxylic acid, racemic cis-2-{1-(4-Bromobenzyl)-6-[(4-chloro-1-methyl-1H-pyrazol-3-yl) methoxy]-1H-benzimidazol-2-yl}cyclohexanecarboxylic acid, racemic cis-2-{6-[(4-Chloro-1-methyl-1H-pyrazol-3-yl) methoxy]-1-(4-piperidin-1-ylbenzyl)-1H-benzimidazol-2-yl}cyclohexanecarboxylic acid, racemic cis-2-{6-[(4-Chloro-1-methyl-1H-pyrazol-3-yl) methoxy]-1-[2-fluoro-4-(trifluoromethoxy)benzyl]-1H-benzimidazol-2-yl}cyclohexanecarboxylic acid, racemic cis-2-{1-[2-Methoxy-4-(trifluoromethoxy)benzyl]-6-[(1-methyl-1H-pyrazol-3-yl) methoxy]-1H-benzimidazol-2-yl}cyclohexanecarboxylic acid, racemic cis-2-{6-[(4-Fluoro-1-methyl-1H-pyrazol-3-yl) methoxy]-1-[2-fluoro-4-(trifluoromethoxy) benzyl]-1H-benzimidazol-2-yl}cyclohexanecarboxylic acid, racemic cis-2-{1-[4-(4,4-Difluoropiperidin-1-yl)benzyl]-6-[(1-methyl-1H-pyrazol-3-yl) methoxy]-1H-benzimidazol-2-yl}cyclohexanecarboxylic acid, racemic cis-2-{6-[(4-Chloro-1-methyl-1H-pyrazol-3-yl) methoxy]-1-[4-(4-fluoropiperidin-1-yl) benzyl]-1H-benzimidazol-2-yl}cyclohexanecarboxylic acid, racemic cis-2-{6-[(1-Methyl-1H-pyrazol-3-yl) methoxy]-1-(4-piperidin-1-ylbenzyl)-1H-benzimidazol-2-yl}cyclohexanecarboxylic acid, racemic cis-2-{1-[4-(3,3-Difluoroazetidin-1-yl)benzyl]-6-[(1-methyl-1H-pyrazol-3-yl) methoxy]-1H-benzimidazol-2-yl}cyclohexanecarboxylic acid, racemic cis-2-{5-Fluoro-1-[2-fluoro-4-(trifluoromethoxy) benzyl]-6-[(1-methyl-1H-pyrazol-3-yl)methoxy]-1H-benzimidazol-2-yl}cyclohexanecarboxylic acid, racemic cis-2-{7-Fluoro-1-[2-fluoro-4-(trifluoromethoxy) benzyl]-6-[(1-methyl-1H-pyrazol-3-yl)methoxy]-1H-benzimidazol-2-yl}cyclohexanecarboxylic acid, 2-Ethyl-2-({6-[(1-methyl-1H-pyrazol-3-yl)methoxy]-1-[2-methyl-4-(trifluoromethoxy) benzyl]-1H-benzimidazol-2-yl}methyl)butanoic acid, racemic cis-2-{1-(4-Bromobenzyl)-4-fluoro-6-[(1-methyl-1H-pyrazol-3-yl) methoxy]-1H-benzimidazol-2-yl}cyclohexanecarboxylic acid, racemic cis-2-{1-(4-Bromo-2-fluorobenzyl)-4-fluoro-6-[(1-methyl-1H-pyrazol-3-yl) methoxy]-1H-benzimidazol-2-yl}cyclohexanecarboxylic acid, racemic cis-2-{4-Fluoro-6-[(1-methyl-1H-pyrazol-3-yl) methoxy]-1-[4-(trifluoromethoxy)benzyl]-1H-benzimidazol-2-yl}cyclohexanecarboxylic acid, racemic cis-2-{4-Fluoro-1-[2-fluoro-4-(trifluoromethoxy) benzyl]-6-[(1-methyl-1H-pyrazol-3-yl)methoxy]-1H-benzimidazol-2-yl}cyclohexanecarboxylic acid, racemic cis-2-{4-Fluoro-1-(4-methylbenzyl)-6-[(1-methyl-1H-pyrazol-3-yl) methoxy]-1H-benzimidazol-2-yl}cyclohexanecarboxylic acid, racemic cis-2-{1-(4-Cyanobenzyl)-4-fluoro-6-[(1-methyl-1H-pyrazol-3-yl) methoxy]-1H-benzimidazol-2-yl}cyclohexanecarboxylic acid, racemic cis-2-{6-[(1-Methyl-1H-pyrazol-3-yl)methoxy]-1-[2-methyl-4-(trifluoromethoxy) benzyl]-1H-benzimidazol-2-yl}cyclohexanecarboxylic acid, racemic cis-2-{6-[(5-Methylpyridin-2-yl)methoxy]-1-[2-methyl-4-(trifluoromethoxy) benzyl]-1H-benzimidazol-2-yl}cyclohexanecarboxylic acid, racemic cis-2-{1-[2-Chloro-4-(trifluoromethoxy)benzyl]-6-[(5-methylpyridin-2-yl) methoxy]-1H-benzimidazol-2-yl}cyclohexanecarboxylic acid, racemic cis-2-{1-[2-Bromo-4-(trifluoromethoxy)benzyl]-6-[(5-methylpyridin-2-yl) methoxy]-1H-benzimidazol-2-yl}cyclohexanecarboxylic acid, racemic cis-2-{1[2--Chloro-4-(trifluoromethoxy) benzyl]-6-[(1-methyl-1H-pyrazol-3-yl)methoxy]-1H-benzimidazol-2-yl}cyclohexanecarboxylic acid, racemic cis-2-{1-[2-Bromo-4-(trifluoromethoxy)benzyl]-6-[(1-methyl-1H-pyrazol-3-yl) methoxy]-1H-benzimidazol-2-yl}cyclohexanecarboxylic acid, 2-Ethyl-2-({6-[(5-methylpyridin-2-yl)methoxy]-1-[2-methyl-4-(trifluoromethoxy) benzyl]-1H-benzimidazol-2-yl}methyl)butanoic acid, racemic cis-2-{6-[(1-Methyl-1H-pyrazol-3-yl)methoxy]-1-[3-methyl-4-(trifluoromethoxy) benzyl]-1H-benzimidazol-2-yl}cyclohexanecarboxylic acid, 3-{1-(4-Bromobenzyl)-6-[(1-methyl-1H-pyrazol-3-yl) methoxy]-1H-benzimidazol-2-yl }-2,2-dimethylpropanoic acid, 3-{1-(4-Bromobenzyl)-6-[(6-methylpyridin-2-yl) methoxy]-1H-benzimidazol-2-yl}-2,2-dimethylpropanoic acid, racemic cis-2-{6-[(5-Methylpyridin-2-yl)methoxy]-1-[3-methyl-4-(trifluoromethoxy) benzyl]-1H-benzimidazol-2-yl}cyclohexanecarboxylic acid, racemic cis-2-{5-Chloro-1-[2-fluoro-4-(trifluoromethoxy) benzyl]-6-[(5-methylpyridin-2-yl) methoxy]-1H-benzimidazol-2-yl}cyclohexanecarboxylic acid, racemic cis-3-{1-(4-Bromobenzyl)-6-[(5-methylpyridin-2-yl) methoxy]-1H-benzimidazol-2-yl }-2,2-dimethylcyclopropanecarboxylic acid, (1S*,3R*)-3-{1-(4-Bromobenzyl)-6-[(5-methylpyridin-2-yl) methoxy]-1H-benzimidazol-2-yl }-2,2-dimethylcyclopropanecarboxylic acid, (1R*,3S*)-3-{1-(4-Bromobenzyl)-6-[(5-methylpyridin-2-yl) methoxy]-1H-benzimidazol-2-yl }-2,2-dimethylcyclopropanecarboxylic acid, racemic trans-3-{1-(4-Bromobenzyl)-6-[(5-methylpyridin-2-yl) methoxy]-1H-benzimidazol-2-yl }-2,2-dimethylcyclopropanecarboxylic acid, (1R*,3R*)-3-{1-(4-Bromobenzyl)-6-[(5-methylpyridin-2-yl) methoxy]-1H-benzimidazol-2-yl }-2,2-dimethylcyclopropanecarboxylic acid, (1S*,3S*)-3-{1-(4-Bromobenzyl)-6-[(5-methylpyridin-2-yl) methoxy]-1H-benzimidazol-2-yl }-2,2-dimethylcyclopropanecarboxylic acid, racemic trans-3-{1-(4-Bromobenzyl)-6-[(1-methyl-1H-pyrazol-3-yl) methoxy]-1H-benzimidazol-2-yl}-2,2-dimethylcyclopropanecarboxylic acid,
3-{1-(4-Bromobenzyl)-6-[(5-methylpyridin-2-yl) methoxy]-1H-benzimidazol-2-yl }-2,2-dimethylpropanoic acid,
racemic cis-2-{1-(4-Methylbenzyl)-6-[(5-methylpyridin-2-yl) methoxy]-1H-benzimidazol-2-yl}cyclohexanecarboxylic acid,
racemic trans-2-{1-(4-Methylbenzyl)-6-[(5-methylpyridin-2-yl) methoxy]-1H-benzimidazol-2-yl}cyclohexanecarboxylic acid,
racemic cis-2,2-Dimethyl-3-{1-(4-methylbenzyl)-6-[(5-methylpyridin-2-yl) methoxy]-1H-benzimidazol-2-yl}cyclopropanecarboxylic acid,
racemic cis-2,2-Dimethyl-3-{6-[(1-methyl-1H-pyrazol-3-yl) methoxy]-1-[4-(trifluoromethoxy)benzyl]-1H-benzimidazol-2-yl}cyclopropanecarboxylic acid,
racemic cis-2-{1-(4-Bromo-2,6-difluorobenzyl)-6-[(3-fluoro-5-methylpyridin-2-yl) methoxy]-1H-benzimidazol-2-yl}cyclohexanecarboxylic acid,
racemic trans-2-{1-(4-Bromo-2,6-difluorobenzyl)-6-[(3-fluoro-5-methylpyridin-2-yl) methoxy]-1H-benzimidazol-2-yl}cyclohexanecarboxylic acid,
racemic cis-2-{1-(4-Bromobenzyl)-6-[(3-fluoro-5-methylpyridin-2-yl) methoxy]-1H-benzimidazol-2-yl}cyclohexanecarboxylic acid,
racemic cis-2-{1-(4-Bromo-2,6-difluorobenzyl)-6-[(5-methylpyridin-2-yl) methoxy]-1H-benzimidazol-2-yl}cyclohexanecarboxylic acid,
3-{1-(2-Fluoro-4-methylbenzyl)-6-[(3-fluoro-5-methylpyridin-2-yl) methoxy]-1H-benzimidazol-2-yl}-2,2-dimethylpropanoic acid,
3-{1-(4-Bromobenzyl)-6-[(3-fluoro-5-methylpyridin-2-yl) methoxy]-1H-benzimidazol-2-yl }-2,2-dimethylpropanoic acid,
3-{1-(4-Bromo-2-fluorobenzyl)-6-[(3-fluoro-5-methylpyridin-2-yl) methoxy]-1H-benzimidazol-2-yl}-2,2-dimethylpropanoic acid,
3-{1-(4-Bromo-2,6-difluorobenzyl)-6-[(3-fluoro-5-methylpyridin-2-yl) methoxy]-1H-benzimidazol-2-yl}-2,2-dimethylpropanoic acid,
3-{6-[(3-Fluoro-5-methylpyridin-2-yl)methoxy]-1-[2-fluoro-4-(trifluoromethoxy) benzyl]-1H-benzimidazol-2-yl}-2,2-dimethylpropanoic acid,
racemic cis-3-{1-(4-Bromobenzyl)-6-[(3-fluoro-5-methylpyridin-2-yl) methoxy]-1H-benzimidazol-2-yl}-2,2-dimethylcyclopropanecarboxylic acid,
racemic cis-3-{1-(4-Bromobenzyl)-6-[(6-methylpyridin-2-yl) methoxy]-1H-benzimidazol-2-yl }-2,2-dimethylcyclopropanecarboxylic acid,
racemic cis-3-{1-(4-Bromobenzyl)-6-[(1-methyl-1H-pyrazol-3-yl) methoxy]-1H-benzimidazol-2-yl}-2,2-dimethylcyclopropanecarboxylic acid,
2-({1-(4-Cyanobenzyl)-6-[(3-fluoro-5-methylpyridin-2-yl) methoxy]-1H-benzimidazol-2-yl}methyl)-2-ethylbutanoic acid,
2-({1-(4-Bromobenzyl)-6-[(3-fluoro-5-methylpyridin-2-yl) methoxy]-1H-benzimidazol-2-yl}methyl)-2-ethylbutanoic acid,
racemic cis-2-(1-{[3,5-Difluoro-4'-(trifluoromethyl) biphenyl-4-yl]methyl}-6-[(3-fluoro-5-methylpyridin-2-yl) methoxy]-1H-benzimidazol-2-yl)cyclohexanecarboxylic acid, racemic cis-2-(1-{[3,5-Difluoro-4'-(trifluoromethyl) biphenyl-4-yl]methyl}-6-[(5-methylpyridin-2-yl) methoxy]-1H-benzimidazol-2-yl)cyclohexanecarboxylic acid,
(1R*,2S*)-2-(6-[(3-Fluoro-5-methylpyridin-2-yl) methoxy]-1-{[4'-(trifluoromethyl)biphenyl-4-yl] methyl}-1H-benzimidazol-2-yl)cyclohexanecarboxylic acid,
racemic trans-2-{1-(4-Bromo-2,6-difluorobenzyl)-6-[(5-methylpyridin-2-yl) methoxy]-1H-benzimidazol-2-yl}cyclohexanecarboxylic acid, 3-(6-[(3-Fluoro-5-methylpyridin-2-yl)methoxy]-1-{[3-fluoro-4'-(trifluoromethyl) biphenyl-4-yl]methyl}-1H-benzimidazol-2-yl)-2,2-dimethylpropanoic acid,
3-(6-[(3-Fluoro-5-methylpyridin-2-yl)methoxy]-1-{[4'-(trifluoromethyl) biphenyl-4-yl]methyl}-1H-benzimidazol-2-yl)-2,2-dimethylpropanoic acid,
3-(6-[(3-Fluoro-5-methylpyridin-2-yl)methoxy]-1-{[4'-(trifluoromethyl) biphenyl-3-yl]methyl}-1H-benzimidazol-2-yl)-2,2-dimethylpropanoic acid,
racemic cis-2-{1-[4(2-Methoxypyrimidin-5-yl)benzyl]-6-[(5-methylpyridin-2-yl) methoxy]-1H-benzimidazol-2-yl}cyclohexanecarboxylic acid,
racemic cis-2-(6-[(5-Methylpyridin-2-yl)methoxy]-1-{[4'-(trifluoromethyl) biphenyl-3-yl]methyl}-1H-benzimidazol-2-yl)cyclohexanecarboxylic acid,
racemic cis-2-(6-[(5-Methylpyridin-2-yl)methoxy]-1-{[4'-(trifluoromethyl) biphenyl-4-yl]methyl}-1H-benzimidazol-2-yl)cyclohexanecarboxylic acid,
(1S,2R)-2-(6-((5-Methylpyridin-2-yl)methoxy)-1-((4'-(trifluoromethyl)-]1,1'-biphenyl]-4-yl) methyl)-1H-benzo[d]imidazol-2-yl)cyclohexanecarboxylic acid,
(1R,2S)-2-(6-[(5-Methylpyridin-2-yl)methoxy]-1-{[4'-(trifluoromethyl) biphenyl-4-yl]methyl}-1H-benzimidazol-2-yl)cyclohexanecarboxylic acid,
2-Ethyl-2-((6-((5-methylpyridin-2-yl)methoxy)-1-((4'-(trifluoromethyl)-[1,1'-biphenyl]-3-yl) methyl)-1H-benzo[d]imidazol-2-yl)methyl)butanoic acid,
racemic cis-2-(6-[(1-Methyl-1H-pyrazol-3-yl)methoxy]-1-{[4'-(trifluoromethyl) biphenyl-3-yl]methyl}-1H-benzimidazol-2-yl)cyclohexanecarboxylic acid,
racemic cis-2-(6-[(4-Chloro-1-methyl-1H-pyrazol-3-yl) methoxy]-1-{[4'-(trifluoromethyl)biphenyl-4-yl] methyl}-1H-benzimidazol-2-yl)cyclohexanecarboxylic acid,
racemic cis-2-{1-[4-(3,3-Difluoropyrrolidin-1-yl)benzyl]-6-[(5-methylpyridin-2-yl) methoxy]-1H-benzimidazol-2-yl}cyclohexanecarboxylic acid,
racemic cis-2-{1-[(3,3-Difluoropiperidin-1-yl)benzyl]-6-[(5-methylpyridin-2-yl) methoxy]-1H-benzimidazol-2-yl}cyclohexanecarboxylic acid,
racemic cis-2-{1-[4(4,4-Difluoropiperidin-1-yl)benzyl]-6-[(5-methylpyridin-2-yl) methoxy]-1H-benzimidazol-2-yl}cyclohexanecarboxylic acid,
2-({1-[4-(3,3-Difluoropiperidin-1-yl)benzyl]-6-[(1-methyl-1H-pyrazol-3-yl) methoxy]-1H-benzimidazol-2-yl}methyl)-2-ethylbutanoic acid,
racemic cis-2-{6-[(5-Methylpyridin-2-yl)methoxy]-1-(4-piperidin-1-ylbenzyl)-1H-benzimidazol-2-yl}cyclohexanecarboxylic acid,
(1S*,2R*)-2-{6-[(5-Methylpyridin-2-yl)methoxy]-1-(4-piperidin-1-ylbenzyl)-1H-benzimidazol-2-yl}cyclohexanecarboxylic acid,
(1R*,2S*)-2-{6-[(5-Methylpyridin-2-yl)methoxy]-1-(4-piperidin-1-ylbenzyl)-1H-benzimidazol-2-yl}cyclohexanecarboxylic acid, racemic cis-2-{1-[4-(3,3-Difluoroazetidin-1-yl)benzyl]-6-[(5-methylpyridin-2-yl) methoxy]-1H-benzimidazol-2-yl}cyclohexanecarboxylic acid, (1S*,2R*)-2-{1-[4-(3,3-Difluoroazetidin-1-yl)benzyl]-6-[(5-methylpyridin-2-yl) methoxy]-1H-benzimidazol-2-yl}cyclohexanecarboxylic acid, racemic cis-2-{1-[4-(4,4-Difluoropiperidin-1-yl)-2-fluorobenzyl]-6-[(5-methylpyridin-2-yl) methoxy]-1H-benzimidazol-2-yl}cyclohexanecarboxylic acid, racemic cis-2-{1-[4-(3,3-Difluoropyrrolidin-1-yl)-2-fluorobenzyl]-6-[(5-methylpyridin-2-yl) methoxy]-1H-benzimidazol-2-yl}cyclohexanecarboxylic acid, (1R*,2S*)-2-{1-[4-(3,3-Difluoropyrrolidin-1-yl)-2-fluorobenzyl]-6-[(5-methylpyridin-2-yl) methoxy]-1H-benzimidazol-2-yl}cyclohexanecarboxylic acid, (1S*,2R*)-2-{1-[4-(3,3-Difluoropyrrolidin-1-yl)-2-fluorobenzyl]-6-[(5-methylpyridin-2-yl) methoxy]-1H-benzimidazol-2-yl}cyclohexanecarboxylic acid, racemic cis-2-{1-[4-(3,3-Difluoroazetidin-1-yl)-2-fluorobenzyl]-6-[(5-methylpyridin-2-yl) methoxy]-1H-benzimidazol-2-yl}cyclohexanecarboxylic acid, (1R*,2S*)-2-{1-[4-(3,3-Difluoroazetidin-1-yl)-2-fluorobenzyl]-6-[(5-methylpyridin-2-yl) methoxy]-1H-benzimidazol-2-yl}cyclohexanecarboxylic acid, (1S*,2R*)-2-{1-[4-(3,3-Difluoroazetidin-1-yl)-2-fluorobenzyl]-6-[(5-methylpyridin-2-yl) methoxy]-1H-benzimidazol-2-yl}cyclohexanecarboxylic acid, racemic cis-2-{1-[4-(3,3-Difluoroazetidin-1-yl)benzyl]-4-fluoro-6-[(1-methyl-1H-pyrazol-3-yl) methoxy]-1H-benzimidazol-2-yl}cyclohexanecarboxylic acid, racemic cis-2-{4-Fluoro-6-[(1-methyl-1H-pyrazol-3-yl) methoxy]-1-(4-piperidin-1-ylbenzyl)-1H-benzimidazol-2-yl}cyclohexanecarboxylic acid, 2-({1-[4-(4,4-Difluoropiperidin-1-yl)benzyl]-6-[(5-methylpyridin-2-yl) methoxy]-1H-benzimidazol-2-yl}methyl)-2-ethylbutanoic acid, racemic trans-2-{1-[4-(3,3-Difluoroazetidin-1-yl)-2-fluorobenzyl]-6-[(5-methylpyridin-2-yl) methoxy]-1H-benzimidazol-2-yl}cyclohexanecarboxylic acid, racemic cis-2-{1-[2,6-Difluoro-4-(4-fluoropiperidin-1-yl)benzyl]-6-[(3-fluoro-5-methylpyridin-2-yl) methoxy]-1H-benzimidazol-2-yl}cyclohexanecarboxylic acid, racemic cis-2-{1-[2-Fluoro-4-(4-fluoropiperidin-1-yl)benzyl]-6-[(3-fluoro-5-methylpyridin-2-yl) methoxy]-1H-benzimidazol-2-yl}cyclohexanecarboxylic acid, (1R*,2S*)-2-{1-[2-Fluoro-4-(4-fluoropiperidin-1-yl)benzyl]-6-[(3-fluoro-5-methylpyridin-2-yl) methoxy]-1H-benzimidazol-2-yl}cyclohexanecarboxylic acid, (1S*,2R*)-2-{1-[2Fluoro-4-(4-fluoropiperidin-1-yl)benzyl]-6-[(3-fluoro-5-methylpyridin-2-yl) methoxy]-1H-benzimidazol-2-yl}cyclohexanecarboxylic acid, (1R*,2S*)-2-6-[(3-Fluoro-5-methylpyridin-2-yl) methoxy]-1-[4-(4-fluoropiperidin-1-yl) benzyl]-1H-benzimidazol-2-yl}clohexanecarboxylic acid, racemic cis-2-{1-[2-Fluoro-4-(4-methylpiperidin-1-yl)benzyl]-6-[(3-fluoro-5-methylpyridin-2-yl) methoxy]-1H-benzimidazol-2-yl}cyclohexanecarboxylic acid, racemic cis-2-{6-[(3-Fluoro-5-methylpyridin-2-yl)methoxy]-1-(4-methylpiperidin-1-yl) benzyl]-1H-benzimidazol-2-yl}cyclohexanecarboxylic acid, racemic cis-2-{6-[(3-Fluoro-5-methylpyridin-2-yl) methoxy]-1-(4-piperidin-1-ylbenzyl)-1H-benzimidazol-2-yl}cyclohexanecarboxylic acid, 2-Ethyl-2-({6-[(3-fluoro-5-methylpyridin-2-yl) methoxy]-1-[4-(4-methylpiperidin-1-yl) benzyl]-1H-benzimidazol-2-yl}methyl)butanoic acid, 2-Ethyl-2-({1-fluoro-4-(4-methylpiperidin-1-yl)benzyl]-6-[(3-fluoro-5-methylpyridin-2-yl) methoxy]-1H-benzimidazol-2-yl}methyl)butanoic acid, 2-Ethyl-2-({6-[(3-fluoro-5-methylpyridin-2-yl) methoxy]-1-[4-(4-fluoropiperidin-1-yl) benzyl]-1H-benzimidazol-2-yl}methyl)butanoic acid, 3-(6-[(3-Fluoro-5-methylpyridin-2-yl)methoxy]-1-{2-fluoro-4-[3-(trifluoromethyl) azetidin-1-yl]benzyl}-1H-benzimidazol-2-yl)-2,2-dimethylpropanoic acid, 3-{1-[4-(4-tert-Butylpiperidin-1-yl)benzyl]-6-[(3-fluoro-5-methylpyridin-2-yl) methoxy]-1H-benzimidazol-2-yl}-2,2-dimethylpropanoic acid, 3-{6-[(3-Fluoro-5-methylpyridin-2-yl)methoxy]-1-[4-(4-methylpiperidin-1-yl) benzyl]-1H-benzimidazol-2-yl}-2,2-dimethylpropanoic acid, 3-{1-[2-Fluoro-4-(4-fluoropiperidin-1-yl)benzyl]-6-[(3-fluoro-5-methylpyridin-2-yl) methoxy]-1H-benzimidazol-2-yl}-2,2-dimethylpropanoic acid, 2-Ethyl-2-((1-((3-fluoro-4'-(trifluoromethyl)-[1,1'-biphenyl]-4-yl) methyl)-6-((1-methyl-1H-pyrazol-3-yl) methoxy)-1H-benzo[d]imidazol-2-yl)methyl)butanoic acid, 2-Ethyl-2-((6-((1-methyl-1H-pyrazol-3-yl)methoxy)-1-((4'-(trifluoromethyl)-[1,1'-biphenyl]-4-yl) methyl)-1H-benzo[d]imidazol-2-yl)methyl)butanoic acid, 2-Ethyl-2-((1-(2-fluoro-4-(4-(trifluoromethyl)piperidin-1-yl)benzyl)-6-((1-methyl-1H-pyrazol-3-yl) methoxy)-1H-benzo[d]imidazol-2-yl)methyl)butanoic acid, 2-Ethyl-2-((6-((1-methyl-1H-pyrazol-3-yl)methoxy)-1-(4-(4-(trifluoromethyl) piperidin-1-yl)benzyl)-1H-benzo[d]imidazol-2-yl)methyl)butanoic acid, 3-{1-(3-Bromobenzyl)-6-[(3-fluoro-5-methylpyridin-2-yl) methoxy]-1H-benzimidazol-2-yl}-2,2-dimethylpropanoic acid, racemic cis-2-(6-[(3-Fluoro-5-methylpyridin-2-yl)methoxy]-1-{2-fluoro-4-[4-(trifluoromethyl) piperidin-1-yl]benzyl}-1H-benzimidazol-2-yl)cyclohexanecarboxylic acid, 3-{1-(5-Bromo-2-fluorobenzyl)-6-[(3-fluoro-5-methylpyridin-2-yl) methoxy]-1H-benzimidazol-2-yl}-2,2-dimethylpropanoic acid, 2-Ethyl-2-[(6-[(3-fluoro-5-methylpyridin-2-yl)methoxy]-1-{4-[4-(trifluoromethyl) piperidin-1-yl]benzyl}-1H-benzimidazol-2-yl)methyl]butanoic acid, racemic cis-2-{1-[3-(2-Methoxypyrimidin-5-yl)benzyl]-6-[(5-methylpyridin-2-yl) methoxy]-1H-benzimidazol-2-yl}cyclohexanecarboxylic acid, 2-Ethyl-2-({1-[3-(2-methoxypyrimidin-5-yl)benzyl]-6-[(5-methylpyridin-2-yl) methoxy]-1H-benzimidazol-2-yl}methyl) butanoic acid, (1S*,2R*)-2-{1-(3-Bromobenzyl)-6-[(1-methyl-1H-pyrazol-3-yl) methoxy]-1H-benzimidazol-2-yl}cyclohexanecarboxylic acid, (1R*,2S*)-2-{1-(3-Bromobenzyl)-6-[(1-methyl-1H-pyrazol-3-yl) methoxy]-1H-benzimidazol-2-yl}cyclohexanecarboxylic acid, racemic cis-2-{1-(3-Cyanobenzyl)-6-[(1-methyl-1H-pyrazol-3-yl) methoxy]-1H-benzimidazol-2-yl}cyclohexanecarboxylic acid, racemic trans-2-{1-(3-Methylbenzyl)-6-[(5-methylpyridin-2-yl) methoxy]-1H-benzimidazol-2-yl}cyclohexanecarboxylic acid, racemic cis-2-{1-(3-Methylbenzyl)-6-[(5-methylpyridin-2-yl) methoxy]-1H-benzimidazol-2-yl}cyclohexanecarboxylic acid, racemic cis-2,2-Dimethyl-3-{1-(3-methylbenzyl)-6-[(5-methylpyridin-2-yl) methoxy]-1H-benzimidazol-2-yl}cyclopropanecarboxylic acid, racemic cis-2-{1-[3-(4,4-Difluoropiperidin-1-yl)benzyl]-6-[(1-methyl-1H-pyrazol-3-yl) methoxy]-1H-benzimidazol-2-yl}cyclohexanecarboxylic acid, racemic cis-2-{6-[(1-Methyl-1H-pyrazol-3-yl) methoxy]-1-(3-piperidin-1-ylbenzyl)-1H-benzimidazol-2-yl}cyclohexanecarboxylic acid, racemic cis-2-{1-[3-(3,3-Difluoroazetidin-1-yl)benzyl]-6-[(1-methyl-1H-pyrazol-3-yl) methoxy]-1H-benzimidazol-2-yl}cyclohexanecarboxylic acid, racemic trans-2-{1-(2-Methylbenzyl)-6-[(5-methylpyridin-2-yl) methoxy]-1H-benzimidazol-2-yl}cyclohexanecarboxylic acid, racemic cis-2-{1-(2-Methylbenzyl)-6-[(5-methylpyridin-2-yl) methoxy]-1H-benzimidazol-2-yl}cyclohexanecarboxylic acid, racemic cis-2-{1-[5-(4,4-Difluoropiperidin-1-yl)-2-fluorobenzyl]-6-[(5-methylpyridin-2-yl) methoxy]-1H-benzimidazol-2-yl}cyclohexanecarboxylic acid, racemic cis-2-{1-(2-Fluoro-5-piperidin-1-ylbenzyl)-6-[(5-methylpyridin-2-yl) methoxy]-1H-benzimidazol-2-yl}cyclohexanecarboxylic acid, racemic cis--2,2-Dimethyl-3-{1-(2-methylbenzyl)-6-[(5-methylpyridin-2-yl) methoxy]-1H-benzimidazol-2-yl}cyclopropanecarboxylic acid, 2-({1-[3-(3,3-Difluoropyrrolidin-1-yl)benzyl]-6-[(1-methyl-1H-pyrazol-3-yl) methoxy]-1H-benzimidazol-2-yl}methyl)-2-ethylbutanoic acid, 2-Ethyl-2-({6-[(1-methyl-1H-pyrazol-3-yl)methoxy]-1-(3-piperidin-1-ylbenzyl)-1H-benzimidazol-2-yl}methyl)butanoic acid, 2-Ethyl-2-({1-[3-(2-methoxypyrimidin-5-yl)benzyl]-6-[(1-methyl-1H-pyrazol-3-yl) methoxy]-1H-benzimidazol-2-yl}methyl)butanoic acid, 2-Ethyl-2-({1-[2-fluoro-4-(2-methoxypyrimidin-5-yl)benzyl]-6-[(1-methyl-1H-pyrazol-3-yl) methoxy]-1H-benzimidazol-2-yl}methyl)butanoic acid, 2-({1-(3-Bromobenzyl)-6-[(1-methyl-1H-pyrazol-3-yl) methoxy]-1H-benzimidazol-2-yl}methyl)-2-ethylbutanoic acid, 2-({1-[4-(3,3-Difluoropyrrolidin-1-yl)benzyl]-6-[(1-methyl-1H-pyrazol-3-yl) methoxy]-1H-benzimidazol-2-yl }methyl)-2-ethylbutanoic acid, racemic trans-2-{1-(3-Bromobenzyl)-6-[(5-methylpyridin-2-yl)methoxy]-1H-benzimidazol-2-yl}cyclohexanecarboxylic acid, racemic trans-2-{1-(5-Bromo-2-fluorobenzyl)-6-[(5-methylpyridin-2-yl) methoxy]-1H-benzimidazol-2-yl}cyclohexanecarboxylic acid, racemic cis-2-{1-[3-(3,3-Difluoroazetidin-1-yl)benzyl]-6-[(5-methylpyridin-2-yl) methoxy]-1H-benzimidazol-2-yl}cyclohexanecarboxylic acid, racemic cis-2-{1-[3-(3,3-Difluoropyrrolidin-1-yl)benzyl]-6-[(5-methylpyridin-2-yl) methoxy]-1H-benzimidazol-2-yl}cyclohexanecarboxylic acid, racemic cis-2-{1-[3-(4,4-Difluoropiperidin-1-yl)benzyl]-6-[(5-methylpyridin-2-yl) methoxy]-1H-benzimidazol-2-yl}cyclohexanecarboxylic acid, racemic cis--2-{1-[3-(3,3-Difluoropiperidin-1-yl)benzyl]-6-[(5-methylpyridin-2-yl) methoxy]-1H-benzimidazol-2-yl}cyclohexanecarboxylic acid, racemic cis-2-{6-[(5-Methylpyridin-2-yl)methoxy]-1-(3-piperidin-1-ylbenzyl)-1H-benzimidazol-2-yl}cyclohexanecarboxylic acid, racemic trans-2-{6-[(5-Methylpyridin-2-yl)methoxy]-1-(3-piperidin-1-ylbenzyl)-1H-benzimidazol-2-yl}cyclohexanecarboxylic acid, 3-{1-(5-Bromo-2-fluorobenzyl)-6-[(5-methylpyridin-2-yl)methoxy]-1H-benzimidazol-2-yl}-2,2-dimethylpropanoic acid, 2-({1-[4-(3,3-Difluoropyrrolidin-1-yl)benzyl]-6-[(5-methylpyridin-2-yl) methoxy]-1H-benzimidazol-2-yl}methyl)-2-ethylbutanoic acid, racemic cis-3-{1-(5-Bromo-2-fluorobenzyl)-6-[(5-methylpyridin-2-yl) methoxy]-1H-benzimidazol-2-yl}-2,2-dimethylcyclopropanecarboxylic acid, racemic cis-2-{1-(3-Bromobenzyl)-6-[(5-methylpyridin-2-yl) methoxy]-1H-benzimidazol-2-yl}cyclohexanecarboxylic acid, racemic-cis-2-{1-(5-Bromo-2-fluorobenzyl)-6-[(5-methylpyridin-2-yl) methoxy]-1H-benzimidazol-2-yl}cyclohexanecarboxylic acid, 1-({1-(3-Bromobenzyl)-4-fluoro-6-[(5-methylpyridin-2-yl) methoxy]-1H-benzimidazol-2-yl}methyl)cyclopentanecarboxylic acid, 1-({1-(2-Bromobenzyl)-4-fluoro-6-[(5-methylpyridin-2-yl) methoxy]-1H-benzimidazol-2-yl}methyl)cyclopentanecarboxylic acid, 3-{1-(3-Bromobenzyl)-6-[(5-methylpyridin-2-yl) methoxy]-1H-benzimidazol-2-yl}-2,2-dimethylpropanoic acid, racemic cis-2-{1-(5-Bromo-2-fluorobenzyl)-6-[(1-methyl-1H-pyrazol-3-yl) methoxy]-1H-benzimidazol-2-yl}cyclohexanecarboxylic acid, 2-({1-(5-Bromo-2-fluorobenzyl)-6-[(1-methyl-1H-pyrazol-3-yl) methoxy]-1H-benzimidazol-2-yl}methyl)-2-ethylbutanoic acid, 2-({1-(5-Bromo-2-fluorobenzyl)-6-[(5-methylpyridin-2-yl) methoxy]-1H-benzimidazol-2-yl}methyl)-2-ethylbutanoic acid, and racemic cis-2-{1-[4-(3,3-Difluoropyrrolidin-1-yl) benzyl]-4-fluoro-6-[(1-methyl-1H-pyrazol-3-yl)methoxy]-1H-benzimidazol-2-yl}cyclohexanecarboxylic acid, and pharmaceutically acceptable salts thereof.

* * * * *

UNITED STATES PATENT AND TRADEMARK OFFICE
CERTIFICATE OF CORRECTION

PATENT NO. : 9,695,149 B2
APPLICATION NO. : 14/777492
DATED : July 4, 2017
INVENTOR(S) : Wenying Chai et al.

Page 1 of 3

It is certified that error appears in the above-identified patent and that said Letters Patent is hereby corrected as shown below:

In the Claims

Column 211, Lines 10-12, "(1R*,3S*)-3-{4-Bromo-2-fluorobenzyl)-6-[(5-methylpyridin-2-yl)methoxy]-1H-benzimidazol-2-yl}-2,2-dimethylcyclopropanecarboxylic acid," should read --(1R*,3S*)-3-{1-(4-Bromo-2-fluorobenzyl)-6-[(5-methylpyridin-2-yl)methoxy]-1H-benzimidazol-2-yl}-2,2-dimethylcyclopropanecarboxylic acid,--

Column 217, Lines 22-24, "2-Ethyl-2-((6-((5-methylpyridin-2-yl)methoxy)-1-{[4'-(trifluoromethyl)-[1,1'-biphenyl]-3-yl)methyl}-1H-benzo[d]imidazol-2-yl)methyl)butanoic acid," should read --2-Ethyl-2-((6-((5-methylpyridin-2-yl)methoxy)-1-((4'-(trifluoromethyl)-[1,1'-biphenyl]-3-yl)methyl)-1H-benzo[d]imidazol-2-yl)methyl)butanoic acid,--

Column 219, Lines 8-11, "2-Ethyl-2-((6-((1-methyl-1H-pyrazol-3-yl)methoxy)-1-(4-(4-(trifluoromethyl)-[1,1'-biphenyl]-4-yl)methyl)-1H-benzo[d]imidazol-2-yl)methyl)butanoic acid," should read --2-Ethyl-2-((6-((1-methyl-1H-pyrazol-3-yl)methoxy)-1-((4'-(trifluoromethyl)-[1,1'-biphenyl]-4-yl)methyl)-1H-benzo[d]imidazol-2-yl)methyl)butanoic acid,--

Column 219, Lines 11-13, "2-Ethyl-2-((1-(2-fluoro-4-(4-(trifluoromethyl)piperidin-1-yl)benzyl)-6-((1-methyl-1H-pyrazol-3-yl)methoxy)-1H-benzo[d]imidazol-2-yl)methyl)butanoic acid," should read --2-Ethyl-2-((1-(2-fluoro-4-(4-(trifluoromethyl)piperidin-1-yl)benzyl)-6-((1-methyl-1H-pyrazol-3-yl)methoxy)-1H-benzo[d]imidazol-2-yl)methyl)butanoic acid, and--

Column 224, Lines 16-19, "racemic cis-2-{1-[2-Fluoro-4-(4-methylpiperidin-1-yl)benzyl]-6-[(3-fluoro-5-methylpyridin-2-yl)methoxy]-1H-benzimidazol-2-yl}cyclohexanecarboxylic acid, and" should read --racemic cis-2-{1-[2-Fluoro-4-(4-methylpiperidin-1-yl)benzyl]-6-[(3-fluoro-5-methylpyridin-2-yl)methoxy]-1H-benzimidazol-2-yl}cyclohexanecarboxylic acid,--

Column 224, Lines 20-22, "racemic cis-2-{6-[(3-Fluoro-5-methylpyridin-2-yl)methoxy]-1-[4-(4-methylpiperidin-1-yl)benzyl]-1H-benzimidazol-2-yl}cyclohexanecarboxylic acid," should read Signed and Sealed this
Seventh Day of May, 2019

Andrei Iancu
*Director of the United States Patent and Trademark Office*

CERTIFICATE OF CORRECTION (continued)
U.S. Pat. No. 9,695,149 B2

--racemic cis-2-{6-[(3-Fluoro-5-methylpyridin-2-yl)methoxy]-1-[4-(4-methylpiperidin-1-yl)benzyl]-1H-benzimidazol-2-yl}cyclohexanecarboxylic acid, and--

Column 224, Lines 47-49, "(1 S*,2R*)-2-{1-(3-Bromobenzyl)-6-[(1-methyl-1H-pyrazol-3-yl)methoxy]-1H-benzimidazol-2-yl}cyclohexanecarboxylic acid," should read --(1S*,2R*)-2-{1-(3-Bromobenzyl)-6-[(1-methyl-1H-pyrazol-3-yl)methoxy]-1H-benzimidazol-2-yl}cyclohexanecarboxylic acid,--

Column 228, beginning at Line 10, insert the following paragraph --1-({1-(4-Bromobenzyl)-6-[(5-methylpyridin-2-yl)methoxy]-1H-benzimidazol-2-yl}methyl)cyclopentanecarboxylic acid,--

Column 228, Lines 10-12, "racemic cis-2-{1-(4-Bromo-3-fluorobenzyl)-6-[(5-methylpyridin-2-yl)methoxy]-1H-benzimidazol-2-yl}cyclohexanecarboxylic acid," should read --racemic cis-2-{1-(4-Bromo-2-fluorobenzyl)-6-[(5-methylpyridin-2-yl)methoxy]-1H-benzimidazol-2-yl}cyclohexanecarboxylic acid,--

Column 228, beginning at Line 13, insert the following paragraphs
--(1R*,2S*)-2-{1-(4-Bromo-2-fluorobenzyl)-6-[(5-methylpyridin-2-yl)methoxy]-1H-benzimidazol-2-yl}cyclohexanecarboxylic acid,
(1S*,2R*)-2-{1-(4-Bromo-2-fluorobenzyl)-6-[(5-methylpyridin-2-yl)methoxy]-1H-benzimidazol-2-yl}cyclohexanecarboxylic acid,--

Column 228, Lines 13-15, "racemic trans-2-{1-(4-Bromobenzyl)-6-[(5-methylpyridin-2-yl)methoxy]-1H-benzimidazol-2-yl}cyclohexanecarboxylic acid," should read --racemic trans-2-{1-(4-Bromo-2-fluorobenzyl)-6-[(5-methylpyridin-2-yl)methoxy]-1H-benzimidazol-2-yl}cyclohexanecarboxylic acid,--

Column 228, Lines 16-22, delete the following paragraphs
"(1S*,2S*)-2-{1-(4-Bromobenzyl)-6-[(5-methylpyridin-2-yl)methoxy]-1H-benzimidazol-2-yl}cyclohexanecarboxylic acid,
(1R*,2R*)-2-{1-(4-Bromobenzyl)-6-[(5-methylpyridin-2-yl)methoxy]-1H-benzimidazol-2-yl}cyclohexanecarboxylic acid,"

Column 228, Lines 23-25, "2-({1-(4-Bromobenzyl)-6-[(5-methylpyridin-2-yl)methoxy]-1H-benzimidazol-2-yl}methyl)-2-ethylbutanoic acid," should read --2-({1-(3-Bromobenzyl)-6-[(5-methylpyridin-2-yl)methoxy]-1H-benzimidazol-2-yl}methyl)-2-ethylbutanoic acid,--

Column 232, Lines 25-27, "racemic cis-2-{1-[2--Chloro-4-(trifluoromethoxy)benzyl]-6-[(1-methyl-1H-pyrazol-3-yl)methoxy]-1H-benzimidazol-2-yl}cyclohexanecarboxylic acid," should read --racemic cis-2-{1-[2-Chloro-4-(trifluoromethoxy)benzyl]-6-[(1-methyl-1H-pyrazol-3-yl)methoxy]-1H-benzimidazol-2-yl}cyclohexanecarboxylic acid,--

Column 234, Lines 22-24, "racemic cis-2-{1-[4(2-Methoxypyrimidin-5-yl)benzyl]-6-[(5-methylpyridin-2-yl)methoxy]-1H-benzimidazol-2-yl}cyclohexanecarboxylic acid," should read --racemic cis-2-{1-[4-(2-Methoxypyrimidin-5-yl)benzyl]-6-[(5-methylpyridin-2-yl)methoxy]-1H-benzimidazol-2-yl}cyclohexanecarboxylic acid,--

CERTIFICATE OF CORRECTION (continued)
U.S. Pat. No. 9,695,149 B2

Column 234, Lines 53-55, "racemic cis-2-{1-[4(4,4-Difluoropiperidin-1-yl)benzyl]-6-[(5-methylpyridin-2-yl)methoxy]-1H-benzimidazol-2-yl}cyclohexanecarboxylic acid," should read --racemic cis-2-{1-[4-(4,4-Difluoropiperidin-1-yl)benzyl]-6-[(5-methylpyridin-2-yl)methoxy]-1H-benzimidazol-2-yl}cyclohexanecarboxylic acid,--

Column 235, Lines 50-52, "(1S*,2R*)-2-{1-[2Fluoro-4-(4-fluoropiperidin-1-yl)benzyl]-6-[(3-fluoro-5-methylpyridin-2-yl)methoxy]-1H-benzimidazol-2-yl}cyclohexanecarboxylic acid," should read --(1S*,2R*)-2-{1-[2-Fluoro-4-(4-fluoropiperidin-1-yl)benzyl]-6-[(3-fluoro-5-methylpyridin-2-yl)methoxy]-1H-benzimidazol-2-yl}cyclohexanecarboxylic acid,--

Column 235, Lines 53-55, "(1R*,2S*)-2-6-[(3-Fluoro-5-methylpyridin-2-yl)methoxy]-1-[4-(4-fluoropiperidin-1-yl)benzyl]-1H-benzimidazol-2-yl}clohexanecarboxylic acid," should read --(1R*,2S*)-2-{6-[(3-Fluoro-5-methylpyridin-2-yl)methoxy]-1-[4-(4-fluoropiperidin-1-yl)benzyl]-1H-benzimidazol-2-yl}cyclohexanecarboxylic acid,--

Column 235, Lines 59-61, "racemic cis-2-{6-[(3-Fluoro-5-methylpyridin-2-yl)methoxy]-1-(4-methylpiperidin-1-yl)benzyl]-1H-benzimidazol-2-yl}cyclohexanecarboxylic acid," should read --racemic cis-2-{6-[(3-Fluoro-5-methylpyridin-2-yl)methoxy]-1-[4-(4-methylpiperidin-1-yl)benzyl]-1H-benzimidazol-2-yl}cyclohexanecarboxylic acid,--

Column 236, Lines 1-3, "2-Ethyl-2-({1-fluoro-4-(4-methylpiperidin-1-yl)benzyl]-6-[(3-fluoro-5-methylpyridin-2-yl)methoxy]-1H-benzimidazol-2-yl}methyl)butanoic acid," should read --2-Ethyl-2-({1-[2-fluoro-4-(4-methylpiperidin-1-yl)benzyl]-6-[(3-fluoro-5-methylpyridin-2-yl)methoxy]-1H-benzimidazol-2-yl}methyl)butanoic acid,--